United States Patent
Bridger et al.

(10) Patent No.: US 7,396,840 B2
(45) Date of Patent: Jul. 8, 2008

(54) CHEMOKINE RECEPTOR BINDING HETEROCYCLIC COMPOUNDS

(75) Inventors: Gary Bridger, Bellingham, WA (US); Renato Skerlj, Vancouver (CA); Al Kaller, Vancouver (CA); Curtis Harwig, Vancouver (CA); David Bogucki, Surrey (CA); Trevor R. Wilson, Langley (CA); Jason Crawford, British Columbia (CA); Ernest J. McEachern, White Rock (CA); Bern Atsma, Abbotsford (CA); Siqiao Nan, ShenZhen (CN); Yuanxi Zhou, Surrey (CA); Dominique Schols, Herent (BE); Christopher Dennis Smith, Toronto (CA); Maria Rosaria Di Fluri, Burnaby (CA)

(73) Assignee: Genzyme Corporation, Watham, MA (US)

( * ) Notice: Subject to any disclaimer, the term of this patent is extended or adjusted under 35 U.S.C. 154(b) by 91 days.

(21) Appl. No.: 11/345,987

(22) Filed: Feb. 2, 2006

(65) Prior Publication Data

US 2006/0128750 A1 Jun. 15, 2006

Related U.S. Application Data

(62) Division of application No. 10/858,910, filed on Jun. 1, 2004, now Pat. No. 7,084,155, which is a division of application No. 09/957,682, filed on Sep. 17, 2001, now Pat. No. 6,864,265.

(60) Provisional application No. 60/232,891, filed on Sep. 15, 2000, provisional application No. 60/234,510, filed on Sep. 22, 2000.

(51) Int. Cl.
*A61K 31/4436* (2006.01)
*A61K 31/44* (2006.01)
*A61K 31/4439* (2006.01)
*C07D 401/02* (2006.01)
*C07D 471/02* (2006.01)

(52) U.S. Cl. .................. 514/336; 544/224; 548/300.1; 548/302.7; 546/268.1; 514/361; 514/277; 514/314

(58) Field of Classification Search .............. 546/268.1; 544/224; 548/300.1, 302.7; 514/336, 361, 514/277, 314
See application file for complete search history.

(56) References Cited

U.S. PATENT DOCUMENTS

| 5,021,409 | A | 6/1991 | Murrer et al. |
| 5,583,131 | A | 12/1996 | Bridger et al. |
| 5,698,546 | A | 12/1997 | Bridger et al. |
| 5,817,807 | A | 10/1998 | Bridger et al. |
| 6,001,826 | A | 12/1999 | Murrer et al. |
| 6,750,348 | B1 | 6/2004 | Bridger et al. |
| 6,864,265 | B2 | 3/2005 | Bridger et al. |

FOREIGN PATENT DOCUMENTS

| EP | 1 163 238 | 12/2001 |
| WO | WO-99/38514 | 8/1999 |
| WO | WO-00/42852 | 7/2000 |
| WO | WO-00/51607 | 9/2000 |
| WO | WO-00/56729 | 9/2000 |
| WO | WO-02/22599 | 3/2002 |
| WO | WO-02/22600 | 3/2002 |

OTHER PUBLICATIONS

Dorwald F. A. Side Reactions in Organic Synthesis, 2005, Wiley: VCH, Weinheim p. IX of Preface.*
U.S. Appl. No. 60/172,153 filed by Bridger et al. on Dec. 17, 1999.
U.S. Appl. No. 09/111,895 filed by Bridger et al. on Jul. 8, 1998.
U.S. Appl. No. 09/495,298 filed by MacFarland et al. on Feb. 1, 2000.
U.S. Appl. No. 09/535,314 filed by Bridger et al. on Mar. 24, 2000.
Abi-Younes et al. (2000). *Circ. Res.* 86:131-138.
Alkhatib et al. (1996). *Science* 272:1955-1958.
Arai et al. (2000). *Eur. J. Haematol.* 64:323-332.
Arenburg et al. (1997). *J. Leukocyte Biol.* 62:554-562.
Auiti et al. (1997). *J. Exp. Med.* 185:111-120.
Baggiolini, M. (1998). *Nature* 392:565-568.
Bajetto et al. (1999). *J. Neurochem.* 73:2348-2357.
Berger et al. (1999). *Annu Rev. Immunol.* 17:657-700.
Biard-Piechaczyk et al. (2000). *Virology* 268:329-344.
Blaak et al. (2000). *Proc. Natl. Acad. Sci.* 97:1269-1274.
Blanco et al. (2000). *Antimigrobial Agents and Chemother* 44:51-56.
Bleul et al. (1998). *J. Exp. Med.* 187:753-762.
Bleul et al. (1996). *Nature* 382:829-833.
Bradstock et al. (2000). *Leukemia* 14:882-888.
Bridger et al. (1999). "Bicyclam Derivatives as HIV Inhibitors" in *Advances in Antiviral Drug Design.* vol. 3., JAI press., pp. 161-229.
Bridger et al. (1999). *J. Med. Chem.* 42:3971-3981.
Burger et al. (1999). *Blood* 94:3658-3667.
Buttini et al. (1998). *Nature Med.* 4:441-446.
Carroll et al. (1997). *Science* 276:273-276.
Cocchi et al. (1995). *Science* 270: 1811-1815.
Connor, R.I., Ho, D.D. (1994). *J. Virol.* 68:4400-4408.
Database WPI AN209951, XP002189031.
Deng et al. (1996). *Nature* 381:661-666.
Donzella et al. (1998). *Nature Medicine* 4:72-77.

(Continued)

*Primary Examiner*—Rita J Desai
(74) *Attorney, Agent, or Firm*—Morrison & Foerster LLP

(57) ABSTRACT

Tertiary amine compounds that bind chemokine receptors such as CXCR4 and CCR5 are disclosed.

9 Claims, No Drawings

OTHER PUBLICATIONS

Dragic et al. (1996). *Nature* 381:667-673.
Egberink et al. (1999). *J. Virol.* 73:6346-6352.
Eitner et al. (1998). *Transplantation* 66:1551-1557.
Fedyk et al. (1999). *J. Leukocyte Biol.* 66:667-673.
Feng et al. (1996). *Science* 272:872-877.
Gonzalo et al. (2000). *J.Immunol.* 165:499-508.
Gupta et al. (1998). *J.Biol. Chem.* 7:4282-4287.
Herbein et al. (1998). *Nature* 395:189-194.
Hesselgesser et al. (1999). "Chemokines and Chemokine receptors in the Brain" in *Chemokines in Disease*, Humana Press, pp. 295-312.
Hesselgesser et al. (1997). *Curr. Biol.* 7:112-121.
Hesselgesser et al. (1998). *Curr. Biol.* 8:595-598.
Ishii et al. (1999). *J.Immunol.* 163:3612-3620.
Lataillade et al. (2000). *Blood* 95:756-768.
Liu et al. (1996). *Cell* 86:367-377.
Locati et al. (1999). *Annu. Rev. Med.* 50:425-40.
Maekawa et al. (2000). *Internal Medicine* 39:90-100.
Michael et al. (1997). *Nature Med.* 3:338-340.
Michael et al. (1998). *J. Virol.* 72:6040-6047.
Miedema et al. (1994). *Immune. Rev.* 140:35-72.
Moore et al. (1998). *J. Invest. Med.* 46:113-120.
Moore et al. (1998). *Trends Cardiovasc. Med.* 8:51-58.
Murdoch et al. (2000). *Blood* 95:3032-3043.
Nagasawa et al. (1996). *Nature* 382:635-638.
Nagase, et al. (2000). *J. Immunol* 164:5935-5943.
Nanki et al. (2000). *J. Immunol* 164:5010-5014.
Oberlin et al. (1996). *Nature* 382:833-835.
O'Brien et al. (1997). *Lancet* 349:1219.
Ohagen et al. (1999). *J. Virol.* 73(2):897-906.
Peled et al. (2000). *Blood* 95(11):3289-3296.
Peled et al. (1999). *Science* 283:845-848.
Ponath, P. (1998). *Exp. Opin. Invest. Drugs* 7(1):1-18.
Qing et al. (1999). *Immunity* 10:463-471.
Rana et al. (1997). *J. Virol.* 71:3219-3227.
Rizzuto et al. (1998). *Science* 280:1949-1953.
Salcedo et al. (1999). *Am. J. Pathol.* 154(4):1125-1135.
Samson et al. (1996). *Nature* 382:722-725.
Sanders et al. (2000). *J. Neuroscience Res.* 59:671-679.
Schols et al. (1997). *Antiviral Research* 35:147-156.
Schols et al. (1997). *J. Exp. Med.* 186(8):1383-1388.
Schuitemaker et al. (1992). *J. Virol.* 66:1354-1360.
Seghal et al. (1998). *J. Surg. Oncol.* 69:99-104.
Simmons et al. (1969). *J. Virol.* 70(12):8355-8360.
Simmons et al. (1988). *J. Virol.* 72(10):8453-8457.
Tachibana et al. (1998). *Nature* 393:591-594.
Tersmette et al. (1988). *J. Virol.* 62(6):2026-2032.
Theodorou et al. (1997). *Lancet* 349:1219-1220.
Viardot et al. (1998). *Ann. Hematol.* 77:193-197.
Volin et al (1998). *Biochem. Biophys Res. Commun.* 242:46-53.
Wyatt et al. (1998). *Science* 280:1884-1888.
Xia et al. (1999). *J. NeuroVirology* 5:32-41.
Yssel et al. (1998). *Clinical and Experimental Allergy* 28:104-109.
Zhang et al. (1997). *AIDS Res. Hum. Retroviruses* 13(16):1357-1366.
Zhang et al. (1998). *J. Virol.* 72:9307-9312.
Zhang et al. (1999). *J. Virol.* 73(4):3443-3448.
Zhang et al. (1999). *J. Virol.* 73(10):8256-8267.

* cited by examiner

CHEMOKINE RECEPTOR BINDING HETEROCYCLIC COMPOUNDS

CROSS-REFERENCE TO RELATED APPLICATIONS

This application is a divisional of U.S. Ser. No. 10/858,910 filed 1 Jun. 2004, which is a divisional of U.S. Ser. No. 09/957,682 filed 17 Sep. 2001, which claims priority under 35 U.S.C. 119(e) to U.S. Provisional Application Ser. Nos. 60/232,891 filed 15 Sep. 2000, and 60/234,510 filed 22 Sep. 2000. The contents of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1-18, 1998; Baggiolini, M., *Nature* 392, 565-568 (1998); Locati et al. *Annu. Rev. Med.* 50, 425-40 (1999)). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR" while those of the α-chemokines are designated "CXCR".

Chemokines are considered to be principal mediators in the initiation and maintenance of inflammation (see *Chemokines in Disease* published by Humana Press (1999), Edited by C. Herbert; Murdoch et al. *Blood* 95, 3032-3043 (2000)). More specifically, chemokines have been found to play an important role in the regulation of endothelial cell function, including proliferation, migration and differentiation during angiogenesis and re-endothelialization after injury (Gupta et al., *J. Biol. Chem.*, 7:4282-4287 (1998); Volin et al *Biochem. Biophys Res. Commun.* 242, 46-53 (1998)). Two specific chemokines have been implicated in the etiology of infection by human immunodeficiency virus (HIV).

In most instances, HIV initially binds via its gp120 envelope protein to the CD4 receptor of the target cell. A conformational change appears to take place in gp120 which results in its subsequent binding to a chemokine receptor, such as CCR5 (Wyatt et al., *Science*, 280:1884-1888 (1998); Rizzuto et al. *Science*, 280:1949-1953 (1998); Berger et al. *Annu. Rev. Immunol.* 17: 657-700 (1999)). HIV-1 isolates arising subsequently in the infection bind to the CXCR4 chemokine receptor.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. Nature 381, 661-666 (1996); Alkhatib et al. *Science* 272, 1955-1958, 1996). During the course of infection within a patient, it appears that a majority of HIV particles shift from the M-tropic to the more pathogenic T-tropic viral phenotype (Blaak et al. *Proc. Natl. Acad. Sci.* 97, 1269-1274 (2000); Miedema et al., *Immune. Rev.*, 140:35 (1994); Simmonds et al. *J. Virol.* 70, 8355-8360 (1996); Tersmette et al. *J. Virol.* 62, 2026-2032, 1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinical observations suggest that patients who possess genetic mutations in CCR5 appear resistant, or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

In addition to serving as a co-factor for HIV entry, the direct interaction of virus-associated gp120 with CXCR4 has been recently suggested as a possible cause of CD8+ T-cell apoptosis and AIDS-related dementia via induction of neuronal cell apoptosis (Hesselgesser et al. *Curr. Biol.* 8, 595-598 (1998); Hesselgesser et al. *Curr. Biol.* 7, 112-121 (1997); Hesselgesser et al. "Chemokines and Chemokine receptors in the Brain" in *Chemokines in Disease* published by Humana Press (1999), Edited by C. Herbert; Herbein et al. *Nature* 395, 189-194 (1998); Buttini et al. *Nature Med.* 4, 441-446 (1998); Ohagen et al. *J. Virol.* 73, 897-906 (1999); Biard-Piechaczyk et al. *Virology* 268, 329-344 (2000); Sanders et al. *J. Neuroscience Res.* 59, 671-679 (2000); Bajetto et al. *J. Neurochem.* 73, 2348-2357 (1999); Zheng et al. *J. Virol.* 73, 8256-8267 (1999)).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou et al., *Nature*, 393:591-594 (1998); Tachibana et al., *Nature*, 393:591-594 (1998); Nagasawa et al. *Nature* 382, 635-638 (1996)). CXCR4-deficient mice also display hematopoietic defects (Nagasawa et al. *Nature* 382, 635-638 (1996)); the migration of CXCR4 expressing leukocytes and hematopoietic progenitors to SDF-1 appears to be important for maintaining B-cell lineage and localization of CD34+ progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)); the known angiogenic growth factors VEG-F and bFGF, up-regulate levels of CXCR4 in endothelial cells, and SDF-1 can induce neovascularization in vivo (Salcedo et al. *Am. J. Pathol.* 154, 1125-1135 (1999)); Leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimers disease (Xia et al. *J. Neurovirology* 5, 32-41 (1999)) and Arthritis (Nanki et al. *J. Immunol.* 164, 5010-5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design* Volume 3, p 161-229; Published by JAI press (1999); Edited by E. De Clercq). Small molecules, such as bicyclams, appear to specifically bind to CXCR4 and not CCR5 (Donzella et al., *Nature Medicine,* 4:72-77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol.* 73, 6346-6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

U.S. Pat. Nos. 5,583,131; 5,698,546; 5,817,807; 5,021,409; and 6,001,826 which are herein incorporated in their entirety by reference, disclose cyclic compounds that are active against HIV-1 and HIV-2 in in vitro tests. It was subsequently discovered and further disclosed in copending application U.S. Ser. No. 09/111,895 and U.S. Ser. No. 60/172,153 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Ser. No. 09/495,298 that these cyclic polyamine antiviral agents described in the above-mentioned patents have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in U.S. Ser. No. 09/535,314, a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

Herein, we disclose novel compounds that exhibit protective effects against HIV infection of target cells by binding to chemokine receptor CXCR4 or CCR5 in a similar manner to the previously disclosed macrocyclic compounds. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

SUMMARY OF THE INVENTION

The present invention provides novel compounds that bind chemokine receptors and interfere with the binding of the natural ligand thereto. The compounds of the present invention are useful as agents demonstrating protective effects on target cells from HIV infection. Other embodiments of the present invention are compounds that act as antagonists or agonists of chemokine receptors, as well as other biological activities related to the ability of these compounds to inhibit the binding of chemokines to their receptors.

The compound of the invention are of Formulas 1-4, including the pharmaceutically acceptable salts and pro-drug forms thereof. The compounds of Formula (1) are of the formula:

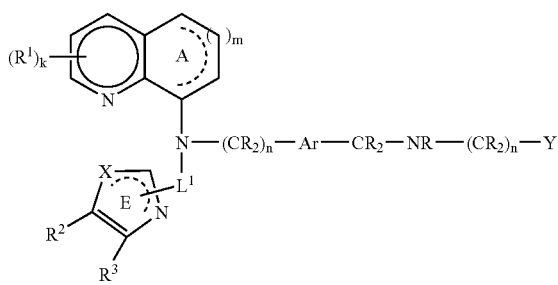

wherein:
ring A optionally comprises a heteroatom selected from N, O and S;
the dotted lines represent optional unsaturation;
$R^1$, $R^2$ and $R^3$ are non-interfering substituents;
k is 0-4;
m is 0-2;
$L^1$ is a linker of 1.5-10 Å;
X is unsubstituted or substituted C or N; or is O or S;
Ar is the residue of an aromatic moiety;
each n is independently 0-2;
each R is independently H or alkyl (1-6C); and
Y is an aromatic or heteroaromatic or other heterocyclic group.

Preferably, the genus of compounds of Formula 1 excludes the compounds

AMD7186: N-(5-ethylthiophene-2-ylmethyl)-N'-(2-pyridinylmethyl)-N-(5,6,7,8-tetrahydro-8-quinolinyl)-1,4-benzenedimethanamine, AMD7208: N-(1-methylpyrrol-2-ylmethyl)-N'-(2-pyridinylmethyl)-N-(5,6,7,8-tetrahydro-8-quinolinyl)-1,4-benzenedimethanamine, AMD7222: N-(1-methylbenzimidazol-2-ylmethyl)-N'-(2-pyridinylmethyl)-N-(5,6,7,8-tetrahydro-8-quinolinyl)-1,4-benzenedimethanamine, AMD8780: N-(2-pyridinylmethyl)-N'-(trans-2-aminocyclohexyl)-N'-(5,6,7,8-tetrahydro-8-quinolinyl)-1,4-benzenedimethanamine(hydrobromide salt), AMD8931: N-(2-pyridinylmethyl)-N-(4-phenyl-1H-imidazol-2-ylmethyl)-N'-(5,6,7,8-tetrahydro-8-quinolinyl)-1,4-benzenedimethanamine, AMD8821: N-(2-pyridinylmethyl)-N'-[2-furanylmethyl]-N'-(5,6,7,8-tetrahydro-8-quinolinyl)-1,4-benzenedimethanamine, AMD8828: N-(2-pyridinylmethyl)-N'-[2-[(2-furanylmethyl)amino]ethyl]-N'-(5,6,7,8-tetrahydro-8-quinolinyl)-1,4-benzenedimethanamine, AMD8835: N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine, AMD8836: N-(2-pyridinylmethyl)-N'-[2-thiopheneylmethyl]-N'-(5,6,7,8-tetrahydro-8-quinolinyl)-1,4-benzenedimethanamine, AMD8839: N-(2-pyridinylmethyl)-N'-(trans-2-aminocyclopentyl)-N'-(5,6,7,8-tetrahydro-8-quinolinyl)-1,4-benzenedimethanamine, AMD8841: N-(2-pyridinylmethyl)-N'-[2-thiazolylmethyl]-N'-(5,6,7,8-tetrahydro-8-quinolinyl)-1,4-benzenedimethanamine, AMD8751: N-(2-pyridinylmethyl)-N'-(1H-imidazol-2-ylmethyl)-N'-(5,6,7,8-tetrahydro-8-quinolinyl)-1,4-benzenedimethanamine, AMD8887: N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine, AMD8728: N-(2-pyridinylmethyl)-N'-[2-pyrrolylmethyl]-N'-(5,6,7,8-tetrahydro-8-quinolinyl)-1,4-benzenedimethanamine, AMD8907: N-(2-pyridinylmethyl)-N'-(1H-benzimidazol-2-ylmethyl)-N'-(5,6,7,8-tetrahydro-8-quinolinyl)-1,4-benzenedimethanamine, AMD8926: N-(2-pyridinylmethyl)-N'-(5-nitro-1H-benzimidazol-2-ylmethyl)-N'-(5,6,7,8-tetrahydro-8-quinolinyl)-1, 4-benzenedimethanamine, AMD8927: N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine, AMD 8929: N-(2-pyridinylmethyl)-N'-[(1H)-5-azabenzimidazol-2-ylmethyl]-N'-(5,6,7,8-tetrahydro-8-quinolinyl)-1, 4-benzenedimethanamine, and AMD8764: N-(2-pyridinylmethyl)-N'-(2-benzoxazolyl)-N'-(5,6,7,8-tetrahydro-8-quinolinyl)-1,4-benzenedimethanamine, which compounds were disclosed in parent application PCT/CA00/00321.

The compounds of Formula 2 are of the formula

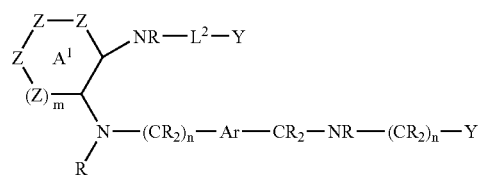

wherein:
R, m, n, Ar, and each Y are defined as in Formula 1;
each Z is independently $CR_2$, NR, O or S, with the proviso that only two Z can be other than $CR_2$; and
$L^2$ is a linker of 1.5-8 Å.

The compounds of Formula 3 are of the formula

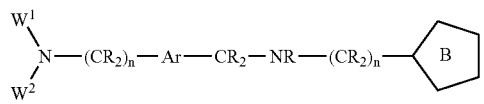

wherein:
$W^1$ is a monocyclic (5-6 membered) or fused bicyclic (8-12 membered) unsubstituted or substituted ring system containing at least one heteroatom selected from N, O and S;
$W^2$ is H, or is selected from the group consisting of: an optionally substituted $C_{1-6}$ alkyl group; a $C_{0-6}$ alkyl group substituted with an optionally substituted aromatic or heterocyclic group; an optionally substituted $C_{0-6}$ alkylamino or $C_{3-7}$ cycloalkylamino group; and an optionally substituted carbonyl group or sulfonyl;

Ar, R and n are defined as in Formula 1, and

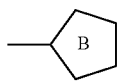

is a saturated or unsaturated 5-membered ring containing 1-2 heteroatoms selected from N, O and S.

The compounds of Formula 4 are of the formula

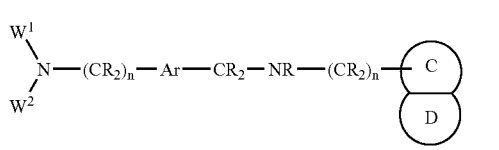

(4)

wherein:
$W^1$ and $W^2$ are defined as in Formula 3 and Ar, R and n are defined as in Formula 1; and

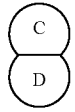

represents a fused ring system of 10 members, optionally containing 1 or 2 heteroatoms selected from N, O and S.

The optional substituents are defined herein infra.

One aspect of the present invention is a pharmaceutical composition comprising a therapeutically effective amount of the compound according to Formulas 1-4. Another aspect is a method of treating a disease of the human body or the bodies of other mammals comprising the administration of such pharmaceutical composition. Still another aspect is a method for blocking or interfering with the binding of a chemokine receptor with its natural ligand, comprising contacting said chemokine receptor with an effective amount of the compound according to Formulas 1-4.

Another aspect is the use of a compound of Formulas 1-4 in the manufacture of a medicament for the treatment of a disease in which blocking or interfering with binding of a chemokine receptor with its natural ligand is advantageous, comprising, for example, formulating a composition comprising a therapeutically effective amount of the compound of Formulas 1-4. The invention includes a method of protecting target cells possessing chemokine receptors, the binding to which by a pathogenic agent results in disease or pathology, comprising administering to a mammalian subject a pharmaceutical composition comprising a therapeutically effective amount of the compound according to Formulas 1-4.

The invention also includes the "pro-drug" forms, that is, protected forms of the compounds, which release the compound after administration to a patient. For example, the compound may carry a protective groups which is split off by hydrolysis in body fluids e.g. in the bloodstream, thus releasing active compound or is oxidized or reduced in body fluids to release the compound. A discussion of pro-drugs may be found in "Smith and Williams' Introduction to the Principles of Drug Design", H. J. Smith, Wright, Second Edition, London 1988.

Acid addition salts, which are pharmaceutically acceptable, such as salt with inorganic base, a salt with organic base, a salt with inorganic acid, a salt with organic acid, a salt with basic or acidic amino acid, etc. are also encompassed in the present invention. Examples of a salt with an inorganic base include a salt with alkali metal (e.g. sodium, potassium, etc.), alkaline earth metal (e.g. calcium, magnesium, etc.), aluminum, ammonium, etc. Examples of the salt with an organic base include a salt with trimethylamine, triethylamine, pyridine, picoline, ethanolamine, diethanolamine, triethanolamine, dicyclohexylamine, N,N'-dibenzylethylenediamine etc. Examples of the salt with an inorganic acid include a salt with hydrochloric acid, hydrobromic acid, nitric acid, sulfuric acid, phosphoric acid, etc. Examples of the salt with an organic acid include a salt with formic acid, oxalic acid, acetic acid, tartaric acid, methanesulfonic acid, benzenesulfonic acid, malic acid, methanesulfonic acid, benzenesulfonic acid, p-toluenesulfonic acid, etc. Examples of salts with basic amino acids include a salt with arginine, lysine, ornithine, etc. Examples of salts with the acidic amino acid include a salt with aspartic acid, glutamic acid, etc. Non-toxic in the present context has to be considered with reference to the prognosis for the infected patient without treatment.

MODES OF CARRYING OUT THE INVENTION

The present invention is directed to compounds of Formulas 1-4 which can act as agents that modulate chemokine receptor activity. Such chemokine receptors include but are not limited to CCR1, CCR2, CCR3, CCR4, CCR5, CCR6, CCR7, CCR8 and CXCR1, CXCR2, CXCR3, CXCR4 and CXCR5.

The present invention provides novel compounds of Formulas 1-4 that demonstrate protective effects on target cells from HIV infection in a manner as to bind specifically to the chemokine receptor, and which affect the binding of a natural ligand or chemokine to a receptor such as CXCR4 and/or CCR5 of a target cell.

In another embodiment, compounds of Formulas 1-4 may be useful as agents which affect chemokine receptors, such as CCR1, CCR2, CCR3, CCR4, CCR5, CCR6, CCR7, CCR8 and CXCR1, CXCR2, CXCR3, CXCR4 and CXCR5 where such chemokine receptors have been correlated as being important mediators of many human inflammatory as well as immunoregulatory diseases and cancer; and a compound that modulates the activity of such chemokine receptors would be useful for the treatment or prevention of such diseases.

The term "modulators" as used herein is intended to encompass antagonist, agonist, partial antagonist, and or partial agonist, inhibitors, and activators. In the preferred embodiment of the present invention, compounds of Formulas 1-4 demonstrate protective effects against HIV infection by inhibiting the binding of HIV to a chemokine receptor such as CXCR4 and/or CCR5 of a target cell, which comprises contacting the target cell with an amount of the compound which is effective at inhibiting the binding of the virus to the chemokine receptor.

The term "therapeutically effective amount" means the amount of the subject compound that will elicit a biological or medical response in a cell, tissue, organ, system, animal or human that is being sought by the researcher, veterinarian, medical doctor or other clinician. The response may be preventive and/or therapeutic.

The term "administration" and or "administering" of the subject compound should be understood to mean as providing a compound of the invention or a pro-drug of a compound of the invention to the individual in need of treatment.

Compounds that inhibit chemokine receptors may be used for the treatment of diseases associated with hematopoiesis, including but not limited to, controlling the side-effects of chemotherapy, enhancing the success of bone marrow transplantation, enhancing wound healing and burn treatment, as well as combating bacterial infections in leukemia.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria, vasculitis (e.g., necrotizing, cutaneous, and hypersensitivity vasculitis); eosinphilic myotis, eosiniphilic fasciitis; and cancers.

Compounds that activate or promote chemokine receptor function may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva *migrans (Ancylostona braziliense, Ancylostoma caninum)*; the malaria-causing protozoan *Plasmodium vivax,* Human cytomegalovirus, *Herpesvirus saimiri,* and Kaposi's sarcoma herpesvirus, also known as human herpesvirus 8, and poxyirus *Moluscum contagiosum.*

Compounds of Formulas 1-4 may be used in combination with any other pharmaceutical composition where such combined therapy may be useful to modulate chemokine receptor activity and thereby prevent and therapeutically treat diseases associated with hematopoiesis, inflammation, autoimmune, inflammatory dermatoses, cancers, inflammatory bowel diseases, and immunoregulatory disorders.

It is also contemplated that the present invention may be used in combinations with one or more agents useful in the prevention or treatment of HIV. Examples of such agents include:

(1) nucleotide reverse transcriptase inhibitor such as zidovudine, didanosine, lamivudine, zalcitabine, abacavir, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and (3) protease inhibitors such as saquinavir, ritonavir, indinavir, nelfinavir, amprenavir, palinavir, lasinavir, etc.

The scope of combinations of compounds of Formulas 1-4 of this invention with HIV agents is not limited to (1), (2), and or (3), but includes in principle, any combination with any pharmaceutical composition useful for the treatment of HIV. Further, in such combinations the compounds of the present invention and other HIV agents may be administered separately or in conjunction. In addition, the administration of one element may be prior to, concurrent to, or subsequent to the administration of other agent(s).

The compounds of Formulas 1-4 in the present invention may be administered by oral, parenteral (e.g., intramuscular, intraperitoneal, intravenous, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of Formulas 1-4 are all active and used to treat animals, including but not limited to, mice, rats, horses, cattle, sheep, dogs, cats, and monkey. The compounds of the invention are also effective for use in humans.

The compounds of Formulas 1-4 of the present invention may form hydrates or solvates, which are included in the scope of the claims. When the compounds of Formulas 1-4 of the present invention exist as regioisomers, configurational isomers, conformers, or diasteroisomeric forms all such forms and various mixtures thereof are included in the generic formulas. It is possible to isolate individual isomers using known separation and purification methods, if desired. For example, when a compound of Formulas 1-4 of the present invention is a racemate, the racemate can be separated into the (S)-compound and (R)-compound by optical resolution. Individual optical isomers and mixtures thereof are included in the scope of the generic formula.

This invention also relates to a pharmaceutical composition comprising a pharmaceutically acceptable carrier or diluent and an effective amount of compound of Formulas 1-4. A compound of Formulas 1-4 may be administered alone or as an admixture with a pharmaceutically acceptable carrier (e.g., solid formulations such as tablets, capsules, granules, powders, etc.; liquid formulations such as syrups, injections, etc.) may be orally or non-orally administered. Examples of non-oral formulations include injections, drops, suppositories, pessaryies.

In the treatment or prevention of conditions which require chemokine receptor modulation an appropriate dosage level will generally be about 0.01 to 500 mg per kg patient body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

The present invention provides novel compounds that bind chemokine receptors and interfere with the binding of the natural ligand thereto. The compounds of the present invention are useful as agents demonstrating protective effects on target cells from HIV infection. The compounds of the present invention are also useful as antagonists or agonists of chemokine receptors, as well as other biological activities related to the ability of these compounds to inhibit the binding of chemokines to their receptors.

In the compounds of Formulas 1-4, the alkyl represented by R may be straight or branched chain or may be cyclic, and may optionally be substituted by 1-2 substituents selected from halo, hydroxy and alkoxy. Preferably each R is H or lower straight chain alkyl, preferably methyl.

Ar is an aromatic or heteroaromatic moiety, which is a single ring or fused ring system of 5-12 ring members. Exemplary embodiments of Ar include benzene, naphthalene, dihydronaphthalene, tetrahydronaphthalene, pyridine, quinoline, isoquinoline, imidazole, benzimidazole, azabenzimidazole, benzotriazole, furan, benzofuran, thiazole, benzothiazole, oxazole, benzoxazole, pyrrole and indole. Preferred embodiments include phenylene, pyridylene or pyridinylene, more preferably the p-forms, and preferably phenylene.

When compounds of Formulas 1-4 contain elements that are "optionally substituted" these substituents are as follows:

The optional substituents may be halogen, nitro, cyano, carboxylic acid, optionally substituted alkyl, alkenyl or cycloalkyl groups, an optionally substituted hydroxyl group, an optionally substituted thiol group, an optionally substituted amino or acyl group, an optionally substituted carboxylate, carbamate, carboxamide or sulfonamide group, an optionally substituted aromatic or heterocyclic group.

Examples of halogen include fluorine, chlorine, bromine, iodine, etc., with fluorine and chlorine preferred.

Examples of alkyl which may be optionally substituted include $C_{1-10}$ alkyl, including methyl, ethyl propyl etc.; examples of alkenyl groups which may be optionally substituted include $C_{2-10}$ alkenyl such as allyl, crotyl, 2-pentenyl, 3-hexenyl, etc.; and examples of cycloalkyl groups which may be optionally substituted, include $C_{3-10}$ cycloalkyl such as cyclopropyl, cyclobutyl, cyclopentyl, cyclohexyl, cycloheptyl, etc. In these cases, $C_{1-6}$ alkyl, alkenyl and cycloalkyl are preferred. The optional substituent may also be an optionally substituted aralkyl (e.g. phenyl $C_{1-4}$ alkyl) or heteroalkyl for example, phenylmethyl(benzyl), phenylethyl, pyridinylmethy, pyridinylethyl, etc. The heterocyclic group may be a 5 or 6 membered ring containing 1-4 heteroatoms.

Examples of optionally substituted hydroxyl and thiol groups include those wherein the substituent is an optionally substituted alkyl (e.g. $C_{1-10}$ alkyl) such as methyl, ethyl, propyl, isopropyl, butyl, isobutyl, sec-butyl, tert-butyl, pentyl, etc., preferably $(C_{1-6})$ alkyl; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted aralkyl (e.g. phenyl-$C_{1-4}$ alkyl, e.g. benzyl, phenethyl, etc.). Where there are two adjacent hydroxyl or thiol substituents, the heteroatoms may be connected via an alkylene group such as $O(CH_2)_nO$ and $S(CH_2)_nS$ (where n=1-5). Examples include methylenedioxy, ethylenedioxy, etc. Oxides of thio-ether groups such as sulfoxides and sulfones are also encompassed.

Further examples of the optionally substituted hydroxyl group include an optionally substituted $C_{2-4}$ alkanoyl (e.g. acetyl, propionyl, butyryl, isobutyryl, etc.), $C_{1-4}$ alkylsufonyl (e.g. methanesulfonyl, ethanesulfonyl, etc.) and an optionally substituted aromatic and heterocyclic carbonyl group including benzoyl, pyridinecarbonyl, etc.

The substituents on optionally substituted amino group may bind to each other to form a cyclic amino group (e.g. 5- to 6-membered cyclic amino, etc., such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.) the number of preferred substituents are 1 to 3.

The amino group may also be substituted once or twice (to form a secondary or tertiary amine) with a group such as an optionally substituted alkyl group including $C_{1-10}$ alkyl (e.g. methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g. phenyl $C_{1-4}$ alkyl) or heteroalkyl for example, phenyl, pyridine, phenylmethyl(benzyl), phenethyl, pyridinylmethyl, pyridinylethyl etc. The heterocyclic group may be a 5 or 6 membered ring containing 1-4 heteroatoms. The optional substituents of the "optionally substituted amino groups are the same as defined above for the "optionally substituted cyclic amino group."

The amino group may be substituted with an optionally substituted $C_{2-4}$ alkanoyl e.g. acetyl, propionyl, butyryl, isobutyryl etc., or a $C_{1-4}$ alkylsulfonyl (e.g. methanesulfonyl, ethanesulfonyl, etc.) or a carbonyl or sulfonyl substituted aromatic or heterocyclic ring, e.g. benzenesulfonyl, benzoyl, pyridinesulfonyl, pyridinecarbonyl etc. The heterocycles are as defined above.

Examples of the optionally substituted acyl groups include a carbonyl group or a sulfinyl or sulfonyl group binding to hydrogen; or to an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower $(C_{1-6})$ alkyl, etc.; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, etc., preferably lower $(C_{2-6})$ alkenyl, etc.); an optionally substituted cycloalkenyl (e.g. $C_{3-7}$ cycloalkenyl, etc., such as 2-cyclopentenyl, 2-cyclohexenyl, 2-cyclopentenylmethyl, 2-cyclohexenylmethyl, etc.) an optionally substituted 5- to 6-membered monocyclic aromatic group (e.g. phenyl, pyridyl, etc.).

Examples of the optionally substituted carboxylate group (ester groups) include an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower $(C_{1-6})$ alkyl, etc.); an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, 3-hexenyl, etc., preferably lower $(C_{2-6})$ alkenyl, etc.); an optionally substituted cycloalkenyl (e.g. $C_{3-7}$ cycloalkenyl, etc., such as 2-cyclohexenylmethyl, etc.); an optionally substituted aryl (e.g. phenyl, naphthyl, etc.) and $C_{1-4}$ aryl for example, benzyl, phenethyl etc. Groups such as methoxymethyl, methoxyethyl, etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups are phenyl, naphthyl, or a 5- or 6-membered heterocyclic ring containing 1-4 heteroatoms. The optional substituents are essentially identical to those listed above.

In the above Formulas 1 and 2, Y is an optionally substituted cyclic or bicyclic group of 5-11 members, for example a six membered heteroaromatic group, such as a heterocyclic group or aromatic including heteroaromatic groups. Examples of optionally substituted aromatic groups include benzene and naphthalene, or dihydronaphthalene and tetrahydronaphthalene. Examples of optionally substituted heterocyclic groups include 5 to 6-membered saturated, partially saturated, or aromatic heterocyclic rings containing 1 to 4 heteroatoms selected from nitrogen, oxygen and sulfur. The heterocycles may be pyridine, quinoline, isoquinoline, imidazole, benzimidazole, azabenzimidazole, benzotriazole, furan, benzofuran, thiazole, benzothiazole, oxazole, benzoxazole, pyrrole, indole, indoline, indazole, pyrrolidine, pyrrolidone, pyrroline, piperidine, piperazine, tetrahydroquinoline, tetrahydroisoquinoline, pyrazole, thiophene, isoxazole, isothiazole, triazole, tetrazole, oxadiazole, thiadiazole, morpholine, thiamorpholine, pyrazolidine, imidazolidine, imidazoline, tetrahydropyran, dihydropyran, benzopyran, dioxane, dithiane, tetrahydrofuran, tetrahydrothiophene, dihydrofuran, dihydrothiophene, etc. Oxides of the nitrogen and sulfur containing heterocycles are also included in the present invention. The optional substituents for the fused or unfused aromatic or heterocyclic rings are identical to those described above.

In the above Formula 1, examples of the optionally substituted ring system containing ring A are dihydroquinoline, tetrahydroquinoline, pyranopyridine, dihydropyranopyridine, thiapyranopyridine, dihydrothiapyranopyridine, dihydronaphthyridine, tetrahydronaphthyridine. Oxides of sulfur-containing heterocycles are also encompassed in the present invention. In the above ring system containing Ring A, the optional nitrogen atom may be substituted with hydrogen, a substituted alkyl, alkenyl, cycloalkyl or aryl group, or may be the nitrogen atom of a carboxamide, carbamate or sulfonamide. Preferred for m is m=1, it is preferred that ring A be saturated. The most preferred embodiment is tetrahydroquinoline.

In the above Formula 1, X may be CH (pyrrole), O (oxazole), S (thiazole), NH or NR (imidazole) where R is a $C_{1-6}$ alkyl group or acyl, sulfonyl group. In Formula 1, two adjacent $R^1$ and/or $R^2$ and $R^3$ may be joined to form an optionally substituted, fused 5-7 membered ring. Examples of fused ring systems include but are not limited to indole, tetrahydroindole, benzimidazole, tetrahydrobenzimidazole, azabenzimidazole, benzoxazole, tetrahydrobenzoxazole, benzothiazole, tetrahydrobenzothiazole. The preferred ring systems resulting from $R^2$ and $R^3$ include benzothiazole and benzoimidazole.

The permitted number of substituents on the fused ring system containing Ring A in Formula 1 is 0-4, preferably 0-2. The substituents ($R^1$) are as described above. Preferred substituents are halogen (fluorine, chlorine etc.), nitro, cyano, hydroxy group, thiol group, amino group, carboxyl group, carboxylate group, sulfonate group, sulfonamide group, carboxamide group, an optionally halogenated $C_{1-4}$alkyl, an optionally halogenated $C_{1-4}$alkoxy (e.g. trifluoromethoxy, etc.), $C_{2-4}$alkanoyl (e.g. acetyl, propionyl, etc.) or aroyl, a $C_{1-4}$ alkylsulfonyl (e.g. methanesulfonyl, ethanesulfonyl, etc.), an optionally substituted aryl or heterocyclic group. The number of substituents (listed above as optional substituents) on the said groups is preferably 0 to 3, more preferably 0-1.

The substituents $R^2$ and $R^3$ are also exemplified by the optional substituents listed above, and preferred embodiments include those which are preferred embodiments for $R^1$. $R^2$ and $R^3$ can also each independently be hydrogen. A preferred embodiment for $R^2$ $R^3$ is that wherein the substituents are covalently linked so as to form a benzene ring. Thus, preferred embodiments of the ring system coupled to $L^1$ include benzimidazole, indole, benzoxazole and benzothiazole.

In Formula 1, $L^1$ is a linker that spaces the attachment atom of the 5-membered ring containing X 1.5-10 Å from N. The attachment atom is preferably position 2; however, as indicated in the formula, alternative positions of attachment may also be employed, preferably positions 4 or 5, in which case, one of the substitutents $R^2$ or $R^3$ as the case may be, will be present at position 2. Typical $L^1$ linkers include a covalent bond, alkylene or heteroalkylene chains of 1-6 members, preferably 1-4, and more preferably 1-2. The heteroatom in heteroalkylene may be N, O, or S, preferably N. A preferred embodiment of $L^1$ is —$CH_2$—.

In Formula 2, $L^2$ spaces the attachment atom of ring $A^1$ to N at a distance of 1.5-8 Å. Typical linkers are similar to those described as $L^1$.

With regard to ring $A^1$ in Formula 2, in preferred embodiments only one Z is other than $CR_2$ and is preferably NR. Preferred embodiments for R in this context are H and lower alkyl, especially methyl. Especially preferred for m is 1.

Preferred embodiments for the Y coupled to $L^2$ are monocylic aromatic/heteromatic rings, such as phenyl, pyridyl, pyrimidyl, imidazolyl or fused rings to, for example, a benzomoiety, and the like.

In the compounds of Formulas 3 and 4, included as preferred embodiments for $W^1$ are phenyl, pyridyl, pyrimidyl, imidazolyl, thiophenylyl, and fused ring systems preferably including heteroatoms including such systems which are partially saturated; all of the foregoing may be substituted as described above. Preferred numbers of substiuents is 0-2 for monocyclic embodiments and 0-4, more preferably 0-3 for fused ring embodiments. Especially preferred are the fused ring system including ring A in Formula 1 and the monocylic ring $A^1$ from Formula 2.

In Formulas 3 and 4, preferred forms of $W^2$ are H, substituents that include aromatic or heteroaromatic substituent. Also preferred are alkyl substiutents as in Formula 2. Especially preferred are those which include the (describe ring) substituent of Formula 1.

In Formula 3, ring B is preferably imidazole, thiazole, pyrrole, which may be substituted by 1-2 substituents, typically lower alkyl, trifluoromethyl, lower alkoxy, phenyl, optionally coupled through sulfonyl or carbonyl, and optionally substituted, or halo.

In Formula 4, the ring system CD is preferably a 9-membered system including at least one heteroatom. Typically the heteroatom is S or N. The CD system is preferably substituted with 0-2, preferably 0-1 substituents, preferably those listed above with respect to ring B.

L¹ is a linker that spaces the C atom of

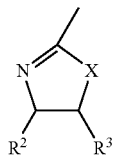

1.5-10 Å from N. Typical linkers include a covalent bond, alkylene or heteroalkylene chains of 1-6, preferably 1-4, more preferably 1-2 atoms. The heteroatom may be O, S or N, preferably N.

In the above Formula 2, examples of the optionally substituted cycloalkyl or heterocyclic ring represented by A¹ include, but are not limited to, cyclopentyl, cyclohexyl, cycloheptyl, tetrahydrofuran, tetrahydrothiophene(thiolane), tetrahydropyran, tetrahydrothiapyran (pentamethylene sulfide), oxepine, thiepin, pyrollidine, piperidine etc., cyclohexyl is preferred.

The novel compounds of Formulas 1-4 of the present invention may be formulated as pharmaceutical compositions that may be administered topically; percutaneously, including intravenously; orally; and by other standard routes of pharmaceutical administration to mammalian subjects as determined according to routine clinical practice.

Having now generally described the invention, the same will be more readily understood through reference to the following examples which are provided by way of illustration, and are not intended to be limiting of the present invention, unless specified. Parent application PCT/CA00/00321 discloses the following compounds:

AMD7186: N-(5-ethylthiophene-2-ylmethyl)-N'-(2-pyridinylmethyl)-N-(5,6,7,8-tetrahydro-8-quinolinyl)-1,4-benzenedimethanamine
AMD7208: N-(1-methylpyrrol-2-ylmethyl)-N'-(2-pyridinylmethyl)-N-(5,6,7,8-tetrahydro-8-quinolinyl)-1,4-benzenedimethanamine
AMD7222: N-(1-methylbenzimidazol-2-ylmethyl)-N'-(2-pyridinylmethyl)-N-(5,6,7,8-tetrahydro-8-quinolinyl)-1,4-benzenedimethanamine
AMD8780: N-(2-pyridinylmethyl)-N'-(trans-2-aminocyclohexyl)-N'-(5,6,7,8-tetrahydro-8-quinolinyl)-1,4-benzenedimethanamine (hydrobromide salt)
AMD8931: N-(2-pyridinylmethyl)-N-(4-phenyl-1H-imidazol-2-ylmethyl)-N'-(5,6,7,8-tetrahydro-8-quinolinyl)-1,4-benzenedimethanamine.
AMD8821: N-(2-pyridinylmethyl)-N'-[2-furanylmethyl]-N'-(5,6,7,8-tetrahydro-8-quinolinyl)-1,4-benzenedimethanamine
AMD8828: N-(2-pyridinylmethyl)-N'-[2-[(2-furanylmethyl)amino]ethyl]-N'-(5,6,7,8-tetrahydro-8-quinolinyl)-1,4-benzenedimethanamine
AMD8835: N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine
AMD8836: N-(2-pyridinylmethyl)-N'-[2-thiopheneylmethyl]-N'-(5,6,7,8-tetrahydro-8-quinolinyl)-1,4-benzenedimethanamine
AMD8839: N-(2-pyridinylmethyl)-N'-(trans-2-aminocyclopentyl)-N'-(5,6,7,8-tetrahydro-8-quinolinyl)-1,4-benzenedimethanamine
AMD8841: N-(2-pyridinylmethyl)-N'-[2-thiazolylmethyl]-N'-(5,6,7,8-tetrahydro-8-quinolinyl)-1,4-benzenedimethanamine
AMD8751: N-(2-pyridinylmethyl)-N'-(1H-imidazol-2-ylmethyl)-N'-(5,6,7,8-tetrahydro-8-quinolinyl)-1,4-benzenedimethanamine
AMD8887: N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine
AMD8728: N-(2-pyridinylmethyl)-N'-[2-pyrrolylmethyl]-N'-(5,6,7,8-tetrahydro-8-quinolinyl)-1,4-benzenedimethanamine.
AMD8907: N-(2-pyridinylmethyl)-N'-(1H-benzimidazol-2-ylmethyl)-N'-(5,6,7,8-tetrahydro-8-quinolinyl)-1,4-benzenedimethanamine
AMD8926: N-(2-pyridinylmethyl)-N'-(5-nitro-1H-benzimidazol-2-ylmethyl)-N'-(5,6,7,8-tetrahydro-8-quinolinyl)-1,4-benzenedimethanamine
AMD8927: N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine
AMD 8929: N-(2-pyridinylmethyl)-N'-[(1H)-5-azabenzimidazol-2-ylmethyl]-N'-(5,6,7,8-tetrahydro-8-quinolinyl)-1,4-benzenedimethanamine
AMD8764: N-(2-pyridinylmethyl)-N'-(2-benzoxazolyl)-N'-(5,6,7,8-tetrahydro-8-quinolinyl)-1,4-benzenedimethanamine In preferred embodiments, the compounds of Formulas 1-4 are described in the above-defined terms, but with the proviso that the group of compounds does not include those listed above. Disclosed herein are additional compounds of Formulas 1-4, such as those set forth in the following examples.

EXPERIMENTAL

The intermediates 8-hydroxy-5,6,7,8-tetrahydroquinoline, 8-amino-5,6,7,8-tetrahydroquinoline, N-(2-nitrobenzenesulfonyl)-N-(2-pyridinylmethyl)-N'-(5,6,7,8-tetrahydro-8-quinolinyl)-1,4-benzenedimethanamine and N-(tert-butoxycarbonyl)-N-(2-pyridinylmethyl)-N'-(5,6,7,8-tetrahydro-8-quinolinyl)-1,4-benzenedimethanamine were prepared according to the procedures described in Bridger et al. PCT International application PCT/CA00/00321.

General Procedures.

The chloromethyl benzimidazole derivatives used for the synthesis of the examples described below were prepared by reaction of substituted ortho-phenylenediamines with chloroacetic acid according to literature procedures (Phillips, M. A. *J. Chem. Soc.* 1928, 2393; Goker, H.; Kus, C. *Arch. Pharm.* (*Weinheim*) 1995, 328, 425-430).

General Procedure for Preparation of 2-chloromethylbenzimidazole Derivatives from o-phenylenediamines:

An appropriately substituted o-phenylenediamine (1.0 mmol) and chloroacetic acid (3.0-5.0 mmol) were refluxed in 4N HCl (10 mL) for 3-16 hours. Upon cooling, the mixture was neutralized to pH~6 with a saturated aqueous solution of sodium carbonate. The precipitated product was then isolated by filtration or by extraction with an appropriate organic solvent, such as ethyl acetate. The isolated substituted 2-chloromethylbenzimidazole could then be used in the next reaction without further purification, or alternatively, could be further purified by flash chromatographic techniques.

In cases where the requisite substituted ortho-phenylenediamine was not commercially available, the intermediate diamine was prepared by a two-step nucleophilic amination of an appropriately substituted nitrobenzene derivative followed by reduction.

General Procedure for Nucleophilic Amination of Nitrobenzenes to Form 2-aminonitrobenzenes:

Using literature procedures (Seko, S.; Kawamura, N. *J. Org. Chem.* 1996, 61, 442-443) a substituted nitrobenzene (10 mmol) and O-Methylhydroxyamine hydrochloride (1.04 g, 12.5 mmol) in DMF (6 mL) were added slowly to a 0° C. solution of potassium t-butoxide (3.36 g, 30 mmol) and copper (I) chloride (200 mg, 2.0 mmol) in DMF (20 mL). The resulting deep-red solution was then stirred, gradually warming to RT for 5-16 hours (monitored by analytical tlc). The reaction was then quenched with saturated $NH_4Cl$ and extracted with dichloromethane. The combined organic fractions were then dried over anhydrous $MgSO_4$ and concentrated. The residue was then purified by column chromatography on silica gel (20-50% ethyl acetate in hexanes) to afford a mixture of isomeric amino-nitrobenzenes, including the desired 1-nitro-2-amino isomer.

General Procedure for Reduction of 2-aminonitrobenzenes to o-phenylenediamines:

To a solution of a substituted 2-aminonitrobenzene (5 mmol) in methanol (50 mL) was added 10% palladium on carbon (100 mg). The resulting suspension was then placed under 1 atm of hydrogen gas, and was stirred for 3 hours at RT. Celite was then added to the reaction, and the contents were filtered through a celite plug. The filtrates were then concentrated to afford the desired substituted o-phenylenediamine in near-quantitative yields.

In order to prepare the required chloromethylbenzoxazole and chloromethylbenzothiazole derivatives, the following procedure was used:

General Procedure for the Preparation of 2-chloromethyl-benzothiazoles or 2-chloromethylbenzoxazoles from 2-aminothiophenols or 2-aminophenols Respectively:

Using literature procedures (Addison, A. W.; Nageswara Rao, T.; Wahlgren, C. G. *J. Heterocyclic Chem.* 1983, 20, 1481-1484) a substituted 2-aminophenol (or a 2-aminothiophenol (5 mmol)) was mixed with chloroacetic acid (940 mg, 10 mmol) in polyphosphoric acid (5 mL), and the viscous mixture was then heated to 120° C. for 3 hours. The reaction was then cooled, and diluted with water (~20 mL) and then neutralized with potassium carbonate to pH~7. The mixture was then extracted with ethyl acetate, and the combined organic fractions were then dried over $MgSO_4$ and concentrated. The residue was then purified by column chromatography on silica gel (50% ethyl acetate in hexanes) to afford the desired 2-chloromethylbenzoxazole (or 2-chloromethylbenzothiazole).

General Procedure for Alkylation of N-(tert-butoxycarbonyl)-N-(2-pyridinylmethyl)-N'-(5,6,7,8-tetrahydro-8-quinolinyl)-1,4-benzenedimethanamine with 2-chloromethyl-benzimidazole Derivatives.

Preparation of N-(tert-butoxycarbonyl)-N-(2-pyridinylmethyl)-N'-(1-H-benzimidazol-2-ylmethyl)-N'-(5,6,7,8-tetrahydro-8-quinolinyl)-1,4-benzenedimethanamine.

To a solution of a substituted 2-chloromethylbenzimidazole (1.0 mmol) in DMF (8 mL) was added N-(tert-butoxycarbonyl)-N-(2-pyridinylmethyl)-N'-(5,6,7,8-tetrahydro-8-quinolinyl)-1,4-benzenedimethanamine (572 mg, 1.25 mmol), then diisopropylethylamine (1.5 mmol, 0.27 mL). The resulting mixture was then heated to 80° C. for 3-16 hours, monitored by analytical thin layer chromatography. After cooling, the reaction was washed with a saturated ammonium chloride solution, then extracted with ethyl acetate. The combined organic fractions were then dried over $MgSO_4$ and concentrated in vacuo to give an oil, which was purified by column chromatography on silica gel (2-10% MeOH in $CH_2Cl_2$) to afford the desired alkylated product.

General Procedure A: Direct Reductive Amination with $NaBH_3CN$

To a stirred solution of the amine (1 equivalent) in anhydrous methanol (concentration ~0.1 M), at room temperature, was added the carbonyl compound (~1-2 equivalents) in one portion. Once the carbonyl had dissolved (~5 minutes), $NaBH_3CN$ (~2-4 equiv.) was added in one portion and the resultant solution was stirred at room temperature. The solvent was removed under reduced pressure and $CH_2Cl_2$ (20 mL/mmol of amine) and brine or 1.0 M aqueous NaOH (10 mL/mmol amine) were added to the residue. The phases were separated and the aqueous phase was extracted with $CH_2Cl_2$ (3×10 mL/mmol amine). The combined organic phases were dried ($Na_2SO_4$) and concentrated. The crude material was purified chromatography.

General Procedure B: Direct Reductive Amination with $NaBH(OAc)_3$

To a stirred solution of the amine (1 equivalent) in $CH_2Cl_2$ (concentration ~0.2 M), at room temperature, was added the carbonyl compound (~1-2 equivalents), glacial acetic acid (0-2 equivalents) and, $NaBH(OAc)_3$ (~1.5-3 equiv.) and the resultant solution was stirred at room temperature. The reaction mixture was poured into either saturated aqueous $NaHCO_3$ or 1.0 M aqueous NaOH (10 mL/mmol amine). The phases were separated and the aqueous phase was extracted with $CH_2Cl_2$ (3×10 mL/mmol amine). The combined organic phases were dried ($Na_2SO_4$) and concentrated. The crude material was purified chromatography.

General Procedure C: Deprotection of the 2-nitobenzenesulfonyl Group (nosyl).

To a stirred solution of the nosyl-protected amine (1 equivalent) in anhydrous $CH_3CN$ (or DMF) (concentration ~0.05 M), at room temperature, was added thiophenol (4-8 equiv.) followed by powdered $K_2CO_3$ (8-12 equivalents). The resulting bright yellow solution was stirred at room temperature (or 50° C.) for 1-24 hours. The solvent was removed under reduced pressure and $CH_2Cl_2$ (10 mL/mmol amine) and water (2 mL/mmol amine) were added to the residue. The phases were separated and the aqueous phase was extracted with $CH_2Cl_2$ (3×5 mL). The combined organic phases were dried ($Na_2SO_4$) and concentrated. Purification of the crude material by chromatography provided the free base.

Alternative work-up: the reaction mixture was filtered and concentrated to provide a yellow oil which was purified by chromatography on basic alumina (eluant $CH_2Cl_2$ then 20:1 $CH_2Cl_2$—$CH_3OH$) and provided the free base as a colorless oil.

General Procedure D: Salt Formation Using Saturated HBr (g) in Acetic Acid.

To a solution of the free base in glacial acetic acid (or dioxane) (2 mL) was added, a saturated solution of HBr(g) in acetic acid (or dioxane) (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification (where necessary), the solid can be dissolved in methanol and re-precipitated with a large volume of ether. Washing the solid with ether by decantation, followed by drying of the solid in vacuo (0.1 Torr) gave the desired compound.

General Procedure E: Reaction of Alcohols with Methanesulfonyl Chloride

To a stirred solution of the alcohol (1 equivalent) and $Et_3N$ (1.5-2 equivalents) in $CH_2Cl_2$ (or THF) (concentration ~0.1 M) at room temperature (or 0° C.) was added methanesulfonyl chloride (~1.5 equivalents) and the reaction stirred at room temperature for 0.5-1 h. The reaction mixture was poured into either saturated aqueous $NaHCO_3$ or saturated $NH_4Cl$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was either purified by chromatography or used without further purification in the N-alkylation step.

General Procedure F: SEM-Deprotection

To a stirred solution of the SEM-protected compound (1 equiv.) was added 6N HCl (30 mL/mmol), and the resultant solution was stirred at 50° C. for indicated time. The solution was diluted with water (50 mL/mmol), and it was neutralised with $NaHCO_3$ and extracted with EtOAc (3×100 mL/mmol).

EXAMPLE: 1

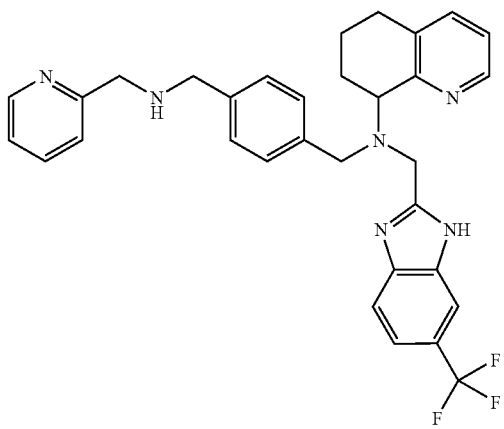

AMD8936: Preparation of N-(2-pyridinylmethyl)-N'-(5-trifluoromethyl-1-H-benzimidazol-2-ylmethyl)-N'-(5,6,7,8-tetrahydro-8-quinolinyl)-1,4-benzenedimethanamine(hydrobromide salt)

A mixture of 4-trifluoromethyl-1,2-phenylenediamine (880 mg, 5.0 mmol) and chloroacetic acid (940 mg, 10 mmol) were refluxed in 4N HCl (10 mL) for 16 hours to give, after work-up and chromatography, 5-trifluoromethyl-2-chloromethylbenzimidazole (380 mg, 32%) as a purple powder: $^1$H NMR (CDCl$_3$) $\delta$4.86 (s, 2H), 7.52 (dd, 1H, J=8.5, 1.0 Hz), 7.67 (d, 1H, J=8.5 Hz), 7.90 (br s, 1H), 10.0 (br s, 1H).

A solution of 5-trifluoromethyl-2-chloromethylbenzimidazole (200 mg, 0.865 mmol), N-(tert-butoxycarbonyl)-N'-(2-pyridinylmethyl)-N'-(5,6,7,8-tetrahydro-8-quinolinyl)-1,4-benzenedimethanamine (440 mg, 0.96 mmol) and diisopropylethylamine (0.25 mL, 1.44 mmol) were stirred at 80° C. in DMF (8 mL) for 16 hours to yield, after work-up and chromatography, the desired N-(tert-butoxycarbonyl)-N-(2-pyridinylmethyl)-N'-(5-trifluoromethyl-1-H-benzimidazol-2-ylmethyl)-N'-(5,6,7,8-tetrahydro-8-quinolinyl)-1,4-benzenedimethanamine as a pale yellow foam (128 mg, 23%). $^1$H NMR (CDCl$_3$) $\delta$1.40 (s, 9H), 2.04 (m, 2H), 2.27 (m, 1H), 2.71 (m, 1H), 2.82-2.88 (m, 2H), 3.72 (s, 2H), 3.95 (d, 1H, J=16.3 Hz), 4.04 (dd, 1H, J=5.8, 6.3 Hz), 4.07 (d, 1H, J=16.3 Hz), 4.37 (br s, 2H), 4.44 (m, 2H), 7.06 (br s, 2H), 7.14-7.26 (m, 5H), 7.24 (m, 2H), 7.45 (d, 2H, J=6 Hz), 7.62 (dd, 1H, J=5.4, 6.1 Hz), 8.44 (d, 1H, J=5.4 Hz), 8.80 (m, 1H).

Using general procedure D: the foam from above was converted to the hydrobromide salt with simultaneous deprotection of the BOC group to provide AMD8936 (110 mg) as a beige solid. $^1$H NMR (D$_2$O) $\delta$1.71-1.79 (m, 1H), 2.08-2.19 (m, 2H), 2.29-2.35 (m, 1H), 2.41-3.45 (m, 1H), 3.01-3.03 (m, 2H), 3.68 (dd, 2H, J=14.1, 13.2 Hz), 3.82 (dd, 2H, J=17.4, 8.1 Hz), 4.04 (s, 2H), 4.47 (d, 1H, J=16.5 Hz), 4.65 (d, 1H, J=16.5 Hz), 4.73 (m, 1H); 7.00 (d, 2H, J=8.1 Hz), 7.20 (d, 2H, J=8.1 Hz), 7.39 (d, 2H, J=8.1 Hz), 7.48 (dd, 1H, J=6.3, 4.8 Hz), 7.70 (s, 2H), 7.88-7.94 (m, 3H), 8.39 (d, 1H, J=7.8 Hz), 8.54 (d, 1H, J=5.4 Hz), 8.75 (d, 1H, J=5.7 Hz). $^{13}$C NMR (D$_2$O) $\delta$ 20.99, 27.84, 49.07, 50.11, 50.32, 56.69, 63.35, 66.47, 113.4 (m), 115.09, 123.59, 126.23 (2C), 126.36, 128.53, 130.06 (2C), 130.23, 130.99, 132.38, 138.24, 139.69, 141.08, 142.58, 147.45, 148.01, 148.36, 150.79, 154.64, 161.19. ES-MS m/z 557 (M+H). Anal. Calcd. for C$_{32}$H$_{31}$N$_6$F$_3$.4.3HBr.4.3H$_2$O: C, 39.22; H, 4.51; N, 8.58; Br, 34.92. Found: C, 38.93; H, 4.32; N, 8.49; Br, 35.21.

EXAMPLE: 2

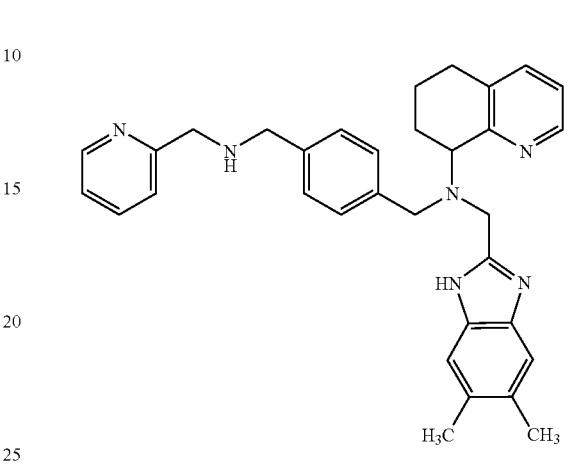

AMD8927: Preparation of N-(2-pyridinylmethyl)-N'-(5,6-dimethyl-1-H-benzimidazol-2-ylmethyl)-N'-(5,6,7,8-tetrahydro-8-quinolinyl)-1,4-benzenedimethanamine(hydrobromide salt)

A mixture of 4,5-dimethyl-1,2-phenylenediamine (680 mg, 5.0 mmol) and chloroacetic acid (940 mg, 10 mmol) were refluxed in 4N HCl (10 mL) for 16 hours to give, after work-up and chromatography, 5-trifluoromethyl-2-chloromethylbenzimidazole (530 mg, 54%) as a beige powder: $^1$H NMR (CDCl$_3$) $\delta$1.25 (br s, 1H) 2.39 (s, 6H), 4.83 (s, 2H), 7.36 (br s, 2H).

A solution of 5-dimethyl-2-chloromethylbenzimidazole (195 mg, 1.0 mmol), N-(2-nitrobenzenesulfonyl)-N-(2-pyridinylmethyl)-N'-(5,6,7,8-tetrahydro-8-quinolinyl)-1,4-benzenedimethanamine (543 mg, 1.0 mmol) and diisopropylethylaamine (0.26 mL, 1.50 mmol) were stirred at 80° C. in DMF (8 mL) for 16 hours to yield, after work-up and chromatography, the desired N-(2-nitrobenzenesulfonyl)-N-(2-pyridinylmethyl)-N'-(5-dimethyl-1-H-benzimidazol-2-ylmethyl)-N'-(5,6,7,8-tetrahydro-8-quinolinyl)-1,4-benzenedimethanamine as a pale yellow foam (280 mg, 39%).

Using general procedure C: N-(2-nitrobenzenesulfonyl)-N-(2-pyridinylmethyl)-N'-(5-dimethyl-1-H-benzimidazol-2-ylmethyl)-N'-(5,6,7,8-tetrahydro-8-quinolinyl)-1,4-benzenedimethanamine (280 mg, 0.39 mmol) was treated with thiophenol (0.160 mL, 1.56 mmol) and potassium carbonate (270 mg, 1.95 mmol) in acetonitrile (8 mL) to afford, after work-up and chromatography, the N-(2-pyridinylmethyl)-N'-(5-dimethyl-1-H-benzimidazol-2-ylmethyl)-N'-(5,6,7,8-tetrahydro-8-quinolinyl)-1,4-benzenedimethanamine (181 mg, 90%). $^1$H NMR (CDCl$_3$) $\delta$1.53 (m, 1H), 1.92 (m, 1H), 2.16 (m, 1H), 2.25 (s, 6H), 2.89-3.01 (m, 2H), 3.36 (br s, 4H), 3.53 (dd, 2H, J=16.8, 11.4 Hz), 3.66 (s, 1H), 3.81 (s, 2H), 3.88 (m, 1H), 7.08-7.30 (m, 10H), 7.68 (t, 1H, J=6.4 Hz), 8.48 (d, 1H, J=5.4 Hz), 8.52 (d, 1H, J=5.9 Hz).

Using general procedure D: the material from above was converted to the hydrobromide salt to provide AMD8927 (188 mg) as a beige solid. $^1$H NMR (D$_2$O) $\delta$1.89 (m, 1H), 2.20 (s, 6H), 2.28 (m, 2H), 2.41 (m, 1H), 3.02 (m, 2H), 3.54 (s, 2H), 3.79 (m, 2H), 3.87 (s, 2H), 4.36 (d, 1H, J=16.8 Hz), 4.57 (d, 1H, J=16.8 Hz), 4.71 (m, 1H), 7.04 (d, 2H, J=7.5 Hz), 7.21 (d, 2H, J=7.5 Hz), 7.29 (s, 2H), 7.63 (d, 1H, J=7.8 Hz), 7.72 (t, 1H, J=6.4 Hz), 7.93 (t, 1H, J=6.8 Hz), 8.19 (t, 1H, J=7.8 Hz), 8.39 (d, 1H, J=7.8 Hz), 8.67 (d, 1H, J=4.8 Hz), 8.74 (d, 1H, J=5.1 Hz). $^{13}$C NMR (D$_2$O) 14.52, 19.81 (2C), 20.44, 27.85, 44.66, 50.14, 56.76, 63.31, 66.46, 113.43 (2C), 116.12, 126.49, 129.00 (2C), 129.71, 130.11 (2C), 130.61, 138.86 (2C), 136.74 (2C), 138.23, 139.68, 141.03, 142.83, 147.42, 147.93, 148.29, 150.33, 150.81. ES-MS m/z 517 (M+H). Anal. Calcd. for C$_{33}$H$_{36}$N$_6$.4.1HBr.1.6H$_2$O.1.1HOAc: C, 44.82; H, 5.10; N, 8.91; Br, 34.73. Found: C, 44.67; H, 5.08; N, 8.88; Br, 34.89.

EXAMPLE: 3:

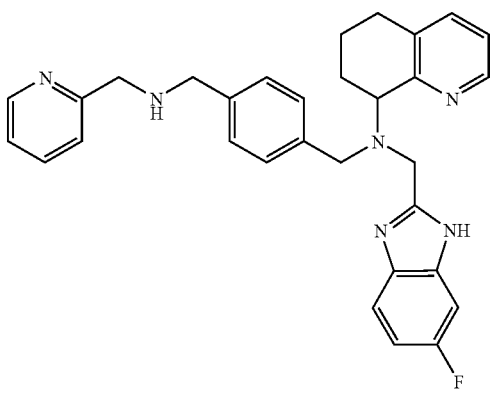

AMD8937: Preparation of N-(2-pyridinylmethyl)-N'-(5-fluoro-1-H-benzimidazol-2-ylmethyl)-N'-(5,6,7,8-tetrahydro-8-quinolinyl)-1,4-benzenedimethanamine(hydrobromide salt)

A mixture of 4-fluoro-1,2-phenylenediamine (630 mg, 5.0 mmol) and chloroacetic acid (940 mg, 10 mmol) were refluxed in 4N HCl (10 mL) for 16 hours to give, after work-up and chromatography, 5-fluoro-2-chloromethylbenzimidazole (330 mg, 36%) as a purple powder: $^1$H NMR (CDCl$_3$) 4.80 (s, 2H), 7.00 (dd, 1H, J=8.2, 1.9 Hz), 7.24 (d, 1H, J=8.2 Hz), 7.50 (dd, 1H, J=2.9, 1.9 Hz), 10.0 (br s, 1H).

A solution of 5-fluoro-2-chloromethylbenzimidazole (158 mg, 0.86 mmol), N-(tert-butoxycarbonyl)-N-(2-pyridinylmethyl)-N'-(5,6,7,8-tetrahydro-8-quinolinyl)-1,4-benzenedimethanamine (440 mg, 0.96 mmol) and diisopropylethylamine (0.25 mL, 1.44 mmol) were stirred at 80° C. in DMF (8 mL) for 16 hours to yield, after work-up and chromatography, the desired N-(tert-butoxycarbonyl)-N-(2-pyridinylmethyl)-N'-(5-trifluoromethyl-1-H-benzimidazol-2-ylmethyl)-N'-(5,6,7,8-tetrahydro-8-quinolinyl)-1,4-benzenedimethanamine as a pale yellow foam (146 mg, 28%). $^1$H NMR (CDCl$_3$) 1.40 (s, 9H), 1.72 (m, 1H), 2.08 (m, 1H), 2.26 (m, 1H), 2.70-2.96 (m, 3H), 3.71 (s, 2H), 3.94 (d, 1H, J=16.9 Hz), 4.04 (m, 2H), 4.38-4.49 (m, 4H), 6.94 (m, 1H), 7.06-7.33 (m, 11H), 8.44 (d, 1H, J=4.8 Hz), 8.68 (d, 1H, J=5.1 Hz).

Using general procedure D: the foam from above was converted to the hydrobromide salt with simultaneous deprotection of the BOC group to provide AMD8937 (171 mg) as a beige solid. $^1$H NMR (D$_2$O) 1.87 (m, 1H), 2.04 (m, 2H), 2.28 (m, 1H), 2.99 (m, 2H), 3.76 (dd, 2H, J=12.6, 8.1 Hz), 3.89 (s, 2H), 4.22 (s, 2H), 4.50 (d, 1H, J=16.5 Hz), 4.62 (d, 1H, J=16.5 Hz), 4.73 (m, 1H), 7.07 (d, 2H, J=8.1 Hz), 7.10 (dd, 1H, J=8.4, 2.4 Hz), 7.23 (d, 2H, J=16.5 Hz), 7.33 (dd, 1H, J=8.4, 2.4 Hz), 7.53 (dd, 1H, J=9.3, 4.5 Hz), 7.66 (d, 1H, J=7.8 Hz), 7.71 (dd, 1H, J=6.9, 5.7 Hz), 7.90 (dd, 1H, J=7.8, 6.9 Hz), 8.18 (dt, 1H, J=7.8, 1.8 Hz), 8.38 (d, 1H, J=7.8 Hz), 8.65 (d, 1H, J=4.8 Hz), 8.73 (d, 1H, J=5.1 Hz). $^{13}$C NMR (D$_2$O). 20.44, 20.92, 48.93, 50.20, 50.46, 57.31, 63.14, 115.52, 120.22, 126.12, 126.34, 126.49, 126.99, 130.02, 130.27 (2C), 130.94 (2C), 138.25, 139.14, 139.66, 141.03, 141.19, 142.98, 145.22, 147.15, 149.30, 151.91, 153.62, 160.48. ES-MS m/z 507 (M+H). Anal. Calcd. for C$_{31}$H$_{31}$N$_6$F.4.1HBr.1.6H$_2$O.0.8HOAc: C, 42.78; H, 4.57; N, 9.18; Br, 35.79. Found: C, 42.75; H, 4.38; N, 9.20; Br, 35.74

EXAMPLE: 4

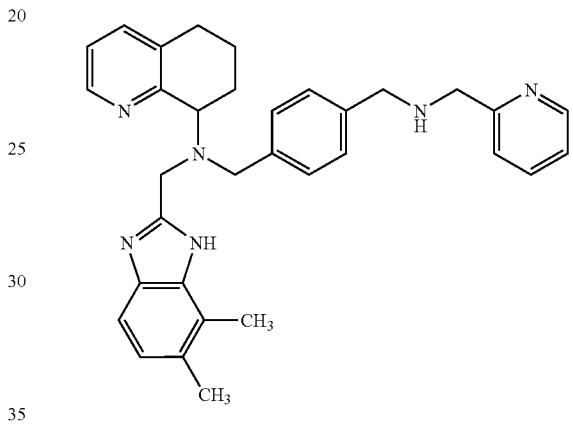

AMD9365: Preparation of N-(2-pyridinylmethyl)-N'-(4,5-dimethyl-1-H-benzimidazol-2-ylmethyl)-N'-(5,6,7,8-tetrahydro-8-quinolinyl)-1,4-benzenedimethanamine(hydrobromide salt)

A mixture of 3,4-dimethyl-1,2-phenylenediamine (680 mg, 5.0 mmol) and chloroacetic acid (940 mg, 10 mmol) were refluxed in 4N HCl (10 mL) for 16 hours to give, after work-up and chromatography, 4,5-dimethyl-2-chloromethylbenzimidazole (760 mg, 78%) as a beige powder: $^1$H NMR (CDCl$_3$) 2.39 (s, 3H), 2.49 (s, 3H), 4.81 (s, 2H), 7.09 (d, 1H, J=8.1 Hz), 7.35 (d, 1H, J=8.1 Hz), 7.49 (br s, 1H).

A solution of 4,5-dimethyl-2-chloromethylbenzimidazole (146 mg, 0.75 mmol), N-(tert-butoxycarbonyl)-N-(2-pyridinylmethyl)-N'-(5,6,7,8-tetrahydro-8-quinolinyl)-1,4-benzenedimethanamine (458 mg, 1.0 mmol) and diisopropylethylamine (0.26 mL, 1.5 mmol) were stirred at 70° C. in DMF (8 mL) for 36 hours to yield, after work-up and chromatography, the desired N-(tert-butoxycarbonyl)-N-(2-pyridinylmethyl)-N'-(4,5-dimethyl-1-H-benzimidazol-2-ylmethyl)-N'-(5,6,7,8-tetrahydro-8-quinolinyl)-1,4-benzenedimethanamine as a pale yellow foam (236 mg, 51%). 1H NMR (CDCl$_3$) 1.37 (s, 9H), 1.77 (m, 2H), 2.00 (m, 2H), 2.24 (m, 1H), 2.24 (s,3H), 2.54 (s, 3H), 2.67 (m, 1H), 3.67 (s, 2H), 3.88 (d, 1H, J=8.1 Hz), 4.05 (m, 1H), 4.15 (d, 1H, J=8.1 Hz), 4.33-4.46 (m, 4H), 6.95-7.05 (m, 6H), 7.29-7.38 (m, 5H), 8.66 (d, 1H, J=4.8 Hz), 8.77 (d, 1H, J=5.1 Hz).

Using general procedure D: the foam from above was converted to the hydrobromide salt with simultaneous deprotection of the BOC group to provide AMD9365 (201 mg) as a beige solid. $^1$H NMR (D$_2$O) □.1.89 (m, 1H), 2.20 (s, 3H), 2.30s (s, 3H), 2.26-2.39 (m, 3H), 3.02 (m, 2H), 3.69 (s, 2H), 3.75 (d, 1H, J=6.9 Hz), 3.80 (d, 1H, J=6.9 Hz), 3.99 (s, 2H), 4.40 (d, 1H, J=16.2 Hz), 4.58 (d, 1H, J=16.2 Hz), 4.75 (m, 1H), 7.00 (d, 2H, J=8.1 Hz), 7.12-7.26 (m, 4H), 7.36 (m, 1H), 7.55 (dd, 1H, J=7.8, 5.6 Hz), 7.93 (dd, 1H, J=5.7, 4,8 Hz), 8.03 (m, 1H), 8.40 (d, 1H, J=8.1 Hz), 8.73 (d, 1H, J=4.1 Hz), 8.74 (d, 1H, J=4.6 Hz). 13C NMR (D2O) □. 13.28, 18.87, 20.46, 20.85, 27.86, 47.35, 50.15, 50.64, 58.85, 63.35, 110.60, 122.31, 126.15, 127.86, 128.06, 128.50, 127.78, 129.34, 130.07 (2C), 130.78 (2C), 133.15, 135.09, 138.52, 139.65, 141.04, 144.73, 145.78, 146.67, 148.27, 150.62, 150.78. ES-MS m/z 517 (M+H). Anal. Calcd. for C33H36N6.4.2HBr.3.2H$_2$O: C, 43.36; H, 5.14; N, 9.19; Br, 36.71. Found: C, 43.40; H, 5.03; N, 8.87; Br, 36.71.

EXAMPLE: 5

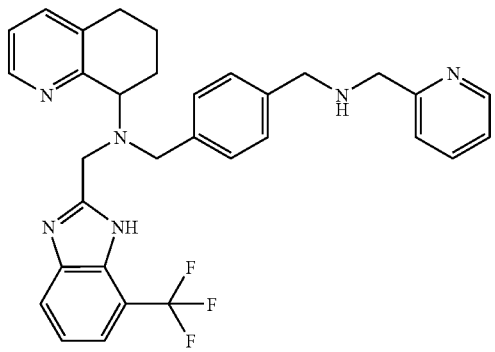

AMD9344: Preparation of N-(2-pyridinylmethyl)-N'-(4-trifluoromethyl-1-H-benzimidazol-2-ylmethyl)-N'-(5,6,7,8-tetrahydro-8-quinolinyl)-1,4-benzenedimethanamine(hydrobromide salt)

3-nitrobenzotrifluoride (1.91 g, 10 mmol) and O-methylhydroxylamine hydrochloride (1.04 g, 12.5 mmol) were reacted in the presence of copper (I) chloride (200 mg, 2 mmol) and potassium t-butoxide (3.36 g, 30 mmol) in DMF (25 mL) to yield, after work-up and chromatography, 2-amino-3-trifluoromethylnitrobenzene (330 mg, 16%) as an orange powder: $^1$H NMR (CDCl$_3$) □7.37 (t, 1H, J=8.1 Hz), 7.97 (d, 1H, J=8.1 Hz), 8.41 (d, 1H, J=8.1 Hz), 8.75 (br s, 2H).

2-amino-3-trifluoromethylnitrobenzene (330 mg, 1.60 mmol) was hydrogenated (1 atmosphere H$_2$) in methanol (20 mL) in the presence of 10% palladium on carbon (30 mg) to yield, after work-up, 3-trifluoromethyl-1,2-phenylenediamine (282 mg, 100%): $^1$H NMR (CDCl$_3$) □3.38 (br s, 4H), 6.35-6.73 (m, 3H).

A mixture of 3-trifluoromethyl-1,2-phenylenediamine (282 mg, 1.60 mmol) and chloroacetic acid (450 mg, 4.8 mmol) were refluxed in 4N HCl (8 mL) for 16 hours to give, after work-up and chromatography, 4-trifluoromethyl-2-chloromethylbenzimidazole (145 mg, 48%) as a purple powder: $^1$H NMR (CDCl$_3$) □4.88 (s, 2H), 7.37 (t, 1H, J=7.8 Hz), 7.55 (d, 1H, J=7.8 Hz), 7.84 (d, 1H, J=7.8 Hz).

A solution of 4-trifluoromethyl-2-chloromethylbenzimidazole (145 mg, 0.78 mmol), N-(tert-butoxycarbonyl)-N-(2-pyridinylmethyl)-N'-(5,6,7,8-tetrahydro-8-quinolinyl)-1,4-benzenedimethanamine (440 mg, 0.96 mmol) and diisopropylethylamine (0.21 mL, 1.17 mmol) were stirred at 80° C. in DMF (8 mL) for 16 hours to yield, after work-up and chromatography, the desired N-(tert-butoxycarbonyl)-N-(2-pyridinylmethyl)-N'-(4-trifluoromethyl-1-H-benzimidazol-2-ylmethyl)-N'-(5,6,7,8-tetrahydro-8-quinolinyl)-1,4-benzenedimethanamine as a pale yellow foam (81 mg, 16%).

Using general procedure D: the foam from above was converted to the hydrobromide salt with simultaneous deprotection of the BOC group to provide AMD9344 (77 mg) as a beige solid. $^1$H NMR (D$_2$O) □1.90 (m, 1H), 2.20-2.35 (m, 2H), 2.43 (m, 1H), 3.03 (m, 2H), 3.73 (s, 2H), 3.78 (d, 1H, J=13.5 Hz), 3.85 (d, 1H, J=13.5 Hz), 4.06 (s, 2H), 4.50 (d, 1H, J=16.5 Hz), 4.67 (d, 1H, J=16.5 Hz), 4.70 (m, 1H), 7.00 (d, 2H, J=7.5 Hz), 7.21 (d, 2H, J=7.5 Hz), 7.42 (d, 1H, J=7.5 Hz), 7.53 (t, 2H, J=7.8 Hz), 7.92 (d, 1H, J=7.2 Hz), 7.97 (d, 1H, J=7.2 Hz), 8.40 (d, 1H, J=8.1 Hz), 8.58 (d, 1H, J=4.8 Hz), 8.75 (d, 1H, J=5.7 Hz). $^{13}$C NMR (D$_2$O) □. 14.53, 20.93, 27.86, 30.68, 48.93, 50.27, 55.65, 63.33, 114.3 (m), 118.51, 124.41, 126.16, 126.28, 126.43, 126.60, 129.94, 130.21 (2C), 130.95 (2C), 131.77, 138.22, 139.67, 141.07, 142.83, 147.19, 147.98, 148.29, 150.70, 154.05. ES-MS m/z 557 (M+H). Anal. Calcd. for C$_{32}$H$_{31}$N$_6$F$_3$.4.3HBr.1.5H$_2$O.1.25HOAc: C, 42.18; H, 4.41; N, 8.55; Br, 32.54. Found: C, 42.13; H, 4.38; N, 8.50; Br, 32.62.

EXAMPLE: 6

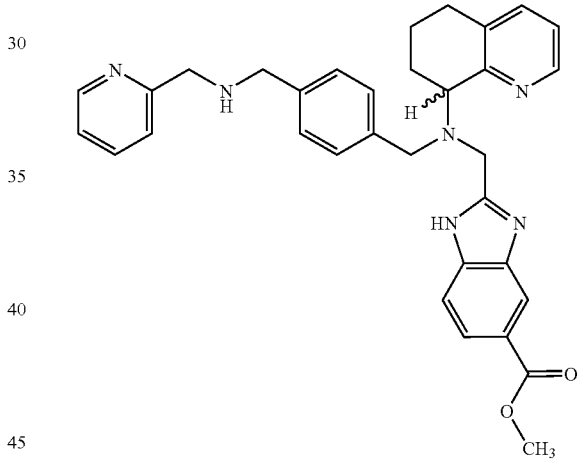

AMD9419: Preparation of N-(2-pyridinylmethyl)-N'-(5-carboxymethyl-1-H-benzimidazol-2-ylmethyl)-N'-(5,6,7,8-tetrahydro-8-quinolinyl)-1,4-benzenedimethanamine(hydrobromide salt)

A mixture of 4-carboxymethyl-1,2-phenylenediamine (833 mg, 5.0 mmol) and chloroacetic acid (940 mg, 10 mmol) were refluxed in 0.5N HCl (10 mL) for 16 hours to give, after work-up and chromatography, 5-carboxymethyl-2-chloromethylbenzimidazole (224 mg, 20%) as a beige powder: $^1$H NMR (CDCl$_3$) □.4.87 (s, 2H), 6.68 (d, 1H, J=7.1 Hz), 8.00 (d, 1H, J=7.1 Hz), 8.34 (s, 1H).

A solution of 5-carboxymethyl-2-chloromethylbenzimidazole (224 mg, 1.0 mmol), N-(tert-butoxycarbonyl)-N-(2-pyridinylmethyl)-N'-(5,6,7,8-tetrahydro-8-quinolinyl)-1,4-benzenedimethanamine (458 mg, 1.0 mmol) and diisopropylethylamine (0.26 mL, 1.5 mmol) were stirred at 70° C. in DMF (8 mL) for 16 hours to yield, after work-up and chromatography, the desired N-(tert-butoxycarbonyl)-N-(2- pyridinylmethyl)-N'-(5-carboxymethyl-1-H-benzimidazol-2-ylmethyl)-N'-(5,6,7,8-tetrahydro-8-quinolinyl)-1,4-benzenedimethanamine as a pale yellow foam (116 mg, 22%). $^1$H NMR (CDCl$_3$) ☐1.40 (s, 9H), 1.77 (m, 1H), 2.04 (m, 2H), 2.22 (m, 1H), 2.75-2.90 (m, 2H), 3.71 (s, 2H), 3.88 (s, 2H), 3.88 (s, 3H), 3.93 (m, 2H), 3.98 (d, 1H, J=7.8 Hz), 4.01 (m, 1H), 4.19 (d, 1H, J=7.8 Hz), 7.21 (dd, 1H, J=5.8, 4.7 Hz), 7.21 (d, 2H, J=7.8 Hz), 7.33 (d, 2H, J=7.8 Hz), 7.45 (d, 1H, J=8.1 Hz), 7.57 (m, 2H), 7.90 (d, 1H, J=8.1 Hz), 8.55 (d, 1H, J=4.8 Hz), 8.71 (d, 1H, J=4.8 Hz).

Using general procedure D: the foam from above was converted to the hydrobromide salt with simultaneous deprotection of the BOC group to provide AMD9419 (38 mg) as a beige solid. $^1$H NMR (D$_2$O) ☐.1.91 (m, 1H), 2.30 (m, 2H), 2.43 (m, 1H), 3.04 (m, 2H), 3.74 (s, 2H), 3.78 (s, 2H), 3.88 (s, 3H), 4.51 (d, 1H, J=16.8 Hz), 4.69 (d, 1H, J=16.8 Hz), 4.71 (m, 1H), 7.07 (d, 2H, J=8.1 Hz), 7.27 (d, 2H, J=8.1 Hz), 7.40 (m, 1H), 7.64 (d, 1H, J=9.0 Hz), 7.94 (m, 3H), 8.19 (s, 1H), 8.40 (d, 1H, J=8.1 Hz), 8.61 (d, 1H, J=4.8 Hz), 8.78 (d, 1H, J=5.8 Hz). $^{13}$C NMR (D$_2$O). 20.42, 21.00, 27.84, 48.91, 50.16, 50.40, 53.30, 56.66, 63.38, 114.21. 116.01, 126.05, 126.23, 127.51, 127.95, 130.22 (2C), 130.49, 131.07, 133.70, 135.33, 138.19, 139.70, 141.09, 142.23, 146.21, 147.72, 148.36, 150.67, 151.69, 154.78, 168.21. ES-MS m/z 547 (M+H). Anal. Calcd. for C$_{33}$H$_{34}$N$_6$O$_2$·4.2HBr·2.1H$_2$O·1.2HOAc: C, 42.67; H, 4.77; N, 8.43; Br, 33.68. Found: C, 42.57; H, 4.93; N, 8.39; Br, 33.86.

EXAMPLE: 7

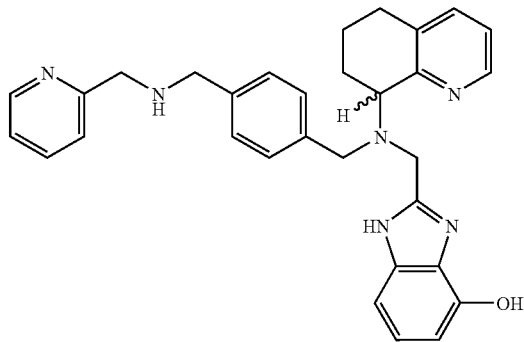

AMD9420: Preparation of N-(2-pyridinylmethyl)-N'-(4-hydroxy-1-H-benzimidazol-2-ylmethyl)-N'-(5,6,7,8-tetrahydro-8-quinolinyl)-1,4-benzenedimethanamine(hydrobromide salt)

A mixture of 3-hydroxy-1,2-phenylenediamine (620 mg, 5.0 mmol) and chloroacetic acid (2.35 g, 25 mmol) were refluxed in 0.5N HCl (10 mL) for 16 hours to give, after work-up and chromatography, 4-hydroxy-2-chloromethylbenzimidazole (120 mg, 13%) as a beige powder: $^1$H NMR (CD$_3$OD) ☐ 4.82 (s, 2H), 6.76 (d, 1H, J=7.8 Hz), 6.99 (d, 1H, J=7.8 Hz), 7.15 (t, 1H, J=7.8 Hz).

A solution of 4-hydroxy-2-chloromethylbenzimidazole (120 mg, 0.65 mmol), N-(tert-butoxycarbonyl)-N-(2-pyridinylmethyl)-N'-(5,6,7,8-tetrahydro-8-quinolinyl)-1,4-benzenedimethanamine (443 mg, 0.97 mmol) and diisopropylethylamine (0.26 mL, 1.5 mmol) were stirred at 70° C. in DMF (8 mL) for 16 hours to yield, after work-up and chromatography, the desired N-(tert-butoxycarbonyl)-N-(2-pyridinylmethyl)-N'-(5-carboxymethyl-1-H-benzimidazol-2-ylmethyl)-N'-(5,6,7,8-tetrahydro-8-quinolinyl)-1,4-benzenedimethanamine as a viscous yellow oil (108 mg, 28%). $^1$H NMR (CDCl$_3$) ☐1.40 (s, 9H), 1.64 (m, 1H), 2.00 (m, 3H), 2.22 (m, 2H), 3.61-3.77 (m, 4H), 3.85-3.91 (m, 3H), 3.91-4.40 (m, 4H), 6.99 (br s, 1H), 7.02 (d, 2H, J=7.8 Hz), 7.13 (d, 2H, J=7.8 Hz), 7.21-7.48 (m, 7H), 8.40 (br s, 1H), 8.55 (d, 1H, J=4.8 Hz), 8.67 (d, 1H, J=5.1 Hz).

Using general procedure D: the foam from above was converted to the hydrobromide salt with simultaneous deprotection of the BOC group to provide AMD9420 (69 mg) as a beige solid. $^1$H NMR (D$_2$O) ☐1.85 (m, 1H), 2.19 (m, 2H), 2.42 (m, 2H), 3.02 (m, 2H), 3.86 (m, 4H), 4.08 (s, 2H), 4.41 (d, 1H, J=16.5 Hz), 4.61 (d, 1H, J=16.5 Hz), 4.71 (m, 1H), 6.72 (d, 1H, J=8.1 Hz), 7.01 (d, 1H, J=8.7 Hz), 7.05 (d, 2H, J=7.8 Hz), 7.15 (t, 1H, J=8.1 Hz), 7.22 (d, 2H, J=7.8 Hz), 7.49 (d, 1H, J=8.1 Hz), 7.60 (dd, 1H, J=7.8, 5.1 Hz), 7.91 (dd, 1H, J=6.8, 4.7 Hz), 8.03 (t, 1H, J=7.8 Hz), 8.39 (d, 1H, J=7.8 Hz), 8.61 (d, 1H, J=5.1 Hz), 8.74 (d, 1H, J=5.7 Hz). $^{13}$C NMR (D$_2$O) ☐ 20.43, 20.84, 27.86, 40.09, 50.13, 60.62, 57.73, 63.24, 105.11, 110.87, 121.31, 126.12, 127.21, 127.71, 129.93, 130.19 (2C), 130.83 (2C), 132.35, 134.45, 138.33, 138.39, 139.69, 141.01, 144.57, 145.03, 145.89, 148.26, 150.84. ES-MS m/z 505 (M+H). Anal. Calcd. for C$_{31}$H$_{32}$N$_6$O·4.1HBr·4.8H$_2$O: C, 40.35; H, 4.99; N, 9.11; Br, 35.50. Found: C, 40.54; H, 4.91; N, 8.81; Br, 35.30.

EXAMPLE: 8

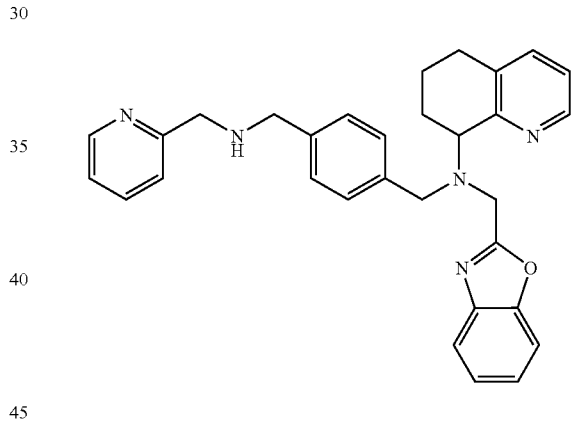

AMD8938: Preparation of N-(2-pyridinylmethyl)-N'-(benzoxazol-2-ylmethyl)-N'-(5,6,7,8-tetrahydro-8-quinolinyl)-1,4-benzenedimethanamine(hydrobromide salt)

A mixture of 2-aminophenol (545 mg, 5.0 mmol) and chloroacetic acid (940 mg, 10 mmol) were heated to 120° C. for 3 hours in polyphosphoric acid (5 mL) to give, after work-up and chromatography, 2-chloromethylbenzoxazole (260 mg, 31%) as pale yellow crystals. $^1$H NMR (CDCl$_3$) ☐4.75 (s), 7.34 (m, 2H), 7.54 (m, 1H), 7.73 (m, 1H). $^{13}$C NMR (CDCl$_3$) ☐36.79, 111.30, 129.95, 125.23, 126.38, 141.22, 151.54, 161.21.

A solution of 2-chloromethylbenzoxazole (182 mg, 1.09 mmol), N-(tert-butoxycarbonyl)-N-(2-pyridinylmethyl)-N'-(5,6,7,8-tetrahydro-8-quinolinyl)-1,4-benzenedimethanamine (400 mg, 0.873 mmol) and diisopropylethylamine (0.225 mL, 1.3 mmol) were stirred at 80° C. in DMF (8 mL) for 16 hours to yield, after work-up and chromatography, the desired N-(tert-butoxycarbonyl)-N-(2-pyridinylmethyl)-N'-(benzoxazol-2-ylmethyl)-N'-(5,6,7,8-tetrahydro-8-quinolinyl)-1,4-benzenedimethanamine as a viscous yellow oil (230 mg, 45%). $^1$H NMR (CDCl$_3$) δ 1.40 (s), 1.47 (s, total of 9H), 1.47 (m, 1H), 2.00-2.09 (m, 3H), 2.68-2.77 (m, 2H), 3.88 (d, 1H, J=12.4 Hz), 4.01-4.06 (m, 2H), 4.15 (dd, 1H, J=6.4, 5.1 Hz), 4.24 (d, 1H, J=12.4 Hz), 4.33-4.49 (m, 4H), 7.04 (m, 1H), 7.08-7.28 (m, 7H), 7.39 (d, 2H, J=7.8 Hz), 7.47 (m, 1H), 7.59 (m, 2H), 8.39 (d, 1H, J=5.4 Hz), 8.55 (d, 1H, J=4.9 Hz).

Using general procedure D: the viscous oil from above was converted to the hydrobromide salt with simultaneous deprotection of the BOC group to provide AMD8938 (220 mg) as a beige solid. $^1$H NMR (D$_2$O) δ 1.13 (m, 1H), 2.03 (m, 2H), 2.11 (m, 1H), 2.91 (br s, 2H), 3.92-3.97 (m, 4H), 4.04 (s, 2H), 4.58-4.72 (m, 3H), 7.22 (d, 2H, J=7.8 Hz), 7.33 (m, 2H), 7.45 (d, 2H, J=7.8 Hz), 7.46-7.50 (m, 2H), 7.63 (t, 1H, J=6.8 Hz), 7.91 (m, 1H), 8.13 (d, 1H, J=8.1 Hz), 8.41 (m, 1H), 8.51 (d, 1H, J=5.7 Hz), 8.75 (d, 1H, J=4.8 Hz). $^{13}$C NMR (D$_2$O) δ 21.01, 27.43, 47.30, 49.34, 51.78, 53.36, 55.19, 60.33, 116.85, 121.00, 124.54, 125.51, 125.67, 128.23, 128.75, 129.86, 129.97 (2C), 130.91 (2C), 131.08, 131.49, 138.33, 140.14, 143.95, 145.12, 145.30, 146.38, 147.63, 150.26, 171.28. ES-MS m/z 491 (M+H). Anal. Calcd. for C$_{31}$H$_{31}$N$_5$O.4 HBr.1 H$_2$O.1 HOAc: C, 44.47; H, 4.64; N, 7.86; Br, 35.86. Found: C, 44.63; H, 4.77; N, 7.87; Br, 35.63.

EXAMPLE: 9

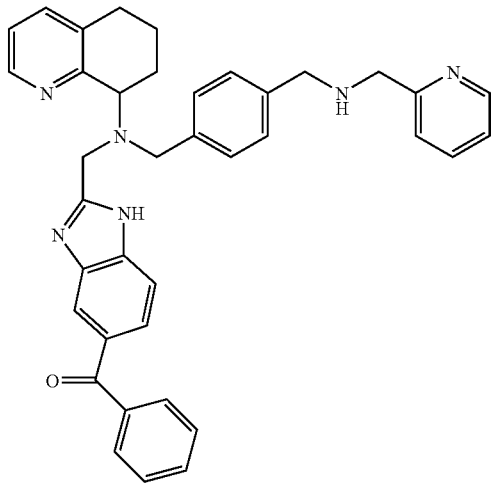

AMD8971: Preparation of N-(2-pyridinylmethyl)-N'-(5-benzoyl-1H-benzimidazol-2-ylmethyl)-N'-(5,6,7,8-tetrahydro-8-quinolinyl)-1,4-benzenedimethanamine(hydrobromide salt)

A mixture of 4-diaminobenzophenone (2.26 g, 0.0106 mol) and chloroacetic acid (2.05 g, 0.022 mol) in 4 M HCl was stirred at reflux for 16 hours. The mixture was cooled to room temperature and diluted with saturated aqueous Na$_2$CO$_3$ (60 mL, pH □□) and ethyl acetate (60 mL). The phases were separated and the aqueous phase was extracted with ethyl acetate (2×50 mL). The combined organic extracts were dried (Na$_2$SO$_4$), filtered and concentrated to afford 5-benzoyl-2-chloromethylbenzimidazole (1.58 g) as an orange solid. $^1$H NMR (CDCl$_3$) δ 4.88 (s, 2H), 7.46-7.51 (m, 2H), 7.57-7.62 (m, 2H), 7.80-7.85 (m, 3H), 8.08 (br s, 1H).

A solution of 5-benzoyl-2-chloromethylbenzimidazole (284 mg, 1.05 mmol), N-(tert-butoxycarbonyl)-N-(2-pyridinylmethyl)-N'-(5,6,7,8-tetrahydro-8-quinolinyl)-1,4-benzenedimethanamine (476 mg, 1.04 mmol) and N,N-diisopropylethylamine (0.36 mL, 2.08 mmol) were stirred at 80 °C in DMF (4 mL) for 16 hours. The reaction was then cooled, concentrated under reduced pressure and diluted with CH$_2$Cl$_2$ (35 mL) and saturated aqueous NaHCO$_3$ (40 mL). The phases were separated and the aqueous phase was washed with CH$_2$Cl$_2$ (2×25 mL). The combined organic extracts were washed with saturated aqueous NaHCO$_3$ (1×40 mL), dried (NaSO$_4$), filtered and concentrated under reduced pressure. Purification of the resultant oil by flash chromatography on silica gel (96:4 CH$_2$Cl$_2$/MeOH) provided the desired alkylated product (468 mg, 65%) as an orange oil.

Using General Procedure D: Conversion of the oil from above (37 mg, 0.063 mmol) to the hydrobromide salt with simultaneous deprotection of the BOC group followed by re-precipitation of the intermediate solid from methanol/ether gave AMD8971 (63 mg, 94%) as a beige solid. $^1$H NMR (D$_2$O) δ 1.80-1.96 (m, 1H), 2.19-2.31 (m, 2H), 2.41-2.46 (m, 1H), 3.01-3.04 (m, 2H), 3.77 (s, 2H), 3.79 (d, 1H, J=12.9 Hz), 3.87 (d, 1H, J=12.9 Hz), 4.12 (s, 2H), 4.50 (d, 1H, J=16.8 Hz), 4.69 (d, 1H, J=16.8 Hz), 4.78-4.80 (m, 1H, overlap with HOD), 7.06 (d, 2H, J=8.1 Hz), 7.24 (d, 2H, J=8.1 Hz), 7.52-7.62 (m, 4H), 7.65-7.77 (m, 5H), 7.90-7.94 (m, 2H), 8.07 (td, 1H, J=7.8, 1.2 Hz), 8.39 (d, 1H, J=7.8 Hz), 8.57 (d, 1H, J=4.8 Hz), 8.76 (d, 1H, J=5.3 Hz); $^{13}$C NMR (D$_2$O) δ 20.44, 21.01, 27.85, 48.96, 50.22, 50.42, 56.70, 63.37, 114.17, 116.73, 126.21 (2 carbons), 126.32, 128.48, 129.16 (2 carbons), 130.06, 130.21 (2 carbons), 130.26, 130.81 (2 carbons), 131.06 (2 carbons), 133.48, 134.40, 135.16, 136.48, 138.23, 139.71, 141.09, 142.50, 147.43, 147.96, 148.37, 150.67, 154.81, 199.02. ES-MS m/z 593 (M+H). Anal. Calcd. for C$_{38}$H$_{36}$N$_6$O.4.0HBr.2.0H$_2$O: C, 47.92; H, 4.66; N, 8.82; Br, 33.56. Found: C, 47.98; H, 4.58; N, 8.55; Br, 33.45.

EXAMPLE: 10

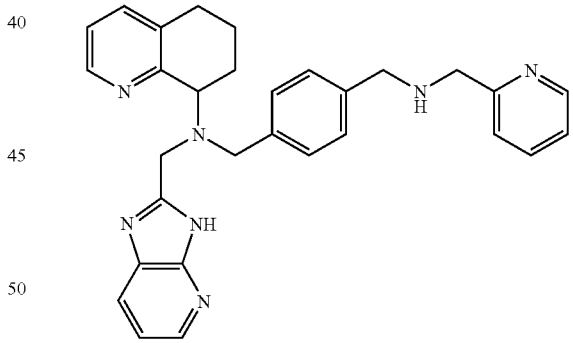

AMD8932: Preparation of N-(2-pyridinylmethyl)-N'-[(1H)-4-azabenzimidazol-2-ylmethyl]-N'-(5,6,7,8-tetrahydro-8-quinolinyl)-1,4-benzenedimethanamine(hydrobromide salt)

Using General Procedure B: Reaction of 1-[[2-(trimethylsilyl)ethoxy]methyl]-(1H)-4-azabenzimidazole-2-carboxaldehyde (prepared as described by Whitten, J. P.; Matthews, D. P.; McCarthy, J. R. *J. Org. Chem.* 1986, 51, 1891-1894.) (0.206 g, 0.74 mmol) and N-(tert-Butoxycarbonyl)-N-(2-pyridinylmethyl)-N'-(5,6,7,8-tetrahydro-8-quinolinyl)-1,4-benzenedimethanamine (0.427 g, 0.93 mmol) with NaBH(OAc)$_3$ (0.400 g, 1.89 mmol) in CH$_2$Cl$_2$ (7.5 mL) for 19 hours followed by purification of the crude material by radial chromatography on silica gel (2 mm plate, 40:1:1 $CH_2Cl_2$—MeOH—$NH_4OH$) provided 0.570 g of a yellow oil. The oil was dissolved in $CH_2Cl_2$ (4 mL) and treated with trifluoroacetic acid (2 mL). The resultant solution was stirred at room temperature for 19 hours then concentrated under reduced pressure. The residue was dissolved in $CH_2Cl_2$ (20 mL) and treated with aqueous NaOH (10 M, ~20 mL) until the aqueous phase was basic (pH 14). The phases were separated and the aqueous phase was extracted with $CH_2Cl_2$ (3×20 mL). The combined organic extracts were dried ($Na_2SO_4$), and concentrated. Purification of the crude material by radial chromatography on silica gel (2 mm plate, 30:1:1 $CH_2Cl_2$—MeOH—$NH_4OH$) provided 0.100 g (28%) of the free base of the title compound as an off-white solid.

Using general procedure D: Conversion of the off-white solid (0.100 g) to the hydrobromide salt, followed by re-precipitation of the intermediate solid from methanol/ether, gave AMD8932(0.151 g) as a white solid. $^1$H NMR ($D_2O$) □ 1.76-1.90(m, 1H), 2.16-2.27(m, 2H), 2.38-2.44 (m, 1H), 2.96-2.99 (m, 2H), 3.85 (s, 2H), 4.01 (s, 2H), 4.35 (d, 1H, J=16.2 Hz), 4.36 (s, 2H), 4.52 (d, 1H, J=16.2 Hz), 4.65 (dd, 1H, J=6.3, 7.5 Hz), 7.11 (d, 2H, J=8.1 Hz), 7.28 (d, 2H, J=7.8 Hz), 7.63 (dd, 1H, J=5.7, 8.1 Hz), 7.73-7.77 (m, 2H), 7.83 (dd, 1H, J=7.8, 6.0 Hz), 8.24 (ddd, 1H, J=7.8, 7.8, 1.5 Hz), 8.30 (d, 1H, J=7.8 Hz), 8.37 (d, 1H, J=8.1 Hz), 8.46 (d, 1H, J=4.8 Hz), 8.67 (d, 2H, J=5.7 Hz); $^{13}$C NMR ($D_2O$) □ 20.49, 20.64, 27.76, 48.63, 50.81, 51.32, 56.21, 61.94, 120.15, 125.85, 126.75, 126.77, 128.44, 129.16, 129.79, 130.20 (2 carbons), 131.03 (2 carbons), 138.63, 138.88, 139.43, 140.71, 143.90, 145.94, 146.45, 147.45, 147.88, 151.34, 160.34; ES-MS m/z 490 (M+H). Anal. Calcd. for $C_{30}H_{31}N_7$·4.4HBr·2.0$H_2O$: C, 40.87; H, 4.50; N, 11.12; Br, 39.88. Found: C, 40.79; H, 4.51; N, 11.00; Br, 39.95.

EXAMPLE: 11

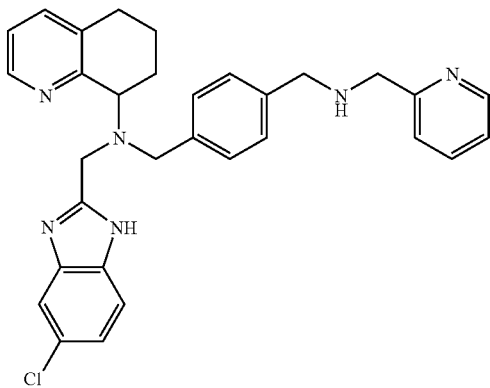

AMD8933: Preparation of N-(2-pyridinylmethyl)-N'-[5-chloro-1H-benzimidazol-2-ylmethyl]-N'-(5,6,7,8-tetrahydro-8-quinolinyl)-1,4-benzenedimethanamine(hydrobromide salt)

General procedures for the protection of benzimidazoles with SEM-Cl and subsequent formylation with DMF are described in Bridger et al. PCT International application PCT/CA00/00321.

1-[[2-(trimethylsilyl)ethoxy]methyl]-5-chloro-1H-benzimidazole-2-carboxaldehyde.

A solution of 5-chloro-1H-benzimidazole (0.345 g, 2.26 mmol) in dry DMF (11 mL) was treated with N,N-diisopropylethylamine (0.60 mL, 3.44 mmol) and 2-(trimethylsilyl)ethoxymethyl chloride (0.50 mL, 2.83 mmol). The resultant solution was heated to 80° C. for 75 minutes. After aqueous work-up, 0.631 g of an orange oil was isolated and was used without further purification. A cold (–40° C.) solution of the oil (0.631 g) in dry THF (22 mL) was treated with tert-butyllithium (1.7 M in pentane, 2.00 mL). The solution turned deep red. After 20 minutes, DMF (0.50 mL, 6.46 mmol) was added to the reaction mixture and the resultant solution was allowed to warm to room temperature overnight. Aqueous work-up followed by purification of the crude material by column chromatography on silica gel (25:1 $CH_2Cl_2$—MeOH) gave 0.470 g (67%) of 1-[[2-(trimethylsilyl)ethoxy]methyl]-5-chloro-1H-benzimidazole-2-carboxaldehyde as a yellow oil. $^1$H NMR analysis of this material indicated a 1:1 mixture of regioisomers. $^1$H NMR ($CDCl_3$) □ 0.08-0.02 (m, 9H), 0.86-0.93 (m, 2H), 3.51-3.58 (m, 2H), 6.00 & 6.02 (s, s, 2H total), 7.40-7.48 (m, 2H), 7.58-7.66 (m, 1H), 7.84-7.93 (m, 1H), 10.09 & 10.10 (s, s, 1H total).

Using General Procedure B: Reaction of 1-[[2-(trimethylsilyl)ethoxy]methyl]-5-chloro-1H-benzimidazole-2-carboxaldehyde (0.448 g, 1.44 mmol) and N-(2-nitrobenzenesulfonyl)-N-(2-pyridinylmethyl)-N'-(5,6,7,8-tetrahydro-8-quinolinyl)-1,4-benzenedimethanamine (0.425 g, 0.78 mmol) with $NaBH(OAc)_3$ (0.515 g, 2.43 mmol) in $CH_2Cl_2$ (7.5 mL) for 21 hours followed by purification of the crude material by column chromatography on silica gel (20:1:1 $CH_2Cl_2$—MeOH containing 2% $NH_4OH$) provided 0.500 g of a yellow solid.

Using general procedure C: the yellow solid from above (0.500 g) was treated with thiophenol (0.37 mL, 3.60 mmol) and $K_2CO_3$ (0.911 g, 6.59 mmol) in $CH_3CN$ (12 mL). Purification of the crude material by column chromatography on silica gel (20:1 $CH_2Cl_2$—MeOH followed by 20:1:1 $CH_2Cl_2$—MeOH—$NH_4OH$) provided 0.322 g of the desired product as an off-white foam.

Using general procedure D: the foam from above (0.322 g) was dissolved in glacial acetic acid (4 mL) and treated with HBr saturated acetic acid (5 mL). The resultant hydrobromide salt was collected and partitioned between $CH_2Cl_2$ (20 mL) and 10 N NaOH (5 mL). The aqueous phase was extracted with $CH_2Cl_2$ (3×10 mL) and the combined organic layers were dried ($Na_2SO_4$), filtered and concentrated under reduced pressure to give the crude free amine as a white solid. Purification of the crude amine by radial chromatography on silica gel (2 mm plate 40:1:1 $CH_2Cl_2$—MeOH—$NH_4OH$) gave 0.113 g (28%) the free base of the title compound as a white solid.

Using general procedure D: Conversion of the free base (0.113 g) to the hydrobromide salt, followed by re-precipitation of the intermediate solid from methanol/ether, gave AMD8933 (0.160 g) as a white solid. $^1$H NMR ($D_2O$) □ 1.70-1.96 (m, 1H), 2.18-2.30 (m, 2H), 2.40-2.45 (m, 1H), 3.02 (br s, 2H), 3.76-3.89 (m, 4H), 4.17 (s, 2H), 4.44 (d, 1H, J=16.5 Hz), 4.62 (d, 1H, J=16.5 Hz), 4.73-4.79 (m, 1H, overlaps with HOD), 7.06 (d, 2H, J=7.8 Hz), 7.21 (d, 2H, J=7.8 Hz), 7.38 (dd, 1H, J=1.5, 8.7 Hz), 7.51 (d, 1H, J=8.7 Hz), 7.61-7.71 (m, 2H), 7.91 (dd, 1H, J=7.8, 6.0 Hz), 8.15 (ddd, 1H, J=8.1, 7.8, 1.2 Hz), 8.39 (d, 1H, J=7.8 Hz), 8.66 (d, 1H, J=5.1 Hz), 8.67 (d, 2H, J=5.7 Hz); $^{13}$C NMR ($D_2O$) □ 20.43, 20.97, 27.84, 49.13, 50.28 (2 carbons), 56.68, 63.31, 113.92, 115.22, 126.21, 126.27, 126.33, 127.25, 129.29, 130.03, 130.22 (2 carbons), 130.94 (2 carbons), 131.20, 131.88, 138.21, 139.68, 141.06, 142.46, 147.61, 148.19, 148.33, 150.71, 153.08; ES-MS m/z 523 (M+H). Anal. Calcd. for $C_{31}H_{31}N_6Cl.4.0HBr.1.6H_2O$: C, 42.53; H, 4.40; N, 9.60; Cl, 4.05; Br, 36.50. Found: C, 42.46; H, 4.38; N, 9.32; Cl, 4.08; Br, 36.77.

EXAMPLE: 12

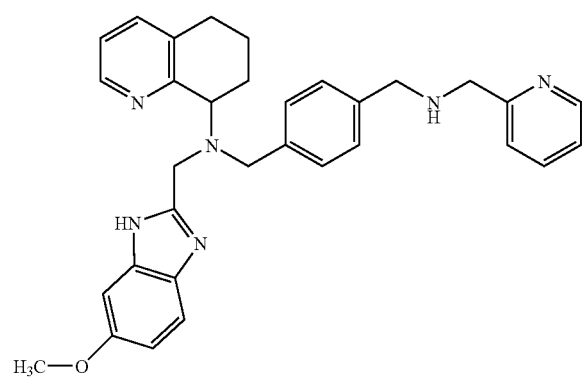

AMD8968: Preparation of N-(2-pyridinylmethyl)-N'-[5-methoxy-1H-benzimidazol-2-ylmethyl]-N'-(5,6,7,8-tetrahydro-8-quinolinyl)-1,4-benzenedimethanamine (free base)

A mixture of 4-methoxy-1,2-phenylenediamine dihydrochloride (1.125 g, 5.33 mmol) and chloroacetic acetic (1.006 g, 10.65 mmol) in 4 N HCl (5 mL) was heated to reflux for 22 hours. Following aqueous work-up, 0.90 g of an orange solid was isolated which was used without further purification.

A solution of 2-chloromethyl-5-methoxy-1H-benzimidazole (0.202 g, 1.03 mmol), N-(2-nitrobenzenesulfonyl)-N-(2-pyridinylmethyl)-N'-(5,6,7,8-tetrahydro-8-quinolinyl)-1,4-benzenedimethanamine (0.558 g, 1.03 mmol) and N,N-diisopropylethylamine (0.60 mL, 3.44 mmol) in DMF (10 mL) was heated to 80° C. for 20 hours. The mixture was concentrated and the residue was partitioned between $CH_2Cl_2$ (30 mL) and brine (10 mL). The phases were separated and the aqueous phase was extracted with $CH_2Cl_2$ (2×10 mL). The combined organic extracts were dried ($Na_2SO_4$) and concentrated. The crude material was purified by column chromatography on silica gel (25:1:1 $CH_2Cl_2$—$CH_3OH$—$NH_4OH$) to provide the desired tertiary amine (0.315 g) as a yellow oil.

Using general procedure C: the yellow oil was treated with thiophenol (0.30 mL, 2.92 mmol) and $K_2CO_3$ (0.638 g, 4.61 mmol) in $CH_3CN$ (9 mL). Purification of the crude material by column chromatography on silica gel (20:1:1 $CH_2Cl_2$—$CH_3OH$—$NH_4OH$) followed by radial chromatography on silica gel (2 mm plate, 50:1:1 $CH_2Cl_2$—$CH_3OH$—$NH_4OH$) provided 0.123 g (23%) of the title compound AMD8968 as a yellow oil. $^1H$ NMR ($CDCl_3$) □ 1.61-1.74 (m, 1H), 1.96-2.29 (m, 3H), 2.71 (dt, 1H, J=16.5, 7.5 Hz), 2.85 (ddd, 1H, J=16.5, 10.5, 4.8 Hz), 3.72 (s, 2H), 3.75 (s, 2H), 3.84-3.95 (m, 6H), 4.04-4.14 (m, 2H), 6.83 (br s, 1H), 7.01 (br s, 1H), 7.10-7.28 (m, 5H), 7.34-7.43 (m, 3H), 7.51 (br d, 1H, J=8.4 Hz), 7.59 (td, 1H, J=7.5, 1.8 Hz), 8.52 (d, 1H, J=4.8 Hz), 8.68 (d, 2H, J=3.9 Hz); $^{13}C$ NMR ($CDCl_3$) □ 21.38, 23.28, 29.24, 48.47, 53.17, 53.71, 54.45, 55.89, 60.08, 121.87, 122.18, 122.32, 128.21, 128.63, 134.70, 136.37, 137.15, 138.07, 139.01, 146.95, 149.25, 155.67, 155.78, 157.53, 159.74; ES-MS m/z 519 (M+H). Anal. Calcd. for $C_{32}H_{34}N_6O.0.4CH_2Cl_2.0.4H_2O$: C, 69.51; H, 6.41; N, 15.01. Found: C, 69.22; H, 6.43; N, 14.85.

EXAMPLE: 13

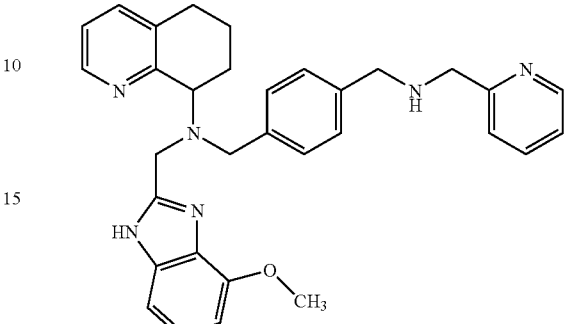

AMD9336: Preparation of N-(2-pyridinylmethyl)-N'-[4-methoxy-1H-benzimidazol-2-ylmethyl]-N'-(5,6,7,8-tetrahydro-8-quinolinyl)-1,4-benzenedimethanamine(hydrobromide salt)

2-chloromethyl-4-methoxy-1H-benzimidazole.

A suspension of 3-nitroanisole (1.550 g, 10.12 mmol) and O-methylhydroxylamine hydrochloride (1.078 g, 12.91 mmol) in DMF (15 mL) was added to a cold (0° C.) solution of potassium tert-butoxide (5.870 g, 52.30 mmol) and copper (I) chloride (0.200 g, 2.02 mmol) in DMF (35 mL). The cooling bath was removed and the resultant slurry was stirred at room temperature for 6 hours. The reaction mixture was poured into saturated aqueous $NH_4Cl$ (50 mL) and the mixture was extracted with $CH_2Cl_2$ (4×50 mL). The combined organic extracts were dried ($Na_2SO_4$) and concentrated. Purification of the crude material by column chromatography on silica gel (5:1 hexanes-ethyl acetate) followed by radial chromatography on silica gel (2 mm plate, 5:1 hexanes-ethyl acetate) provided 0.860 g (50%) of 2-amino-3-methoxy-nitrobenzene as a red solid. $^1H$ NMR ($CDCl_3$) □ 3.92 (s, 3H), 6.44 (br s, 2H), 6.61 (dd, 1H, J=9.0, 9.0 Hz), 6.88 (d, 1H, J=9.0 Hz), 7.74 (d, 1H, J=9.0 Hz).

A solution of 2-amino-3-methoxy-1-nitrobenzene (0.860 g, 5.11 mmol) in MeOH (50 mL) was hydrogenated (1 atm) over palladium, 10 wt. % on activated carbon (0.163 g). The resultant crude 3-methoxy-1,2-phenylenediamine was reacted with chloroacetic acid (0.953 g, 10.08 mmol) in refluxing 4 N HCl (10 mL) overnight. After aqueous workup, 0.87 g of 2-chloromethyl-4-methoxy-1H-benzimidazole was isolated as a red-brown solid, which was used without further purification.

A solution of the crude 2-chloromethyl-4-methoxy-1H-benzimidazole (0.209 g), N-(2-nitrobenzenesulfonyl)-N-(2-pyridinylmethyl)-N'-(5,6,7,8-tetrahydro-8-quinolinyl)-1,4-benzenedimethanamine (0.588 g, 1.08 mmol) and N,N-diisopropylethylamine (0.56 mL, 3.21 mmol) in DMF (11 mL) was heated to 80° C. for 19 hours. The mixture was concentrated and the residue was partitioned between $CH_2Cl_2$ (20 mL) and brine (10 mL). The phases were separated and the aqueous phase was extracted with $CH_2Cl_2$ (3×10 mL). The combined organic extracts were dried ($Na_2SO_4$) and concentrated. The crude material was purified by column chromatography on silica gel (30:1:1 CH$_2$Cl$_2$—CH$_3$OH—NH$_4$OH) to provide the desired tertiary amine (0.359 g) as a yellow oil.

Using general procedures C and D: the yellow oil was treated with thiophenol (0.37 mL, 3.60 mmol) and K$_2$CO$_3$ (0.742 g, 5.36 mmol) in CH$_3$CN (10 mL). Purification of the crude material by column chromatography on silica gel (20:1:1 CH$_2$Cl$_2$—CH$_3$OH—NH$_4$OH) followed by radial chromatography on silica gel (2 mm plate, 50:1:1 CH$_2$Cl$_2$—CH$_3$OH—NH$_4$OH) provided 0.073 g (13%) of the free base of the title compound as a white solid. Conversion of the free base (0.073 g) to the hydrobromide salt, followed by re-precipitation of the intermediate solid from methanol/ether, gave AMD9336 (0.098 g) as a white solid. $^1$H NMR (D$_2$O) □ 1.81-1.95 (m, 1H), 2.18-2.27 (m, 2H), 2.41-2.45 (m, 1H), 3.02 (br s, 2H), 3.76-3.87 (m, 4H), 3.94 (s, 3H), 4.12 (s, 2H), 4.41 (d, 1H, J=16.5 Hz), 4.60 (d, 1H, J=16.5 Hz), 4.73-4.78 (m, 1H, overlaps with HOD), 6.87 (d, 1H, J=8.1 Hz), 7.04 (d, 2H, J=7.8 Hz), 7.09 (d, 1H, J=8.1 Hz), 7.20 (d, 2H, J=7.8 Hz), 7.29 (dd, 1H, J=8.1, 8.4 Hz), 7.62 (d, 1H, J=8.1 Hz), 7.69 (dd, 1H, J=6.0, 7.8 Hz), 7.91 (dd, 1H, J=6.0, 7.8 Hz), 8.16 (ddd, 1H, J=7.8, 7.8, 1.5 Hz), 8.38 (d, 1H, J=7.5 Hz), 8.66 (d, 1H, J=5.1 Hz), 8.74 (d, 1H, J=5.7 Hz); $^{13}$C NMR (D$_2$O) □ 20.45, 20.93, 27.85, 48.96, 50.17, 50.31, 56.67, 56.75, 63.34, 105.83, 107.01, 121.37, 126.12, 126.24, 126.35, 127.82, 129.92, 130.10 (2 carbons), 130.84 (2 carbons), 131.91, 138.27, 139.68, 141.03, 142.51, 147.22, 147.49, 148.26 (2 carbons), 150.79, 150.88; ES-MS m/z 519 (M+H). Anal. Calcd. for C$_{32}$H$_{34}$N$_6$O.4.0HBr.3.0H$_2$O: C, 42.88; H, 4.95; N, 9.38; Br, 35.66. Found: C, 42.94; H, 4.90; N, 9.22; Br, 35.63.

EXAMPLE: 14

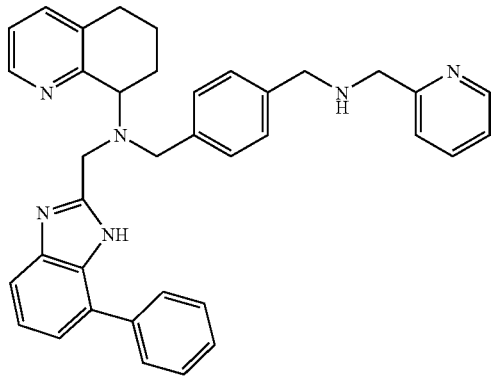

AMD9368: Preparation of N-(2-pyridinylmethyl)-N'-[4-phenyl-1H-benzimidazol-2-ylmethyl]-N'-(5,6,7,8-tetrahydro-8-quinolinyl)-1,4-benzenedimethanamine(hydrobromide salt)

2-Chloromethyl-4-phenyl-1H-benzimidazole.

A suspension of 2-nitrobiphenyl (2.061 g, 10.34 mmol) and O-methylhydroxylamine hydrochloride (1.088 g, 13.02 mmol) in DMF (15 mL) was added to a cold (0° C.) solution of potassium tert-butoxide (5.993 g, 53.40 mmol) and copper (I) chloride (0.246 g, 2.48 mmol) in DMF (35 mL). The cooling bath was removed and the resultant slurry was stirred at room temperature for 20 hours. The reaction mixture was poured into saturated aqueous NH$_4$Cl (50 mL) and the mixture was extracted with CH$_2$Cl$_2$ (4×50 mL). The combined organic extracts were dried (Na$_2$SO$_4$) and concentrated. Purification of the crude material by column chromatography on silica gel (4:1 hexanes-ethyl acetate followed by 2:1 hexanes-ethyl acetate) provided 0.600 g (27%) 2-amino-6-phenyl-nitrobenzene as a yellow oil. $^1$H NMR (CDCl$_3$) □ 4.99 (br s, 2H), 6.70 (dd, 1H, J=7.2, 1.2 Hz), 6.80 (dd, 1H, J=8.4, 1.2 Hz), 7.29-7.41 (m, 6H).

A solution of 2-amino-6-phenyl-nitrobenzene (0.600 g, 2.80 mmol) in MeOH (28 mL) was hydrogenated (30 psi) over palladium, 10 wt. % on activated carbon (0.121 g). The resultant crude 3-phenyl-1,2-phenylenediamine was reacted with chloroacetic acid (0.537 g, 5.68 mmol) in refluxing 4 N H1 (6 mL) overnight. After normal workup, 0.63 g (92%) of 2-chloromethyl-4-phenyl-1H-benzimidazole was isolated as a brown solid, which was used without further purification.

A solution of the crude 2-chloromethyl-4-phenyl-1H-benzimidazole (0.249 g), N-(tert-butoxycarbonyl)-N-(2-pyridinylmethyl)-N'-(5,6,7,8-tetrahydro-8-quinolinyl)-1,4-benzenedimethanamine (0.468 g, 1.02 mmol) and N,N-diisopropylethylamine (0.55 mL, 3.15 mmol) in DMF (10 mL) was heated to 80° C. for 17 hours. The mixture was concentrated and the residue was partitioned between CH$_2$Cl$_2$ (30 mL) and brine (10 mL). The phases were separated and the aqueous phase was extracted with CH$_2$Cl$_2$ (3×10 mL). The combined organic extracts were dried (Na$_2$SO$_4$) and concentrated. The crude material was purified by radial chromatography on silica gel (25:1 CH$_2$Cl$_2$—CH$_3$OH containing 2% NH$_4$OH) to provide 0.121 g (20%) of the desired tertiary amine as a yellow solid.

Using general procedure D: Conversion of the yellow solid to the hydrobromide salt with simultaneous removal of the BOC-protecting group, followed by re-precipitation of the intermediate solid from methanol/ether, gave AMD9368 (0.130 g) as a white solid. $^1$H NMR D$_2$O) □ 1.81-1.95 (m, 1H), 2.17-2.29 (m, 2H), 2.40-2.45 (m, 1H), 3.01 (br s, 2H), 3.73-3.83 (m, 4H), 4.12 (s, 2H), 4.43 (d, 1H, J=16.5 Hz), 4.63 (d, 1H, J=16.5 Hz), 4.74-4.79 (m, 1H, overlaps with HOD), 6.97 (d, 2H, J=7.8 Hz), 7.15 (d, 2H, J=7.8 Hz), 7.34 (d, 1H, J=6.6 Hz), 7.43-7.68 (m, 9H), 7.91 (dd, 1H, J=6.0, 7.8 Hz), 8.11 (ddd, 1H, J=7.8, 7.8, 1.5 Hz), 8.38 (d, 1H, J=7.8 Hz), 8.61 (d, 1H, J=4.8 Hz), 8.71 (d, 1H, J=5.7 Hz); $^{13}$C NMR (D$_2$O) □ 20.43, 20.91, 27.84, 48.97, 50.22, 50.23, 56.67, 63.44, 112.86, 126.12, 126.28, 126.36, 127.11, 128.79, 129.55, 129.85, 129.97, 130.81, 131.14, 135.71, 138.24, 139.67, 141.07, 142.36, 147.52, 148.24, 148.27, 150.76, 152.38; ES-MS m/z 565 (M+H). Anal. Calcd. for C$_{37}$H$_{36}$N$_6$.4.0HBr.2.7H$_2$O: C, 47.43; H, 4.88; N, 8.97; Br, 34.11. Found: C, 47.42; H, 4.89; N, 8.77; Br, 34.08.

EXAMPLE: 15

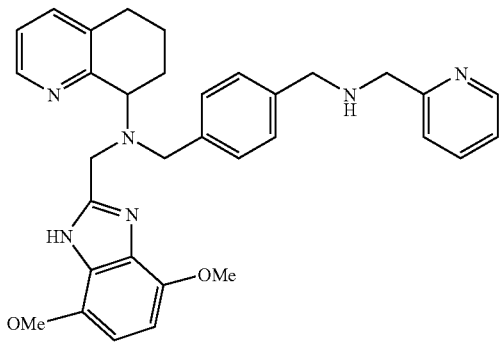

AMD9387: Preparation of N-(2-pyridinylmethyl)-N'-[4,7-dimethoxy-1H-benzimidazol-2-ylmethyl]-N'-(5,6,7,8-tetrahydro-8-quinolinyl)-1,4-benzene-dimethanamine(hydrobromide salt)

3,6-Dimethoxy-1,2-phenylenediamine

A suspension of 2,5-dimethoxynitrobenzene (1.831 g, 10.00 mmol) and O-methylhydroxylamine hydrochloride (1.086 g, 13.01 mmol) in DMF (15 mL) was added to a cold (0° C.) solution of potassium tert-butoxide (5.84 g, 52.04 mmol) and copper(I) chloride (0.198 g, 2.00 mmol) in DMF (35 mL). The cooling bath was removed and the resultant slurry was stirred at room temperature for 23 hours. The reaction mixture was poured into saturated aqueous $NH_4Cl$ (50 mL) and the mixture was extracted with $CH_2Cl_2$ (4×50 mL). The combined organic extracts were dried ($Na_2SO_4$) and concentrated. Purification of the crude material by column chromatography on silica gel (5:1 hexanes-ethyl acetate followed by 3:1 hexanes-ethyl acetate) provided 0.400 g of an orange oil. The oil was dissolved in MeOH (10 mL) and the mixture was hydrogenated (1 atm) over palladium, 10 wt. % on activated carbon (0.088 g). The mixture was vacuum filter through celite and the cake was washed with methanol. The solvent was removed from the filtrate under reduced pressure and the oil thus obtained was purified by column chromatography on silica gel (2:1 hexanes-ethyl acetate) and afforded 0.179 g (11%) of 3,6-dimethoxy-1,2-phenylenediamine as a yellow oil. $^1$H NMR (CDCl$_3$) □ 3.52 (br s, 4H), 3.81 (s, 6H), 6.31 (s, 2H).

3,6-Dimethoxy-1,2-phenylenediamine was reacted with chloroacetic acid (0.537 g, 5.68 mmol) in refluxing 4 N HCl (6 mL) overnight. After aqueous workup, 0.371 g of an orange solid was isolated and this was used without further purification in the next step. A solution of the crude 2-chloromethyl-4,7-dimethoxy-1H-benzimidazole (0.371 g), N-(tert-butoxycarbonyl)-N-(2-pyridinylmethyl)-N'-(5,6,7,8-tetrahydro-8-quinolinyl)-1,4-benzenedimethanamine (0.460 g, 1.00 mmol) and N,N-diisopropylethylamine (0.55 mL, 3.15 mmol) in DMF (10 mL) was heated to 80° C. for 23 hours. The mixture was concentrated and the residue was partitioned between $CH_2Cl_2$ (40 mL) and brine (10 mL). The phases were separated and the aqueous phase was extracted with $CH_2Cl_2$ (3×10 mL). The combined organic extracts were dried ($Na_2SO_4$) and concentrated. The crude material was purified by column chromatography on silica gel (50:1:1 $CH_2Cl_2$—$CH_3OH$—$NH_4OH$) followed by radial chromatography on silica gel (40:1:1 $CH_2Cl_2$—$CH_3OH$—$NH_4OH$) to provide 0.092 g (17%) of the desired tertiary amine as a yellow oil.

Using general procedure D: Conversion of the yellow oil to the hydrobromide salt with simultaneous removal of the BOC-protecting group, followed by re-precipitation of the intermediate solid from methanol/ether, gave AMD9387 (0.089 g) as a white solid. $^1$H NMR D$_2$O □ 1.80-1.96 (m, 1H), 2.17-2.29 (m, 2H), 2.38-2.45 (m, 1H), 3.02 (br s, 2H), 3.75-3.82 (m, 4H), 3.88 (s, 6H), 4.06 (s, 2H), 4.38 (d, 1H, J=16.2 Hz), 4.59 (d, 1H, J=16.2 Hz), 4.73-4.79 (m, 1H, overlaps with HOD), 6.77 (s, 2H), 7.02 (d, 2H, J=8.1 Hz), 7.18 (d, 2H, J=8.1 Hz), 7.54 (d, 1H, J=7.8 Hz), 7.62 (dd, 1H, J=5.4, 7.2 Hz), 7.91 (dd, 1H, J=6.0, 7.8 Hz), 8.07 (ddd, 1H, J=7.8, 7.8, 1.5 Hz), 8.38 (d, 1H, J=7.5 Hz), 8.63 (d, 1H, J=4.5 Hz), 8.73 (d, 1H, J=5.1 Hz); $^{13}$C NMR (D$_2$O) □ 20.44, 20.90, 27.85, 49.35, 50.11, 56.79, 56.99, 63.45, 107.44, 122.62, 125.77, 125.95, 126.11, 129.90, 129.99, 130.80, 138.27, 139.65, 141.07, 141.37, 148.23, 148.31, 148.91, 150.62, 150.77; ES-MS m/z 549 (M+H). Anal. Calcd. for $C_{33}H_{36}N_6O_2$.4.0HBr.3.6H$_2$O: C, 42.29; H, 5.08; N, 8.97; Br, 34.10. Found: C, 42.37; H, 5.03; N, 8.82; Br, 34.06.

EXAMPLE: 16

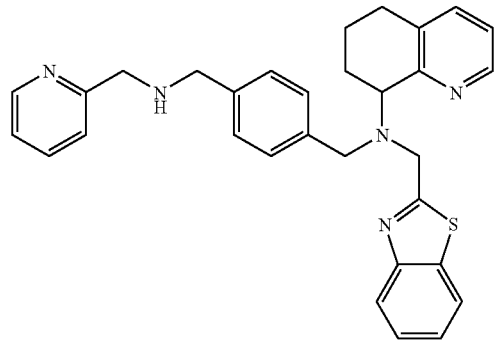

AMD8969: Preparation of N-(2-pyridinylmethyl)-N'-(benzothiazol-2-ylmethyl)-N'-(5,6,7,8-tetrahydro-8-quinolinyl)-1,4-benzenedimethanamine(hydrobromide salt)

A mixture of 2-aminothiophenol (630 mg, 5.0 mmol) and chloroacetic acid (945 mg, 10 mmol) was stirred in polyphosphoric acid (5 mL) for 2 hours at 120° C. to give, after work-up and chromatography, 2-chloromethylbenzothiazole (260 mg, 28%) as colorless crystals. $^1$H NMR (CDCl$_3$) δ 4.95 (s, 2H), 7.45 (t, 1H, J=6 Hz), 7.51 (t, 1H, J=6 Hz), 7.90 (d, 1H, J=9 Hz), 8.03 (d, 1H, J=6 Hz).

A solution of 2-chloromethylbenzothiazole (260 mg, 1.4 mmol), N-(tert-butoxycarbonyl)-N-(2-pyridinylmethyl)-N'-(5,6,7,8-tetrahydro-8-quinolinyl)-1,4-benzenedimethanamine (713 mg, 1.56 mmol) and diisopropylethylamine (0.38 mL, 2.1 mmol) were stirred at 80° C. in DMF (12 mL) for 64 hours to yield, after work-up and chromatography, the desired N-(tert-butoxycarbonyl)-N-(2-pyridinylmethyl)-N'-(benzothiazol-2-ylmethyl)-N'-(5,6,7,8-tetrahydro-8-quinolinyl)-1,4-benzenedimethanamine as a pale brown foam (400 mg, 47%). $^1$H NMR (CDCl$_3$) δ 1.45 (m, 9H), 1.65 (m, 1H), 1.87 (m, 1H), 1.94 (m, 1H), 2.26 (m, 1H), 2.74 (m, 2H), 3.83 (d, 1H, J=15 Hz), 3.98 (d, 1H, J=18 Hz), 4.09 (m, 1H), 4.24 (d, 1H, J=12 Hz), 4.43 (s, 2H), 4.54 (s, 2H), 4.59 (s, 1H), 7.05 (m, 3H), 7.21 (m, 3H), 7.31 (t, 3H, J=7.0 Hz), 7.35 (t, 1H, J=7.5 Hz), 7.53 (d, 2H, J=9 Hz), 7.57 (m, 1H), 7.89 (t, 1H, J=7.5 Hz), 8.51 (t, 1H, J=6.5 Hz).

Using general procedure D: the foam from above was converted to the hydrobromide salt with simultaneous deprotection of the BOC group to provide AMD8969 (0.42 g) as a pale yellow solid. $^1$H NMR (D$_2$O) □1.67-1.79 (m, 1H), 2.04-2.19 (m, 2H), 2.26-2.35 (m, 1H), 2.91 (d, 2H), 3.94 (m, 2H), 4.18 (s, 2H), 4.23 (t, 2H, J=8.7 Hz), 4.27 (s, 2H), 4.48 (dd, 1H, J=6.0, 10.2 Hz), 7.27 (d, 2H J=7.8 Hz), 7.31 (t, 1H J=7.2 Hz), 7.42 (t, 1H, J=8.4 Hz), 7.47 (d, 2H, J=7.8 Hz), 7.68 (m, 3H), 7.81 (d, 1H, J=8.1 Hz), 7.89 (d, 1H, J=7.8 Hz), 8.17 (m, 2H), 8.51 (d, 1H, J=5.1 Hz), 8.66 (d, 1H, J=5.5 Hz); $^{13}$C NMR (D$_2$O) □ 20.38, 27.73, 47.41, 51.44, 53.35, 55.91, 59.91, 66.46, 120.85, 123.15, 125.73, 126.85, 127.97 (2 carbons), 128.27, 129.69, 130.65 (2 carbons), 131.02 (2 carbons), 133.58, 139.03, 139.53, 140.55, 144.45, 145.69, 146.93, 147.61, 148.37, 151.31, 174.26. ES-MS m/z 506 (M+H). Anal. Calcd. for $C_{31}H_{31}N_5S$.4.0HBr.2.3H$_2$O: C, 42.76; H, 4.58; N, 8.04; Br, 36.71. Found: C, 42.75; H, 14.55; N, 7.84; Br, 36.70.

EXAMPLE: 17

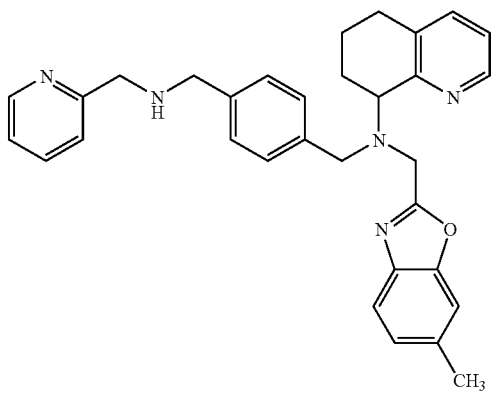

AMD8970: Preparation of N-(2-pyridinylmethyl)-N'-(6-methylbenzoxazol-2-ylmethyl)-N'-(5,6,7,8-tetrahydro-8-quinolinyl)-1,4-benzenedimethanamine (hydrobromide salt)

A mixture of 2-amino-5-methylphenol (616 mg, 5.0 mmol) and chloroacetic acid (945 mg, 10 mmol) was stirred in polyphosphoric acid (5 mL) for 2 hours at 120° C. to give, after work-up and chromatography, 2-chloromethyl-5-methylbenzoxazole (340 mg, 37%) as a yellow liquid. $^1$H NMR (CDCl$_3$) δ 2.50 (s, 3H), 4.74 (s, 2H), 7.18 (d, 1H, J=6 Hz), 7.35 (s, 1H), 7.60 (d, 1H, J=9 Hz).

A solution of 2-chloromethyl-5-methyl-benzoxazole (340 mg, 1.9 mmol), N-(tert-butoxycarbonyl)-N-(2-pyridinylmethyl)-N'-(5,6,7,8-tetrahydro-8-quinolinyl)-1,4-benzenedimethanamine (940 mg, 2.06 mmol) and diisopropylethylamine (0.50 mL, 2.8 mmol) were stirred at 80° C. in DMF (15 mL) for 16 hours to yield, after work-up and chromatography, the desired N-(tert-butoxycarbonyl)-N-(2-pyridinylmethyl)-N'-(6-methylbenzoxazol-2-ylmethyl)-N'-(5,6,7,8-tetrahydro-8-quinolinyl)-1,4-benzenedimethanamine as a pale brown foam (700 mg, 61%). $^1$H NMR (CDCl$_3$) δ 1.45 (m, 9H), 1.67 (m, 2H), 1.96 (m, 1H), 2.06 (m, 1H), 2.47 (s, 3H), 2.68 (m, 1H), 2.76 (m, 1H), 3.88 (d, 1H, J=15 Hz), 4.01 (d, 1H, J=15 Hz), 4.04 (d, 1H, J=15 Hz), 4.17 (m, 1H), 4.27 (d, 1H, J=15 Hz), 4.39 (s, 2H), 4.50 (s, 2H), 7.03 (m, 2H), 7.11 (m, 4H), 7.31 (s, 2H), 7.40 (d, 2H, J=9 Hz), 7.51 (d, 1H, J=6 Hz), 7.60 (t, 1H), 8.43 (d, 1H, J=4 Hz), 8.51 (d, 1H, J=5 Hz).

Using general procedure D: the foam from above was converted to the hydrobromide salt with simultaneous deprotection of the BOC group to provide AMD8970 (0.77 g) as a pale yellow solid. $^1$H NMR (D$_2$O) δ 1.67-1.81 (m, 1H), 2.09-2.19 (m, 2H), 2.22-2.30 (m, 1H), 2.36 (s, 3H), 2.89 (d, 2H, J=5.1 Hz), 3.97 (s, 1H), 4.02 (d, 2H), 4.08 (s, 1H), 4.17 (s, 2H), 4.38 (s, 2H), 4.49 (dd, 1H, J=6.0, 10.5 Hz), 7.06 (d, 1H, J=8.2 Hz), 7.25 (d, 2H J=8.4 Hz), 7.30 (s, 1H), 7.33 (d, 1H J=4.5 Hz), 7.46 (d, 2H, J=8.1 Hz), 7.61 (dd, 1H, J=6.0, 7.8 Hz), 7.81 (d, 1H, J=8.4 Hz), 7.83 (d, 1H, J=7.8 Hz), 8.12 (d, 1H, J=8.1 Hz), 8.32 (dt, 1H, J=1.8, 7.8 Hz), 8.49 (d, 1H, J=5.7 Hz), 8.72 (dd, 1H, J=2.0, 5.9 Hz); $^{13}$C NMR (D$_2$O) δ 20.73, 27.43, 46.88, 47.48, 51.50, 53.31, 55.20, 60.43, 61.99, 117.13, 121.56, 124.08, 125.28, 128.11, 128.48, 129.86, 130.82 (2 carbons), 131.10, 138.40, 139.50, 140.13, 141.76, 144.40, 145.49, 146.26, 146.67, 147.15, 149.07, 149.98, 151.12, 175.37. ES-MS m/z 504 (M+H). Anal. Calcd. for C$_{32}$H$_{33}$N$_5$O.4.5HBr.2.3H$_2$O: C, 42.27; H, 4.67; N, 7.70; Br, 39.55. Found: C, 42.17; H, 4.70; N, 7.46; Br, 39.70.

EXAMPLE: 18

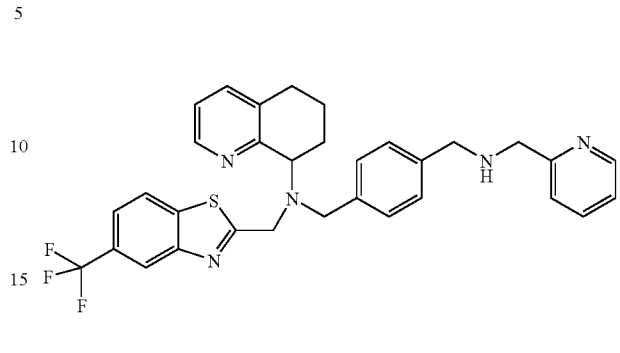

AMD8988: Preparation of N-(2-pyridinylmethyl)-N'-(5-trifluoromethylbenzothioazol-2-ylmethyl)-N'-(5,6,7,8-tetrahydro-8-quinolinyl)-1,4-benzenedimethanamine(hydrobromide salt)

A mixture of 2-amino-4-trifluoromethylthiophenol (1.25 g, 5.0 mmol) and chloroacetic acid (945 mg, 10 mmol) were refluxed in polyphosphoric acid (5 mL) for 16 hours to give, after work-up and chromatography, 2-chloromethyl-5-trifluoromethylbenzothiazole (740 mg, 59%) as a colorless solid. $^1$H NMR (CDCl$_3$) δ 4.97 (s, 2H), 7.67 (d, 1H, J=9 Hz), 8.02 (d, 1H, J=9 Hz), 8.29 (d, 1H).

A solution of 2-chloromethyl-5-trifluoromethylbenzothiazole (740 mg, 2.94 mmol), N-(tert-butoxycarbonyl)-N-(2-pyridinylmethyl)-N'-(5,6,7,8-tetrahydro-8-quinolinyl)-1,4-benzenedimethanamine (1.48 g, 3.23 mmol) and diisopropylethylamine (0.80 mL, 4.4 mmol) were stirred at 80° C. in DMF (15 mL) for 16 hours to yield, after work-up and chromatography, the desired N-(tert-butoxycarbonyl)-N-(2-pyridinylmethyl)-N'-(5-trifluoromethylbenzothiazol-2-ylmethyl)-N'-(5,6,7,8-tetrahydro-8-quinolinyl)-1,4-benzenedimethanamine as a pale yellow foam (550 mg, 28%). $^1$H NMR (CDCl$_3$) δ 1.44 (m, 9H), 1.67 (m, 1H), 1.87 (m, 1H), 1.94 (m, 1H), 2.28 (m, 1H), 2.75 (m, 2H), 3.84 (d, 1H, J=12 Hz), 4.00 (d, 1H, J=15 Hz), 4.09 (m, 1H), 4.24 (d, 1H, J=15 Hz), 4.43 (s, 2H), 4.54 (s, 2H), 4.60 (d, 1H, J=15 Hz), 7.08 (m, 3H), 7.22 (m, 3H), 7.33 (d, 1H, J=9 Hz), 7.52 (d, 2H, J=9 Hz), 7.57 (d, 1H, J=9 Hz), 7.97 (d, 1H, J=9 Hz), 8.14 (s, 1H), 8.52 (m, 2H).

Using general procedure D: the foam from above was converted to the hydrobromide salt with simultaneous deprotection of the BOC group to provide AMD8988 (0.19 g) as a pale yellow solid. $^1$H NMR (D$_2$O) δ 1.63-1.77 (m, 1H), 2.00-2.14 (m, 2H), 2.20-2.30 (m, 1H), 2.88 (brd, 2H), 3.81 (s, 2H), 4.07 (d, 2H, J=15.2 Hz), 4.20 (s, 2H), 4.39 (dd, 1H), 4.47 (s, 2H), 7.28 (d, 2H, J=8.1 Hz), 7.43 (d, 2H J=7.8 Hz), 7.50 (d, 1H, J=8.4 Hz), 7.68 (t, 1H J=6.9 Hz), 7.91 (t, 2H, J=7.8 Hz), 7.96 (s, 2H), 8.17 (d, 1H, J=8.1 Hz), 8.42 (t, 1H, J=8.0 Hz), 8.52 (d, 1H, J=5.4 Hz), 8.73 (d, 1H, J=5.1 Hz); $^{13}$C NMR (D$_2$O) δ 14.54, 20.35, 27.67, 47.41, 51.50, 53.78, 55.60, 59.14, 66.43, 119.09, 123.66, 125.64, 128.00 (2 carbons), 128.34 (2 carbons), 129.60, 130.65 (2 carbons), 130.86 (2 carbons), 138.45, 139.04, 139.53, 140.41, 144.35, 145.58, 147.03, 147.48, 151.15, 151.51, 174.82. ES-MS m/z 575 (M+H). Anal. Calcd. for C$_{32}$H$_{30}$F$_3$N$_5$S.3.9HBr.1.8H$_2$O.0.4 (CH$_3$CH$_2$)$_2$O: C, 42.42; H, 4.40; N, 7.36; Br, 32.76. Found: C, 42.38; H, 4.23; N, 7.21; Br, 32.73.

EXAMPLE: 19

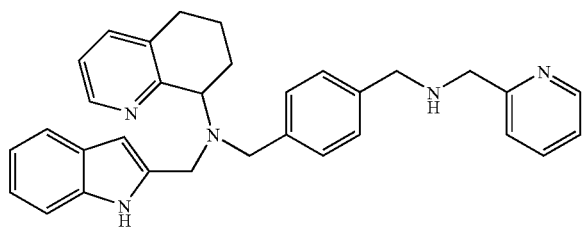

AMD9337: Preparation of N-(2-pyridinylmethyl)-N'-(indol-2-ylmethyl)-N'-(5,6,7,8-tetrahydro-8-quinolinyl)-1,4-benzenedimethanamine (free base)

A solution of indole-2-carboxylic acid (514 mg, 3.2 mmol) in anhydrous THF (20 mL) at 0° C. was treated with lithium aluminum hydride (1.0M in hexanes, 6.4 mL, 6.4 mmol) dropwise over 5 minutes. This gave, after work-up, 2-hydroxymethylindole (300 mg, 64%) as an orange powder. $^1$H NMR (CDCl$_3$) δ 1.90 (br s, 1H), 4.82 (s, 2H), 6.41 (s, 1H), 7.11 (t, 1H, J=7.5 Hz), 7.19 (t, 1H, J=7.5 Hz), 7.34 (d, 1H, J=8.1 Hz), 7.59 (d, 1H, J=7.8 Hz), 8.37 (br s, 1H).

A solution of 2-hydroxymethylindole (135 mg, 0.91 mmol) in dichloromethane (5 mL) was treated with 5 μm activated manganese dioxide (790 mg, 9.1 mmol) for 5 hours at room temperature. This gave, after work-up, the desired indole-2-carboxaldehyde (85 mg, 62%) as a brown solid. $^1$H NMR (CDCl$_3$) δ7.19 (t, 1H, J=7.5 Hz), 7.29(s, 1H), 7.43 (m, 2H), 7.75 (d, 1H, J=7.5 Hz), 9.04 (br s, 1H), 9.86 (s, 1H).

Using general procedure B: Indole-2-carboxaldehyde (85 mg, 0.58 mmol), N-(2-nitrophenylsulfonyl)-N-(2-pyridinylmethyl)-N'-(5,6,7,8-tetrahydro-8-quinolinyl)-1,4-benzenedimethanamine (320 mg, 0.58 mmol) and sodium triacetoxyborohydride (170 mg, 0.81 mmol) were stirred at room temperature in dichloromethane (6 mL) for 16 hours to yield, after work-up and chromatography, the desired N-(2-nitrophenylsulfonyl)-N-(2-pyridinylmethyl)-N'-(indol-2-ylmethyl)-N'-(5,6,7,8-tetrahydro-8-quinolinyl)-1,4-benzenedimethanamine as a brown foam (300 mg, 77%). $^1$H NMR (CDCl$_3$) δ 1.65 (m, 1H), 1.90 (m, 1H), 2.02 (m, 1H), 2.18 (m, 1H), 2.70 (m, 1H), 2.82 (m, 1H), 3.57 (d, 1H, J=15 Hz), 3.70 (d, 1H, J=15 Hz), 3.80 (d, 2H, J=15 Hz), 4.00 (m, 1H), 4.52 (d, 2H, J=3 Hz), 4.59 (s, 2H), 6.25 (s, 1H), 6.95 (m, 1H), 7.05 (m, 3H), 7.09 (m, 2H), 7.18 (d, 1H, J=7.0 Hz), 7.27 (d, 4H, J=6 Hz), 7.33 (m, 3H), 7.45 (d, 1H, J=7.5 Hz), 7.50 (d, 1H, J=7.8 Hz), 7.81 (d, 1H, J=8.5 Hz), 8.33 (d, 1H, J=4.5 Hz), 8.68 (d, 1H, J=5.0 Hz).

Using general procedure C: The solid from above (0.15 g, 0.22 mmol) was treated with thiophenol (0.1 mL, 0.9 mmol) and potassium carbonate (0.15 g, 1.1 mmol) in anhydrous acetonitrile (2 mL) to provide, after chromatography, AMD9337 (55 mg) as a pale yellow solid. $^1$H NMR (CDCl$_3$) □1.63-1.72 (m, 1H), 1.85-1.95 (m, 1H), 1.97-2.09 (m, 1H), 2.12-2.22 (m, 1H), 2.68 (d, 1H, J=16.2 Hz), 2.77-2.90 (m, 1H), 3.65 (d, 1H, J=13.5 Hz), 3.78 (s, 2H), 3.80 (d, 1H, J=14.1 Hz), 3.85 (s, 2H), 3.90 (s, 2H), 4.05 (dd, 1H, J=5.7, 9.0 Hz), 6.24 (s, 1H), 7.02 (t, 1H, J=7.5 Hz), 7.11 (t, 2H, J=7.2 Hz), 7.13 (t, 2H, J=7.2 Hz), 7.27 (d, 3H, J=7.8 Hz), 7.37 (dd, 1H, J=12.3, 13.8 Hz), 7.41 (d, 3H, J=8.1 Hz), 7.45 (d, 1H, J=8.1, 8.4 Hz), 7.61 (dt, 1H, J=1.8, 7.5 Hz), 8.55 (d, 1H, J=7.2), 8.63 (d, 1H, J=7.2 Hz); $^{13}$C NMR (CDCl$_3$) □ 21.09, 23.69, 29.15, 47.41, 53.25, 53.82, 54.48, 59.15, 99.14, 110.98, 118.85, 119.65, 120.57, 121.89 (2 carbons), 122.35, 128.15 (2 carbons), 128.68 (2 carbons), 128.85, 134.44, 135.89, 136.40, 136.86, 138.77 (2 carbons), 139.11, 147.01, 149.25, 158.04, 159.78. ES-MS m/z488 (M+H). Anal. Calcd. for C$_{32}$H$_{33}$N$_5$: C, 77.11; H, 6.92; N, 14.05. Found: C, 77.02; H, 6.82; N, 13.75.

EXAMPLE: 20

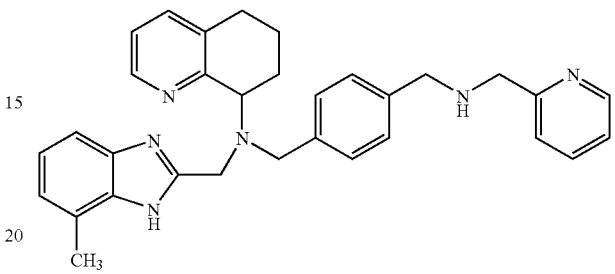

AMD9338: Preparation of N-(2-pyridinylmethyl)-N'-(4-methylbenzimidazol-2-ylmethyl)-N'-(5,6,7,8-tetrahydro-8-quinolinyl)-1,4-benzenedimethanamine (hydrobromide salt)

A mixture of 2-amino-3-methylaniline (826 mg, 6.8 mmol) and chloroacetic acid (1.03 g, 10.9 mmol) were refluxed in 4N hydrochloric acid (6 mL) for 2 hours to give, after work-up, 2-chloromethyl-4-methylbenzimidazole (781 mg, 64%) as a brown solid. $^1$H NMR (CDCl$_3$) δ 2.59 (s, 3H), 4.85 (s, 2H), 7.07 (d, 1H, J=6 Hz), 7.17 (t, 1H, J=7.5 Hz), 7.42 (d, 1H, J=9 Hz).

A solution of 2-chloromethyl-4-methylbenzimidazole (150 mg, 0.83 mmol), N-(tert-butoxycarbonyl)-N-(2-pyridinylmethyl)-N'-(5,6,7,8-tetrahydro-8-quinolinyl)-1,4-benzenedimethanamine (480 mg, 1.0 mmol) and diisopropylethylamine (0.22 mL, 1.25 mmol) were stirred at 80° C. in DMF (5 mL) for 16 hours to yield, after work-up and chromatography, the desired N-(tert-butoxycarbonyl)-N-(2-pyridinylmethyl)-N'-(4-methylbenzimidazol-2-ylmethyl)-N'-(5,6,7,8-tetrahydro-8-quinolinyl)-1,4-benzenedimethanamine as a pale brown foam (100 mg, 25%). $^1$H NMR (CDCl$_3$) δ 1.39 (br s, 9H), 1.74 (br, 3H), 2.06 (m, 2H), 2.25 (m, 1H), 2.65 (d, 2H, J=15 Hz), 2.85 (m, 1H), 3.71 (s, 2H), 3.95 (d, 1H, J=15 Hz), 4.08 (m, 1 Hz), 4.21 (d, 1H, J=18 Hz), 4.44 (m, 4H), 6.99 (m, 1H, J=9 Hz), 7.02-7.18 (br m, 7H), 7.33 (d, 2H, J=9 Hz), 7.43 (d, 1H, J=7.5 Hz), 7.49 (d, 1H, J=7.5 Hz), 8.44 (d, 1H, J=4 Hz), 8.70 (d, 1H, J=3 Hz).

Using general procedure D: the residue from above was converted to the hydrobromide salt with simultaneous deprotection of the BOC group to provide AMD9338 (0.10 g) as a white solid. $^1$H NMR (D$_2$O) □1.82-1.95 (m, 1H), 2.17-2.31 (m, 2H), 2.42 (s, 3H), 2.43 (m, 1H), 3.03 (brd, 2H), 3.72 (d, 2H, J=3.6 Hz), 3.81 (d, 2H, J=7.2 Hz), 3.98 (s, 2H), 4.42 (dd, 1H, J=16.2 Hz), 4.61 (d, 1H, J=17.5 Hz), 4.75 (m, 1H), 7.00 (d, 2H, J=8.1 Hz), 7.11 (d, 1H J=7.5 Hz), 7.19 (d, 2H, J=7.8 Hz), 7.24 (d, 1H J=7.5 Hz), 7.35 (d, 1H, J=8.4 Hz), 7.42 (d, 1H, J=7.8 Hz), 7.53 (dd, 1H, J=5.7, 7.2 Hz), 7.92 (dt, 1H, J=2.1, 6.6 Hz), 7.96 (dt, 1H, J=1.5, 7.8 Hz), 8.40 (d, 1H, J=7.8 Hz), 8.59 (d, 1H, J=7.2 Hz); $^{13}$C NMR (D$_2$O) □ 16.33, 20.46, 20.90, 27.87, 48.25, 50.23, 50.49, 56.87, 63.42, 111.24, 124.69, 126.15, 126.75, 127.06 (3 carbons), 129.78, 130.06 (2 carbons), 130.23, 130.38, 130.83 (2 carbons), 138.44, 139.65, 141.05, 144.45, 146.12, 147.07, 148.29, 150.80, 151.16. ES-MS m/z 503 (M+H). Anal. Calcd. for $C_{32}H_{34}N_6 \cdot 4.1HBr \cdot 3.1H_2O$: C, 43.17; H, 5.02; N, 9.44; Br, 36.80. Found: C, 43.36; H, 4.97; N, 9.33; Br, 36.58.

EXAMPLE: 21

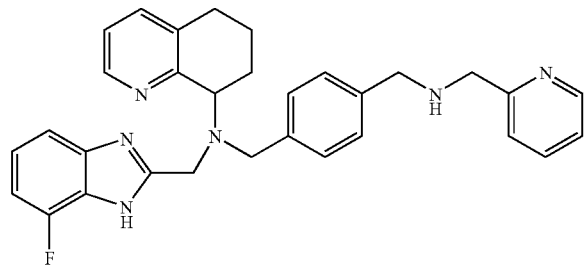

AMD9345: Preparation of N-(2-pryidinylmethyl)-N'-(4-fluorobenzimidazol-2-ylmethyl)-N'-(5,6,7,8-tetrahydro-8-quinolinyl)-1,4-benzenedimethanamine (hydrobromide salt)

A mixture of 2-amino-3-fluoroaniline (130 mg, 1.0 mmol) and chloroacetic acid (190 mg, 2.0 mmol) were refluxed in 4N hydrochloric acid (1.5 mL) for 16 hours to give, after work-up and chromatography, 2-chloromethyl-4-fluorobenzimidazole (89 mg, 47%) as a brown solid. $^1$H NMR (CDCl$_3$) δ 4.86 (s, 2H), 7.00 (m, 1H), 7.17 (m, 1H), 7.25 (d, 1H, J=9 Hz).

A solution of 2-chloromethyl-4-fluorobenzimidazole (89 mg, 0.5 mmol), N-(tert-butoxycarbonyl)-N-(2-pyridinylmethyl)-N'-(5,6,7,8-tetrahydro-8-quinolinyl)-1,4-benzenedimethanamine (270 mg, 0.59 mmol) and diisopropylethylamine (0.13 mL, 0.71 mmol) were stirred at 80° C. in DMF (5 mL) for 16 hours to yield, after work-up and chromatography, the desired N-(tert-butoxycarbonyl)-N-(2-pyridinylmethyl)-N'-(4-fluorobenzimidazol-2-ylmethyl)-N'-(5,6,7,8-tetrahydro-8-quinolinyl)-1,4-benzenedimethanamine as a pale brown foam (25 mg, 9%). $^1$H NMR (CDCl$_3$) δ 1.41 (m, 9H), 1.69 (m, 1H), 2.05 (m, 2H), 2.25 (m, 1H), 2.72 (m, 1H), 2.83 (m, 1H), 3.73 (d, 2H, J=6 Hz), 4.00 (d, 1H, J=15 Hz), 4.07 (m, 1H), 4.17 (d, 1H, J=9 Hz), 4.24 (d, 1H, J=9 Hz), 4.38 (s, 2H), 4.47 (d, 1H, J=12 Hz), 6.90 (m, 1H), 7.07-7.15 (m, 7H), 7.26 (t, 2H, J=7 Hz), 7.44 (d, 1H, J=9 Hz), 7.50 (m, 1H), 8.44 (d, 1H, J=4.5 Hz), 8.69 (d, 1H, J=5.5 Hz).

Using general procedure D: the residue from above was converted to the hydrobromide salt with simultaneous deprotection of the BOC group to provide AMD9345 (0.02 g) as a pale yellow solid. $^1$H NMR (D$_2$O) δ 1.82-1.95 (m, 1H), 2.17-2.31 (m, 2H), 2.40-2.45 (m, 1H), 3.02 (br d, 2H), 3.81 (s, 2H), 3.82 (d, 2H, J=9.0 Hz), 4.03 (s, 2H), 4.45 (d, 1H, J=16.8 Hz), 4.63 (d, 1H, J=16.8 Hz), 4.79 (m, 1H), 7.05 (d, 2H, J=7.8 Hz), 7.12 (t, 1H J=9.3 Hz), 7.22 (d, 2H, J=7.8 Hz), 7.30 (m, 1H), 7.34 (s, 1H), 7.39 (d, 1H, J=7.8 Hz), 7.48 (t, 1H, J=6.2 Hz), 7.91 (t, 2H, J=7.2 Hz), 8.38 (d, 1H, J=8.1 Hz), 8.56 (d, 1H, J=4.8 Hz), 8.72 (d, 1H, J=5.7 Hz); $^{13}$C NMR (D$_2$O) δ 20.44, 20.95, 27.85, 49.38, 50.27 (2 carbons), 56.65, 63.26, 110.12, 111.81, 112.17, 114.22, 125.81, 126.14 (2 carbons), 130.21 (3 carbons), 130.94 (2 carbons), 138.23, 139.65, 141.04, 141.79, 142.74, 147.94, 148.30, 148.63, 150.73, 152.82, 155.19. ES-MS m/z 507 (M+H). Anal. Calcd. for $C_{31}H_{31}N_6F \cdot 3.9HBr \cdot 3.5H_2O$: C, 42.06; H, 4.77; N, 9.49; Br, 35.20. Found: C, 42.06; H, 4.56; N, 9.19; Br, 35.16.

EXAMPLE: 22

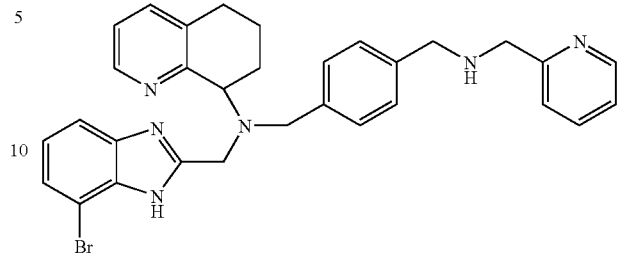

AMD9383: Preparation of N-(2-pyridinylmethyl)-N'-(4-bromobenzimidazol-2-ylmethyl)-N'-(5,6,7,8-tetrahydro-8-quinolinyl)-1,4-benzenedimethanamine (hydrobromide salt)

A mixture of 3-bromonitrobenzene (6.06 g, 30 mmol) and o-methylhydroxylamine hydrochloride (3.13 g, 37.5 mmol) were reacted in the presence of copper (I) chloride (0.59 g, 6 mmol) and potassium t-butoxide (10.1 g, 90 mmol) in DMF (75 mL). Aqueous work-up and chromatography gave 2-amino-3-bromonitrobenzene (0.36 g, 6%) as an orange powder. $^1$H NMR (CDCl$_3$) δ 6.60 (t, 1H, J=9 Hz), 7.70 (d, 1H, J=9 Hz), 8.14 (d, 1H, J=9 Hz).

The powder from above (0.36 g, 1.66 mmol) was dissolved in methanol (17 mL) and treated with iron powder (0.93 g, 16.6 mmol) and concentrated hydrochloric acid (6.8 mL) at 0° C. for 30 minutes. This gave, after work-up, 2-amino-3-bromoaniline (0.25 g, 79%) as a dark green solid. $^1$H NMR (CDCl$_3$) δ 6.62 (d, 2H, J=9 Hz), 6.97 (t, 1H, J=9 Hz).

A mixture of 2-amino-3-bromoaniline (245 mg, 1.3 mmol) and chloroacetic acid (250 mg, 2.6 mmol) were refluxed in 4N hydrochloric acid (1.5 mL) for 16 hours to give, after work-up and chromatography, 4-bromo-2-chloromethylbenzimidazole (160 mg, 50%) as a brown solid. $^1$H NMR (CDCl$_3$) δ 4.89 (s, 2H), 7.15 (t, 1H, J=6 Hz), 7.44 (d, 1H, J=6 Hz), 7.69 (d, 1H, J=9 Hz), 8.53 (br, 1H).

A solution of 4-bromo-2-chloromethylbenzimidazole (250 mg, 1.0 mmol), N-(tert-butoxycarbonyl)-N-(2-pyridinylmethyl)-N'-(5,6,7,8-tetrahydro-8-quinolinyl)-1,4-benzenedimethanamine (584 mg, 1.25 mmol) and diisopropylethylamine (0.27 mL, 1.5 mmol) were stirred at 80° C. in DMF (10 mL) for 16 hours to yield, after work-up and chromatography, the desired N-(tert-butoxycarbonyl)-N-(2-pyridinylmethyl)-N'-(4-bromobenzimidazol-2-ylmethyl)-N'-(5,6,7,8-tetrahydro-8-quinolinyl)-1,4-benzenedimethanamine as a pale brown foam (50 mg, 7%). $^1$H NMR (CDCl$_3$) δ 1.45 (m, 9H), 1.65 (m, 1H), 2.05 (m, 2H), 2.26 (m, 1H), 2.75 (m, 1H), 2.86 (m, 1H), 3.72 (d, 2H, J=9 Hz), 3.95 (d, 1H, J=15 Hz), 4.08 (m, 1H), 4.26 (d, 1H, J=15 Hz), 4.37 (s, 2H), 4.48 (d, 2H, J=15 Hz), 7.00-7.30 (m, 6H), 7.31 (m, 3H), 7.45 (t, 2H, J=7.0 Hz), 7.5 (d, 1H, J=7.5 Hz), 8.41 (d, 1H, J=4.5 Hz), 8.88 (d, 1H, J=5.5 Hz).

Using general procedure D: the residue from above was converted to the hydrobromide salt with simultaneous deprotection of the BOC group to provide AMD9383 (0.02 g) as a pale yellow solid. $^1$H NMR (D$_2$O) δ 1.82-1.95 (m, 1H), 2.17-2.31 (m, 2H), 2.40-2.45 (m, 1H), 3.02 (brd, 2H), 3.77 (d, 2H, J=2.4 Hz), 3.81 (d, 2H, J=6.9 Hz), 4.13 (s, 2H), 4.44 (d, 1H, J=16.2 Hz), 4.63 (d, 1H, J=16.2 Hz), 4.79 (m, 1H), 7.02 (d, 2H, J=8.1 Hz), 7.18 (d, 2H, J=8.1 Hz), 7.30 (t, 1H, J=8.1 Hz), 7.55 (t, 1H, J=7.8 Hz), 7.56 (d, 2H, J=8.1 Hz), 7.61 (t, 1H, J=6.1 Hz), 7.92 (t, 1H, J=6.9 Hz), 8.06 (dt, 1H, J=1.5, 8.0 Hz), 8.39 (d, 1H, J=8.1 Hz), 8.62 (d, 1H, J=4.8 Hz), 8.74 (d, 1H, J=5.1 Hz); $^{13}$C NMR (D$_2$O) □ 20.41, 20.91, 27.84, 49.44, 50.16 (2 carbons), 63.50 (2 carbons), 105.55, 113.34, 125.73, 125.96, 126.16, 127.83, 129.54, 130.15 (3 carbons), 138.80 (3 carbons), 131.24, 138.35, 139.63, 141.08, 141.54, 148.13, 148.28, 148.76, 150.75, 152.80. ES-MS m/z 569 (M+H). Anal. Calcd. for C$_{31}$H$_{31}$N$_6$Br.4.4HBr.4.4H$_2$O: C, 37.13; H, 4.44; N, 8.38; Br, 43.03. Found: C, 37.23; H, 4.18; N, 8.30; Br, 42.84.

EXAMPLE: 23

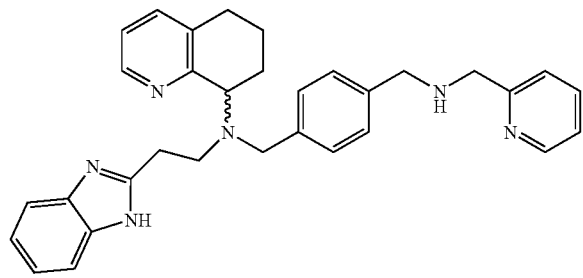

AMD9333: Preparation of N-(2-pyridinylmethyl)-N'-[2-(1H-benzimidazole-2-yl)eth-1-yl]-N'-(5,6,7,8-tetrahydro-8-quinolinyl)-1,4-benzenedimethanamine (hydrobromide salt)

2-(2-Chloroethyl)-1H-benzimidazole

A mixture of 1,2-Phenylenediamine (1.3 g, 12.0 mmol) and 3-chloropropionic acid (2.0 g, 18.5 mmol) were refluxed in 4N HCl (13 mL) for 16 hours to give the title compound as white solid (700 mg, 32%). $^1$H NMR (CD$_3$OD) □ 3.35 (t, 2H, J=6.8 Hz), 4.00 (t, 2H, J=6.8 Hz), 7.18-7.25 (m, 2H), 7.49-7.55 (m, 2H); ES-MS m/z 181.0 (M+H).

N-(tert-butoxycarbonyl)-2-(2-Chloroethyl)-benzimidazole

To a solution of 2-(2-Chloroethyl)-1H-benzimidazole (205 mg. 1.13 mmol) in DMF (8 mL) was added N,N-diisopropylethylamine (0.42 mL, 2.41 mmol) and di-tert-butyl dicarbonate (272 mg, 1.24 mmol). The resulting solution was allowed to stir for 16 hours at room temperature under N$_2$ and then concentrated. The residues was diluted with 300-mL ethyl acetate, and washed with sat. NaHCO$_3$, brine and dried over Na$_2$SO$_4$. Evaporation of the solvent and purification of the residue by column chromatography on silica gel (50% ethyl acetate in CH$_2$Cl$_2$) gave the title compound (183 mg, 57%) as a white solid. $^1$H NMR (CDCl$_3$) □ 1.73 (s, 9H), 3.69 (t, 2H, J=7.4 Hz), 4.05 (t, 2H, J=7.4 Hz), 7.30-7.36 (m, 2H), 7.68-7.74 (m, 1H), 7.90-7.95 (m, 1H); ES-MS m/z 281.0 (M+H).

A mixture of N-(tert-butoxycarbonyl)-N-(2-pyridinylmethyl)-N'-(5,6,7,8-tetrahydro-8-quinolinyl)-1,4-benzenedimethanamine (143 mg, 0.31 mmol), 1-(tert-butoxycarbonyl)-2-(2-Chloroethyl)-benzimidazole (83 mg, 0.29 mmol), NaI (2 mg) and diisopropylethylamine (0.1 mL, 0.57 mmol) were heated to reflux in CH$_3$CN (2 mL) for 24 hours under N$_2$. The reaction mixture was diluted with 200-mL ethyl acetate, and washed with sat. NaHCO$_3$, brine and dried over Na$_2$SO$_4$. Evaporation of the solvent and purification of the residue by flash chromatograph on silica gel, followed by radial chromatograph on silica gel (1 mm plate), using 3:3:94 CH$_3$OH—NH$_3$H$_2$O—CH$_2$Cl$_2$, gave the desired intermediate (88 mg, 43%) as a white solid. $^1$H NMR (CDCl$_3$) □ 1.44 (br, d, 9H), 1.61 (s, 9H), 1.84-1.95 (m, 2H), 2.05-2.08 (m, 1H), 2.67-2.75 (m, 2H), 3.13-3.14 (m, 1H), 3.41-3.45 (m, 4H), 3.72 (d, 1H, J=15 Hz), 3.97 (d, 1H, J=15 Hz), 4.12-4.17 (m, 1H), 4.39 (d, 2H, J=6.0 Hz), 4.50 (d, 2H, J=12 Hz), 7.00-7.22 (m, 6H), 7.25-7.30 (m, 4H), 7.64-7.73 (m, 2H), 7.88-7.92 (m, 1H), 8.44 (d, 1H), 8.52 (d, 1H); ES-MS m/z 703.5 (M+H).

Using general procedure D: the intermediate from above was converted to the corresponding hydrobromide salt with simultaneous deprotection of the BOC group to afford AMD9333 as a white solid. $^1$H NMR (D$_2$O) □ 1.77-1.84 (m, 1H), 1.99-2.14 (m, 2H), 2.32-2.34 (m, 1H), 2.93 (s, 2H), 3.07-3.13 (m, 1H), 3.36-3.48(m, 3H), 3.73 (s, 2H), 4.02 (d, 1H, J=12.9 Hz), 4.10 (d, 1H, J=13.2 Hz), 4.42-4.44 (br, 3H), 7.16 (d, 2H, J=8.1 Hz), 7.28 (d, 2H, J=7.8 Hz), 7.47-7.53 (m, 2H), 7.58-7.64 (m, 2H), 7.73-7.76 (m, 3H), 8.23 (d, 2H, J=7.8 Hz), 8.37 (d, 1H, J=4.8 Hz), 8.65 (d, 1H, J=4.5 Hz); $^{13}$C NMR (D$_2$O) □ 20.50, 26.74, 27.80, 48.97, 49.32, 51.11, 54.56, 59.30, 114.08, 125.65, 126.56, 129.84, 130.59, 139.31, 139.52, 140.64, 143.10, 146.78, 147.49, 152.02; ES-MS m/z 503.2 (M+H); Anal. Calcd. for (C$_{32}$H$_{34}$N$_6$).4.0(HBr).2.0 (H$_2$O): C, 44.57; H, 4.91; N, 9.75; Br, 37.06. Found: C, 44.33; H, 5.03; N, 9.52; Br, 37.35.

EXAMPLE: 24

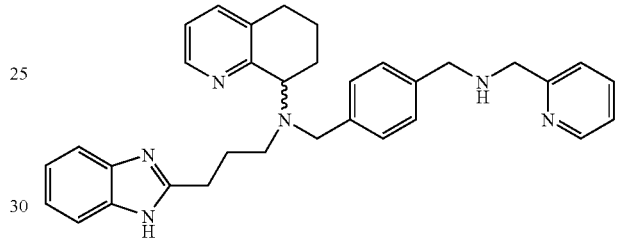

AMD9334: Preparation of N-(2-pyridinylmethyl)-N'-[3-(1H-benzimidazol-2-yl)prop-1-yl]-N'-(5,6,7,8-tetrahydro-8-quinolinyl)-1,4-benzenedimethanamine (hydrobromide salt)

3-(1H-Benzimidazol-2-yl)propan-1-ol

A mixture of 1,2-Phenylenediamine (1.0 g, 12.0 mmol) and 4-chlorobutyric acid (1.5 mL, 15.17 mmol) were refluxed in 4N HCl (13 mL) for 16 hours under N$_2$ to give the title compound as white solid (900 mg, 50%). $^1$H NMR (CD$_3$OD) □ 2.04-2.08 (m, 2H), 2.97 (t, 2H, J=7.8 Hz), 5.64 (t, 2H, J=6.6 Hz), 7.15-7.21 (m, 2H), 7.47-7.49 (m, 2H); ES-MS m/z 177.1 (M+H).

3-(1-tert-butoxycarbonyl-Benzimidazol-2-yl)-propan-1-ol

To a solution of 3-(1H-Benzimidazol-2-yl)propan-1-ol (249 mg. 1.41 mmol) in DMF (7 mL) was added N,N-diisopropylethylamine (0.50 mL, 2.80 mmol) and di-tert-butyl dicarbonate (307 mg, 1.41 mmol). The resulting solution was allowed to stir for 16 hours at room temperature under N$_2$ and then concentrated. The residues was diluted with 300-mL ethyl acetate, and washed with sat. NaHCO$_3$, brine and dried over Na$_2$SO$_4$. Evaporation of the solvent and flash chromatograph of residue over silica gel, using 50% ethyl acetate in CH$_2$Cl$_2$, gave the title compound (372 mg, 95%) as pure white solid. $^1$H NMR (CDCl$_3$) □ 1.72 (s, 9H), 2.14-2.22 (m, 2H), 3.37 (t, 2H, J=6.9 Hz), 3.80 (t, 2H, J=5.7), 7.28-7.34 (m, 2H), 7.66-7.70 (m, 1H), 7.87-7.91 (m, 1H); ES-MS m/z 277.1 (M+H).

3-(1-tert-butoxycarbonyl-Benzimidazol-2-yl)propionaldehyde

To a solution of 3-(1-tert-butoxycarbonyl-Benzimidazol-2-yl)propan-1-ol (186 mg, 0.67 mmol) in CH$_2$Cl$_2$ (4 mL) was added Dess-Martin reagent (314 mg, 0.74 mmol) and the resulting mixture was allowed to stir at room temperature under N₂ for 1 hour. The mixture was further diluted with 300-mL ethyl acetate, and washed with 1N NaOH, brine and dried over Na₂SO₄. Evaporation of the solvent and flash chromatograph of residue over silica gel, using 20% ethyl acetate in CH₂Cl₂, gave the title compound (141 mg, 76%) as pure white solid. ¹H NMR (CDCl₃) ☐ 1.72 (s, 9H), 3.13 (t, 2H, J=6.8 Hz), 3.52 (t, 2H, J=6.8 Hz), 7.28-7.34 (m, 2H), 7.66-7.67 (m, 1H), 7.87-7.91 (m, 1H), 9.97 (s, 1H).

Using general procedure B: Reaction of 3-(1-tert-butoxycarbonyl-Benzimidazol-2-yl)-propionaldehyde (141 mg, 0.51 mmol), N-(tert-butoxycarbonyl)-N-(2-pyridinylmethyl)-N'-(5,6,7,8-tetrahydro-8-quinolinyl)-1,4-benzenedimethanamine (235 mg, 0.512 mmol), acetic acid (0.05 mL) and sodium triacetoxyborohydride (326 mg, 1.54 mmol) in THF(5 mL) at room temperature under N₂ for 40 min., followed by purification of crude material using radial chromatography on silica gel (2 mm plate, 3:3:94 CH₃OH—NH₃H₂O—CH₂Cl₂), afforded the desired intermediate (320 mg, 87%) as white foam. ¹H NMR (CDCl₃) ☐ 1.44 (d, 9H, J=23.1 Hz), 1.67 (s, 9H), 1.84-2.05 (m, 6H), 2.65-2.74 (m, 3H), 2.89-2.98 (m, 1H), 3.10-3.23 (m, 2H), 3.65 (d, 1H, J=14.4 Hz), 3.93 (d, 1H, J=14.4 Hz), 4.05-4.10 (m, 1H), 4.40 (br, d, 2H), 4.50 (br, d, 2H), 6.98 (dd, 1H, J=4.5, 7.8 Hz), 7.08-7.15 (m, 3H), 7.25-7.28 (m, 4H), 7.36 (d, 2H, J=8.1 Hz), 7.59-7.66 (m, 2H), 7.68-7.91 (m, 1H), 8.43 (d, 1H, J=3.6 Hz), 8.51 (d, 1H, J=4.2 Hz); ES-MS m/z 717.6 (M+H).

Using general procedure D: N-tert-butoxycarbonyl)-N-(2-pyridinylmethyl)-N'-[3-[3-(tert-butoxycarbonyl)-benzimidazol-2-yl]prop-1-yl]-N'-(5,6,7,8-tetrahydro-8-quinolinyl)-1,4-benzenedimethanamine from above was converted to the corresponding hydrobromide salt with simultaneous deprotection of BOC groups to afford AMD9334 as a white solid. ¹H NMR (D₂O) ☐ 1.71-1.81 (m, 1H), 2.06-2.13 (m, 3H), 2.21-2.41 (m, 2H), 2.81 (s, 2H), 2.88-2.97 (m, 1H), 3.15 (ddd, 2H, J=6.6, 7.2, 7.2 Hz), 3.23-3.29 (m, 1H), 4.07 (d, 1H, J=13.5 Hz), 4.16 (d, 1H, J=13.5 Hz), 4.31 (s, 2H), 3.63 (br, 3H), 7.32-7.43 (m, 3H), 7.45-7.54 (m, 4H), 7.59-7.63 (m, 2H), 7.75 (d, 1H, J=7.8 Hz), 8.00 (ddd, 1H, J=0.9, 8.1, 5.7 Hz), 8.05 (d, 1H, J=8.1 Hz), 8.41 (d, 1H, J=5.1 Hz), 8.52 (ddd, 1H, J=1.5, 8.1, 8.1 Hz), 8.77-8.79 (m, 1H); ¹³C NMR (D₂O) ☐ 20.38, 20.84, 23.86, 23.96, 27.43, 47.58, 50.08, 51.58, 55.22, 61.36, 114.03, 124.98, 126.62, 128.06, 128.42, 130.62, 131.11, 131.48, 134.56, 137.35, 142.22, 144.35, 145.58, 147.14, 149.78, 152.20; ES-MS m/z 517.3 (M+H); Anal. Calcd. for (C₃₃H₃₆N₆).4.8(HBr).3.0(H₂O).0.4(C₄H₁₀O): C, 42.03; H, 5.18; N, 8.50; Br, 38.79. Found: C, 41.98; H, 5.08; N, 8.34; Br, 38.78.

EXAMPLE: 25

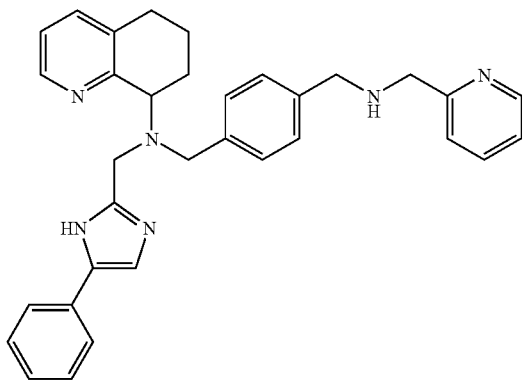

AMD8931: Preparation of N-(2-pyridinylmethyl)-N'-(4-Phenyl-1H-imidazol-2-ylmethyl)-N'-(5,6,7,8-tetrahydro-8-quinolinyl)-1,4-benzenedimethanamine (free base)

The following general procedures were used for the synthesis of functionalized imidazole derivatives:

General Procedure for Bromination of Aryl Ketones

To a stirred solution of ketone (1 equiv.), acetic acid (1 equiv.) in water (~4.2 M), at 79° C., was added bromine (1.15 equiv.) slowly (over two hours) from an addition funnel. The resultant solution was stirred till the solution decolourised. Water (~0.12 mL/mmol of ketone) was added. The mixture was cooled to room temperature, and neutralised with Na₂CO₃. The oil was separated from aqueous layer, and the aqueous layer was extracted with CH₂Cl₂ (3×10 mL/mmol). The combined organic phases were dried (Na₂SO₄) and concentrated. The crude material was purified by re-crystallisation or silica gel chromatography.

Preparation of 2-Bromo-1-phenyl-ethanone

Reaction of acetophenone (5.0 g, 42.00 mmol), acetic acid (2.4 mL, 42.00 mmol), and bromine (2.5 mL, 48.00 mmol) followed by recrystallisation from cold EtOAc/Hexane gave the title compound (3.4 g, 41%) as a white crystal. ¹H NMR (300 MHz, CDCl₃) δ 4.47 (s, 2H), 7.51 (d, 2H, J=7.5 Hz), 7.63 (t, 1H, J=7.5 Hz), 8.00 (d, 2H, J=7.2 Hz).

General Procedure for Preparation of Imidazoles from ☐☐romo-Ketones

To a stirred suspension of the ☐bromo-ketone (1 equiv.), at room temperature, was added formamide (~7 equiv.). The resultant solution was stirred at 170° C. for the indicated time (~4 h). CHCl₃ was added (10 mL/mmol), and the solution was washed with H₂O. The aqueous layer was extracted with CHCl₃ (3×5 mL/mmol). The combined organic phases were dried (Na₂SO₄) and concentrated. The crude material was purified by recrystallisation or chromatography.

Preparation of 4-phenylimidazole

Reaction of 2-bromo-1-phenyl-ethanone (3.4 g, 17.09 mmol), and formamide (4.3 mL/107.64 mmol), followed by chromatography on silica gel (EtOAc) gave the title compound (902 mg, 37%) as a yellow solid. ¹H NMR (300 MHz, CDCl₃) δ 7.29 (s, 1H), 7.36 (s, 1H), 7.40 (dd, 2H, J=7.5, 7.5 Hz), 7.72-7.75 (m, 3H).

General Procedure for SEM protection of Imidazoles

To a stirred suspension of NaH (1 equiv.), at room temperature, was added the imidazole (1.03 equiv.) anhydrous DMF solution (~0.6 M) dropwise. After the resultant solution was stirred at room temperature for the indicated time (~1.5 h), SEMCl (1.09 equiv.) was added. The solution was stirred for the indicated time (~1 h). Water (~2 mL/mmol of imidazole) was added, extracted with EtOAC (3×10 mL/mmol of imidazole). The combined organic phases were dried (Na₂SO₄) and concentrated. The crude material was purified by silica gel chromatography.

Preparation of 4-Phenyl-1-(2-trimethylsilanyl-ethoxymethyl)-1H-imidazole

Reaction of 4-phenylimidazole (400 mg, 2.78 mmol), NaH (60%, 108 mg, 2.70 mmol), and SEMCl (520 uL/2.94 mmol) followed by column chromatography on silica gel (hexane/EtOAC 1:1) gave the title compound (500 mg, 67%) as a yellow oil. ¹H NMR (300 MHz, CDCl₃) δ 0.00 (s, 9H), 0.92 (t, 2H, J=9.0 Hz), 3.54 (t, 2H, J=9.0 Hz), 5.27 (s, 2H), 7.17 (s, 1H), 7.37-7.47 (m, 3H), 7.56 (d, 2H, J=9.0 Hz), 7.68 (s, 1H). ES-MS m/z 275 (M+H).

General Procedure for the Reparation of 2-Carboxaldehyde Imidazole Derivatives from SEM-Protected Imidazoles To a stirred solution of the SEM-protected imidazole (1 equiv.) in anhydrous THF (~0.2 M), at −40° C., was added 2.5 M n-BuLi Hexane solution (1.3 equiv.). After the resulting solution was stirred at −40° C. for the indicated time (~20 min), DMF (3-4 equiv.) was added, and the stirring was continued for indicated time (1-4 h) at −40° C. Saturated NH$_4$Cl solution (~3 mL/mmol of imidazole) was added, extracted with EtOAC (3×60 mL/mmol of imidazole). The combined organic phases were dried (Na$_2$SO$_4$) and concentrated. The crude material was purified by chromatography.

Preparation of 4-Phenyl-1-(2-trimethylsilanyl-ethoxymethyl)-1H-imidazole-2-carbaldehyde Reaction of 4-phenyl-1-(2-trimethylsilanyl-ethoxymethyl)-1H-imidazole (380 mg, 1.39 mmol), 2.5 M n-BuLi (720 uL, 1.80 mmol), and DMF (323 uL, 4.17 mmol) for 4 h at −40° C. gave the title compound (411 mg, 98%) as a yellow oil. $^1$H NMR (300 MHz, CDCl$_3$) δ 0.00 (s, 9H), 0.93 (t, 2H, J=9.0 Hz), 3.61 (t, 2H, J=9.0 Hz), 5.83 (s, 2H), 7.26-7.46 (m, 3H), 7.65 (s, 1H), 7.83 (d, 2H, J=9.0 Hz), 9.89 (s, 1H).

Using general procedure B: Reaction of N-(2-nitrobezenesulfonyl)-N-(2-pyridinylmethyl)-N'-(5,6,7,8-tetrahydro-8-quinolinyl)-1,4-benzenedimethanamine (244 mg, 0.45 mmol), 4-phenyl-1-(2-trimethylsilanyl-ethoxymethyl)-1H-imidazole-2-carbaldehyde (150 mg, 0.50 mmol), and NaBH(OAc)$_3$ (286 mg, 1.35 mmol) for 1 h at room temperature followed by column chromatography on silica gel (CH$_2$Cl$_2$/MeOH/NH$_4$OH 98:1:1) gave N-(2-nitrobezenesulfonyl)-N-(2-pyridinylmethyl)-N'-[4-phenyl-1-[(2-trimethylsilyl)ethoxy]methyl-imidazol-2-ylmethyl]-N'-(5,6,7,8-tetrahydro-8-quinolinyl)-1,4-benzenedimethanamine (266 mg, 71%) as a yellow foam. $^1$H NMR (300 MHz, CDCl$_3$) δ 0.00 (s, 9H), 0.82 (dd, 2H, J=9.0, 9.0 Hz), 1.59-1.61 (m, 2H), 1.99-2.03 (m, 2H), 2.67-2.72 (m, 2H), 3.32-3.39 (m, 2H), 3.66 (d, 1H, J=15.0 Hz), 3.83-4.03 (m, 4H), 4.50 (s, 2H), 4.51 (s, 2H), 5.45 (d, 1H, J=12.0 Hz), 5.73 (d, 1H, J=12.0 Hz), 6.97-7.35 (m, 12H), 7.49-7.71 (m, 6H), 7.90 (d, 1H, J=9.0 Hz), 8.30 (d, 1H, J=4.2 Hz), 8.50 (d, 1H, J=4.2 Hz). ES-MS m/z 830 (M+H).

General Procedure E: SEM-Deprotection.

To a stirred solution of the SEM-protected compound (1 equiv.) was added 6N HCl (30 mL/mmol), and the resultant solution was stirred at 50° C. for indicated time. The solution was diluted with water (50 mL/mmol), and it was neutralised with NaHCO$_3$ and extracted with EtOAc (3×100 mL/mmol). The combined organic phases were dried (Na$_2$SO$_4$) and concentrated. The crude material was purified by chromatography.

Preparation of N-(2-nitrobezenesulfonyl)-N-(2-pyridinylmethyl)-N'-(4-phenyl-1H-imidazol-2-ylmethyl)-N'-(5,6,7,8-tetrahydro-8-quinolinyl)-1,4-benzenedimethanamine Using general procedure E: Reaction of N-(2-nitrobezenesulfonyl)-N-(2-pyridinylmethyl)-N'-[4-phenyl-1-[(2-trimethylsilyl)ethoxy]methyl-imidazol-2-ylmethyl]-N'-(5,6,7,8-tetrahydro-8-quinolinyl)-1,4-benzenedimethanamine (190 mg, 0.23 mmol), and 6N HCl (6.0 mL) for 3 h at 50° C. followed by column chromatography on silica gel (CH$_2$Cl$_2$/MeOH/NH$_4$OH 98:1:1) gave the title compound (141 mg, 88%) as a yellow foam. 1H NMR (300 MHz, CDCl$_3$) δ 1.65-1.66 (m, 1H), 2.01-2.05 (m, 2H), 2.21-2.23 (m, 1H), 2.69-2.85 (m, 2H), 3.59 (br s, 2H), 3.64 (d, 1H, J=16.2 Hz), 4.06 (d, 2H, J=16.2 Hz), 4.44-4.49 (m, 2H), 4.56 (br s, 2H), 6.70-7.06 (m, 3H), 7.19-7.22 (m, 5H), 7.33-7.53 (m, 8H), 7.66-7.83 (m, 3H), 8.32 (d, 1H, J=4.2 Hz), 8.63 (d, 1H, J=4.2 Hz). ES-MS m/z 700 (M+H).

Using general procedures C: Reaction of N-(2-nitrobezenesulfonyl)-N-(2-pyridinylmethyl)-N'-(4-phenyl-1H-imidazol-2-ylmethyl)-N'-(5,6,7,8-tetrahydro-8-quinolinyl)-1,4-benzenedimethanamine (135 mg, 0.19 mmol), thiophenol (57 uL, 0.56 mmol), and K$_2$CO$_3$ (128 mg, 0.93 mmol) for 4 h at room temperature followed by radial chromatography (Chromatotron, 1 mm plate, CH$_2$Cl$_2$/MeOH/NH$_4$OH 48:1:1), gave AMD8931 (61 mg, 61%) as a white foam. $^1$H NMR (300 MHz, CDCl$_3$) δ 1.50-1.71 (m, 1H), 1.75-2.03 (m, 2H), 2.22-2.23 (m, 2H), 2.68-2.89 (m, 2H), 3.68 (br s, 2H), 3.76 (br s, 2H), 3.82 (br s, 1H), 3.87 (br s, 2H), 4.06 (d, 2H, J=16.2 Hz), 7.10-7.42 (m, 13H), 7.59 (dd, 1H, J=7.5, 7.5 Hz), 7.72 (br s, 2H), 8.53 (d, 1H, J=3.6 Hz), 8.63 (br s, 1H); $^{13}$C NMR (75.5 MHz, CDCl$_3$) δ 21.29, 23.18, 29.26, 47.99, 53.19. 53.64, 54.48, 59.75, 121.85, 122.12, 122.32, 124.52, 126.12, 128.15, 128.57, 134.67, 136.36, 137.06, 138.29, 138.97, 147.09. 149.23, 157.71, 159.79. ES-MS m/z 515 (M+H). Anal. Calcd. for C$_{33}$H$_{34}$N$_6$.0.9H$_2$O: C, 74.66; H. 6.80; N, 15.83. Found: C, 74.53; H. 6.61; N, 15.86.

EXAMPLE: 26

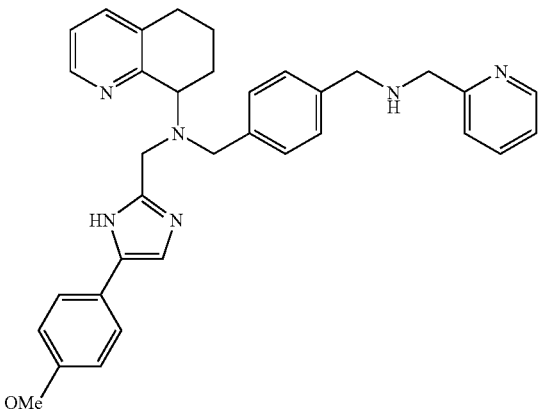

AMD8939: Preparation of N-(2-pyridinylmethyl)-N'-[4-(4-methoxyphenyl)-1H-imidazol-2-ylmethyl]-N'-(5,6,7,8-tetrahydro-8-quinolinyl)-1,4-benzene-dimethanamine (free base)

Preparation of 4-(4-Methoxy-phenyl)-1H-imidazole

Reaction of 2-bromo-1-(4-methoxy-phenyl)ethanone (3.0 g, 13.00 mmol), and formamide (3.63 mL, 92.00 mmol), followed by recrystallisation from cold EtOAc gave the title compound (1.4 g, 62%) as a yellow solid. $^1$H NMR (300 MHz, CDCl$_3$) δ 3.81 (s, 3H), 6.93 (d, 2H, J=8.7 Hz), 7.29 (s, 1H), 7.61 (d, 2H, J=8.7 Hz), 7.68 (s, 1H).

Preparation of 4-(4-Methoxyphenyl)-1-(2-trimethylsilanyl-ethoxymethyl)-1H-imidazole Reaction of 4-(4-methoxyphenyl)-1H-imidazole (610 mg, 3.51 mmol), NaH (60%, 136 mg, 3.40 mmol), and SEMCl (656 uL, 3.71 mmol) followed by column chromatography on silica gel (hexane/EtOAC 1:1) gave the title compound (654 mg, 64%) as a yellow solid. $^1$H NMR (300 MHz, CDCl$_3$) major isomer: δ 0.00 (s, 9H), 0.93 (t, 2H, J=7.5 Hz), 3.52 (t, 2H, J=7.5 Hz), 3.83 (s, 3H), 5.28 (s, 2H), 6.94 (d, 2H, J=9.0 Hz), 7.24 (s, 1H), 7.60 (s, 1H), 7.72 (d, 2H, J=9.0 Hz); minor isomer: δ 0.00 (s, 9H), 0.92 (t, 2H, J=7.5 Hz), 3.54 (t, 2H, J=7.5 Hz), 3.85 (s, 3H), 5.23 (s, 2H), 6.98 (d, 2H, J=9.0 Hz), 7.09 (s, 1H), 7.47 (d, 2H, J=9.0 Hz), 7.65 (s, 1H). ES-MS m/z 305 (M+H).

Preparation of 5-(4-Methoxyphenyl)-1-(2-trimethylsilanyl-ethoxymethyl)-1H-imidazole 2-carbaldehyde.

Reaction of 4-(4-methoxy-phenyl)-1-(2-trimethylsilanyl-ethoxymethyl)-1H-imidazole (400 mg, 1.32 mmol), 2.5 M n-BuLi (684 uL, 1.71 mmol), and DMF (306 uL, 3.95 mmol) for 2 h at −40° C., followed by column chromatography on silica gel (EtOAc/hexane 9:1), gave the title compound (337 mg, 77%) as a pink oil. $^1$H NMR (300 MHz, CDCl$_3$) δ 0.00 (s, 9H), 0.94 (t, 2H, J=7.5 Hz), 3.61 (t, 2H, J=7.5 Hz), 3.85 (s, 3H), 5.81 (s, 2H), 6.97 (d, 2H, J=9.0 Hz), 7.56 (s, 1H), 7.75 (d, 2H, J=9.0 Hz), 9.87 (s, 1H).

Preparation of N-(tert-Butoxycarbonyl)-N-(2-pyridinylmethyl)-N'-[4-[4-methoxyphenyl]-1-[(2-trimethylsilyl)

ethoxy]methyl-imidazol-2-ylmethyl]-N'-(5,6,7,8-tetrahydro-8-quinolinyl)-1,4-benzenedimethanamine Reaction of N-(tert-butoxycarbonyl)-N-(2-pyridinylmethyl)-N'-(5,6,7,8-tetrahydro-8-quinolinyl)-1,4-benzenedimethanamine (188 mg, 0.41 mmol), 5-(4-methoxy-phenyl)-1-(2-trimethylsilanyl-ethoxymethyl)-1H-imidazole-2-carbaldehyde (150 mg, 0.45 mmol), and NaBH(OAc)$_3$ (261 mg, 1.23 mmol) for 1 h at room temperature followed by column chromatography on silica gel (CH$_2$Cl$_2$/MeOH/NH$_4$OH 99:1:1) gave the title compound (276 mg, 87%) as a yellow foam. $^1$H NMR (300 MHz, CDCl$_3$) δ 0.00 (s, 9H), 0.81 (dd, 2H, J=9.0, 9.0 Hz), 1.25-1.40 (m, 1H), 1.57 (s, 9H), 1.96-1.98 (m, 2H), 1.99-2.02 (m, 1H), 2.52-2.70 (m, 2H), 3.34 (dd, 2H, J=12.0, 9.0 Hz), 3.78 (d, 1H, J=15.0 Hz), 3.81 (s, 3H), 3.88 (d, 1H, J=15.0 Hz), 3.96 (d, 2H, J=3 Hz), 4.01-4.05 (m, 1H), 4.39 (br s, 2H), 4.49 (br s, 2H), 5.48 (d, 1H, J=12.0 Hz), 5.77 (d, 1H, J=12.0 Hz), 6.88 (d, 2H, J=9.0 Hz), 7.05-7.15 (m, 6H), 7.30-7.33 (m, 3H), 7.61 (s, 1H), 7.63 (d, 2H, J=9.0 Hz), 8.51-8.55 (m, 2H). ES-MS m/z 775 (M+H).

Using general procedure E: Reaction of N-(tert-butoxycarbonyl)-N-(2-pyridinylmethyl)-N'-[4-[4-methoxy-phenyl]-1-[(2-trimethylsilyl)ethoxy]methyl-imidazol-2-ylmethyl]-N'-(5,6,7,8-tetrahydro-8-quinolinyl)-1,4-benzenedimethanamine (120 mg, 0.16 mmol), and 6N HCl (4.1 mL) for 3 h at 50° C. followed by purification of the crude product by column chromatography on silica gel (CH$_2$Cl$_2$MeOH/NH$_4$OH 98:1:1) afforded AMD8939 (69 mg, 84%) as a yellow foam. $^1$H NMR (300 MHz, CDCl$_3$) δ 1.66-1.69 (m, 1H), 1.99-2.05 (m, 2H), 2.20-2.21 (m, 2H), 2.66-2.83 (m, 2H), 3.67 (br s, 2H), 3.75 (br s, 2H), 3.81 (s, 3H), 3.87 (br s, 2H), 4.01 (brs, 1H), 4.07 (brs, 1H), 6.90 (d, 2H, J=6.3 Hz), 7.09-7.40 (m, 9H), 7.55-7.64 (m, 3H), 8.51 (d, 1H, J=4.5 Hz), 8.61 (d, 1H, J=4.5 Hz); $^{13}$C NMR (75.5 MHz, CDCl$_3$) δ 21.69, 23.57, 29.66, 48.41, 53.59, 54.06, 54.87, 55.68, 60.12, 114.45, 122.26, 122.50, 122.72, 126.04, 128.55, 128.98, 135.06, 136.77, 137.45, 138.73, 139.33, 147.47, 149.63, 149.85, 158.12, 158.61, 160.17. ES-MS m/z 545 (M+H). Anal. Calcd. for C$_{34}$H$_{36}$N$_6$O.1.1H$_2$O: C, 72.34; H, 6.82; N, 14.89. Found: C, 72.31; H, 6.71; N, 14.89.

EXAMPLE: 27

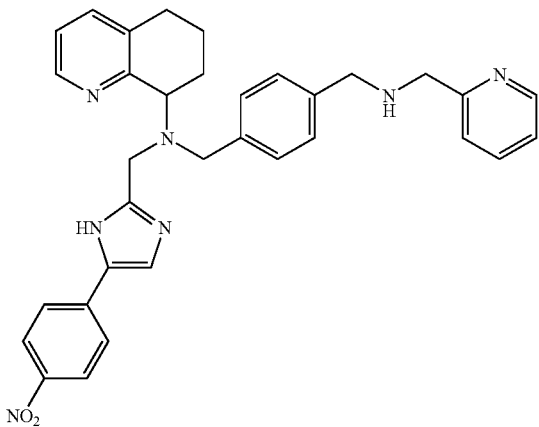

AMD8985: Preparation of N-(2-pyridinylmethyl)-N'-[4-(4-nitrophenyl)-1H-imidazol-2-ylmethyl]-N'-(5,6,7,8-tetrahydro-8-quinolinyl)-1,4-benzenedimethanamine (free base)

Preparation of 4-(4-Nitrophenyl)-1H-imidazole
Reaction of 2-Bromo-1-(4-nitro-phenyl)-ethanone (3.0 g, 12.30 mmol), and formamide (3.1 mL, 77.40 mmol) followed by column chromatography on silica gel (EtOAc/MeOH 49:1) gave the title compound (178 mg, 8%) as a yellow solid. $^1$H NMR (300 MHz, CDCl$_3$) δ 7.52 (s, 1H), 7.78 (s, 1H), 7.97 (d, 2H, J=9.0 Hz), 8.27 (d, 2H, J=9.0 Hz). ES-MS m/z 190 (M+H).

Preparation of 5-(4-Nitrophenyl)-1-(2-trimethylsilanyl-ethoxymethyl)-1H-imidazole.

Reaction of 4-(4-nitrophenyl)-1H-imidazole (160 mg, 0.85 mmol), NaH (60%, 33 mg, 0.82 mmol), and SEMCl (158 uL, 0.89 mmol) followed by column chromatography on silica gel (hexane/EtOAC 3:2) gave the title compound (170 mg, 65%) as a yellow solid. $^1$H NMR (300 MHz, CDCl$_3$) δ 0.00 (s, 9H), 0.94 (t, 2H, J=7.5 Hz), 3.55 (t, 2H, J=7.5 Hz), 5.33 (s, 2H), 7.50 (s, 1H), 7.69 (s, 1H), 7.94 (d, 2H, J=6.0 Hz), 8.26 (d, 2H, J=6.0 Hz).

Preparation of 4-(4-Nitrophenyl)-1-(2-trimethylsilanyl-ethoxymethyl)-1H-imidazole-2-carbaldehyde.

Reaction of 4-(4-nitro-phenyl)-1-(2-trimethylsilanyl-ethoxymethyl)-1H-imidazole (170 mg, 0.53 mmol), 0.53 M LDA (1 mL, 0.53 mmol), and DMF (232 uL, 1.60 mmol) for 4 h at −40° C. followed by column chromatography on silica gel (EtOAc/hexane 9:1) gave the title compound (55 mg, 30%) as a yellow oil. $^1$H NMR (300 MHz, CDCl$_3$) δ 0.00 (s, 9H), 0.95 (t, 2H, J=9.0 Hz), 3.63 (t, 2H, J=9.0 Hz), 5.82 (s, 2H), 7.79 (s, 1H), 7.98 (d, 2H, J=9.0 Hz), 8.27 (d, 2H, J=9 Hz), 9.89 (s, 1H).

Preparation of N-(tert-Butoxycarbonyl)-N-(2-pyridinylmethyl)-N'-[4-[4-nitrophenyl]-1-[(2-trimethylsilyl)ethoxy]methyl-imidazol-2-ylmethyl]-N'-(5,6,7,8-tetrahydro-8-quinolinyl)-1,4-benzenedimethanamine.

Reaction of N-(tert-butoxycarbonyl)-N-(2-pyridinylmethyl)-N'-(5,6,7,8-tetrahydro-8-quinolinyl)-1,4-benzenedimethanamine (87 mg, 0.19 mmol), 5-(4-nitrophenyl)-1-(2-trimethylsilanyl-ethoxymethyl)-1H-imidazole-2-carbaldehyde (55 mg, 0.16 mmol), and NaBH(OAc)$_3$ (121 mg, 0.57 mmol) for 2 h at room temperature followed by purification of the crude product by column chromatography on silica gel (CH$_2$Cl$_2$/MeOH/NH$_4$OH 98:1:1) gave the title compound (57 mg, 45%) as a yellow foam. $^1$H NMR (300 MHz, CDCl$_3$) δ 0.00 (s, 9H), 0.81-0.90 (m, 2H), 1.26-1.41 (m, 1H), 1.55 (s, 9H), 1.96-1.98 (m, 2H), 1.98-2.04 (m, 1H), 2.52-2.70 (m, 2H), 3.34-3.37 (m, 2H), 3.69 (d, 1H, J=15.0 Hz), 3.85 (d, 1H, J=12.0 Hz), 4.02 (br s, 2H), 4.04-4.06 (m, 1H), 4.37 (br s, 2H), 4.46 (br s, 2H), 5.53 (d, 1H, J=6.0 Hz), 5.76 (d, 1H, J=6.0 Hz), 6.92-7.27 (m, 9H), 7.61-7.63 (m, 1H), 7.84 (d, 2H, J=9.0 Hz), 8.19 (d, 2H, J=9.0 Hz), 8.51-8.53 (m, 2H). ES-MS m/z 790 (M+H).

Using general procedure E: Reaction of N-(tert-butoxycarbonyl)-N-(2-pyridinylmethyl)-N'-[4-[4-nitro-phenyl]-1-[(2-trimethylsilyl)ethoxy]methyl-imidazol-2-ylmethyl]-N'-(5,6,7,8-tetrahydro-8-quinolinyl)-1,4-benzenedimethanamine (57 mg, 0.07 mmol), and 6N HCl (1.9 mL) for 3 h at 50° C. followed by purification of the crude product by column chromatography on silica gel (CH$_2$Cl$_2$/MeOH/NH$_4$OH 48:1:1) gave AMD8939 (31 mg, 77%) as a yellow foam. $^1$H NMR (300 MHz, acetone-d$_6$) δ 1.68-172. (m, 1H), 2.25-2.28 (m, 2H), 2.69-2.93 (m, 4H), 3.70 (br s, 2H), 3.74 (br s, 2H), 3.78 (br s, 2H), 3.79-3.40 (m, 2H), 4.05 (dd, 1H, J=7.5, 7.5 Hz), 7.15 (dd, 1H, J=6.2, 6.2 Hz), 7.24 (d, 4H, J=7.8 Hz), 7.37 (d, 4H, J=8.1 Hz), 7.53 (d, 1H, J=7.5 Hz), 7.66 (m, 1H), 7.79 (br s, 1H), 7.99 (d, 2H, J=8.7 Hz), 8.17 (d, 1H, J=7.8 Hz), 8.45 (d, 1H, J=4.2 Hz), 8.80 (br s, 1H); $^{13}$C NMR (75.5 MHz, acetone-d$_6$) δ 19.90, 22.51, 25.68, 49.37, 53.92, 55.09, 55.43, 61.31, 116.22, 122.89, 123.03, 123.44, 125.12, 125.76, 129.15, 129.74, 136.11, 137.38, 138.48, 139.67, 140.96, 146.77, 148.24, 150.19, 151.35, 159.05, 161.87. ES-MS m/z 560

(M+H). Anal. Calcd. for $C_{33}H_{33}N_7O_2 \cdot 1.0H_2O$: C, 68.61; H, 6.11; N, 16.97. Found: C, 68.65; H, 5.99; N, 16.66.

EXAMPLE: 28

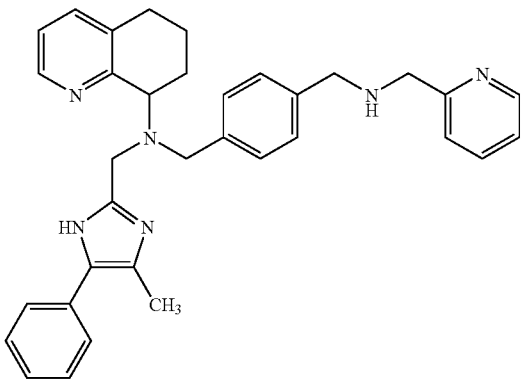

AMD8989: Preparation of N-(2-Pyridinylmethyl)-N'-(4-methyl-5-phenyl-1H-imidazol-2-ylmethyl)-N'-(5,6,7,8-tetrahydro-8-quinolinyl)-1,4-benzene-dimethanamine (free base)

Preparation of 4-Methyl-5-phenyl-1H-imidazole.

Reaction of 2-bromo-1-phenyl-propan-1-one (3.0 g, 14.00 mmol), and formamide (3.9 mL, 99.00 mmol), followed by recrystallisation from cold EtOAc gave the title compound (1.97 g, 88%) as a yellow solid. $^1$H NMR (300 MHz, MD$_3$OD) δ 2.40 (s, 3H), 7.28 (t, 1H, J=7.5 Hz), 7.42 (dd, 2H, J=7.5, 7.5 Hz), 7.55 (d, 2H, J=9.0 Hz), 7.76 (s, 1H). ES-MS m/z 159 (M+H).

Preparation of 4-methyl-5-phenyl-1-(2-trimethylsilanyl-ethoxymethyl)-1H-imidazole Reaction of 4-methyl-5-phenyl-1H-imidazole (400 mg, 2.53 mmol), NaH (60%, 98 mg, 2.46 mmol), and SEMCl (474 uL, 2.68 mmol) followed by column chromatography on silica gel (hexane/EtOAC 3:2) gave the title compound (323 mg, 46%) as a yellow solid. $^1$H NMR (300 MHz, CDCl$_3$) δ 0.00 (s, 9H), 0.92 (t, 2H, J=7.5 Hz), 2.47 (s, 3H), 3.52 (t, 2H, J=7.5 Hz), 5.26 (s, 2H), 7.26-7.27 (m, 1H), 7.41 (dd, 2H, J=7.5, 7.5 Hz), 7.57 (s, 1H), 7.68 (d, 2H, J=9.0 Hz).

Preparation of 4-Methyl-5-phenyl-1-(2-trimethylsilanyl-ethoxymethyl)-1H-imidazole-2-carbaldehyde.

Reaction of 4-methyl-5-phenyl-1-(2-trimethylsilanyl-ethoxymethyl)-1H-imidazole (187 mg, 0.65 mmol), 2.5 M n-BuLi (338 uL, 0.84 mmol), and DMF (151 uL, 1.95 mmol) for 2 h at −40° C. gave the title compound (199 mg, 99%) as a yellow oil. $^1$H NMR (300 MHz, CDCl$_3$) δ 0.00 (s, 9H), 0.94 (t, 2H, J=7.5 Hz), 2.54 (s, 3H), 3.61 (t, 2H, J=7.5 Hz), 5.88 (s, 2H), 7.33-7.38 (m, 1H), 7.46 (dd, 2H, J=7.5, 7.5 Hz), 7.68 (d, 2H, J=6.0 Hz), 9.82 (s, 1H).

Preparation of 4-Methyl-5-phenyl-1H-imidazole.

Reaction of 2-bromo-1-phenyl-propan-1-one (3.0 g, 14.00 mmol), and formamide (3.9 mL, 99.00 mmol), followed by recrystallisation from cold EtOAc gave the title compound (1.97 g, 88%) as a yellow solid. $^1$H NMR (300 MHz, MD$_3$OD) δ 2.40 (s, 3H), 7.28 (t, 1H, J=7.5 Hz), 7.42 (dd, 2H, J=7.5, 7.5 Hz), 7.55 (d, 2H, J=9.0 Hz), 7.76 (s, 1H). ES-MS m/z 159 (M+H).

Preparation of 4-methyl-5-phenyl-1-(2-trimethylsilanyl-ethoxymethyl)-1H-imidazole Reaction of 4-methyl-5-phenyl-1H-imidazole (400 mg, 2.53 mmol), NaH (60%, 98 mg, 2.46 mmol), and SEMCl (474 uL, 2.68 mmol) followed by column chromatography on silica gel (hexane/EtOAC 3:2) gave the title compound (323 mg, 46%) as a yellow solid. $^1$H NMR (300 MHz, CDCl$_3$) δ 0.00 (s, 9H), 0.92 (t, 2H, J=7.5 Hz), 2.47 (s, 3H), 3.52 (t, 2H, J=7.5 Hz), 5.26 (s, 2H), 7.26-7.27 (m, 1H), 7.41 (dd, 2H, J=7.5, 7.5 Hz), 7.57 (s, 1H), 7.68 (d, 2H, J=9.0 Hz).

Preparation of 4-Methyl-5-phenyl-1-(2-trimethylsilanyl-ethoxymethyl)-1H-imidazole-2-carbaldehyde.

Reaction of 4-methyl-5-phenyl-1-(2-trimethylsilanyl-ethoxymethyl)-1H-imidazole (187 mg, 0.65 mmol), 2.5 M n-BuLi (338 uL, 0.84 mmol), and DMF (151 uL, 1.95 mmol) for 2 h at 40° C. gave the title compound (199 mg, 99%) as a yellow oil. $^1$H NMR (300 MHz, CDCl$_3$) δ 0.00 (s, 9H), 0.94 (t, 2H, J=7.5 Hz), 2.54 (s, 3H), 3.61 (t, 2H, J=7.5 Hz), 5.88 (s, 2H), 7.33-7.38 (m, 1H), 7.46 (dd, 2H, J=7.5, 7.5 Hz), 7.68 (d, 2H, J=6.0 Hz), 9.82 (s, 1H).

Preparation of N-(tert-Butoxycarbonyl)-N-(2-pyridinylmethyl)-N'-[4-methyl-5-phenyl-1-[(2-trimethylsilyl)ethoxy]methyl-imidazol-2-ylmethyl]-N'-(5,6,7,8-tetrahydro-8-quinolinyl)-1,4-benzenedimethanamine Using general procedure B: Reaction of N-(tert-butoxycarbonyl)-N-(2-pyridinylmethyl)-N'-(5,6,7,8-tetrahydro-8-quinolinyl)-1,4-benzenedimethanamine (229 mg, 0.50 mmol), 4-methyl-5-phenyl-1-(2-trimethylsilanyl-ethoxymethyl)-1H-imidazole-2-carbaldehyde (190 mg, 0.60 mmol), and NaBH(OAc)$_3$ (318 mg, 1.50 mmol) for 1 h at room temperature followed by purification of the crude product by column chromatography on silica gel (CH$_2$Cl$_2$/MeOH/NH$_4$OH 98:1:1) gave the title compound (108 mg, 28%) as a yellow foam. $^1$H NMR (300 MHz, CDCl$_3$) δ 0.00 (s, 9H), 0.77 (dd, 2H, J=7.5 Hz), 1.25-1.41 (m 1H), 1.58 (br s, 3H), 1.64 (br s, 3H), 1.68 (br s, 3H), 2.00-2.04 (m, 2H), 2.08-2.18 (m, 1H), 2.24 (s, 3H), 2.63-2.80 (m, 2H), 3.23 (m, 2H), 3.69 (d, 1H, J=15.0 Hz), 3.84 (d, 1H, J=15.0 Hz), 3.97 (m, 2H), 4.04-4.10 (m, 1H), 4.39 (s, 2H), 4.48 (s, 2H), 5.35 (d, 1H, J=9.0 Hz), 5.78 (d, 1H, J=12.0 Hz), 7.06-7.38 (m, 11H), 7.55-7.61 (m, 2H), 7.61-7.64 (m, 1H), 8.51 (d, 1H, J=5.1 Hz), 8.55 (d, 1H, J=3.9 Hz).

Using general procedure E: Reaction of N-(tert-Butoxycarbonyl)-N-(2-pyridinylmethyl)-N'-[4-methyl-5-phenyl-1-[(2-trimethylsilyl)ethoxy]methyl-imidazol-2-ylmethyl]-N'-(5,6,7,8-tetrahydro-8-quinolinyl)-1,4-benzenedimethanamine (108 mg, 0.14 mmol), and 6N HCl (4.0 mL) for 3 h at 50° C. followed by purification of the crude product by column chromatography on silica gel (CH$_2$Cl$_2$/MeOH/NH$_4$OH 48:1:1) gave AMD8989 (57 mg, 76%) as a yellow foam. $^1$H NMR (300 MHz, CDCl$_3$) δ 1.66-1.70 (m, 1H), 2.00-2.04 (m, 2H), 2.20-2.21 (m, 1H), 2.44 (s, 3H), 2.65-2.83 (m, 2H), 3.67 (br s, 2H), 3.75 (br s, 2H), 3.81 (br s, 1H), 3.87 (br s, 2H), 3.92 (d, 1H, J=16.2 Hz), 4.09-4.14 (m, 1H), 7.10-7.13 (m, 2H), 7.20-7.28 (m, 4H), 7.32-7.39 (m, 6H), 7.58-7.63 (m, 3H), 8.51 (d, 1H, J=4.5 Hz), 8.61 (d, 1H, J=4.5 Hz); $^{13}$C NMR (75.5 MHz, CDCl$_3$) δ 21.75, 23.64, 29.68, 48.36, 53.60, 54.02, 54.89, 60.16, 122.26, 122.51, 122.72, 126.02, 126.38, 128.55, 128.95, 135.06, 136.76, 137.42, 138.77, 139.33, 147.40, 147.99, 149.63, 158.15, 160.19. ES-MS m/z 529 (M+H). Anal. Calcd. for $C_{34}H_{36}N_6 \cdot 1.4H_2O$: C, 73.72; H, 7.06; N, 15.17. Found: C, 73.67; H, 6.79; N, 14.98.

EXAMPLE: 29

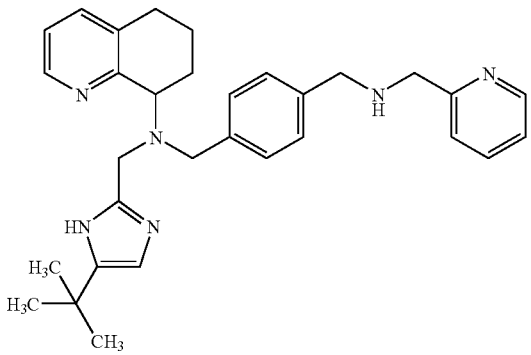

AMD8990: Preparation of N-(2-Pyridinylmethyl)-N'-(5-tert-butyl-1H-imidazol-2-ylmethyl)-N'-(5,6,7,8-tetrahydro-8-quinolinyl)-1,4-benzenedimethanamine (free base)

Preparation of 5-tert-Butyl-1H-imidazole

Reaction of 1-bromo-3,3-dimethyl-butan-2-one (3.0 g, 16.80 mmol), and formamide (4.7 mL, 117.20 mmol), followed by chromatography ($CH_2Cl_2$/MeOH/$NH_4OH$ 94:3:3) gave the title compound (450 mg, 21%) as a yellow foam. $^1$H NMR (300 MHz, $CDCl_3$) δ 1.29 (s, 9H), 6.77 (s, 1H), 7.57, (s, 1H). ES-MS m/z 125 (M+H).

Preparation of 5-tert-Butyl-1-(2-trimethylsilanyl-ethoxymethyl)-1H-imidazole

Reaction of 5-tert-butyl-1H-imidazole (423 mg, 3.41 mmol), NaH (60%, 132 mg, 3.31 mmol), and SEMCl (639 uL, 3.61 mmol) followed by column chromatography on, silica gel (hexane/EtOAC 3:2) gave the title compound (500 mg, 57%) as a yellow oil. $^1$H NMR (300 MHz, $CDCl_3$) δ major isomer: 0.00 (s, 9H), 0.89 (t, 2H, J=7.5 Hz), 1.29 (s, 9H), 3.47 (t, 2H, J=7.5 Hz), 5.19 (s, 2H), 6.73 (s, 1H), 7.50 (s, 1H).

Preparation of 5-tert-Butyl-1-(2-trimethylsilanyl-ethoxymethyl)-1H-imidazole-2-carbaldehyde Reaction 5-tert-butyl-1-(2-trimethylsilanyl-ethoxymethyl)-1H-imidazole (276 mg, 1.09 mmol), 2.5 M n-BuLi (567 uL, 1.42 mmol), and DMF (253 uL, 3.27 mmol) for 2 h at −40° C. gave the title compound (304 mg, 99%) as a yellow solid. $^1$H NMR (300 MHz, $CDCl_3$) δ 0.00 (s, 9H), 0.91 (t, 2H, J=9.0 Hz), 1.33 (s, 9H), 3.57 (t, 2H, J=7.5 Hz), 5.72 (s, 2H), 7.10 (s, 1H), 9.80 (s, 1H).

Preparation of N-(tert-Butoxycarbonyl)-N-(2-pyridinylmethyl)-N'-[5-tert-butyl-1-[(2-trimethylsilyl)ethoxy]methyl-imidazol-2-ylmethyl]-N'-(5,6,7,8-tetrahrydro-8-quinolinyl)-1,4-benzenedimethanamine Using general procedure B: Reaction of N-(tert-butoxycarbonyl)-N-(2-pyridinylmethyl)-N'-(5,6,7,8-tetrahydro-8-quinolinyl)-1,4-benzenedimethanamine (271 mg, 0.59 mmol), 5-tert-butyl-1-(2-trimethylsilanyl-ethoxymethyl)-1H-imidazole-2-carbaldehyde (200 mg, 0.71 mmol), and NaBH(OAc)$_3$ (375 mg, 1.77 mmol) for 1 h at room temperature followed by purification of the crude product by column chromatography on silica gel ($CH_2Cl_2$/MeOH/$NH_4OH$ 98:1:1) gave the title compound (265 mg, 62%) as a yellow foam. $^1$H NMR (300 MHz, $CDCl_3$) δ 0.00 (s, 9H), 0.80 (dd, 2H, J=9.0, 9.0 Hz), 1.21 (br s, 5H), 1.25 (br s, 4H), 1.41 (br s, 5H), 1.49 (br s, 4H), 1.91-1.95 (m, 2H), 2.01-2.10 (m, 1H), 2.62-2.82 (m, 2H), 3.28-3.33 (m, 2H), 3.53 (d, 1H, J=14.4 Hz), 3.79-4.00 (m, 3H), 4.40 (s, 2H), 4.48 (s, 2H), 5.27 (s, 2H), 5.41 (d, 1H, J=10.8 Hz), 5.66 (d, 1H, J=10.8 Hz), 7.01-7.05 (m, 1H), 7.11-7.15 (m, 3H), 7.23-7.26 (m, 3H), 7.30-7.33 (m, 2H), 7.62 (dd, 1H, J=7.8, 7.8 Hz), 8.52 (br s, 2H).

Using general procedure E: Reaction of N-(tert-butoxycarbonyl)-N-(2-pyridinylmethyl)-N'-[5-tert-butyl-1-[(2-trimethylsilyl)ethoxy]methyl-imidazol-2-ylmethyl]-N'-(5,6,7,8-tetrahydro-8-quinolinyl)-1,4-benzenedimethanamine (260 mg, 0.36 mmol), and 6N HCl (10.0 mL) for 3 h at 50° C. followed by purification of the crude product by column chromatography on silica gel ($CH_2Cl_2$/MeOH/$NH_4OH$ 98:1:1) gave AMD8990 (97 mg, 55%) as a white foam. $^1$H NMR (300 MHz, $CDCl_3$) δ 1.25 (s, 3H), 1.29 (s, 3H), 1.34 (s, 3H), 1.71 (br s, 1H), 1.97-2.00 (m, 3H), 2.17-2.21 (m, 1H), 2.73-2.83 (m, 2H), 3.33-3.69(m, 3H), 3.77 (br s, 2H), 3.92 (br s, 2H), 3.94-4.04 (m, 2H), 6.59 (br s, 1H), 6.70 (br s, 1H), 7.11-7.15 (m, 2H), 7.19-7.22 (m, 2H), 7.30-7.34 (m, 4H), 7.58-7.62 (m, 1H), 8.54 (d, 1H, J=3.0 Hz), 8.59 (br s, 1H); $^{13}$C NMR (75.5 MHz, $CDCl_3$) δ 21.68, 23.51, 29.68, 30.68 (3C), 48.46, 53.65, 54.15, 54.93, 60.01, 122.26, 122.36, 122.72, 128.47, 128.94, 134.96, 136.76, 137.30, 138.94, 139.24, 147.55, 148.52, 149.65, 158.25, 160.20. ES-MS m/z 495 (M+H). Anal. Calcd. for $C_{31}H_{38}N_6 \cdot 1.0H_2O$: C, 72.62; H, 7.86; N, 16.39. Found: C, 72.78; H, 7.77; N, 16.10.

EXAMPLE: 30

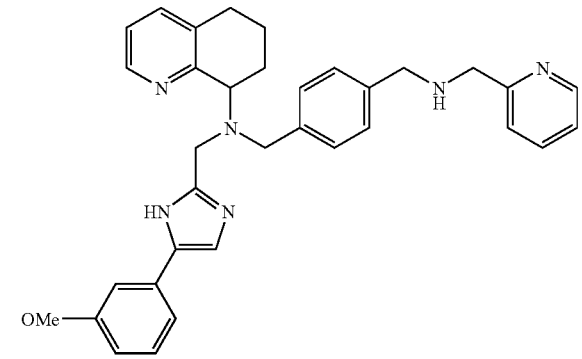

AMD8999: Preparation of N-(2-Pyridinylmethyl)-N'-[5-(3-methoxyphenyl)-1H-imidazol-2-ylmethyl]-N'-(5,6,7,8-tetrahydro-8-quinolinyl)-1,4-benzenedimethanamine (free base)

Preparation of 2-Bromo-1-(3-methoxy-phenyl)-ethanone

Reaction of 1-(3-methoxy-phenyl)-ethanone (5.0 g, 33.30 mmol), acetic acid (1.9 mL, 33.30 mmol), and bromine (1.9 mL, 38.30 mmol) followed by recrystallisation from cold EtOAc/Hexane gave the title compound (2.5 g, 33%) as a yellow powder. $^1$H NMR (300 MHz, $CDCl_3$) δ 3.87 (s, 3H), 4.46 (s, 2H), 7.16 (d, 1H, J=8.4 Hz), 7.63 (dd, 1H, J=8.1, 8.1 Hz), 7.52 (s, 1H), 7.56 (d, 1H, J=7.5 Hz).

Preparation of 5-(3-Methoxy-phenyl)-1H-imidazole

Reaction of 2-bromo-1-(3-methoxy-phenyl)-ethanone (2.5 g, 10.90 mmol), and formamide (3.1 mL, 76.40 mmol), followed by chromatography ($CH_2Cl_2$/MeOH/$NH_4OH$ 48:1:1) gave the title compound (820 mg, 43%) as a white solid. $^1$H NMR (300 MHz, $CD_3OD$) δ 3.83 (s, 3H), 6.78-6.82 (m, 1H), 7.26-7.28 (m, 3H), 7.42 (s, 1H), 7.72 (s, 1H).

Preparation of 5-(3-Methoxy-phenyl)-1-(2-trimethylsilanyl-ethoxymethyl)-1H-imidazole Reaction of 5-(3-methoxy-phenyl)-1H-imidazole (500 mg, 2.87 mmol), NaH (60%, 112 mg, 2.79 mmol), and SEMCl (598 uL, 3.35 mmol) followed by column chromatography on silica gel (hexane/EtOAC 3:2) gave the title compound (505 mg, 60%) as a brown oil. $^1$H NMR (300 MHz, CDCl$_3$) δ 0.00 (s, 9H), 0.93 (t, 2H, J=7.5 Hz), 3.52 (t, 2H, J=9.0 Hz), 3.87 (s, 3H), 5.30 (s, 2H), 6.80-6.83 (m, 1H), 7.26-7.39 (m, 3H), 7.40 (s, 1H), 7.63 (s, 1H).

Preparation of 5-(3-Methoxy-phenyl)-1-(2-trimethylsilanyl-ethoxymethyl)-1H-imidazole-2-carbaldehyde Reaction of 5-(3-methoxy-phenyl)-1-(2-trimethylsilanyl-ethoxymethyl)-1H-imidazole (470 mg, 1.55 mmol), 2.5 M n-BuLi (800 uL, 2.00 mmol), and DMF (479 uL, 6.18 mmol) for 2 h at −40° C. followed by column chromatography on silica gel (EtOAc/hexane 9:1) gave the title compound (111 mg, 22%) as a yellow oil. $^1$H NMR (300 MHz, CDCl$_3$) δ 0.00 (s, 9H), 0.95 (t, 2H, J=9.0 Hz), 3.61 (t, 2H, J=9.0 Hz), 3.89 (s, 3H), 5.8s (s, 2H), 6.90 (d, 2H, J=9.0 Hz), 7.34-7.42 (m, 3H), 9.89 (s, 1H).

Preparation of N-(tert-Butoxycarbonyl)-N-(2-pyridinylmethyl)-N'-[5-[3-methoxyphenyl]-1-[(2-trimethylsilyl)ethoxy]methyl-imidazol-2-ylmethyl]-N'-(5,6,7,8-tetrahydro-8-quinolinyl)-1,4-benzenedimethanamine Using general procedure B: Reaction of N-(tert-butoxycarbonyl)-N-(2-pyridinylmethyl)-N'-(5,6,7,8-tetrahydro-8-quinolinyl)-1,4-benzenedimethanamine (166 mg, 0.36 mmol), 5-(3-methoxyphenyl)-1-(2-trimethylsilanyl-ethoxymethyl)-1H-imidazole-2-carbaldehyde (100 mg, 0.30 mmol), and NaBH(OAc)$_3$ (191 mg, 0.90 mmol) for 1 h at room temperature followed by purification of the crude product by column chromatography on silica gel (CH$_2$Cl$_2$/MeOH/NH$_4$OH 198:1:1) gave the title compound (156 mg, 67%) as a yellow foam. $^1$H NMR (300 MHz, CDCl$_3$) δ 0.00 (s, 9H), 0.82 (dd, 2H, J=10.5, 7.5 Hz), 1.24-1.25 (m, 1H), 1.45 (d, 9H), 1.90-2.08 (m, 2H), 2.11-2.18 (m, 1H), 2.63-2.83 (m, 2H), 3.30-3.37 (m, 2H), 3.67 (d, 1H, J=14.4 Hz), 3.84 (s, 3H), 3.91-3.92 (m, 1H), 3.97 (br s, 2H), 4.02-4.04 (m, 1H), 4.39 (br s, 2H), 4.49 (br s, 2H), 5.49 (d, 1H, J=10.8 Hz), 5.78 (d, 1H, J=9.0 Hz), 6.74-6.78 (m, 1H), 7.05-7.34 (m, 12H), 7.61 (ddd, 1H, J=7.8, 7.8, 1.6 Hz), 8.45-8.56 (m, 2H).

Using general procedure E: Reaction of N-(tert-butoxycarbonyl)-N-(2-pyridinylmethyl)-N'-[5-[3-methoxy-phenyl]-1-[(2-trimethylsilyl)ethoxy]methyl-imidazol-2-ylmethyl]-N'-(5,6,7,8-tetrahydro-8-quinolinyl)-1,4-benzenedimethanamine (156 mg, 0.20 mmol), and 6N HCl (5.7 mL) for 3 h at 50° C. followed by purification of the crude product by column chromatography on silica gel (CH$_2$Cl$_2$/MeOH/NH$_4$OH 48:1:1) gave AMD8999 (103 mg, 94%) as a yellow foam. $^1$H NMR (300 MHz, CD$_3$COCD$_3$) δ 1.67-1.71 (m, 1H), 2.23-2.24 (m, 2H), 2.69-2.74 (m, 2H), 2.85-2.88 (m, 2H), 3.68-3.79 (m, 7H), 3.80 (s, 3H), 3.94 (d, 1H, J=15.0 Hz), 4.02-4.07 (m, 1H), 6.72 (d, 1H, J=6.9 Hz), 7.21-7.44 (m, 12H), 7.52 (d, 1H, J=9.0 Hz), 7.66 (ddd, 1H, J=7.5, 7.5, 1.5 Hz), 8.45 (d, 1H, J=4.5 Hz), 8.67 (br s, 1H); $^{13}$C NMR (75.5 MHz, CD$_3$COCD$_3$) δ 22.50, 25.44, 49.36, 53.98, 55.00, 55.50, 61.10, 110,92, 112.64, 117.91, 122.89, 123.04, 123.41, 129.14, 129.74, 130.62, 136.10, 137.39, 138.41, 139.81, 140.92, 148.28, 150.19, 159.16, 161.37, 161.90. ES-MS m/z 545 (M+H). Anal. Calcd. for C$_{34}$H$_{36}$N$_6$O.0.9H$_2$O: C, 72.81; H, 6.79; N, 14.98. Found: C, 71.81; H, 6.79; N, 14.83.

EXAMPLE: 31

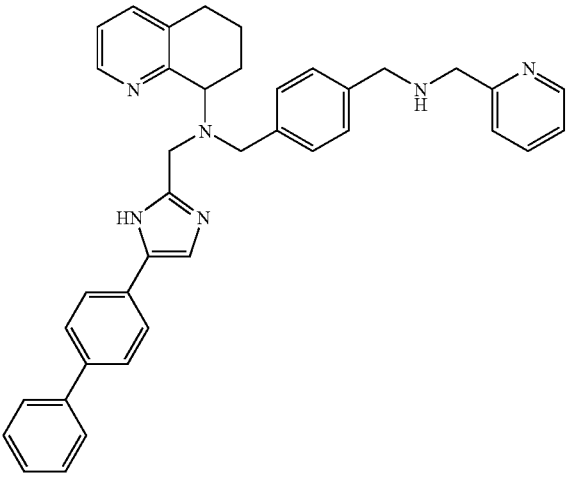

AMD9321: Preparation of N-(2-Pyridinylmethyl)-N'-(4-(4-biphenyl)-1H-imidazol-2-ylmethyl)-N'-(5,6,7,8-tetrahydro-8-quinolinyl)-1,4-benzenedimethanamine (free base)

Preparation of 4-(4-Biphenyl)-1H-imidazole

Reaction of 1-(4-biphenyl)-2-bromo-ethanone (3.0 g, 10.90 mmol), and formamide (3.1 mL, 76.30 mmol), followed by recrystallisation from cold EtOAc gave the title compound (1.4 g, 59%) as a yellow solid. $^1$H NMR (300 MHz, CD$_3$OD) δ 7.32-7.34 (m, 1H), 7.41-7.47 (m, 3H), 7.62-7.65 (m, 4H), 7.76-7.79 (m, 3H). ES-MS m/z 221 (M+H).

Preparation of 4-(4-Biphenyl)-1-(2-trimethylsilanyl-ethoxymethyl)-1H-imidazole

Reaction of 4-(4-biphenyl)-1H-imidazole (400 mg, 1.82 mmol), NaH (60%, 71 mg, 1.77 mmol), and SEMCl (341 uL, 1.92 mmol) followed by column chromatography on silica gel (hexane/EtOAC 3:2) gave the title compound (358 mg, 58%) as a yellow solid. $^1$H NMR (300 MHz, CDCl$_3$) δ 0.00 (s, 9H), 0.94 (t, 2H, J=8.3 Hz), 3.54 (t, 2H, J=8.1 Hz), 5.31 (s, 2H), 7.26 (s, 1H), 7.27-7.38 (m, 2H), 7.45 (dd, 2H, J=7.5, 7.5 Hz), 7.64 (d, 4H, J=8.1 Hz), 7.87 (d, 2H, J=8.1 Hz).

Preparation of 5-(4-Biphenyl)-1-(2-trimethylsilanyl-ethoxymethyl)-1H-imidazole-2-carbaldehyde.

Reaction of 5-(4-biphenyl)-1-(2-trimethylsilanyl-ethoxymethyl)-1H-imidazole (282 mg, 0.81 mmol), 2.5 M n-BuLi (420 uL, 1.05 mmol), and DMF (249 uL, 3.22 mmol) for 2 h at −40° C. followed by column chromatography on silica gel (EtOAc/hexane 9:1) gave the title compound (192 mg, 63%) as a yellow solid. $^1$H NMR (300 MHz, CDCl$_3$) δ 0.00 (s, 9H), 0.96 (t, 2H, J=7.5 Hz), 3.63 (t, 2H, J=7.5 Hz), 5.84 (s, 2H), 7.26-7.36 (m, 1H), 7.44-7.49 (m, 2H), 7.64-7.69 (m, 5H), 7.92 (d, 2H, J=9.0 Hz), 9.91 (s, 1H).

Preparation of N-(tert-Butoxycarbonyl)-N-(2-pyridinylmethyl)-N'-[5-(4-Biphenyl)-1-[(2-trimethylsilyl)ethoxy]methyl-imidazol-2-ylmethyl]-N'-(5,6,7,8-tetrahydro-8-quinolinyl)-1,4-benzenedimethanamine.

Using general procedure B: Reaction of N-(tert-butoxycarbonyl)-N-(2-pyridinylmethyl)-N'-(5,6,7,8-tetrahydro-8-quinolinyl)-1,4-benzenedimethanamine (194 mg, 0.42 mmol), 5-(4-biphenyl)-1-(2-trimethylsilanyl-ethoxymethyl)-1H-imidazole-2-carbaldehyde (192 mg, 0.51 mmol), and NaBH(OAc)$_3$ (267 mg, 1.26 mmol) for 2 h at room temperature followed by purification of the crude product by column chromatography on silica gel (CH$_2$Cl$_2$/MeOH/NH$_4$OH 198:1:1) gave the title compound (267 mg, 77%) as a yellow foam. $^1$H NMR (300 MHz, CDCl$_3$) δ 0.00 (s, 9H), 0.82 (dd, 2H, J=7.5, 7.5 Hz), 1.22-1.25 (m, 1H), 1.44 (d, 9H), 1.93-2.00 (m, 2H), 2.14-2.18 (m, 1H), 3.32-3.39 (m, 2H), 3.69 (d, 1H, J=14.4 Hz), 3.99 (d, 1H, J=14.4 Hz), 3.99 (d, 2H, J=4.2 Hz), 4.03-4.09 (m, 1H), 4.39 (br s, 2H), 4.49 (brs, 2H), 5.51 (d, 1H, J=9.0 Hz), 5.80 (d, 1H, J=9.0 Hz), 7.04-7.34 (m, 10H), 7.43 (dd, 2H, J=7.5, 7.5 Hz), 7.57-7.63 (m, 5H), 7.78 (d, 2H, J=8.4 Hz), 8.51 (d, 1H, J=3.9 Hz), 8.55 (d, 1H, J=4.2 Hz). ES-MS m/z 821 (M+H).

Using general procedure E: Reaction of N-(tert-butoxycarbonyl)-N-(2-pyridinylmethyl)-N'-[5-(4-Biphenyl)-1-[(2-trimethylsilyl)ethoxy]methyl-imidazol-2-ylmethyl]-N'-(5,6,7,8-tetrahydro-8-quinolinyl)-1,4-benzenedimethanamine (250 mg, 0.31 mmol), and 6N HCl (8.6 mL) for 3 h at 50° C. followed by purification of the crude product by column chromatography on silica gel (CH$_2$Cl$_2$/MeOH/NH$_4$OH 48:1:1) gave AMD9321 (89 mg, 49%) as a yellow foam. $^1$H NMR (300 MHz, CD$_3$COCD$_3$) δ 1.60-1.69 (m, 1H), 2 04-2.22 (m, 1H), 2.68-2.91 (m, 4H), 3.71 (br s, 2H), 3.73 (br s, 2H), 3.81-3.85 (m, 4H), 3.93-4.06 (m, 2H), 7.17-7.88 (m, 20 H), 8.50 (br s, 1H), 8.75 (br s, 1H); $^{13}$C NMR (75.5 MHz, CD$_3$COCD$_3$) δ 22.54, 25.67, 49.48, 54.04, 54.72, 55.13, 55.54, 61.10, 113.05, 122.90, 123.05, 123.36, 125.50, 126.13, 127.77, 127.98, 128.20, 128.70, 129.15, 129.76, 130.07, 136.03, 136.31, 137.40, 138.37, 139.84, 140.92, 141.77, 148.25, 150.20, 159.16, 161.92. ES-MS m/z 591 (M+H). Anal. Calcd. for C$_{39}$H$_{38}$N$_6$.0.9H$_2$O: C, 77.17; H, 6.61; N, 13.85. Found: C, 77.16; H, 6.62; N, 13.75.

EXAMPLE: 32

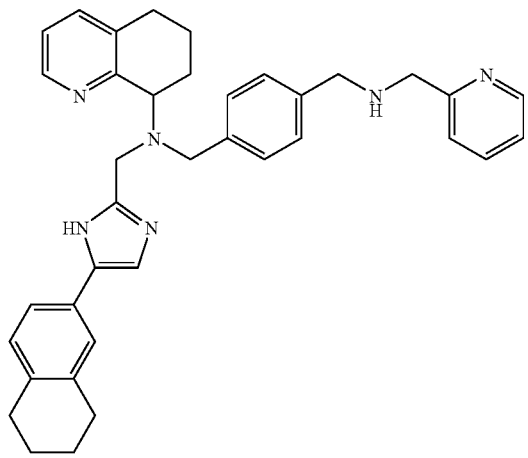

AMD9335: Preparation of N-(2-Pyridinylmethyl)-N'-[5-(5,6,7,8-tetrahydronaphthalen-2-yl)-1H-imidazol-2-ylmethyl]-N'-(5,6,7,8-tetrahydro-8-quinolinyl)-1,4-benzenedimethanamine (free base)

Preparation of 2-Bromo-1-(3-methoxy-phenyl)-ethanone

Reaction of 1-(5,6,7,8-tetrahydro-naphthalen-2-yl)-ethanone (5 g, 28.70 mmol), acetic acid (1.6 mL, 28.70 mmol), and bromine (1.7 mL, 33.00 mmol) followed by recrystallisation from cold EtOAc/Hexane gave the title compound (1.9 g, 26%) as a yellow powder. $^1$H NMR (300 MHz, CD$_3$OD) δ 1.84 (t, 4H, J=6.6 Hz), 2.80-2.85 (m, 4H), 4.61 (s, 2H), 7.19 (d, 1H, J=8.7 Hz), 7.70-7.78 (m, 2H). ES-MS m/z 253 (M+H).

Preparation of 5-(5,6,7,8-Tetrahydro-naphthalen-2-yl)-1H-imidazole

Reaction of 2-bromo-1-(5,6,7,8-tetrahydro-naphthalen-2-yl)-ethanone (1.9 g, 7.6 mmol), and formamide (2.1 mL, 53 mmol), followed by chromatography (CH$_2$Cl$_2$/MeOH 19:1) gave the title compound (603 mg, 42%) as a brown foam. $^1$H NMR (300 MHz, CD$_3$OD) $^1$H NMR (300 MHz, CD$_3$OD) δ 1.80-1.84 (m, 4H), 2.76-2.80 (m, 4H), 7.03 (d, 1H, J=8.4 Hz), 7.32 (s, 1H), 7.37 (br s, 2H), 7.68 (s, 1H).

Preparation of 5-(5,6,7,8-Tetrahydro-naphthalen-2-yl)-1-(2-trimethylsilanyl ethoxymethyl)-1H-imidazole Reaction of 5-(5,6,7,8-tetrahydro-naphthalen-2-yl)-1H-imidazole (387 mg, 1.95 mmol), NaH (60%, 76 mg, 1.89 mmol), and SEMCl (474 uL, 2.28 mmol) followed by column chromatography on silica gel (hexane/EtOAC 3:2) gave the title compound (321 mg, 52%) as a brown oil. $^1$H NMR (300 MHz, CDCl$_3$) δ 0.00 (s, 9H), 0.92 (t, 2H, J=9.0 Hz), 1.80-1.83 (m, 4H), 2.77-2.81 (m, 4H), 3.51 (t, 2H, J=9.0 Hz), 5.28 (s, 2H), 7.08 (d, 1H, J=9.0 Hz), 7.29 (s, 1H), 7.48 (d, 1H, J=6.0 Hz), 7.54 (s, 1H), 7.61 (s, 1H).

Preparation of 5-(5,6,7,8-Tetrahydro-naphthalen-2-yl)-1-(2-trimethylsilanyl-ethoxymethyl)-1H-imidazole-2-carbaldehyde Reaction of 5-(5,6,7,8-tetrahydro-naphthalen-2-yl)-1-(2-trimethylsilanyl ethoxymethyl)-1H-imidazole (268 mg, 0.82 mmol), 2.5 M n-BuLi (424 uL, 1.06 mmol), and DMF (253 uL, 3.27 mmol) for 2 h at −40° C. followed by column chromatography on silica gel (EtOAc/hexane 9:1) gave the title compound (166 mg, 57%) as a yellow oil. $^1$H NMR (300 MHz, CDCl$_3$) δ 0.00 (s, 9H), 0.94 (t, 2H, J=7.5 Hz), 1.80-1.85 (m, 4H), 2.80-2.83 (m, 4H), 3.60 (t, 2H, J=9.0 Hz), 5.81 (s, 2H), 7.13 (d, 1H, J=6.0 Hz), 7.51 (d, 1H, J=6.0 Hz), 7.57 (s, 1H), 7.60 (s, 1H). 9.88 (s, 1H).

Preparation of N-(tert-Butoxycarbonyl)-N-(2-pyridinylmethyl)-N'-[5-(5,6,7,8-tetrahydro-naphthalen-2-yl)-1-[(2-trimethylsilyl)ethoxy]methyl-imidazol-2-ylmethyl]-N'-(5,6,7,8-tetrahydro-8-quinolinyl)-1,4-benzenedimethanamine Reaction of N-(tert-butoxycarbonyl)-N-(2-pyridinylmethyl)-N'-(5,6,7,8-tetrahydro-8-quinolinyl)-1,4-benzenedimethanamine (178 mg, 0.39 mmol), 5-(5,6,7,8-tetrahydronaphthalen-2-yl)-1-(2-trimethylsilanyl-ethoxymethyl)-1H-imidazole-2-carbaldehyde (166 mg, 0.47 mmol), and NaBH(OAc)$_3$ (247 mg, 1.16 mmol) for 1 h at room temperature followed by purification of the crude product by column chromatography on silica gel (CH$_2$Cl$_2$/MeOH/NH$_4$OH 98:1:1) gave the title compound (230 mg, 74%) as a yellow foam. $^1$H NMR (300 MHz, CDCl$_3$) δ 0.00 (s, 9H), 0.81 (dd, 2H, J=7.5, 7.5 Hz), 1.25-1.30 (m, 1H), 1.41 (s, 3H), 1.48 (s, 3H), 1.57 (s, 3H), 1.60-1.78 (m, 4H), 1.95-1.98 (m, 3H), 2.68-2.78 (m, 6H), 3.29-3.33 (m, 2H), 3.67 (d, 1H, J=15.0 Hz), 3.89 (d, 1H, J=9.0 Hz), 3.96 (d, 2H, J=9.0 Hz), 3.97-4.01 m, 1H), 4.39 (brs, 1H), 4.49 (br s, 2H), 5.48 (d, 1H, J=12.0 Hz), 5.80 (d, 1H, J=9.0 Hz), 7.00-7.15 (m, 7H), 7.30-7.34 (m, 4H), 7.46 (s, 1H), 7.61 (ddd, 1H, J=7.65, 7.65, 1.5 Hz), 8.51-8.54 (m, 2H). ES-MS m/z 799 (M+H).

Using general procedure E: Reaction of N-(tert-butoxycarbonyl)-N-(2-pyridinylmethyl)-N'-[5-(5,6,7,8-tetrahydronaphthalen-2-yl)-1-[(2-trimethylsilyl)ethoxy]methyl-imidazol-2-ylmethyl]-N'-(5,6,7,8-tetrahydro-8-quinolinyl)-1,4-benzenedimethanamine (230 mg, 0.29 mmol), and 6N HCl (8.0 mL) for 3 h at 50° C. followed by purification of the crude product by column chromatography on silica gel (CH$_2$Cl$_2$/MeOH/NH$_4$OH 48:1:1) gave AMD9335 (144 mg, 87%) as a yellow foam. ¹H NMR (300 MHz, CD₃COCD₃) δ 1.62-1.75 (m, 1H), 1.95-1.99 (m, 5H), 2.03-2.07 (m, 2H), 2.69-2.74 (m, 7H), 3.71 (br s, 2H), 3.72-3.77 (m, 3H), 3.80 (br s, 2H), 3.94 (d, 1H, J=15.9 Hz), 4.02-4.06 (m, 1H), 6.99 (d, 1H, J=9.0 Hz), 7.19-7.21 (m, 1H), 7.24-7.39 (m, 3H), 7.44-7.50 (m, 8H), 7.64 (ddd, 1H, J=7.8, 7.8, 1.5 Hz), 8.45 (d, 1H, J=4.2 Hz), 8.67 (d, 1H, J=3 Hz); ¹³C NMR (75.5 MHz, CD₃COCD₃) δ 22.52, 24.51, 25.28, 49.40, 53.94, 55.00, 55.43, 61.08, 122.93, 123.07, 123.42, 125.98, 129.16, 129.75, 130.42, 132.67, 135.77, 136.12, 137.41, 138.00, 138.42, 139.85, 140.80, 148.29, 149.81, 150.20, 159.16, 161.81. ES-MS m/z 569 (M+H). Anal. Calcd. for C₃₇H₄₀N₆·1.0H₂O: C, 75.74; H, 7.21; N, 14.32. Found: C, 75.68; H, 6.96; N, 14.08.

EXAMPLE: 33

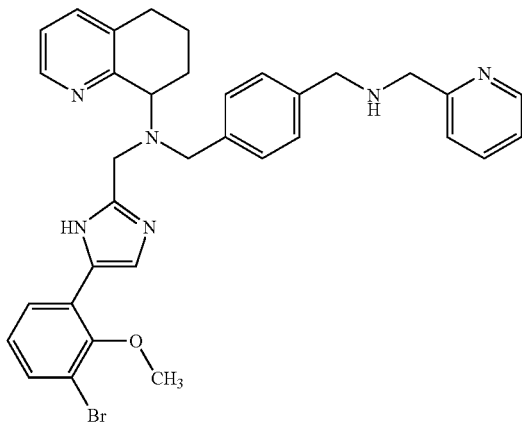

AMD9340: Preparation of N-(2-Pyridinylmethyl)-N'-[5-(3-Bromo-2-methoxy-phenyl)-1H-imidazol-2-ylmethyl]-N'-(5,6,7,8-tetrahydro-8-quinolinyl)-1,4-benzenedimethanamine (free base)

Preparation of 2-Bromo-1-(3-bromo-2-methoxy-phenyl)-ethanone

Reaction of 1-(2-methoxy-phenyl)-ethanone (5 g, 33 mmol), acetic acid (1.9 mL, 33 mmol), and bromine (1.97 mL, 38 mmol) followed by recrystallisation from cold EtOAc/Hexane gave the title compound (1.5 g, 25%) as a yellow powder. ¹H NMR (300 MHz, CDCl₃) δ 3.95 (s, 3H), 4.56 (s, 2H), 6.90 (d, 1H, J=8.7 Hz), 7.60 (dd, 1H, J=6.6, 2.4 Hz), 7.93 (d, 1H, J=2.4 Hz).

Preparation of 5-(3-Bromo-2-methoxy-phenyl)-1H-imidazole

Reaction of 2-bromo-1-(3-bromo-2-methoxy-phenyl)-ethanone (1.50 g, 4.87 mmol), and formamide (1.35 mL, 3.41 mmol), followed recrystallisation from cold EtOAc/Hexane gave the title compound (532 mg, 43%) as a white solid. ¹H NMR (300 MHz, CD₃OD) δ 3.92 (s, 3H), 6.97 (d, 1H, J=8.7 Hz), 7.31 (dd, 1H, J=8.7, 2.4 Hz), 7.58 (s, 1H), 7.71 (s, 1H), 8.02 (d, 1H, J=2.1 Hz).

Preparation of 5-(3-Bromo-2-methoxy-phenyl)-1-(2-trimethylsilanyl-ethoxymethyl)-1H-imidazole.

Reaction of 5-(3-bromo-2-methoxy-phenyl)-1H-imidazole (539 mg, 3.10 mmol), NaH (60%, 120 mg, 3.00 mmol), and SEMCl (751 uL, 3.61 mmol) followed by column chromatography on silica gel (hexane/EtOAC 3:2) gave the title compound (485 mg, 60%) as a brown oil. ¹H NMR (300 MHz, CDCl₃) δ 0.00 (s, 9H), 0.93 (t, 2H, J=7.5 Hz), 3.52 (t, 2H, J=7.5 Hz), 3.93 (s, 3H), 5.31 (s, 2H), 6.82 (d, 1H, J=6.0 Hz), 7.31 (dd, 1H, J=9.0, 3.0 Hz), 7.63 (s, 1H), 7.66 (s, 1H), 8.36 (d, 1H, J=2.1 Hz). ES-MS m/z 385 (M+H).

Preparation of 5-(3-Bromo-2-methoxy-phenyl)-1-(2-trimethylsilanyl-ethoxymethyl)-1H-imidazole-2-carbaldehyde.

Reaction 5-(3-bromo-2-methoxy-phenyl)-1-(2-trimethylsilanyl-ethoxymethyl)-1H-imidazole (485 mg, 1.26 mmol), 2.5 M n-BuLi (828 uL, 2.07 mmol), and DMF (494 uL, 6.38 mmol) for 2 h at −40° C. followed by column chromatography on silica gel (EtOAc/hexane 9:1) gave the title compound (240 mg, 47%) as a yellow oil. ¹H NMR (300 MHz, CDCl₃) δ 0.00 (s, 9H), 0.94 (t, 2H, J=9.0 Hz), 3.61 (t, 2H, J=7.5 Hz), 3.93 (s, 3H), 5.83 (s, 2H), 6.86 (d, 1H, J=9.0 Hz), 7.38 (dd, 1H, J=9.0, 3.0 Hz), 7.94 (s, 1H), 8.38 (d, 1H, J=3.0 Hz), 9.89 (s, 1H). ES-MS m/z 413 (M+H).

Preparation of N-(tert-Butoxycarbonyl)-N-(2-pyridinylmethyl)-N'-[5-(3-Bromo-2-methoxy-phenyl)-1-[(2-trimethylsilyl)ethoxy]methyl-imidazol-2-ylmethyl]-N'-(5,6,7,8-tetrahydro-8-quinolinyl)-1,4-benzenedimethanamine Using general procedure B: Reaction of N-(tert-butoxycarbonyl)-N-(2-pyridinylmethyl)-N'-(5,6,7,8-tetrahydro-8-quinolinyl)-1,4-benzenedimethanamine (193 mg, 0.42 mmol), 5-(3-bromo-2-methoxy-phenyl)-1-(2-trimethylsilanyl-ethoxymethyl)-1H-imidazole-2-carbaldehyde (190 mg, 0.46 mmol), and NaBH(OAc)₃ (267 mg, 1.26 mmol) for 1.5 h at room temperature followed by purification of the crude product by column chromatography on silica gel (CH₂Cl₂/MeOH/NH₄OH 98:1:1) gave the title compound (171 mg, 48%) as a yellow foam. ¹H NMR (300 MHz, CDCl₃) δ 0.00 (s, 9H), 0.81 (dd, 2H, J=10.5, 7.5 Hz), 1.45 (d, 9H), 1.61-1.76 (m, 1H), 1.89-2.13 (m, 3H), 2.63-2.83 (m, 2H), 3.30-3.34 (m, 2H), 3.68 (d, 1H, J=14.1 Hz), 3.87 (s, 3H), 3.90-3.92 (m, 1H), 3.96 (br s, 2H), 4.02 (dd, 1H, J=9.8, 6.5 Hz), 4.39 (br s, 2H), 4.49 (br s, 2H), 5.52 (d, 1H, J=9.0 Hz), 6.76 (d, 1H, J=8.7 Hz), 6.76 (d, 1H, J=8.7 Hz), 7.11-7.32 (m, 9H), 7.50 (s, 1H), 7.60(ddd, 1H, J=7.5, 7.5, 1.8 Hz), 8.28 (d, 1H, J=2.4 Hz), 8.50 (d, 1H, J=4.5 Hz), 8.55 (d, 1H, J=5.7 Hz).

Using general procedure E: Reaction of N-(tert-butoxycarbonyl)-N-(2-pyridinylmethyl)-N'-[5-(3-Bromo-2-methoxy-phenyl)-1-[(2-trimethylsilyl)ethoxy]methyl-imidazol-2-ylmethyl]-N'-(5,6,7,8-tetrahydro-8-quinolinyl)-1,4-benzenedimethanamine (170 mg, 0.20 mmol), and 6N HCl (6.0 mL) for 3 h at 50° C. followed by purification of the crude product by column chromatography on silica gel (CH₂Cl₂/MeOH/NH₄OH 48:1:1) gave AMD9340 (112 mg, 90%) as a white foam. ¹H NMR (300 MHz, CD₃COCD₃) δ 1.64-1.71 (m, 1H), 1.96-2.06 (m, 2H), 2.20-2.24 (m, 1H), 2.66-2.91 (m, 3H), 3.72 (br s, 2H), 3.78 (br s, 2H), 3.80 (s, 3H), 3.89 (brs, 1H), 3.94 (brs, 3H), 4.01 (dd, 1H, J=8.9, 6.5 Hz), 6.95 (d, 1H, J=8.7 Hz), 7.18-7.25 (m, 6H), 7.36-7.41 (m, 3H), 7.48 (d, 1H, J=7.5 Hz), 7.62-7.65 (m, 2H), 8.26 (br s, 1H), 8.45 (d, 1H, J=4.2 Hz), 8.66 (d, 1H, J=3.9 Hz); ¹³C NMR (75.5 MHz, CD₃COCD₃) δ 22.51, 25.38, 49.33, 53.98, 55.06, 55.48, 56.40, 61.06, 113,88, 114.19, 122.89, 123.05, 123.36, 129.15, 129.73, 136.04, 137.39, 138.38, 139.80, 140.89, 148.31, 149.26, 150.19, 156.19, 159.11, 161.88. ES-MS m/z 625 (M+H). Anal. Calcd. for C₃₄H₃₅N₆OBr.0.3H₂O: C, 64.92; H, 5.70; N, 13.36; Br, 12.70. Found: C, 64.97; H, 5.71; N, 13.11, Br, 12.61.

EXAMPLE: 34

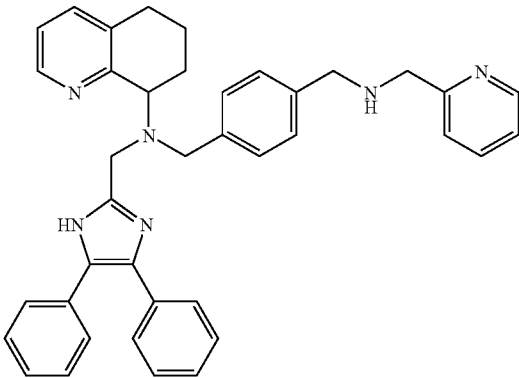

AMD9360: Preparation of N-(2-pyridinylmethyl)-N'-(4,5-Diphenyl-1H-imidazol-2-ylmethyl)-N'-(5,6,7,8-tetrahydro-8-quinolinyl)-1,4-benzenedimethanamine (free base)

Preparation of 4,5-Diphenyl-1-(2-trimethylsilanyl-ethoxymethyl)-1H-imidazole

Reaction of 4,5-diphenyl-1H-imidazole (300 mg, 1.36 mmol), NaH (60%, 55 mg, 1.36 mmol), and SEMCl (289 uL, 1.63 mmol) followed by column chromatography on silica gel (hexane/EtOAC 3:2) gave the title compound (304 mg, 64%) as a white solid. $^1$H NMR (300 MHz, CDCl$_3$) δ 0.00 (s, 9H), 0.88 (t, 2H, J=7.5 Hz), 3.46 (t, 2H, J=9.0 Hz), 5.12 (s, 2H), 7.27-7.38 (m, 3H), 7.40-1.52 (m, 7H), 7.75 (s, 1H).

Preparation of 4,5-Diphenyl-1-(2-trimethylsilanyl-ethoxymethyl)-1H-imidazole-2-carbaldehyde.

Reaction of 4,5-diphenyl-1-(2-trimethylsilanyl-ethoxymethyl)-1H-imidazole (304 mg, 0.87 mmol), 2.5 M n-BuLi (452 uL, 1.13 mmol), and DMF (269 uL, 3.48 mmol) for 1 h at −40° C. gave the title compound (257 mg, 78%) as a yellow solid. $^1$H NMR (300 MHz, CDCl$_3$) δ 0.00 (s, 9H), 0.89 (t, 2H, J=9.0 Hz), 3.58 (t, 2H, J=7.5 Hz), 5.61 (s, 2H), 7.26 (br s, 5H), 7.47 (br s, 5H), 9.95 (s, 1H).

Preparation of N-(tert-Butoxycarbonyl)-N-(2-pyridinylmethyl)-N'-[4,5-Diphenyl-1-[(2-trimethylsilyl)ethoxy]methyl-imidazol-2-ylmethyl]-N'-(5,6,7,8-tetrahydro-8-quinolinyl)-1,4-benzenedimethanamine.

Using general procedure B: Reaction of N-(tert-butoxycarbonyl)-N-(2-pyridinylmethyl)-N'-(5,6,7,8-tetrahydro-8-quinolinyl)-1,4-benzenedimethanamine (257 mg, 0.56 mmol), 4,5-diphenyl-1-(2-trimethylsilanyl-ethoxymethyl)-1H-imidazole-2-carbaldehyde (231 mg, 0.61 mmol), and NaBH(OAc)$_3$ (353 mg, 1.67 mmol) for 1 h at room temperature followed by purification of the crude product by column chromatography on silica gel (CH$_2$Cl$_2$/MeOH/NH$_4$OH 98:1:1) gave the title compound (231 mg, 50%) as a white foam. $^1$H NMR (300 MHz, CDCl$_3$) δ 0.00 (s, 9H), 0.67 (dd, 2H, J=7.5, 7.5 Hz), 1.43 (d, 9H), 1.60-1.70 (m, 1H), 2.03-2.09 (m, 3H), 2.65-2.73 (m, 2H), 3.09-3.72 (m, 2H), 3.79 (d, 1H, J=15.0 Hz), 4.00 (d, 1H, J=15.0 Hz), 4.05-4.19 (m, 3H), 4.37 (d, 2H, J=4.8 Hz), 4.46 (brs, 2H), 5.33 (d, 1H, J=12.0 Hz), 5.48 (d, 1H, J=9.0 Hz), 7.05-7.19 (m, 11H), 7.30-7.37 (m, 7H), 7.60 (td, 1H, J=5.7, 1.8 Hz), 8.50-8.52 (m, 2H). ES-MS m/z 821 (M+H).

Using general procedure E: Reaction of N-(tert-Butoxycarbonyl)-N-(2-pyridinylmethyl)-N'-[4,5-Diphenyl-1-[(2-trimethylsilyl)ethoxy]methyl-imidazol-2-ylmethyl]-N'-(5,6,7,8-tetrahydro-8-quinolinyl)-1,4-benzenedimethanamine (223 mg, 0.27 mmol), and 6N HCl (9.0 mL) for 3 h at 50° C. followed by purification of the crude product by column chromatography on silica gel (CH$_2$Cl$_2$/MeOH/NH$_4$OH 48:1:1) gave AMD9360 (123 mg, 77%) as a white foam. $^1$H NMR (300 MHz, CD$_3$COCD$_3$) δ 1.74-1.77 (m, 1H), 2 12-2.19 (m, 1H), 2.27 (br s, 1H), 2.70-2.90 (m, 4H), 3.69 (br s, 2H), 3.73 (br s, 2H), 3.79 (br s, 3H), 4.05 (d, 1H, J=16.5 Hz), 4.16 (t, 1H, J=7.2 Hz), 7.15-7.65 (m, 20 H), 8.44 (br s, 1H), 8.57 (d, 1H, J=3.3 Hz); $^{13}$C NMR (75.5 MHz, CD$_3$COCD$_3$) δ 22.50, 24.94, 49.21, 53.93, 54.75, 55.48, 61.52, 122.87, 123.03, 123.60, 128.61, 129.16, 129.73, 136.30, 137.38, 138.58, 139.77, 141.00, 148.18, 149.86, 150.18, 159.10, 161.89. ES-MS m/z 591 (M+H). Anal. Calcd. for C$_{39}$H$_{38}$N$_6$·0.7H$_2$O: C, 77.63; H, 6.58; N, 13.93. Found: C, 77.52; H, 6.49; N, 14.01.

EXAMPLE: 35

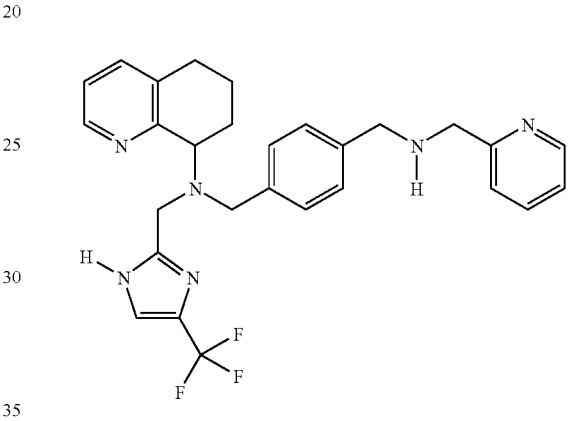

AMD8998: Preparation of N-(2-pyridinylmethyl)-N'-(4-trifluormethyl-1H-imidazol-2-ylmethyl)-N'-(5,6,7,8-tetrahydro-8-quinolinyl)-1,4-benzenedimethanamine(hydrobromide salt)

Preparation of 4-trifluoromethyl-1H-imidazole.

3-Bromo-1,1,1-trifluoroacetone (3.50 g, 18.3 mmol) and formamide (4.40 mL, 111 mmol) were heated (neat) at 170° C. for 3 hours. The mixture was partitioned between water (30 mL) and EtOAc (100 mL). The organic phase was washed with water (3×30 mL) and brine (15 mL), then dried (MgSO$_4$) and concentrated. The title compound was obtained as a brown solid (308 mg, 12%) and was used without further purification. $^1$H NMR (CD$_3$OD) □ 7.58 (s, 1H), 7.81 (s, 1H).

4-Trifluoromethyl-1-(2-trimethylsilanyl-ethoxymethyl)-1H-imidazole.

Reaction of 4-trifluoromethyl-1H-imidazole (301 mg, 2.21 mmol), 95% NaH (61 mg, 2.4 mmol), and SEMCl (406 mg, 2.44 mmol) gave the title compound as a brown oil that was used without further purification. $^1$H NMR (CDCl$_3$) □ 0.00 (s, 9H), 0.93 (m, 2H), 3.51 (m, 2H), 5.30 (s, 2H), 7.39 (s, 1H), 7.64 (s, 1H).

4-Trifluoromethyl-1-(2-trimethylsilanyl-ethoxymethyl)-1H-imidazole-2-carbaldehyde.

Reaction of 4-trifluoromethyl-1-(2-trimethylsilanyl-ethoxymethyl)-1H-imidazole (590 mg, 2.2 mmol), 2.3 M n-BuLi (1.3 mL, 3.0 mmol), and DMF (0.51 mL, 6.6 mmol) followed by purification of the crude material on silica gel (10% EtOAc/hexanes) gave the title compound as a yellow oil (92 mg, 14% over two steps). $^1$H NMR (CDCl$_3$) □ 0.02 (s, 9H), 0.95 (m, 2H), 3.60 (m, 2H), 5.79 (s, 2H), 7.28 (s, 1H), 7.67 (s, 1H), 9.86 (s, 1H).

Preparation of N-(tert-Butoxycarbonyl)-N-(2-pyridinylmethyl)-N'-[4-trifluoromethyl-1-[(2-trimethylsilyl)ethoxy]methyl-imidazol-2-ylmethyl]-N'-(5,6,7,8-tetrahydro-8-quinolinyl)-1,4-benzenedimethanamine.

Reaction of 4-trifluoromethyl-1-(2-trimethylsilanyl-ethoxymethyl)-1H-imidazole-2-carbaldehyde (87 mg, 0.30 mmol), N-(tert-butoxycarbonyl)-N-(2-pyridinylmethyl)-N'-(5,6,7,8-tetrahydro-8-quinolinyl)-1,4-benzenedimethanamine (145 mg, 0.316 mmol), acetic acid (0.017 mL, 0.30 mmol), and NaBH(OAc)$_3$ (188 mg, 0.887 mmol) for 15 hours followed by purification of the crude material on silica gel (100:3:0.2 CH$_2$Cl$_2$/MeOH/NH$_4$OH) gave the title compound as a yellow oil (168 mg, 77%). $^1$H NMR (CDCl$_3$) □ −0.07 (s, 9H), 0.81 (m, 2H), 1.46 (m, 9H), 1.68 (m, 1H), 1.97 (m, 2H), 2.16 (m, 1H), 2.74 (m, 2H), 3.32 (m, 2H), 3.64 (d, 1H, J=14 Hz), 3.79 (d, 1H, J=14 Hz), 3.98 (m, 3H), 4.44 (m, 4H), 5.47 (d, 1H, J=11 Hz), 5.67 (d, 1H, J=11 Hz), 7.03-7.35 (m, 9H), 7.63 (m, 1H), 8.51 (m, 2H).

The intermediate from above (162 mg, 0.220 mmol) was dissolved in trifluoroacetic acid (4 mL) and stirred at room temperature for 19 hours then concentrated. The residue was dissolved in EtOAc (25 mL) and washed with saturated NaHCO$_3$(aq) (2×15 mL) and brine (5 mL), then dried (MgSO$_4$) and concentrated. The crude material was purified by chromatography on silica gel (100:3:0.2 CH$_2$Cl$_2$/MeOH/NH$_4$OH) to give a colourless oil (66 mg, 59%).

Using General Procedure D: The colourless oil from above (61 mg, 0.12 mmol) was converted to the hydrobromide salt providing AMD8998 as a colourless solid (81 mg, 77%). $^1$H NMR (D$_2$O) □ 1.83 (m, 1H), 2.20 (m, 2H), 2.34 (m, 1H), 2.97 (m, 2H), 3.80 (m, 2H), 4.26 (d, 1H, J=16 Hz), 4.29 (s, 2H), 4.40 (d, 1H, J=16 Hz), 4.56 (s, 2H), 4.63 (m, 1H), 7.24 (d, 2H, J=7.8 Hz), 7.32 (d, 2H, J=7.8 Hz), 7.67 (s, 1H), 7.85 (m, 2H), 7.92 (d, 1H, J=8.4 Hz), 8.32 (d, 1H, J=8.1 Hz), 8.39 (m, 1H), 8.62 (d, 1H, J=5.4 Hz), 8.74 (d, 1H, J=5.4 Hz); $^{13}$C NMR (D$_2$O) □ 20.44, 20.64, 27.78, 48.19, 49.73, 51.33, 56.23, 62.31, 120.46, 125.98, 127.42, 127.55, 129.94, 130.81, 138.61, 139.48, 140.76, 145.38, 145.54, 146.55, 148.07, 148.65, 150.94. ES-MS m/z 507 (M+H). Anal Calcd for (C$_{28}$H$_{29}$N$_6$F$_3$) 4.0(HBr) 2.2(H$_2$O): C, 38.66; H, 4.33; N, 9.66; Br, 36.74. Found: C, 38.67; H, 4.37; N, 9.44; Br, 36.75.

EXAMPLE: 36

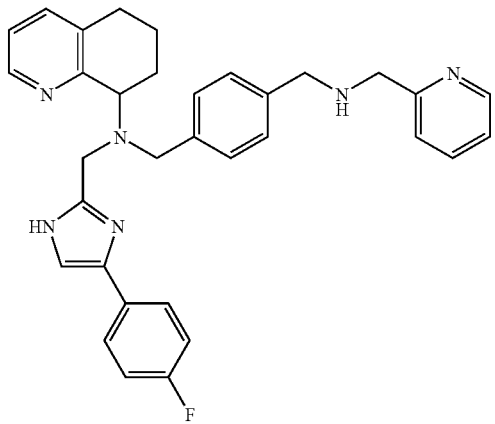

AMD8991: Preparation of N-(2-Pyridinylmethyl)-N'-[4-(4-fluorophenyl)-1H-imidazol-2-ylmethyl]-N'-(5,6,7,8-tetrahydro-8-quinolinyl)-1,4-benzene-dimethanamine(hydrobromide salt)

Preparation of 4-(4-fluorophenyl)-1H-imidazole.
2-Bromo-4'-fluoroacetophenone (4.00 g, 18.4 mmol) and formamide (4.40 mL, 111 mmol) were heated (neat) at 170° C. for 3 hours. The mixture was partitioned between water (50 mL) and CHCl$_3$ (25 mL). The aqueous phase was extracted with CHCl$_3$ (3×15 mL) and concentrated. The crude material was purified by chromatography on silica gel (EtOAc) to give the title compound as yellow crystals (581 mg, 19%). $^1$H NMR (CDCl$_3$) □ 7.06 (m, 2H), 7.24 (s, 1H), 7.67 (m, 3H).

4-(4-Fluorophenyl)-1-(2-trimethylsilanyl-ethoxymethyl)-1H-imidazole.

Reaction of 4-(4-fluoro-phenyl)-1H-imidazole (573 mg, 3.53 mmol), 95% NaH (100 mg, 4.0 mmol), and SEMCl (650 mg, 3.90 mmol) followed by purification of the crude material on silica gel (50% EtOAc/hexanes) gave the title compound as yellow crystals (695 mg, 67%). $^1$H NMR (CDCl$_3$) □ −0.01 (s, 9H), 0.93 (m, 2H), 3.52 (m, 2H), 5.29 (s, 2H), 7.07 (m, 2H), 7.28 (s, 1H), 7.62 (s, 1H), 7.75 (m, 2H).

4-(4-Fluorophenyl)-1-(2-trimethylsilanyl-ethoxymethyl)-1H-imidazole-2-carbaldehyde.

Reaction of 4-(4-fluoro-phenyl)-1-(2-trimethylsilanyl-ethoxymethyl)-1H-imidazole (688 mg, 2.35 mmol), 1.5 M n-BuLi (2.0 mL, 3.0 mmol), and DMF (0.55 mL, 7.1 mmol) gave the title compound as a brown oil that was used without further purification in the next step. $^1$H NMR (CDCl$_3$) □ 0.00 (s, 9H), 0.95 (m, 2H), 3.61 (m, 2H), 5.82 (s, 2H), 7.12 (m, 2H), 7.28 (s, 1H), 7.59 (s, 1H), 7.80 (m, 2H), 9.88 (s, 1H).

Preparation of N-(tert-Butoxycarbonyl)-N-(2-pyridinylmethyl)-N'-[[4-(4-fluorophenyl)-1-[(2-trimethylsilyl)ethoxy]methyl]imidazol-2-ylmethyl]-N'-(5,6,7,8-tetrahydro-8-quinolinyl)-1,4-benzenedimethanamine.

Using general procedure B: Reaction of 4-(4-fluorophenyl)-1-(2-trimethylsilanyl-ethoxymethyl)-1H-imidazole-2-carbaldehyde (285 mg, 0.889 mmol), ), N-(tert-butoxycarbonyl)-N-(2-pyridinylmethyl)-N'-(5,6,7,8-tetrahydro-8-quinolinyl)-1,4-benzenedimethanamine (315 mg, 0.687 mmol), acetic acid (0.04 mL, 0.70 mmol), and NaBH(OAc)$_3$ (420 mg, 1.98 mmol) for 2 hours followed by purification of the crude material on silica gel (100:3:0.2 CH$_2$Cl$_2$/MeOH/NH$_4$OH) gave the title compound as a yellow oil (334 mg, 64% over two steps). $^1$H NMR (CDCl$_3$) □ −0.07 (s, 9H), 0.82 (m, 2H), 1.45 (m, 9H), 1.66 (m, 1H), 1.99 (m, 2H), 2.14 (m, 1H), 2.73 (m, 2H), 3.34 (m, 2H), 3.67 (d, 1H, J=14 Hz), 3.87 (d, 1H, J=14 Hz), 3.97 (m, 2H), 4.05 (m, 1H), 4.43 (m, 4H), 5.48 (d, 1H, J=11 Hz), 5.76 (d, 1H, J=11 Hz), 6.98-7.16 (m, 8H), 7.30 (m, 3H), 7.63 (m, 3H), 8.53 (m, 2H).

A solution of the oil from above (324 mg, 0.425 mmol) in trifluoroacetic acid (4 mL) was stirred at room temperature for 67 hours then concentrated. The residue was dissolved in EtOAc (30 mL) and washed with saturated NaHCO$_3$(aq) (2×15 mL) and brine (5 mL), then dried (MgSO$_4$) and concentrated. The crude material was purified by chromatography on silica gel (100:3:0.2 CH$_2$Cl$_2$/MeOH/NH$_4$OH) to give a yellow foam (142 mg, 63%).

Using General Procedure D: The yellow foam from above (135 mg, 0.253 mmol) was converted to the hydrobromide salt affording AMD8991 as a colourless solid (190 mg, 84%). $^1$H NMR (D$_2$O) □ 1.87 (m, 1H), 2.21 (m, 2H), 2.41 (m, 1H), 3.00 (m, 2H), 3.76-3.98 (m, 4H), 4.25 (s, 2H), 4.27 (d, J=16 Hz), 4.44 (d, 1H, J=16 Hz), 4.71 (m, 1H), 7.17 (m, 6H), 7.40 (m, 3H), 7.66 (d, 1H, J=7.8 Hz), 7.75 (m, 1H), 7.89 (dd, 1H, J=7.8, 5.7 Hz), 8.22 (m, 1H), 8.36 (d, 1H, J=7.8 Hz), 8.66

(d, 1H, J=5.4 Hz), 8.71 (d, 1H, J=5.7 Hz); $^{13}$C NMR D$_2$O) □ 20.47, 20.75, 27.83, 48.08, 49.48, 50.86, 56.69, 62.98, 114.57, 116.64, 116.93, 122.70, 126.08, 127.31, 127.37, 127.99, 128.10, 129.50, 130.57, 130.65, 132.67, 138.95, 139.59, 140.92, 145.06, 145.52, 145.75, 146.59, 148.20, 150.88, 161.69, 164.98. ES-MS m/z 533 (M+H). Anal Calcd for (C$_{33}$H$_{33}$N$_6$F) 3.9(HBr) 2.4(H$_2$O): C, 44.46; H, 4.71; N, 9.43; Br, 34.96. Found: C, 44.44; H, 4.77; N, 9.25; Br, 35.15.

EXAMPLE: 37

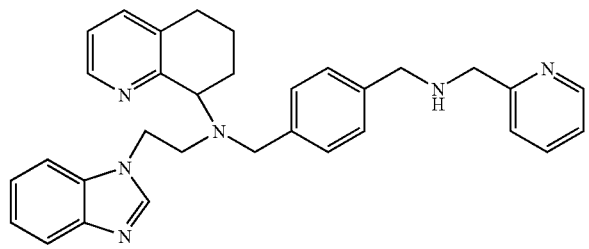

AMD9366: Preparation of N-(2-pyridinylmethyl)-N'-[2-(benzimidazol-1-yl)eth-1-yl]-N'-(5,6,7,8-tetrahydro-8-quinolinyl)-1,4-benzenedimethanamine (hydrobromide salt)

Benzimidazole (590 mg, 5.0 mmol) and 3-bromo-1,2-propanediol (0.52 mL, 6.0 mmol) were dissolved in anhydrous acetonitrile (50 mL) and dry potassium carbonate (2.07 g, 15 mmol) was added. The solution was then heated to reflux for 3 days. Upon cooling the mixture was filtered and the filtrates were concentrated, giving the desired N-benzimidazolyl-1,2-propanediol (0.66 g, 69%) as a pale yellow solid. $^1$H NMR (CDCl$_3$) δ 3.60 (m, 2H), 3.78 (m, 2H), 4.17 (m, 1H), 4.27 (m, 2H), 7.25 (m, 2H), 7.42 (d, 1H, J=6 Hz), 7.67 (d, 1H, J=6 Hz), 7.87 (s, 1H).

The intermediate, N-benzimidazolyl-1,2-propanediol (0.66 g, 3.4 mmol) from above was dissolved in water (25 mL) and treated with sodium periodate (0.88 g, 4.1 mmol) with stirring for 1.5 hours. The solution was then extracted with dichloromethane, dried (MgSO$_4$), filtered and concentrated to yield 2-(benzimidazol-1-yl)-ethanal (0.22 g, 1.4 mmol) which was used immediately without further purification in the next reaction.

Using general procedure B: 2-(benzimidazol-1-yl)ethanal (0.22 g, 2.0 mmol), N-(tert-butoxycarbonyl)-N-(2-pyridinylmethyl)-N'-(5,6,7,8-tetrahydro-8-quinolinyl)-1,4-benzenedimethanamine (780 mg, 1.7 mmol) and sodium triacetoxyborohydride (590 mg, 2.8 mmol) were stirred at room temperature in dichloromethane (20 mL) for 64 hours to yield, after work-up and chromatography, the desired N-(tert-butoxycarbonyl)-N-(2-pyridinylmethyl)-N'-[2-(benzimidazol-1-yl)eth-1-yl]-N'-5,6,7,8-tetrahydroquinolinyl)-1,4-benzenedimethanamine as a brown foam (25 mg, 2.5%). $^1$H NMR (CDCl$_3$) δ 1.45 (m, 9H), 1.63 (t, 2H, J=7.5 Hz), 1.88 (m, 1H), 1.98 (m, 1H), 2.64 (br d, 2H), 3.00 (m, 1H), 3.25 (m, 1H), 3.76 (d, 2H, J=12 Hz), 3.95 (m, 4H), 4.41 (s, 2H), 4.52 (s, 2H), 7.02 (m, 2H), 7.18 (m, 5H), 7.27 (m, 4H), 7.62 (t, 1H), 7.75 (d, 1H, J=7.5 Hz), 7.90 (s, 1H), 8.46 (d, 1H, J=3 Hz), 8.53 (d, 1H, J=4.5 Hz).

Using general procedure D: the residue from above was converted to the hydrobromide salt with simultaneous deprotection of the BOC group to provide AMD9366 (0.03 g) as a pale yellow solid. $^1$H NMR (D$_2$O) □1.66-1.75 (m, 1H), 1.98-2.07 (m, 2H), 2.23-2.28 (m, 1H), 2.89 (br d, 2H), 3.10-3.21 (m, 1H), 3.35 (d, 1H, J=14.4 Hz), 3.82 (d, 1H, J=13.2 Hz), 3.92 (d, 1H, J=13.2 Hz), 4.28 (s, 2H), 4.35 (t, 1H, J=8.4 Hz), 4.43 (d, 2H, J=7.2 Hz), 4.63 (br, 2H), 7.31 (d, 2H, J=7.5 Hz), 7.38 (d, 2H J=7.5 Hz), 7.42 (s, 2H), 7.50-7.61 (m, 2H), 7.63-7.73 (m, 2H), 7.80 (d, 1H, J=8.4 Hz), 8.03-8.11 (br, 1H), 8.15 (d, 2H, J=7.8 Hz), 8.62-8.67 (br, 1H), 9.25 (s, 1H); $^{13}$C NMR (D$_2$O) □ 20.32, 20.45, 27.71, 46.15, 48.78, 48.91, 51.38, 54.89, 58.62, 112.90, 115.31, 125.46, 126.80, 127.56, 130.03, 130.59, 130.74, 130.98, 139.23 (2 carbons), 140.83, 143.93, 146.45, 147.30, 147.55, 151.37. ES-MS m/z 503 (M+H). Anal. Calcd. for C$_{32}$H$_{34}$N$_6$.5.4HBr.4.7H$_2$O.1.1CH$_3$CO$_2$H: C, 37.68; H, 4.92; N, 7.71; Br, 39.57. Found: C, 37.70; H, 4.85; N, 7.74; Br, 39.50.

EXAMPLE: 38

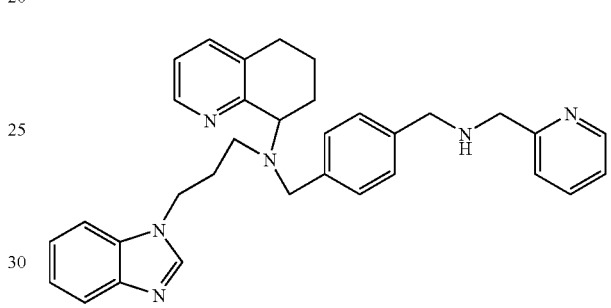

AMD9382: Preparation of N-(2-pyridinylmethyl)-N'-[3-(benzimidazol-1-yl)prop-1-yl]-N'-(5,6,7,8-tetrahydro-8-quinolinyl)-1,4-benzenedimethanamine (hydrobromide salt)

A solution of 3-bromopropanol (1.39 g, 10.0 mmol), acetic anhydride (1.23 mL, 13.0 mmol), and triethylamine (2.09 mL, 15 mmol) in dichloromethane (50 mL) was treated with 4-dimethylaminopyridine (0.24 g, 2.0 mmol) and the mixture was stirred for 2.5 hours at room temperature. The mixture was then acidified with saturated ammonium chloride (25 mL), extracted with dichloromethane (2×25 mL), dried (MgSO$_4$), filtered, and concentrated to give ethyl-3-bromopropanoate (1.29 g, 71%) as a yellow oil. $^1$H NMR (CDCl$_3$) δ 2.05 (s, 3H), 2.15 (qn, 2H, J=6 Hz), 3.46 (t, 2H, J=6 Hz), 4.20 (t, 2H, J=6 Hz).

Ethyl-3-bromopropanoate (1.29 g, 7.1 mmol), benzimidazole (0.70 g, 5.9 mmol), and potassium carbonate (2.44 g, 17.7 mmol) were combined in anhydrous acetonitrile (60 mL) and heated to reflux for 3 days. Aqueous work-up gave ethyl-3-(benzimidazol-1-yl)propanoate (1.17 g, 91%). $^1$H NMR (CDCl$_3$) δ 2.02 (s, 3H), 2.26 (m, 2H), 4.10 (t, 2H, J=6 Hz), 4.30 (t, 2H, J=6 Hz), 7.28 (br, 2H), 7.33 (br, 1H), 7.84 (br, 1H), 7.94 (br, 1H), 7.60 (br, 1H).

Ethyl-3-(benzimidazol-1-yl)propanoate (590 mg, 2.7 mmol) was dissolved in anhydrous methanol (13 mL), and treated with potassium carbonate (0.75 g, 5.4 mmol) and allowed to stir overnight. This provided, after work-up with ammonium chloride, 3-(benzimidazol-1-yl)-propanol (0.22 g, 49%) as a brown liquid. $^1$H NMR (CDCl$_3$) δ 2.11 (qn, 2H, J=6 Hz), 2.57 (br, 1H), 3.61 (t, 2H, J=6 Hz), 4.38 (t, 2H, J=6 Hz), 7.27 (m, 2H), 7.45. (d, 1H, J=6 Hz), 7.80 (d, 1H, J=7.5 Hz), 7.93 (s, 1H).

3-(benzimidazol-1-yl)propan-1-ol (100 mg, 0.57 mmol) was dissolved in dichloromethane (6 mL), and treated with sodium periodinane (290 mg, 0.68 mmol). After stirring 5 hours, the mixture was treated with sodium bicarbonate (10 mL), ethyl acetate (10 mL), sodium thiosulfate (2 g) and extracted with ethyl acetate (2×10 mL). The organic phases were combined and washed with brine (15 mL), dried (MgSO$_4$), filtered, and concentrated to yield the desired 3-(benzimidazol-1-yl)propanal (81 mg, 80%) as a yellow oil. $^1$H NMR (CDCl$_3$) δ 3.09 (t, 2H, J=6 Hz), 4.54 (t, 2H, J=6 Hz), 7.32 (m, 2H), 7.38 (m, 1H), 7.80 (d, 1H, J=6 Hz), 8.00 (s, 1H), 9.81 (s, 1H).

Using general procedure B: 3-(benzimidazol-1-yl)propanal (75 mg, 0.43 mmol), N-(tert-butoxycarbonyl)-N-(2-pyridinylmethyl)-N'-(5,6,7,8-tetrahydro-8-quinolinyl)-1,4-benzenedimethanamine (200 mg, 0.43 mmol) and sodium cyanoborohydride (38 mg, 0.60 mmol) were stirred at room temperature in methanol (2.5 mL) for 16 hours to yield, after work-up and chromatography, N-(tert-butoxycarbonyl)-N-(2-pyridinylmethyl)-N'-(N-(benzimidazol-2-yl)prop-1-yl)-N'-(5,6,7,8-tetrahydro-8-quinolinyl)-1,4-benzenedimethanamine as a brown foam (25 mg, 10%). $^1$H NMR (CDCl$_3$) δ 1.39 (m, 9H), 1.70 (m, 1H), 1.89 (m, 4H), 2.08 (m, 1H), 2.70 (m, 3H), 2.81 (m, 1H), 3.60 (d, 1H, J=12 Hz), 3.82 (d, 1H, J=12 Hz), 4.05 (m, 2H), 4.26 (m, 1H), 4.44 (s, 2H), 4.54 (s, 2H), 7.03 (m, 1H), 7.20 (m, 6H), 7.33 (d, 2H, J=4.5 Hz), 7.40 (d, 2H, J=6 Hz), 7.63 (t, 1H, J=6 Hz), 7.69 (s, 1H), 7.75 (d, 1H, J=6 Hz), 8.51 (m, 2H).

Using general procedure D: the residue from above was converted to the hydrobromide salt with simultaneous deprotection of the BOC group to provide AMD9382 (0.04 g) as a pale yellow solid. $^1$H NMR (D$_2$O) □1.66-1.75 (m, 1H), 1.87-2.00 (m, 1H), 2.01-2.11 (m, 1H), 2.13-2.26 (m, 1H), 2.28-3.37 (br, 2H), 2.70-2.81 (br, 3H), 3.25 (dt, 1H, J=5.1, 12.0 Hz), 4.10 (d, 1H, J=13.5 Hz), 4.22 (d, 1H, J=13.2 Hz), 4.30 (s, 2H), 4.34 (s, 2H), 4.34-4.56 (m, 3H), 7.38 (d, 3H, J=7.8 Hz), 7.47 (d, 2H, J=7.8 Hz), 7.62-7.67 (m, 4H), 7.71-7.81 (m, 3H), 8.10 (t, 1H, J=7.8 Hz), 8.26 (d, 1H, J=4.8 Hz), 8.63 (d, 1H, J=5.1 Hz), 9.13 (s, 1H); $^{13}$C NMR (D$_2$O) □ 20.30, 20.78, 26.70, 27.37, 44.70, 48.60, 48.81, 51.27, 55.43, 61.69, 113.09, 115.34, 124.91, 126.89 (2 carbons), 127.37, 127.70, 130.83, 131.01 (3 carbons), 131.34 (3 carbons), 134.58, 137.26, 140.37, 142.12, 144.01, 144.22, 146.42, 147.45, 149.93. ES-MS m/z 517 (M+H). Anal. Calcd. for C$_{33}$H$_{36}$N$_6$.5.4HBr.3.9H$_2$O.0.2CH$_3$CO$_2$H: C, 38.73; H, 4.86; N, 8.11; Br, 41.65. Found: C, 38.91; H, 5.05; N, 8.12; Br, 41.58.

EXAMPLE: 39

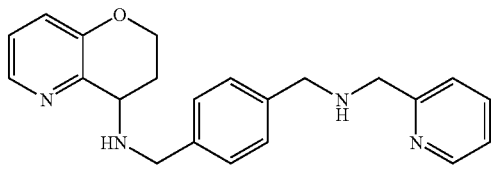

AMD9410: Preparation of N-(2-pyridinylmethyl)-N'-(3,4-dihydro-2H-pyrano[3,2-b]pyridinyl)-1,4-benzenedimethanamine 2-Bromo-3-but-3-enyloxy-pyridine.

To a solution of triphenylphosphine (903 mg, 3.44 mmol), 3-buten-1-ol (0.25 mL, 2.88 mmol) and 2-bromo-3-pyridinol (500 mg, 2.87 mmol) in THF (26 mL) at 0° C. was added dropwise diethyl azodicarboxylate (0.50 mL, 3.14 mmol). The ice bath was removed and the mixture was allowed to stir at 50° C. for 18 hours under N$_2$. The reaction mixture was diluted with ethyl acetate (300 mL), and washed with sat. NaHCO$_3$, then brine and dried over Na$_2$SO$_4$. Evaporation of the solvent and purification of the residue by flash chromatography on silica gel, using 10% ethyl acetate in hexanes, afforded the title compound (514 mg, 78%) as pale yellow solid. $^1$H NMR (CDCl$_3$) □ 2.58-2.66 (m, 2H), 4.08 (t, 2H, J=6.9 Hz), 5.13-5.24 (m, 2H), 5.87-5.98 (m, 1H), 7.10-7.14 (m, 1H), 7.18-7.22 (m, 1H), 7.97 (dd, 1H, J=1.5, 6.0 Hz).

4-Methylene-3,4-dihydro-2H-pyrano[3,2-b]pyridine.

A reaction tube was charged with 2-Bromo-3-but-3-enyloxy-pyridine (106 mg, 0.45 mmol), triphenylphosphine (35 mg, 0.133 mmol), palladium acetate (10 mg, 0.044 mmol), potassium acetate (223 mg, 2.27 mmol), tetraethylammonium chloride hydrate (151 mg, 0.91 mmol) and degassed DMF (2mL). A rubber septum was used to seal the tube and the contents were then flushed several times with argon, then closed tightly with a cap. The mixture was heated at 110° C. under argon for 18 hours, cooled to room temperature then diluted with 200 mL ethyl acetate. The organic layer was washed with sat. NaHCO$_3$, then brine and dried over Na$_2$SO$_4$. Evaporation of the solvent and purification of the residue by flash chromatography on silica gel, using 5% ethyl acetate in hexanes, afforded the title compound (35 mg, 52%) as white solid. $^1$H NMR (CDCl$_3$) □ 2.79-2.84 (m, 2H), 4.25 (t, 2H, J=5.7 Hz), 5.06-5.08 (m, 1H), 6.19 (d, 1H, J=1.6 Hz), 7.08-7.17 (m, 2H), 8.20 (dd, 1H, J=1.6, 4.7 Hz); ES-MS m/z 148.0 (M+H).

4-Hydroxymethyl-3,4-dihydro-2H-pyrano[3,2-b]pyridinyl-4-ol.

To a solution of 4-methylene-3,4-dihydro-2H-pyrano[3,2-b]pyridine (247 mg, 1.69 mmol) and 4-methylmorpholine N-oxide (608 mg, 5.03 mmol) in CH$_2$Cl$_2$ (4 mL) was added osmium tetroxide (2.5 wt. % solution in 2-methyl-2-propanol, 0.4 mL, 0.03 mmol). The mixture was stirred at room temperature under N$_2$ for 24 hours, diluted with 200 mL ethyl acetate, then filtered though a pad of celite. Evaporation of the solvent and purification of the residue by flash chromatograph on silica gel, using 3:3:94 CH$_3$OH—NH$_3$H$_2$O—CH$_2$Cl$_2$, afforded the title compound (276 mg, 90%) as white solid. $^1$H NMR (CD$_3$OD) □ 2.00 (ddd, 1H, J=3.0, 5.1, 14.1 Hz), 2.32 (ddd, 1H, J=5.1, 9.6, 14.4 Hz), 3.84 (d, 1H, J=11.1 Hz), 3.95 (d, 1H, J=11.1 Hz), 4.30-4.36 (m, 2H), 7.21-7.23 (m, 2H), 8.13 (dd, 1H, J=3.0, 3.0 Hz); ES-MS m/z 182.0 (M+H).

2,3-Dihydro-pyrano[3,2-b]pyridinyl-4-one.

To a solution of 4-hydroxymethyl-3,4-dihydro-2H-pyrano [3,2-b]pyridinyl-4-ol (276 mg, 1.52 mmol) in H$_2$O (2 mL) was added sodium periodate (649 mg, 3.04 mmol). The mixture was allowed to stir at room temperature for 2 hours and diluted with large volume of ethyl acetate, then dried over Na$_2$SO$_4$. Evaporation of the solvent and purification of the residue by flash chromatography on silica gel, using 20% ethyl acetate in CH$_2$Cl$_2$, gave the title compound (126 mg, 74%) as white solid. $^1$H NMR (CDCl$_3$) □ 2.97 (t, 2H, J=6.6 Hz), 4.61 (t, 2H, J=6.6 Hz), 7.36-7.43 (m, 2H), 8.44 (dd, 1H, J=2.1, 12.6 Hz); ES-MS m/z 150.1 (M+H).

N-(2-nitrobenzenesulfonyl)-N-(2-pyridinylmethyl)-N'-(3,4-dihydro-2H-pyrano[3,2-b]pyridinyl)-1,4-benzenedimethanamine.

Using general procedure B: Reaction of 2,3-dihydro-pyrano[3,2-b]pyridinyl-4-one (45 mg, 0.30 mmol), N-(2-nitrobenzenesulfonyl)-N-(2-pyridinyl)-1,4-benzenedimethanamine (137 mg, 0.33 mmol), acetic acid (0.05 mL) and sodium triacetoxyborohydride (189 mg, 0.90 mmol) in THF (5 mL) at 50° C. for 40 min., followed by purification of crude material using radial chromatography on silica gel (2 mm plate, 3:3:94 CH$_3$OH—NH$_3$H$_2$O—CH$_2$Cl$_2$), afforded the title compound (107 mg, 66%) as white form. $^1$H NMR (CDCl₃) □ 1.99-2.09 (m, 1H), 2.18-2.21 (m, 1H), 3.83-3.95 (m, 3H), 4.13-4.22 (m, 1H), 4.34-4.41 (m, 1H), 4.58 (s, 2H), 4.59 (s, 2H), 7.06-7.15 (m, 6H), 7.20-7.24 (m, 2H), 7.51-7.57 (m, 2H), 7.61-7.67 (m, 2H), 7.94 (d, 1H, J=8.0 Hz), 8.14 (dd, 1H, J=2.1, 3.9 Hz), 8.40 (d, 1H); ES-MS m/z 546.1 (M+H).

Using general procedure C: Reaction of N-(2-nitrobenzenesulfonyl)-N-(2-pyridinylmethyl)-N'-(3,4-dihydro-2H-pyrano[3,2-b]pyridinyl)-1,4-benzenedimethanamine (96 mg, 0.17 mmol) with thiophenol (0.037 mL, 0.36 mmol) and K₂CO₃ (73 mg, 0.54 mmol) in DMF (1.5 mL) at room temperature under N₂ for 16 hours followed by purification of crude material using radial chromatography on silica gel (1 mm plate, 3:3:94 CH₃OH—NH₃H₂O—CH₂Cl₂), afforded AMD9410 (55 mg, 87%). ¹H NMR (CDCl₃) □ 2.01-2.22 (m, 2H), 2.34 (br, s, 2H), 3.81(s, 2H), 3.88-3.99 (m, 5H), 4.14-4.20 (m, 1H), 4.33-4.38 (m, 1H), 7.03-7.16 (m, 3H), 7.26-7.37 (m, 5H), 7.62 (ddd, 1H, J=1.5, 7.5, 7.8 Hz), 8.13 (dd, 1H, J=1.8, 4.2 Hz), 8.53 (d, 1H); ¹³C NMR (CDCl₃) □ 28.15, 51.85, 53.62, 53.93, 54.85, 63.94, 122.33, 122.75, 123.86, 124.47, 128.67, 128.78, 136.82, 139.20, 139.48, 141.79, 144.85, 149.71, 151.72, 160.11; ES-MS m/z 361.2 (M+H); Anal. Calcd. for (C₂₂H₂₄N₄O).0.3(H₂O): C, 72.22; H, 6.78; N, 15.31. Found: C, 72.19; H, 6.71; N, 15.16.

EXAMPLE: 40

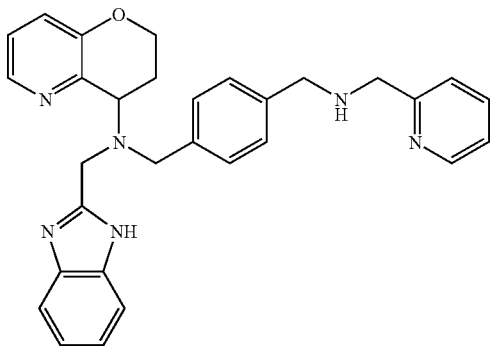

AMD9418: Preparation of N-(2-pyridinylmethyl)-N'-(1-H-benzimidazol-2-ylmethyl)-N'-(3,4-dihydro-2H-pyrano[3,2-b]pyridinyl)-1,4-benzenedimethanamine(hydrobromide salt)

Preparation of N-(tert-butoxycarbonyl)-N-(2-pyridinylmethyl)-N'-(3,4-dihydro-2H-pyrano[3,2-b]pyridinyl)-1,4-benzenedimethanamine Using general procedure B: Reaction of 2,3-Dihydropyrano[3,2-b]pyridinyl-4-one (126 mg, 0.84 mmol), N-(tert-butoxycarbonyl)-N-(2-pyridinyl)-1,4-benzenedimethanamine (303 mg, 0.92 mmol), acetic acid (0.4 mL) and sodium triacetoxyborohydride (534 mg, 2.50 mmol) in THF (8 mL) at room temperature under N₂ for 40 min., followed by purification of crude material using radial chromatography on silica gel (2 mm plate, 3:3:94 CH₃OH—NH₃H₂O—CH₂Cl₂), afforded the title compound (290 mg, 74%) as white form. ¹H NMR (CDCl₃) □ 1.44 (br, d, 9H), 2.08-2.22 (m, 2H), 3.89 (d, 1H, J=13.2 Hz), 3.99 (d, 1H, J=13.2 Hz), 4.16-4.22 (m, 1H), 4.33-4.38 (m, 1H), 4.39-4.44 (m, 5H), 7.05-7.19 (m, 6H), 7.32 (d, 2H, J=8.1 Hz), 7.63 (ddd, 1H, J=1.8, 7.5, 7.8 Hz), 8.14 (dd, 1H, J=1.8, 4.2 Hz), 8.51 (d, 1H, J=4.2 Hz); ES-MS m/z 461.1 (M+H).

N-(tert-butoxycarbonyl)-N-(2-pyridinylmethyl)-N'-[1-(2-trimethylsilyl)ethoxy]methyl-benzimidazol-2-ylmethyl]-N'-(3 4-dihydro-2H-pyrano[3,2-b]pyridinyl)-1,4-benzenedimethanamine Using general procedure B: Reaction of N-(tert-butoxycarbonyl)-N-(2-pyridinylmethyl)-N'-(3,4-dihydro-2H-pyrano[3,2-b]pyridinyl)-1,4-benzenedimethanamine (270 mg, 0.59 mmol), 1-[(2-trimethylsily)ethoxy]methyl-benzimidazol-2-carboxaldehyde (174 mg, 0.63 mmol), acetic acid (0.2 mL) and sodium triacetoxyborohydride (400 mg, 1.88 mmol) in THF (6.3 mL) at room temperature under N₂ for 40 min., followed by purification of the crude material using radial chromatography on silica gel (2 mm plate, 3:3:94 CH₃OH—NH₃H₂O—CH₂Cl₂), afforded the title compound (209 mg, 78% yield, 63% conversion) as pale yellow foam. ¹H NMR (CDCl₃) □ 0.15 (s, 6H), 0.74 (dd, 2H, J=8.1, 8.1 Hz), 1.45 (br, d, 9H), 2.17-2.22 (m, 1H), 2.35-2.40 (m, 1H), 3.26 (dd, 2H, J=8.1, 8.1 Hz), 3.64 (d, 1H, J=14.1 Hz), 3.86 (d, 1H, J=14.1 Hz), 4.03-4.18 (m, 3H), 4.27 (d, 1H, J=13.2 Hz), 4.33-4.38 (m, 3H), 4.44-4.47 (m, 2H), 5.64 (d, 1H, J=11.1 Hz), 5.96 (d, 1H, J=12.3 Hz), 7.06 (d, 2H, J=3.0 Hz), 7.11-7.15 (m, 3H), 7.17-7.22 (m, 3H), 7.29 (d, 2H, J=8.1 Hz), 7.38-7.42 (m, 1H), 7.61 (ddd, 1H, J=1.5, 7.8, 7.8 Hz), 7.66-7.71 (m, 1H), 8.29 (dd, 1H, J=3.0, 3.0 Hz), 8.50 (d, 1H); ES-MS m/z 721.6 (M+H).

Using general procedure E: Reaction of N-(tert-butoxycarbonyl)-N-(2-pyridinylmethyl)-N'-{[1-(2-trimethylsilyl) ethoxy]methyl-benzimidazol-2-ylmethyl}-N'-(3,4-dihydro-2H-pyrano[3,2-b]pyridinyl)-1,4benzenedimethanamine (209 mg, 0.29 mmol) and 6N HCl (3 mL) at 50° C. for 3 hours under N₂ followed by purification of crude material using radial chromatography on silica gel (2 mm plate, 3:3:94 CH₃OH—NH₃H₂O—CH₂Cl₂), afford the desired intermediate (130 mg, 93%) as pale yellow oil.

Using general procedure D: The oil from above was converted to the corresponding hydrobromide salt to afford AMD9418. ¹H NMR (D₂O) □ 2.55-2.70 (m, 2H), 3.80 (s, 2H), 3.86 (s, 2H), 4.11 (s, 2H), 4.41-4.71 (m, 4H), 4.95 (dd, 1H, J=6.6, 9.6 Hz), 7.04 (d, 2H, J=7.8 Hz), 7.22 (d, 2H, J=7.8 Hz), 7.33-7.36 (m, 2H), 7.51-7.54 (m, 2H), 7.59 (d, 1H, J=7.8 Hz), 7.67 (dd, 1H, J=5.7, 6.9 Hz), 7.88-7.93 (m, 1H), 8.04 (d, 1H, J=8.7 Hz), 8.14 (dd, 1H, J=6.9, 7.5 Hz), 8.53 (d, 1H, J=5.4 Hz), 8.64 (d, 1H, J=4.5 Hz); ¹³C NMR (D₂O) □ 20.31, 49.09, 49.78, 50.35, 56.54, 58.86, 67.40, 113.90, 126.15, 126.28, 126.67, 127.80, 130.24, 130.42, 130.91, 135.09, 135.45, 137.91, 138.38, 142.38, 147.54, 148.27, 151.66, 156.19; ES-MS m/z 491.2 (M+H); Anal. Calcd. for (C₃₀H₃₀N₆O).3.8 (HBr).2.4(H₂O): C, 42.83; H, 4.62; N, 9.99; Br, 36.09. Found: C, 42.99; H, 4.57; N, 9.90; Br, 35.95.

EXAMPLE: 41

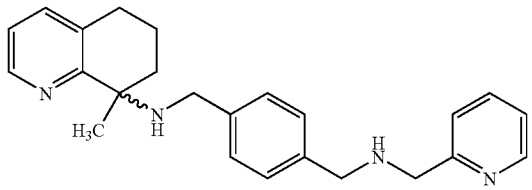

AMD9361: Preparation of N-(2-pyridinylmethyl)-N'-(8-methyl-5,6,7,8-tetrahydro-8-quinolinyl)-1,4-benzenedimethanamine(hydrobromide salt)

6,7-Dihydro-5H-quinolin-8-one 8-hydroxy-5,6,7,8-tetrahydroquinoline was prepared as described in Bridger et al. PCT International Application PCT/CA00/00321. To a stirred solution of 8-hydroxy-5,6,7,8-tetrahydroquinoline (1.37 g, 9.18 mmol) in dry CH₂Cl₂ (50 mL) was added activated manganese dioxide (85% purity, 7.51 g, 73.5 mmol) in one portion. The resulting heterogeneous mixture was stirred vigorously for 4 days, at which point the black slurry was filtered through a cake of celite and washed with CH$_2$Cl$_2$ (3×50 mL). The combined filtrates were concentrated to afford 1.15 g (85%) of the title compound as an off-white solid. This material was used directly in subsequent steps without further purification. $^1$H NMR (CDCl$_3$) □ 2.17-2.25 (m, 2H), 2.82 (t, 2H, J=6 Hz), 3.04 (t, 2H, J=6 Hz), 7.39 (dd, 1H, J=9, 5 Hz), 7.66 (dt, 1H, J=9, 1 Hz), 8.71 (dd, 1H, J=5, 1 Hz); $^{13}$C NMR (CDCl$_3$) □ 22.2, 28.6, 39.2, 126.6, 137.3, 140.4, 147.6, 148.6, 196.5.

8-Methyl-5,6,7,8-tetrahydroquinolin-8-ol

A 3.0 M solution of methylmagnesium bromide in THF (6.80 mL, 20.4 mmol) was added dropwise to a cold (0° C.), stirred solution of 6,7-dihydro-5H-quinolin-8-one (2.00 g, 13.6 mmol) in dry CH$_2$Cl$_2$ (50 mL). The resulting solution was stirred at 0° C. for 1 h, then warmed slowly to room temperature and stirred for a further 1 h. Saturated aqueous NH$_4$Cl (50 mL) was added cautiously and the phases were separated. The aqueous layer was extracted with CH$_2$Cl$_2$ (3×50 mL) and the combined organic extracts were dried (MgSO$_4$) and concentrated. Flash chromatography (silica gel, EtOAc) of the crude material afforded 0.80 g (40% recovery) starting material and 1.06 g (48%) of the title compound as a white crystalline solid. $^1$H NMR (CDCl$_3$) □ 1.53 (s, 3H), 1.67-1.83 (m, 1H), 1.85-2.06 (m, 3H), 2.78-2.83 (m, 2H), 3.77 (br s, 1H), 7.09 (dd, 1H, J=8, 4 Hz), 7.38 (dt, 1H, J=8, 1 Hz), 8.40 (dd, 1H, J=4, 1 Hz); $^{13}$C NMR (CDCl$_3$) □ 19.7, 28.7, 30.3, 36.8, 70.6, 122.1, 130.5, 136.8, 146.9, 160.8.

8-Methyl-5,6,7,8-tetrahydroquinolin-8-ylamine

To a cold (0° C.) stirred solution of 8-methyl-5,6,7,8-tetrahydroquinolin-8-ol (1.06 g, 6.49 mmol) in dry CH$_2$Cl$_2$ (30 mL) was added triethylamine (2.0 mL, 14 mmol) followed by methanesulfonyl chloride (0.80 mL, 10.3 mmol). The resulting mixture was stirred at 0° C. for 1 h, then warmed slowly to room temperature and stirred for a further 1 h. Saturated aqueous NaHCO$_3$ (30 mL) was added and the phases were separated. The aqueous layer was extracted with CH$_2$Cl$_2$ (3×30 mL) and the combined organic extracts were dried (MgSO$_4$) and concentrated (note: the resulting mesylate is relatively unstable and should be used immediately upon preparation). The resulting pale yellow oil was taken up in dry DMF (15 mL) and solid sodium azide (844 mg, 13.0 mmol) was added; the suspension was then heated to 60° C. and stirred vigorously for 3 h. Next, the reaction mixture was cooled to room temperature, diluted with CH$_2$Cl$_2$ (30 mL) and poured into saturated aqueous NaHCO$_3$ (50 mL). The phases were separated and the aqueous layer was extracted with CH$_2$Cl$_2$ (3×30 mL), then the combined organic extracts were washed once with brine (20 mL), dried (MgSO$_4$), and concentrated in vacuo (a reduced pressure of ~0.5 Torr was required to remove all traces of DMF). Flash chromatography (silica gel, 4:1 hexanes-EtOAc) of the crude material afforded 1 g of a pale yellow oil that $^1$H NMR and MS analysis indicated was a 59:20:21 mixture of 8-methyl-5,6-dihydro-quinoline, 8-methylene-5,6,7,8-tetrahydro-quinoline and 8-azido-8-methyl-5,6,7,8-tetrahydroquinoline, respectively. This material was taken up in dry MeOH (20 mL), flushed with nitrogen, and 10% palladium on carbon (100 mg) was added; the mixture was hydrogenated (50 psi) on a Parr Shaker for 5 h. The crude material was filtered through a cake of celite and washed with MeOH (3×20 mL) then the combined washings were concentrated. Flash chromatography (silica gel, 20:2:1 CHCl$_3$—MeOH—NH$_4$OH) of the crude material afforded 180 mg (17%) of the title compound as a pale yellow oil. $^1$H NMR (CDCl$_3$) □ 1.46 (s, 3H), 1.82-1.89 (m, 3H), 1.90-2.03 (m, 3H), 2.77-2.81 (m, 2H), 7.04 (dd, 1H, J=9, 5 Hz), 7.35 (dt, 1H, J=9, 1 Hz), 8.42 (dd, 1H, J=5, 1 Hz); $^{13}$C NMR (CDCl$_3$) □ 19.6, 29.5, 30.9, 38.6, 52.3, 121.4, 130.3, 136.7, 147.1, 163.1. ES-MS m/z 163 (M+H).

Preparation of N-(2-Pyridinylmethyl)-N'-(8-methyl-5,6,7,8-tetrahydro-8-quinolinyl)-1,4-benzenedimethanamine (AMD9361)

Using general procedure B: 8-Methyl-5,6,7,8-tetrahydro-quinolin-8-ylamine (44 mg, 0.30 mmol) and 4-[[N-(tert-butoxycarbonyl)-N-(2-pyridinylmethyl)amino]methyl]benzylaldehyde (97 mg, 0.30 mmol) were converted into the corresponding reductive amination adduct using the following quantities of reagents and solvents: NaBH(OAc)$_3$ (127 mg, 0.60 mmol), CH$_2$Cl$_2$ (3 mL). The reaction time in this case was 18 h. Purification of the crude material by radial chromatography (2 mm plate, 20:2:1 CHCl$_3$—MeOH—NH$_4$OH) afforded 121 mg (89%) of N-tert-butoxycarbonyl-N-(2-pyridinylmethyl)-N'-(8-methyl-5,6,7,8-tetrahydro-8-quinolinyl)-1,4-benzenedimethanamine as a colourless oil.

Using general procedure D: the intermediate from above (121 mg, 0.26 mmol) was converted to the hydrobromide salt with simultaneous deprotection of the BOC group to afford 89 mg (79%) of AMD9361 as a white solid. $^1$H NMR (D$_2$O) □ 1.84 (s, 3H), 2.02-2.11 (m, 2H), 2.27-2.35 (m, 1H), 2.44-2.53 (m, 1H), 2.93-3.08 (m, 2H), 4.02 (d, 1H, J=12 Hz), 4.30 (d, 1H, J=12 Hz), 4.50 (s, 2H), 4.75 (s, 2H), 7.50-7.60 (m, 5H), 7.93 (dd, 1H, J=8, 1 Hz), 8.05-8.10 (m, 1H), 8.15 (d, 1H, J=8 Hz), 8.57-8.63 (m, 2H), 8.87 (br d, 1H, J=6 Hz); $^{13}$C NMR (D$_2$O) □ 18.5, 25.7, 27.8, 31.2, 46.2, 47.7, 51.7, 62.6, 125.5, 128.1, 128.4, 131.3, 131.6, 133.1, 136.4, 142.2, 144.4, 145.6, 146.4, 147.1, 150.6. ES-MS m/z 373 (M+H). Anal. Calcd. for C$_{24}$H$_{28}$N$_4$.4.6HBr.1.8H$_2$O: C, 37.09; H, 4.69; N, 7.21; Br, 47.30. Found: C, 36.99; H, 4.68; N, 6.99; Br, 47.43.

EXAMPLE: 42

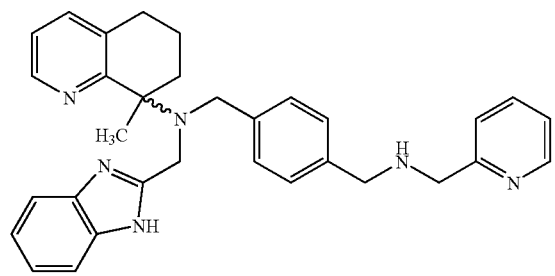

AMD9405: Preparation of N-(2-pyridinylmethyl)-N'-(1H-benzimidazol-2-ylmethyl)-N'-(8-methyl-5,6,7,8-tetrahydro-8-quinolinyl)-1,4-benzenedimethanamine (free base)

2-Chloromethyl-1-(2-trimethylsilylethoxymethyl)-1H-benzimidazole

To a stirred solution of 2-chloromethylbenzimidazole (1.89 g, 11.4 mmol) in dry THF (57 mL) was added N,N-diisopropylethylamine (3.00 mL, 17.2 mmol) and 2-(trimethylsilyl)ethoxymethyl chloride (1.90 mL, 10.8 mmol) both via syringe under nitrogen at room temperature. The mixture was stirred for 3 days at which time the solvent was removed in vacuo. The residue was taken up in CH$_2$Cl$_2$ (100 mL) and washed with water (100 mL) and brine (100 mL). The organic layer was dried over sodium sulfate, filtered, and concentrated in vacuo to afford the crude product as a yellow oil.

Purification by flash chromatography (silica gel, 100:2:1 $CH_2Cl_2$-methanol-ammonium hydroxide) provided 2.17 g (65%) of the title compound as a yellow oil, which solidified on standing. $^1$H NMR ($CDCl_3$) δ −0.06 (s, 9H), 0.92 (t, 2H, J=7.5 Hz), 3.57 (t, 2H, J=7.5 Hz), 4.91 (s, 2H), 5.65 (s, 2H), 7.31-7.36 (m, 2H), 7.50 (d, 1H, J=7.5 Hz), 7.78 (d, 1H, J=7.5 Hz).

N-(2-Pyridinylmethyl)-N'-(1H-benzimidazol-2-ylmethyl)-N'-(8-methyl-5,6,7,8-tetrahydro-8-quinolinyl)-1,4-benzenedimethanamine (AMD9405)

Reaction of N-tert-Butoxycarbonyl-N-(2-pyridinylmethyl)-N'-(8-methyl-5,6,7,8-tetrahydro-8-quinolinyl)-1,4-benzenedimethanamine (120 mg, 0.26 mmol), 2-chloromethyl-1-(2-trimethylsilylethoxymethyl)-1H-benzimidazole (234 mg, 0.79 mmol) and diisopropylethylamine (229 µL, 1.31 mmol) in DMF (2.6 mL) for 18 h at 90° C. followed by purification of the crude material by radial chromatography (2 mm plate, 20:2:1 $CHCl_3$—MeOH—$NH_4OH$) afforded 90 mg (48%) of N-tert-butoxycarbonyl-N-(2-pyridinylmethyl)-N'-(1-(2-trimethylsilylethoxymethyl)-1H-benzimidazol-2-ylmethyl)-N'-(8-methyl-5,6,7,8-tetrahydro-8-quinolinyl)-1,4-benzenedimethanamine as a colourless oil.

The compound from above was taken up in dry $CH_2Cl_2$ (1 mL) and trifluoroacetic acid (1 mL) was added, then the mixture was stirred 18 h. At this time the solvent was removed in vacuo and the residue was dissolved in dry MeOH (3 mL) and anhydrous $K_2CO_3$ (87 mg, 0.63 mmol) was added. The resulting suspension was stirred for 2 h, then the solvent was removed in vacuo, and the residue was dissolved in $CHCl_3$ (5 mL). This material was filtered through a cake of celite and washed with $CHCl_3$ (3×10 mL), then the combined washings were concentrated. Purification of the crude material by radial chromatography (1 mm plate, 50:1:1 $CHCl_3$—MeOH—$NH_4OH$) afforded 36 mg (57%) of AMD9405 as an off-white foam. $^1$H NMR ($CDCl_3$) □ 1.60 (s, 3H), 1.79-1.93 (m, 2H), 2.01-2.12 (m, 2H), 2.26 (td, 1H, J=12, 3 Hz), 2.81-2.87 (m, 2H), 3.62 (d, 1H, J=15 Hz), 3.64 (s, 2H), 3.74 (s, 2H), 3.82 (d, 1H, J=15 Hz), 3.98 (d, 1H, J=18 Hz), 4.35 (d, 1H, J=18 Hz), 7.08-7.22 (m, 10H), 7.42-7.46 (m, 2H), 7.53 (br s, 1H), 7.62 (td, 1H, J=8, 2 Hz), 8.54 (br d, 1H, J=5 Hz), 8.61 (dd, 1H, J=5, 2 Hz); $^{13}$C NMR ($CDCl_3$) □ 20.7, 28.1, 29.6, 33.8, 47.1, 52.9, 54.2, 54.5, 62.8, 121.8, 122.0, 122.4, 127.9, 128.7, 133.8, 136.3, 137.7, 138.3, 138.6, 146.7, 149.2, 157.1, 159.8, 161.9. ES-MS m/z 503 (M+H). Anal. Calcd. for $C_{32}H_{34}N_6.0.6H_2O.1.4C_2H_6O$: C, 72.32; H, 7.60; N, 14.54. Found: C, 72.67; H, 7.21; N, 14.14.

EXAMPLE: 43

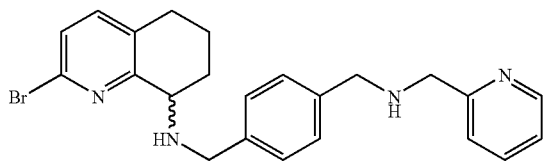

AMD9412: Preparation of N-(2-pyridinylmethyl)-N'-(2-bromo-5,6,7,8-tetrahydro-8-quinolinyl)-1,4-benzenedimethanamine(hydrobromide salt)

2-Bromo-5,6,7,8-tetrahydroquinolin-8-ol was prepared according to the procedure described by Zimmerman et al. (Zimmerman, S. C.; Zeng, Z.; Wu, W.; Reichert, D. E. J. Am. Chem. Soc. 1991, 113, 183-196).

To a cold (0° C.) stirred solution of 2-bromo-5,6,7,8-tetrahydroquinolin-8-ol (500 mg, 2.36 mmol) in dry $CH_2Cl_2$ (10 mL) was added triethylamine (0.72 mL, 5.2 mmol) followed by methanesulfonyl chloride (0.35 mL, 3.6 mmol). The resulting mixture was stirred at 0° C. for 1 h, then warmed slowly to room temperature and stirred a further 1 h. Saturated aqueous $NaHCO_3$ (30 mL) was added and the phases were separated. The aqueous layer was extracted with $CH_2Cl_2$ (3×30 mL) and the combined organic extracts were dried ($MgSO_4$) and concentrated to give 605 mg (88%) of 2-bromo-5,6,7,8-tetrahydroquinolin-8-yl methanesulfonate as an orange solid.

The material from above (216 mg, 0.74 mmol) was taken up in dry DMSO (6 mL) and triethylamine (0.40 mL, 3.7 mmol) and N-tert-butoxycarbonyl-N-(2-pyridinylmethyl)-1,4-benzenedimethanamine (244 mg, 0.74 mmol) were added. The mixture was stirred at 80° C. for 18 h, at which point the reaction was cooled to room temperature and diluted with $CH_2Cl_2$ (150 mL); the resulting solution was washed with water (20 mL) and brine (20 mL), dried ($MgSO_4$), and concentrated. Purification of the crude material by flash chromatography (silica gel, 20:1:1 $CH_2Cl_2$—MeOH—$NH_4OH$) afforded 175 mg (44%) of N-tert-butoxycarbonyl-N-(2-pyridinylmethyl)-N'-(2-bromo-5,6,7,8-tetrahydro-8-quinolinyl)-1,4-benzenedimethanamine as a pale yellow oil.

Using general procedure D: the intermediate from above (40 mg, 0.074 mmol) was converted to the hydrobromide salt with simultaneous deprotection of the BOC group to afford 33 mg (57%) of the title compound as a white solid. $^1$H NMR ($D_2O$) □ 1.81-1.89 (m, 1H), 1.99-2.11 (m, 2H), 2.44-2.50 (m, 1H), 2.82-2.85 (m, 2H), 4.44 (br s, 2H), 4.49 (s, 2H), 4.57 (dd, 1H), J=10, 6 Hz), 7.52 (d, 1H, J=8 Hz), 7.57 (d, 1H, J=8 Hz), 7.60 (d, 2H, J=10 Hz), 7.64 (d, 2H, J=10 Hz), 7.98 (dd, 1H, J=6,7 Hz), 8.04 (d, 1H, J=8 Hz), 8.50 (td, 1H, J=8, 1 Hz), 8.82 (d, 1H, J=5 Hz); $^{13}$C NMR ($D_2O$) □ 22.2, 27.4, 29.5, 50.6 (2 peaks), 54.1, 59.5, 130.2, 130.4, 131.3, 133.7, 133.8, 134.2, 135.7, 136.9, 141.1, 144.3, 147.6, 148.6, 148.9, 153.3. ES-MS m/z 437 (M+H). Anal. Calcd. for $C_{23}H_{25}BrN_4.3.8HBr2.1H_2O$: C, 35.30; H, 4.25; N, 7.16; Br, 49.00. Found: C, 35.50; H, 4.44; N, 6.90; Br, 48.88.

EXAMPLE: 44

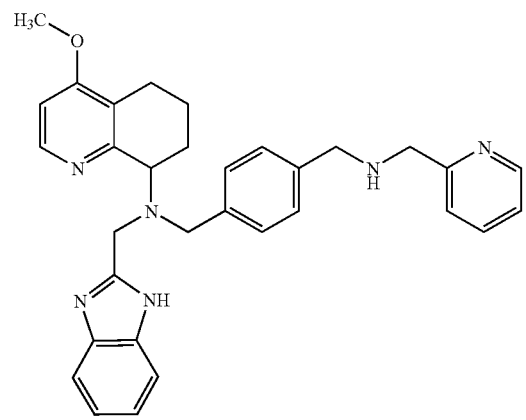

AMD9343: Preparation of N-(2-pyridinylmethyl)-N'-[1H-benzimidazol-2-ylmethyl]-N'-(4-methoxy-5,6,7,8-tetrahydro-8-quinolinyl)-1,4-benzenedimethanamine(hydrobromide salt)

8-amino-4-methoxy-5,6,7,8-tetrahydroquinoline 8-amino-4-methoxy-5,6,7,8-tetrahydroquinoline was prepared in 68% yield from 8-hydroxy-4-methoxy-5,6,7,8-tetrahydroquinoline (preparation and characterization described by: Uchida, M.; Morita, S.; Chihiro, M.; Kanbe, T.; Yamasaki, K.; Yabuuchi, Y.; Nakagawa, K. *Chem. Pharm. Bull.* 1989, 37, 1517-1523) using the same procedure employed to prepare 8-amino-5,6,7,8-tetrahydroquinoline (see Bridger et al. PCT International Application PCT/CA00/00321). $^1$H NMR (CDCl$_3$) ☐ 1.59-2.15 (m, 6H), 2.60-2.65 (m, 2H), 3.84 (s, 3H), 3.95 (dd, 1H, J=6.0, 9.0 Hz), 6.61 (d, 1H, J=6.0 Hz). 8.32 (d, 1H, J=6.0 Hz); $^{13}$C NMR (CDCl$_3$) ☐ 19.53, 22.89, 31.94, 51.57, 55.62, 104.04, 120.94, 148.52, 160.42, 163.71; ES-MS m/z 179 (M+H).

N-(2-pyridinylmethyl)-N-(2-nitrobenzenesulfonyl)-N'-(4-methoxy-5,6,7,8-tetrahydro-8-quinolinyl)-1,4-benzenedimethanamine Using General Procedure B: Reaction of 8-amino-4-methoxy-5,6,7,8-tetrahydroquinoline (0.860 g, 4.83 mmol) and N-[1-methylene-4-(carboxaldehyde)phenylene]-N-(2-nitrobenzenesulfonyl)-2-(aminomethyl)pyridine (PCT Int. Application PCT/CA00/00321) (1.981 g, 4.82 mmol) with NaBH(OAc)$_3$ (1.555 g, 7.34 mmol) in CH$_2$Cl$_2$ (24 mL) for 21 hours followed by purification of the crude material by column chromatography on silica gel (20:1:1 CH$_2$Cl$_2$—MeOH—NH$_4$OH) provided 1.68 g (61%) of the title compound as a white solid. $^1$H NMR (CDCl$_3$) ☐ 1.64-1.80 (m, 2H), 1.97-2.23 (m, 2H), 2.56-2.73 (m, 2H), 3.75-3.93 (m, 6H), 4.57 (s, 2H), 4.60 (s, 2H), 6.62 (d, 1H, J=5.7 Hz). 7.07-7.12 (m, 3H), 7.21-7.27 (m, 3H), 7.52-7.57 (m, 2H), 7.60-7.65 (m, 2H), 7.93 (d, 1H, J=7.8 Hz), 8.31 (d, 1H, J=5.7 Hz); 8.42 (d, 1H, J=7.2 Hz);

A solution of N-(2-pyridinylmethyl)-N-(2-nitrobenzenesulfonyl)-N'-(4-methoxy-5,6,7,8-tetrahydro-8-quinolinyl)-1,4-benzenedimethanamine (0.337 g, 0.621 mmol), tert-butoxycarbonyl)-2-(chloromethyl)benzimidazole (0.302 g, 1.13 mmol) and N,N-diisopropylethylamine (0.3 mL, 1.725 mmol) in CH$_3$CN (6 mL) was heated at 80° C. for 5 days. Purification of the crude material by radial chromatography on silica gel (2 mm plate, 20:1:1 CH$_2$Cl$_2$—MeOH—NH$_4$OH) provided 0.360 g of the alkylated material as a tan solid.

Using general procedure C: the tan solid from above (0.360 g) was treated with thiophenol (0.30 mL, 2.92 mmol) and K$_2$CO$_3$ (0.664 g, 4.81 mmol) in CH$_3$CN (9 mL). Purification of the crude material by column chromatography on silica gel (20:1 CH$_2$Cl$_2$—MeOH followed by 20:1:1 CH$_2$Cl$_2$—MeOH—NH$_4$OH) provided 0.098 g (30%) of the free base of the title compound and 0.052 g (14%) of N-(2-pyridinylmethyl)-N'-[2-(tert-butoxycarbonyl)-1H-benzimidazol-2-ylmethyl]-N'-(4-methoxy-5,6,7,8-tetrahydro-8-quinolinyl)-1,4-benzenedimethanamine.

Using general procedure D: N-(2-pyridinylmethyl)-N'-[2-(tert-butoxycarbonyl)-1H-benzimidazol-2-ylmethyl]-N'-(4-methoxy-5,6,7,8-tetrahydro-8-quinolinyl)-1,4-benzenedimethanamine (0.052 g) was converted to the corresponding hydrobromide salt with simultaneous de-protection of the BOC group. The salt was purified by re-precipitation from methanol/ether to give AMD9343 as an orange-brown solid (0.055 g). $^1$H NMR (D$_2$O) ☐ 1.75-1.84 (m, 1H), 2.09-2.21 (m, 2H), 2.34-2.39 (m, 1H), 2.58-2.69 (m, 1H), 2.88 (br d, 1H, J=16.5 Hz), 3.74-3.86 (m, 4H), 4.12 (s, 3H), 4.18 (s, 2H), 4.40 (d, 1H, J=16.5 Hz), 4.58 (d, 1H, J=16.5 Hz), 4.65 (dd, 1H, J=6.6, 9.9 Hz), 7.04 (d, 2H, J=7.8 Hz), 7.23 (d, 2H, J=7.8 Hz), 7.37 (dd, 2H, J=6.0, 3.0 Hz), 7.42 (d, 1H, J=6.9 Hz), 7.53 (dd, 2H, J=6.0, 3.0 Hz), 7.70 (d, 1H, J=7.8 Hz), 7.76 (dd, 1H, J=6.3, 6.3 Hz), 8.24 (ddd, 1H, J=7.8, 7.8, 1.2 Hz), 8.64 (d, 1H, J=6.9 Hz), 8.68 (d, 1H, J=5.1 Hz); $^{13}$C NMR (D$_2$O) ☐ 19.77, 20.61, 21.83, 48.65, 50.03, 50.49, 56.65, 58.18, 62.92, 107.71, 113.89 (2 carbons), 126.61 (2 carbons), 126.70, 128.63, 129.93, 130.19 (2 carbons), 130.45, 130.90 (2 carbons), 138.41, 141.43 (2 carbons), 143.49 (2 carbons), 146.79, 147.64, 149.67, 151.86, 171.08; ES-MS m/z 519 (M+H). Anal. Calcd. for C$_{32}$H$_{34}$N$_6$O.4.0HBr.4.2H$_2$O: C, 41.87; H, 5.09; N, 9.15; Br, 34.82. Found: C, 41.84; H, 4.79; N, 9.02; Br, 34.85.

EXAMPLE: 45

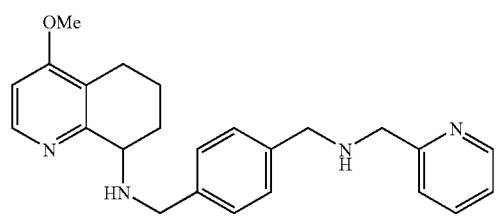

AMD9358: Preparation of N-(2-pyridinylmethyl)-N'-(4-methoxy-5,6,7,8-tetrahydro-8-quinolinyl)-1,4-benzenedimethanamine(hydrobromide salt)

N-(2-pyridinylmethyl)-N'-(4-methoxy-5,6,7,8-tetrahydro-8-quinolinyl)-1,4-benzenedimethanamine Using general procedure C: N-(2-pyridinylmethyl)-N-(2-nitrobenzenesulfonyl)-N'-(4-methoxy-5,6,7,8-tetrahydro-8-quinolinyl)-1,4-benzenedimethanamine (0.269 g, 0.50 mmol) was treated with thiophenol (0.35 mL, 3.41 mmol) and K$_2$CO$_3$ (0.757 g, 5.48 mmol) in CH$_3$CN (10 mL). Purification of the crude material by radial chromatography on silica gel (2 mm plate, 20:1:1 CH$_2$Cl$_2$—CH$_3$OH—NH$_4$OH) provided 0.158 g (82%) of the title compound as a yellow oil. $^1$H NMR (CDCl$_3$) ☐ 1.61-1.80 (m, 2H), 1.98-2.17 (m, 2H) 2.56-2.70 (m, 2H), 3.79-3.83 (m, 6H), 3.88-3.98 (m, 4H), 6.60 (d, 1H, J=5.7 Hz). 7.15 (dd, 1H, J=5.1, 6.9 Hz), 7.23-7.41 (m, 5H) 7.63 (ddd, 1H, J=7.8, 7.8, 1.8 Hz), 8.30 (d, 1H, J=5.7 Hz); 8.55 (d, 1H, J=3.9 Hz);

Using general procedure D: Conversion of the free base (0.051 g, 0.13 mmol) to the hydrobromide salt, followed by re-precipitation of the intermediate solid from methanol/ether, gave AMD9358 as a white solid (0.078 g). $^1$H NMR (D$_2$O) ☐ 1.80-1.97 (m, 1H), 2.04-2.22 (m, 2H), 2.48-2.55 (m, 1H), 2.64-2.76 (m, 1H), 2.90-2.98 (m, 1H), 4.13 (s, 3H), 4.42 (s, 2H), 4.43 (d, 1H, J=12.9 Hz), 4.57 (s, 2H), 4.61 (d, 1H, J=12.9 Hz), 4.87 (dd, 1H, J=3.3, 3.6 Hz), 7.49 (d, 1H, J=7.2 Hz), 7.54-7.62 (m, 4H), 7.76-7.85 (m, 2H), 8.27 (ddd, 1H, J=7.8, 7.8, 1.8 Hz), 8.59 (d, 1H, J=6.9 Hz), 8.71 (dd, 1H, J=5.4, 0.9 Hz); $^{13}$C NMR (D$_2$O) ☐ 15.03, 21.07, 23.35, 49.07, 50.18, 51.28, 53.53, 58.51, 109.11, 126.81 (2 carbons), 129.20, 131.30 (2 carbons), 131.48 (2 carbons), 131.99, 132.32, 141.80, 143.11, 143.80, 146.67, 147.63, 171.67; ES-MS m/z 389 (M+H). Anal. Calcd. for C$_{24}$H$_{28}$N$_4$O.4.0HBr.2.6H$_2$O: C, 37.98; H, 4.94; N, 7.38; Br, 42.11. Found: C, 38.15; H, 4.93; N, 7.26; Br, 41.97.

EXAMPLE: 46

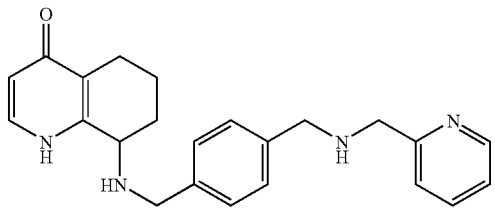

AMD9359: Preparation of N-(2-pyridinylmethyl)-N'-(5,6,7,8-tetrahydro-1H-quinol-4-on-8-yl)-1,4-benzenedimethanamine(hydrobromide salt)

Using a modification of general procedure D: N-(2-pyridinylmethyl)-N'-(4-methoxy-5,6,7,8-tetrahydro-8-quinolinyl)-1,4-benzenedimethanamine (0.102 g, 0.26 mmol) was dissolved in glacial acetic acid (2 mL), treated with HBr saturated acetic acid (2 mL) and heated to reflux for 22 hours. The reaction mixture was cooled to room temperature. The salts were precipitated in the usual manner giving 0.166 g the title compound AMD9359 as a beige solid. $^1$H NMR D$_2$O) □ 1.80-1.96 (m, 1H), 2.06-2.22 (m, 2H), 2.47-2.53 (m, 1H), 2.61-2.73 (m, 1H), 2.83-2.98 (m, 1H), 4.10-4.45 (m, 3H), 4.58-4.62 (m, 3H), 4.79-4.83 (m, 1H, overlaps with HOD), 7.20 (d, 1H, J=6.6 Hz), 7.55-7.62 (m, 4H), 7.79-7.88 (m, 2H), 8.28-8.36 (m, 2H), 8.72 (d, 1H, J=5.4 Hz); $^{13}$C NMR (D$_2$O) □ 15.15, 21.03, 23.47, 48.87, 50.13, 51.32, 53.61, 113.04, 126.98, 127.02, 128.07, 131.30 (2 carbons), 131.46 (2 carbons), 132.03, 132.24, 141.54, 142.25, 144.26, 146.34, 147.34, 172.04; ES-MS m/z 375 (M+H). Anal. Calcd. for C$_{23}$H$_{26}$N$_4$O.4.0HBr.2.4H$_2$O: C, 37.26; H, 4.73; N, 7.56; Br, 43.11. Found: C, 37.47; H, 4.71; N, 7.56; Br, 42.81.

EXAMPLE: 47

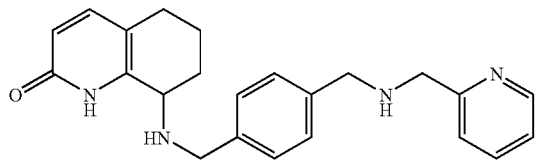

AMD9460: Preparation of N-(2-pyridinylmethyl)-N'-(5,6,7,8-tetrahydro-1H-quinol-2-on-8-yl)-1,4-benzenedimethanamine(hydrobromide salt)

8-amino-5,6,7,8-tetrahydro-2-quinolone

Following a modification of the procedure described by Meidert et al. German Patent DE 78-2840437: To a warm (35° C.) solution of 3,4,5,6,7,8-hexahydro-2(1H)-quinolone (5.18 g, 34.3 mmol) in 1,2-dichloroethane (52 mL) was added, by syringe pump (over 4 hours), a solution of bromine (15.61 g, 97.67 mmol) in 1,2-dichloroethane (45 mL). After the addition of bromine was complete, the reaction mixture was warmed to 60° C. and the mixture was maintained at that temperature for 10 minutes to allow the escape of hydrogen bromide gas. The reaction mixture was cooled to room temperature and a stream of nitrogen gas was blown over the solution for 1 hour. The mixture was concentrated and dried under vacuum overnight. The resultant orange gummy solid was dissolved in CH$_2$Cl$_2$ (100 mL) and treated with saturated aqueous NaHCO$_3$ (50 mL) until basic (pH ~8) to litmus paper. The phases were separated and the aqueous phase was extracted with CH$_2$Cl$_2$ (3×50 mL). The combined organic extracts were dried (Na$_2$SO$_4$) and concentrated. The crude material was purified by column chromatography on silica gel (10:1 CH$_2$Cl$_2$—MeOH followed by 4:1 CH$_2$Cl$_2$—MeOH) and provided 8.64 g of an off-white solid.

The solid was dissolved in DMF (135 mL), treated with NaN$_3$ (5.07 g, 78.00 mmol), and heated to 60° C. for 2 days. The reaction mixture was cooled to room temperature and diluted with ethyl acetate (270 mL), brine (135 mL), and water (85 mL). The phases were separated and the aqueous phase was extracted with ethyl acetate (2×100 mL). The combined organic extracts were washed with brine (4×50 mL), dried (MgSO$_4$), and concentrated. Purification of the crude material by column chromatography on silica gel (10:1 CH$_2$Cl$_2$—MeOH) provided 4.90 g of a brown paste. This was used without further purification.

The brown paste was dissolved in MeOH (100 mL) and hydrogenated (30 psi) over palladium, 10 wt. % on activated carbon (0.503 g). The mixture was vacuum filter through celite and the cake was washed with methanol. The combined filtrates were evaporated under reduced pressure and the residual oil was purified by column chromatography on silica gel (10:1 CH$_2$Cl$_2$—MeOH followed by 10:1:1 CH$_2$Cl$_2$—MeOH—NH$_4$OH) to give 0.731 g (10%) of 8-amino-5,6,7,8-tetrahydro-2-quinolone as a blue solid. $^1$H NMR (CDCl$_3$) □ 1.53-1.71 (m, 2H), 1.83-1.90 (m.1H), 2.03-2.09 (m, 1H), 2.38-2.65 (m, 2H), 3.79 (dd, 1H, J=5.7, 6.9 Hz), 6.39 (d, 1H, J=9.0 Hz). 7.17 (d, 1H, J=9.0 Hz); $^{13}$C NMR (CDCl$_3$) □ 20.15, 26.27, 32.78, 47.49, 114.44, 118.30, 143.60, 144.99, 164.28; ES-MS m/z 165 (M+H).

Using General Procedure B: Reaction of 8-amino-5,6,7,8-tetrahydro-2-quinolone (0.600 g, 3.66 mmol) and N-[1-methylene-4-(carboxaldehyde)phenylene]-N-(tert-butoxycarbonyl)-2-(aminomethyl)pyridine (1.062 g, 3.23 mmol) with NaBH(OAc)$_3$ (1.566 g, 7.38 mmol) in CH$_2$Cl$_2$ (18 mL) for 16 hours followed by purification of the crude material by column chromatography on silica gel (20:1 CH$_2$Cl$_2$—MeOH followed by 20:1:1 CH$_2$Cl$_2$—MeOH—NH$_4$OH) provided 1.09 g (71%) of N-(2-pyridinylmethyl)-N-(tert-butoxycarbonyl)-N'-(5,6,7,8-tetrahydro-1H-quinol-2-on-8-yl)-1,4-benzenedimethanamine as a white solid.

Using general procedure D: Conversion of the white solid from above (0.101 g) to the hydrobromide salt with simultaneous removal of the BOC-protecting group, followed by re-precipitation of the intermediate solid from methanol/ether, gave AMD9460 (0.113 g) as a white solid. $^1$H NMR (D$_2$O) □ 1.86-1.92 (m, 2H), 2.11-2.21 (m, 1H), 2.27-2.35 (m, 1H), 2.54-2.74 (m, 2H), 4.38 (d, 1H, J=13.2 Hz), 4.41 (s, 2H), 4.48 (d, 1H, J=13.2 Hz), 4.52 (dd, 1H, J=4.5, 4.5 Hz), 4.57 (s, 2H), 6.60 (d, 1H, J=9.0 Hz), 7.51-7.64 (m, 5H), 7.77-7.85 (m, 2H), 8.26-8.31 (m, 1H), 8.72 (d, 1H, J=4.8 Hz); $^{13}$C NMR (D$_2$O) □ 17.27, 23.93, 25.39, 48.90, 49.21, 51.27, 53.80, 120.35, 122.23, 126.87, 131.24, 131.28, 132.08, 132.51, 134.73, 144.04, 145.98, 146.48, 147.49, 164.26; ES-MS m/z 375 (M+H). Anal. Calcd. for C$_{23}$H$_{26}$N$_4$O.4.0HBr.2.0H$_2$O: C, 37.63; H, 4.67; N, 7.63; Br, 43.53. Found: C, 37.73; H, 4.74; N, 7.53; Br, 43.37.

EXAMPLE: 48

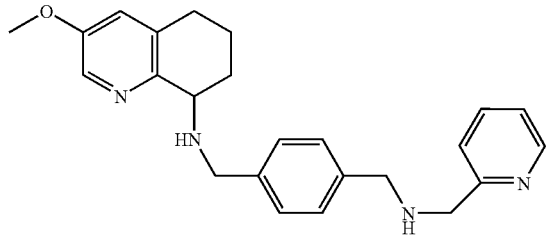

AMD9542: Preparation of (3-methoxy-5,6,7,8-tetrahydroquinolin-8-yl)-(4-{[(pyridin-2-ylmethyl)-amino]-methyl}-benzyl)-amine(hydrobromide salt)

Preparation of (3-methoxy-5,6,7,8-tetrahydroquinolin-8-yl)-alcohol:

A solution of 3-bromoquinoline (22.54 g, 108 mmol) in anhydrous DMF (110 mL) was treated with sodium methoxide (11.70 g, 217 mmol) and stirred at 80° C. for 16 hours. The reaction mixture was then concentrated and the residue taken up in ethyl acetate (300 mL) and water (60 mL). The organic phase was separated, washed with brine (2×60 mL), dried (MgSO$_4$), filtered, concentrated and purified by column chromatography on silica gel (ethyl acetate/hexane; 1:3) to give 3-methoxyquinoline (1.06 g, 6%). $^1$H NMR (CDCl$_3$) δ 3.95 (s, 3H), 7.38 (d, 1H, J=1.5 Hz), 7.54 (m, 2H), 7.72 (d, 1H, J=7.5 Hz), 8.04 (d, 1H, J=7.5 Hz), 8.67 (d, 1H, J=1.5 Hz).

To a solution of 3-methoxyquinoline (1.06 g, 6.7 mmol) in TFA (22 mL) under nitrogen was added platinum oxide (225 mg, 1.3 mmol) and the suspension bubbled with hydrogen gas 16 h at 60° C. The mixture was then cooled to room temperature, neutralized to pH 12 with 10 N NaOH and extracted with CH$_2$Cl$_2$ (3×50 mL). The organic extracts were dried (MgSO$_4$), filtered, concentrated and purified by column chromatography on silica gel (ethyl acetate/hexane; 1:2) to give the desired 3-methoxy-5,6,7,8-tetrahydroquinoline (0.95 g, 87%). $^1$H NMR (CDCl$_3$) δ 1.77 (m, 2H), 1.85 (m, 2H), 2.75 (t, 2H, J=6.0 Hz), 2.85 (t, 2H, J=6.0 Hz), 3.81 (s, 3H), 6.88 (d, 1H, J=1.5 Hz), 8.07 (d, 1H, J=1.5 Hz).

To a solution of 3-methoxy-5,6,7,8-tetrahydroquinoline (0.95 g, 5.8 mmol) in acetic acid (12 mL) was added hydrogen peroxide (30%, 0.60 mL, 5.8 mmol) and the reaction heated to 70° C. for 4 h. A second equivalent of hydrogen peroxide (30%, 0.60 mL, 5.8 mmol) was then added and the solution stirred another 16 h at 70° C. The mixture was concentrated under reduced pressure to provide the desired N-oxide salt as a yellow crystalline solid that was used without purification in the next reaction. $^1$H NMR (CDCl$_3$) δ 1.77 (m, 2H), 1.85 (m, 2H), 2.75 (t, 2H, J=6.0 Hz), 2.90 (t, 2H, J=6.0 Hz), 3.80 (s, 3H), 6.76 (d, 1H, J=1.5 Hz), 8.12 (d, 1H, J=1.5 Hz).

A solution of the N-oxide from above in acetic anhydride (4.76 mL, 50.5 mmol) was heated to 90° C. for 4.5 h. The mixture was concentrated under reduced pressure and the resultant crude brown oil was used immediately in the next reaction without further purification. $^1$H NMR (CDCl$_3$) δ 1.83 (m, 2H), 2.09 (s, 3H), 2.11 (m, 2H), 2.80 (m, 3H), 3.84 (s, 3H), 5.95 (t, 1H, J=4.5 Hz), 6.95 (d, 1H, J=1.5 Hz), 8.22 (d, 1H, J=1.5 Hz).

A solution of 8-acetyl-3-methoxy-5,6,7,8-tetrahydroquinoline in anhydrous MeOH (6 mL) was treated with K$_2$CO$_3$ and stirred at room temperature for 16 h. Water (15 ml) was added and the mixture was extracted with CH$_2$Cl$_2$ (2×20 mL). The organic phase was then dried (MgSO$_4$), filtered, concentrated and purified by column chromatography on silica gel (5% MeOH/CH$_2$Cl$_2$) to give (3-methoxy-5,6,7,8-tetrahydroquinolin-8-yl)-alcohol as a brown oil (0.68 g, 65% 3 steps). $^1$H NMR (CDCl$_3$) δ 1.81 (m, 2H), 2.00 (m, 1H), 2.20 (m, 1H), 2.78 (m, 2H), 3.83 (s, 3H), 3.95 (s, 1H (O*H*)), 4.70 (t, 1H, J=7.5 Hz), 6.93 (d, 1H, J=3.0 Hz), 8.12 (d, 1H, J=3.0 Hz).

Following General Procedure E: To a solution of (3-methoxy-5,6,7,8-tetrahydroquinolin-8-yl)-alcohol (0.66 g, 3.7 mmol) and triethylamine (0.87 mL, 6.3 mmol) in CH$_2$Cl$_2$ (12 mL) was added methanesulfonyl chloride (0.45 mL, 3.7 mmol) and the mixture stirred at room temperature for 1 hour. The resultant crude mesylate (0.55 g) was used without further purification in the next reaction.

To a solution of the crude material from above (0.55 g) in anhydrous DMF (10 mL) was added sodium azide (0.50 g, 7.4 mmol) and the mixture heated at 60° C. for 16 h. The reaction mixture was then concentrated and diluted with brine (4 mL) and EtOAc (10 mL). The organic phase was washed with brine (2×5 mL), dried (MgSO$_4$), filtered, concentrated and purified by column chromatography on silica gel (3% MeOH/CH$_2$Cl$_2$) to give the desired (3-methoxy-5,6,7,8-tetrahydroquinolin-8-yl)-azide (0.33 g, 55%). $^1$H NMR (CDCl$_3$) δ 1.81 (m, 1H), 2.00 (m, 3H), 2.80 (m, 2H), 3.84 (s, 3H), 4.69 (t, 1H, J=4.5 Hz), 6.93 (d, 1H, J=1.5 Hz), 8.20 (d, 1H, J=1.5 Hz).

To a solution of (3-methoxy-5,6,7,8-tetrahydroquinolin-8-yl)-azide (0.33 g, 1.6 mmol) in MeOH (16 mL) was added palladium on activated carbon, (10%, 50 mg) and the reaction mixture stirred under 1 atmosphere of hydrogen for 4 h. The mixture was filtered through celite, the cake washed with methanol and the solvent from the eluent removed in vacuo to give crude (3-methoxy-5,6,7,8-tetrahydroquinolin-8-yl)-amine as a yellow oil (0.28 g, 96%). $^1$H NMR (CDCl$_3$) δ 1.75 (m, 2H), 1.97 (m, 1H), 2.17 (m, 1H), 2.77 (m, 2H), 3.81 (s, 3H), 3.98 (t, 1H, J=4.5 Hz), 6.88 (d, 1H, J=1.5 Hz), 8.12 (d, 1H, J=1.5 Hz).

Using General Procedure B: To a solution of (3-methoxy-5,6,7,8-tetrahydroquinolin-8-yl)-amine (0.27 g, 1.5 mmol) and 4-[[N-(t-butoxycarbonyl)-N-(2-pyridinylmethyl)amino]methyl]benzaldehyde (prepared as described by Bridger et al, U.S. patent application Ser. No. 09/535,314) (0.57 g, 1.7 mmol) in CH$_2$Cl$_2$ (15 mL) was added NaBH(OAc)$_3$ (0.48 g, 2.3 mmol) and the mixture stirred at room temperature for 16 h. Purification of the crude material by column chromatography on silica gel (5% MeOH/CH$_2$Cl$_2$) gave {4-[(3-methoxy-5,6,7,8-tetrahydroquinolin-8-ylamino)-methyl]-benzyl}-pyridin-2-ylmethyl-carbamic acid tert-butyl ester (0.43 g, 58%). $^1$H NMR (CDCl$_3$) δ 1.45 (m, 9H), 1.77 (m, 2H), 2.00 (m, 1H), 2.12 (m, 1H), 2.77 (m, 2H), 3.80 (m, 1H), 3.81 (s, 3H), 3.85 (d, 1H, J=12.0 Hz), 3.95 (d, 1H, J=12.0 Hz), 4.44 (br s, 2H), 4.55 (br s, 2H), 6.88 (d, 1H, J=1.5 Hz), 7.15 (m, 2H), 7.23 (br s, 2H), 7.34 (d, 2H, J=6.0 Hz), 7.62 (t, 1H, J=7.5 Hz), 8.11 (d, 1H, J=1.5 Hz), 8.52 (d, 1H, J=6.0 Hz).

Using General Procedure D: Conversion of the material from above (60 mg) to the hydrobromide salt with simultaneous removal of the Boc group provided AMD9542 (0.069 g) as a white solid. $^1$H NMR (D$_2$O) □1.86 (m, 1H), 1.97 (m, 1H), 2.14 (m, 1H), 2.35 (m, 1H), 2.87 (m, 2H), 3.87 (s, 3H), 4.40 (s, 4H), 4.52 (s, 2H), 4.55 (m, 1H), 7.39 (d, 1H, J=2.1 Hz), 7.55 (m, 4H), 7.71 (m, 2H), 8.19 (m, 2H), 8.67 (m, 1H, J=4.8 Hz); $^{13}$C NMR (D$_2$O) □ 18.17, 24.89, 27.55, 48.67, 48.78, 51.37, 55.79, 56.66, 125.28, 127.09, 127.17, 131.19 (2C), 131.27 (2C), 131.92, 132.76, 134.36, 137.93, 139.19, 144.61, 146.07, 147.15, 156.80. ES-MS m/z 389 (M+H).

Anal. Calcd. for $C_{24}H_{28}N_4O \cdot 4.0HBr \cdot 2.6H_2O$: C, 38.06; H, 4.95; N, 7.40; Br, 41.97. Found: C, 38.13; H, 5.04; N, 7.14; Br, 42.01.

EXAMPLE: 49

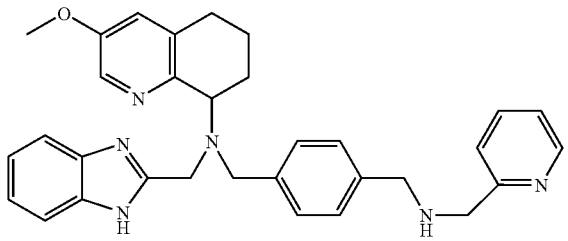

AMD9543: Preparation of (1H-Benzimidazole-2-ylmethyl)-(3-methoxy-5,6,7,8-tetrahydroquinolin-8-yl)-(4-{[(pyridin-2-ylmethyl)-amino]-methyl}-benzyl)-amine(hydrobromide salt)

To a solution of {4-[(3-methoxy-5,6,7,8-tetrahydroquinolin-8-ylamino)-methyl]-benzyl}-pyridin-2-ylmethyl-carbamic acid tert-butyl ester (81 mg, 0.17 mmol), N,N-diisopropylethylamine (0.05 mL, 0.18 mmol) and potassium iodide (10 mg, 0.04 mmol) in anhydrous $CH_3CN$ (2 mL) was added (N-tert-butoxycarbonyl)-2-chloromethylbenzimidazole (50 mg, 0.18 mmol) and the reaction stirred at 60° C. for 16 h. Purification of the crude product by column chromatography on silica gel (5% $MeOH/CH_2Cl_2$) gave the desired 2-{[{4-[(tert-butoxycarbonyl-pyridin-2-ylmethyl-amino)-methyl]-benzyl}-(3-methoxy-5,6,7,8-tetrahydroquinolin-8-yl)-amino]-methyl}-benzimidazole-1-carboxylic acid tert-butyl ester as a pale yellow solid (69 mg, 58%). $^1H$ NMR ($CDCl_3$) δ 1.45 (m, 9H), 1.67 (m, 9H), 1.70 (m, 1H), 1.97 (m, 2H), 2.17 (m, 1H), 2.65 (m, 1H), 2.78 (m, 1H), 3.78 (d, 1H, J=15.0 Hz), 3.80 (s, 3H), 4.28 (m, 4H), 4.40 (m, 1H), 4.60 (s, 2H), 6.79 (d, 1H, J=1.5 Hz), 6.90 (m, 2H), 7.13 (m, 2H), 7.18 (d, 4H, J=6.0 Hz), 7.59 (d, 2H, J=6.0 Hz), 7.68 (m, 1H), 8.16 (d, 1H, J=1.5 Hz), 8.51 (d, 1H, J=2.0 Hz).

Using General Procedure D: Conversion of the solid from above to the hydrobromide salt with simultaneous removal of the Boc group provided AMD9543 (0.064 g) as a white solid. $^1H$ NMR ($D_2O$) □1.85 (m, 1H), 2.18 (m, 2H), 2.38 (m, 1H), 2.99 (m, 2H), 3.78 (s, 3H), 3.79 (m, 1H), 4.00 (s, 3H), 4.01 (s, 2H), 4.41 (d, 1H, J=16.8 Hz), 4.59 (d, 1H, J=16.8 Hz), 4.66 (m, 1H), 7.02 (d, 2H, J=8.1 Hz), 7.20 (d, 2H, J=8.1 Hz), 7.33 (m, 2H), 7.45 (d, 1H, J=8.1 Hz), 7.51 (m, 2H), 7.55 (d, 1H, J=8.1 Hz), 7.99 (m, 2H), 8.42 (d, 1H, J=2.7 Hz), 8.60 (d, 1H, J=4.2 Hz); $^{13}C$ NMR ($D_2O$) □ 20.53, 21.10, 28.22, 49.24, 50.02, 50.30, 56.54, 57.47, 62.77, 113.86 (2C), 125.94, 126.13, 126.61 (2C), 127.00, 130.04, 130.17 (3C), 130.44, 130.83 (2C), 132.03, 138.35, 141.88, 141.96, 143.06, 147.83, 148.53, 151.53, 157.35. ES-MS m/z 519 (M+H). Anal. Calcd. for $C_{32}H_{34}N_6O \cdot 4.0HBr \cdot 2.9H_2O$: C, 42.94; H, 4.93; N, 9.39; Br, 35.78. Found: C, 42.96; H, 4.79; N, 9.39; Br, 35.78.

EXAMPLE: 50

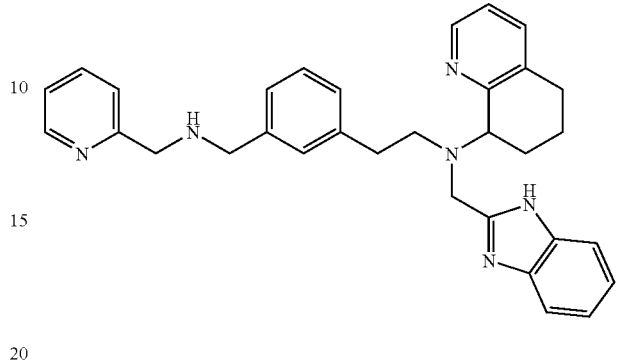

AMD9522: Preparation of (1H-Benzimidazol-2-ylmethyl)-[2-(3-{[(pyridin-2-ylmethyl)-amino]-methyl}-phenyl)-ethyl]-(5,6,7,8-tetrahydroquinolin-8-yl)-amine(hydrobromide salt)

Preparation of 6,7-Dihydro-5H-quinolin-8-one:

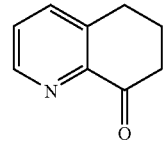

To a stirred solution of 8-hydroxy-5,6,7,8-tetrahydroquinoline (13.96 g, 93.6 mmol) in dry $CH_2Cl_2$ (400 mL) was added activated manganese dioxide (85% purity, 82.22 g, 804 mmol). The resulting heterogeneous mixture was stirred 18 h, at which point the black slurry was filtered through a cake of celite and washed with $CH_2Cl_2$ (3×50 mL). The combined washings were concentrated to afford 11.27 g (82%) of the title compound as a pale yellow solid, which was used in subsequent reactions without further purification. $^1H$ NMR ($CDCl_3$) δ 2.17-2.25 (m, 2H), 2.82 (t, 2H, J=7 Hz), 3.04 (t, 2H, J=6 Hz), 7.37 (dd, 1H, J=9, 6 Hz), 7.66 (dd, 1H, J=9, 1 Hz), 8.71 (dd, 1H, J=6, 1 Hz); $^{13}C$ NMR ($CDCl_3$) δ 22.2, 28.6, 39.2, 126.6, 137.3, 140.5, 147.6, 148.6, 196.5. ES-MS m/z 148 (M+H).

Preparation of 2-(3-{[(pyridin-2-ylmethyl)-2-nitrobenzenesulfonylamino]-methyl}-phenyl)-ethylamine:

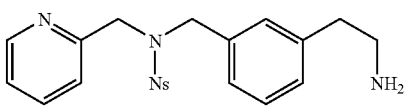

Preparation of 3-{[(Pyridin-2-ylmethyl)-N-(2-nitrobenzenesylfonyl)-amino]-methyl}-benzyl alcohol:

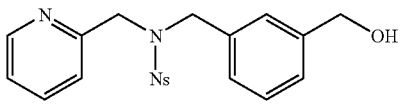

To a solution of 2-aminomethylpyridine (2.05 mL, 20.0 mmol) in CH$_3$CN (80 mL) was added K$_2$CO$_3$ (4.14 g, 30.0 mmol) followed by 2-nitrobenzenesulfonyl chloride (4.88 g, 22.0 mmol) and the reaction stirred at room temperature for 3 h. The mixture was concentrated under reduced pressure and diluted with CH$_2$Cl$_2$ (40 mL) and saturated aqueous NH$_4$Cl (40 mL). The phases were separated, the aqueous phase extracted with CH$_2$Cl$_2$ (2×20 mL) and the combined organic extracts dried (Na$_2$SO$_4$), filtered and concentrated. Purification of the crude material by column chromatography on silica gel (CH$_2$Cl$_2$/MeOH, 19:1 then 9:1) afforded the nosyl-protected amine (5.07 g, 86%). $^1$H NMR (CDCl$_3$): δ 4.43 (d, 2H, J=6 Hz), 6.63 (br s, 1H), 7.14 (dd, 1H, J=9, 6 Hz), 7.25 (d, 1H, J=6 Hz), 7.61-7.69 (m, 3H), 7.87 (d, 1H, J=9 Hz), 8.07 (d, 1H, J=9 Hz), 8.39 (d, 1H, J=5.7 Hz).

To a solution of the nosyl-protected amine from above (1.47 g, 5.00 mmol) in CH$_3$CN (60 mL) was K$_2$CO$_3$ (1.38 g, 10.0 mmol) and methyl 3-bromomethylbenzoate (1.14 g, 5.00 mmol) and the mixture stirred at 50° C. overnight. The mixture was concentrated under reduced pressure and diluted with CH$_2$Cl$_2$ (40 mL) and saturated aqueous NH$_4$Cl (40 mL). The phases were separated, the aqueous phase extracted with CH$_2$Cl$_2$ (2×20 mL) and the combined organic extracts dried (Na$_2$SO$_4$), filtered and concentrated. Purification of the crude material by column chromatography on silica gel (CH$_2$Cl$_2$/MeOH, 19:1) afforded the alkylated material (2.18 g, 98%). $^1$H NMR (CDCl$_3$): δ 3.89 (s, 3H), 4.61 (s, 2H), 4.66 (s, 2H), 7.12 (dd, 1H, J=9, 6 Hz), 7.21-7.34 (m, 2H), 7.43 (d, 1H, J=9 Hz), 7.54-7.58 (m, 2H), 7.67 (d, 2H, J=3.9 Hz), 7.73 (s, 1H), 7.88 (d, 1H, J=9 Hz), 7.99 (d, 1H, J=9 Hz), 8.41 (d, 1H, J=5.7 Hz).

To a solution of the ester from above (2.18 g, 4.94 mmol) in CH$_2$Cl$_2$ (50 mL) at –78° C. was added a solution of DIBAL-H (15 mL, 1.0 M in CH$_2$Cl$_2$, 15 mmol) and the reaction stirred at –78° C. for 1.5 h. The mixture was quenched with a saturated potassium sodium tartrate solution (30 mL) and the biphasic mixture stirred vigorously overnight. The phases were separated and the organic layer dried (MgSO$_4$), filtered, concentrated and purified by column chromatography on silica gel (CH$_2$Cl$_2$/MeOH, 19:1) to give the desired title alcohol (1.90 g, 92%). $^1$H NMR (CDCl$_3$): δ 4.57 (s, 2H), 4.59 (s, 2H), 7.08-7.12 (m, 2H), 7.20-7.26 (m, 4H), 7.54-7.59 (m, 2H), 7.68 (d, 2H, J=3 Hz), 7.98 (d, 1H, J=9 Hz), 8.39 (d, 1H, J=5.7 Hz).

To a stirred solution of 3-{[(Pyridin-2-ylmethyl)-N-(2-nitrobenzenesylfonyl)-amino]-methyl}-benzyl alcohol (1.06 g, 2.57 mmol) in CH$_2$Cl$_2$ (30 mL) was added methanesulfonyl chloride (0.25 mL, 3.34 mmol) and triethylamine (0.54 mL, 3.85 mmol) and the resultant suspension stirred at room temperature for 2 h. The mixture was washed with aqueous ammonium chloride (1×30 mL) and the organic layer dried (Na$_2$SO$_4$) and concentrated under reduced pressure. The mesylate was used immediately in the next reaction without further purification as a 1 M stock solution in THF (2.5 mL).

To a stirred solution of the mesylate from above (1.1 mL of a 1 M stock solution in THF, 1.1 mmol) in benzene (15 mL) and water (5 mL) was added sodium cyanide (294 mg, 6 mmol) and cetyltrimethylammonium bromide (91 mg, 0.25 mmol). The reaction was heated to 80° C. and stirred overnight. After cooling, the reaction was extracted with ethyl acetate (3×15 mL). The combined organic fractions were dried (Na$_2$SO$_4$), concentrated under reduced pressure and purified by column chromatography on silica gel (CH$_2$Cl$_2$/MeOH, 19:1) to afford the desired nitrile (364 mg, 78%) as a yellow oil. $^1$H NMR (CDCl$_3$) δ 3.64 (s, 2H), 4.59 (s, 4H), 7.20 (m, 6H), 7.57 (m, 2H), 7.67 (m, 2H), 7.97 (d, 2H, J=6.1 Hz), 8.48 (d, 1H, J=5.1 Hz).

To a solution of the nitrile from above (364 mg, 0.863 mmol) in THF (15 mL) was added borane (5 mL of a 1 M solution in THF, 5 mmol) and the mixture heated at 50° C. for 3 h. The reaction was cooled, quenched with MeOH (5 mL) and stirred at room temperature for 30 minutes. The mixture was then concentrated under reduced pressure, diluted with 1N HCl (10 mL) and heated at 50° C. for 1 h. The mixture was cooled, diluted with 15% NaOH (to pH~12) and extracted with CH$_2$Cl$_2$ (3×15 mL). The combined organic fractions were dried (Na$_2$SO$_4$), concentrated under reduced pressure and purified by column chromatography on silica gel (CH$_2$Cl$_2$/MeOH, 19:1) to afford the title amine as a yellow foam (160 mg, 38%). $^1$H NMR (CDCl$_3$) δ 2.84 (t, 2H, J=6.8 Hz), 3.02 (m, 2H), 3.67 (m, 2H (NH$_2$)), 4.57 (s, 4H), 6.99-7.16 (m, 6H), 7.57-7.71 (m, 4H), 8.01 (d, 1H, J=8.1 Hz), 8.48 (d, 1H, J=4.9 Hz).

Using General Procedure B: To a solution of 2-(3-{[(pyridin-2-ylmethyl)-2-nitrobenzenesulfonylamino]-methyl}-phenyl)-ethylamine (255 mg, 0.6 mmol) and 6,7-dihydro-5H-quinolin-8-one (110 mg, 0.75 mmol) in CH$_2$Cl$_2$ (10 mL) was added sodium triacetoxyborohydride (190 mg, 0.9 mmol). Purification of the crude residue by column chromatography on silica gel (CH$_2$Cl$_2$/MeOH, 19:1) gave the N-alkylated product (192 mg, 57%). $^1$H NMR (CDCl$_3$) δ 1.78-1.99 (m, 4H), 2.71-2.89 (m, 6H), 3.78 (t, 1H, J=5.8 Hz), 4.56 (s, 2H), 4.61 (s, 2H), 6.94-7.08 (m, 6H), 7.13 (s, 1H), J=5.8 Hz), 7.28 (d, 1H, J=8.1 Hz), 7.55 (m, 2H), 7.64 (m, 2H), 7.93 (d, 1H, J=8.1 Hz), 8. 28 (d, 1H, J=5.2 Hz), 8.40 (d, 1H, J=4.9 Hz).

The material from above (192 mg, 0.345 mmol) was reacted with N-(tert-butoxycarbonyl)-2-chloromethylbenzimidazole (133 mg, 0.5 mmol) in CH$_3$CN (4 mL) in the presence of N,N-diisopropylamine (0.09 mL, 0.5 mmol) at 60° C. for 16 h. Purification by column chromatography on silica gel (CH$_2$Cl$_2$/MeOH, 10:1) afforded N-(tert-butoxycarbonyl-1H-benzimidazol-2-ylmethyl)-[2-(3-{[(pyridin-2-yl-methyl)-2-nitrobenzenesulfonylamino]-methyl}-phenyl)-ethyl]-(5,6,7,8-tetrahydroquinolin-8-yl)-amine (160 mg, 59%) as a pale foam.

Using General Procedure C: To a solution of the material from above (160 mg, 0.203 mmol) in anhydrous CH$_3$CN (5 mL) was added thiophenol (0.08 mL, 0.8 mmol) and potassium carbonate (140 mg, 1.01 mmol) and the mixture stirred at room temperature for 2 h. Purification of the crude product by column chromatography on silica gel (CH$_2$Cl$_2$/MeOH, 85:15) afforded the free amine (34 mg, 33%) as a pale foam. $^1$H NMR (CDCl$_3$) δ 1.41 (s, 9H), 1.73 (m, 1H), 1.89 (dq, 1H, J=12.6, 2.4 Hz), 2.02 (m, 1H), 2.21 (m, 1H), 2.68 (dd, 2H, J=13.8, 6.3 Hz), 2.83 (m, 2H), 2.92 (m, 2H), 3.71 (s, 2H), 3.86 (s, 2H), 4.08 (m, 1H), 4.11 (d, 2H, J=7.1 Hz), 6.89 (dt, 1H, J=3.9, 1.5 Hz), 7.01 (s, 1H), 7.10-7.20 (m, 6H), 7.25 (d, 1H, J=6.0 Hz), 7.39 (d, 1H, J=7.8 Hz), 7.58 (m, 2H), 7.61 (dt, J=7.5, 1.5 Hz), 8.45 (d, 1H, J=4.2 Hz), 8.53 (d, 1H, J=4.3 Hz).

Using General Procedure D: Conversion of the foam from above (34 mg) to the hydrobromide salt with simultaneous removal of the BOC-protecting group, followed by re-precipitation of the intermediate solid from methanol/ether, gave AMD9522 as a white solid (28 mg). $^1$H NMR (D$_2$O). δ 1.83 (m, 1H), 2.14 (t, 1H, J=13.5 Hz), 2.36 (m, 1H), 2.78 (m, 3H), 2.87 (m, 1H), 2.99 (m, 2H), 3.19 (m, 1H), 3.84 (m, 2H), 4.33 (m, 3H), 4.54 (m, 2H), 6.82 (d, 1H, J=9.0 Hz), 7.14-7.34 (m, 3H), 7.58 (m, 4H), 7.70 (m, 2H), 7.85 (dd, 1H, J=6.9, 5.8 Hz), 8.06 (m, 1H), 8.33 (d, 1H, J=7.8 Hz), 8.49 (d, 1H, J=5.1 Hz), 8.60 (m, 1H). $^{13}$C NMR (D$_2$O) ☐ 20.44, 20.85, 27.70, 34.39, 48.86, 49.28, 51.08, 52.80, 62.01, 114.26, 125.89, 126.55, 126.96, 128.48, 129.94, 130.04, 130.43, 130.74, 130.89, 139.24, 140.49, 140.76, 143.25, 146.87, 147.82, 148.15, 150.90, 151.71. ES-MS m/z 503 (M+H); Anal. Calcd. for (C$_{32}$H$_{34}$N$_6$×4 HBr×3.8 H$_2$O): C, 42.96; H, 5.14; N, 9.39; Br 35.72. Found: C, 43.22; H, 4.93; N, 9.39; Br, 35.38.

EXAMPLE: 51

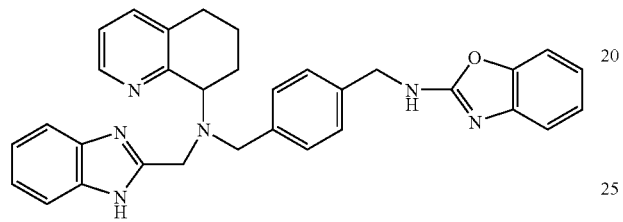

AMD9611: Preparation of N-(benzoxazol-2-yl)-N'-(1H-benzimidazol-2-ylmethyl)-N'-(5,6,7,8-tetrahydro-8-quinolinyl)-1,4-benzenedimethanamine(hydrobromide salt)

Using the General N-Alkylation Procedure: To a stirred solution of N'-(1H-benzimidazol-2-ylmethyl)-N'-(5,6,7,8-tetrahydro-8-quinolinyl)-1,4-benzenedimethanamine (128 mg, 0.32 mmol) and triethylamine (100 ul, 0.72 mmol) in THF (5 mL) was added 2-chlorobenzoxazole (50 uL, 0.44 mmol) and the mixture was stirred at reflux for 16 h. Purification of the crude material by radial chromatography on silica gel (1 mm plate, CH$_2$Cl$_2$/MeOH/NH$_4$OH, 125:1:1) afforded the desired amine (83 mg, 37%) as a yellow foam.

Using General Procedure D: Conversion of the foam from above (83 mg, 0.16 mmol) to the hydrobromide salt followed by re-precipitation of the intermediate solid from methanol/ether gave AMD9611 (105 mg, 82%) as a white solid. $^1$H NMR (D$_2$O) ☐1.79-1.96 (m, 1H), 2.14-2.32 (m, 2H), 2.36-2.48 (m, 1H), 2.98-3.06 (m, 2H), 3.73 (d, 1H, J=12.2 Hz), 3.82 (d, 1H, J=12.6 Hz), 4.20 (s, 2H), 4.43 (d, 1H, J=16.6 Hz), 4.60 (d, 1H, J=16.7 Hz), 7.02 (d, 2H, J=8.0 Hz), 7.10-7.20 (m, 4H), 7.31-7.46 (m, 5H), 7.53 (d, 1H, J=7.9 Hz), 7.90 (dd, 1H, J=7.9, 5.8 Hz), 8.37 (d, 1H, J=7.8 Hz), 8.74 (d, 1H, J=5.8 Hz). $^{13}$C NMR (D$_2$O) ☐ 20.44, 20.91, 27.83, 45.70, 50.25, 56.67, 63.30, 111.27, 113.11, 113.53 (2 carbons), 124.83, 126.06, 126.21 (2 carbons), 126.64, 128.07 (2 carbons), 130.35, 130.65 (2 carbons), 135.63, 136.43, 139.62 (2 carbons), 140.98, 148.24 (2 carbons), 150.85, 151.87. ES-MS m/z 515 (M+H) Anal Calc. for C$_{32}$H$_{30}$N$_6$O.3.0HBr 2.1H$_2$O: C, 48.33; H, 4.72; N, 10.57; Br, 30.15. Found: C, 48.47; H, 4.70; N, 10.40; Br, 30.05.

EXAMPLE: 52

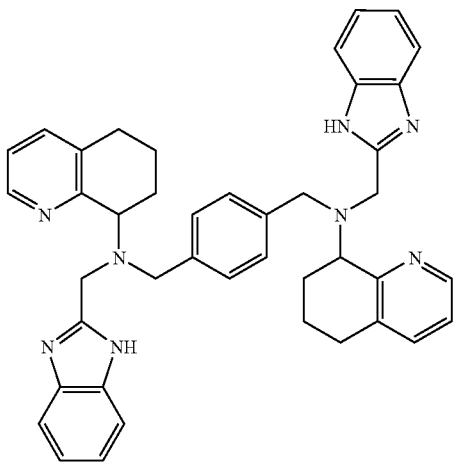

AMD9718: Preparation of Bis[N'-(1H-benzimidazol-2-ylmethyl)-N'-(5,6,7,8-tetrahydro-8-quinolinyl)]-1,4-benzenedimethanamine(hydrobromide salt)

To a stirred solution of 8-amino-5,6,7,8-tetrahydroquinoline (0.312 g, 2.1 mmol) in dry MeOH (10 mL) was added terephthaldehyde (0.142 g, 1.05 mmol) and the mixture stirred at room temperature for 2 h. The reaction mixture was concentrated under reduced pressure and the residue analyzed by $^1$H NMR for imine formation. To a solution of the residue in dry MeOH/CH$_2$Cl$_2$ (1:1, 12 mL) was added sodium borohydride (80 mg, 2.1 mmol) and the mixture stirred overnight at room temperature (see General Procedures XX). The desired dimer (0.345 g, 83%) was obtained as a yellow oil and used in the next step without any further purification.

Using the General alkylation Procedure: To a stirred solution of the dimer (0.193 g, 0.48 mmol) in dry CH$_3$CN (5 mL) was added 1-N-tert-butoxycarbonyl-2-chloromethylbenzimidazole (0.260 g, 0.97 mmol), N,N-diisopropylethylamine (0.34 mL, 1.9 mmol) and potassium iodide (12 mg, 0.048 mmol). The mixture was stirred under an argon atmosphere at 60° C. overnight. Purification of the crude material by column chromatography on silica gel (CH$_2$Cl$_2$/MeOH, 97:3 followed by 96:4 and 93:7) gave the alkylated product (0.218 g, 53%).

The purified material was dissolved in dry CH$_2$Cl$_2$ (2.5 mL) and trifluoroacetic acid (2 mL) was added. The resultant mixture was stirred for 2.5 h at room temperature. The reaction mixture was diluted with CH$_2$Cl$_2$ (20 mL) and then concentrated in vacuo to remove any excess trifluoroacetic acid. The concentrate was diluted with CH$_2$Cl$_2$ (25 mL) and 2N NaOH (25 mL), the aqueous layer extracted with CH$_2$Cl$_2$ (2×15 mL), the phases separated and the combined organic extracts dried (Na$_2$SO$_4$), filtered and concentrated in vacuo. Purification of the crude material by radial chromatography on a 1 mm TLC grade silica gel plate (CH$_2$Cl$_2$/MeOH/NH$_4$OH, 100:1:1) afforded the deprotected material (56 mg, 34%).

Using General Procedure D: Conversion of the free amine from above (56 mg, 0.085 mmol) to the hydrobromide salt with simultaneous removal of the Boc group gave AMD9718 (68 mg) as an off-white solid. $^1$H NMR (D$_2$O) ☐ 1.70-1.91 (br m, 1H), 1.99-2.22 (br m, 2H), 2.23-2.38 (br m, 1H), 2.95-3.13

(br m, 3H), 3.34 (dd, 1H, J=12.9, 8.1 Hz), 4.16 (t, 1H, J=16.2 Hz), 4.41 (dd, 1H, J=16.5, 6.0 Hz), 4.56 (d, 1H, J=8.7 Hz), 6.69 (d, 2H, J=3.9 Hz), 7.18 (dd, 2H, J=7.8, 4.5 Hz), 7.33-7.50 (m, 2H), 7.95 (t, 1H, J=6.9 Hz), 8.42 (d, 1H, J=8.1 Hz), 8.72 (d, 1H, J=5.7 Hz); $^{13}$C NMR (D$_2$O) 19.04, 19.43, 26.53, 48.31, 48.52, 54.48, 60.99, 61.09, 112.48, 124.90, 125.06, 128.15, 129.22, 134.75, 134.84, 139.74, 147.02, 149.49, 149.56, 150.22, 150.29; ES-MS m/z 659 (M+H); Anal. Calcd. for C$_{42}$H$_{42}$N$_8$·4.0HBr·3.7H$_2$O: C, 48.08; H, 5.13; N, 10.68; Br, 30.46. Found: C, 48.27; H, 5.09; N, 10.48; Br, 30.29.

EXAMPLE: 53

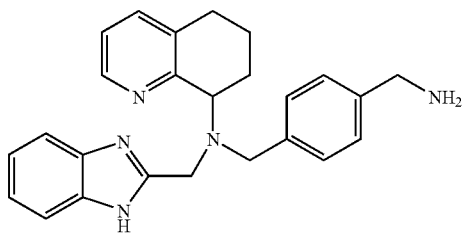

AMD9381: Preparation of N-(1H-benzimidazol-2-ylmethyl)-N-(5,6,7,8-tetrahydro-8-quinolinyl)-1,4-benzenedimethanamine To a stirred solution of 8-amino-5,6,7,8-tetrahydroquinoline (24.3 g, 164 mmol) in dichloromethane (600 mL), at room temperature, was added 4-cyanobenzaldehyde (21.5 g, 164 mmol) and sodium triacetoxyborohydride (45 g, 210 mmol). After 42 hours, the reaction was quenched with 1N NaOH (250 mL). The phases were separated and the organic phase was washed once with brine (200 mL), dried (Na$_2$SO$_4$), and concentrated. Purification of the crude material by flash chromatography on silica gel (5% CH$_3$OH/CH$_2$Cl$_2$) provided 30.9 g (72%) of N-(5,6,7,8-tetrahydro-8-quinolinyl)-4-cyanobenzylamine as a pale yellow solid.

The material from above (30.1 g, 114 mmol) was reacted with N-(tert-butoxycarbonyl)-2-chloromethylbenzimidazole (30.5 g, 114 mmol) in DMF in the presence of N,N-diisopropylethylamine, and the crude material was purified by flash chromatography on silica gel (3% CH$_3$OH/CH$_2$Cl$_2$) to give 38.0 g (67%) of N-(N-(tert-butoxycarbonyl)benzimidazol-2-ylmethyl)-N-(5,6,7,8-tetrahydro-8-quinolinyl)-4-cyanobenzylamine as a pale orange foam.

The intermediate from above (35 g, 70.9 mmol) was dissolved in NH$_3$ saturated methanol, treated with Raney nickel, and placed under 50 psi H$_2$ on a Parr shaker, for 16 h. The mixture was filtered through Celite 521, concentrated, and purified by flash chromatography on silica gel (5% CH$_3$OH/CH$_2$Cl$_2$) to give 25.1 g (90%) of N-(1H-benzimidazol-2-ylmethyl)-N-(5,6,7,8-tetrahydro-8-quinolinyl)-1,4-benzenedimethanamine (AMD9381) as a yellow powder. $^1$H NMR (CDCl$_3$) δ 1.63-1.74 (m, 1H), 1.98-2.06 (m, 2H), 2.24-2.30 (m, 1H), 2.67-2.91 (m, 2H), 3.69 (s, 2H), 3.75 (s, 2H), 3.91-4.17 (m, 3H), 7.14-7.19 (m, 5H), 7.33 (d, 2H, J=7.5 Hz), 7.43 (d, 1H, J=7.5 Hz), 7.54-7.58 (m, 2H), 8.69 (d, 1H, J=4.2 Hz). $^{13}$C NMR (CDCl$_3$) δ 21.66, 23.57, 29.53, 44.85, 49.00, 54.06, 60.93, 115.15, 115.26, 122.09 (2), 122.66, 128.46(2), 129.36 (2), 135.21, 137.71, 137.78, 138.75, 138.95, 147.12, 155.90, 157.35. ES-MS m/z 398 (M+H). Anal. Calcd. for C$_{25}$H$_{27}$N$_5$·0.6H$_2$O·0.4CH$_2$Cl$_2$: C, 68.98 H, 6.61; N, 15.83. Found: C, 69.34; H, 6.67; N, 15.82.

EXAMPLE: 54

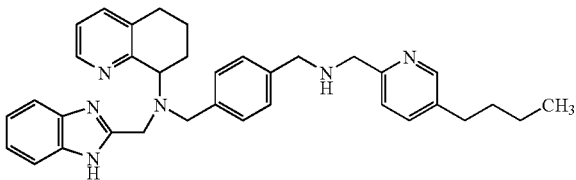

AMD9398: Preparation of N-(5-butyl-2-pyridinylmethyl)-N'-(1H-benzimidazol-2-ylmethyl)-N'-(5,6,7,8-tetrahydro-8-quinolinyl)-1,4-benzenedimethanamine (hydrobromide salt)

Using general procedure B: N-(1H-benzimidazol-2-ylmethyl)-N-(5,6,7,8-tetrahydro-8-quinolinyl)-1,4-benzenedimethanamine (0.1258 g, 0.316 mmol) and 5-n-butylpyridine-2-carboxaldehyde (0.0603 g, 0.294 mmol) were reacted with NaBH(OAc)$_3$ (0.0942 g, 0.444 mmol) in CH$_2$Cl$_2$ (2.5 mL). Purification of the crude material by radial chromatography (2mm TLC plate, 50:1:1 CH$_2$Cl$_2$:CH$_3$OH:NH$_4$OH) provided 0.0713 g (45%) of AMD9398 (free base).

Using General Procedure D: the free base was converted to 0.1009 g (84%) of AMD9398. $^1$H NMR (D$_2$O) 0.86 (t, 3H, J=7.4 Hz), 1.28 (sextet, 2H, J=7.4 Hz), 1.59 (pentet, 2H, J=7.4 Hz), 1.80-1.98 (m, 1H), 2.15-2.33 (m, 2H), 2.36-2.50 (m, 1H), 2.74 (t, 2H, J=7.4 Hz), 2.99-3.08 (m, 2H), 3.74-3.90 (m, 4H), 4.18 (s, 2H), 4.63 (d, 1H, J=16.8 Hz), 4.44 (d, 1H, J=16.2 Hz), 7.02 (d, 2H, J=7.9 Hz), 7.21 (d, 2H, J=7.9 Hz), 7.36 (dd, 2H, J=6.4, 3.3 Hz), 7.54 (dd, 2H, J=6.1, 3.0 Hz), 7.64 (d, 1H, J=8.3 Hz), 7.92 (t, 1H, J=6.9 Hz), 8.14 (dd, 1H, J=3.8, 1.5 Hz), 8.39 (d, 1H, J=7.9 Hz), 8.54 (s, 1H), 8.76 (d, 1H, J=5.6 Hz). $^{13}$C NMR (D$_2$O) 13.46, 20.44, 20.95, 21.84, 27.85, 31.94, 32.49, 48.08, 50.19, 50.51, 56.68, 63.24, 113.90 (2 carbons), 126.15, 126.60 (2 carbons), 126.77, 129.96, 130.18 (2 carbons), 130.46 (2 carbons), 130.90 (2 carbons), 138.19, 139.70, 141.04, 143.03, 144.12, 144.19, 145.66, 148.32, 150.78, 151.78. ES-MS m/z 545 (M+H) Anal Calc. for C$_{35}$H$_{40}$N$_6$·4.0HBr·2.9H$_2$O: C, 45.66; H, 5.45; N, 9.13; Br, 34.72. Found: C, 45.58; H, 5.43; N, 9.00; Br, 34.80.

EXAMPLE: 55

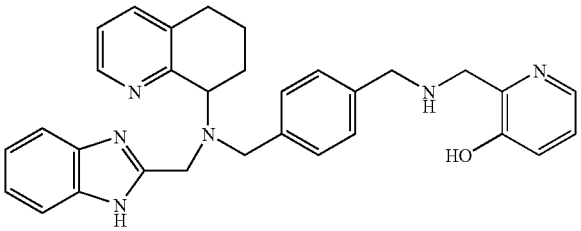

AMD9399: Preparation of N-(3-hydroxy-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-hydroxypyridine-2-carboxaldehyde

To a stirred suspension of 3-hydroxypicolinic acid (5.0570 g, 36.35 mmol) in dry THF (150 mL) at room temperature was added BH$_3$·THF (1.0 M, 145 mL, 145 mmol). The mixture was heated to 70° C. with stirring for 20 hrs, after which time the solution was allowed to cool to room temperature. Dry CH$_3$OH (40 mL) was carefully added, then the mixture heated to 70° C. for 6 hrs. The mixture was concentrated and additional CH₃OH (20 mL) was added. Evaporation of the solution for a second time gave 5.82 g of a light yellow foam.

The foam from above was dissolved in CH₂Cl₂ (150 mL) and CH₃OH (3 mL) at room temperature and treated with MnO₂ (~85%, 40.59 g, 397 mmol). The mixture was stirred for 64 hrs then filtered through celite. The filtrates were concentrated and the residue was purified by flash chromatography (50 g silica, 5:1 hexanes:ethyl acetate) to give 1.43 g (32%) of 3-hydroxypyridine-2-carboxaldehyde as yellow crystals. ¹H NMR (CDCl₃) d 7.38 (d, 1H, J=8.5 Hz), 7.46 (dd, 1H, J=8.7, 4.4 Hz), 8.37 (dd, 1H, J=3.8, 1.3 Hz), 10.08 (s, 1H), 10.74 (s, 1H).

Using General procedure B: N-(1H-benzimidazol-2-ylmethyl)-N-(5,6,7,8-tetrahydro-8-quinolinyl)-1,4-benzenedimethanamine (0.1244 g, 0.313 mmol) and 3-hydroxypyridine-2-carboxaldehyde (0.0342 g, 0.278 mmol) were reacted with NaBH(OAc)₃ (0.0854 g, 0.403 mmol) in CH₂Cl₂ (2.5 mL). Purification of the crude material by radial chromatography (2mm TLC plate, 50:1:1 CH₂Cl₂:CH₃OH:NH₄OH) provided 0.0811 g (58%) of AMD9399 (free base).

Using General Procedure D: the free base from above was converted to the corresponding hydrobromide salt giving 0.1218 g (87%) of AMD9399 as a white solid. ¹H NMR D₂O) ⬜1.80-1.98 (m, 1H), 2.15-2.33 (m, 2H), 2.36-2.50 (m, 1H), 2.99-3.07 (m, 2H), 3.74-3.89 (m, 4H), 3.93-4.05 (m, 2H), 4.63 (d, 1H, J=16.7 Hz), 4.45 (d, 1H, J=16.7 Hz), 7.04 (d, 2H, J=7.7 Hz), 7.22 (d, 2H, J=7.9 Hz), 7.31 (dd, 2H, J=6.1, 3.0 Hz), 7.52 (dd, 2H, J=6.2, 3.1 Hz), 7.65-7.82 (m, 2H), 7.92 (dd, 1H, J=7.9, 6.1 Hz), 8.18 (dd, 1H, J=4.8, 1.3), 8.39 (d, 1H, J=7.9 Hz), 8.76 (d, 1H, J=4.8 Hz). ¹³C NMR (D₂O) ⬜20.46, 20.98, 27.87, 44.33, 50.24, 50.41, 56.71, 63.32, 113.91 (2 carbons), 126.15, 126.52 (2 carbons), 128.60, 129.56, 130.04 (2 carbons), 130.33, 130.44 (2 carbons), 130.92 (2 carbons), 134.19, 136.59, 138.19, 139.71, 141.07, 148.34, 150.77, 151.88, 154.70. ES-MS m/z 505 (M+H) Anal Calc. for C₃₁H₃₂N₆O.4.0HBr.2.4H₂O: C, 42.72; H, 4.72; N, 9.64; Br, 36.67. Found: C, 42.75; H, 4.74; N, 9.39; Br, 36.74

EXAMPLE: 56

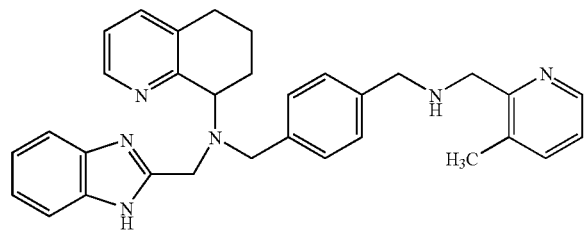

AMD9402: Preparation of N-(3-methyl-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 2-(hydroxymethyl)-3-methylpyridine

To a stirred solution of 2,3-lutidine (4.8363 g, 45.13 mmol) in glacial acetic acid (30 mL) at room temperature was added 30% H₂O₂ (4.6 mL) and the resultant solution was heated to 70° C. After 6 hours, the reaction mixture was cooled to room temperature, additional H₂O₂ (4.6 mL) was added, and the solution was heated at 70° C. overnight. The reaction mixture was allowed to cool to room temperature and then concentrated under reduced pressure. The residue was dissolved in CHCl₃ (100 mL) and treated with solid Na₂CO₃ (14.12 g). After 1 hour, the supernatant was decanted and the residue was washed with warm CHCl₃ (3×50 mL). The combined supernatants were filtered and concentrated to provide 4.6951 g as a yellow solid. The solid was dissolved in acetic anhydride (38 mL) and heated at 90° C. overnight. The mixture was cooled to room temperature and concentrated and the crude product was filtered through a silica plug (33 g silica, ethyl acetate) to give 6.13 g of 2-acetoxymethyl-3-methylpyridine as an orange oil.

To a stirred solution of the oil from above (6.13 g, 37.1 mmol) in dry CH₃OH (75 mL) was added K₂CO₃ (10.30 g, 74.5 mmol). The mixture was stirred for 20 hrs, then distilled water (50 mL) was added to dissolve the K₂CO₃. The mixture was extracted with CHCl₃ (4×100 mL). The combined organic phases were dried (Na₂SO₄) and concentrated to give 3.26 g (59%) of 2-(hydroxymethyl)-3-methylpyridine as a brown solid. ¹H NMR (CDCl₃) ⬜ 2.21 (s, 3H), 4.68 (s, 2H), 7.15 (dd, 1H, J=7.4, 4.7 Hz), 7.46 (d, 1H, J=6.9 Hz), 8.40 (d, 1H, J=4.7 Hz).

Preparation of 3-methylpyridine-2-carboxaldehyde

To a stirred solution of 2-(hydroxymethyl)-3-methylpyridine (1.08 g, 8.77 mmol) in dry CH₂Cl₂ (45 mL) at room temperature was added MnO₂ (8.09 g, 79.1 mmol). The mixture was stirred for 21 hrs then filtered through celite. The filtrate was concentrated to give 0.68 g (64%) of 3-methylpyridine-2-carboxaldehyde. ¹H NMR (CDCl₃) ⬜ 2.66 (s, 3H), 7.39 (dd, 1H, J=8.3, 4.3 Hz), 7.63 (d, 1H, J=7.9 Hz), 8.66 (d, 1H, J=3.3 Hz), 10.19 (s, 1H). This was used without further purification.

Using general procedure B: N-(1H-benzimidazol-2-ylmethyl)-N-(5,6,7,8-tetrahydro-8-quinolinyl)-1,4-benzenedimethanamine (0.1281 g, 0.322 mmol) and 3-methylpyridine-2-carboxaldehyde (0.0376 g, 0.310 mmoll) were reacted with NaBH(OAc)₃ (0.0877 g, 0.414 mmol) in CH₂Cl₂ (2.5 mL). Purification of the crude material by radial chromatography (2mm TLC plate, 50:1:1 CH₂Cl₂:CH₃OH:NH₄OH) followed by a second radial chromatography (1 mm TLC plate, 75:1:1 CH₂Cl₂:CH₃OH:NH₄OH) provided 0.0791 g (51%) of AMD9402 (free base).

Using General Procedure D: the free base was converted to the corresponding hydrobromide salt giving 0.1541 g (98%) of AMD9402. ¹H NMR (D₂O) ⬜1.82-1.98 (m, 1H), 2.16-2.35 (m, 2H), 2.28 (s, 3H), 2.39-2.51 (m, 1H), 3.00-3.08 (m, 2H), 3.77-3.91 (m, 4H), 4.17 (s, 2H), 4.44 (d, 1H, J=16.5 Hz), 4.63 (d, 1H, J=16.2 Hz), 7.07 (d, 2H, J=7.7 Hz), 7.24 (d, 2H, J=7.7 Hz), 7.39 (dd, 2H, J=6.2, 3.1 Hz), 7.55 (dd, 2H, J=6.2, 3.1 Hz), 7.60 (dd, 1H, J=8.0, 5.1 Hz), 7.92 (dd, 1H, J=7.9, 5.9 Hz), 8.39 (d, 1H, J=7.1 Hz), 8.49 (d, 1H, J=3.9 Hz), 8.76 (d, 1H, J=4.9 Hz). ¹³C NMR (D₂O) ⬜17.30, 20.44, 20.93, 27.85, 46.24, 50.15, 50.59, 56.68, 63.19, 113.88 (2 carbons), 126.16 (2 carbons), 126.64 (2 carbons), 130.12, 130.24 (2 carbons), 130.47, 130.90 (2 carbons), 135.86, 138.25, 139.69, 141.03, 144.17, 144.31, 145.91, 148.30, 150.80, 151.76. ES-MS m/z 503 (M+H) Anal Calc. for C₃₂H₃₄N₆.4.0HBr.2.8H₂O: C, 43.84; H, 5.01; N, 9.59; Br, 36.45. Found: C, 43.81; H, 5.10; N, 9.45; Br, 36.58.

EXAMPLE: 57

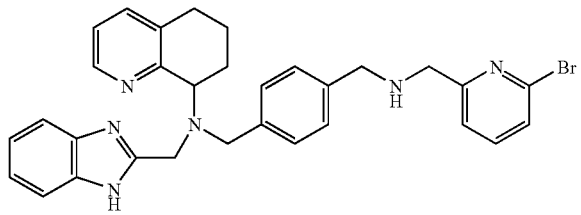

AMD9411: Preparation of N-(6-bromo-2-pyridinyl-methyl)-N'-(1H-benzimidazol-2-ylmethyl)-N'-(5,6,7,8-tetrahydro-8-quinolinyl)-1,4-benzenedimethanamine(hydrobromide salt)

Preparation of 6-bromopyridine-2-carboxaldehyde

To a stirred solution of 6-bromopicolinic acid (0.4998 g, 2.47 mmol) in dry THF (13 mL) at room temperature was added $BH_3$.THF (1.0M, 10.0 mL, 10.0 mmol). The reaction was stirred for 19 hrs then quenched with the addition of dry $CH_3OH$ (9 mL) followed by heating to 70° C. for 20 hrs. The clear solution was concentrated and methanol (20 mL) was added, and the mixture was evaporated once again (repeated three times). The residue was purified by flash chromatography (31 g silica, 49:1 $CH_2Cl_2$:$CH_3OH$) to afford 0.2218 g of a yellow oil.

This yellow oil was dissolved in $CH_2Cl_2$ (10 mL) and treated with $MnO_2$ (~85%, 0.9306 g, 10.7 mmol). The suspension was stirred for 63 hrs at room temperature, then for 3 hrs at 40° C. The suspension was then filtered through celite and concentrated. The orange residue obtained was purified by flash chromatography (7 g silica, 99:1 $CH_2Cl_2$:$CH_3OH$) to afford 0.0655 g (19%) 6-bromopyridine-2-carboxaldehyde as an orange crystalline solid. $^1$H NMR (CDCl$_3$): δ 7.74 (m, 2H), 7.93 (dd, J=3 Hz, 9 Hz, 1H), 10.01 (s, 1H).

Using general procedure B: N-(1H-benzimidazol-2-ylmethyl)-N-(5,6,7,8-tetrahydro-8-quinolinyl)-1,4-benzenedimethanamine (0.0847 g, 0.213 mmol) and 6-bromopyridine-2-carboxaldehyde (0.0379 g, 0.204 mmol) were reacted with NaBH(OAc)$_3$ (0.0637 g, 0.301 mmol) in $CH_2Cl_2$ (5 mL). Purification of the crude material by radial chromatography (2mm TLC plate, 100:1:1 $CH_2Cl_2$:$CH_3OH$:$NH_4OH$) provided 0.0666 g (58%) of AMD9411 (free base).

Using General Procedure D: the free base was converted to the corresponding hydrobromide salt giving 0.0835 g (82%) of AMD9411. $^1$H NMR (D$_2$O) □1.82-1.97 (m, 1H), 2.16-2.33 (m, 2H), 2.39-2.49 (m, 1H), 2.99-3.09 (m, 2H), 3.70-3.88 (m, 4H), 3.96 (s, 2H), 4.44 (d, 1H, J=16.7 Hz), 4.63 (d, 1H, J=16.6 Hz), 7.03 (d, 2H, J=8.1 Hz), 7.22 (d, 2H, J=8.0 Hz), 7.30-7.36 (m, 3H), 7.54 (dd, 2H, J=6.1, 3.0 Hz), 7.62 (d, 1H, J=7.5 Hz), 7.72 (t, 1H, J=7.9 Hz), 7.92 (dd, 1H, J=7.9,6.1 Hz), 8.39 (d, 1H, J=7.0 Hz), 8.76 (d, 1H, J=4.4 Hz). $^{13}$C NMR (D$_2$O) □20.48, 20.93, 27.85, 49.62, 49.97, 50.21, 56.69, 63.27, 113.88 (2 carbons), 123.31, 126.13, 126.62 (2 carbons), 129.10, 130.19 (2 carbons), 130.28, 130.45, 130.81 (2 carbons), 138.06, 139.68, 141.06 (2 carbons), 141.65, 148.31 (2 carbons), 150.74, 151.75, 151.85. ES-MS m/z 569 (M+H).

Anal Calc. for $C_{31}H_{31}N_6Br.3.4HBr$ 1.5$H_2O$: C, 42.81; H, 4.33; N, 9.66; Br, 40.43. Found: C, 42.93; H, 4.49; N, 9.37; Br, 40.30.

EXAMPLE: 58

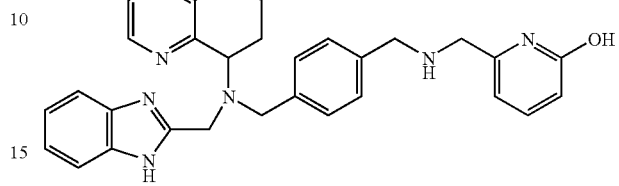

AMD9421: Preparation of N-(6-hydroxy-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 6-hydroxypyridine-2-carboxaldehyde

To a stirred solution of 6-hydroxypicolinic acid (0.5236 g, 3.76 mmol) in dry THF (20 mL) at room temperature was added $BH_3$THF (1.0 M, 19.0 mL, 19.0 mmol). The mixture was heated to 65° C. with stirring for 17 hrs. The mixture was cooled to room temperature and dry $CH_3OH$ (20 mL) was added. The mixture was heated at 65° C. for a further 3.5 hrs then concentrated. Additional $CH_3OH$ (10 mL) was added and the mixture was concentrated once again to give 0.5465 g of a yellow solid. This was used without further purification in the next step.

The yellow solid from above (0.4451 g, 3.62 mmol) was dissolved in pyridine (30 ml) and treated with $MnO_2$ (~85%, 3.21 g, 31.4 mmol). The mixture was stirred for 19 hrs then filtered through celite and the filter cake was washed with CHCl$_3$. The filtrates were concentrated to afford a green oil which was purified by flash chromatography (12 g silica, 19:1 $CH_2Cl_2$:$CH_3OH$) to give 0.1487 g (34%) of 6-hydroxypyridine-2-carboxaldehyde as a white solid. $^1$H NMR (CDCl$_3$) □ 6.79 (dd, 1H, J=6.6, 1.3 Hz), 6.90 (dd, 1H, J=9.1, 1.4), 7.56 (dd, 1H, J=9.2, 6.6 Hz), 9.26 (br s, 1H), 9.55 (s, 1H).

Using general procedure B: N-(1H-benzimidazol-2-ylmethyl)-N-(5,6,7,8-tetrahydro-8-quinolinyl)-1,4-benzenedimethanamine (0.1186 g, 0.298 mmol) and 6-hydroxypyridine-2-carboxaldehyde (0.0333 g, 0.270 mmol) were reacted with NaBH(OAc)$_3$ (0.0881 g, 0.415 mmol) in $CH_2Cl_2$ (5 mL). Purification of the crude material by radial chromatography (2 mm TLC plate, 50:1:1 $CH_2Cl_2$:$CH_3OH$:$NH_4OH$) followed by a second radial chromatography (1 mm TLC plate, 75:1:1 $CH_2Cl_2$:$CH_3OH$:$NH_4OH$) provided 0.0522 g (38%) of the AMD9421 (free base).

Using General Procedure D: the free base was converted to the corresponding hydrobromide salt giving 0.0715 g (80%) of AMD9421 as a white solid. $^1$H NMR (D$_2$O) □1.85-1.99 (m, 1H), 2.16-2.33 (m, 2H), 2.39-2.49 (m, 1H), 3.00-3.09 (m, 2H), 3.75-3.90 (m, 6H), 4.45 (d, 1H, J=16.2 Hz), 4.63 (d, 1H, J=16.7 Hz), 6.52 (d, 1H, J=6.6 Hz), 6.64 (d, 1H, J=9.1 Hz), 7.02 (d, 2H, J=7.9 Hz), 7.23 (d, 2H, J=7.9 Hz), 7.39 (dd, 2H, J=6.4, 3.3 Hz), 7.55 (dd, 2H, J=6.1, 3.1 Hz), 7.67 (dd, 1H, J=9.2, 7.0 Hz), 7.93 (dd, 1H, J=7.9, 6.1 Hz), 8.40 (d, 1H, J=7.9 Hz), 8.76 (d, 1H, J=4.8 Hz). $^{13}$C NMR (D$_2$O) □20.43, 20.94, 27.84, 46.89, 50.15, 50.33, 56.68, 63.26, 111.50, 113.92 (2 carbons), 120.61, 126.13, 126.57 (2 carbons), 129.91, 130.18 (2 carbons), 130.46, 130.88 (2 carbons), 137.82, 138.23, 138.68, 141.06, 143.79 (2 carbons), 148.32, 150.77, 151.84, 165.35. ES-MS m/z 505 (M+H) Anal Calc. for $C_{31}H_{32}N_6O.3.8HBr.2.6H_2O$: C, 43.35; H, 4.81; N, 9.78; Br, 35.35. Found: C, 43.54; H, 4.73; N, 9.69; Br, 35.05

EXAMPLE: 59

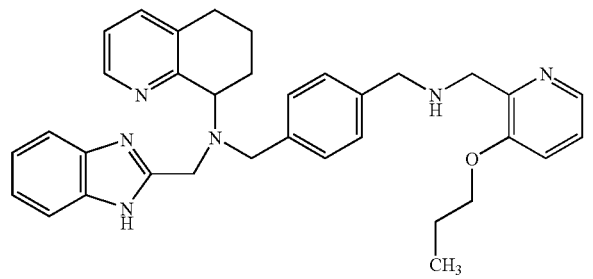

AMD9422: Preparation of N-(3-propoxy-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-n-propoxypyridine-2-carboxaldehyde

To a stirred solution of 3-n-propoxypicolinic acid n-propyl ester (0.1209 g, 0.541 mmol) in dry $CH_2Cl_2$ (5 mL) at −78° C. was added DIBAL-H (1.0 M, 2.5 mL, 2.5 mmol). The mixture was stirred at −78° C. for 1 hr, then at room temperature for 3 hrs. The mixture was poured into saturated aqueous sodium potassium tartrate (15 mL), diluted with $CH_2Cl_2$ (15 mL) and stirred vigorously for 65 hrs. The phases were separated and the aqueous phase extracted with $CH_2Cl_2$ (3×20 mL). The combined organic phases were dried ($Na_2SO_4$) and concentrated to give a yellow oil. The yellow oil was dissolved in $CH_2Cl_2$ (5 mL) and treated with $MnO_2$ (85%, 0.4549 g, 4.45 mmol). The mixture was stirred for 19 hrs then filtered through celite. The filtrate was concentrated to give 0.1014 g of 3-n-propoxypyridine-2-carboxaldehyde as an orange oil. $^1H$ NMR ($CDCl_3$) d 1.09 (t, 3H, J=7.4 Hz), 1.91 (sextet, 2H, J=7.1 Hz), 4.07 (t, 2H, J=6.6 Hz), 7.38-7.47 (m, 2H), 8.39 (dd, 2H, J=4.4, 1.4 Hz), 10.43 (s, 1H).

Using general procedure B: N-(1H-benzimidazol-2-ylmethyl)-N-(5,6,7,8-tetrahydro-8-quinolinyl)-1,4-benzenedimethanamine (0.1211 g, 0.305 mmol) and 3-n-propoxypyridine-2-carboxaldehyde (0.0470 g, 0.285 mmol) were reacted with $NaBH(OAc)_3$ (0.0850 g, 0.401 mmol) in $CH_2Cl_2$ (5 mL). Purification of the crude material by radial chromatography (2 mm TLC plate, 75:1:1 $CH_2Cl_2$:$CH_3OH$:$NH_4OH$) provided 0.0476 g (31%) of AMD9422 (free base) as a white solid.

Using General Procedure D: the free base was converted to the corresponding hydrobromide salt giving 0.0669 g (82%) of AMD9422 as a white powder. $^1H$ NMR ($D_2O$) 0.91 (t, 3H, J=7.5 Hz), 1.74 (sextet, 2H, J=7.1 Hz), 1.84-1.98 (m, 1H), 2.16-2.33 (m, 2H), 2.40-2.51 (m, 1H), 3.00-3.09 (m, 2H), 3.75-3.94 (m, 6H), 4.08 (t, 2H, J=6.6 Hz), 4.46 (d, 1H, J=16.8 Hz), 4.65 (d, 1H, J=17.1 Hz), 7.07 (d, 2H, J=8.4 Hz), 7.22-7.29 (m, 4H), 7.51 (dd, 2H, J=6.1, 3.0 Hz), 7.63 (dd, 1H, J=8.6, 4.9 Hz), 7.72 (d, 1H, J=8.8 Hz), 7.93 (dd, 1H, J=7.0, 7.0 Hz), 8.19 (d, 1H J=5.1 Hz), 8.41 (d, 1H, J=8.0 Hz), 8.77 (d, 1H, J=5.7 Hz). $^{13}C$ NMR $D_2O$) 14.96, 25.26, 25.79, 26.93, 32.68, 49.79, 55.02 (2 carbons), 61.65, 68.21, 76.28, 118.63 (2 carbons), 128.93, 130.97, 131.32 (2 carbons), 132.52 (2 carbons), 134.83 (2 carbons), 135.20, 135.72 (2 carbons), 142.40, 143.01, 143.48, 144.51, 145.91, 153.16, 155.56, 156.73, 159.68. ES-MS m/z 547 (M+H) Anal Calc. for $C_{34}H_{38}N_6O.4.0HBr.3.4H_2O$: C, 43.84; H, 5.28; N, 9.02; Br, 34.31. Found: C, 43.71; H, 5.19; N, 8.91; Br, 34.52.

EXAMPLE: 60

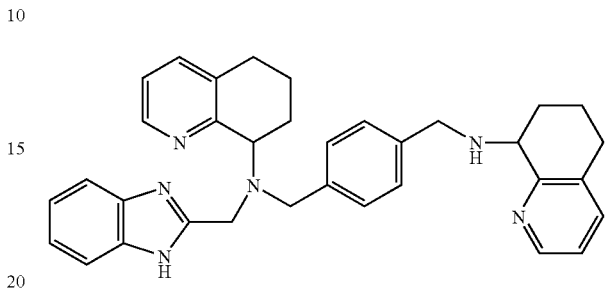

AMD9425: Preparation of N-(5,6,7,8-tetrahydro-8-quinolinyl)-N'-(1H-benzimidazol-2-ylmethyl)-N'-(5,6,7,8-tetrahydro-8-quinolinyl)-1,4-benzenedimethanamine(hydrobromide salt)

Using general procedure B: N-(1H-benzimidazol-2-ylmethyl)-N-(5,6,7,8-tetrahydro-8-quinolinyl)-1,4-benzenedimethanamine (0.1135 g, 0.286 mmol) and 6,7-dihydro-5H-quinolin-8-one (0.0415 g, 0.282 mmol) were reacted with $NaBH(OAc)_3$ (0.0858 g, 0.404 mmol) in $CH_2Cl_2$ (5 mL). Purification of the crude material by radial chromatography (2 mm TLC plate, 75:1:1 $CH_2Cl_2$:$CH_3OH$:$NH_4OH$) provided 0.0716 g (48%) of AMD9425 (free base) as a colourless film.

Using General Procedure D: the free base was converted to the corresponding hydrobromide salt giving 0.1090 g (85%) of AMD9425 as a white powder. $^1H$ NMR ($D_2O$) 1.74-2.07 (m, 4H), 2.11-2.32 (m, 3H), 2.38-2.49 (m, 1H), 2.85-2.93 (m, 2H), 3.00-3.08 (m, 2H), 3.76-3.89 (m, 4H), 4.01-4.10 (m, 1H), 4.08 (t, 2H, J 6.6 Hz), 4.45 (dd, 1H, J=16.6, 4.0 Hz), 4.63 (d, 1H, J=16.6 Hz), 7.09 (d, 2H, J=8.1 Hz), 7.24 (d, 2H, J=7.8 Hz), 7.27-7.34 (m, 2H), 7.48-7.56 (m, 3H), 7.86-7.94 (m, 2H), 8.39 (d, 1H, J=8.0 Hz), 8.49 (br s, 1H), 8.76 (d, 1H, J=5.8 Hz). $^{13}C$ NMR ($D_2O$) 18.30, 20.43, 20.94, 24.28, 27.17, 27.84, 47.68, 50.21, 55.33, 56.68, 63.29, 113.78 (2 carbons), 125.65, 126.11, 126.55 (2 carbons), 130.04(2 carbons), 130.41, 130.90 (2 carbons), 136.55, 136.58, 138.05, 139.67, 141.03, 141.99, 145.80, 145.87, 148.29, 150.78, 151.85. ES-MS m/z 529 (M+H) Anal Calc. for $C_{34}H_{36}N_6.4.5HBr.2.7H_2O$: C, 43.38; H, 4.91; N, 8.93; Br, 38.19. Found: C, 43.39; H, 5.06; N, 8.89; Br, 38.13.

EXAMPLE: 61

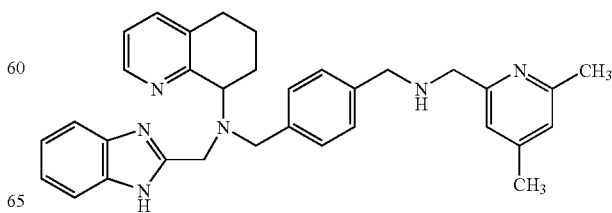

AMD9437: Preparation of N-(4,6-dimethyl-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 2-acetoxymethyl-4,6-dimethylpyridine and 4-acetoxymethyl-2,6-dimethylpyridine.

To a stirred solution of 2,4,6-collidine (3.22 g, 26.6 mmol) in glacial acetic acid (21 mL) at room temperature was added 30% $H_2O_2$ (3.0 mL) and the resultant solution was heated to 70° C. After 6 hours, the reaction mixture was cooled to room temperature, additional $H_2O_2$ (3.0 mL) was added, and the solution was heated at 70° C. overnight. The reaction mixture was cooled to room temperature and concentrated under reduced pressure. The residue was dissolved in $CHCl_3$ (50 mL) and treated with solid $Na_2CO_3$ (9.9 g). After 1 hour, the supernatant was decanted and the residue was washed with warm $CHCl_3$ (3×75 mL). The combined supernatants were filtered and concentrated to provide 2.43 g as a yellow oil. The oil was dissolved in acetic anhydride (22.5 mL) and heated at 90° C. overnight. The mixture was cooled to room temperature and concentrated. The crude product was purified by flash chromatography (40 g silica gel, 2:1 hexanes/ethyl acetate) to give 1.05 g (24%) of 2-acetoxymethyl-4,6-dimethylpyridine: $^1$H NMR ($CDCl_3$) ☐ 2.31 (s, 3H), 2.35 (s, 3H), 2.51 (s, 3H), 5.14 (s, 2H), 6.92 (s, 1H), 6.97 (s, 1H); and 0.35 g (8%) of 4-acetoxymethyl-2,5-dimethylpyridine: $^1$H NMR ($CDCl_3$) ☐ 2.15 (s, 3H), 2.53 (s, 6H), 5.04 (s, 2H), 6.92 (s, 2H).

Preparation of 4,6-dimethylpyridine-2-carboxaldehyde.

To a stirred solution of 2-acetoxymethyl-4,6-dimethylpyridine (1.05 g, 6.28 mmol) in dry $CH_3OH$ (50 mL) at room temperature was added $K_2CO_3$ (1.89 g, 13.7 mmol). The mixture was stirred for 19 hrs then poured into distilled water (25 mL) and the solution was extracted with $CHCl_3$ (4×30 mL). The combined organic phase were dried ($Na_2SO_4$) and concentrated to 0.45 g yellow solid. The solid was dissolved in $CH_2Cl_2$ (20 mL) and treated with $MnO_2$ (~85%, 2.94 g, 28.7 mmol). After stirring for 21 hrs the mixture was filtered through celite. The filtrate was concentrated to afford 0.28 g of a yellow oil, which was a mixture of the desired aldehyde (74%) and the intermediate alcohol (26%). The overall yield was 24%. 4,6-dimethylpyridine-2-carboxaldehyde: $^1$H NMR ($CDCl_3$) ☐ 2.39 (s, 3H), 2.61 (s, 3H), 7.20 (s, 1H), 7.60 (s, 1H), 10.02 (s, 1H).

Preparation of 2,6-dimethylpyridine-4-carboxaldehyde.

To a stirred solution of 4-acetoxymethyl-2,5-dimethylpyridine (0.35 g, 2.09 mmol) in dry $CH_3OH$ (25 mL) at room temperature was added $K_2CO_3$ (0.77 g, 5.57 mmol). The mixture was stirred for 19 hrs then poured into distilled water (20 mL). The mixture was extracted with $CHCl_3$ (4×30 mL) and the combined organic phase were dried ($Na_2SO_4$) and concentrated to give 0.24 g white solid. This solid was dissolved in $CH_2Cl_2$ (20 mL) and treated with $MnO_2$ (~85%, 1.56 g, 15.3 mmol). After stirring for 21 hrs the mixture was filtered through celite. The filtrate was concentrated to afford 0.150 g (53%) of 2,6-dimethylpyridine-4-carboxaldehyde as yellow oil. $^1$H NMR ($CDCl_3$) ☐ 2.63 (s, 6H), 7.36 (s, 2H), 10.01 (s, 1H).

Using general procedure B: N-(1H-benzimidazol-2-ylmethyl)-N-(5,6,7,8-tetrahydro-8-quinolinyl)-1,4-benzenedimethanamine (0.1200 g, 0.302 mmol) and 4,6-dimethylpyridine-2-carboxaldehyde (0.0510 g, 0.282 mmol) were reacted with $NaBH(OAc)_3$ (0.0827 g, 0.390 mmol) in $CH_2Cl_2$ (5 mL). Purification of the crude material by radial chromatography (2 mm TLC plate, 75:1:1 $CH_2Cl_2$:$CH_3OH$:$NH_4OH$) provided 0.0689 g (47%) of AMD9437 (free base) as a white foam.

Using General Procedure D: the free base was converted to the corresponding hydrobromide salt giving 0.1067 g (88%) of AMD9437 as a white powder. $^1$H NMR ($D_2O$) ☐ 1.83-1.99 (m, 1H), 2.18-2.35 (m, 2H), 2.40-2.60 (m, 4H), 2.67 (s, 3H), 3.01-3.11 (m, 2H), 3.79-3.93 (m, 4H), 4.30 (s, 2H), 4.46 (d, 1H, J=16.6 Hz), 4.65 (d, 1H, J=16.6 Hz), 7.07 (d, 2H, J=7.5 Hz), 7.26 (d, 2H, J=7.8 Hz), 7.45 (dd, 2H, J=6.4, 3.3 Hz), 7.55-7.68 (m, 4H), 7.95 (t, 1H, J=7.5 Hz), 8.32 (d, 1H, J=8.0 Hz), 8.78 (d, 1H, J=5.6 Hz). $^{13}$C NMR ($D_2O$) ☐ 20.87, 21.76, 22.24, 23.16, 29.16, 48.07, 51.41, 52.15, 57.99, 64.48, 115.27 (2 carbons), 127.45, 127.66, 127.94 (2 carbons), 130.40, 131.06, 131.61 (2 carbons), 131.83, 132.23 (2 carbons), 139.72, 141.01, 142.36, 144.65, 149.63 (2 carbons), 152.09, 153.04, 156.68, 162.58. ES-MS m/z 517 (M+H) Anal Calc. for $C_{33}H_{36}N_6$.4.0HBr.3.6$H_2O$: C, 43.49; H, 5.26; N, 9.28; Br, 35.31. Found: C, 43.88; H, 5.01; N, 9.21; Br, 35.24.

EXAMPLE: 62

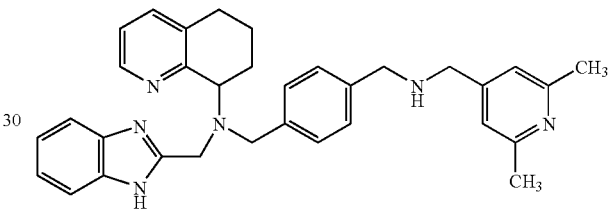

AMD9438: Preparation of N-(2,6-dimethyl-4-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Using general procedure B: N-(1H-benzimidazol-2-ylmethyl)-N-(5,6,7,8-tetrahydro-8-quinolinyl)-1,4-benzenedimethanamine (0.1276 g, 0.321 mmol) and 2,6-dimethylpyridine-4-carboxaldehyde (0.0420 g, 0.311 mmol) were reacted with $NaBH(OAc)_3$ (0.0919 g, 0.434 mmol) in $CH_2Cl_2$ (5 mL). Purification of the crude material by radial chromatography (2mm TLC plate, 75:1:1 $CH_2Cl_2$:$CH_3OH$:$NH_4OH$) followed by a second radial chromatography (1 mm TLC plate, 100:1:1 $CH_2Cl_2$:$CH_3OH$:$NH_4OH$) provided 0.0493 g (31%) of AMD9438 (free base) as a white solid.

Using General Procedure D: the free base was converted to the corresponding hydrobromide salt giving 0.0767 g (88%) of AMD9438 as a white powder. $^1$H NMR ($D_2O$) ☐ 1.83-2.00 (m, 1H), 2.18-2.36 (m, 2H), 2.42-2.52 (m, 1H), 2.71 (s, 6H), 3.02-3.10 (m, 2H), 3.80-3.94 (m, 4H), 4.16 (s, 2H), 4.47 (d, 1H, J=16.7 Hz), 4.66 (d, 1H, J=16.4 Hz), 7.09 (d, 2H, J=8.0 Hz), 7.27 (d, 2H, J=8.0 Hz), 7.45 (dd, 2H, J=6.1, 3.0 Hz), 7.54-7.62 (m, 4H), 7.95 (dd, 1H, J=7.7, 6.1 Hz), 8.42 (d, 1H, J=7.8 Hz), 8.78 (d, 1H, J=5.4 Hz). $^{13}$C NMR ($D_2O$) ☐ 19.24 (2 carbons), 20.44, 20.93, 27.85, 48.62, 50.13, 50.77, 56.68, 63.18, 113.95 (2 carbons), 125.10 (2 carbons), 126.12, 126.62 (2 carbons), 129.78, 130.40 (2 carbons), 130.52 (2 carbons), 130.89, 138.36, 139.69, 141.04, 148.29 (2 carbons), 150.40, 150.79, 151.77, 154.54. ES-MS m/z 517 (M+H) Anal Calc. for $C_{33}H_{36}N_6$.4.0HBr.4.1$H_2O$: C, 43.36; H, 5.31; N, 9.19; Br, 34.96. Found: C, 43.50; H, 5.30; N, 8.99; Br, 34.74.

EXAMPLE: 63

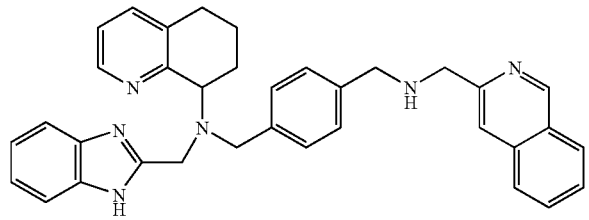

AMD9439: Preparation of N-(3-isoquinolinylmethyl)-N'-(1H-benzimidazol-2-ylmethyl)-N'-(5,6,7,8-tetrahydro-8-quinolinyl)-1,4-benzenedimethanamine (hydrobromide salt)

Preparation of isoquinoline-3-carboxaldehyde

To a stirred solution of isoquinoline-3-carboxylic acid (0.3179 g, 1.84 mmol) in dry THF (10 mL) at room temperature was added $BH_3$—THF (1.0 M, 7.5 mL, 7.5 mmol). The mixture was stirred for 17 hrs, dry $CH_3OH$ (10 mL) was added, and the reaction was heated to 75° C. with stirring for a further 24 hrs. The mixture was concentrated and the residue was treated with dry $CH_3OH$ (3×10 mL), removing the solvent by evaporation each time. The crude product was purified by column chromatography (12 g silica gel, 19:1 $CH_2Cl_2$:$CH_3OH$) to give 0.0359 g of 3-(hydroxymethyl)isoquinoline as a white film. The solid was dissolved in dry $CH_2Cl_2$ (5 mL) and treated with $MnO_2$ (~85%, 0.2978 g, 2.91 mmol) with stirring for 19 hrs then filtered through celite. Concentration of the filtrate afforded 0.0252 g (9%) of isoquinoline-3-carboxaldehyde as yellow oil. $^1H$ NMR ($CDCl_3$) d 7.73-7.82 (m, 2H), 7.97-8.07 (m, 2H), 8.37 (s, 1H), 9.36 (s, 1H), 10.25 (s, 1H).

Using general procedure B: N-(1H-benzimidazol-2-ylmethyl)-N-(5,6,7,8-tetrahydro-8-quinolinyl)-1,4-benzenedimethanamine (0.0666 g, 0.168 mmol) and isoquinoline-3-carboxaldehyde (0.0252 g, 0.159 mmol) were reacted with $NaBH(OAc)_3$ (0.0481 g, 0.227 mmol) in $CH_2Cl_2$ (5 mL). Purification of the crude material by radial chromatography (2 mm TLC plate, 100:1:1 $CH_2Cl_2$:$CH_3OH$:$NH_4OH$) provided 0.0455 g (53%) of AMD9439 (free base) as a white solid.

Using General Procedure D, the free base was converted to the corresponding hydrobromide salt giving 0.0720 g (92%) of AMD9439 as a white powder. $^1H$ NMR ($D_2O$) $\delta$ 1.80-1.96 (m, 1H), 2.14-2.31 (m, 2H), 2.37-2.47 (m, 1H), 3.65 (d, 1H, J=12.8 Hz), 3.78 (d, 1H, J=12.7 Hz), 3.84 (s, 2H), 4.28 (s, 2H), 4.41 (d, 1H, J=16.2 Hz), 4.60 (d, 1H, J=16.6 Hz), 4.70-4.75 (m, 1H), 7.02 (d, 2H, J=8.4 Hz), 7.15 (d, 2H, J=7.9 Hz), 7.29 (dd, 2H, J=6.3, 3.2 Hz), 7.52 (dd, 2H, J=6.2, 3.1 Hz), 7.85, (t, 1H, J=7.5 Hz), 7.93 (dd, 1H, J=8.2, 5.9 Hz), 7.98-8.08 (m, 3H), 8.27 (d, 1H, J=8.4 Hz), 8.40 (d, 1H, J=6.7 Hz), 8.75 (d, 1H, J=4.3 Hz), 9.43 (s, 1H). $^{13}C$ NMR ($D_2O$) $\delta$ 20.41, 20.91, 27.84, 48.89, 50.13, 50.32, 56.53, 63.09, 113.88 (2 carbons), 125.22, 126.15, 126.57 (2 carbons), 127.65, 127.87, 129.71 (2 carbons), 130.11, 130.44 (2 carbons), 130.75, 130.89, 135.37, 137.54, 138.07, 138.34, 139.68, 141.05, 148.32 (2 carbons), 150.77, 151.35 (2 carbons), 151.74. ES-MS m/z 539 (M+H) Anal Calc. for $C_{35}H_{34}N_6$·4.0HBr·3.6$H_2O$: C, 45.34; H, 4.91; N, 9.06; Br, 34.47. Found: C, 45.39; H, 4.99; N, 8.96; Br, 34.35.

EXAMPLE: 64

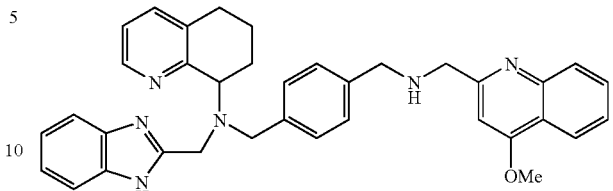

AMD9440: Preparation of N-(4-methoxy-2-quinolinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 4-methoxyquinoline-2-carboxaldehyde.

To a stirred solution of 4-methoxyquinoline-2-carboxylic acid (0.3069 g, 1.78 mmol) in dry THF (9 mL) at 0° C. was added $BH_3$—THF. The mixture was allowed to warm to room temperature and stirred for 6.5 hrs. Dry $CH_3OH$ (10 mL) was added and the mixture heated to 70° C. for 17 hrs and then concentrated. The resulting crude residue was dissolved in methanol (20 mL) and concentrated (repeat 3 times) and the residual oil was purified by flash chromatography (20 g silica, 39:1 $CH_2Cl_2$:$CH_3OH$) to afford 0.23 g of an orange oil.

The oil from above was dissolved in dry $CH_2Cl_2$ (7 mL) and treated with $MnO_2$ (85%, 1.0956 g, 12.6 mmol) at room temperature. The suspension was stirred for 63 hrs then filtered through celite. The filtrate was concentrated to give 0.17 g (51%) 4-methyoxyquinoline-2-carboxaldehyde as a yellow solid. $^1H$ NMR ($CDCl_3$): $\delta$ 4.13 (s, 3H), 7.39 (s, 1H), 7.64 (dd, J=6 Hz, 9 Hz, 1H), 7.80 (dd, J=6 Hz, 9 Hz, 1H), 8.18 (d, J=6 Hz, 1H), 8.26 (d, J=6 Hz, 1H), 10.16 (s, 1H).

Using general procedure B: N-(1H-benzimidazol-2-ylmethyl)-N-(5,6,7,8-tetrahydro-8-quinolinyl)-1,4-benzenedimethanamine (0.1133 g, 0.285 mmol) and 4-methoxyquinoline-2-carboxaldehyde (0.0490 g, 0.262 mmol) were reacted with $NaBH(OAc)_3$ (0.0831 g, 0.392 mmol) in $CH_2Cl_2$ (5 mL). Purification of the crude material by radial chromatography (2 mm TLC plate, 100:1:1 $CH_2Cl_2$:$CH_3OH$:$NH_4OH$) provided 0.0520 g (35%) of AMD9440 (free base) as a white foam.

Using General Procedure D: the free base was converted to the corresponding hydrobromide salt giving 0.0762 g (86%) of AMD9440 as a white powder. $^1H$ NMR ($D_2O$) $\delta$ 1.80-1.94 (m, 1H), 2.12-2.27 (m, 2H), 2.99-3.07 (m, 1H), 3.48 (d, 1H, J=12.7 Hz), 3.68 (d, 1H, J=12.7 Hz), 3.94 (s, 2H), 4.20 (s, 3H), 4.35 (d, 1H, J=16.7 Hz), 4.50 (s, 2H), 4.56 (d, 1H, J=15.3 Hz), 4.64-4.72 (m, 1H), 7.02 (q, 4H, J=7.5 Hz), 7.28 (s, 1H), 7.40 (dd, 2H, J=6.1, 3.1 Hz), 7.55 (dd, 2H, J=6.6, 3.1 Hz), 7.65, (t, 1H, J=7.5 Hz), 7.88-7.98 (m, 3H), 8.22 (d, 1H, J=8.3 Hz), 8.40 (d, 1H, J=7.0 Hz), 8.72 (d, 1H, J=4.4 Hz). $^{13}C$ NMR ($D_2O$) $\delta$ 20.39, 20.83, 27.84, 48.10, 49.94, 51.08, 56.23, 58.70, 62.70, 102.55, 113.96 (2 carbons), 120.53, 121.18, 123.39, 126.19, 126.70 (2 carbons), 129.44, 129.71, 130.42 (2 carbons), 130.52 (2 carbons), 135.37, 138.29, 139.69, 140.20, 141.06, 148.34 (2 carbons), 149.99, 150.74, 151.52, 169.78. ES-MS m/z 569 (M+H) Anal Calc. for $C_{36}H_{36}N_6O$·4.0HBr·4.1$H_2O$: C, 44.75; H, 5.03; N, 8.70; Br, 33.08. Found: C, 44.99; H, 5.04; N, 8.52; Br, 32.82.

EXAMPLE: 65

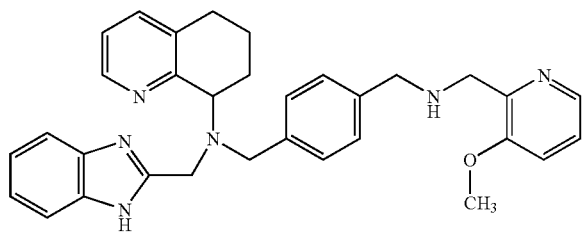

AMD9455: Preparation of N-(3-methoxy-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-methoxypyridine-2-carboxaldehyde.

To a stirred solution of 3-hydroxypicolinic acid (0.7122 g, 5.1 mmol) in $CH_3OH$ (32 mL) at room temperature was added concentrated $H_2SO_4$ (4 mL). The mixture was heated to reflux for 18 hrs then concentrated. The residue was diluted with saturated aqueous $Na_2CO_3$ (45 mL) and extracted with $CH_2Cl_2$ (4×30 mL). The combined organic phases were dried ($Na_2SO_4$) and concentrated to give 0.73 g 3-hydroxypicolinic acid methyl ester as a white powder.

The powder (0.55 g, 3.6 mmol) was dissolved in dry N,N-dimethylformamide (25 mL) and treated with $K_2CO_3$ (0.6218 g, 4.4 mmol) followed by $CH_3I$ (0.63 mL, 10.1 mmol) and the mixture was stirred for 2 hrs then concentrated to afford a bright yellow solid. The solid was dissolved in $CH_2Cl_2$ (25 mL) and washed with brine (25 mL). The aqueous phase was extracted with $CH_2Cl_2$ (4×20 mL). The combined organic phases were dried ($Na_2SO_4$) and concentrated to give a crude brown syrup which was purified by flash chromatography (20 g silica, 39:1 $CH_2Cl_2$:$CH_3OH$) to afford 0.4547 g 3-methoxypicolinic acid methyl ester as yellow oil.

To a stirred solution of the oil from above (0.40 g, 2.4 mmol) in dry THF (5 mL) at 0° C. was added $BH_3$.THF (1.0M, 9.6 mL, 9.6 mmol). The mixture was stirred at room temperature for 17 hr, at which point a further 4 equivalents of $BH_3$—THF were added. The resulting mixture was stirred for a further 4 hrs then quenched with dry $CH_3OH$ (25 mL). The mixture was concentrated, diluted with $CH_3OH$ (25 mL) and refluxed for 17 hrs and concentrated once again. The residue was dissolved in methanol (15 mL) and concentrated (repeat 3 times) to give a yellow oil. The oil was purified by flash chromatography (24 g silica, 49:1 $CH_2Cl_2$:$CH_3OH$) to afford 0.0843 g of a mixture of 3-methoxypicolinic acid methyl ester (17%) and 2-(hydroxymethyl)-3-methoxypyridine (83% as shown by NMR).

This mixture was dissolved in $CH_2Cl_2$ (6 mL) and treated with $MnO_2$ (0.4743 g, 5.5 mmol). The suspension was stirred at room temperature for 63 hrs then filtered through celite. The filtrate was concentrated to afford 0.0800 g of a colourless oil (50% 3-methoxypyridine-2-carboxaldehyde and 50% 3-methoxypicolinic acid methyl ester). Purification of the mixture by column chromatography on silica gel gave the desired 3-methoxypyridine-2-carboxaldehyde (10% overall yield for 4 steps): $^1H$ NMR ($CDCl_3$): δ 3.98 (s, 3H), 7.39 (m, 2H), 8.40 (d, 1H, J=3.6 Hz), 10.30 (s, 1H).

Using general procedure B: N-(1H-benzimidazol-2-ylmethyl)-N'-(5,6,7,8-tetrahydro-8-quinolinyl)-1,4-benzene-dimethanamine (0.131 g, 0.330 mmol) and 3-methoxypyridine-2-carboxaldehyde (0.0400 g, 0.292 mmol) were reacted with $NaBH(OAc)_3$ (0.0850 g, 0.401 mmol) in $CH_2Cl_2$ (10 mL). Purification of the crude material by radial chromatography (2 mm TLC plate, 75:1:1 $CH_2Cl_2$:$CH_3OH$:$NH_4OH$) provided 0.0728 g (48%) of AMD9455 (free base) as a white foam.

Using General Procedure D: the free base was converted to the corresponding hydrobromide salt giving 0.1102 g (88%) of AMD9455 as a white powder. $^1H$ NMR ($D_2O$) 1.85-1.99 (m, 1H), 2.18-2.35 (m, 2H), 2.41-2.52 (m, 1H), 3.02-3.09 (m, 2H), 3.78-3.98 (m, 9H), 4.47 (d, 1H, J=16.6 Hz), 4.66 (d, 1H, J=16.7 Hz), 7.06 (d, 2H, J=7.9 Hz), 7.23-7.31 (m, 4H), 7.53 (dd, 2H, J=6.1, 3.1 Hz), 7.69 (dd, 1H, J=8.8, 5.2 Hz), 7.77, d 1H, J=8.2 Hz), 7.94 (dd, 1H, J=7.8, 5.9 Hz), 8.21 (d, 1H, J=5.0 Hz), 8.41 (d, 1H, J=7.9 Hz), 8.78 (d, 1H, J=5.3 Hz). $^{13}C$ NMR ($D_2O$) 20.46, 20.99, 27.87, 45.09, 50.22 (2 carbons), 56.68 (2 carbons), 63.36, 113.84 (2 carbons), 123.81, 126.15, 126.51 (2 carbons), 127.98, 130.00 (2 carbons), 130.41, 130.88 (2 carbons), 137.28, 138.14, 138.41, 139.71 (2 carbons), 141.08, 148.35 (2 carbons), 150.75, 151.91, 155.54. ES-MS m/z 519 (M+H) Anal Calc. for $C_{32}H_{34}N_6O.4.0HBr.2.6H_2O$: C, 43.23; H, 4.90; N, 9.45; Br, 35.95. Found: C, 43.40; H, 4.81; N, 9.35; Br, 35.76.

EXAMPLE: 66

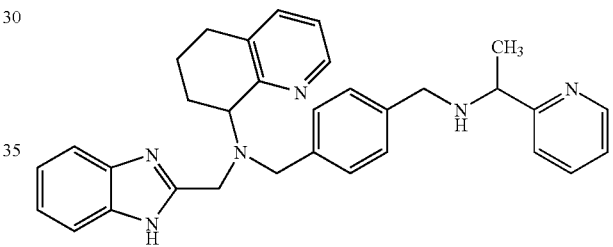

AMD9481: Preparation of N-[1-(2-pyridinyl)eth-1-yl]-N'-(1H-benzimidazol-2-ylmethyl)-N'-(5,6,7,8-tetrahydro-8-quinolinyl)-1,4-benzenedimethanamine (hydrobromide salt)

Using general procedure B: 2-acetylpyridine (46 mg, 0.4 mmol) and N-(1H-benzimidazol-2-ylmethyl)-N-(5,6,7,8-tetrahydro-8-quinolinyl)-1,4-benzenedimethanamine (150 mg, 0.4 mmol) were reacted with sodium triacetoxyborohydride (120 mg, 0.57 mmol) at room temperature in dichloromethane (5 mL) for 16 hours to yield, after work-up and chromatography, the desired N-[1-(2-pyridinyl)eth-1-yl]-N'-(N-benzimidazol-2-ylmethyl)-N'-(5,6,7,8-tetrahydro-8-quinolinyl)-1,4-benzenedimethanamine as a flakey white solid (18 mg, 9.5%). $^1H$ NMR ($CDCl_3$) δ 1.35 (m, 3H), 1.69 (m, 1H), 2.05 (m, 2H), 2.24 (m, 2H), 2.73 (m, 1H), 2.84 (m, 1H), 3.52 (d, 2H, J=15 Hz), 3.70 (s, 1H), 3.85 (q, 1H, J=5 Hz), 3.95 (d, 1H, J=18 Hz), 4.06 (m, 1H), 4.15 (d, 1H, J=15 Hz), 7.12-7.21 (m, 6H), 7.31 (d, 1H, J=7 Hz), 7.34 (d, 3H, J=9 Hz), 7.41 (d, 1H, J=9 Hz), 7.53 (br, 1H), 7.59 (m, 2H), 8.53 (d, 1H, J=4 Hz), 8.67 (d, 1H, J=5 Hz).

Using general procedure D: the solid from above was converted to the corresponding hydrobromide salt to give AMD9481 (0.02 g) as a white solid. $^1H$ NMR ($D_2O$) 1.56 (m, 3H), 1.90 (m, 1H), 2.23 (m, 2H), 2.43 (m, 1H), 3.04 (br d, 2H), 3.43 (m, 1H), 3.62 (m, 1H), 3.83 (d, 2H, J=8.4 Hz), 4.31

(m, 1H), 4.42 (dd, 1H, J=5.7, 16.5 Hz), 4.62 (d, 1H, J=16.2 Hz), 4.79 (m, 1H), 6.95 (d, 2H, J=7.8 Hz), 7.18 (dd, 2H, J=2.7, 8.1 Hz), 7.37 (d, 1H, J=3 Hz), 7.40 (d, 1H, J=3.6 Hz), 7.47 (m, 1H), 7.50-7.60 (m, 3H), 7.94 (t, 1H, J=6.9 Hz), 8.01 (br t, 1H, J=7.8 Hz), 8.41 (d, 1H, J=7.8 Hz), 8.64 (d, 1H, J=7.8 Hz), 8.77 (d, 1H, J=7.8 Hz); $^{13}$C NMR (D$_2$O) □ 18.31, 20.43, 20.92, 27.83, 48.58, 50.18, 56.65, 57.65, 63.22, 113.84 (3 carbons), 123.87, 125.45, 126.12, 126.59 (3 carbons), 129.88 (3 carbons), 130.47, 130.78, 137.94, 139.67, 140.28, 141.03, 148.29, 149.18, 150.80, 151.78, 153.86. ES-MS m/z 503 (M+H). Anal. Calcd. for C$_{32}$H$_{34}$N$_6$.4.0HBr.3.5H$_2$O: C, 43.22; H, 5.10; N, 9.45; Br, 35.94. Found: C, 43.36; H, 4.98; N, 9.07; Br, 35.88.

EXAMPLE: 67

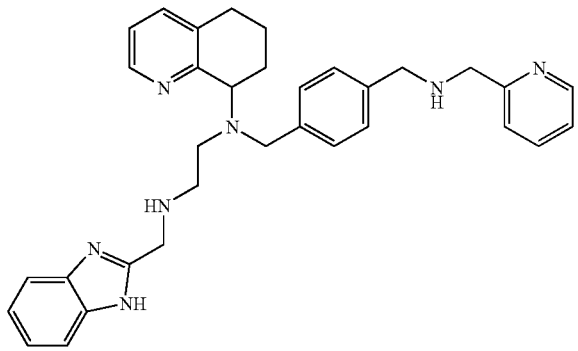

AMD9388: Preparation of N-(2-pyridinylmethyl)-N'-[2-[(1H-benzimidazol-2-ylmethyl)amino]ethyl]-N'-(5,6,7,8-tetrahydro-8-quinolinyl)-1,4-benzene-dimethanamine(hydrobromide salt)

Using General Procedure B: To a stirred solution of N-(2-nitrobenzenesulfonyl)-N-(2-pyridinylmethyl)-N'-(5,6,7,8-tetrahydro-8-quinolinyl)-1,4-benzenedimethanamine (1.55 g, 2.83 mmol) and N-(t-butyloxycarbonyl)-aminoacetaldehyde (0.500 g, 3.14 mmol) in CH$_2$Cl$_2$ (15 mL) was added NaBH(OAc)$_3$ (0.908 g, 4.28 mmol) and the mixture was stirred at room temperature for 16 hours. Aqueous work-up gave a yellow foam (2.05 g) which was used without further purification in the next step.

The foam from above (2.05 g) was dissolved in CH$_2$Cl$_2$ (4 mL) and treated with trifluoroacetic acid (2 mL) and the mixture stirred for 2 days. Work-up gave the amine as a dark foam (1.65 g). To a solution of the crude amine (0.830 g) and triethylamine (0.34 mL, 2.5 mmol) in CH$_2$Cl$_2$ (7.5 mL) at 0 □C was added a solution of 2-nitrobenzenesulfonyl chloride (0.380 g, 1.7 mmol) in CH$_2$Cl$_2$ (7.5 mL) and the mixture stirred for 1.5 hours. The reaction was diluted with CH$_2$Cl$_2$ (10 mL) and brine (15 mL) and the phases separated. The aqueous phase was washed with CH$_2$Cl$_2$ (2×10 mL) and the combined organic extracts dried (Na$_2$SO$_4$), filtered and concentrated under reduced pressure. Purification of the resultant brown foam by column chromatography on silica gel (CH$_2$Cl$_2$/MeOH, 96:4) afforded the desired nosyl-protected amine (0.890 mg, 81% over 3 steps) as a yellow foam.

To a solution of the foam from above (0.890 mg, 1.15 mmol) and 1-(tert-butoxycarbonyl)-2-(chloromethyl)benzimidazole (0.462 g, 1.73 mmol) in CH$_3$CN (7 mL) was added powdered K$_2$CO$_3$ (0.409 g, 2.96 mmol) and the mixture was stirred at room temperature overnight then at 50 □C for 23 hours. The mixture was concentrated under reduced pressure and diluted with CH$_2$Cl$_2$ (25 mL) and water (25 mL). The phases were separated and the aqueous phase was washed with CH$_2$Cl$_2$ (2×10 mL). The combined organic extracts were dried (Na$_2$SO$_4$), filtered and concentrated under reduced pressure. The resulting orange foam (1.36 g) was used without further purification in the next step.

The foam from above (0.588 g) was dissolved in CH$_2$Cl$_2$ (4 mL) and treated with trifluoroacetic acid (2 mL) and the mixture stirred for 2 hours. The resulting intermediate (0.521 g) was then subjected to Nosyl deprotection using General Procedure C:

A solution of the foam from above (0.521 g) was reacted with thiophenol (0.6 mL, 5.84 mmol) and K$_2$CO$_3$ (1.11 g, 8.04 mmol) and the mixture stirred at room temperature for 2.5 hours. Purification of the resultant orange oil by column chromatography on silica gel (20:1:1 CH$_2$Cl$_2$/MeOH/NH$_4$OH) gave the desired free base (219 mg, 35% over 3 steps) as a yellow foam.

Using General Procedure D: The free base (0.219 g, 0.306 mmol) was converted to the corresponding hydrobromide salt giving AMD9388 (0.336 g) as a pale yellow solid. $^1$H NMR (D$_2$O) □1.70-1.78 (m, 1H), 2.04-2.14 (m, 2H), 2.30-2.35 (m, 1H), 2.89-2.92 (m, 2H), 3.09-3.13 (m, 1H), 3.22-3.38 (m, 3H), 3.83 (s, 2H), 3.99 (d, 1H, J=13.2 Hz, 412 (d, 1H, J=13.2 Hz), 4.36 (S, 2H), 4.36-4.43 (m, 1H), 4.56 (d, 1H, J=15.3 Hz), 4.64 (d, 1H, J=15.3 Hz), 7.29 (d, 2H, J=8.1 Hz), 7.41 (d, 2H, J=8.1 Hz, 7.52-7.56 (m, 2H), 7.61-7.75 (m, 5H), 8.10 (td, 1H, J=7.8, 1.5 Hz), 8.14 (d, 1H, J=8.1 Hz), 8.47 (d, 1H, J=4.5 Hz), 8.62 (d, 1H, J=5.1 Hz); $^{13}$C NMR (D$_2$O) □ 19.95, 20.48, 27.68, 41.90, 46.81, 48.33, 48.85, 51.30, 54.70, 59.83, 115.01 (2 carbons), 125.57, 127.23, 127.36, 127.51 (2 carbons), 130.06, 130.87 (4 carbons), 132.11 (2 carbons), 139.09, 139.60, 140.17, 142.34, 145.02, 145.75, 146.84, 147.24, 151.53. ES-MS m/z 532 (M+H). Anal. Calcd. for C$_{33}$H$_{37}$N$_7$.5.1HBr.3.3H$_2$O: C, 39.49; H, 4.89; N, 9.77; Br, 40.60. Found: C, 39.44; H, 4.68; N, 9.46; Br, 40.75.

EXAMPLE: 68

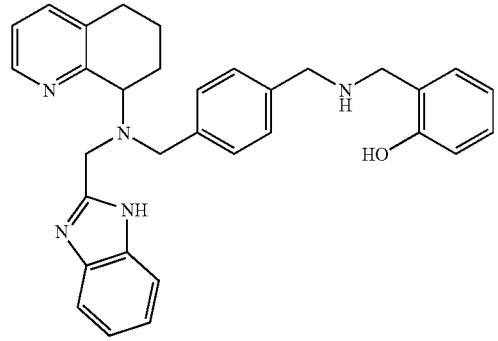

AMD9495: Preparation of N-(2-hydroxyphenylmethyl)-N'-(1H-benzimidazol-2-ylmethyl)-N'-(5,6,7,8-tetrahydro-8-quinolinyl)-1,4-benzenedimethanamine (hydrobromide salt)

Using General Procedure B: To a stirred solution of N'-(1H-benzimidazol-2-ylmethyl)-N'-(5,6,7,8-tetrahydro-8-quinolinyl)-1,4-benzenedimethanamine (147 mg, 0.37 mmol) and salicylaldehyde (0.04 mL, 0.38 mmol) in CH$_2$Cl$_2$ (5 mL) was added NaBH(OAc)$_3$ (100 mg, 0.47 mmol) and the resultant mixture was stirred at room temperature for 16 hours. Purification of the crude material by radial chromatography on silica gel gel (2 mm plate, 75:1:1 CH$_2$Cl$_2$/MeOH/NH$_4$OH) afforded the free amine (100 mg, 54%) as a white foam.

Using General Procedure D: Conversion of the foam from above (51 mg, 0.063 mmol) to the hydrobromide salt followed by re-precipitation of the intermediate solid from methanol/ether gave AMD9495 (75 mg, 95%) as a white solid. $^1$H NMR (D$_2$O) ☐1.80-1.97 (m, 1H), 2.19-2.33 (m, 2H), 2.41-2.44 (m, 1H), 3.01-3.04 (m, 2H), 3.59 (d, 1H, J=13.2 Hz), 3.65 (d, 1H, J=13.22 Hz), 3.70 (s, 2H), 3.78 (d, 1H, J=12.9 Hz), 3.86 (d, 1H, J=12.9 Hz), 4.46 (d, 1H, J=16.5 Hz), 4.65 (d, 1H, J=16.5 Hz), 4.69-4.79 (m, 1H, overlap with HOD), 6.95 (d, 2H, J=7.5 Hz), 7.02 (d, 2H, J=7.5 Hz), 7.14 (d, 1H, J=6.9 Hz), 7.21-7.25 (m, 4H), 7.35 (t, 1H, J=7.5 Hz), 7.46-7.50 (m, 2H), 7.93 (t, 1H, J=6.6 Hz), 8.40 (d, 1H, J=7.8 Hz), 8.77 (d, 1H, J=5.7 Hz); $^{13}$C NMR (D$_2$O) ☐ 20.45, 21.00, 27.87, 46.32, 49.30, 50.33, 56.73, 63.42, 113.78 (2 carbons), 115.84, 117.50, 120.93, 126.14, 126.58 (2 carbons), 129.81 (2 carbons), 130.34, 130.56, 130.85 (2 carbons), 131.97, 132.17, 137.79, 139.70 (2 carbons), 141.05, 148.32, 150.77, 151.89, 155.37. ES-MS m/z 504 (M+H). Anal. Calcd. for C$_{32}$H$_{33}$N$_5$O.3.0HBr.1.9H$_2$O: C, 49.24; H, 5.14; N, 8.97; Br, 30.71. Found: C, 49.28; H, 5.23; N, 8.80; Br, 30.71.

EXAMPLE 69

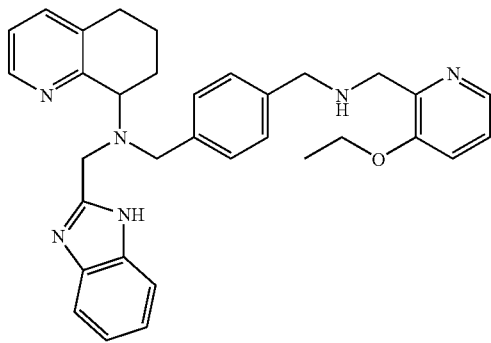

AMD9507: Preparation of N-(3-ethoxy-2-pyridinyl-methyl)-N'-(1H-benzimidazol-2-ylmethyl)-N'-(5,6,7,8-tetrahydro-8-quinolinyl)-1,4-benzenedimethanamine(hydrobromide salt)

Preparation of 3-fluoropyridine 1-oxide

To a solution of 3-fluoropyridine (2.2 mL, 25.6 mmol) in glacial acetic acid (18 mL) was added a 30 wt. % hydrogen peroxide solution in water (2.7 mL, 24 mmol) and the reaction mixture stirred at 70° C. for 3 hours. An additional portion of hydrogen peroxide (2.7 mL, 24 mmol) was then added and the reaction was stirred at 70° C. for an additional 17 hours. The mixture was concentrated under reduced pressure and the resultant crude was diluted with CHCl$_3$ (35 mL) and solid Na$_2$CO$_3$ (2.8 g). The mixture was allowed to stand for 1 hour before the organic layer was decanted off through filter paper. The remaining solid was diluted with CHCl$_3$ (25 mL) and the mixture was heated to 60° C. in a water bath before the organic layer was decanted off through filter paper. This extraction process was repeated 8 times. The filtrates were combined and concentrated to give the title compound as a yellow solid (2.77 g, 96% crude yield). $^1$H NMR (CDCl$_3$): δ 7.06-7.12 (m, 1H), 7.26 (dd, 1H, J=15.3, 6.6 Hz), 8.09 (d, 1H, J=6.6 Hz), 8.14-8.23 (m, 1H).

Preparation of 3-fluoro-2-pyridinecarbonitrile

To a solution of 3-fluoropyridine 1-oxide (1.21 g, 10.7 mmol) in CH$_3$CN (10 mL) was added Et$_3$N (4.4 mL, 31.6 mmol) followed by TMSCN (4.3 mL, 32.2 mmol) and the reaction was stirred at reflux for 6.5 hours. The mixture was diluted with CH$_2$Cl$_2$ (100 mL) and washed with saturated aqueous NaHCO$_3$ (50 mL). The aqueous layer was extracted with CH$_2$Cl$_2$ (3×40 mL) and the combined organic layers were dried (Na$_2$SO$_4$), filtered and concentrated to give a crude dark red oil. Purification of the crude material by column chromatography on silica gel (CH$_2$Cl$_2$/MeOH, 98:2) afforded the title compound as a yellow solid (1.01 g, 77%). $^1$H NMR (CDCl$_3$): δ 7.58-7.67 (m, 2H), 8.54-8.57 (m, 1H).

Preparation of 3-ethoxypicolinic acid

To a solution of 3-fluoro-2-pyridinecarbonitrile (0.99 g, 8.1 mmol) in H$_2$O (3.1 mL) and EtOH (3.1 mL) was added solid NaOH pellets (3.24 g, 81 mmol) and the reaction stirred at 100° C. for 2 hours. The reaction mixture was cooled to room temperature, diluted with H$_2$O (30 mL) and washed with Et$_2$O (2×15 mL). The aqueous phase was acidified with 1N HCl (81 mL, pH 3-4) and extracted with a 2:1 mixture of CH$_2$Cl$_2$/EtOAc (20×30 mL) to give the desired acid as a yellow powdered solid (0.58 g, 43%). $^1$H NMR (CDCl$_3$+CD$_3$OD): δ 1.39 (t, 3H, J=7.0 Hz), 4.10 (q, 2H, J=7.0), 7.42-7.53 (m, 2H), 8.20-8.21 (m, 1H).

Preparation of 3-ethoxy-2-hydroxymethylpyridine

To a solution of 3-ethoxypicolinic acid (0.202 g, 1.21 mmol) in dry THF (1 mL) was added BH$_3$.THF (1.0 M in THF, 5.0 mL, 5.0 mmol) and the reaction mixture stirred at room temperature for 2.5 hours. The mixture was then quenched with methanol (20 mL), stirred at reflux for 4 hours and concentrated under reduced pressure. The resultant crude product was dissolved in methanol (3×15 mL) and concentrated to give the desired crude alcohol (0.231 g) as an orange solid. $^1$H NMR (CDCl$_3$): δ 1.46 (t, 3H, J=7.0 Hz), 4.07 (q, 2H, J=7.0 Hz), 4.74 (s, 2H), 7.09-7.20 (m, 2H), 8.14 (d, 1H, J=4.5 Hz).

Preparation of 3-ethoxy-2-pyridinecarboxaldehyde

To a solution of the crude alcohol from above (0.231 g) in CH$_2$Cl$_2$ (5.4 mL) was added activated manganese(IV) oxide (0.963 g, 11.1 mmol) and the reaction mixture stirred at room temperature for 15 hours. The resultant black suspension was filtered through celite and the cake was washed with CH$_2$Cl$_2$. The combined filtrates were evaporated under reduced pressure to give a yellow syrup (0.12 g). Purification of the crude oil by column chromatography on silica gel (CH$_2$Cl$_2$/MeOH, 98:2) gave the title compound as a clear oil (0.063 g, 34% over 2 steps). $^1$H NMR (CDCl$_3$): δ 1.49 (t, 3H, J=7.0 Hz), 4.21 (q, 2H, J=7.0 Hz), 7.38 (d, 1H, J=8.6 Hz), 7.43 (dd, 1H, J=8.6, 4.4 Hz), 8.35 (d, 1H, J=4.4 Hz), 10.39 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (145 mg, 0.37 mmol) and 3-ethoxy-2-pyridinecarboxaldehyde (54 mg, 0.36 mmol) in CH$_2$Cl$_2$ (5 mL) was added NaBH(OAc)$_3$ (110 mg, 0.52 mmol) and the resultant mixture was stirred at room temperature for 2.5 days. Purification of the crude material by radial chromatography on silica gel gel (2 mm plate, 75:1:1 CH$_2$Cl$_2$/MeOH/NH$_4$OH) afforded the free amine (87 mg, 44%) as a white foam.

Using General Procedure D: Conversion of the foam from above (77 mg, 0.14 mmol) to the hydrobromide salt followed by re-precipitation of the intermediate solid from methanol/ether gave AMD9507 (110 mg, 95%) as a white solid. $^1$H NMR (D₂O) □1.35 (t, 3H, J=6.9 Hz), 1.86-1.90 (m, 1H), 2.17-2.26 (m, 2H), 2.40-2.45 (m, 1H), 3.01-3.03 (m, 2H), 3.78 (d, 1H, J=12.6 Hz), 3.83 (d, 1H, J=12.6 Hz), 3.87 (d, 1H, J=13.8 Hz), 3.93 (d, 1H, J=13.8 Hz), 3.95 (d, 1H, J=14.1 Hz), 4.08 (d, 1H, J=14.1 Hz), 4.26 (q, 2H, J=6.9 Hz), 4.45 (d, 1H, J=16.5 Hz), ), 4.64 (d, 1H, J=16.5 Hz), 4.77-4.79 (m, 1H, overlap with HOD), 7.06 (d, 2H, J=7.5 Hz), 7.25 (d, 2H, J=7.5 Hz), 7.29 (dd, 2H, J=6, 3 Hz), 7.51 (dd, 2H, J=6, 3 Hz), 7.89-7.93 (m, 2H), 8.06 (d, 1H, J=9 Hz), 8.29 (d, 1H, J=5.4 Hz), 8.38 (d, 1H, J=7.8 Hz), 8.76 (d, 1H, J=5.7 Hz); $^{13}$C NMR (D₂O) □ 11.94, 18.27, 18.82, 25.70, 41.00, 48.03, 48.42, 54.61, 61.14, 64.96, 111.74 (2 carbons), 123.99, 124.31 (2 carbons), 126.61, 127.48, 127.85 (2 carbons), 128.21, 128.82 (2 carbons), 132.40, 133.11, 136.17, 137.54 (2 carbons), 138.88, 146.17 (2 carbons), 148.51, 149.70, 154.06. ES-MS m/z 533 (M+H). Anal. Calcd. for $C_{33}H_{36}N_6O·4.0HBr·2.8H_2O$: C, 43.71; H, 5.07; N, 9.27; Br, 35.25. Found: C, 43.65; H, 5.12; N, 9.12; Br, 35.41.

EXAMPLE 70

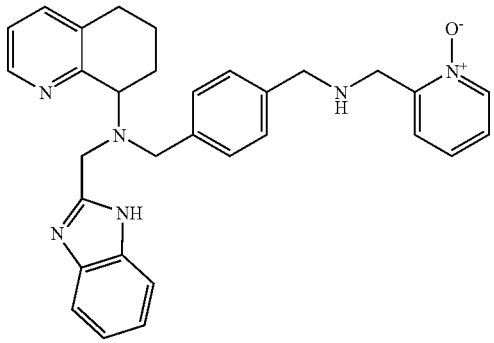

AMD9508: Preparation of N-(1-oxo-2-pyridinylmethyl)-N'-(1H-benzimidazol-2-ylmethyl)-N'-(5,6,7,8-tetrahydro-8-quinolinyl)-1,4-benzenedimethanamine (hydrobromide salt)

Preparation of 2-hydroxymethyl-pyridine 1-oxide

To a solution of 2-pyridine carbinol (1.3 mL, 13.5 mmol) in acetic acid (glacial, 9 mL) was added a 30% solution of hydrogen peroxide in water (1.4 mL, 12 mmol) and the reaction stirred at 70° C. for 2 hours. A second portion of hydrogen peroxide was then added and the mixture stirred at 70° C. for an additional 15 hours. The reaction was concentrated and the resultant crude diluted with CHCl₃ (20 mL) and solid Na₂CO₃ (1.56 g) and stirred for 1 hour before the organic layer was decanted off through filter paper. The remaining solid was diluted with CHCl₃ (20 mL) and the mixture heated to 60° C. in a water bath before the organic layer was again decanted off through filter paper. This process was repeated 8 times. The filtrates were combined and concentrated to give the oxide as a white powdered solid. Purification by column chromatography on silica gel (CH₂Cl₂/MeOH, 92:8) afforded the title compound (1.08 g, 64%). $^1$H NMR (CDCl₃): δ 4.84 (s, 2H), 7.35-7.50 (m, 3H), 8.32 (d, 1H, J=6 Hz).

Preparation of 2-pyridine carboxaldehyde 1-oxide

To a solution of 2-hydroxymethyl-pyridine 1-oxide (0.23 g, 1.84 mmol) in CHCl₃ (8 mL) was added activated manganese(IV) oxide (1.48 g, 17.0 mmol) and the reaction stirred at room temperature for 4 hours. The black suspension was then filtered through celite and the cake was washed with CHCl₃ (100 mL). The combined filtrates were concentrated under reduced pressure to give a yellow oil (0.22 g). Purification of the crude product by column chromatography on silica gel (CH₂Cl₂/MeOH, 95:5) afforded the desired aldehyde (0.046 g, 20% but 66% based on recovered starting material). $^1$H NMR (CDCl₃): δ 7.6-7.7 (m, 3H), 7.76 (dd, 1H, J=7.5, 1.8 Hz), 8.20 (d, 1H, J=6 Hz), 10.56 (s, 1H).

Using General Procedure A: To a stirred solution of N'-(1H-benzimidazol-2-ylmethyl)-N'-(5,6,7,8-tetrahydro-8-quinolinyl)-1,4-benzenedimethanamine (155 mg, 0.39 mmol) and 2-pyridine carboxaldehyde 1-oxide (45 mg, 0.37 mmol) in MeOH (4.5 mL) was added NaCNBH₃ (50 mg, 0.8 mmol) and the resultant mixture was stirred at room temperature for 16 hours. Purification of the crude material by radial chromatography on silica gel gel (2 mm plate, 75:1:1 CH₂Cl₂/MeOH/NH₄OH) afforded the free amine (71 mg, 38%) as a white foam.

Using General Procedure D: Conversion of the foam from above (71 mg, 0.14 mmol) to the hydrobromide salt followed by re-precipitation of the intermediate solid from methanol/ether gave AMD9508 (75 mg, 95%) as a pale yellow solid. $^1$H NMR (D₂O) □1.85-1.93 (m, 1H), 2.18-2.31 (m, 2H), 2.40-2.45 (m, 1H), 3.02-3.04 (m, 2H), 3.76 (d, 1H, J=12.6 Hz), 3.82 (s, 2H), 3.84 (d, 1H, J=12.6 Hz), 3.90 (s, 2H), 4.45 (d, 1H, J=16.8 Hz), 4.64 (d, 1H, J=16.8 Hz), 4.75-4.79 (m, 1H, overlap with HOD), 7.04 (d, 2H, J=7.8 Hz), 7.21 (d, 2H, J=7.8 Hz), 7.27 (dd, 2H, J=6, 3 Hz), 7.51 (dd, 2H, J=6, 3 Hz), 7.56-7.68 (m, 3H), 7.93 (dd, 1H, J=7.5, 6 Hz), 8.28 (d, 1H, J=6 Hz), 8.40 (d, 1H, J=8.1 Hz), 8.77 (d, 1H, J=5.7 Hz); $^{13}$C NMR (D₂O) □ 20.44, 20.98, 27.86, 45.81, 49.95, 50.27, 56.68, 63.37, 113.84 (2 carbons), 126.15, 126.46 (2 carbons), 128.56, 129.45, 129.81 (2 carbons), 130.40, 130.90 (2 carbons), 132.02, 138.11, 139.71 (2 carbons), 140.03 (2 carbons), 141.06, 148.34 (2 carbons), 150.75, 151.92. ES-MS m/z 505 (M+H). Anal. Calcd. for $C_{31}H_{32}N_6·4.0HBr·2.2H_2O$: C, 42.90; H, 4.69; N, 9.68; Br, 36.83. Found: C, 43.06; H, 4.84; N, 9.55; Br, 36.73.

EXAMPLE 71

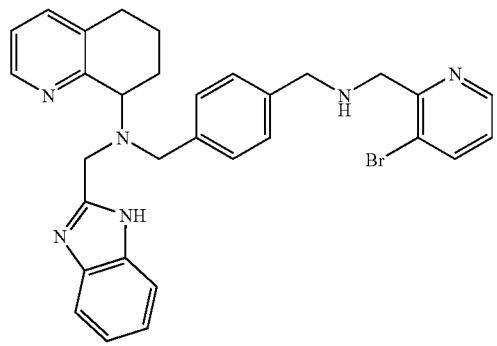

AMD9540: Preparation of N-(3-bromo-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-bromo-2-pyridinecarboxaldehyde:

To a solution of 3-bromo-2-picoline (prepared as described by Guthikonda, R. N.; Cama, L. D.; Quesada, M.; Woods, M. F.; Salzmann, T. N.; Christensen, B. G. *J. Med. Chem.* 1987, 30, 871-880) (249 mg, 1.45 mmol) in dioxane (2 mL) was added selenium(IV) oxide (212 mg, 1.91 mmol) and the mixture stirred at reflux overnight. The reaction mixture was concentrated under reduced pressure and purified by column chromatography on silica gel (Hexanes/ether, 3:1) to afford the title compound (78 mg, 29%) as a pale yellow solid. $^1$H NMR (CDCl$_3$): δ 7.38 (dd, 1H, J=9, 6 Hz), 8.05 (d, 1H, J=9 Hz), 8.76 (d, 1H, J=3 Hz), 10.25 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (170 mg, 0.43 mmol) and 3-bromo-2-pyridinecarboxaldehyde (78 mg, 0.42 mmol) in CH$_2$Cl$_2$ (7 mL) was added NaBH(OAc)$_3$ (152 mg, 0.72 mmol) and the resultant mixture was stirred at room temperature over the weekend. Purification of the crude material by radial chromatography on silica gel gel (2 mm plate, 75:1:1 CH$_2$Cl$_2$/MeOH/NH$_4$OH) afforded the free amine (143 mg, 44%) as a white foam.

Using General Procedure D: Conversion of the foam from above (106 mg, 0.19 mmol) to the hydrobromide salt followed by re-precipitation of the intermediate solid from methanol/ether gave AMD9540 (140 mg, 86%) as a pale yellow solid. $^1$H NMR (D$_2$O) ☐1.86-1.90 (m, 1H), 2.17-2.30 (m, 2H), 2.40-2.45 (m, 1H), 3.01-3.03 (br m, 2H), 3.77 (d, 1H, J=12.6 Hz), 3.83 (s, 2H), 3.85 (d, 1H, J=12.6 Hz), 4.07 (s, 2H), 4.44 (d, 1H, J=16.5 Hz), 4.63 (d, 1H, J=16.5 Hz), 4.66-4.79 (m, 1H, overlap with HOD), 7.07 (d, 2H, J=7.8 Hz), 7.23 (d, 2H, J=8.1 Hz), 7.31 (dd, 2H, J=6.3, 3.3 Hz), 7.52 (dd, 2H, J=6.3, 3.3 Hz), 7.91 (dd, 2H, J=7.8, 6.3 Hz), 8.03 (d, 1H, J=8.1 Hz), 8.38 (d, 1H, J=8.1 Hz), 8.50 (d, 1H, J=4.8 Hz), 8.76 (d, 1H, J=7.8 Hz); $^{13}$C NMR (D$_2$O) ☐ 20.46, 20.95, 27.86, 49.33, 50.08, 50.24, 56.69, 63.22, 113.86, 120.28, 125.83, 126.13, 126.61, 130.30, 130.32, 130.40, 130.86, 138.08, 139.71, 141.02, 141.91, 148.12, 148.31, 149.04, 150.77, 151.78. ES-MS m/z 569 (M+H). Anal. Calcd. for C$_{31}$H$_{31}$N$_6$Br.3.3HBr.2.1H$_2$O: C, 42.68; H, 4.45; N, 9.63; Br, 39.39. Found: C, 42.68; H, 4.45; N, 9.30; Br, 39.44.

EXAMPLE 72

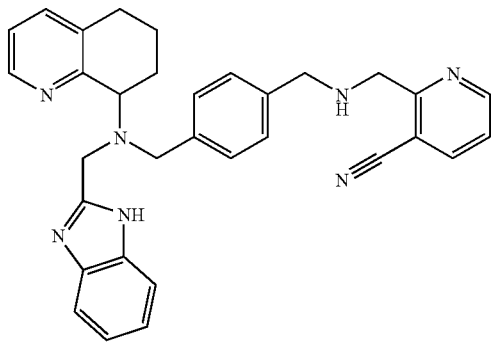

AMD9565: Preparation of N-(3-cyano-2-pyridinlymethyl)-N'-(1H-benzimidazol-2-ylmethyl)-N'-(5,6,7,8-tetrahydro-8-quinolinyl)-1,4-benzenedimethanamine (hydrobromide salt)

Preparation of 3-cyano-2-picoline:

To a mixture of 3-cyano-2-chloro-pyridine (422 mg, 3.05 mmol), methylboronic acid (209 mg, 3.49 mmol) and K$_2$CO$_3$ (1.22 g, 8.83 mmol) in degassed dioxane (5 mL) under argon was added Pd(PPh$_3$)$_4$ (222 mg, 0.19 mmol) and the mixture stirred at reflux over the weekend. The reaction was cooled to room temperature, diluted with CH$_2$Cl$_2$ (20 mL) and filtered through Celite, washing the cake with CH$_2$Cl$_2$ and MeOH. The filtrate was concentrated in vacuo and purified by column chromatography on silica gel (Hexanes/ethyl acetate, 9:1 then 4:1) to afford the desired product (166 mg, 46%) as a white solid. $^1$H NMR (CDCl$_3$): δ 2.78 (s, 3H), 7.25 (dd, 1H, J=9, 6 Hz), 7.90 (dd, 1H, J=6, 3 Hz), 8.69 (d, 1H, J=3 Hz).

Preparation of 3-cyano-2-pyridinecarboxaldehyde:

To a solution of 3-cyano-2-picoline (166 mg, 1.41 mmol) in dioxane (3 mL) was added water (0.2 mL) and selenium (IV) oxide (228 mg, 2.05 mmol) and the mixture stirred at reflux overnight. The reaction mixture was concentrated under reduced pressure and purified by column chromatography on silica gel (Hexanes/ether, 3:1 then 1:1) to afford the title compound (18 mg, 10%) as a pale yellow solid. $^1$H NMR (CDCl$_3$): δ 7.69 (dd, 1H, J=9, 6 Hz), 8.20 (d, 1H, J=9 Hz), 9.00 (d, 1H, J=3 Hz), 10.13 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (60 mg, 0.15 mmol) and 3-cyano-2-pyridinecarboxaldehyde (18 mg, 0.14 mmol) in CH$_2$Cl$_2$ (4 mL) was added NaBH(OAc)$_3$ (45 mg, 0.21 mmol) and the mixture stirred at room temperature for 5 h. Purification of the crude material by radial chromatography on silica gel gel (1 mm plate, CH$_2$Cl$_2$/MeOH/NH$_4$OH, 75:1:1 followed by 50:1:1) afforded the free amine (29 mg, 45%) as a yellow foam.

Using General Procedure D: Conversion of the foam from above (29 mg, 0.057 mmol) to the hydrobromide salt followed by re-precipitation of the intermediate solid from methanol/ether gave AMD9565 (46 mg, 92%) as a pale yellow solid. $^1$H NMR (D$_2$O) ☐1.86-1.90 (m, 1H), 2.17-2.28 (m, 2H), 2.35-2.41 (m, 1H), 3.01-3.03 (br m, 2H), 3.76 (d, 1H, J=12.6 Hz), 3.85 (d, 1H, J=12.6 Hz), 4.40 (s, 2H), 4.46 (d, 1H, J=16.5 Hz), 4.56 (s, 2H), 4.63 (d, 1H, J=16.5 Hz), 4.77-4.79 (m, 1H, overlap with HOD), 7.02 (d, 2H, J=7.8 Hz), 7.07 (dd, 2H, J=6, 3 Hz), 7.23 (d, 2H, J=7.8 Hz), 7.44 (dd, 2H, J=6, 3 Hz), 7.75 (dd, 1H, J=7.8, 5.1 Hz), 7.92 (dd, 1H, J=7.2, 6.6 Hz), 8.39 (d, 1H, J=8.1 Hz), 8.44 (d, 1H, J=8.1 Hz), 8.76 (d, 1H, J=6 Hz), 8.90 (d, 1H, J=5.1 Hz); $^{13}$C NMR (D$_2$O) ☐20.44, 20.98, 27.86, 48.70, 50.40, 56.76 (2 carbons), 63.50, 113.54, 123.64, 124.92, 126.12, 126.27, 128.39, 130.29, 130.97, 133.07, 133.55, 136.96, 139.67, 141.06, 148.31, 150.80, 152.08, 154.43, 160.94, 161.16. ES-MS m/z 514 (M+H). Anal. Calcd. for C$_{32}$H$_{31}$N$_7$.3.7HBr.4.1H$_2$O: C, 43.34; H, 4.88; N, 11.06; Br, 33.34. Found: C, 43.59; H, 4.81; N, 10.92; Br, 33.09.

EXAMPLE 73

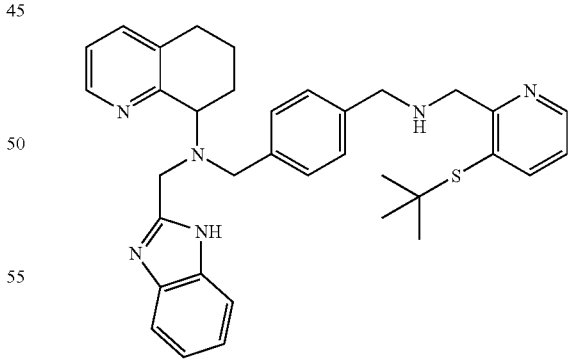

AMD9604: Preparation of N-(3-t-butylthio-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 2-(3-tert-butylthio)pyridylmethyl acetate:

To a solution of 3-bromo-2-picoline (prepared as described by Guthikonda, R. N.; Cama, L. D.; Quesada, M.; Woods, M.

F.; Salzmann, T. N.; Christensen, B. G. *J. Med. Chem.* 1987, 30, 871-880) (1.102 g, 6.41 mmol) in acetic acid (10 mL) was added a 30% wt. aqueous solution of hydrogen peroxide in water (2 mL) and the mixture warmed to 70° C. overnight. An additional portion of hydrogen peroxide (1 mL) was then added and the mixture stirred at 70° C. for another 4 h before being cooled to room temperature and concentrated under reduced pressure. The resultant crude was diluted with $CHCl_3$ (25 mL) and solid $Na_2CO_3$ (1.8 g) and the mixture allowed to stand for 1 h with occasional stirring. The solution was then filtered and the remaining $Na_2CO_3$ solid extracted with $CHCl_3$ (4×20 mL). The combined $CHCl_3$ extracts were concentrated to afford the crude N-oxide (1.29 g) which was used without further purification in the next reaction.

To a solution of the N-oxide from above (1.29 g, 6.4 mmol) in DMF (20 mL) was added the sodium salt of 2-methyl-2-propanethiol (2.10 g, 19.0 mmol) and the resultant suspension stirred at 80° C. for 1 h then at room temperature overnight. The mixture was concentrated under reduced pressure and diluted with ethyl acetate (100 mL). The organic layer was washed with brine (3×75 mL), dried ($Na_2SO_4$), filtered and concentrated under reduced pressure. The resultant crude yellow oil (1.02 g) was used without further purification in the next step.

A solution of the crude N-oxide from above (1.02 g) in acetic anhydride (5 mL) was heated to 80° C. for 2 d. The mixture was then cooled to room temperature, diluted with $CH_2Cl_2$ (15 mL) and MeOH (3 mL) and concentrated under reduced pressure. The residue was diluted with $CH_2Cl_2$ (40 mL) and saturated aqueous sodium bicarbonate (40 mL), the phases separated and the aqueous layer extracted with $CH_2Cl_2$ (2×25 mL). The combined organic extracts were dried ($Na_2SO_4$), filtered and concentrated under reduced pressure. Purification by column chromatography on silica gel (Hexanes/EtOAc, 4:1) afforded the title compound (0.66 g, 43% over 3 steps). $^1$H NMR ($CDCl_3$) ☐1.33 (s, 9H), 2.16 (s, 3H), 5.52 (s, 2H), 7.26 (dd, 1H, J=9, 6 Hz), 7.87 (d, 1H, J=9 Hz), 8.62 (d, 1 H, J=6 Hz).

Preparation of 3-(tert-butylthio)pyridine-2-carboxaldehyde:

To a solution of the acetate from above (0.284 g, 1.20 mmol) in MeOH (5 mL) was added powdered $K_2CO_3$ (0.335 g, 2.43 mmol) and the mixture stirred at room temperature for 3 h. The reaction was diluted with $CH_2Cl_2$ (40 mL) and water (30 mL). The phases were separated and the aqueous layer was extracted with $CH_2Cl_2$ (2×20 mL). The combined organic extracts were dried ($Na_2SO_4$), filtered and concentrated under reduced pressure. The resultant alcohol (0.22 g) was used without further purification in the next reaction.

To a solution of the alcohol from above (0.22 g) in $CH_2Cl_2$ (10 mL) was added activated $MnO_2$ (1.221 g, 14.2 mmol) and the mixture stirred at room temperature overnight. The reaction mixture was filtered through Celite and the cake was washed with $CH_2Cl_2$. The solvent was removed from the filtrate under reduced pressure and purification of the resultant crude yellow oil by column chromatography on silica gel (Hexanes/EtOAc, 3:1) afforded the desired aldehyde (0.14 g, 60% over 2 steps) as a yellow oil. $^1$H NMR ($CDCl_3$) ☐1.34 (s, 9H), 7.48 (dd, 1H, J=9, 6 Hz), 8.00 (d, 1H, J=9 Hz), 8.83 (d, 1H, J=6 Hz), 10.78 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (81 mg, 0.20 mmol) and 3-(tert-butylthio)pyridine-2-carboxaldehyde (40 mg, 0.21 mmol) in $CH_2Cl_2$ (5 mL) was added $NaBH(OAc)_3$ (60 mg, 0.28 mmol) and the mixture was stirred at room temperature for 3 h. Purification of the crude material by radial chromatography on silica gel (1 mm plate, $CH_2Cl_2$/MeOH/ $NH_4OH$, 75:1:1 then 50:1:1) afforded the desired amine (43 mg, 37%) as a yellow foam.

Using General Procedure D: Conversion of the foam from above (25 mg, 0.043 mmol) to the hydrobromide salt followed by re-precipitation of the intermediate solid from methanol/ether gave AMD9604 (39 mg, 98%) as a white solid. $^1$H NMR ($D_2O$) ☐1.15 (s, 9H), 186-1.91 (m, 1H), 2.18-2.26 (m, 2H), 2.41-2.46 (m, 1H), 3.02-3.04 (br m, 2H), 3.77 (d, 1H, J=12.6 Hz), 3.79 (s, 2H), 3.85 (d, 1H, J=12.6 Hz), 4.35 (s, 2H), 4.41 (d, 1H, J=16.5 Hz), 4.61 (d, 1H, J=16.5 Hz), 4.70-4.79 (m, 1H, overlap with HOD), 7.04 (d, 2H, J=7.8 Hz), 7.21 (d, 2H, J=7.8 Hz), 7.36-7.44 (m, 3H), 7.55 (dd, 2H, J=6, 3 Hz), 7.92 (dd, 1H, J=7.8, 6 Hz), 7.95 (dd, 1H, J=7.8, 1.5 Hz), 8.39 (d, 1H, J=7.8 Hz), 8.56 (dd, 1H, J=4.8, 1.5 Hz), 8.75 (d, 1H, J=5.1 Hz); $^{13}$C NMR ($D_2O$) ☐ 20.44, 20.85, 27.83, 30.32, 48.53, 49.39, 49.98 (2 carbons), 56.57, 62.94, 113.89, 124.82, 126.14, 126.67, 129.00, 130.25, 130.37, 130.49, 130.73, 138.08, 139.70, 141.04, 148.16, 148.32, 149.45, 150.79, 151.66, 154.45. ES-MS m/z 577 (M+H). Anal. Calcd. for $C_{35}H_{40}N_6S.3.7HBr.2H_2O$: C, 46.08; H, 5.27; N, 9.21; Br, 32.41. Found: C, 46.16; H, 5.15; N, 8.99; Br, 32.33.

EXAMPLE 74

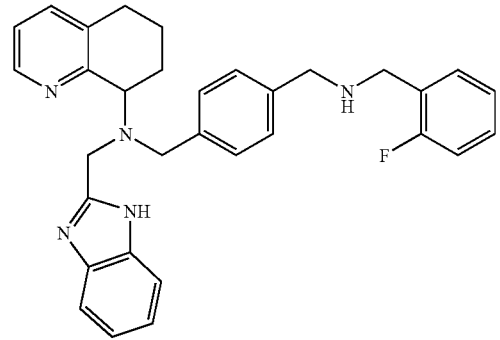

AMD9602: Preparation of N-(2-fluorobenzyl)-N'-(1H-benzimidazol-2-ylmethyl)-N'-(5,6,7,8-tetrahydro-8-quinolinyl)-1,4-benzenedimethanamine(hydrobromide salt)

2-Fluorobenzaldehyde (0.05 mL, 0.5 mmol) was condensed with N'-(1H-benzimidazol-2-ylmethyl)-N'-(5,6,7,8-tetrahydro-8-quinolinyl)-1,4-benzenedimethanamine (200 mg, 0.529 mmol) in MeOH (5 mL) for 1 hour at room temperature and the resultant imine was reduced with sodium borohydride (38 mg, 1.0 mmol) for 2 h (see General Procedures A and B). Purification of the crude residue by column chromatography on silica gel ($CH_2Cl_2$/MeOH, 95:5) yielded the alkylated product (215 mg, 81%) as a pale foam. $^1$H NMR ($CDCl_3$) ☐1.65 (m, 1H), 1.99 (m, 1H), 2.24 (m, 1H), 2.71 (m, 2H), 3.47 (s, 2H), 3.63 (d, 2H, J=5.1 Hz), 3.68 (s, 2H), 3.78 (s, 2H), 3.95 (d, 1H, J=16.1 Hz), 4.02 (m, 1H), 4.12 (d, 1H, J=16.1 Hz), 6.99 (t, 1H, J=9.0 Hz), 7.07 (t, 1H, J=7.4 Hz), 7.17 (m, 6H), 7.29 (dd, 1H, J=7.4, 1.2 Hz), 7.35-7.42 (m, 3H), 7.55 (br s, 2H), 8.60 (d, 1H, J=5.8 Hz).

Conversion of the foam from above (110 mg, 0.2 mmol) to the hydrobromide salt using General Procedure D followed by re-precipitation of the intermediate solid from methanol/ ether gave AMD9602 (115 mg) as a white solid. $^1$H NMR ($D_2O$) ☐ 1.90 (m, 1H), 2.25 (m, 2H), 2.43 (m, 1H), 3.04 (m, 2H), 3.74 (s, 2H), 3.79 (d, 1H, J=12.3 Hz), 3.82 (s, 2H), 3.87 (d, 1H, J=12.3 Hz), 4.46 (d, 1H, J=16.8 Hz), 4.64 (d, 1H, J=16.8 Hz), 4.78 (m, 1H), 7.03 (d, 2H, J=7.8 Hz), 7.27 (m, 8H), 7.51 (m, 3H), 7.94 (dd, 1H, J=5.8, 8.1 Hz), 8.39 (d, 1H, J=8.1 Hz), 8.77 (d, 1H, J=5.7 Hz). $^{13}$C NMR (D$_2$O) ☐20.44, 21.08, 27.85, 44.01, 49.70, 50.27, 56.70, 63.36, 113.85 (2C), 116.21 (d, $J_{C-F}$=21.0 Hz), 118.04(d, $J_{C-F}$=14.9 Hz), 125.48, 126.13, 126.59 (2C), 129.92 (2C), 130.39, 130.88 (2C), 132.56, 132.80 (d, $J_{C-F}$=8.2 Hz), 137.94, 139.69, 141.04, 148.31, 151.32 (d, $J_{C-F}$=83.6 Hz), 161.03 (d, $J_{C-F}$=247 Hz). ES-MS m/z 506 (M+H); Anal. Calcd. for (C$_{32}$H$_{32}$N$_5$F×2 HBr×3 H$_2$O): C, 49.00; H, 5.01; N, 8.93; Br 30.56. Found: C, 49.37; H, 4.89; N, 8.77; Br, 30.21.

EXAMPLE 75

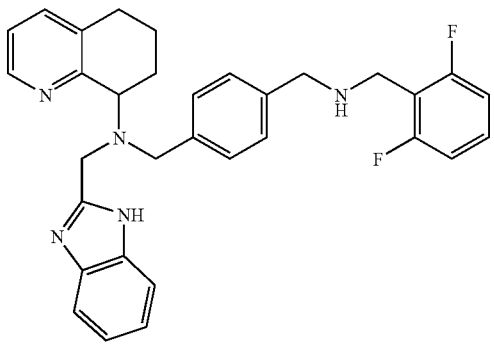

AMD9621: Preparation of N-(2,6-difluorobenzyl)-N'-(1H-benzimidazol-2-ylmethyl)-N'-(5,6,7,8-tetrahydro-8-quinolinyl)-1,4-benzenedimethanamine (hydrobromide salt) (hydrobromide salt)

2,6-Difluorobenzaldehyde (79 mg, 0.56 mmol) was condensed with N'-(1H-benzimidazol-2-ylmethyl)-N'-(5,6,7,8-tetrahydro-8-quinolinyl)-1,4-benzenedimethanamine (217 mg, 0.55 mmol) in dry MeOH (5 mL) for 1.5 hour at room temperature and the resultant imine was reduced with sodium borohydride (45 mg, 1.19 mmol) for 1 h (see General Procedures A and B). Purification of the crude material by radial chromatography on silica gel gel (4 mm plate, CH$_2$Cl$_2$/MeOH/NH$_4$OH, 100:1:1 then 50:1:1) afforded the free amine (234 mg, 81%) as a white foam.

Conversion of the foam from above (134 mg, 0.26 mmol) to the hydrobromide salt using General Procedure D followed by re-precipitation of the intermediate solid from methanol/ether gave AMD9621 (165 mg, 81%) as a white solid. $^1$H NMR (D$_2$O) ☐1.86-1.91 (m, 1H), 2.18-2.27 (m, 2H), 2.41-2.46 (m, 1H), 3.01-3.03 (br m, 2H), 3.72 (d, 1H, J=12.3 Hz), 3.75 (s, 2H), 3.79 (s, 2H), 3.85 (d, 1H, J=12.3 Hz), 4.45 (d, 1H, J=16.5 Hz), 4.64 (d, 1H, J=16.5 Hz), 4.76-4.79 (m, 1H, overlap with HOD), 7.02-7.10 (m, 4H), 7.24 (d, 2H, J=7.5 Hz), 7.31 (dd, 2H, J=6, 3 Hz), 7.46-7.56 (m, 3H), 7.92 (dd, 1H, J=7.2, 6.6 Hz), 8.39 (d, 1H, J=7.8 Hz), 8.77 (d, 1H, J=5.7 Hz); $^{13}$C NMR (D$_2$O) ☐ 20.47, 21.01, 27.88, 37.55, 49.84, 50.28, 56.69, 63.33, 107.10 (t, $^2J_{C-F}$=19.1 Hz), 112.36 (d, $^2J_{C-F}$=23.6 Hz), 113.89, 126.15, 126.56, 129.88, 130.21, 130.40, 130.94, 133.42 (t, $^3J_{C-F}$=10.6 Hz), 137.96, 139.72, 141.04, 148.33, 150.76, 151.89, 161.55 (dd, $^1J_{C-F}$=248.2 Hz, $^3J_{C-F}$=26.4 Hz). ES-MS m/z 524 (M+H). Anal. Calcd. for C$_{32}$H$_{31}$N$_5$F$_2$.3.0HBr.1.7H$_2$O: C, 48.23; H, 4.73; N, 8.79; Br, 30.08. Found: C, 48.25; H, 4.82; N, 8.76; Br, 30.02.

EXAMPLE 76

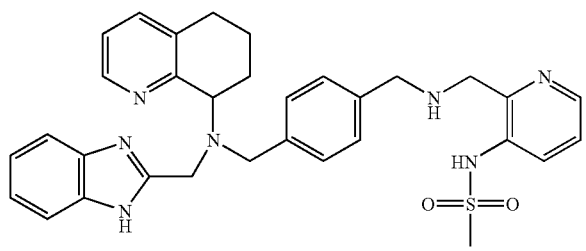

AMD9674: Preparation of N-(3-methylsulphonamido-pyridin-2-ylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-methylsulfonamido-2-pyridinecarboxaldehyde:

To a solution of 2-methyl-3-nitropyridine (prepared as described by Liu, M.-C.; Lin, T.-S.; Sartorelli, A. C. *Synthetic Comm.* 1990, 20, 2965-2970) (5.21 g, 37.7 mmol) in MeOH (20 mL) in a Parr bottle was added 10% palladium on carbon (521 mg) and the mixture hydrogenated at 35 psi hydrogen in a Parr hydrogenator for 1 h. The product mixture was filtered through celite and the solvent from the eluent removed in vacuo to afford 2-methyl-3aminopyridine (4.00 g, 99%) as a brown solid.

To a solution of the solid from above (998 mg, 9.33 mmol) in THF (46 mL) at room temperature was added triethylamine (1.95 mL, 14.0 mmol) and methanesulfonyl chloride (0.65 mL, 8.40 mmol) and the mixture stirred overnight. The reaction was diluted with CH$_2$Cl$_2$ (50 mL) and saturated aqueous NaHCO$_3$ (25 mL) and the aqueous layer extracted with CH$_2$Cl$_2$ (3×15 mL). The combined organic extracts were dried (Na$_2$SO$_4$), filtered and concentrated under reduced pressure. Purification of the resultant brown oil by column chromatography on silica gel (EtOAc/MeOH, 19:1) afforded the desired 3-methylsulfonamido-2-methylpyridine (310 mg, 18%) along with some of the bis-sulfonylated product (484 mg, 20%). 3-Methylsulfonamido-2-methylpyridine: $^1$H NMR (CDCl$_3$) ☐ 2.58 (s, 3H), 3.05 (s, 3H), 6.37 (br s, 1H, NH), 7.20 (dd, 1H, J=9, 6 Hz), 7.81 (dd, 1H, J=9, 3 Hz), 8.38 (dd, 1H, J=6, 3 Hz).

To a solution of 3-methylsulfonamido-2-methylpyridine (310 mg, 1.66 mmol) in dioxane (8 mL) was added water (0.8 mL) and selenium(IV) oxide (241 mg, 2.17 mmol) and the mixture stirred at reflux overnight. The reaction mixture was concentrated under reduced pressure and purified by column chromatography on silica gel (Hexanes/ethyl acetate, 1:1) to afford the title compound (278 mg, 83%). $^1$H NMR (CDCl$_3$) ☐ 3.14 (s, 3H), 7.53 (dd, 1H, J=9, 6 Hz), 8.16 (dd, 1H, J=9, 3 Hz), 8.53 (dd, 1H, J=6, 3 Hz), 10.09 (s, 1H), 10.41 (br s, 1H, NH).

3-Methylsulfonamido-2-pyridinecarboxaldehyde (0.100 mL, 0.50 mmol) was condensed with N'-(1H-benzimidazol-2-ylmethyl)-N'-(5,6,7,8-tetrahydro-8-quinolinyl)-1,4-benzenedimethanamine (204 mg, 0.51 mmol) in dry MeOH (5 mL) for 17 h at room temperature and the resultant imine was reduced with sodium borohydride (38 mg, 1.00 mmol) for 1 h (see General Procedures A and B). Purification of the crude product by radial chromatography (2 mm TLC plate, CH$_2$Cl$_2$/CH$_3$OH/NH$_4$OH, 50:1:1) followed followed by basic alumina flash chromatography (8 g alumina, CH$_2$Cl$_2$/CH$_3$OH, 60: 1) afforded the alkylated amine (59 mg, 20%) as a foam.

Using General Procedure D: Conversion of the foam from above (59 mg) to the hydrobromide salt followed by re-precipitation of the intermediate solid from methanol/ether gave AMD9674 (74 mg, 78%) as a solid. $^1$H NMR (D$_2$O) ☐ 1.81-1.96 (m, 1H), 2.14-2.34 (m, 2H), 2.37-2.48 (m, 1H), 2.99-3.06 (m, 2H), 3.08 (s, 3H), 3.74-3.87 (m, 4H), 4.17 (s, 2H), 4.43 (d, 1H, J=16.2 Hz), 4.61 (d, 1H, J=16.2 Hz), 7.03 (d, 2H, J=7.7 Hz), 7.21 (d, 2H, J=7.6 Hz), 7.36 (dd, 2H, J=6.3, 3.1 Hz), 7.46-7.57 (m, 3H), 7.79, (d, 1H, J=7.8 Hz), 7.90 (t, 1H, J=6.8 Hz), 8.38 (d, 1H, J=8.4 Hz), 8.54 (d, 1H, J=4.8 Hz), 8.74 (d, 1H, J=5.8 Hz). $^{13}$C NMR D$_2$O) d 20.43, 20.86, 27.83, 39.32, 46.80, 50.08, 56.59, 63.06, 113.86 (2 carbons), 125.61, 126.10, 126.61 (2 carbons), 130.21 (2 carbons), 130.47, 130.77 (2 carbons), 136.73, 138.05, 139.66, 141.01, 148.28 (2 carbons), 148.73 (2 carbons), 149.49, 150.81, 151.74. ES-MS m/z 582 (M+H) Anal Calc. for C$_{32}$H$_{35}$N$_7$SO$_2$.4.0HBr.2.1H$_2$O: C, 40.75; H, 4.62; N, 10.39; S, 3.40; Br, 33.89. Found: C, 40.81; H, 4.56; N, 10.31; S, 3.33; Br, 33.75.

EXAMPLE 77

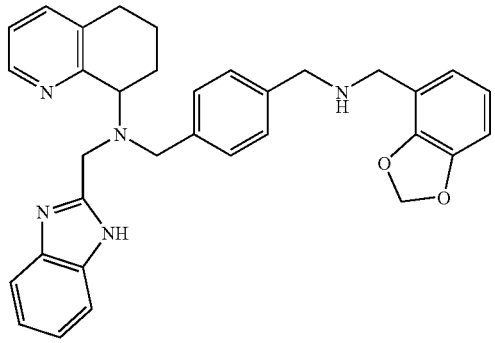

AMD9682: Preparation of N-((methylene-2,3-dioxy)benzenemethyl)-N'-(1H-benzimidazol-2-ylmethyl)-N'-(5,6,7,8-tetrahydro-8-quinolinyl)-1,4-benzenedimethanamine 3-(Methylenedioxy)benzaldehyde (0.100 mL, 0.50 mmol) was condensed with N'-(1H-benzimidazol-2-ylmethyl)-N'-(5,6,7,8-tetrahydro-8-quinolinyl)-1,4-benzenedimethanamine (226 mg, 0.59 mmol) in dry MeOH (2.5 mL) for 2 h at room temperature and the resultant imine was reduced with sodium borohydride (43 mg, 1.14 mmol) for 18 h (see General Procedures A and B). Purification of the crude product by column chromatography on silica gel afforded the title compound (57 mg, 19%) as a white solid. $^1$H NMR (CDCl$_3$) ☐ 1.97-2.08 (m, 2H), 2.23-2.29 (m, 1H), 2.69-2.86 (m, 2H), 3.07 (br s, 2H), 3.73 (s, 2H), 3.74 (s, 4H), 3.96 (d, 1H, J=17.1 Hz), 4.08 (dd, 1H, J=9.3, 6.3 Hz, 4.17 (d, 1H, J=16.8 Hz), 5.91 (s, 2H), 6.7-6.77 (m, 5H), 7.15-7.21 (m, 6H), 7.34 (s, 1H), 7.37 (s, 1H), 7.43 (d, 1H, J=7.2 Hz), 7.21-7.81 (m, 1H), 7.32-7.92 (m,1H), 8.69 (d, 1H, J=4.5 Hz); $^{13}$C NMR (CDCl$_3$) δ 21.79, 23.78, 29.63, 47.73, 48.90, 53.08, 54.12, 60.62, 101.12, 107.84, 121.85, 121.91 (2C), 122.64 (2C), 128.62 (2C), 129.04 (2C), 135.12, 137.60, 138.47, 139.18, 145.90, 147.31, 147.58, 156.70, 157.86;ES-MS m/z 532 (M+H). Anal. Calcd. for C$_{31}$H$_{32}$N$_6$.0.9H$_2$O: C, 72.35; H, 6.40; N, 12.78. Found: C, 72.40; H, 6.16; N, 12.54.

EXAMPLE 78

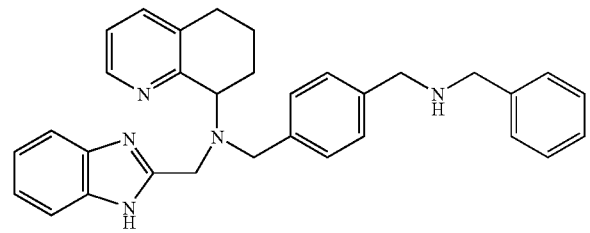

AMD9683: Preparation of N-benzyl-N'-(1H-benzimidazol-2-ylmethyl)-N'-(5,6,7,8-tetrahydro-8-quinolinyl)-1,4-benzenedimethanamine(hydrobromide salt)

Benzaldehyde (0.5 mL, 4.92 mmol) was condensed with N'-(1H-benzimidazol-2-ylmethyl)-N'-(5,6,7,8-tetrahydro-8-quinolinyl)-1,4-benzenedimethanamine (170 mg, 0.428 mmol) in dry MeOH (3 mL) for 17 h at room temperature and the resultant imine was reduced with sodium borohydride (329 mg, 8.70 mmol) for 1 h (see General Procedures A and B). Purification of the crude product by flash chromatography (14 g silica, 30:1:1 EtOAc/CH$_3$OH/NH$_4$OH) followed by radial chromatography (2 mm TLC plate, 100:1:1 CH$_2$Cl$_2$/CH$_3$OH/NH$_4$OH) gave the N-alkylated product (54 mg, 26%) as a foam.

Using General Procedure D: Conversion of the foam from above (68 mg, 81%) to the hydrobromide salt followed by re-precipitation of the intermediate solid from methanol/ether AMD9683 (68 mg, 81%) as a solid. $^1$H NMR (D$_2$O) ☐ 1.81-1.96 (m, 1H), 2.15-2.33 (m, 2H), 2.37-2.49 (m, 1H), 2.98-3.07 (m, 2H), 3.66 (s, 2H), 3.76-3.88 (m, 4H), 4.44 (d, 1H, J=16.6 Hz), 4.63 (d, 1H, J=16.6 Hz), 7.00 (d, 2H, J=7.9 Hz), 7.22 (d, 2H, J=7.8 Hz), 7.27 (dd, 2H, J=6.2, 3.1 Hz), 7.30-7.34 (m, 2H), 7.45-7.52 (m, 5H), 7.92 (dd, 1H, J=7.6, 6.1 Hz), 8.39 (d, 1H, J=7.9 Hz), 8.76 (d, 1H, J=5.3 Hz). $^{13}$C (D$_2$O) ☐ 20.44, 20.97, 27.85, 49.59, 50.27, 50.64, 56.72, 63.37, 113.85 (2 carbons), 126.13, 126.62 (2 carbons), 129.71 (2 carbons), 130.02 (2 carbons), 130.21, 130.36 (2 carbons), 130.43, 130.57, 130.73, 130.86 (2 carbons), 137.93, 139.70, 141.04, 148.30 (2 carbons), 150.79, 151.57. ES-MS m/z 488 (M+H) Anal Calc. for C$_{32}$H$_{33}$N$_5$.3.2HBr.0.6H$_2$O: C, 50.75; H, 4.98; N, 9.25; Br, 33.76. Found: C, 50.66; H, 5.18; N, 9.23; Br, 33.92.

EXAMPLE: 79

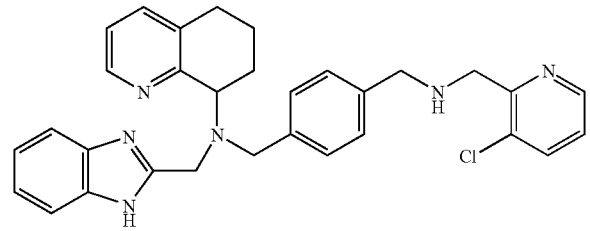

115

AMD9544: Preparation of N-(3-chloro-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-chloro-pyridine-2-carboxaldehyde:

To a solution of TMEDA (660 µL, 2.58 mmol) in ether (20 mL) at −78° C. was added a solution of n-butyl lithium in ether (2.5 M, 1.76 mL, 4.40 mmol). After 30 minutes at −78° C., 3-chloropyridine (419 µL, 4.40 mmol) was added. After another 2 hours at −78° C., DMF (375 µL, 4.84 mmol) was added. After a further 2 hours at −78° C., the reaction was quenched with saturated aqueous $NaHCO_3$ (20 mL), extracted with ether (4×15mL), dried ($Na_2SO_4$), filtered and concentrated in vacuo to give the crude oil. Purification by column chromatography on silica gel (Hexanes:EtOAc 4:1) afforded the title compound as a crystalline solid (168 mg, 27%). $^1$H NMR ($CDCl_3$) 7.45 (dd, 1H, J=8.3, 4.4 Hz), 7.83 (dd, 1H, J=4.8, 1.4 Hz), 8.70 (dd, 1H, J=4.8, 1.5 Hz), 10.28 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (171 mg, 0.43 mmol) and 3-chloro-pyridine-2-carboxaldehyde (56 mg, 0.40 mmol) in $CH_2Cl_2$ (5 mL) was added $NaBH(OAc)_3$ (123 mg, 0.58 mmol) and the mixture was stirred at room temperature for 22 h. Purification of the crude material by radial chromatography on silica gel (1 mm plate, $CH_2Cl_2$/MeOH/$NH_4OH$, 200:1:1) afforded the desired amine (94 mg, 45%) as a yellow foam.

Using General Procedure D: Conversion of the foam from above (94 mg, 0.18 mmol) to the hydrobromide salt followed by re-precipitation of the intermediate solid from methanol/ether gave AMD9544 (138 mg, 90%) as a white solid. $^1$H NMR ($D_2O$) 1.81-1.98 (m, 1H), 2.16-2.34 (m, 2H), 2.39-2.50 (m, 1H), 3.00-3.08 (m, 2H), 3.76-3.91 (m, 4H), 4.12 (s, 2H), 4.46 (d, 1H, J=16.2 Hz), 4.65 (d, 1H, J=16.7 Hz), 7.09 (d, 2H, J=7.9 Hz), 7.25 (d, 2H, J=7.9 Hz), 7.34 (dd, 2H, J=6.4, 2.8 Hz), 7.42 (dd, 1H, J=8.0, 4.9 Hz), 7.55 (dd, 2H, J=6.2, 3.1 Hz), 7.90 (d, 1H, J=8.0 Hz), 7.94 (d, 1H, J=5.8 Hz), 8.40 (d, 1H, J=8.0 Hz), 8.49 (d, 1H, J=4.8 Hz), 8.77 (d, 1H, J=5.7 Hz). $^{13}$C NMR ($D_2O$) 20.46, 20.96, 27.86, 47.54, 50.13, 20.24, 56.70, 63.26, 113.86 (2 carbons), 125.74, 126.13, 126.61 (2 carbons), 130.27 (2 carbons), 130.42, 130.86 (2 carbons), 138.09, 138.69 (2 carbons), 139.70, 141.03, 147.70 (2 carbons), 147.84, 148.31 (2 carbons), 150.79, 151.81. ES-MS m/z 523 (M+H) Anal Calc. for $C_{31}H_{31}N_6Cl.3.5HBr.2.4H_2O$: C, 43.83; H, 4.66; N, 9.89; Cl, 4.17; Br, 32.92. Found: C, 43.88; H, 4.58; N, 9.63; Cl, 4.16; Br, 32.82.

EXAMPLE: 80

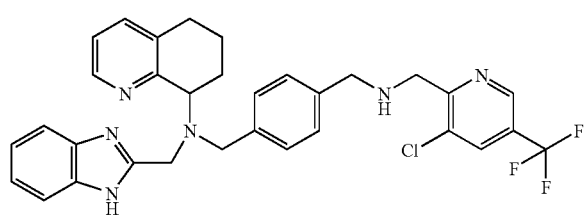

116

AMD9545: Preparation of N-(3-chloro-5-(trifluoromethyl)-2-pyridinylmethyl)-N'-(1H-benzimidazol-2-ylmethyl)-N'-(5,6,7,8-tetrahydro-8-quinolinyl)-1,4-benzenedimethanamine(hydrobromide salt)

Using General Procedure B: To a stirred solution of N'-(1H-benzimidazol-2-ylmethyl)-N'-(5,6,7,8-tetrahydro-8-quinolinyl)-1,4-benzenedimethanamine (133 mg, 0.34 mmol) and 3-chloro-5-(trifluoromethyl)-pyridine-2-carboxaldehyde (66 mg, 0.32 mmol) in $CH_2Cl_2$ (5 mL) was added $NaBH(OAc)_3$ (93 mg, 0.44 mmol) and the mixture was stirred at room temperature for 16 h. Purification of the crude material by radial chromatography on silica gel (1 mm plate, $CH_2Cl_2$/MeOH/$NH_4OH$, 75:1:1) afforded the desired amine (48 mg, 26%) as a yellow foam.

Using General Procedure D: Conversion of the foam from above (48 mg, 0.081 mmol) to the hydrobromide salt followed by re-precipitation of the intermediate solid from methanol/ether gave AMD9545 (42 mg, 58%) as a white solid. $^1$H NMR ($D_2O$) 1.82-1.98 (m, 1H), 2.14-2.34 (m, 2H), 2.99-3.07 (m, 2H), 3.74-3.89 (m, 4H), 4.26 (s, 2H), 4.45 (d, 1H, J=16.3 Hz), 4.63 (d, 1H, J=16.3 Hz), 7.06 (d, 2H, J=7.7 Hz), 7.22 (d, 2H, J=7.7 Hz), 7.37 (dd, 2H, J=6.3, 3.2 Hz), 7.55 (dd, 2H, J=6.3, 3.2 Hz), 7.92 (dd, 1H, J=7.9, 6.1 Hz), 8.26 (s, 1H), 8.39 (d, 1H, J=6.9 Hz), 8.76 (d, 1H, J=4.4 Hz), 8.80 (s, 1H). $^{13}$C NMR ($D_2O$) 20.44, 20.92, 27.84, 47.65, 50.25 (2 carbons), 56.64, 63.20, 113.87 (2 carbons), 126.11, 126.57 (2 carbons), 130.15, 130.34 (2 carbons), 130.52, 130.78 (2 carbons), 135.85 (2 carbons), 138.17, 139.69, 141.07, 144.42 (2 carbons), 148.26, 150.83, 151.82, 152.29. ES-MS m/z 591 (M+H) Anal Calc. for $C_{31}H_{32}N_6O.2.9HBr.3.3H_2O$: C, 43.42; H, 4.50; N, 9.49; Cl, 4.01; Br, 26.18. Found: C, 43.53; H, 4.35; N, 9.37; Cl, 3.97; Br, 25.98.

EXAMPLE: 81

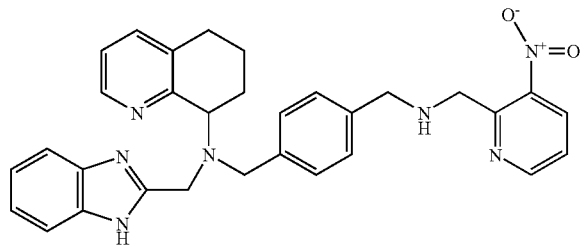

AMD9658: Preparation of N-(3-Nitro-pyrid-2-ylmethyl)-N'-(1H-benzimidazol-2-ylmethyl)-N'-(5,6,7,8-tetrahydro-8-quinolinyl)-1,4-benzenedimethanamine (hydrobromide salt)

Using General Procedure B: To a stirred solution of N'-(1H-benzimidazol-2-ylmethyl)-N'-(5,6,7,8-tetrahydro-8-quinolinyl)-1,4-benzenedimethanamine (582 mg, 1.46 mmol) and 3-nitro-pyridine-2-carboxaldehyde (208 mg, 1.37 mmol) in $CH_2Cl_2$ (5 mL) was added $NaBH(OAc)_3$ (407 mg, 1.92 mmol) and the mixture was stirred at room temperature for 19 h. Purification of the crude material by column chromatography on silica gel (20:1 $CH_2Cl_2$:$CH_3OH$) followed by radial chromatography on silica gel (1 mm plate, $CH_2Cl_2$/MeOH/$NH_4OH$, 150:1:1) afforded the desired amine as a mixture with the benzenedimethanamine starting material.

To facilitate the purification, a solution of the mixture obtained from the reaction above (205 mg) in THF (10 mL), TEA (7 drops) and distilled water (7 drops) was treated with di-tert-butyl dicarbonate (147 mg, 0.674 mmol). After 1.5 hours the reaction was poured over brine (35 mL), extracted with EtOAc (3×30 mL), dried ($Na_2SO_4$), filtered and concentrated in vacuo to give the di-BOC protected crude product. Purification by column chromatography on silica gel (40:1:1 $CH_2Cl_2$:$CH_3OH$:$NH_4OH$) followed by radial chromatography on silica gel (1 mm plate, $CH_2Cl_2$/MeOH/$NH_4OH$, 75:1:1) afforded the desired protected amine (107 mg, 38%) as a pale yellow oil.

Using General Procedure D: Conversion of the oil from above (56 mg, 0.076 mmol) to the hydrobromide salt followed by re-precipitation of the intermediate solid from methanol/ether gave AMD9658 (56 mg, 87%) as a white solid. $^1$H NMR ($D_2O$) ☐1.79-1.96 (m, 1H), 2.15-2.33 (m, 2H), 2.38-2.49 (m, 1H), 2.99-3.06 (m, 2H), 3.77-3.89 (m, 4H), 4.45 (d, 1H, J=16.7 Hz), 4.55 (s, 2H), 4.63 (d, 1H, J=16.6 Hz), 7.10 (d, 2H, J=7.8 Hz), 7.24 (d, 2H, J=8.4 Hz), 7.36 (dd, 2H, J=6.4, 3.4 Hz), 7.54 (dd, 2H, J=6.1, 3.0 Hz), 7.70 (dd, 1H, J=8.4, 4.8 Hz), 7.92 (dd, 1H, J=7.9, 6.2 Hz), 8.39 (d, 1H, J=7.9 Hz), 8.64 (d, 1H, J=8.4 Hz), 8.75 (d, 1H, J=5.6 Hz), 8.85 (d, 1H, J=4.8 Hz). $^{13}$C NMR ($D_2O$) ☐20.44, 20.92, 27.84, 49.29, 50.24, 56.66, 63.20, 113.67 (2 carbons), 125.30, 126.11, 126.55 (2 carbons), 130.34 (2 carbons), 130.49, 130.84 (2 carbons), 134.86, 138.16, 139.67, 141.02, 146.60, 148.29, 150.81, 151.80, 153.84. ES-MS m/z 534 (M+H) Anal Calc. for $C_{31}H_{31}N_7O_2$.3.2HBr.3.0$H_2O$: C, 43.98; H, 4.79; N, 11.58; Br, 30.20. Found: C, 44.05; H, 4.80; N, 11.35; Br, 30.15.

EXAMPLE: 82

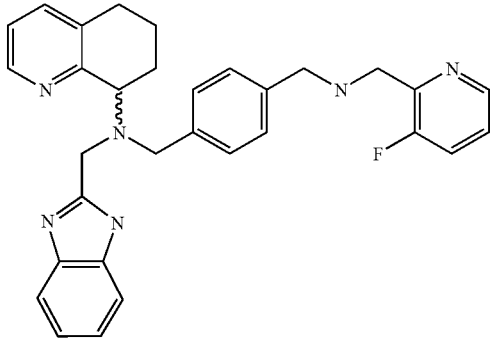

AMD9538: Preparation of (1H-benzoimidazol-2-ylmethyl)-(4-{[(3-fluoro-pyridin-2-ylmethyl)-amino]-methyl}-benzyl)-(5,6,7,8-tetrahydro-quinolin-8-yl)-amine Following the General Procedure for reductive amination B, (4-aminomethyl-benzyl)-(1H-benzoimidazol-2-ylmethyl)-(5,6,7,8-tetrahydro-quinolin-8-yl)-amine (190 mg, 0.48 mmol) and 3-fluoro-2-formylpyridine (prepared as described by Marsais, F.; Qeuquiner, G. *Tetrahedron*, 1983, 39, 2009-2021) (60 mg, 0.48 mmol) were converted into the corresponding reductive amination product using the following quantities of reagents and solvents: sodium triacetoxyborohydride (203 mg, 0.96 mmol), $CH_2Cl_2$ (4 mL). The reaction time in this case was 18 h. Purification of the crude material thus obtained by radial chromatography (silica gel, 1 mm plate, 50:2:1 $CH_2Cl_2$—MeOH—$NH_4OH$) afforded 185 mg (72%) of AMD9538 as a white foam. $^1$H NMR (CDCl$_3$) ☐ 1.43-1.47 (m, 1H), 2.00-2.05 (m, 2H), 2.16-2.28 (m, 2H), 3.71 (s, 2H), 3.76 (s, 2H), 3.94-3.95 (m, 2H), 3.95 (d, 1H, J=16 Hz), 4.08 (dd, 1H, J=9, 6 Hz), 4.16 (d, 1H, J=16 Hz), 7.13-7.29 (m, 8H), 7.34 (s, 1H), 7.36 (s, 1H), 7.41 (dd, 1H, J=8, 1 Hz), 7.50-7.52 (m, 1H), 7.63-7.65 (m, 1H), 8.33 (dt, 1H, J=5, 1 Hz), 8.67 (dd, 1H, J=5, 1 Hz); $^{13}$C NMR (CDCl$_3$) ☐ 21.4, 23.2, 29.2, 47.8, 48.5, 53.1, 53.7, 60.1, 110.9, 118.7, 121.2, 121.7, 122.1, 122.4, 122.7, 123.2 128.2, 128.6, 137.7, 137.2, 138.0, 138.9, 144.8, 146.9, 156.2,157.4. ES-MS m/z 507 (M+H). Anal. Calcd. for $C_{31}H_{31}N_6F$.1.4$H_2O$: C, 70.01; H, 6.41; N, 15.80. Found: C, 70.01; H, 6.32; N, 15.57.

EXAMPLE: 83

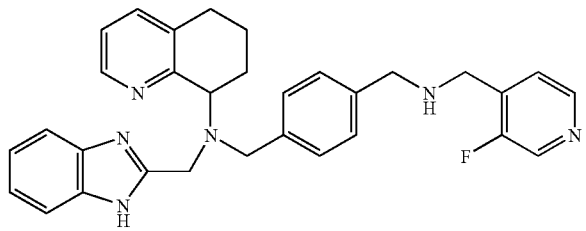

AMD9539: Preparation of N-(3-fluoro-4-pyridinylmethyl)-N'-(1H-benzimidazol-2-ylmethyl)-N'-(5,6,7,8-tetrahydro-8-quinolinyl)-1,4-benzenedimethanamine Preparation of 3-fluoro-pyridine-4-carboxaldehyde:

To a solution of TMEDA (389 uL, 2.58 mmol) in THF (10 mL) at −78° C. was added a solution of n-butyl lithium in THF (2.5M, 1.03 mL, 2.58 mmol). After 30 minutes at −78° C., 3-fluoropyridine (221 μL, 2.57 mmol) was added. After another 2 hours at −78° C., DMF (219 μL, 2.83 mmol) was added. After a further 2 hours at −78° C., the reaction was quenched with saturated aqueous NaHCO$_3$ (20 mL), extracted with ether (4×15 mL), dried (Na$_2$SO$_4$), filtered and concentrated in vacuo to give the crude oil. Purification by column chromatography on silica gel (Hexanes:EtOAc 4:1) afforded the title compound as a pale yellow oil (120 mg, 37%). $^1$H NMR (CDCl$_3$) 7.68 (t, 1H, J=5.2 Hz), 8.62 (d, 1H, J=4.7 Hz), 8.70 (s, 1H), 10.42 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (111 mg, 0.28 mmol) and 3-fluoro-pyridine-4-carboxaldehyde (35 mg, 0.28 mmol) in CH$_2$Cl$_2$ (4 mL) was added NaBH(OAc)$_3$ (159 mg, 0.75 mmol) and the mixture was stirred at room temperature for 3 h. Purification of the crude material by radial chromatography on silica gel (1 mm plate, CH$_2$Cl$_2$/MeOH/NH$_4$OH, 75:1:1) afforded the desired amine (56.4 mg, 40%) as a yellow foam. $^1$H NMR (CDCl$_3$) ☐1.59-1.71 (m, 1H), 1.94-2.09 (m, 2H), 2.20-2.31 (m, 1H), 2.65-2.91 (m, 2H), 3.69 (s, 2H), 3.71 (s, 2H), 3.80 (s, 2H), 3.95 (d, 1H, J=16.7 Hz), 4.08 (dd, 1H, J=8.9, 6.6 Hz) 4.16 (d, 1H, J=16.7 Hz), 7.14-7.20 (m, 5H), 7.31-7.44 (m, 4H), 7.46-7.66 (m, 2H), 8.33 (d, 1H, J=4.8 Hz), 8.35 (d, 1H, J=1.6 Hz), 8.67 (d, 1H, J=3.2 Hz). $^{13}$C NMR (CDCl$_3$) ☐21.78, 23.66, 29.63, 45.60, 48.94, 53.30, 54.45, 60.73, 121.95, 122.67, 122.79 (J=18.2 Hz), 124.39, 128.47 (2 carbons), 129.18 (2 carbons), 135.21, 137.69 (2 carbons), 137.82, 138.14, 138.69, 138.86, 146.14, 146.21, 147.29 (2 carbons), 156.57, 157.76, 158.50 (J=254.5 Hz). ES-MS m/z 507 (M+H) Anal Calc. for C$_{31}$H$_{31}$N$_6$F.1.0H$_2$O.0.4CH$_2$Cl$_2$: C, 67.51; H, 6.10; N, 15.04. Found: C, 67.32; H, 6.21; N, 14.69.

EXAMPLE: 84

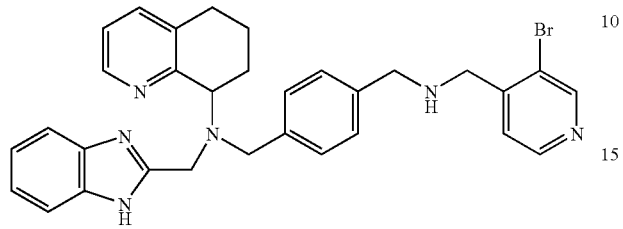

AMD9614: Preparation of N-(3-Bromo-pyrid-4-ylmethyl)-N'-(1H-benzimidazol-2-ylmethyl)-N'-(5,6,7,8-tetrahydro-8-quinolinyl)-1,4-benzenedimethanamine(hydrobromide salt)

Preparation of 3-bromo-pyridine-4-carboxaldehyde:

To a solution of TMEDA (1.91 mL, 12.7 mmol) and LDA (12.7 mmol) in ether (50 mL) at −78° C. was added 3-bromopyridine (1.22 mL, 12.7 mmol). After 60 minutes at −78° C., DMF (1.08 mL, 13.9 mmol) was added, and the mixture allowed to warm to room temperature. After 1 hour at room temperature the reaction was quenched with saturated aqueous NaHCO$_3$ (100 mL), extracted with CH$_2$Cl$_2$ (4×15 mL), dried (MgSO$_4$), filtered and concentrated in vacuo to give the crude oil. Purification by column chromatography on silica gel (Hexanes:EtOAc 4:1) afforded the title compound as a crystalline solid (1.2 g, 51%). $^1$H NMR (CDCl$_3$) 7.70 (d, 1H, J=4.8 Hz), 8.71 (d, 1H, J=4.8 Hz), 8.91 (s, 1H), 10.36 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (183 mg, 0.46 mmol) and 3-bromo-pyridine-4-carboxaldehyde (82 mg, 0.44 mmol) in CH$_2$Cl$_2$ (5 mL) was added NaBH(OAc)$_3$ (143 mg, 0.68 mmol) and the mixture was stirred at room temperature for 23 h. Purification of the crude material by radial chromatography on silica gel (1 mm plate, CH$_2$Cl$_2$/MeOH/NH$_4$OH, 150:1:1) afforded the desired amine (42 mg, 17%) as a colourless oil.

Using General Procedure D: Conversion of the foam from above (42 mg, 0.074 mmol) to the hydrobromide salt followed by re-precipitation of the intermediate solid from methanol/ether gave AMD9614 (68 mg, 99%) as a white solid. $^1$H NMR (D$_2$O) 1.80-1.97 (m, 1H), 2.14-2.32 (m, 2H), 2.38-2.49 (m, 1H), 2.99-3.07 (m, 2H), 3.77-3.93 (m, 4H), 3.98 (d, 1H, J=15.0 Hz), 4.04 (d, 1H, J=15.0 Hz), 4.45 (d, 1H, J=16.7 Hz), 4.64 (d, 1H, J=16.7 Hz), 7.09 (d, 2H, J=8.0 Hz), 7.26 (d, 2H, J=8.0), 7.35 (dd, 2H, J=6.2, 3.1 Hz), 7.54 (dd, 2H, J=6.2, 3.0 Hz), 7.62 (d, 1H, J=5.1 Hz), 7.92 (dd, 1H, J=6.7, 6.7 Hz), 8.39 (d, 1H, J=7.9 Hz), 8.63 (d, 1H, J=5.4 Hz), 8.76 (d, 1H, J=5.3 Hz), 8.88 (s, 1H). $^{13}$C NMR (D$_2$O) 20.44, 20.97, 27.86, 48.58, 50.17, 50.64, 56.72, 63.29, 113.92 (2 carbons), 123.56, 126.14 (2 carbons), 126.61, 126.78, 129.70, 130.32 (2 carbons), 130.44, 130.97 (2 carbons), 138.35, 139.35, 139.70, 141.06, 144.81, 145.91, 148.33, 149.37, 150.76, 151.86. ES-MS m/z 569 (M+H) Anal Calc. for C$_{31}$H$_{31}$N$_6$Br.4.0HBr.2.3H$_2$O: C, 39.92; H, 4.28; N, 9.01; Br, 42.84. Found: C, 39.88; H, 4.18; N, 8.90; Br, 42.94.

EXAMPLE: 85

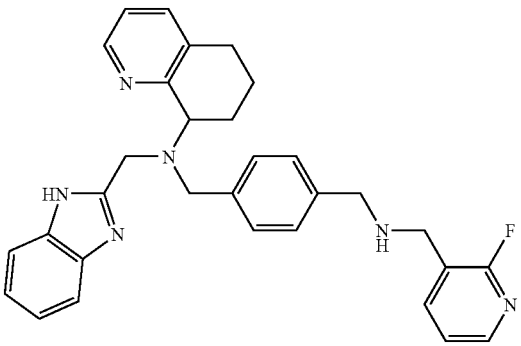

AMD9597: Preparation of (1H-benzimidazol-2-ylmethyl)-(4-{[(2-fluoro-pyridin-3-ylmethyl)-amino]-methyl}-benzyl)-(5,6,7,8-tetrahydro-quinolin-8-yl)-amine(hydrobromide salt)

Preparation of 2-fluoro-pyridine-3-carbaldehyde:

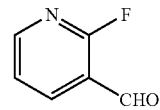

A solution of 2-fluoropyridine (306 mg, 3.15 mmol) in THF (1 mL) was added to a solution of lithium diisopropylamide in THF (0.20 M, 17 mL, 3.4 mmol) at −78° C. The solution was stirred at −78° C. for 4 h, then DMF (0.73 mL, 9.4 mmol) was added dropwise and stirring was continued at −78° C. for 2.5 h. Saturated NH$_4$Cl(aq) (2 mL) was added, and the mixture was allowed to warm to room temperature. The mixture was diluted with EtOAc (20 mL), and the organic phase was washed with saturated NaHCO$_3$(aq) (20 mL) and brine (10 mL), then dried (MgSO$_4$) and concentrated in vacuo. Purification of the crude material by chromatography on silica gel (10% EtOAc/hexanes) gave the title compound as a yellow liquid (58 mg, 15%). $^1$H NMR (CDCl$_3$) 7.39 (m, 1H), 8.32 (m, 1H), 8.48 (m, 1H), 10.33 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (178 mg, 0.448 mmol), 2-fluoro-pyridine-3-carbaldehyde (56 mg, 0.448 mmol), and AcOH (0.026 mL, 0.45 mmol) in THF (4.5 mL) was added NaBH(OAc)$_3$ (285 mg, 1.34 mmol) and the mixture was stirred at room temperature for 1.5 h. Purification of the crude material by column chromatography on silica gel (400:5:1 CH$_2$Cl$_2$/MeOH/NH$_4$OH) afforded a colourless oil (117 mg).

Using General Procedure D: Conversion of the oil from above (113 mg, 0.223 mmol) to the hydrobromide salt followed by re-precipitation of the intermediate solid from methanol/ether gave AMD9597 (145 mg, 39%) as a colourless solid. $^1$H NMR (D$_2$O) 1.89 (m, 1H), 2.24 (m, 2H), 2.44 (m, 1H), 3.02 (m, 2H), 3.71-3.90 (m, 6H), 4.45 (d, 1H, J=17 Hz), 4.64 (d, 1H, J=17 Hz), 4.79 (m, 1H), 7.03 (d, 2H, J=8.1 Hz), 7.24 (d, 2H, J=7.8 Hz), 7.31 (m, 2H), 7.39 (m, 1H), 7.51 (m, 2H), 7.91 (m, 2H), 8.24 (dd, 1H, J=5.0, 1.4 Hz), 8.39 (d, 1H, J=7.8 Hz), 8.76 (d, 1H, J=4.8 Hz); $^{13}$C NMR (D$_2$O) 20.45, 20.99, 27.87, 43.58, 50.03, 50.26, 56.70, 63.33, 113.91, 123.19, 126.15, 126.55, 130.01, 130.12, 130.43, 130.93, 138.07, 139.71, 141.06, 144.80, 144.85, 148.33, 149.15, 149.32, 150.77, 151.91. ES-MS m/z 507 (M+H). Anal. Calcd. for C$_{31}$H$_{31}$N$_6$F.3.6HBr.3.9H$_2$O: C, 42.89; H, 4.92; N, 9.68; Br, 33.13. Found: C, 42.94; H, 4.96; N, 9.54; Br, 33.08.

EXAMPLE: 86

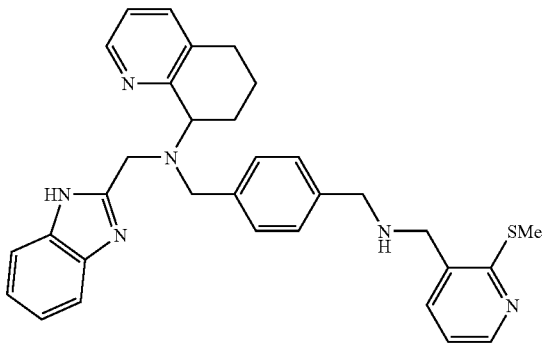

AMD9598: Preparation of (1H-benzimidazol-2-ylmethyl)-(4-{[(2-methylsulfanyl-pyridin-3-ylmethyl)-amino]-methyl}-benzyl)-(5,6,7,8-tetrahydro-quinolin-8-yl)-amine(hydrobromide salt)

Preparation of (2-methylsulfanyl-pyridin-3-yl)-methanol:

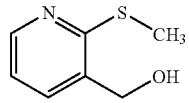

To 2-(methylthio)picolinic acid (1.00 g, 5.91 mmol) was added BH$_3$.THF (1.0 M/THF, 15 mL, 15 mmol) and the mixture heated at 80° C. for 24 h. Methanol (30 mL) was carefully added at room temperature and the solution was concentrated in vacuo. Purification of the crude material on silica gel (20% EtOAc/hexanes) gave the title compound as colourless crystals (278 mg, 30%). $^1$H NMR (CDCl$_3$) □ 1.99 (t, 1H, J=6.0 Hz), 2.61 (s, 3H), 4.70 (d, 2H, J=6.0 Hz), 7.04 (dd, 1H, J=6, 3 Hz), 7.62 (d, 1H, J=6 Hz), 8.40 (d, 1H, J=3 Hz).

2-Methylsulfanyl-pyridine-3-carbaldehyde:

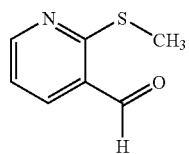

To a solution of (2-methylsulfanyl-pyridin-3-yl)-methanol (278 mg, 1.79 mmol) in CH$_2$Cl$_2$ (10 mL) was added activated MnO$_2$ (85%, 1.83 g, 17.9 mmol) and the suspension stirred at room temperature for 18 h. The mixture was filtered through Celite, and the solvent was removed from the filtrate under reduced pressure. Purification of the crude product by chromatography on silica gel (10% EtOAc/hexanes) gave the titlw compound as colourless crystals (202 mg, 74%). $^1$H NMR (CDCl$_3$) □ 2.61 (s, 3H), 7.17 (dd, 1H, J=9, 6 Hz), 8.00 (dd, 1H, J=9, 3 Hz), 8.62 (dd, 1H, J=6, 3 Hz), 10.24 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (200 mg, 0.503 mmol), 2-methylsulfanyl-pyridine-3-carbaldehyde (77 mg, 0.503 mmol) and AcOH (0.03 mL, 0.52 mmol) in THF (5 mL) was added NaBH(OAc)$_3$ (320 mg, 1.51 mmol) and the mixture was stirred at room temperature for 1.5 h. Purification of the crude material by column chromatography on silica gel (400:5:1 CH$_2$Cl$_2$/MeOH/NH$_4$OH) afforded a colourless foam (94 mg).

Using General Procedure D: Conversion of the foam from above (75 mg, 0.14 mmol) to the hydrobromide salt followed by re-precipitation of the intermediate solid from methanol/ether gave AMD9598 (89 mg, 23%) as a colourless solid. $^1$H NMR (D$_2$O) □ 1.89 (m, 1H), 2.26 (m, 2H), 2.45 (m, 1H), 2.72 (s, 3H), 3.04 (m, 2H), 3.78-3.97 (m, 6H), 4.46 (d, 1H, J=17 Hz), 4.65 (d, 1H, J=17 Hz), 4.79 (m, 1H), 7.09 (d, 2H, J=8.1 Hz), 7.27 (d, 2H, J=7.8 Hz), 7.35 (m, 2H), 7.54 (m, 3H), 7.92 (dd, 1H, J=8.1, 6.0 Hz), 8.01 (dd, 1H, J=7.8, 1.2 Hz), 8.39 (d, 1H, J=7.5 Hz), 8.52 (dd, 1H, J=1.2 Hz), 8.77 (d, 1H, J=5.1 Hz); $^{13}$C NMR (D$_2$O) □ 14.40, 20.46, 21.01, 27.88, 45.97, 50.21, 50.47, 56.75, 63.30, 113.94, 122.23, 126.16, 126.60, 127.98, 129.82, 130.20, 130.44, 130.98, 138.26, 139.74, 141.07, 143.86, 146.19, 148.35, 150.75, 151.85, 158.77. ES-MS m/z 535 (M+H). Anal. Calcd. for C$_{32}$H$_{34}$N$_6$S.4.2HBr.4.4H$_2$O: C, 40.30; H, 4.97; N, 8.81; S, 3.36; Br, 35.18. Found: C, 40.40; H, 4.79; N, 8.71; S, 3.24; Br, 35.01.

EXAMPLE: 87

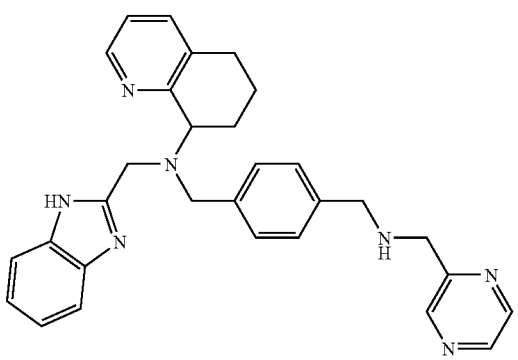

AMD9625: Preparation of (1H-benzimidazol-2-ylmethyl)-(4-{[(pyrazin-2-ylmethyl)-amino]-methyl}-benzyl)-(5,6,7,8-tetrahydroquinolin-8-yl)-amine(hydrobromide salt)

Preparation of pyrazine-2-carboxylic acid methyl ester:

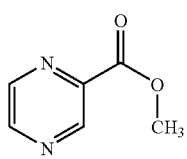

A solution of 2-pyrazinecarboxylic acid (2.00 g, 16.1 mmol) and H$_2$SO$_4$ (catalytic) in MeOH (50 mL) was heated at reflux for 45 minutes, then concentrated in vacuo. The residue was partitioned between EtOAc (40 mL) and saturated NaHCO$_3$(aq) (20 mL). The organic phase was washed with saturated NaHCO₃(aq) (20 mL) and brine (10 mL), then dried (MgSO₄) and concentrated in vacuo to give colourless crystals (1.32 g, 59%). ¹H NMR (CDCl₃) ☐ 4.04 (s, 3H), 8.72 (dd, 1H, J=2.4, 1.2 Hz), 8.77 (d, 1H, J=2.4 Hz), 9.32 (d, 1H, J=1.2 Hz).

Preparation of pyrazine-2-carbaldehyde:

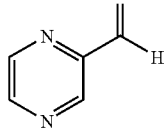

To a solution of pyrazine-2-carboxylic acid methyl ester (1.00 g, 7.24 mmol) in THF (20 mL) at −78° C. was added LiAlH₄ (1.0 M/THF, 3.62 mL, 3.62 mmol) over 40 minutes, and the solution was stirred at −78° C. for 20 min. Acetic acid (1.0 mL, 17 mmol) was added dropwise, and the solution was allowed to warm to room temperature then concentrated in vacuo. The residue was partitioned between 2.5 N HCl(aq) (7 mL) and CHCl₃ (10 mL). The aqueous phase was diluted with H₂O (5 mL) and extracted with CHCl₃ (6×7 mL). The combined extracts were washed with saturated NaHCO₃(aq), then dried (MgSO₄) and concentrated in vacuo to give an orange oil (740 mg, 95%). ¹H NMR (CDCl₃) ☐ 8.77 (m, 1H), 8.82 (d, 1H, J=3 Hz), 9.19 (d, 1H, J=3 Hz), 10.16 (s, 1H).

Using General Procedure B: To a stirred solution of N'-(1H-benzimidazol-2-ylmethyl)-N'-(5,6,7,8-tetrahydro-8-quinolinyl)-1,4-benzenedimethanamine (302 mg, 0.760 mmol) and pyrazine-2-carbaldehyde (100 mg, 0.925 mmol) in THF (8 mL) was added NaBH(OAc)₃ (258 mg, 1.22 mmol) and the mixture was stirred at room temperature for 15 h. Purification of the crude material by column chromatography on silica gel (300:5:1 CH₂Cl₂/MeOH/NH₄OH) afforded a colourless oil (81 mg).

Using General Procedure D: Conversion of the oil from above (76 mg, 0.16 mmol) to the hydrobromide salt followed by re-precipitation of the intermediate solid from methanol/ether gave AMD9625 (108 mg, 17%) as a colourless solid. ¹H NMR. (D₂O) ☐ 1.88 (m, 1H), 2.24 (m, 2H), 2.42 (m, 1H), 3.01 (m, 2H), 3.75-3.87 (m, 4H), 4.09 (s, 2H), 4.44 (d, 1H, J=17 Hz), 4.63 (d, 1H, J=17 Hz), 4.79 (d, 2H, J=8.1 Hz), 7.21 (d, 2H, J=7.8 Hz), 7.34 (m, 2H), 7.52 (m, 2H), 7.91 (dd, 1H, J=7.8, 6.0 Hz), 8.38 (d, 1H, J=8.1 Hz), 8.49 (s, 1H), 8.57 (d, 1H, J=2.7 Hz), 8.67 (m, 1H), 8.75 (d, 1H, J=5.7 Hz); ¹³C NMR (D₂O) ☐ 19.53, 20.03, 26.94, 47.04, 49.23, 49.32, 55.76, 62.32, 112.97, 125.21, 125.68, 129.20, 129.34, 129.50, 129.94, 137.20, 138.78, 140.10, 143.07, 143.66, 144.49, 146.71, 147.38, 149.84, 150.87. ES-MS m/z 490 (M+H). Anal. Calcd. for C₃₀H₃₁N₇.4.0HBr.3.7H₂O: C, 40.95; H, 4.86; N, 11.14; Br, 36.32. Found: C, 40.97; H, 4.88; N, 10.84; Br, 36.48.

EXAMPLE: 88

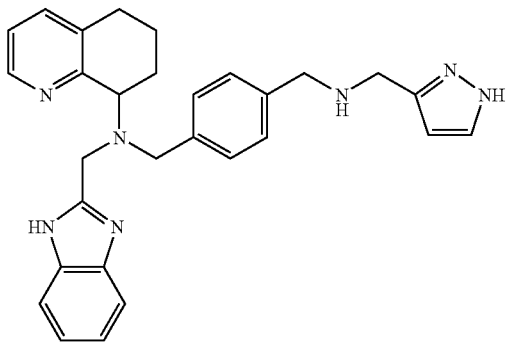

AMD11087: Preparation of (1H-benzoimidazol-2-ylmethyl)-(4-{[(1H-pyrazol-3-ylmethyl)-amino]-methyl}-benzyl)-(5,6,7,8-tetrahydro-quinolin-8-yl)-amine(hydrobromide salt)

Using General Procedure B: A solution of pyrazol-3-carboxaldehyde (26.6 mg, 0.28 mmol) and (4-aminomethyl-benzyl)-(1H-benzoimidazol-2-ylmethyl)-(5,6,7,8-tetrahydro-quinolin-8-yl)-amine (110 mg, 0.28 mmol) in MeOH (2.0 mL) was stirred overnight at room temperature. NaBH₄ (21.2 mg, 0.56 mmol) was added and the resultant mixture stirred for an additional 15 minutes. Purification by column chromatography on silica gel (CH₂Cl₂/MeOH/NH₄OH, 100:1:1) afforded the desired amine (80 mg, 60%) as a white foam.

Using General Procedure D: Conversion of the foam from above to the hydrobromide salt afforded AMD11087 as a white solid. ¹H NMR (D₂O) δ 1.90-1.96 (m, 1H), 2.20-2.32 (m, 2H), 2.42-2.46 (m, 1H), 3.03 (br s, 2H), 3.62-3.71 (m, 2H), 3.78 (d, 1H, J=12.6 Hz), 3.86 (d, 1H, J=12.9 Hz), 3.91 (s, 2H), 4.45 (d, 1H, J=16.5 Hz), 4.64 (d, 1H, J=16.8 Hz), 4.79 (m, 1H, overlap with HOD), 6.42 (d, 1H, J=2.4 Hz), 6.99 (d, 2H, J=8.1 Hz), 7.22 (d, 2H, J=8.1 Hz), 7.33-7.36 (m, 2H), 7.51-7.54 (m, 2H), 7.77 (d, 1H, J=2.4 Hz), 7.92 (dd, 1H, J=7.8, 6.3 Hz), 8.39 (d, 1H, J=7.8 Hz), 8.77 (d, 1H, J=5.4 Hz); ¹³C NMR (D₂O) δ 20.46, 20.99, 27.87, 43.14, 49.46, 50.29, 56.72, 63.33, 106.44, 113.88, 126.15, 126.63, 130.00, 130.41, 130.44, 130.86, 132.08, 137.95, 139.71, 141.04, 142.06, 148.32, 150.77, 151.82. ES-MS m/z 478.3 (M+H). Anal. Calcd. for C₂₉H₃₁N₇.4.0HBr.2.3H₂O.0.4C₄H₁₀O: C, 42.13; H, 5.04; N, 11.24; Br, 36.64. Found: C, 42.19; H, 4.87; N, 11.23; Br, 36.56.

EXAMPLE: 89

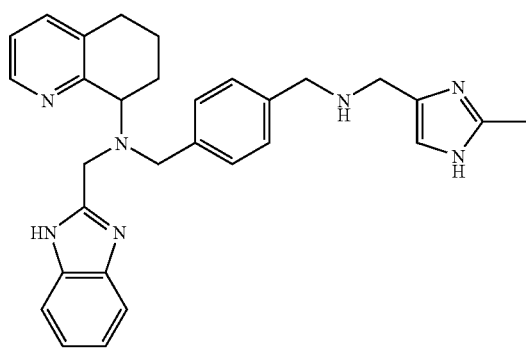

AMD11095: Preparation of (1H-benzoimidazol-2-ylmethyl)-(4-{[(2-methyl-1H-imidazol-4-ylmethyl)-amino]-methyl}-benzyl)-(5,6,7,8-tetrahydro-quinolin-8-yl)-amine(hydrobromide salt)

Using General Procedure B: A solution of 2-methyl-1H-imidazole-4-carbaldehyde (27.7 mg, 0.25 mmol) and (4-aminomethyl-benzyl)-(1H-benzoimidazol-2-ylmethyl)-(5,6,7,8-tetrahydro-quinolin-8-yl)-amine (100 mg, 0.25 mmol) in MeOH (2.0 mL) was stirred overnight at room temperature. NaBH₄ (18.9 mg, 0.50 mmol) was added and the resultant mixture stirred for an additional 15 minutes. Purification of the crude yellow foam by column chromatography on silica gel (CH₂Cl₂/MeOH/NH₄OH, 200:3:3) afforded the desired amine (65 mg, 53%) as a white foam.

Using General Procedure D: Conversion of the foam above to the hydrobromide salt afforded AMD11095 as a white solid. $^1$H NMR (D$_2$O) δ 1.92-1.95 (m, 1H), 2.23-2.34 (m, 2H), 2.45-2.49 (m, 1H), 2.62 (s, 3H), 3.04-3.06 (m, 2H), 3.73-3.92 (m, 4H), 4.12 (s, 2H), 4.48 (d, 1H, J=16.5 Hz), 4.66 (d, 1H, J=16.8 Hz), 4.80 (m, 1H, overlap with HOD), 7.06 (d, 2H, J=8.1 Hz), 7.27 (d, 2H, J=8.1 Hz), 7.44-7.50 (m, 3H), 7.57-7.61 (m, 2H), 7.95 (dd, 1H, J=7.8, 6.0 Hz), 8.42 (d, 1H, J=7.8 Hz), 8.79 (d, 1H, J=5.7 Hz); $^{13}$C NMR (D$_2$O) δ 11.27, 20.46, 20.95, 27.86, 39.87, 49.96, 50.18, 56.68, 63.16, 113.98, 120.81, 122.40, 126.13, 126.61, 130.02, 130.10, 130.51, 130.91, 138.21, 139.71, 141.02, 146.73, 148.30, 150.78, 151.77. ES-MS m/z 492.3 (M+H). Anal. Calcd. for C$_{30}$H$_{33}$N$_7$.4.0HBr.2.8H$_2$O.0.3C$_4$H$_{10}$O: C, 42.20; H, 5.18; N, 11.04; Br, 35.99. Found: C, 42.14; H, 5.07; N, 11.01; Br, 36.14.

EXAMPLE: 90

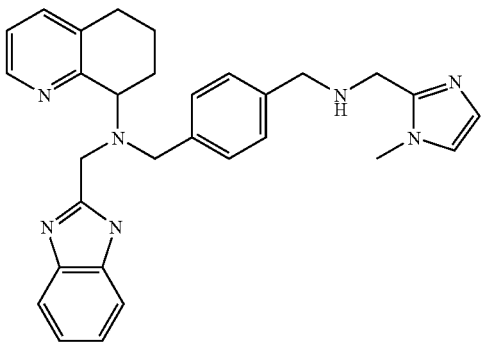

AMD 11096: Preparation of (1H-benzoimidazol-2-ylmethyl)-(4-{[(1-methyl-1H-imidazol-2-ylmethyl)-amino]-methyl}-benzyl)-(5,6,7,8-tetrahydro-quinolin-8-yl)-amine(hydrobromide salt)

Using General Procedure B: A solution of 1-methyl-2-imidazole carboxaldehyde (27.5 mg, 0.25 mmol) and (4-aminomethyl-benzyl)-(1H-benzoimidazol-2-ylmethyl)-(5,6,7,8-tetrahydro-quinolin-8-yl)-amine (100 mg, 0.25 mmol) in MeOH (2.0 mL) was stirred overnight at room temperature. NaBH$_4$ (37.5, 0.75 mmol) was added and the resultant mixture stirred for an additional 15 minutes. Purification of the crude white foam by column chromatography on silica gel (CH$_2$Cl$_2$/MeOH/NH$_4$OH, 50:1:1) followed by radial chromatography on silica gel (CH$_2$Cl$_2$/MeOH/NH$_4$OH, 200:3:2) afforded the desired amine (83 mg, 67%) as a white foam.

Using General Procedure D: Conversion of the foam from above to the hydrobromide salt afforded AMD11096 as a white solid. $^1$H NMR (D$_2$O) δ 1.85-1.98 (m, 1H), 2.22-2.33 (m, 2H), 2.44-2.48 (m, 1H), 3.04-3.06 (m, 2H), 3.81-3.92 (m, 7H), 4.47 (d, 1H, J=16.5 Hz), 4.50 (s, 2H), 4.66 (d, 1H, J=16.5 Hz), 4.80 (m, 1H, overlap with HOD), 7.08 (d, 2H, J=7.8 Hz), 7.27 (d, 2H, J=7.8 Hz), 7.47-7.52 (m, 4H), 7.58-7.62 (m, 2H), 7.94 (dd, 1H, J=7.8, 6.0 Hz), 8.41 (d, 1H, J=7.8 Hz), 8.78 (d, 1H, J=5.4 Hz); $^{13}$C NMR (D$_2$O) δ 20.45, 20.93, 27.85, 35.42, 38.33, 50.10, 50.93, 56.66, 63.10, 113.98, 121.09, 125.76, 126.13, 126.66, 129.78, 130.14, 130.52, 130.98, 136.55, 138.43, 139.70, 141.02, 148.30, 150.77, 151.67. ES-MS m/z 492.3 (M+H). Anal. Calcd. for C$_{30}$H$_{33}$N$_7$.3.9HBr.1.7H$_2$O: C, 43.01; H, 4.85; N, 11.70; Br, 37.19. Found: C, 42.85; H, 4.77; N, 11.51; Br, 37.45.

EXAMPLE: 91

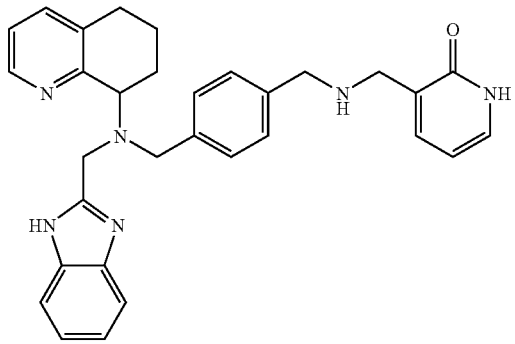

AMD9566: Preparation of 3-[(4-{[(1H-benzimidazol-2-ylmethyl)-(5,6,7,8-tetrahydro-quinolin-8-yl)-amino]-methyl}-benzylamino)-methyl]-1H-pyridin-2-one(hydrobromide salt)

Preparation of 3-hydroxymethyl-pyridin-2-ol:

To a suspension of 2-Hydroxynicotinic acid (1.01 g, 7.26 mmol) in THF (2 mL) was added BH$_3$.THF (1.0 m in THF, 18 mL, 18 mmol) and the mixture was heated to 80° C. for 18 hours. MeOH (2 mL) was added and the mixture was heated to 80° C. for an additional 2 hours before being cooled to room temperature and concentrated under reduced pressure. The resultant crude syrup was repeatedly dissolved in MeOH (5 mL) and concentrated (3×). Purification by column chromatography on silica gel (20:1—CH$_2$Cl$_2$:MeOH) afforded the desired alcohol (260 mg, 29%) as a white solid. $^1$H NMR (CD$_3$OD) δ 4.50 (s, 2H), 6.43 (t, 1H, J=6.6 Hz), 7.34 (d, 1H, J=4.5 Hz), 7.65 (d, 1H, J=6.3 Hz).

Preparation of 2-hydroxy-pyridine-3-carbaldehyde:

To a solution of the diol (260 mg, 2.05 mmol) from above in CH$_2$Cl$_2$ (10 mL) and MeOH (0.5 mL) was added MnO$_2$ (85%, 2.23 g, 21.8 mmol) and the resulting suspension was stirred at 40° C. overnight. The reaction mixture was diluted with CH$_2$Cl$_2$/MeOH (2:1) filtered through Celite and the cake was washed with CH$_2$Cl$_2$. The filtrate was concentrated under reduced pressure and purification by column chromatography on silica gel (50:1—CH$_2$Cl$_2$:MeOH) afforded the desired aldehyde (66 mg, 41%) as a light yellow solid. $^1$H NMR (CDCl$_3$) δ 6.52 (t, 1H, J=6.0 Hz), 7.77 (dd, 1H, J=6.0, 3.0 Hz), 8.15 (dd, 1H, J=6.0, 3.0 Hz), 10.16 (s, 1H).

Using General Procedure B: To a stirred solution of 2-hydroxy-pyridine-3-carbaldehyde (65 mg, 0.53 mmol), N'-(1H-benzimidazol-2-ylmethyl)-N'-(5,6,7,8-tetrahydro-8-quinolinyl)-1,4-benzenedimethanamine (211 mg, 0.53 mmol) and AcOH (30 μL, 0.53 mmol) in THF (5 mL) was added NaBH (OAc)$_3$ (337 mg, 1.59 mmol) and the mixture was stirred at room temperature overnight. Purification of the crude yellow foam (320 mg) by column chromatography on silica gel (90:5:1—CH$_2$Cl$_2$:MeOH:NH$_4$OH) followed by radial chromatography on silica gel (98:1:1—CH$_2$Cl$_2$:MeOH:NH$_4$OH followed by 48:1:1—CH$_2$Cl$_2$:MeOH:NH$_4$OH) afforded the desired product (139 mg, 52%) as a colorless syrup.

Using General Procedure D: Conversion of the syrup from above to the hydrobromide salt afforded AMD9566 as a white solid. $^1$H NMR (CD$_3$OD) δ 1.82-1.99 (m, 1H), 2.19-2.34 (m, 2H), 2.40-2.50 (m, 1H), 3.03-3.07 (m, 2H), 3.79 (s, 2H), 3.83-3.94 (m, 4H), 4.42 (d, H, J=16.2 Hz), 4.61 (d, 1H, J=16.5

Hz), 4.67-4.74 (m, 1H), 6.43 (t, 1H, J=6.6 Hz), 7.26 (d, 2H, J=8.1 Hz), 7.49-7.56 (m, 3H), 7.59-7.66 (m, 3H), 7.71-7.75 (m, 2H), 7.92-7.97 (m, 1H), 8.37-8.40 (m, 1H), 8.69-8.99 (m, 1H); $^{13}$C NMR (CD$_3$OD) δ 21.91 (2 carbons), 29.25, 48.13, 50.59, 51.30, 57.74, 62.75, 108.42, 115.32, 123.13, 127.30, 127.95, 131.40, 132.23, 132.38, 132.61, 138.08, 139.11, 141.73, 142.16, 145.22, 149.42, 152.07, 152.91, 164.77. ES-MS m/z 505.3 (M+H). Anal. Calcd. for C$_{31}$H$_{32}$N$_6$O.3.0HBr.4.4H$_2$O: C, 45.93; H, 5.45; N, 10.37; Br, 29.57. Found: C, 46.06; H, 5.22; N, 10.19; Br, 29.46.

EXAMPLE: 92

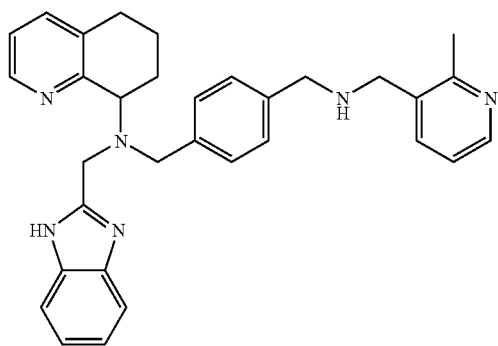

AMD9567: Preparation of (1H-benzimidazol-2-ylmethyl)-(4-{[(2-methyl-pyridin-3-ylmethyl)-amino]-methyl}-benzyl)-(5,6,7,8-tetrahydro-quinolin-8-yl)-amine(hydrobromide salt)

Preparation of (2-methyl-pyridin-3-yl)-methanol:

To 2-Methylnicotinic acid (1.00 g, 7.29 mmol) was added BH$_3$.THF (1.0 m in THF, 18 mL, 18 mmol) and the resultant mixture was heated to 80° C. for 20 hours. MeOH (6 mL) was added and the mixture was heated to 80° C. for an additional 2 hours before being cooled to room temperature and concentrated under reduced pressure. The resultant crude syrup was repeatedly dissolved in MeOH (5 mL) and concentrated (3×). Purification by column chromatography on silica gel (4:1-EtOAc:Hexanes) afforded the desired alcohol (700 mg, 80%) as a white solid. $^1$H NMR (CDCl$_3$) δ 1.96 (t, 1H, J=5.4 Hz), 2.73 (s, 3H), 4.81 (d, 2H, J=5.4 Hz), 7.32 (dd, 1H, J=7.8, 6.3 Hz), 8.03 (d, 1H, J=7.8 Hz), 8.73 (d, 1H, J=5.7 Hz).

To a solution of the alcohol (270 mg, 2.19 mmol) from above in CH$_2$Cl$_2$ (10 mL) was added MnO$_2$ (85%, 2.24 g, 21.9 mmol) and the resulting suspension was stirred at 40° C. overnight. The reaction mixture was diluted with CH$_2$Cl$_2$, filtered through Celite and the cake was washed with CH$_2$Cl$_2$. The filtrate was concentrated under reduced pressure to afford the desired aldehyde (66 mg, 41%) as a yellow syrup which was used without further purification in the next reaction.

Using General Procedure B: To a stirred solution of 2-methyl-pyridine-3-carbaldehyde (75 mg, 0.62 mmol), N'-(1H-benzimidazol-2-ylmethyl)-N'-(5,6,7,8-tetrahydro-8-quinolinyl)-1,4-benzenedimethanamine (246 mg, 0.62 mmol) and AcOH (40 μL, 0.62 mmol) in THF (6.2 mL) was added NaBH(OAc)$_3$ (394 mg, 1.86 mmol) and the mixture was stirred at room temperature overnight. Purification of the crude white foam (280 mg) by column chromatography on silica gel (200:3:1—CH$_2$Cl$_2$:MeOH:NH$_4$OH) afforded the desired product (116 mg, 37%) as a colorless syrup.

Using General Procedure D: Conversion of the syrup from above to the hydrobromide salt afforded AMD9567 as a white solid. $^1$H NMR (D$_2$O) δ 1.93-2.00 (m, 1H), 2.18-2.32 (m, 1H), 2.35-2.52 (m, 1H), 2.82 (s, 3H), 3.01-3.10 (m, 2H), 3.87 (d, 1H, J=12.9 Hz), 3.94 (d, 1H, J=13.2 Hz), 4.18 (s, 2H), 4.42-4.70 (m, 3H), 4.63 (d, 1H, J=16.2 Hz), 4.71 (m, 1H), 7.42 (d, 2H, J=8.1 Hz), 7.54 (dd, 2H, J=6.3, 3.0 Hz), 7.64 (d, 2H, J=7.8 Hz), 7.77 (dd, 2H, J=6.0, 3.0 Hz), 7.89-7.95 (m, 2H), 8.37 (d, 1H, J=7.8 Hz), 8.65 (d, 1H, J=8.1 Hz), 8.73 (dd, 1H, J=5.7, 1.2 Hz), 8.97 (d, 1H, J=4.8 Hz); $^{13}$C NMR (CD$_3$OD) δ 19.65, 21.98, 22.19, 29.31, 47.33, 50.27 (overlap with CD$_3$OD), 52.51, 57.46, 62.49, 115.38, 126.34, 127.11, 127.92, 131.98, 132.12, 132.18, 132.48 (2 carbons), 139.62, 141.83, 142.16, 144.15, 148.57, 148.73, 152.56, 153.08, 156.44. ES-MS m/z 503.3 (M+H). Anal. Calcd. for C$_{32}$H$_{34}$N$_6$.3.8HBr.5.2H$_2$O: C, 42.53; H, 5.38; N, 9.30; Br, 33.60. Found: C, 42.43; H, 5.30; N, 8.94; Br, 33.88.

EXAMPLE: 93

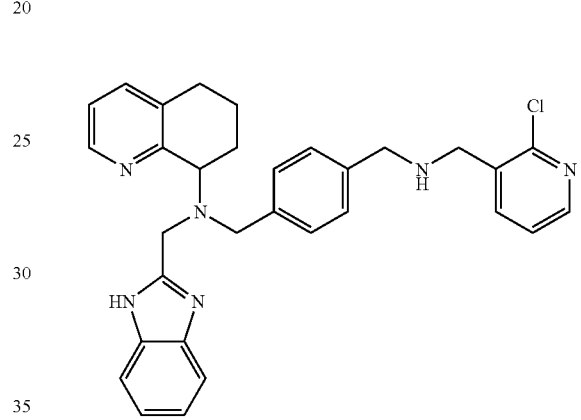

AMD9666: Preparation of (1H-benzimidazol-2-ylmethyl)-(4-{[(2-chloro-pyridin-3-ylmethyl)-amino]-methyl}-benzyl)-(5,6,7,8-tetrahydro-quinolin-8-yl)-amine(hydrochloride salt)

To a suspension of 2-Chloronicotinic acid (500 mg, 3.17 mmol) in THF (10 mL) was added BH$_3$.THF (1.0 m in THF, 25 mL, 25 mmol) and the mixture was heated to 65° C. for 18 hours. The mixture was allowed to cool to room temperature, MeOH (4 mL) was added slowly and the solution concentrated under reduced pressure. The resultant crude mixture was partially dissolved in 6N HCl and heated to 80° C. for 4 hours before being cooled to room temperature. H$_2$O (10 mL) was added and the aqueous layer washed with Et$_2$O (4×20 mL). The aqueous layer was neutralized to basic pH (pH>10) using NaOH (s) followed by 1N NaOH, saturated with NaHCO$_3$ (s) and washed with CH$_2$Cl$_2$ (4×50 mL). The combined organic extracts were dried (MgSO$_4$) and concentrated under reduced pressure to afford the desired alcohol (350 mg, 77%) as a white solid which was used without further purification in the next reaction.

To a solution of the alcohol (340 mg, 2.37 mmol) from above in CH$_2$Cl$_2$ (12 mL) was added MnO$_2$ (85%, 2.42 g, 23.7 mmol) and the resulting suspension was stirred at 40° C. overnight. The reaction mixture was diluted with CH$_2$Cl$_2$, filtered through Celite and the cake was washed with CH$_2$Cl$_2$. The filtrate was concentrated under reduced pressure to afford the desired aldehyde (207 mg, 60%) as a white solid which was used without further purification in the next reaction.

Using General Procedure B: To a stirred solution of the aldehyde from above (50 mg, 0.35 mmol) and N'-(1H-benzimidazol-2-ylmethyl)-N'-(5,6,7,8-tetrahydro-8-quinolinyl)-1,4-benzenedimethanamine (140 mg, 0.35 mmol) in THF (3.5 mL) was added NaBH(OAc)$_3$ (223 mg, 1.05 mmol) and the mixture was stirred at room temperature overnight. Purification of the crude white foam (280 mg) by column chromatography on silica gel (125:1:1—CH$_2$Cl$_2$:MeOH:NH$_4$OH) afforded the desired product (140 mg, 76%) as a colorless syrup.

Using General Procedure D: Conversion of the syrup from above to the hydrochloride salt afforded AMD9666 as a light green solid. $^1$H NMR (CD$_3$OD) δ 1.81-1.97 (m, 1H), 2.18-2.32 (m, 2H), 2.42-2.53 (m, 1H), 3.00-3.06 (m, 2H), 3.85 (d, 1H, J=12.9 Hz), 3.93 (d, 1H, J=12.9 Hz), 4.06 (s, 2H), 4.15 (s, 2H), 4.41 (d, 1H, J=16.5 Hz), 4.59 (d, 1H, J=16.5 Hz), 4.64-4.67 (m, 1H), 7.32 (d, 2H, J=8.1 Hz), 7.45-7.53 (m, 3H), 7.68-7.77 (m, 4H), 7.94-8.01 (m, 2H), 8.37-8.44 (m, 2H), 8.94 (d, 1H, J=5.1 Hz); $^{13}$C NMR (CD$_3$OD) δ 21.86, 21.91, 29.26, 48.56-50.27 (2 carbons overlap with CD$_3$OD), 52.10, 57.63, 62.45, 115.32, 125.18, 127.34, 127.87, 128.12, 128.83, 131.71, 132.01, 132.38, 132.60, 139.42, 141.72, 142.12, 143.08, 194.25, 152.16, 152.28, 152.86, 152.99. ES-MS m/z 523.4 (M+H). Anal. Calcd. for C$_{31}$H$_{31}$N$_6$Cl.3.0HCl.3.7H$_2$O.0.5C$_4$H$_{10}$O: C, 53.84; H, 6.35; N, 11.42; Cl, 19.26. Found: C, 54.00; H, 6.16; N, 11.33; Cl, 19.03.

EXAMPLE: 94

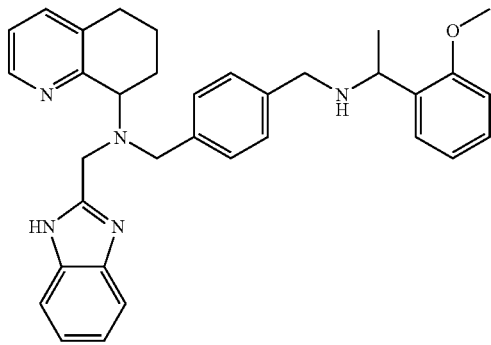

AMD9644: Preparation of (1H-benzimidazol-2-ylmethyl)-(4-{[1-(2-methoxy-phenyl)-ethylamino]-methyl}-benzyl)-(5,6,7,8-tetrahydro-quinolin-8-yl)-amine(hydrobromide salt)

Using General Procedure B: To a stirred solution of 1-(2-methoxy-phenyl)-ethanone (69 μL, 0.50 mmol), N'-(1H-benzimidazol-2-ylmethyl)-N'-(5,6,7,8-tetrahydro-8-quinolinyl)-1,4-benzenedimethanamine (200 mg, 0.50 mmol) and AcOH (0.10 mL, 1.4 mmol) in THF (5 mL) was added NaBH(OAc)$_3$ and the mixture was stirred at room temperature for 48 hours. Purification of the crude light yellow foam (267 mg) by column chromatography on silica gel (100:1:1—CH$_2$Cl$_2$:MeOH:NH$_4$OH) followed by radial chromatography on silica gel (100:1:1—CH$_2$Cl$_2$:MeOH:NH$_4$OH) afforded the desired product (83 mg, 27%) as a white foam.

Using General Procedure D: Conversion of the foam from above to the hydrobromide salt afforded AMD9644 as a white solid. $^1$H NMR (CD$_3$OD) δ 1.56 (d, 3H, J=6.9 Hz), 1.85-1.97 (m, 1H), 2.20-2.35 (m, 2H), 2.40-2.52 (m, 1H), 3.03-3.12 (m, 2H), 3.56-3.62 (m, 1H), 3.59 (dd, 1H, J=13.2, 7.2 Hz), 3.75 (dd, 1H, J=13.5, 1.8 Hz), 3.83-3.95 (m, 5H), 4.28-4.34 (m, 1H), 4.45 (dd, 1H, J=16.2, 3.9 Hz), 4.61 (d, 1H, J=16.2 Hz), 4.69-4.74 (m, 1H), 7.02-7.15 (m, 4H), 7.27 (ddd, 1H, J=5.7, 4.2, 1.5 Hz), 7.41-7.47 (m, 3H), 7.63 (d, 2H, J=8.1 Hz), 7.72 (dd, 2H, J=6.0, 3.0 Hz), 7.97 (dd, 1H, J=7.8, 5.7 Hz), 8.42 (d, 1H, J=7.8 Hz), 9.01 (d, 1H, J=5.7 Hz); $^{13}$C NMR (CD$_3$OD) δ 18.33, 21.93 (2 carbons), 29.25, 50.44, 55.54, 55.60, 56.63, 57.75, 62.69, 113.04, 115.25, 122.88, 124.86, 127.29, 127.88, 130.34, 131.43, 132.21, 132.42, 132.54, 132.64, 139.03, 141.75, 142.18, 149.43, 152.05, 152.90, 158.74. ES-MS m/z 532.4 (M+H). Anal. Calcd. for C$_{34}$H$_{37}$N$_5$O.2.9HBr.2.7H$_2$O: C, 50.11; H, 5.60; N, 8.59; Br, 28.43; O, 7.26. Found: C, 50.28; H, 5.63; N, 8.36; Br, 28.44; O, 7.35.

EXAMPLE: 95

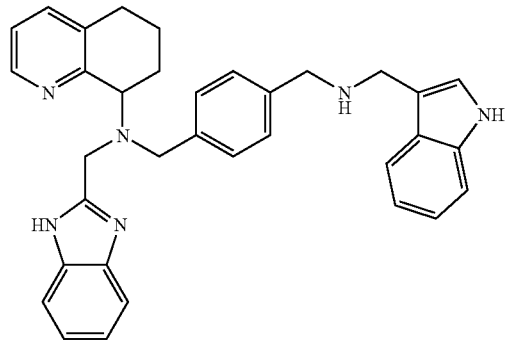

AMD9673: Preparation of (1H-benzimidazol-2-ylmethyl)-(4-{[(1H-indol-3-ylmethyl)-amino]-methyl}-benzyl)-(5,6,7,8-tetrahydro-quinolin-8-yl)-amine Using General Procedure B: 1H-Indole-3-carbaldehyde (73 mg, 0.50 mmol) and N'-(1H-benzimidazol-2-ylmethyl)-N'-(5,6,7,8-tetrahydro-8-quinolinyl)-1,4-benzenedimethanamine (200 mg, 0.50 mmol) were stirred at 40° C. in MeOH (5 mL) for 4 hours. NaBH$_4$ (38 mg, 1.0 mmol) was added and the resultant mixture stirred at room temperature for an additional 15 minutes. Purification of the crude white foam by column chromatography on silica gel (200:1:1—EtOAc:MeOH:NH$_4$OH) afforded AMD9673 (80 mg, 31%) as a white foam. $^1$H NMR (CDCl$_3$) δ 1.59-1.75 (m, 1H), 1.81-2.09 (m, 2H), 2.16-2.30 (m, 1H), 2.64-2.76 (m, 1H), 2.76-2.91 (m, 1H), 3.69 (s, 2H), 3.78 (s, 2H), 3.92-3.98 (m, 3H), 4.04-4.09 (m, 1H), 4.15 (d, 1H, J=16.5 Hz), 7.02-7.07 (m, 2H), 7.11-7.21 (m, 6H), 7.25-7.34 (m, 3H), 7.41 (d, 1H, J=7.2 Hz), 7.54-7.57 (m, 3H), 8.68 (d, 1H, J=3.9 Hz), 8.75 (br s, 1H); $^{13}$C NMR (CDCl$_3$) δ 21.74, 23.88, 29.60, 44.05, 48.89, 52.95, 54.06, 60.72, 111.68, 113.70, 119.08, 119.77, 121.97, 122.30, 122.66, 123.71, 127.40, 128.84, 129.07, 135.15, 136.70, 137.66, 138.60 (2 carbons), 147.27, 156.70, 157.79. ES-MS m/z 532.4 (M—C$_9$H$_8$N). Anal. Calcd. for C$_{34}$H$_{34}$N$_6$.0.7H$_2$O.0.2CH$_2$Cl$_2$: C, 73.84; H, 6.49; N, 15.11. Found: C, 73.95; H, 6.60; N, 14.81.

EXAMPLE: 96

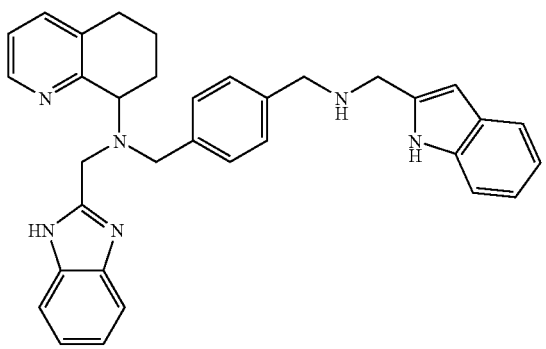

AMD9692: Preparation of (1H-Benzimidazol-2-ylmethyl)-(4-{[(1H-indol-2-ylmethyl)-amino]-methyl}-benzyl)-(5,6,7,8-tetrahydro-quinolin-8-yl)-amine Preparation of (1H-indol-2-yl) methanol:

LiAlH$_4$ (1.0 m in THF, 5.0 mL, 5.0 mmol) was slowly added to a solution of indole-2-carboxylic acid (403 mg, 2.5 mmol) in dry THF (18 mL) at 0° C. The resultant yellow solution was warmed to room temperature and stirred for 18 hours. MeOH (0.5 mL) was added and the solution concentrated under reduced pressure (3×). The resultant orange syrup was partially dissolved in CHCl$_3$ (150 mL) and washed consecutively with H$_2$O (10 mL) and NH$_4$Cl (10 mL). The aqueous layer was extracted with CHCl$_3$ (2×25 mL). The combined organic extracts were dried (MgSO$_4$) and concentrated under reduced pressure. Purification by column chromatography on silica gel (100% CH$_2$Cl$_2$) afforded the desired alcohol (250 mg, 68%) as a yellow solid. $^1$H NMR (CDCl$_3$) δ 4.84 (s, 2H), 6.42 (d, 1H, J=0.9 Hz), 7.11-7.20 (m, 2H), 7.36 (d, 1H, J=7.5 Hz), 7.59 (d, 1H, J=7.5 Hz), 8.31 (br s, 1H).

To a solution of the alcohol (250 mg, 1.70 mmol) from above in CH$_2$Cl$_2$ (8.5 mL) was added MnO$_2$ (85%, 1.74 g, 17.0 mmol) and the resulting suspension was stirred at room temperature for 4 hours. The reaction mixture was diluted with CH$_2$Cl$_2$, filtered through Celite and the cake was washed with CH$_2$Cl$_2$. The filtrate was concentrated under reduced pressure to afford the desired aldehyde (120 mg, 41%) as an orange-pink solid which was used without further purification in the next reaction.

Using General Procedure B: 1H-Indole-2-carbaldehyde (73 mg, 0.50 mmol) and N'-(1H-benzimidazol-2-ylmethyl)-N'-(5,6,7,8-tetrahydro-8-quinolinyl)-1,4-benzenedimethanamine (200 mg, 0.50 mmol) were stirred stirred at room temperature in MeOH (5 mL) for 4.5 hours. NaBH$_4$ (38 mg, 1.0 mmol) was added and the resultant mixture stirred for an additional 15 minutes. Purification of the crude light yellow foam by column chromatography on silica gel (200:1:1-EtOAc:MeOH:NH$_4$OH followed by 100:1:1-EtOAc:MeOH:NH$_4$OH) afforded AMD9692 (180 mg, 68%) as a tan foam. $^1$H NMR (CDCl$_3$) δ 1.60-1.78 (m, 1H), 1.97-2.11 (m, 2H), 2.21-2.34 (m, 1H), 2.65-2.79 (m, 1H), 2.79-2.95 (m, 1H), 3.70 (s, 2H), 3.74 (s, 2H), 3.89 (s, 2H), 3.97 (d, 1H, J=16.8 Hz), 4.05-4.14 (m, 1H), 4.18 (d, 1H, J=16.8 Hz), 6.31 (s, 1H), 7.04-7.23 (m, 7H), 7.30 (d, 1H, J=8.1 Hz), 7.37 (d, 2H, J=8.1 Hz), 7.43 (d, 1H, J=7.2 Hz), 7.53 (d, 2H, 7.2 Hz), 7.65 (d, 1H, J=7.5 Hz), 8.59 (br s, 1H), 8.71 (d, 1H, J=3.9 Hz); $^{13}$C NMR (CDCl$_3$) δ 20.58, 22.65, 28.42, 45.21, 47.76, 51.92, 52.97, 59.60, 99.48, 109.96 (2 carbons), 117.87, 118.67, 119.25, 120.51 (2 carbons), 121.47, 127.35, 127.66, 127.93, 133.96, 135.21, 136.45, 136.77, 137.40, 137.91, 146.12, 155.53, 156.63. ES-MS m/z 527.4 (M+H). Anal. Calcd. for C$_{34}$H$_{34}$N$_6$.0.9H$_2$O: C, 75.22; H, 6.65; N, 15.48. Found: C, 75.20; H, 6.58; N, 15.12.

EXAMPLE: 97

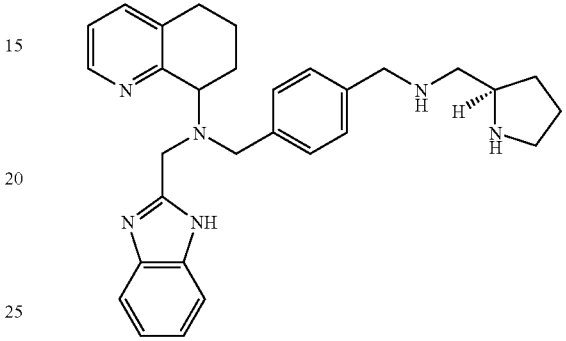

AMD9618: Preparation of (1H-Benzoimidazol-2-ylmethyl)-(4-{[(pyrrolidin-2-ylmethyl)-amino]-methyl}-benzyl)-(5,6,7,8-tetrahydro-quinolin-8-yl)-amine(hydrobromide salt)

Using General Procedure B: To a stirred solution of N-(tert-butoxycarbonyl)-D-prolinal (0.121 g, 0.61 mmol) in dry CH$_2$Cl$_2$ (9 mL) was added N'-(1H-benzimidazol-2-ylmethyl)-N'-(5,6,7,8-tetrahydro-8-quinolinyl)-1,4-benzenedimethanamine (0.236 g, 0.59 mmol) at room temperature and the mixture stirred for 40 min. To the resultant mixture was added sodium triacetoxyborohydride (0.174 g, 0.82 mmol) and the mixture stirred overnight at room temperature. Purification and separation of the crude material by radial chromatography on a 2 mm TLC grade silica gel plate (CH$_2$Cl$_2$/MeOH/NH$_4$OH, 50:1:1) afforded the more polar mono-alkylated (77 mg, 23%) and the less polar dialkylated (70 mg, 21%) products, both as white foams.

Using General Procedure D: Conversion of the more polar monoalkylated amine from above (77 mg, 0.13 mmol) to the hydrobromide salt with simultaneous removal of the Boc group gave AMD9618 (46 mg) as a white solid. $^1$H NMR (D$_2$O) δ 1.63-1.89 (m, 1H), 1.91-2.12 (br m, 4H), 2.15-2.32 (m, 3H), 2.37-2.48 (br m, 1H), 2.98-3.06 (m, 2H); 3.20-3.37 (m, 4H), 3.72 (s, 2H), 3.75-3.85 (m, 3H), 4.42 (d, 1H, J=16.5 Hz), 4.61 (d, 1H, J=16.5 Hz), 7.03 (d, 2H, J=7.8 Hz), 7.22 (d, 2H, J=7.8 Hz), 7.46-7.52 (m, 2H), 7.53-7.60 (m, 2H), 7.91 (dd, 1H, J=7.8, 1.8 Hz), 8.38 (d, 1H, J=8.1 Hz), 8.74 (d, 1H, J=5.7 Hz); $^{13}$C NMR (D$_2$O) δ 20.43, 20.89, 23.17, 27.83, 28.98, 46.51, 47.50, 50.04, 51.08, 56.56, 56.65, 63.06, 113.93, 126.10, 126.68, 129.89, 130.22, 130.56, 130.84, 138.32, 139.68, 141.00, 148.25, 150.82, 151.64; ES-MS m/z 481 (M+H); Anal. Calcd. for C$_{30}$H$_{36}$N$_6$.4.0HBr.3.5H$_2$O: C, 41.54; H, 5.46; N, 9.69; Br, 36.85. Found: C, 41.67; H, 5.39; N, 9.61; Br, 36.78.

EXAMPLE: 98

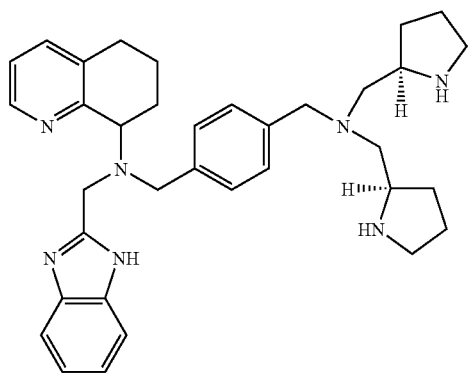

AMD9619: (1H-Benzoimidazol-2-ylmethyl)-{4-[(bis-pyrrolidin-2-ylmethyl-amino)-methyl]-benzyl}-(5,6,7,8-tetrahydro-quinolin-8-yl)-amine(hydrobromide salt)

Using General Procedure D: Conversion of the less polar dialkylated amine from above (70 mg, 0.092 mmol) to the hydrobromide salt with simultaneous removal of the Boc group gave AMD9619 (42 mg) as a white solid. $^1$H NMR (D$_2$O) ☐ 1.50-1.64 (m, 2H), 1.74-1.83 (m, 2H), 1.84-2.07 (br m, 4H), 2.08-2.47 (br m, 10H), 3.00-3.06 (m, 2H), 3.18-3.31 (m, 5H), 3.38 (s, 2H), 3.64-3.88 (m, 5H), 4.48 (d, 1H, J=16.8 Hz), 4.65 (d, 1H, J=16.5 Hz), 6.92 (d, 2H, J=7.8 Hz), 7.20 (d, 2H, J=7.2 Hz), 7.45-7.52 (m, 2H), 7.57-7.63 (m, 2H), 7.93 (t, 1H, J=7.2 Hz), 8.40 (d, 1H, J=8.1 Hz), 8.78 (d, 1H, J=5.7 Hz); $^{13}$C NMR (D$_2$O) ☐ 20.47, 20.99, 23.18, 27.88, 28.07, 29.15, 45.60, 53.87, 53.93, 57.39, 63.45, 63.52, 114.04, 114.07, 126.12, 126.73, 130.33, 130.37, 130.53, 130.58, 136.02, 136.06, 139.69, 141.08, 148.34, 150.83, 152.46; ES-MS m/z 564 (M+H); Anal. Calcd. for C$_{35}$H$_{45}$N$_7$.4.9HBr.3.8H$_2$O: C, 40.87; H, 5.63; N, 9.53; Br, 39.06. Found: C, 40.86; H, 5.62; N, 9.30; Br, 38.06.

EXAMPLE: 99

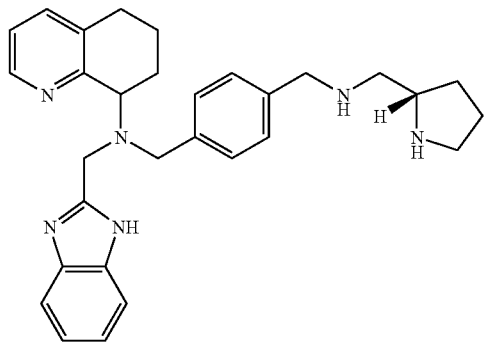

AMD9669: Preparation of (1H-Benzoimidazol-2-ylmethyl)-(4-{[(pyrrolidin-2-ylmethyl)-amino]-methyl}-benzyl)-(5,6,7,8-tetrahydro-quinolin-8-yl)-amine(hydrobromide salt)

To a stirred solution of N'-(1H-benzimidazol-2-ylmethyl)-N'-(5,6,7,8-tetrahydro-8-quinolinyl)-1,4-benzenedimethanamine (0.231 g, 0.58 mmol) in dry MeOH (5.5 mL) was added N-(tert-butoxycarbonyl)-L-prolinal (0.116 g, 0.58 mmol) and the mixture was stirred at room temperature for 2.5 h. The reaction mixture was concentrated under reduced pressure and subjected to high vacuum for 1 h. The residue was dissolved in dry MeOH (5 mL) and to the resultant solution was added sodium borohydride (44 mg, 1.16 mmol), which was stirred for 0.5 h (see General Procedures XX). Purification by radial chromatography on a 2mm TLC grade silica gel plate (CH$_2$Cl$_2$/MeOH/NH$_4$OH, 100:1:1 followed by 50:1:1) afforded the desired product (0.151 g, 45%) as a colourless oil.

Using General Procedure D: Conversion of the free amine from above (151 mg, 0.26 mmol) to the hydrobromide salt with simultaneous removal of the Boc group gave AMD9669 (188 mg) as an off-white solid. $^1$H NMR (D$_2$O) ☐ 1.60-1.76 (m, 1H), 1.78-2.13 (br m, 4H), 2.14-2.35 (m, 3H), 2.36-2.48 (br m, 1H), 2.98-3.04 (m, 2H), 3.20-3.37 (m, 4H), 3.71 (s, 2H), 3.75-3.90 (m, 3H), 4.42 (d, 1H, J=16.5 Hz), 4.60 (d, 1H, J=16.5 Hz), 7.02 (d, 2H, J=7.8 Hz), 7.21 (d, 2H, J=7.5 Hz), 7.45-7.52 (m, 2H), 7.52-7.59 (m, 2H), 7.90 (t, 1H, J=6.6 Hz), 8.37 (d, 1H, J=8.1 Hz), 8.73 (d, 1H, J=5.7 Hz); $^{13}$C NMR (D$_2$O) ☐ 20.25, 20.71, 27.65, 28.80, 46.33, 47.31, 49.86, 50.89, 56.38, 62.88, 113.75, 125.92, 126.51, 129.71, 130.04, 130.35, 130.66, 138.13, 139.49, 140.83, 148.09, 150.63, 151.44; ES-MS m/z 481 (M+H); Anal. Calcd. for C$_{30}$H$_{36}$N$_6$.4.0HBr.2.5H$_2$O: C, 42.42; H, 5.34; N, 9.89; Br, 37.63. Found: C, 42.54; H, 5.30; N, 9.75; Br, 37.53.

EXAMPLE: 100

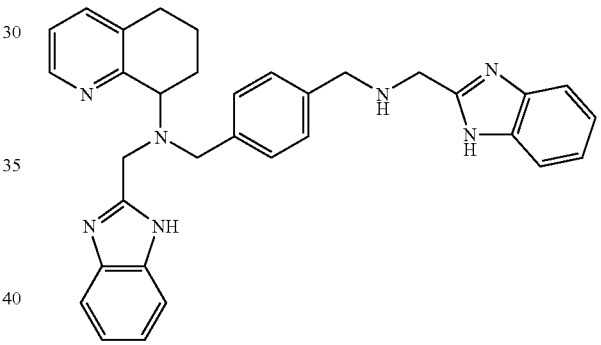

AMD9668: Preparation of (1H-Benzimidazol-2-ylmethyl)-(4-{[(1H-benzimidazol-2-ylmethyl)-amino]-methyl}-benzyl)-(5,6,7,8-tetrahydro-quinolin-8-yl)-amine(hydrobromide salt)

To a stirred solution of 1-(2-trimethylsilylethoxymethyl)-2-formyl-benzimidazole (prepared as described by Bridger et al. U.S. patent application Ser. No. 09/535,314) (0.150 g, 0.54 mmol) in dry MeOH (2.5 mL) was added a dry MeOH (2.5 mL) solution of N'-(1H-benzimidazol-2-ylmethyl)-N'-(5,6,7,8-tetrahydro-8-quinolinyl)-1,4-benzenedimethanamine (0.215 g, 0.54 mmol) under an argon atmosphere. The mixture was stirred at room temperature for 1.5 h then concentrated under reduced pressure and analyzed by $^1$H NMR. The residue was dissolved in dry MeOH (5 mL) and to the resultant solution was added sodium borohydride (41 mg, 1.08 mmol) and the reaction mixture stirred for 16 h (see General Procedures XX). Purification of the crude product by radial chromatography on a 2 mm TLC grade silica gel plate (CH$_2$Cl$_2$/MeOH/NH$_4$OH, 100:1:1 followed by 50:1:1) afforded the desired product (0.165 g, 47%) as a pale yellow oil.

The material from above (0.110 g, 0.17 mmol) was dissolved in dry CH$_2$Cl$_2$ (2 mL) and trifluoroacetic acid (1 mL)

was added dropwise. The resultant mixture was stirred overnight at room temperature. The reaction mixture was diluted with CH$_2$Cl$_2$ (15 mL) and then concentrated in vacuo. The resultant residue was diluted with CH$_2$Cl$_2$ (20 mL) and 1N NaOH (20 mL), the aqueous layer extracted with CH$_2$Cl$_2$ (2×15 mL), the phases separated and the combined organic extracts dried (Na$_2$SO$_4$), filtered, and concentrated in vacuo. Purification of the crude material by radial chromatography on a 1 mm TLC grade silica gel plate (CH$_2$Cl$_2$/MeOH/NH$_4$OH, 100:1:1 followed by 75:1:1 and 50:1:1) afforded the desired product (45 mg, 51%) as a colourless oil.

Using General Procedure D: Conversion of the free amine from above (45 mg, 0.085 mmol) to the hydrobromide salt with simultaneous removal of the Boc group gave AMD9668 (68 mg) as a white solid. $^1$H NMR (D$_2$O) □1.75-1.94 (br m, 1H), 2.11-2.30 (m, 2H), 2.30-2.45 (br m, 1H), 3.01 (br s, 2H), 3.60 (d, 1H, J=12 Hz), 3.73 (d, 1H, J=12.6 Hz), 3.87 (s, 2H), 4.37 (d, 1H, J=16.2 Hz), 4.49 (s, 2H), 4.57 (d, 1H, J=16.5 Hz), 6.98 (d, 2H, J=7.5 Hz), 7.09 (d, 2H, J=7.5 Hz), 7.26-7.40 (m, 2H), 7.40-7.49 (m, 2H), 7.49-7.61 (m, 2H), 7.59-7.73 (m, 2H), 7.91 (t, 1H, J=7.2 Hz), 8.38 (d, 1H, J=7.8 Hz) 8.72 (d, 1H, J=5.7 Hz); $^{13}$C NMR (D$_2$O) □20.39, 20.85, 27.82, 41.56, 50.02, 50.83, 56.41, 62.92, 113.91 (2 carbons), 115.01 (2 carbons), 126.15, 126.60 (4 carbons), 129.78, 129.92 (2 carbons), 130.45, 130.65 (2 carbons), 133.25, 138.19, 139.67, 141.04, 142.99, 148.31, 150.75, 151.62; ES-MS m/z 528 (M+H). Anal. Calcd. for C$_{29}$H$_{33}$N$_5$O.3.0HBr.2.0H$_2$O: C, 43.69; H, 4.80; N, 10.81; Br, 35.23. Found: C, 43.80; H, 4.80; N, 10.57; Br, 35.09.

EXAMPLE: 101

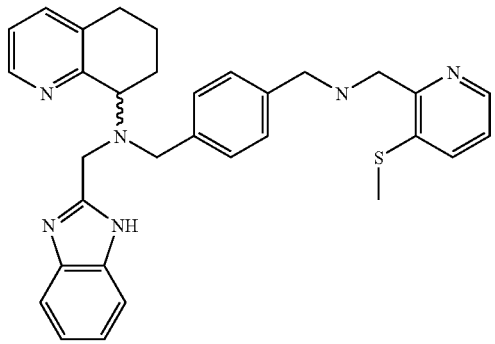

AMD9574: Preparation of (1H-benzoimidazol-2-ylmethyl)-(4-{[(3-methylsulfanyl-pyridin-2-ylmethyl)-amino]-methyl}-benzyl)-(5,6,7,8-tetrahydroquinolin-8-yl)-amine

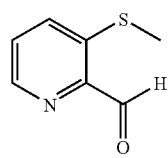

Preparation of 3-methylsulfanyl-pyridine-2-carbaldehyde:

To a cold (−78° C.) stirred solution of TMEDA (0.60 mL, 4.0 mmol) in dry diethyl ether (15 mL) was added a 2.5 M solution of $^n$BuLi in hexanes (1.6 mL, 4.0 mmol). The resulting mixture was stirred 30 min at −78° C., at which point a solution of 3-(methylthio)pyridine (prepared as described by Trecourt, F.; Breton, G.; Bonnet, V.; Mongin, F.; Marsais, F.; Queguiner, G. *Tetrahedron* 2000, 56, 1349-1360) (500 mg, 4.0 mmol) in dry diethyl ether (5 mL) was added dropwise. The resulting red/orange solution was stirred 2 h at −78° C., then neat DMF (0.31 mL, 4.4 mmol) was added dropwise and stirring was continued for a further 2 h. Saturated aqueous sodium bicarbonate (20 mL) was added, then the phases were separated and the aqueous layer was extracted with CH$_2$Cl$_2$ (3×30 mL). The combined organic extracts were dried (MgSO$_4$), and concentrated in vacuo. Purification of the crude material thus obtained by flash chromatography (silica gel, 4:1 hexanes-EtOAc) afforded 119 mg (19%) of 3-methylsulfanyl-pyridine-2-carbaldehyde. $^1$H NMR (CDCl$_3$) □ 2.45 (s, 3H), 7.42 (dd, 1H, J=8, 5 Hz), 7.67 (d, 1H, J=9 Hz), 8.50-8.52 (m, 1H), 10.14 (s, 1H).

Following the General Procedure B: (4-aminomethyl-benzyl)-(1H-benzoimidazol-2-ylmethyl)-(5,6,7,8-tetrahydroquinolin-8-yl)-amine (122 mg, 0.31 mmol) and 3-methylsulfanyl-pyridine-2-carbaldehyde (47 mg, 0.31 mmol) were converted into the corresponding reductive amination product using the following quantities of reagents and solvents: sodium triacetoxyborohydride (130 mg, 0.62 mmol), CH$_2$Cl$_2$ (3 mL). The reaction time in this case was 18 h. Purification of the crude material thus obtained by radial chromatography (silica gel, 1 mm plate, 50:2:1 CH$_2$Cl$_2$—MeOH—NH$_4$OH) afforded 48 mg (29%) of AMD9574 as a white foam. $^1$H NMR (CDCl$_3$) □ 1.66-1.74 (m, 1H), 1.87-2.08 (m, 3H), 2.22-2.26 (m, 1H), 2.37 (s, 3H), 2.70-2.74 (m, 1H), 2.82-2.85 (m, 1H), 3.73 (s, 2H), 3.79 (s, 2H), 3.93 (s, 2H), 3.96 (d, 1H, J=16 Hz), 4.07 (dd, 1H, J=9, 6 Hz), 4.17 (d, 1H, J=16 Hz), 7.12 (dd, 1H, J=11, 7 Hz), 7.16-7.25 (m, 6H), 7.35 (d, 2H, J=8 Hz), 7.41 (dt, 2H, J=8, 1 Hz), 7.50-7.52 (m, 1H), 7.63-7.66 (m, 1H), 8.29 (dd, 1H, J=5, 1 Hz), 8.69 (dd, 1H, J=5, 1 Hz); $^{13}$C NMR (CDCl$_3$) □ 15.1, 21.4, 23.3, 29.2, 48.5, 51.9, 53.3, 53.7, 60.0, 110.9, 118.7, 121.2, 121.6, 122.1, 128.2, 128.5, 132.6, 133.8, 134.6, 137.1, 137.9, 139.2, 144.7, 146.9, 156.2, 156.4, 157.5. ES-MS m/z 535 (M+H). Anal. Calcd. for C$_{32}$H$_{34}$N$_6$S.0.4CH$_2$Cl$_2$.0.2H$_2$O: C, 68.00; H, 6.20; N, 14.68; S, 5.60. Found: C, 68.40; H, 6.42; N, 14.31; S, 5.42.

EXAMPLE: 102

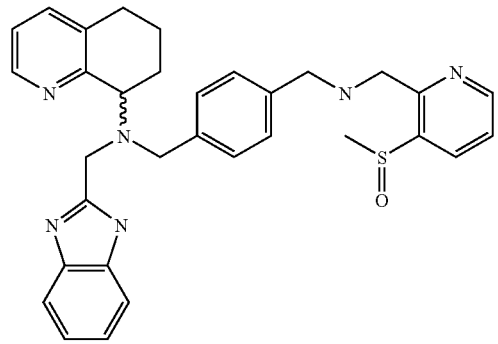

AMD9612: Preparation of (1H-benzoimidazol-2-ylmethyl)-(4-{[(3-methanesulfinyl-pyridin-2-ylmethyl)-amino]-methyl}-benzyl)-(5,6,7,8-tetrahydro-quinolin-8-yl)-amine

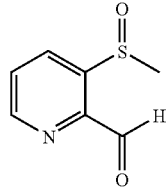

Preparation of 3-methanesulfinyl-pyridine-2-carbaldehyde:

To a cold (0° C.), stirred solution of 3-methylsulfanyl-pyridine-2-carbaldehyde (prepared as described for AMD9574) (280 mg, 1.83 mmol) in a mixture of MeOH (20 mL) and water (2 mL) was added solid oxone (2.25 g, 3.66 mmol) and the resulting heterogeneous mixture was stirred for 5 h. At this point, the reaction mixture was diluted with CH$_2$Cl$_2$ (50 mL), and then filtered through celite, washed with CH$_2$Cl$_2$ (3×20 mL) and concentrated and dried in vacuo. Flash chromatography (silica gel, 4:1 hexanes-EtOAc) of the residue thus obtained afforded 70 mg (23%) of 3-methane-sulfinyl-pyridine-2-carbaldehyde. $^1$H NMR (CDCl$_3$) □ 2.86 (s, 3H), 7.81 (dd, 1H, J=8, 5 Hz), 8.66-8.69 (m, 1H), 8.90 (d, 1H, J=3 Hz), 10.12 (s, 1H).

Following the General Procedure B: (4-aminomethyl-benzyl)-(1H-benzoimidazol-2-ylmethyl)-(5,6,7,8-tetrahydro-quinolin-8-yl)-amine (164 mg, 0.41 mmol) and 3-methane-sulfinyl-pyridine-2-carbaldehyde (70 mg, 0.41 mmol) were converted into the corresponding reductive amination product using the following quantities of reagents and solvents: sodium triacetoxyborohydride (175 mg, 0.82 mmol), CH$_2$Cl$_2$ (4 mL). The reaction time in this case was 18 h. Purification of the crude material thus obtained by radial chromatography (silica gel, 1 mm plate, 50:2:1 CH$_2$Cl$_2$—MeOH—NH$_4$OH) afforded 80 mg (34%) of AMD9612 as a white foam. $^1$H NMR (CDCl$_3$) □ 1.66-1.70 (m, 1H), 2.00-2.07 (m, 4H), 2.23-2.25 (m, 1H), 2.73-2.82 (m, 5H), 3.70 (s, 2H), 2.72 (s, 2H), 3.91 (s, 2H), 3.94 (d, 1H, J=15 Hz), 4.07 (dd, 1H, J=9, 6 Hz), 4.17 (dd, 1H, J=15 Hz), 7.14-7.24 (m, 5H), 7.34-7.37 (m, 2H), 7.39-7.42 (m, 2H), 7.50-7.52 (m, 1H), 7.60-7.61 (m, 1H), 8.33 (dt, 1H, J=8, 1 Hz), 8.57 (d, 1H, J=5 Hz), 8.70 (d, 1H, J=5 Hz); $^{13}$C NMR (CDCl$_3$) □ 21.3, 23.4, 29.1, 43.6, 48.4, 52.5, 53.3, 53.6, 60.2, 121.4, 122.2, 123.6, 128.2, 128.7, 132.2, 134.7, 137.2, 138.2, 138.3, 141.9, 146.9, 150.6, 155.4, 156.2, 157.3. ES-MS m/z 551 (M+H). Anal. Calcd. for C$_{32}$H$_{34}$N$_6$OS.1.3CH$_4$O.0.3H$_2$O: C, 66.91; H, 6.71; N, 14.06; S, 5.36. Found: C, 66.88; H, 6.39; N, 13.93; S, 5.26.

EXAMPLE: 103

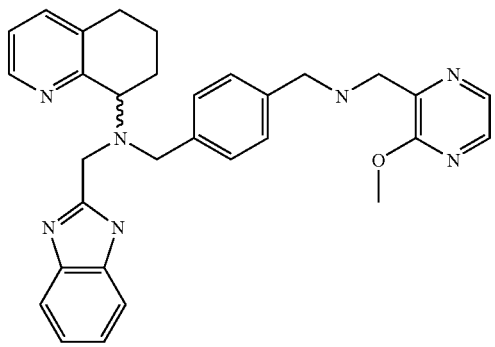

AMD9624: Preparation of (1H-benzoimidazol-2-ylmethyl)-(4-{[(3-methoxy-pyrazin-2-ylmethyl)-amino]-methyl}-benzyl)-(5,6,7,8-tetrahydro-quinolin-8-yl)-amine Following the General Procedure B: (4-aminomethyl-benzyl)-(1H-benzoimidazol-2-ylmethyl)-(5,6,7,8-tetrahydro-quinolin-8-yl)-amine (118 mg, 0.30 mmol) and 3-methoxy-pyrazinecarboxaldehyde (prepared as described by Lepretre, A.; Turck, A.; Ple, N.; Knochel, P.; Quequiner, G. *Tetrahedron* 1999, 56, 265-273) (41 mg, 0.30 mmol) were converted into the corresponding reductive amination product using the following quantities of reagents and solvents: sodium triacetoxyborohydride (126 mg, 0.60 mmol), CH$_2$Cl$_2$ (3 mL). The reaction time in this case was 18 h. Purification of the crude material thus obtained by radial chromatography (silica gel, 1 mm plate, 50:2:1 CH$_2$Cl$_2$—MeOH—NH$_4$OH) afforded 36 mg (23%) of AMD9624 as a white foam. $^1$H NMR (CDCl$_3$) □ 1.68-1.72 (m, 1H), 2.00-2.08 (m, 3H), 2.22-2.26 (m, 1H), 2.70-2.74 (m, 1H), 2.84-2.87 (m, 1H), 3.72 (s, 2H), 3.78 (s, 2H), 3.89 (s, 2H), 3.91 (s, 3H), 3.95 (d, 1H, J=16 Hz), 4.07 (dd, 1H, J=9, 6 Hz), 4.17 (d, 1H, J=16 Hz), 7.14-7.23 (m, 5H), 7.36 (d, 2H, J=8 Hz), 7.42 (dd, 1H, J=8, 1 Hz), 7.50-7.53 (m, 1H), 7.63-7.66 (m, 1H), 7.92 (d, 1H, J=3 Hz), 8.02 (d, 1H, J=3 Hz), 8.68 (dd, 1H, J=5, 1 Hz); $^{13}$C NMR (CDCl$_3$) □ 21.4, 23.3, 29.2, 48.5, 49.0, 53.2, 53.4, 53.7, 60.1, 110.9, 118.7, 121.5, 122.2, 128.2, 128.6, 134.7, 135.4, 137.1, 138.0, 138.7, 139.0, 145.2, 146.9, 156.3, 157.4, 158.1. ES-MS m/z 542 (M+Na). Anal. Calcd. for C$_{31}$H$_{33}$N$_7$O.0.4C$_4$H$_8$O$_2$.1.8H$_2$O: C, 66.67; H, 6.83; N, 16.69. Found: C, 66.31; H, 6.44; N, 16.39.

EXAMPLE: 104

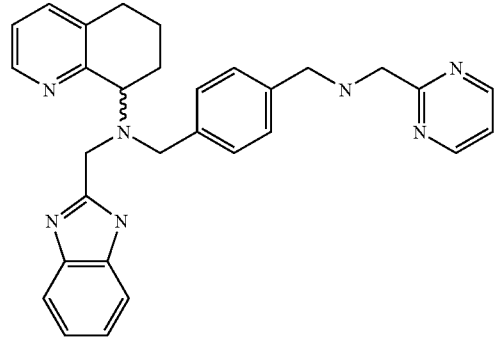

AMD9675: Preparation of (1H-benzoimidazol-2-ylmethyl)-(4-{[(pyrimidin-2-ylmethyl)-amino]-methyl}-benzyl)-(5,6,7,8-tetrahydro-quinolin-8-yl)-amine Following the General Procedure for alkylation: (4-aminomethyl-benzyl)-(1H-benzoimidazol-2-ylmethyl)-(5,6,7,8-tetrahydro-quinolin-8-yl)-amine (300 mg, 0.76 mmol) and 2-(chloromethyl)pyrimidine (prepared as described by Sakamoto, T.; Kaneda, S.; Hama, Y.; Yoshizawa, H.; Yamanaka, H. *Heterocycles* 1983, 20, 991-994) (88 mg, 0.68 mmol) were converted into the corresponding alkylation product using the following quantities of reagents and solvents: diisopropyl-ethylamine (260 μL, 1.37 mmol), CH$_3$CN (4 mL). The reaction time in this case was 24 h, while the reaction temperature was 40° C. The resulting crude material was purified by flash chromatography (silica gel, 20:2:1 CH$_2$Cl$_2$—MeOH—NH$_4$OH) to provide a ~2:1 mixture of mono- and di-alkylation products; in our hands, separation of these compounds proved to be problematic. Thus, the mixture was taken up in THF (4 mL), and water (2 drops) and di-tert-butyl dicarbonate (436 mg, 2.0 mmol) were added. The resulting solution was stirred 2 h, then concentrated in vacuo and filtered through a plug of silica (elution with 20:2:1 CH$_2$Cl$_2$—MeOH—NH$_4$OH). Radial chromatography (silica gel, 1 mm plate, 50:2:1 CH$_2$Cl$_2$—MeOH—NH$_4$OH) of the crude material thus obtained afforded ~120 mg of a mixture of the mono- and di-BOC-protected mono-alkylation products. This mixture was taken up in neat TFA (1 mL) and stirred 30 min. Saturated aqueous sodium bicarbonate (5 mL) was cautiously added, and the resulting mixture was extracted with CH$_2$Cl$_2$ (3×10 mL) then the combined organic extracts were dried (MgSO$_4$), and concentrated in vacuo. Purification of the crude material thus obtained by radial chromatography (silica gel, 1 mm plate, 50:1:1 CH$_2$Cl$_2$—MeOH—NH$_4$OH) afforded 35 mg (9%) of AMD9675 as a white foam. $^1$H NMR (CDCl$_3$) δ 1.68-1.72 (m, 1H), 2.00-2.06 (m, 2H), 2.24-2.35 (m, 2H), 2.70-2.74 (m, 1H), 2.84-2.87 (m, 1H), 3.72 (s, 2H), 3.92 (s, 2H), 3.95 (d, 1H, J=16 Hz), 4.02 (s, 2H), 4.07 (dd, 1H, J=9, 6 Hz), 4.17 (d, 1H, J=16 Hz), 7.10 (t, 1H, J=5 Hz), 7.15-7.24 (m, 5H), 7.35 (d, 2H, J=8 Hz), 7.42 (d, 1H, J=8 Hz), 7.58 (br s, 2H), 8.63 (d, 2H, J=5 Hz), 8.68 (dd, 1H, J=5, 1 Hz); $^{13}$C NMR (CDCl$_3$) δ 21.4, 23.2, 29.2, 48.5, 53.2, 53.7, 54.9, 60.1, 110.9, 118.7, 119.0, 121.4, 122.2, 128.3, 128.6, 134.7, 137.1, 138.0, 138.9, 146.9, 156.2, 156.9, 157.4, 168.9. ES-MS m/z 490 (M+H). Anal. Calcd. for C$_{30}$H$_{31}$N$_7$.0.1CH$_2$Cl$_2$.1.1H$_2$O: C, 69.80; H, 6.50; N, 18.93. Found: C, 69.75; H, 6.35; N, 19.28.

EXAMPLE: 105

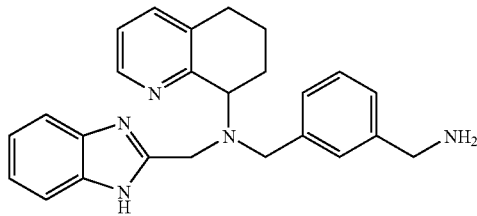

AMD9679: Preparation of N'-(1H-benzimidazol-2-ylmethyl)-N'-(5,6,7,8-tetrahydro-8-quinolinyl)-1,3-benzenedimethanamine To a stirred solution of 8-amino-5,6,7,8-tetrahydroquinoline (6.43 g, 43 mmol) in CH$_2$Cl$_2$ (450 mL) at room temperature was added 3-cyanobenzaldehyde (5.69 g, 43 mmol) and sodium triacetoxyborohydride (17.0 g, 80 mmol) and the mixture stirred 16 h. The reaction was quenched with 1N NaOH (200 mL) and the phases separated. The organic phase was dried (Na$_2$SO$_4$) and concentrated under reduced pressure to give a yellow oil (11.7 g) which was purified by flash chromatography on silica gel (97:3 CH$_2$Cl$_2$/CH$_3$OH) to provide N-(5,6,7,8-tetrahydro-8-quinolinyl)-3-cyanobenzylamine (9.10 g, 81%) as a pale yellow solid.

Using General Procedure for alkylation: A solution of the material from above (4.17 g, 15.8 mmol), potassium iodide (130 mg, 0.80 mmol) and N,N-diisopropylethylamine (5.2 mL, 30 mmol) in CH$_3$CN (160 mL) was reacted with N-(tert-butoxycarbonyl)-2-chloromethylbenzimidazole (prepared as described by An, H.; Wang, T.; Mohan, V.; Griffey, R. H.; Cook, P. D *Tetrahedron* 1998, 54, 3999-4012) (4.22 g, 15.8 mmol). Purification of the crude material by flash chromatography on silica gel (1:1 EtOAc/hexanes) gave the alkylated product (6.86 g, 88%) as a yellow foam.

To a solution of the material from above (6.86 g, 13.9 mmol) in NH$_3$ saturated methanol (100 mL) in a Parr bottle was added Raney nickel (approx 1 g) and the mixture hydrogenated at 50 psi hydrogen in a Parr hydrogenator for 17 h. The product mixture was filtered through Celite 521 and the solvent from the eluent removed in vacuo. Purification of the crude material by flash chromatography on silica gel (5% CH$_2$Cl$_2$/CH$_3$OH/NH$_4$OH, 19:1:0 followed by 18:1:1) gave AMD9679 (4.36 g, 79%) as a yellow foamy solid. $^1$H NMR (CDCl$_3$) δ 1.58-1.75 (m, 1H), 1.96-2.09 (m, 2H), 2.24-2.30 (m, 1H), 2.70-2.94 (m, 2H), 3.74 (s, 2H), 3.78 (s, 2H), 3.94-4.20 (m, 3H), 7.07 (d, 1H, J=7.5 Hz), 7.15-7.21 (m, 4H), 7.30 (d, 1H, J=7.5 Hz), 7.36 (s, 1H), 7.43 (d, 1H, J=7.5 Hz), 7.47 (s br, 2H), 8.67 (d, 1H, J=4.2 Hz). $^{13}$C NMR (CDCl$_3$) δ 21.77, 23.70, 29.65, 46.47, 49.12, 54.51, 60.78, 121.93(2), 122.65, 126.45, 127.61, 127.98, 128.83, 135.23, 137.70, 140.08, 142.72, 147.27, 156.35, 157.72. ES-MS m/z 398 (M+H). Anal. Calcd. for C$_{25}$H$_{27}$N$_5$.1.0H$_2$O.0.23CH$_2$Cl$_2$: C, 69.65; H, 6.82; N, 16.10. Found: C, 69.57; H, 6.91; N, 16.30.

EXAMPLE: 106

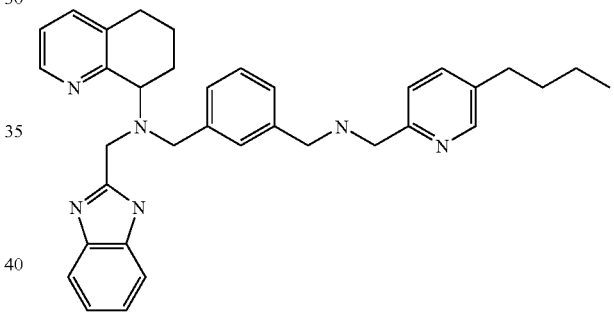

AMD9590: Preparation of (1H-Benzimidazol-2-ylmethyl)-(3-{[(5-butyl-pyridin-2-ylmethyl)-amino]-methyl}-benzyl)-(5,6,7,8-tetrahydro-quinolin-8-yl)-amine Using the reductive amination general procedure B: Reaction of (3-aminomethyl-benzyl)-1H-benzimidazol-2-ylmethyl)-(5,6,7,8-tetrahydro-quinolin-8-yl)-amine (155 mg, 0.39 mmol), 5-butyl-pyridine-2-carbaldehyde (64 mg, 0.39 mmol), NaBH(OAc)$_3$ (248 mg, 1.17 mmol), and AcOH (200 uL) for 1 h at room temperature followed by column chromatography on silica gel (EtOAc/MeOH/NH$_4$OH 199:1:1) gave the title compound (67 mg, 32%) as a white foam.

Using general procedure D: Conversion of the foam from above to the hydrobromide salt gave AMD9590 as a white powder. $^1$H NMR (300 MHz, D$_2$O) δ 0.85 (t, 3H, J=7.2 Hz), 1.23-1.30 (m, 2H), 1.53-1.60 (m, 2H), 1.75-2.00 (m, 1H), 2.18-2.27 (m, 2H), 2.41-2.42 (m, 1H), 2.72 (t, 2H, J=7.5 Hz), 3.02 (br s, 2H), 3.77 (d, 1H, J=12.9 Hz), 3.85 (d, 1H, J=12.9 Hz), 3.88 (s, 2H), 4.36 (s, 2H), 4.40 (d, 1H, J=16.5 Hz), 4.60 (d, 1H, J=16.5 Hz), 4.72-4.74 (m, 1H), 6.85 (d, 1H, J=7.8 Hz), 7.14 (t, 2H, J=7.8 Hz), 7.28 (d, 1H, J=7.8 Hz), 7.45-7.49 (m, 2H), 7.51-7.56 (m, 2H), 7.67 (d, 1H, J=8.1 Hz), 7.90 (dd, 1H, J=8.1, 6.3 Hz), 8.13 (dd, 1H, J=8.1, 2.1 Hz), 8.38 (d, 1H, J=7.5 Hz), 8.51 (d, 1H, J=1.8 Hz), 8.75 (d, 1H, J=4.8 Hz); $^{13}$C NMR (75.5 MHz, D$_2$O) δ 13.45, 20.44, 20.89, 21.83, 27.85, 31.91, 32.38, 48.09, 49.88, 50.84, 56.66, 62.88, 113.86, 126.13, 126.80, 126.90, 129.60, 129.96, 130.20, 130.45, 131.28, 131.68, 137.62, 139.76, 140.99, 143.09, 143.93, 144.47, 145.34, 148.30, 150.72, 151.56. ES-MS m/z 545 (M+H). Anal. Calcd. C$_{35}$H$_{40}$N$_6$.3.9(HBr).3.9H$_2$O.0.1 (C$_4$H$_{10}$O): C, 45.33; H, 5.66; N, 8.96; Br, 33.22; Found: C, 45.53; H, 5.65; N, 8.95; Br, 32.86.

EXAMPLE: 107

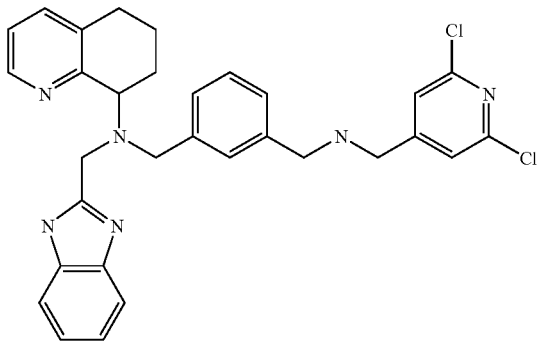

AMD9599: Preparation of (1H-benzimidazol-2-ylmethyl)-(3-{[(2,6-dichloro-pyridin-4-ylmethyl)-amino]-methyl}-benzyl)-(5,6,7,8-tetrahydro-quinolin-8-yl)-amine Using general procedure B: Reaction of (3-aminomethyl-benzyl)-1H-benzimidazol-2-ylmethyl)-(5,6,7,8-tetrahydro-quinolin-8-yl)-amine (90 mg, 0.23 mmol), 2,6-dichloro-pyridine-4-carbaldehyde (40 mg, 0.23 mmol), and NaBH(OAc)$_3$ (97 mg, 0.46 mmol) for 4 h at room temperature followed by column chromatography on silica gel (EtOAc/MeOH/NH$_4$OH 199:1:1) gave the title compound (57 mg, 45%) as a white foam.

Using general procedure D: Conversion of the foam from above to the hydrobromide salt gave AMD9599 as a white powder. $^1$H NMR (300 MHz, D$_2$O) δ 1.80-2.00 (m, 1H), 2.18-2.30 (m, 2H), 2.40-2.44 (m, 1H), 3.01 (br s, 2H), 3.72-3.86 (m, 4H), 4.11 (s, 2H), 4.38 (d, 1H, J=16.2 Hz), 4.58 (d, 1H, J=16.2 Hz), 4.70-4.73 (m, 1H), 6.84 (d, 1H, J=7.5 Hz), 7.05 (s, 1H), 7.14 (t, 1H, J=7.8 Hz), 7.27 (d, 1H, J=7.8 Hz), 7.31 (s, 2H), 7.44-7.47 (m, 2H), 7.50-7.55 (m, 2H), 7.90 (dd, 1H, J=7.5, 5.7 Hz), 8.37 (d, 1H, J=7.8 Hz), 8.74 (d, 1H, J=5.4 Hz); $^{13}$C NMR (75.5 MHz, D$_2$O) δ 20.44, 20.86, 27.85, 48.19, 49.84, 50.62, 56.53, 62.76, 113.88, 124.21, 126.10, 126.66, 129.60, 129.89, 130.23, 130.68, 131.26, 131.65, 137.59, 139.79, 140.95, 146.49, 148.18, 150.80, 151.61. ES-MS m/z 557 (M+H). Anal. Calcd. C$_{31}$H$_{30}$N$_6$Cl$_2$.2.9(HBr).2.8H$_2$O: C, 44.19; H, 4.61; N, 9.97; Cl, 8.42; Br, 27.50; Found: C, 44.37; H, 4.43; N, 9.91; Cl, 8.33; Br, 27.21.

EXAMPLE: 108

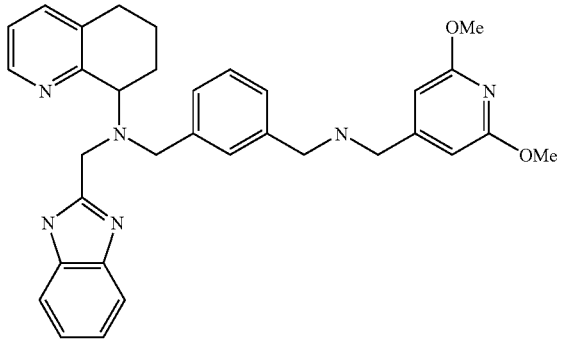

AMD 9600: Preparation of (1H-benzimidazol-2-ylmethyl)-(3-{[(2,6-dimethoxy-pyridin-4-ylmethyl)-amino]-methyl}-benzyl)-(5,6,7,8-tetrahydro-quinolin-8-yl)-amine Using general procedure B: Reaction of (3-aminomethyl-benzyl)-1H-benzimidazol-2-ylmethyl)-(5,6,7,8-tetrahydro-quinolin-8-yl)-amine (144 mg, 0.36 mmol), 2,6-dimethoxy-pyridine-4-carbaldehyde (60 mg, 0.36 mmol), and NaBH(OAc)$_3$ (153 mg, 0.72 mmol) for 19 h at room temperature followed by column chromatography on silica gel (EtOAc/MeOH/NH$_4$OH 199:1:1) gave AMD9600 (100 mg, 51%) as a white foam. $^1$H NMR (300 MHz, CDCl$_3$) δ 1.66-1.70 (m, 1H), 2.00-2.10 (m, 4H), 2.26-2.30 (m, 1H), 2.74-2.85 (m, 2H), 3.66 (s, 2H), 3.69 (s, 2H), 3.73 (s, 2H), 3.91 (s, 6H), 3.96 (d, 1H, J=16.5 Hz), 4.04-4.13 (m, 1H), 4.18 (d, 1H, J=16.5 Hz), 6.30 (s, 2H), 7.08 (d, 1H, J=7.5 Hz), 7.15-7.20 (m, 4H), 7.41-7.44 (m, 2H), 7.56 (br s, 2H), 8.68 (d, 1H, J=5.2 Hz); $^{13}$C NMR (75.5 MHz, CDCl$_3$) δ 21.78, 23.59, 29.66, 49.06, 52.23, 53.24, 53.92, 54.47, 60.66, 100.57, 121.97, 122.67, 127.43, 127.76, 128.70, 128.81, 135.23, 137.71, 139.95, 140.11, 147.33, 155.26, 156.38, 157.68, 163.86. ES-MS m/z 549 (M+H). Anal. Calcd. C$_{33}$H$_{36}$N$_6$O$_2$.1.0(H$_2$O): C, 69.94; H, 6.76; N, 14.83; O, 8.47; Found: C, 69.75; H, 6.67; N, 14.45; O, 8.41.

EXAMPLE: 109

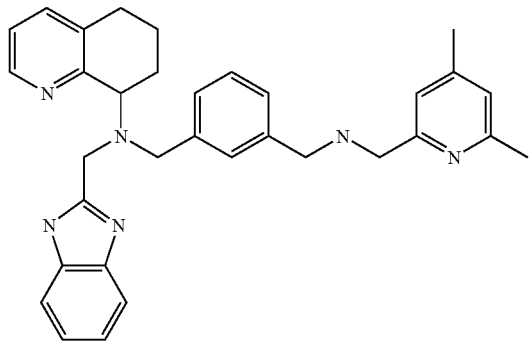

AMD9616: Preparation of (1H-benzimidazol-2-ylmethyl)-(3-{[(4,6-dimethyl-pyridin-2-ylmethyl)-amino]-methyl}-benzyl)-(5,6,7,8-tetrahydro-quinolin-8-yl)-amine(hydrobromide salt)

Using general procedure B: Reaction of (3-aminomethyl-benzyl)-1H-benzimidazol-2-ylmethyl)-(5,6,7,8-tetrahydro-quinolin-8-yl)-amine (150 mg, 0.38 mmol), 4,6-dimethyl-pyridine-2-carbaldehyde (52 mg, 0.38 mmol), and NaBH(OAc)$_3$ (160 mg, 0.76 mmol) for 18 h at room temperature followed by column chromatography on silica gel (EtOAc/MeOH/NH$_4$OH 199:1:1) gave the title compound (129 mg, 66%) as a white foam.

Using general procedure D: Conversion of the foam from above to the hydrobromide salt gave AMD9616 as a white powder. $^1$H NMR (300 MHz, D$_2$O) δ 1.89-2.05 (m, 1H), 2.02-2.32 (m, 2H), 2.44-2.47 (m, 1H), 2.51 (s, 3H), 2.63 (s, 3H), 3.03 (br s, 2H), 3.85 (dd, 2H, J=24.33, 12.9 Hz), 3.96 (s, 2H), 4.42-4.46 (m, 3H), 4.62 (d, 1H, J=17.4 Hz), 6.88 (d, 1H, J=7.5 Hz), 7.16 (dd, 1H, J=7.8, 7.5 Hz), 7.22 (s, 1H), 7.32 (d, 1H, J=7.5 Hz), 7.48-7.63 (m, 6H), 7.92 (dd, 1H, J=7.2, 6.3 Hz), 8.39 (d, 1H, J=8.1 Hz), 8.78 (d, 1H, J=5.4 Hz); $^{13}$C NMR (75.5 MHz, D$_2$O) δ 19.55, 20.46, 20.89, 21.89, 27.86, 46.81, 49.86, 51.15, 56.66, 63.84, 113.89, 126.11, 126.48, 126.80, 129.10, 129.71, 129.94, 130.45, 131.44, 131.83, 137.70, 139.80, 140.97, 143.24, 148.28, 150.68, 151.51, 155.22, 161.32. ES-MS m/z 517 (M+H). Anal. Calcd. C$_{33}$H$_{36}$N$_6$.3.7(HBr).2.6(H$_2$O): C, 45.93; H, 5.24; N, 9.74; Br, 34.26; Found: C, 45.89; H, 5.17; N, 9.41; Br, 34.39.

EXAMPLE: 110

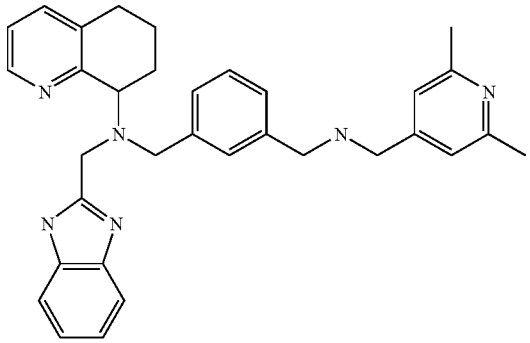

AMD9617: Preparation of (1H-benzimidazol-2-ylmethyl)-(3-{[(2,6-dimethyl-pyridin-4-ylmethyl)-amino]-methyl}-benzyl)-(5,6,7,8-tetrahydro-quinolin-8-yl)-amine Using general procedure B: Reaction of (3-aminomethyl-benzyl)-1H-benzimidazol-2-ylmethyl)-(5,6,7,8-tetrahydro-quinolin-8-yl)-amine (150 mg, 0.38 mmol), 2,6-dimethyl-pyridine-4-carbaldehyde (52 mg, 0.38 mmol), and NaBH(OAc)$_3$ (160 mg, 0.76 mmol) for 18 h at room temperature followed by column chromatography on silica gel (EtOAc/MeOH/NH$_4$OH 199:1:1) gave the title compound (125 mg, 64%) as a white foam.

Using general procedure D: Conversion of the foam from above to the hydrobromide salt gave AMD9617 as a white powder. $^1$H NMR (300 MHz, D$_2$O) δ 1.88-1.90 (m, 1H), 2.20-2.33 (m, 2H), 2.43-2.46 (m, 1H), 2.68 (s, 6H), 3.03 (br s, 2H), 3.81-3.88 (m, 3H), 3.92 (s, 2H), 4.32 (s, 2H), 4.43 (d, 1H, J=16.2 Hz), 4.62 (d, 1H, J=16.2 Hz), 6.89 (d, 1H, J=7.5 Hz), 7.16 (dd, 1H, J=7.8, 7.5 Hz), 7.25 (s, 1H), 7.33 (d, 1H, J=7.5 Hz), 7.48-7.58 (m, 6H), 7.91 (dd, 1H, J=7.5, 6.0 Hz), 8.39 (d, 1H, J=7.8 Hz), 8.79 (d, 1H, J=5.4 Hz); $^{13}$C NMR (75.5 MHz, D$_2$O) δ 18.34, 19.51, 19.94, 26.91, 47.89, 48.93, 50.14, 55.70, 61.88, 112.94, 124.26, 125.15, 125.82, 128.84, 128.92, 129.16, 129.54, 130.60, 130.84, 136.70, 138.86, 140.00, 147.31, 149.39, 149.74, 150.60, 153.49. ES-MS m/z 517 (M+H). Anal. Calcd. C$_{33}$H$_{36}$N$_6$.3.8(HBr).3.8(H$_2$O): C, 44.40; H, 5.35; N, 9.42; Br, 34.02; Found: C, 44.35; H, 5.15; N, 9.17; Br, 34.04.

EXAMPLE: 111

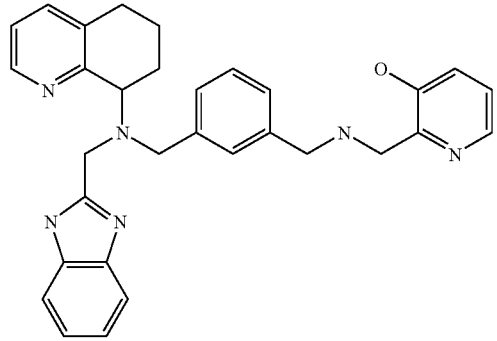

AMD9626: Preparation of (1H-benzimidazol-2-ylmethyl)-(5,6,7,8-tetrahydro-quinolin-8-yl)-amino]-methyl}-benzylamino)-methyl]-pyridin-3-ol Using general procedure B: Reaction of (3-aminomethyl-benzyl)-1H-benzimidazol-2-ylmethyl)-(5,6,7,8-tetrahydro-quinolin-8-yl)-amine (158 mg, 0.40 mmol), 3-hydroxy-pyridine-2-carbaldehyde (49 mg, 0.40 mmol), and NaBH(OAc)$_3$ (101 mg, 0.48 mmol) for 48 h at room temperature followed by column chromatography on silica gel (CH$_2$Cl$_2$MeOH/NH$_4$OH 194:3:3) gave AMD9626 (98 mg, 49%) as a white foam. $^1$H NMR (300 MHz, CDCl$_3$) δ 1.72-1.73 (m, 1H), 2.00-2.08 (m, 2H), 2.26-2.31 (m, 1H), 2.75-2.86 (m, 2H), 3.72 (d, 1H, J=3.6 Hz), 3.77 (s, 2H), 3.98 (d, 1H, J=16.5 Hz), 4.08-4.11 (m, 1H), 4.14 (s, 1H), 4.16 (s, 2H), 7.08 (dd, 1H, J=7.2, 5.1 Hz), 7.10-7.22 (m, 6H), 7.28-7.30 (m, 1H), 7.42 (d, 1H, J=7.8 Hz), 7.46 (s, 1H), 7.50-7.51 (m, 1H), 7.61 (br s, 1H), 8.05 (dd, 1H, J=4.2, 1.5 Hz), 8.69-8.70 (m, 1H); $^{13}$C NMR (75.5 MHz, CDCl$_3$) δ 21.84, 24.21, 29.63, 49.28, 53.30, 54.57, 61.05, 111.46, 119.07, 121.74, 122.65, 123.67, 123.96, 127.65, 128.34, 128.99, 135.08, 137.61, 138.36, 140.27, 140.42, 143.83, 147.45, 155.12, 156.49, 157.77. ES-MS m/z 505 (M+H). Anal. Calcd. C$_{31}$H$_{32}$N$_6$O.0.7(CH$_2$Cl$_2$).1.4(H$_2$O): C, 64.61; H, 6.19; N, 14.26; O, 6.52; Found: C, 64.50; H, 5.92; N, 14.12; O, 6.55.

EXAMPLE: 112

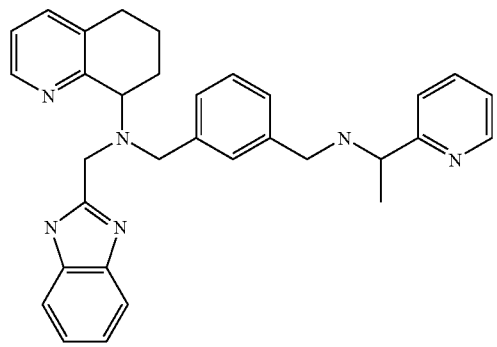

AMD9627: Preparation of (1H-benzimidazol-2-ylmethyl)-{3-[(1-pyridin-2-yl-ethylamino)-methyl]-benzyl}-(5,6,7,8-tetrahydro-quinolin-8-yl)-amine Using the general procedure B: Reaction of (3-aminomethyl-benzyl)-1H-benzimidazol-2-ylmethyl)-(5,6,7,8-tetrahydro-quinolin-8-yl)-amine (150 mg, 0.38 mmol), 1-pyridin-2-yl-ethanone (42 uL, 0.38 mmol), NaBH(OAc)$_3$ (97 mg, 0.46 mmol), and AcOH (150 uL) for 18 h at room temperature followed by column chromatography on silica gel (EtOAc/MeOH/NH$_4$OH 199:1:1) gave the title compound (101 mg, 53%) as a white foam.

Using the general procedure D: Conversion of the foam from above to the hydrobromide salt gave AMD9627 as a white powder. $^1$H NMR (300 MHz, D$_2$O) δ 1.60 (d, 3H, J=6.9 Hz), 1.75-2.06 (m, 1H), 2.20-2.24 (m, 2H), 2.28-2.40 (m, 1H), 3.03 (br s, 2H), 3.49-3.55 (m, 1H), 3.69 (d, 1H, J=13.2 Hz), 3.82 (dd, 2H, J=20.4, 13.2 Hz), 4.36-4.43 (m, 1H), 4.58 (d, 1H, J=16.5 Hz), 4.73-4.76 (m, 1H), 6.79 (d, 1H, J=7.5 Hz), 6.99 (s, 1H), 7.13 (dd, 1H, J=7.8, 7.5 Hz), 7.27 (d, 1H, J=7.5 Hz), 7.42-7.52 (m, 4H), 7.57 (d, 1H, J=7.8 Hz), 7.62 (ddd, 1H, J=6.3, 6.3, 0.9 Hz), 7.93 (dd, 1H, J=6.9, 6.6 Hz), 8.08 (dd, 1H, J=7.8, 7.8 Hz), 8.40 (d, 1H, J=7.8 Hz), 8.63-8.65 (m, 1H), 8.75 (d, 1H, J=5.4 Hz); $^{13}$C NMR (75.5 MHz, D$_2$O) δ 18.36, 20.43, 20.87, 27.83, 49.07, 49.86, 56.65, 57.52, 62.93, 113.79, 124.22, 125.87, 126.11, 126.73, 129.37, 129.88, 130.41, 130.56, 130.99, 131.46, 137.55, 139.68, 141.00, 141.40, 148.28, 148.37, 150.73, 151.54, 153.34. ES-MS m/z 503 (M+H). Anal. Calcd. C$_{32}$H$_{34}$N$_6$.3.6(HBr).3.4(H$_2$O): C, 44.94; H, 5.23; N, 9.83; Br, 33.64; Found: C, 44.94; H, 5.00; N, 9.61; Br, 33.61.

EXAMPLE: 113

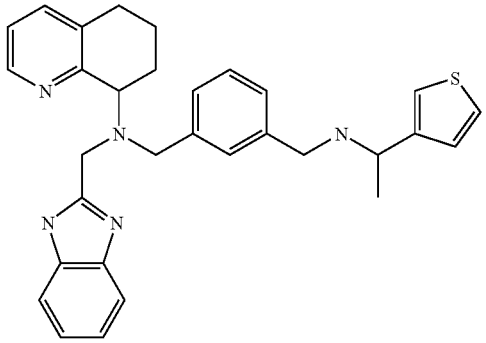

AMD9628: Preparation of (1H-benzimidazol-2-ylmethyl)-(5,6,7,8-tetrahydro-quinolin-8-yl)-{3-[(1-thiophen-3-yl-ethylamino)-methyl]-benzyl}-amine Using general procedure B: Reaction of (3-aminomethyl-benzyl)-1H-benzimidazol-2-ylmethyl)-(5,6,7,8-tetrahydro-quinolin-8-yl)-amine (150 mg, 0.38 mmol), 3-acetylthiophene (48 mg, 0.38 mmol), NaBH(OAc)$_3$ (104 mg, 0.49 mmol), and AcOH (150 uL) for 48 h at room temperature followed by column chromatography on silica gel (EtOAc/MeOH/NH$_4$OH 199:1:1) gave the title compound (87 mg, 46%) as a white foam.

Using the general procedure D: Conversion of the foam from above to the hydrobromide salt gave AMD9628 as a white powder. $^1$H NMR (300 MHz, D$_2$O) δ 1.59 (d, 3H, J=6.9 Hz), 1.90-1.99 (m, 1H), 2.20-2.28 (m, 2H), 2.42-2.50 (m, 1H), 3.03 (br s, 2H), 3.25 (dd, 1H, J=13.2, 6.6 Hz), 3.47-3.56 (m, 1H), 3.77-3.87 (m, 2H), 4.35-4.47 (m, 2H), 4.59 (d, 1H, J=16.5 Hz), 4.73-4.81 (m, 1H), 6.74 (d, 1H, J=6.9 Hz), 6.87-6.88 (m, 1H), 7.13-7.18 (m, 2H), 7.26 (d, 1H, J=7.5 Hz), 7.44-7.51 (m, 4H), 7.54-7.55 (m, 1H), 7.59-7.62 (m, 1H), 7.93 (dd, 1H, J=7.2, 6.6 Hz), 8.40 (d, 1H, J=7.8 Hz), 8.72-8.75 (m, 1H); $^{13}$C NMR (75.5 MHz, D$_2$O) δ 18.68, 20.43, 20.88, 27.82, 48.34, 49.91, 53.81, 56.69, 63.01, 113.80, 126.10, 126.26, 126.57, 126.76, 128.69, 129.09, 129.86, 130.48, 130.70, 130.79, 130.99, 131.25, 136.48, 137.50, 139.67, 140.98, 148.23, 150.77, 151.59. ES-MS m/z 508 (M+H). Anal. Calcd. C$_{31}$H$_{33}$N$_5$S.2.9(HBr).2.7(H$_2$O): C, 47.07; H, 5.26; N, 8.85; S, 4.05; Br, 29.30; Found: C, 46.95; H, 5.20; N, 8.61; S, 3.71; Br, 29.62.

EXAMPLE: 114

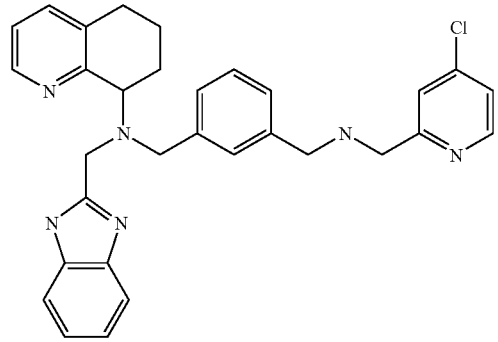

AMD9667: Preparation of (1H-benzimidazol-2-ylmethyl)-(3-{[(4-chloro-pyridin-2-ylmethyl)-amino]-methyl}-benzyl)-(5,6,7,8-tetrahydro-quinolin-8-yl)-amine Using general procedure B: Reaction of (3-aminomethyl-benzyl)-1H-benzimidazol-2-ylmethyl)-(5,6,7,8-tetrahydro-quinolin-8-yl)-amine (133 mg, 0.33 mmol), 4-chloro-pyridine-2-carbaldehyde (47 mg, 0.33 mmol), NaBH$_4$ (25 mg, 0.66 mmol), for 36 h at room temperature followed by column chromatography on silica gel (EtOAc/MeOH/NH$_4$OH 199:1:1) gave the title compound (118 mg, 69%) as a white foam. $^1$H NMR (300 MHz, CDCl$_3$) δ 1.63-1.66 (m, 1H), 1.94-2.04 (m, 2H), 2.24-2.26 (m, 1H), 2.65-2.86 (m, 2H), 3.72 (s, 2H), 3.75 (s, 2H), 3.82 (s, 2H), 3.97 (d, 1H, J=16.5 Hz), 4.04-4.09 (m, 1H), 4.17 (d, 1H, J=16.2 Hz), 7.09-7.20 (m, 6H), 7.28-7.30 (m, 2H), 7.38 (d, 1H, J=7.5 Hz), 7.48 (s, 1H), 7.55 (br s, 2H), 8.41 (d, 1H, J=5.1 Hz), 8.64 (d, 1H, J=3.6 Hz); $^{13}$C NMR (75.5 MHz, CDCl$_3$) δ 19.59, 21.47, 27.45, 46.97, 51.54, 52.14, 52.25, 58.44, 110.29, 116.63, 119.72, 120.43, 120.55, 120.82, 125.28, 125.55, 126.56, 126.73, 133.00, 135.47, 137.80, 137.92, 142.68, 145.10, 148.27, 154.19, 155.53, 159.79. ES-MS m/z 523 (M+H). Anal. Calcd. C$_{31}$H$_{31}$N$_6$Cl.1.0(H$_2$O): C, 68.81; H, 6.15; N, 15.53; Cl, 6.55; Found: C, 68.82; H, 5.99; N, 15.50; Cl, 6.74.

EXAMPLE: 115

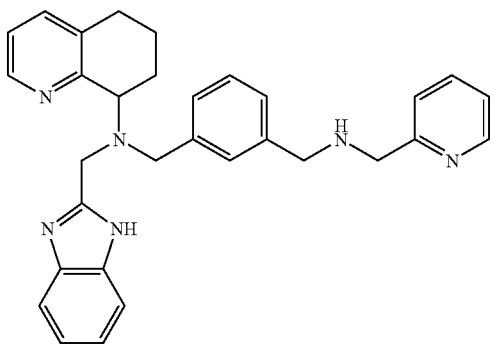

AMD9665: Preparation of (1H-Benzimidazol-2-ylmethyl)-(3-{[(pyridin-2-ylmethyl)-amino]-methyl}-benzyl)-(5,6,7,8-tetrahydro-quinolin-8-yl)-amine(hydrobromide salt)

Using general procedure B: Reaction of Pyridine-2-carbaldehyde (17.7 uL, 0.19 mmol), (3-aminomethyl-benzyl)-1H-benzimidazol-2-ylmethyl)-(5,6,7,8-tetrahydro-quinolin-8-yl)-amine (74 mg, 0.19 mmol) and sodium triacetoxyborohydride (36 mg, 0.22 mmol) in MeOH (1.8 mL) at room temperature under $N_2$ for 18 h, followed by purification of the crude material by chromatography on silica gel (2:2:96 $CH_3OH$—$NH_3H_2O$—$CH_2Cl_2$) afforded the title compound (61 mg, 67%) as a white foam.

Using General Procedure D: Conversion of the foam from above (61 mg, 0.12 mmol) to the hydrobromide salt using an acetic acid/HBr solution, followed by re-precipitation of the salt from diethyl ether gave AMD9665 as a white solid. $^1$H NMR ($CD_3OD$) ☐i☐☐-2.02 (m, 1H), 2.21-2.32 (m, 2H), 2.48-2.53 (m, 1H), 3.02-3.15 (m, 2H), 3.85 (d, 1H, J=12.9 Hz), 3.94 (d, 1H, J=12.9 Hz), 4.29-4.63 (m, 6H), 4.71 (dd, 1H, J=5.7, 10.8 Hz), 7.17-7.21 (m, 2H), 7.43-7.46 (m, 1H), 7.51-7.59 (m, 2H), 7.69-7.87 (m, 4H), 7.97 (dd, 1H, J=6, 7.8 Hz), 8.17 (s, 1H), 8.17-8.20 (m, 1H); 8.41 (dd, 1H, J=1.2, 7.5 Hz), 8.75 (d, 1H, J=5.1 Hz), 9.06 (dd, 1H, J=1.2, 5.4 Hz); $^{13}$C NMR ($CD_3OD$) δ 21.72, 21.87, two peaks overlapped with methanol, 52.25, 57.69, 62.22, 115.29, 127.21, 128.04, 130.60, 131.19, 132.31, 132.57, 132.95, 133.88, 138.73, 142.07, 143.22, 148.49, 149.43, 151.98,152.66; ES-MS m/z 490.3 (M+H); Anal. Calcd. For $(C_{31}H_{29}N_5O)$.3.7(HBr).4.0 $(H_2O)$: C, 43.29; H, 5.12; N, 9.77; Br, 34.37. Found: C, 43.21; H, 4.99; N, 9.65; Br, 34.50.

EXAMPLE: 116

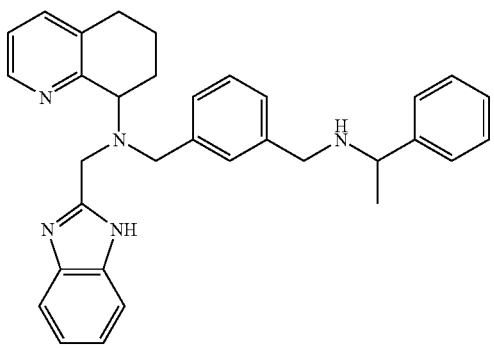

AMD9672: (1H-Benzimidazol-2-ylmethyl)-{3-[(1-phenyl-ethylamino)-methyl]-benzyl}-(5,6,7,8-tetrahydro-quinolin-8-yl)-amine(hydrobromide salt)

Using general procedure B: Reaction of acetophenone (40 mg, 0.34 mmol), (3-aminomethyl-benzyl)-1H-benzimidazol-2-ylmethyl)-(5,6,7,8-tetrahydro-quinolin-8-yl)-amine (134 mg, 0.34 mmol) in MeOH (2 mL) at 60° C. overnight under $N_2$ and 2 min of stirring after addition of sodium borohydride (25 mg, 0.66 mmol), followed by purification of the crude material by chromatography on silica gel (2:2:96 $CH_3OH$—$NH_3$ $H_2O$—$CH_2Cl_2$) afforded the title compound (41 mg, 24%) as a white foam.

Using General Procedure D: Conversion of the foam from above (41 mg, 0.08 mmol) to the hydrobromide salt using an acetic acid/HBr solution, followed by re-precipitation of the salt from diethyl ether gave AMD9672 as a white solid. $^1$H NMR ($CD_3OD$) ☐i☐☐ (t, 3H, J=6.6 Hz), 1.89-1.98 (m, 1H), 2.23-2.27 (m, 2H), 2.48 (b, 1H), 3.06 (b, 2H), 3.69-4.09 (m, 4H), 4.36-4.66 (m, 4H), 6.98 (d, 1H, J=7.2 Hz), 7.16 (dd, 1H, J=7.1, 7.1 Hz), 7.38 (d, 1H, J=6.9 Hz), 7.50-7.58 (m, 7H), 7.73-7.76 (m, 2H), 7.98 (dd, 1H, J=3.5, 3.5 Hz), 8.07 (s, 1H), 8.41 (d, 1H, J=7.5 Hz), 9.04 (s, 1H); $^{13}$C NMR ($CD_3OD$) δ 20.35, 21.75, 21.88, 29.24, two peaks overlapped with methanol, 57.59, 60.62, 62.18, 115.28, 127.19, 128.00, 129.50, 130.55, 130.90, 131.01, 131.26, 132.33, 133.34, 133.48, 137.82, 138.65, 142.07, 149.32, 152.10, 152.78; ES-MS m/z 502.3 (M+H); Anal. Calcd. For $(C_{33}H_{35}N_5)$.3(HBr).2.3 $(H_2O)$: C, 50.44; H, 5.46; N, 8.91; Br, 30.50. Found: C, 50.74; H, 5.35; N, 8.73; Br, 30.24.

EXAMPLE: 117

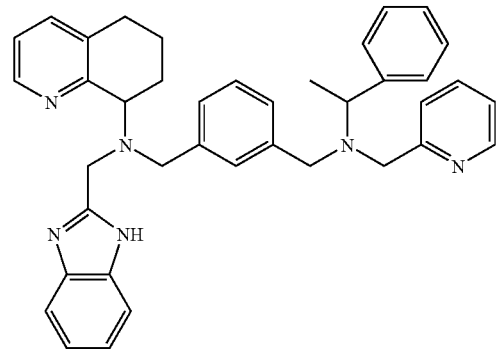

AMD9686: (1H-Benzimidazol-2-ylmethyl)-(3-{[(1-phenyl-ethyl)-pyridin-2-ylmethyl-amino]-methyl}-benzyl)-(5,6,7,8-tetrahydro-quinolin-8-yl)-amine (hydrobromide salt)

Using general procedure B: Reaction of Pyridine-2-carbaldehyde (22 mg, 0.20 mmol, (1H-Benzimidazol-2-ylmethyl)-{3-[(1-phenyl-ethylamino)-methyl]-benzyl}-(5,6,7,8-tetrahydro-quinolin-8-yl)-amine (101 mg, 0.20 mmol) and sodium triacetoxyborohydride (58 mg, 0.26 mmol) in $CH_2Cl_2$ (2 mL) at room temperature under $N_2$ for 20 h, followed by purification of the crude material by chromatography on silica gel (2:2:96 $CH_3OH$—$NH_3$ $H_2O$—$CH_2Cl_2$) afforded the title compound (60 mg, 50%) as a white foam.

Using General Procedure D: Conversion of the foam from above (60 mg, 0.10 mmol) to the hydrobromide salt using an acetic acid/HBr solution, followed by re-precipitation of the salt from diethyl ether gave AMD9686 as a white solid. $^1$H NMR (CD$_3$OD) □1.91 (d, 3H, J=6.6 Hz), 1.98-2.01 (m, 1H), 2.23-2.30 (m, 2H), 2.45-2.49 (m, 1H), 3.01-3.06 (m, 2H), 3.30 (s, 1H), 3.70-3.76 (m, 1H), 3.84 (d, 1H, J=12.3 Hz), 4.16-4.66 (m, 7H), 6.99 (d, 2H, J=4.2 Hz), 7.18 (b, 1H), 7.29 (b, 2H), 7.44-7.45 (m, 3H), 7.48-7.53 (m, 2H), 7.65-7.66 (m, 3H), 7.74-7.77 (m, 2H), 7.98-8.03 (m, 1H), 8.09 (s, 1H), 8.31 (s, 1H), 8.42 (d, 1H, J=7.8 Hz), 9.08 (dd, 1H, J=5.5, 5.5 Hz); $^{13}$C NMR (CD$_3$OD) δ 16.95, 17.30, 21.77, 21.88, 29.23, 54.14, 57.64, 58.28, 58.56, 62.34, 67.03, 67.29, 115.27, 125.70, 127.27, 128.01, 130.36, 130.78, 130.97, 131.49, 131.70, 132.26, 132.51, 132.79, 134.44, 134.51, 136.55, 138.32, 141.03, 141.96, 142.19, 148.45, 149.49, 151.98, 152.76; ES-MS m/z 593.4 (M+H); Anal. Calcd. For (C$_{38}$H$_{38}$N$_6$).3.9(HBr).1.3(H$_2$O).0.6(C$_4$H$_{10}$O): C, 50.43; H, 5.29; N, 8.73; Br, 32.39. Found: C, 50.45; H, 5.32; N, 8.71; Br, 32.35.

EXAMPLE: 118

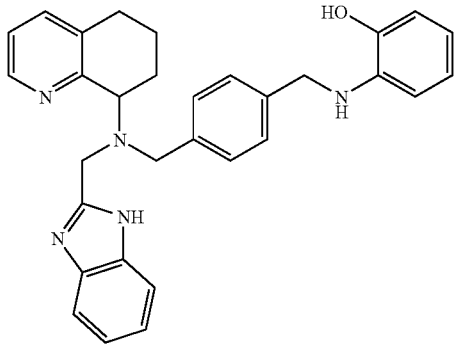

AMD9740: Preparation of 2-(4-{[(1H-Benzimidazol-2-ylmethyl)-(5,6,7,8-tetrahydro-quinolin-8-yl)-amino]-methyl}-benzylamino)-phenol(hydrobromide salt)

Preparation of 4-hydroxymethylbenzaldehyde:

Terephthaldicarboxaldehyde (30.02 g, 224 mmol), methanol (200 mL), palladium on activated carbon, (10%, 3.02 g) and 2-(aminomethyl)pyridine (2.3 mL, 22 mol, 0.01 mol equiv) were combined in a hydrogenation vessel and the reaction mixture was shaken on a Parr hydrogenator for 2.5 hours at 40 psi of hydrogen. The mixture was filtered through celite, the cake washed with methanol and the solvent from the eluent removed in vacuo. Purification of the crude product by column chromatography on silica gel (EtOAc/Hexanes, 1:1) afforded the title compound (23.8 g, 78%) as a white solid. $^1$H NMR (CDCl$_3$) □ 4.80 (s, 2H), 7.53 (d, 2H, J=9 Hz), 7.87 (d, 2H, J=9 Hz), 10.00 (s, 1H).

Preparation of 4-{[(1H-Benzimidazol-2-ylmethyl)-(5,6,7,8-tetrahydro-quinolin-8-yl)-amino]-methyl}-benzaldehyde:

To a stirred solution of 8-amino-5,6,7,8-tetrahydroquinoline (5.56 g, 37.5 mmol) in dry MeOH (150 mL) was added 4-hydroxymethylbenzaldehyde (7.22 g, 52.5 mmol) under an argon atmosphere and the mixture was stirred overnight at room temperature. To the resultant solution was added sodium borohydride (2.85 g, 75 mmol) in three portions over 45 minutes and the reaction mixture stirred for 24 h to afford a pale yellow oil which was used in the next step without any further purification (see General Procedures A and B).

To a stirred solution of the oil from above (7.64 g) in dry CH$_3$CN (100 mL) was added N,N-diisopropylethylamine (10 mL, 57 mmol), potassium iodide (0.24 g, 1.4 mmol) and 1-N-tert-butoxycarbonyl-2-chloromethylbenzimidazole (7.98 g, 29.9 mmol) as a solution in CH$_3$CN (50 mL). The mixture was stirred under an argon atmosphere at 60° C. overnight. The reaction mixture was concentrated in vacuo, diluted with CH$_2$Cl$_2$ (100 mL) and washed with saturated aqueous ammonium chloride (150 mL). The aqueous layer was extracted with CH$_2$Cl$_2$ (2×50 mL) and the combined organic layers were dried (Na$_2$SO$_4$), filtered, and concentrated in vacuo.

A solution of the crude material from above in CH$_2$Cl$_2$/trifluoroacetic acid (2:1, 30 mL) was stirred for 3 h at room temperature. The reaction mixture was diluted with CH$_2$Cl$_2$ (30 mL) and concentrated in vacuo. The residue was diluted with CH$_2$Cl$_2$ (50 mL) and washed with 1N NaOH (50 mL). The aqueous layer was extracted with CH$_2$Cl$_2$ (2×30 mL) and the combined organic layers were dried (Na$_2$SO$_4$), filtered, and concentrated in vacuo to afford a brown foam. The resultant alcohol was used in the next step without any further purification.

To a stirred solution of the alcohol from above (9.29 g) in dry CH$_2$Cl$_2$ (200 mL) was added MnO$_2$ (20.3 g, 233 mmol) and the mixture stirred for 4 h at room temperature. An additional portion of MnO$_2$ (8.5 g, 97.8 mmol) was then added and the mixture stirred overnight at room temperature. The reaction mixture was filtered through a celite pad, the cake washed with CHCl$_3$ and the resultant filtrate concentrated in vacuo. Purification of the crude product by column chromatography on silica gel (CH$_2$Cl$_2$/MeOH, 97:3 followed by 96:4) afforded the aldehyde (5.08 g, 34%, 5 steps) as a pale yellow solid. $^1$H NMR (CDCl$_3$) □ 1.56-1.74 (br m, 2H), 1.92-2.09 (m, 2H), 2.28-2.32 (m, 1H), 2.70-2.94 (m, 2H), 3.84 (s, 2H), 3.94 (d, 1H, J=16.5 Hz), 4.08-4.14 (m, 1H), 4.23 (d, 1H, J=16.5 Hz), 7.18-7.26 (m, 4H), 7.45 (d, 1H, J=7.8 Hz), 7.56 (d within m, 4H, J=13.5 Hz), 7.76 (d, 2H, J=8.1 Hz), 8.72 (d, 1H, J=4.2 Hz), 9.92 (s, 1H). ES-MS m/z 397 (M+H).

Using General Procedure B: To a stirred solution of 4-{[(1H-Benzimidazol-2-ylmethyl)-(5,6,7,8-tetrahydro-quinolin-8-yl)-amino]-methyl}-benzaldehyde (190 mg, 0.48 mmol) and 2-aminophenol (65 mg, 0.60 mmol) in THF (5 mL) and acetic acid (0.25 mL) was added NaBH(OAc)$_3$ (147 mg, 0.69 mmol) and the mixture stirred at room temperature overnight. Purification of the crude material by column chromatography on silica gel gel (CH$_2$Cl$_2$/MeOH/NH$_4$OH, 95:4:1) afforded the desired product (157 mg, 67%) as a yellow foam.

Using General Procedure D: Conversion of the foam from above (54 mg, 0.11 mmol) to the hydrobromide salt followed by re-precipitation of the intermediate solid from methanol/ether gave AMD9740 (72 mg, 86%) as a rose solid. $^1$H NMR (D$_2$O) □1.87-1.92 (m, 1H), 2.18-2.25 (m, 2H), 2.39-2.42 (m, 1H), 3.02-3.04 (m, 2H), 3.77 (d, 1H, J=12.6 Hz), 3.83 (d, 1H, J=12.6 Hz), 3.96 (d, 1H, J=13.5 Hz), 4.01 (d, 1H, J=13.5 Hz), 4.40 (d, 1H, J=16.5 Hz), 4.59 (d, 1H, J=16.5 Hz), 4.69-4.79 (m, 1H, overlap with HOD), 6.79 (t, 1H, J=7.8 Hz), 6.86-6.96 (m, 4H), 7.13 (d, 2H, J=7.8 Hz), 7.24 (t, 1H, J=7.8 Hz), 7.48 (dd, 2H, J=6, 3 Hz), 7.57 (dd, 2H, J=6, 3 Hz), 7.92 (dd, 1H, J=7.8, 6 Hz), 8.39 (d, 1H, J=8.1 Hz), 8.75 (d, 1H, J=5.5 Hz); $^{13}$C NMR (D$_2$O) □ 20.46, 20.88, 27.83, 49.94, 52.87, 56.61, 62.93, 113.92, 117.17, 120.82, 121.63, 124.30, 126.12, 126.71, 130.48, 131.37, 137.93, 139.66, 140.99, 148.28, 150.06, 150.82, 151.61. ES-MS m/z 490 (M+H). Anal. Calcd. for C$_{31}$H$_{31}$N$_5$O.3.0HBr.1.8H$_2$O: C, 48.79; H, 4.96; N, 9.18; Br, 31.20. Found: C, 49.13; H, 4.91; N, 8.80; Br, 30.82.

EXAMPLE: 119

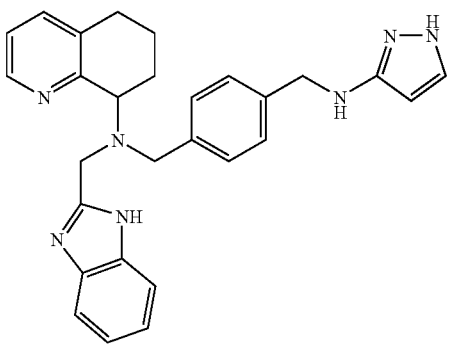

AMD9744: Preparation of (1H-Benzimidazol-2-ylmethyl)-{4-[(1H-pyrazol-3-ylamino)-methyl]-benzyl}-(5,6,7,8-tetrahydro-quinolin-8-yl)-amine(hydrobromide salt)

Using General Procedure B: To a stirred solution of 4-{[(1H-Benzimidazol-2-ylmethyl)-(5,6,7,8-tetrahydro-quinolin-8-yl)-amino]-methyl}-benzaldehyde (199 mg, 0.50 mmol) and 3-aminopyrazole (60 mg, 0.72 mmol) in THF (5 mL) and acetic acid (0.2 mL) was added NaBH(OAc)$_3$ (166 mg, 0.78 mmol) and the resultant mixture stirred at room temperature for 2.5 days. Purification of the crude material by radial chromatography on silica gel gel (2 mm plate, CH$_2$Cl$_2$/MeOH/NH$_4$OH, 100:1:1 then 50:1:1) afforded the desired amine (52 mg, 23%) as a white foam.

Using General Procedure D: Conversion of the foam from above (43 mg, 0.093 mmol) to the hydrobromide salt followed by re-precipitation of the intermediate solid from methanol/ether gave AMD9744 (54 mg, 78%) as a grey solid. $^1$H NMR (D$_2$O) ☐1.91-1.94 (m, 1H), 2.22-2.34 (m, 2H), 2.41-2.46 (m, 1H), 3.04-3.05 (m, 2H), 3.77 (d, 1H, J=12.6 Hz), 3.84 (d, 1H, J=12.6 Hz), 3.90 (s, 2H), 4.46 (d, 1H, J=16.5 Hz), 4.64 (d, 1H, J=16.5 Hz), 4.74-4.79 (m, 1H, overlap with HOD), 5.70 (s, 1H), 6.94 (d, 2H, J=7.8 Hz), 7.15 (d, 2H, J=7.8 Hz), 7.47 (dd, 2H, J=6, 3 Hz), 7.57 (dd, 2H, J=6, 3 Hz), 7.72 (s, 1H), 7.91 (dd, 1H, J=7.2, 6.6 Hz), 8.39 (d, 1H, J=7.8 Hz), 8.75 (d, 1H, J=5.7 Hz); $^{13}$C NMR (D$_2$O) ☐ 20.48, 20.91, 27.85, 47.20, 50.33, 56.62, 63.19, 113.76, 126.04, 126.52, 127.59, 130.46, 135.53, 135.80, 137.40, 139.61, 140.91, 148.20, 150.92, 151.40, 151.87. ES-MS m/z 464 (M+H). Anal. Calcd. for C$_{28}$H$_{29}$N$_7$.3.1HBr.1.6H$_2$O: C, 45.25; H, 4.79; N, 13.19; Br, 33.33. Found: C, 45.55; H, 4.83; N, 12.92; Br, 32.98.

EXAMPLE: 120

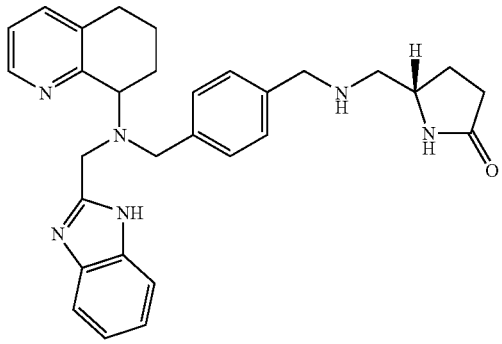

AMD9703: Preparation of (S)-5-[(4-{[(1H-Benzimidazol-2-ylmethyl)-(5,6,7,8-tetrahydro-quinolin-8-yl)-amino]-methyl}-benzylamino)-methyl]-pyrrolidin-2-one(hydrobromide salt)

Preparation of (S)-5-(aminomethyl)-2-pyrrolidinone:

To a suspension of (S)-5-(hydroxymethyl)-2-pyrrolidinone p-toluenesulfonate (1.358 g, 5.04 mmol) and sodium azide (1.65 g, 25.4 mmol) in DMF (5 mL) was added sodium hydride (25 mg, 1.04 mmol) and the mixture stirred at 60° C. overnight. The reaction was concentrated in vacuo then redissolved in CH$_2$Cl$_2$ (40 mL) and brine (40 mL). The aqueous layer was extracted with CH$_2$Cl$_2$ (2×25 mL), the phases separated and the combined organic extracts dried (Na$_2$SO$_4$), filtered and concentrated. The resultant crude oil (1.07 g) was used without further purification in the next step.

To a solution of the crude azide from above (0.57 g) in MeOH (10 mL) was added palladium on activated carbon (10%, 100 mg) and the mixture was hydrogenated (Parr hydrogenator, 45 psi) for 3 h. The reaction mixture was filtered through Celite and the cake was washed with methanol and CH$_2$Cl$_2$. The combined filtrates were evaporated under reduced pressure to afford the title compound as a clear oil (0.368 g, 63% over 2 steps). $^1$H NMR (CDCl$_3$) ☐1.27 (brs, 2H), 1.73-1.78 (m, 1H), 2.18-2.27 (m, 1H), 2.33-2.39 (m, 2H), 2.65 (dd, 1H, J=12, 9 Hz), 2.87 (dd, 1H, J=12, 3 Hz), 3.64-3.70 (m, 1H), 6.52 (br s, 1H).

4-{[(1H-Benzimidazol-2-ylmethyl)-(5,6,7,8-tetrahydro-quinolin-8-yl)-amino]-methyl}-benzaldehyde (192 mg, 0.48 mmol) was condensed with (S)-5-(aminomethyl)-2-pyrrolidinone (92 mg, 0.79 mmol) in dry MeOH (5 mL) for 2.5 h at room temperature and the resultant imine was reduced with sodium borohydride (48 mg, 1.27 mmol) for 1 h (see General Procedures A and B). Purification of the crude material by radial chromatography on silica gel gel (2 mm plate, CH$_2$Cl$_2$/MeOH/NH$_4$OH, 50:1:1 then 25:1: 1) afforded the free amine (227 mg, 95%) as a white foam.

Using General Procedure D: Conversion of the foam from above (146 mg, 0.30 mmol) to the hydrobromide salt followed by re-precipitation of the intermediate solid from methanol/ether gave AMD9703 (186 mg, 75%) as a white solid. $^1$H NMR (D$_2$O) ☐1.72-1.90 (m, 2H), 2.20-2.43 (m, 6H), 2.94 (d, 2H, J=6 Hz), 3.01-3.03 (br m, 2H), 3.71 (s , 2H), 3.79 (d, 1H, J=12.6 Hz), 3.87 (d, 1H, J=12.6 Hz), 3.94-4.00 (m, 1H), 4.45 (d, 1H, J=16.5 Hz), 4.64 (d, 1H, J=16.5 Hz), 4.75-4.79 (m, 1H, overlap with HOD), 7.04 (d, 2H, J=7.8 Hz), 7.23 (d, 2H, J=7.8 Hz), 7.49 (dd, 2H, J=6.3, 3 Hz), 7.58 (dd, 2H, J=6.3, 3 Hz), 7.92 (dd, 1H, J=7.5, 6.3 Hz), 8.39 (d, 1H, J=7.8 Hz), 8.76 (d, 1H, J=5.7 Hz); $^{13}$C NMR (D$_2$O) ☐ 18.31, 18.80, 22.35, 25.71, 27.48, 48.01, 48.69, 48.89, 49.51, 54.52, 60.97, 111.81, 123.99, 124.55, 127.97, 128.08, 128.34, 128.68, 135.96, 137.56, 138.87, 146.15, 148.63, 149.55, 179.87. ES-MS m/z 495 (M+H). Anal. Calcd. for C$_{30}$H$_{34}$N$_6$O.3.5HBr.1.3H$_2$O.0.5C$_4$H$_{10}$O: C, 45.85; H, 5.42; N, 10.02; Br, 33.36. Found: C, 45.70; H, 5.36; N, 9.96; Br, 33.59.

EXAMPLE: 121

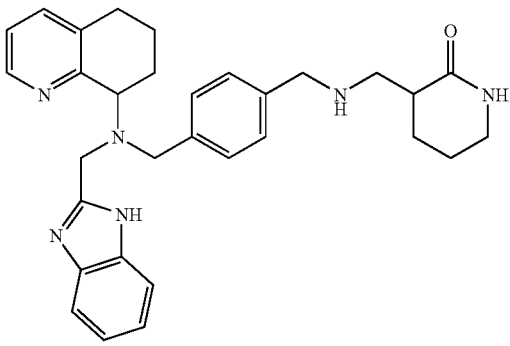

AMD9751: Preparation of 3-[(4-{[(1H-Benzimidazol-2-ylmethyl)-(5,6,7,8-tetrahydro-quinolin-8-yl)-amino]-methyl}-benzylamino)-methyl]-piperidin-2-one(hydrobromide salt)

Preparation of $HN_3$ solution in $CHCl_3$

To an ice-cooled solution of $NaN_3$ in $H_2O$ (10 mL) was added $CHCl_3$ (10 mL) followed by 1 N $H_2SO_4$ (5 mL) dropwise. The biphasic mixture was stirred vigorously at 0° C. for 30 min then transferred to a separatory funnel and the layers separated. The organic layer was dried ($Na_2SO_4$), filtered and used in the following reaction.

Preparation of 3-(aminomethyl)-2-piperidone:

To a suspension of 3-(hydroxymethyl)-2-piperidone (prepared as described by Altman, J.; Ben-Ishai, D. *Tetrahedron: Asymmetry* 1993, 4, 91-100) (0.438 g, 3.39 mmol) and triphenylphosphine (0.97 g, 3.70 mmol) in THF (10 mL) was added the $HN_3$ solution in $CHCl_3$ from above (5 mL, 5 mmol). The mixture was cooled to 0° C. and diethyl azodicarboxylate (0.65 mL, 4.1 mmol) added dropwise. The reaction was stirred at room temperature overnight then concentrated in vacuo and purified by column chromatography on silica gel ($CHCl_3$/MeOH, 96:4) to afford the desired azide (0.183 g, 35%) as a white solid.

To a solution of the azide from above (85 mg, 0.55 mmol) in MeOH (5 mL) was added palladium on activated carbon (10%, 28 mg) and the mixture was stirred under hydrogen (βatmosphere) for 2 d. The reaction mixture was filtered through Celite and the cake was washed with methanol and $CH_2Cl_2$. The combined filtrates were evaporated under reduced pressure to afford the title compound as a clear oil (68 mg, 96%).

4-{[(1H-Benzimidazol-2-ylmethyl)-(5,6,7,8-tetrahydro-quinolin-8-yl)-amino]-methyl}-benzaldehyde (147 mg, 0.37 mmol) was condensed with 3-(aminomethyl)-2-piperidone (68 mg, 0.53 mmol) in dry MeOH (5 mL) for 2 h at room temperature and the resultant imine was reduced with sodium borohydride (50 mg, 1.32 mmol) overnight (see General Procedures A and B). Purification of the crude material by radial chromatography on silica gel gel (2 mm plate, $CH_2Cl_2$/MeOH/$NH_4OH$, 50:1:1) afforded the free amine (115 mg, 61%) as a white foam.

Using General Procedure D: Conversion of the foam from above (95 mg, 0.19 mmol) to the hydrobromide salt followed by re-precipitation of the intermediate solid from methanol/ether gave AMD9751 (134 mg, 83%) as a yellow solid. $^1$H NMR ($D_2O$) □1.38-1.45 (m, 1H), 1.62-1.79 (m, 1H), 1.84-1.90 (m, 3H), 2.24-2.30 (m, 2H), 2.42-2.46 (m, 1H), 2.57-2.62 (m, 1H), 2.86-2.89 (m, 1H), 2.95-3.03 (m, 3H), 3.19-3.25 (m, 2H), 3.65-3.76 (m, 2H), 3.78 (d, 1H, J=12.9 Hz), 3.86 (d, 1H, J=12.9 Hz), 4.46 (d, 1H, J=16.5 Hz), 4.65 (d, 1H, J=16.5 Hz), 4.74-4.79 (m, 1H, overlap with HOD), 7.03 (d, 2H, J=7.8 Hz), 7.24 (d, 2H, J=7.8 Hz), 7.49 (dd, 2H, J=6, 3.3 Hz), 7.58 (dd, 2H, J=6, 3.3 Hz), 7.93 (dd, 1H, J=7.2, 6.6 Hz), 8.40 (d, 1H, J=7.8 Hz), 8.77 (d, 1H, J=5.7 Hz); $^{13}$C NMR ($D_2O$) □ 20.49, 20.93, 20.98, 24.32, 27.89, 36.68, 41.75, 48.22, 50.07, 50.27, 56.68, 63.20, 113.99, 126.16, 126.73 (2 carbons), 129.92 (2 carbons), 130.49, 130.90 (2 carbons), 137.99, 139.73 (2 carbons), 141.02, 148.32 (2 carbons), 150.80, 151.78, 174.97. ES-MS m/z 509 (M+H). Anal. Calcd. for $C_{31}H_{36}N_6O$.3.5HBr.91.$H_2O$0.5$C_4H_{10}O$: C, 45.92; H, 5.64; N, 9.74; Br, 32.40. Found: C, 45.81; H, 5.50; N, 9.69; Br, 32.54.

EXAMPLE: 122

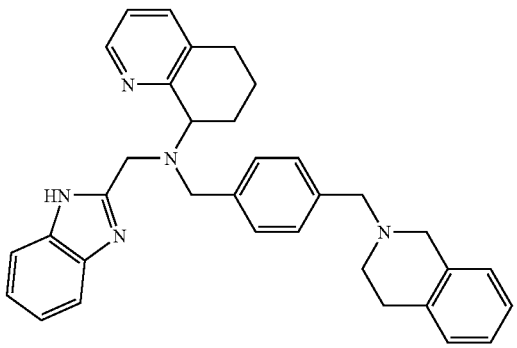

AMD9678: Preparation of (1H-benzimidazol-2-ylmethyl)-[4-(3,4-dihydro-1H-isoquinolin-2-ylmethyl)-benzyl]-(5,6,7,8-tetrahydro-quinolin-8-yl)-amine (hydrobromide salt)

Using General Procedure B: To a stirred solution of 1,2,3,4-tetrahydroisoquinoline (49 mg, 0.37 mmol), 4-{[(1H-benzimidazol-2-ylmethyl)-(5,6,7,8-tetrahydro-quinolin-8-yl)-amino]-methyl}-benzaldehyde (140 mg, 0.34 mmol), and AcOH 0.020 mL, 0.35 mmol) in THF (3.5 mL) was added $NaBH(OAc)_3$ (94 mg, 0.44 mmol) and the mixture was stirred at room temperature for 2 h. Purification of the crude material by column chromatography on silica gel (500:5:1 $CH_2Cl_2$/MeOH/$NH_4OH$) afforded a colourless foam (137 mg).

Using General Procedure D: Conversion of the foam from above (131 mg, 0.255 mmol) to the hydrobromide salt followed by re-precipitation of the intermediate solid from methanol/ether gave AMD9678 (171 mg, 64%) as a colourless solid. $^1$H NMR ($D_2O$) □ 1.90 (m, 1H), 2.18-2.54 (m, 4H), 3.03 (m, 4H), 3.42-3.66 (m, 2H), 3.83 (m, 2H), 4.01 (m, 2H), 4.15 (dd, 1H, J=15, 6 Hz), 4.49 (dd, 1H, J=17, 3.6 Hz), 4.67 (d, 1H, J=17 Hz), 4.78 (m, 1H), 7.11 (m, 5H), 7.30 (m, 5H), 7.48 (m, 2H), 7.93 (m, 1H), 8.40 (d, 1H, J=8.1 Hz), 8.79 (m, 1H); $^{13}$C NMR ($D_2O$) □ 20.45, 21.02, 25.17, 27.88, 49.07, 50.48, 52.17, 56.79, 58.15, 63.49, 113.64, 126.16, 126.64, 127.24, 127.43, 127.54, 127.77, 128.91, 129.22, 130.27, 130.88, 131.85, 138.59, 139.74, 141.09, 148.34, 150.73, 151.94. ES-MS m/z 514 (M+H). Anal. Calcd. for $C_{34}H_{35}N_5$.3.1HBr.2.8$H_2O$: C, 50.11; H, 5.40; N, 8.59; Br, 30.39. Found: C, 49.94; H, 5.30; N, 8.44; Br, 30.56.

EXAMPLE: 123

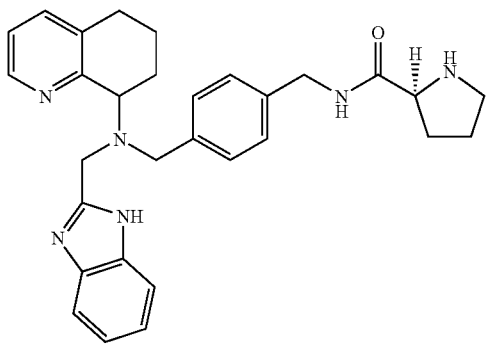

AMD9684: Preparation of (S)-Pyrrolidine-2-carboxylic acid 4-{[(1H-benzimidazol-2-ylmethyl)-(5,6,7,8-tetrahydro-quinolin-8-yl)-amino]-methyl}-benzylamide(hydrobromide salt)

To a stirred solution of N'-(1H-benzimidazol-2-ylmethyl)-N'-(5,6,7,8-tetrahydro-8-quinolinyl)-1,4-benzenedimethanamine (148 mg, 0.37 mmol) in dry $CH_2Cl_2$ (5 mL) was added N-(tert-butoxycarbonyl)-L-proline (88 mg, 0.41 mmol), N,N-diisopropylethylamine (0.13 mL, 0.75 mmol), 1-hydroxybenzotriazole hydrate (68mg, 0.50 mmol) and 1-(3-dimethylaminopropyl)-3-ethyl carbodiimide HCl (EDC) (99 mg, 0.52 mmol) and the mixture stirred at room temperature overnight. The reaction mixture was diluted with $CH_2Cl_2$ (25 mL) and saturated aqueous sodium bicarbonate (30 mL) and the aqueous layer was separated and extracted with $CH_2Cl_2$ (2×15 mL). The combined organic phases were dried ($Na_2SO_4$), filtered and evaporated in vacuo to give the crude product as a white foam. Purification by column chromatography on silica gel ($CH_2Cl_2$/MeOH, 96:4) gave the desired amide (214 mg, 85%) as a white foam.

Using General Procedure D: Conversion of the foam from above (185 mg, 0.31 mmol) to the hydrobromide salt with simultaneous removal of the N-tert-butoxycarbonyl protecting group followed by re-precipitation of the intermediate solid from methanol/ether gave AMD9684 (208 mg, 83%) as a white solid. $^1$H NMR ($D_2O$) $\delta$ 1.86-2.03 (m, 4H), 2.18-2.24 (m, 2H), 2.36-2.42 (m, 2H), 3.00-3.02 (br m, 2H), 3.33-3.38 (m, 2H), 3.70-3.81 (m, 3H), 3.86-3.93 (m, 1H), 4.28 (t, 1H, J=7.2 Hz), 4.41 (d, 1H, J=16.5 Hz), 4.59 (d, 1H, J=16.5 Hz), 4.70-4.79 (m, 1H, overlap with HOD), 6.81 (d, 2H, J=7.8 Hz), 7.10 (d, 2H, J=7.8 Hz), 7.48 (dd, 2H, J=6.6, 3.3 Hz), 7.56 (dd, 2H, J=6.6, 3.3 Hz), 7.89 (dd, 1H, J=7.5, 6.3 Hz), 8.36 (d, 1H, J=8.1 Hz), 8.72 (d, 1H, J=6 Hz); $^{13}$C NMR ($D_2O$) $\delta$ 20.46, 20.85, 24.19, 27.83, 30.23, 42.75, 46.91, 50.18, 56.56, 60.10, 63.05, 113.83, 126.02, 126.61, 127.24, 130.38, 130.52, 135.63, 137.64, 139.59, 140.88, 148.17, 150.92, 151.80, 169.57. ES-MS m/z 495 (M+H). Anal. Calcd. for $C_{30}H_{34}N_6O\cdot3.1HBr\cdot1.9H_2O\cdot0.3C_4H_{10}O$: C, 46.73; H, 5.52; N, 10.48; Br, 30.89. Found: C, 46.79; H, 5.42; N, 10.42; Br, 30.73.

EXAMPLE: 124

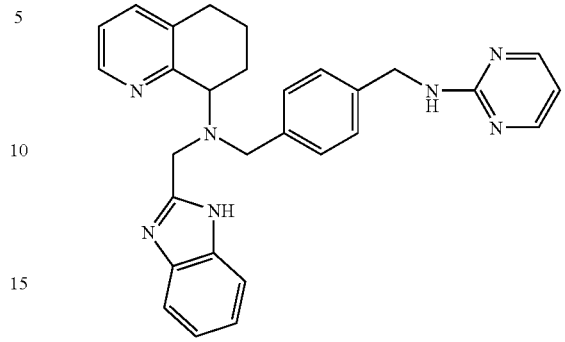

AMD 9705: Preparation of (1H-Benzimidazol-2-ylmethyl)-[4-(pyrimidin-2-ylaminomethyl)-benzyl]-(5,6,7,8-tetrahydro-quinolin-8-yl)-amine(hydrobromide salt)

Preparation of of 4-(pyrimidin-2-ylaminomethyl)-benzaldehyde:

Using General Procedure B: Reaction of 4-hydroxymethylbenzaldehyde (4.05 g, 29.8 mmol) and 2-aminopyrimidine (1.43 g, 15.0 mmol) with $NaBH(OAc)_3$ (9.11 g, 43.0 mmol) in $CH_2Cl_2$ (75 mL) and glacial acetic acid (3.5 mL) for 18 hours followed by purification of the crude material by column chromatography on silica gel (25:1 $CH_2Cl_2$—$CH_3OH$) gave 1.50 g of a white solid. The solid (1.50 g) from above was dissolved in $CH_2Cl_2$ (75 mL), treated with activated $MnO_2$ (6.10 g, 70.1 mmol) and stirred at room temperature overnight. The mixture was filtered through celite and the cake was washed with $CH_2Cl_2$. The solvent was removed from the filtrate under reduced pressure and the crude material was purified by column chromatography on silica gel (50:1 $CH_2Cl_2$—$CH_3OH$) to afford the title compound (0.57 g, 18% from 2-aminopyrimidine) as a white solid. $^1$H NMR ($CDCl_3$) $\delta$ 4.75 (d, 2H, J=6.3 Hz), 5.78 (br s, 1H), 6.58 (t, 1H, J=4.8 Hz), 7.51 (d, 2H, J=7.8 Hz), 7.85 (d, 2H, J=7.8 Hz), 8.28 (d, 2H, J=4.8 Hz), 9.99 (s, 1H);

Using General Procedure B: Reaction of 4-(pyrimidin-2-ylaminomethyl)-benzaldehyde (0.142 g, 0.66 mmol) and (1-tert-butoxycarbonyl-1H-benzimidazol-2-ylmethyl)-(5,6,7,8-tetrahydro-quinolin-8-yl)-amine (0.171 g, 0.45 mmol) with $NaBH(OAc)_3$ (0.230 g, 1.08 mmol) in $CH_2Cl_2$ (5 mL) for 44 hours followed by purification of the crude material by radial chromatography on silica gel (2 mm plate, 10:1 $CH_2Cl_2$—$CH_3OH$, followed by 25:1:1 $CH_2Cl_2$—$CH_3OH$—$NH_4OH$) provided the desired tertiary amine (0.118 g, 45%) as a white solid.

Using General Procedure D: Conversion of the white solid (118 mg) to the hydrobromide salt with simultaneous removal of the BOC-protecting group, followed by re-precipitation of the intermediate solid from methanol/ether, gave AMD9705 (125 mg) as a white solid. $^1$H NMR ($D_2O$) $\delta$ 1.82-1.97 (m, 1H), 2.20-2.32 (m, 2H), 2.39-2.48 (m, 1H), 3.04 (br s, 2H), 3.76 (d, 1H, J=12.3 Hz), 3.83 (d, 1H, J=12.3 Hz), 4.17 (s, 2H), 4.44 (d, 1H, J=16.5 Hz), 4.62 (d, 1H, J=16.5 Hz), 4.73-4.79 (m, 1., overlaps with HOD), 6.96 (d, 2H, J=7.8 Hz), 7.01 (t, 2H, J=5.4 Hz), 7.14 (d, 2H, J=7.8 Hz), 7.41 (dd, 2H, J=3.0, 6.0 Hz), 7.54 (dd, 2H, J=3.0, 6.0 Hz), 7.92 (dd, 1H, J=7.5, 6.0 Hz), 8.39 (d, 1H, J=7.8 Hz), 8.50 (d, 1H, J=5.1 Hz), 8.74 (d, 1H, J=5.4 Hz); $^{13}$C NMR ($D_2O$) $\delta$ 20.47, 20.90, 44.13, 50.24, 56.65, 63.21, 110.74, 113.74, 126.05, 126.48, 127.60, 130.44, 135.87, 136.91, 139.60, 140.95, 148.22, 150.93, 151.91; ES-MS m/z 476 (M+H). Anal. Calcd. for C$_{29}$H$_{29}$N$_7$.3.0HBr.1.8 H$_2$O: C, 46.40; H, 4.78; N, 13.06; Br, 31.93. Found: C, 46.47; H, 4.79; N, 12.83; Br, 31.99.

EXAMPLE: 125

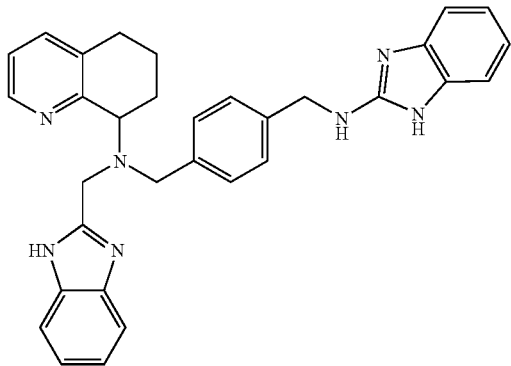

AMD9693: Preparation of {4-[(1H-Benzimidazol-2-ylamino)-methyl]-benzyl}-(1H-benzimidazol-2-ylmethyl)-(5,6,7,8-tetrahydro-quinolin-8-yl)-amine Using General Procedure A: To a stirred solution of 4-{[(1H-benzimidazol-2-ylmethyl)-(5,6,7,8-tetrahydro-quinolin-8-yl)-amino]-methyl}-benzaldehyde (140 mg, 0.34 mmol) and 2-aminobenzimidazole (45 mg, 0.0.34 mmol) in MeOH (4 mL) was added NaBH$_3$CN (64 mg, 1.1 mmol) and the mixture was stirred at room temperature for 20 hours. Purification of the crude yellow foam by column chromatography on silica gel (200: 1:1—EtOAc:MeOH:NH$_4$OH) followed by radial chromatography on silica gel (100:1:1—CH$_2$Cl$_2$:MeOH:NH$_4$OH) afforded AMD9693 (26 mg, 15%) as a white solid. $^1$H NMR (CDCl$_3$) δ 1.57-1.74 (m, 1H), 1.87-2.05 (m, 2H), 2.10-2.20 (m, 1H), 2.63-2.75 (m, 1H), 2.75-2.90 (m, 1H), 3.54 (s, 2H), 3.86 (d, 1H, J=16.8 Hz), 4.03-4.16 (m, 2H), 4.24-4.35 (m, 2H), 5.44 (br s, 1H), 6.88-6.91 (m, 4H), 7.10-7.19 (m, 7H), 7.42 (d, 1H, J=7.5 Hz), 7.54 (br s, 2H), 8.65 (d, 1H, J=4.2 Hz); $^{13}$C NMR (CDCl$_3$) δ 21.16, 24.26, 29.10, 46.66, 48.40, 53.29, 60.62, 111.39 (br), 118.11 (br), 120.13, 121.81, 122.37, 127.22, 128.57, 133.86, 134.79, 137.41, 138.17, 143.78, 146.67, 155.56, 156.41, 157.20. ES-MS m/z 514.4 (M+H). Anal. Calcd. for C$_{32}$H$_{31}$N$_7$.0.8CH$_2$Cl$_2$.0.4C$_4$H$_8$O$_2$: C, 66.98; H, 5.85; N, 15.90. Found: C, 67.14; H, 5.66; N, 15.87.

EXAMPLE: 126

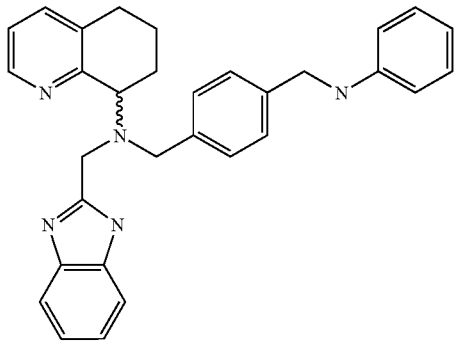

AMD9704: Preparation of (1H-benzoimidazol-2-ylmethyl)-(4-phenylaminomethyl-benzyl)-(5,6,7,8-tetrahydro-quinolin-8-yl)-amine Following the General Procedure A: 4-{[(1H-benzoimidazol-2-ylmethyl)-(5,6,7,8-tetrahydro-quinolin-8-yl)-amino]-methyl}-benzaldehyde (200 mg, 0.50 mmol) and aniline (46 μL, 0.50 mmol) were converted into the corresponding reductive amination product using the following quantities of reagents and solvents: sodium cyanoborohydride (47 mg, 0.75 mmol), MeOH (3 mL). The reaction time in this case was 18 h. The residue was taken up in MeOH (3 mL) and sodium borohydride (38 mg, 1.0 mmol) was added to reduce any unreacted starting material. After stirring 30 min, saturated aqueous sodium bicarbonate (5 mL) was added, then the phases were separated and the aqueous layer was extracted with CH$_2$Cl$_2$ (3×10 mL). The combined organic extracts were dried (MgSO$_4$), and concentrated in vacuo. Purification of the crude material thus obtained by radial chromatography (silica gel, 1 mm plate, 50:2:1 CH$_2$Cl$_2$—MeOH—NH$_4$OH) afforded 49 mg (22%) of AMD9704 as a white foam. $^1$H NMR (CDCl$_3$) □ 1.68-1.72 (m, 1H), 2.02-2.09 (m, 2H), 2.25-2.27 (m, 1H), 2.71-2.75 (m, 1H), 2.83-2.87 (m, 1H), 3.74 (s, 2H), 3.91-3.93 (m, 1H), 3.97 (d, 1H, J=16 Hz), 4.10 (dd, 1H, J=9, 6 Hz), 4.16-4.23 (in, 3H), 6.59 (dd, 2H, J=9, 1 Hz), 6.71 (t, 1H, J=7 Hz), 7.12-7.24 (m, 7H), 7.38 (d, 2H, J=8 Hz), 7.43 (dd, 1H, J=8, 1 Hz), 7.51-7.53 (in, 1H), 7.64-7.67 (in, 1H), 8.71 (dd, 1H, J=5, 1 Hz); $^{13}$C NMR (CDCl$_3$) □ 21.3, 23.4, 29.2, 47.9, 48.5, 53.6, 60.3, 110.9, 112.7, 117.3, 118.7, 121.3, 121.6, 122.2, 127.4, 128.8, 129.2, 134.6, 137.1, 138.3, 146.9, 148.1, 156.3, 157.4. ES-MS m/z 474 (M+H). Anal. Calcd. for C$_{31}$H$_{31}$N$_5$.0.9H$_2$O: C, 76.01; H, 6.75; N, 14.30. Found: C, 76.04; H, 6.57; N, 14.18.

EXAMPLE: 127

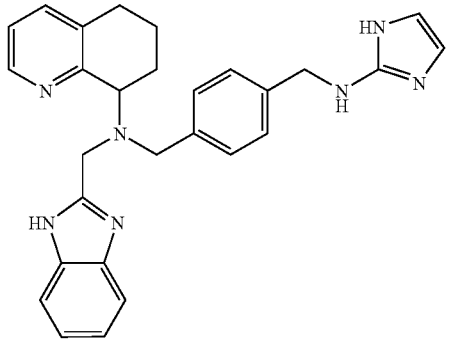

AMD9741: Preparation of (1H-benzimidazol-2-ylmethyl)-{4-[(1H-imidazol-2-ylamino)-methyl]-benzyl}-(5,6,7,8-tetrahydro-quinolin-8-yl)-amine To a suspension of of 2-aminoimidazole sulphate (150 mg, 0.57 mmol) in anhydrous MeOH (10 mL) was added excess K$_2$CO$_3$. After 18 hours the reaction mixture was diluted with CH$_2$Cl$_2$ (40 mL), filtered through Celite and the cake was washed with CH$_2$Cl$_2$. The filtrate was concentrated under reduced pressure to afford a brown syrup (150 mg) which was used without further purification in the next reaction.

Using General Procedure A: To a stirred solution of 4-{[(1H-benzimidazol-2-ylmethyl)-(5,6,7,8-tetrahydro-quinolin-8-yl)-amino]-methyl}-benzaldehyde (200 mg, 0.49 mmol) and the amine (41 mg, 0.49 mmol) from above in MeOH (5 mL) was added NaBH$_3$CN (94.3 mg, 1.5 mmol) and the mixture was stirred at room temperature for 5 days. Purification of the crude yellow foam by column chromatography on silica gel (100:1:1—CH$_2$Cl$_2$:MeOH:NH$_4$OH) afforded AMD9741 (26 mg, 15%) as a brown solid (22mg, 10%). $^1$H NMR (CDCl$_3$) δ 1.61-1.76 (m, 1H), 1.92-2.09 (m, 2H), 2.17-2.27 (m, 1H), 2.68-2.76 (m, 1H), 2.80-2.90 (m, 1H), 3.64 (s, 2H), 3.89 (d, 1H, J=16.5 Hz), 4.05-4.14 (m, 2H), 4.22 (s, 2H), 4.39 (br s, 1H), 6.54 (s, 2H), 7.06 (d, 2H, J=7.8 Hz), 7.15-7.20 (m, 3H), 7.25 (d, 2H, J=6.9 Hz), 7.43 (d, 1H, J=7.8 Hz), 7.54 (br s, 2H), 8.67 (d, 1H, J=4.5 Hz); $^{13}$C NMR (CDCl$_3$) δ 19.22, 21.83, 27.12, 45.73, 46.41, 51.49, 58.49, 111.83, 112.90, 115.59, 119.64, 120.29, 125.33, 126.71, 132.76, 135.33, 135.86, 136.22, 144.75, 148.75, 154.19, 155.23. ES-MS m/z 464.3 (M+H). Anal. Calcd. for C$_{28}$H$_{29}$N$_7$.1.4CH$_2$Cl$_2$: C, 60.62; H, 5.50; N, 16.83. Found: C, 60.53; H, 5.48; N, 16.94.

EXAMPLE: 128

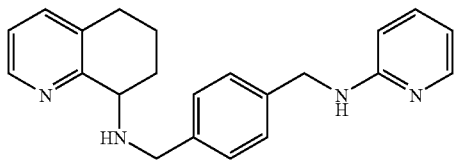

AMD9458: Preparation of [4-(Pyridin-2-ylaminomethyl)-benzyl]-(5,6,7,8-tetrahydro-quinolin-8-yl)-amine(hydrobromide salt)

Preparation of [4-(Pyridin-2-ylaminomethyl)-phenyl]-methanol:

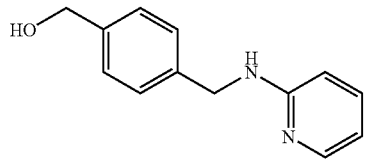

Using general procedure B: Reaction of 4-hydroxymethyl-benzaldehyde (1.01 g, 7.42 mmol), 2-aminopyridine (697 mg, 7.42 mmol), acetic acid (0.5 mL) and sodium triacetoxyborohydride (3.2 g, 14.8 mmol) in THF (20 mL) at room temperature under N$_2$ for 40 min., then one hour at 50° C., followed by purification of crude material using chromatography on silica gel (2:2:96 CH$_3$OH—NH$_3$ H$_2$O—CH$_2$Cl$_2$), afforded the title compound (1.17 g, 74%) as white foam.

Preparation of 4-(Pyridin-2-ylaminomethyl)-benzaldehyde:

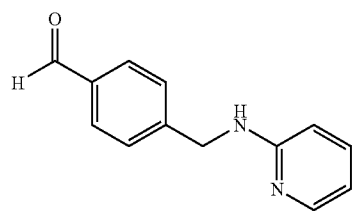

To a solution of oxalyl chloride (0.9 ml, 10.32 mmol) in CH$_2$Cl$_2$ (15 ml) at −78° C. was added a solution of DMSO (1.5 ml, 21.11 mmol) in CH$_2$Cl$_2$ (10 ml) and the mixture allowed to stir for 20 min. at −78° C., after which [4-(Pyridin-2-ylaminomethyl)-phenyl]-methanol (1.1 g, 5.13 mmol) in CH$_2$Cl$_2$ (10 ml) was added dropwise. Stirring was continued for 2 hours and then Et$_3$N (2.9 ml, 21.30 mmol) was added dropwise. The cooling bath was removed, stirring was continued for 3 h, and the mixture was diluted with 300 mL ethyl acetate, washed with sat. NaHCO$_3$, brine and dried over Na$_2$SO$_4$. Evaporation of the solvent and purification of the residue by flash chromatography on silica gel, using 30% ethyl acetate in CH$_2$Cl$_2$, gave the title compound (335 mg, 31%) as a pure white solid.

Using general procedure B: Reaction of 4-(Pyridin-2-ylaminomethyl)-benzaldehyde (335 mg, 1.58 mmol), 5,6,7,8-Tetrahydro-quinolin-8-ylamine (235 mg, 1.58 mmol), acetic acid (0.2 mL) and sodium triacetoxyborohydride (1.0 g, 4.74 mmol) in THF (10 mL) at room temperature under N$_2$ for 40 min., followed by purification of crude material using chromatography on silica gel (1:1:98 CH$_3$OH—NH$_3$H$_2$O—CH$_2$Cl$_2$), afforded the title compound (485 mg, 86%) as a white foam.

Using General Procedure D: Conversion of the foam from above (30 mg, 0.084 mmol) to the hydrobromide salt using an acetic acid/HBr solution, followed by re-precipitation of the salt from diethyl ether gave AMD9458 as a white solid. $^1$H NMR (D$_2$O) ⎕i⎕⎕-2.07 (m, 2H), 2.30-2.36 (m, 2H), 2.88-3.07 (m, 2H), 4.40 (d, 1H, J=12.6 Hz), 4.50 (d, 1H, J=13.2 Hz), 4.64 (s, 2H), 6.88 (dd, 1H, J=6.8, 6.8 Hz), 7.00 (d, 1H, J=9 Hz), 7.45 (d, 2H, J=8.4 Hz), 7.53 (d, 2H, J=8.4 Hz), 7.68 (dd, 1H, J=5.7, 7.5 Hz), 7.77 (d, 1H, J=6.6 Hz), 7.87 (ddd, 1H, J=1.5, 5.7, 9 Hz), 8.09 (d, 1H, J=7.8 Hz), 8.57 (d, 1H, J=4.5 Hz); $^{13}$C NMR (D$_2$O) ⎕ 17.71, 24.43, 27.12, 45.23, 49.36, 55.32, 113.36, 126.37, 128.40, 130.43, 130.95, 135.53, 137.89, 144.20, 144.52, 145.94, 152.99; ES-MS m/z 345.2 (M+H); Anal. Calcd. for (C$_{22}$H$_{24}$N$_4$).3.3(HBr).0.6(H$_2$O).0.4 (C$_4$H$_{10}$O): C, 43.48; H, 5.02; N, 8.59; Br, 40.45. Found: C, 43.29; H, 5.32; N, 8.69; Br, 40.82.

EXAMPLE:129

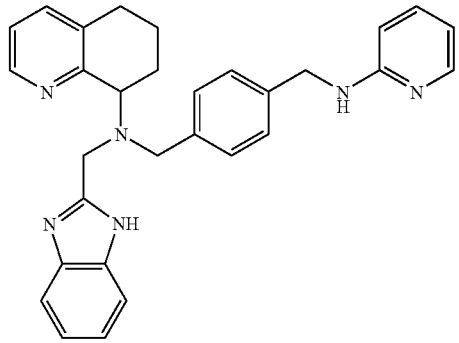

AMD9496: Preparation of Benzimidazol-2-ylmethyl)-[4-(pyridin-2-ylaminomethyl)-benzyl]-(5,6,7,8-tetrahydro-quinolin-8-yl)-amine(hydrobromide salt)

Using general procedure B: Reaction of 1-(2-Trimethylsilanyl-ethoxymethyl)-1H-benzimidazole-2-carbaldehyde (243 mg, 0.88 mmol), [4-(Pyridin-2-ylaminomethyl)-benzyl]-(5,6,7,8-tetrahydro-quinolin-8-yl)-amine (315 mg, 0.87 mmol), acetic acid (0.2 mL) and sodium triacetoxyborohydride (553 mg, 2.61 mmol) in THF (9 mL) at room temperature under N$_2$ for 40 min., followed by purification of the crude material by chromatography on silica gel (1:1:98 CH₃OH—NH₃H₂O—CH₂Cl₂), afforded the title compound (315 mg, 60%) as a white foam.

Using general procedure F: Reaction of [4-(Pyridin-2-ylaminomethyl)-benzyl]-(5,6,7,8-tetrahydro-quinolin-8-yl)-[1-(2-trimethylsilanyl-ethoxymethyl)-1H-benzimidazol-2-ylmethyl]-amine (315 mg, 0.52 mmol), 6 N HCl solution (5 ml) at 50° C. for 3 h, followed by purification of crude material using chromatography on silica gel (1:1:98 CH₃OH—NH₃H₂O—CH₂Cl₂), afforded the title compound (215 mg, 87%) as a white foam.

Using General Procedure D: Conversion of the foam from above (50 mg, 0.11 mmol) to the hydrobromide salt using an acetic acid/HBr solution, followed by re-precipitation of the salt from diethyl ether gave AMD9496. ¹H NMR (D₂O) δ 1.77-1.90 (m, 1H), 2.14-2.26 (m, 2H), 2.35-2.40 (m, 1H), 2.96-2.98 (m, 2H), 3.67 (d, 1H, J=12.6 Hz), 3.75 (d, 1H, J=12.6 Hz), 4.02 (s, 2H), 4.38 (d, 1H, J=16.5 Hz), 4.56 (d, 1H, J=16.5 Hz), 4.68-4.74 (m, 1H), 6.76 (d, 1H, J=9.3 Hz), 6.84 (dd, 1H, J=6.75, 6.75 Hz), 6.91 (d, 2H, J=7.8 Hz), 7.10 (d, 2H, J=7.8 Hz), 7.32-7.37 (m, 2H), 7.47-7.51 (m, 2H), 7.69 (d, 1H, J=6.3 Hz), 7.79-7.87(m, 2H), 8.31 (d, 1H, J=7.5 Hz), 8.70 (d, 1H, J=5.4 Hz); ¹³CNMR (D₂O) δ 20.49, 20.92, 27.86, 44.65, 50.29, 56.57, 63.07, 112.95, 113.28, 113.80, 126.00, 126.41, 127.43, 130.59, 135.54, 135.97, 136.06, 139.71, 140.83, 144.59, 148.08, 150.94, 151.88, 152.59; ES-MS m/z 475.4 (M+H); Anal. Calcd. for (C₃₀H₃₀N₆).3.0(HBr).1.8(H₂O): C, 48.08; H, 4.92; N, 11.21; Br, 31.97. Found: C, 48.01; H, 4.91; N, 11.06; Br, 32.07.

EXAMPLE: 130

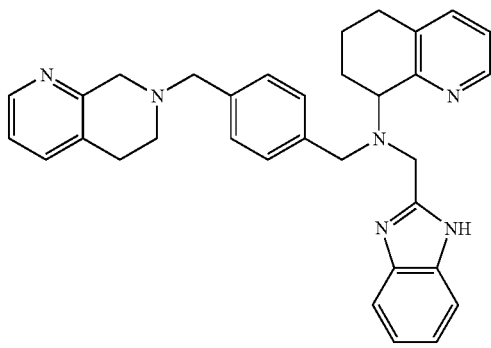

AMD9670: Preparation of (1H-Benzimidazol-2-ylmethyl)-[4-(5,8-dihydro-6H-[1,7]naphthylpyridine-7-ylmethyl)-benzyl]-(5,6,7,8-tetrahydroquinolin-8-yl)-amine(hydrobromide salt)

Preparation of N-benzyl-2-[2-(hydroxymethyl)-pyridin-3-yl]-acetamide:

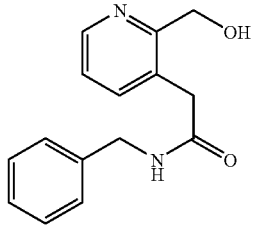

To a stirred solution of ethyl-2-[2-(acetoxymethyl)-pyridin-3-yl]-acetate (prepared from 2-methylnicotinic acid as described by Y. Sato et al., Chem. Pharm. Bull.; EN. 1960, 8, 427) (2.37 g, 10 mmol) in EtOH (50 mL) was added KOH (3 g, 53 mmol) and the mixture stirred at reflux overnight. The mixture was cooled, concentrated under reduced pressure and diluted with brine (5 mL) and CH₂Cl₂ (25 mL). The aqueous phase was extracted with CH₂Cl₂ (2×20 mL), the phases separated and the combined organic extracts dried (Na₂SO₄), filtered and concentrated to afford ethyl-2-[2-(hydroxymethyl)-pyridin-3-yl]-acetate (1.03 g, 52%).

To the product from above (97mg, 0.5 mmol) was added benzylamine (107 mg, 1.0 mmol) and the resultant solution was heated at 150° C. for 8 h. The reaction was cooled, concentrated in vacuo and purified by chromatography on silica gel (CH₂Cl₂/MeOH, 10:1) to afford the title compound (105 mg, 88%). ¹H NMR (CDCl₃) δ 3.55 (s, 2H), 4.41 (d, 1H, J=5.7 Hz), 4.59 (br s, 1H (OH)), 4.75 (s, 2H), 6.04 (br s, 1H (NH)), 7.28 (m, 6H), 7.61 (d, 1H, J=5.8 Hz), 8.47 (d, 1H, J=4.9 Hz).

Preparation of 5,6,7,8-tetrahydro-[1,7]-naphthylpyridine:

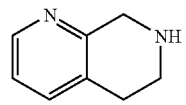

To a solution of N-benzyl-2-[2-(hydroxymethyl)-pyridin-3-yl]-acetamide (357 mg, 1.5 mmol) in THF (2 mL) was added borane in THF (5 mL of a 1.0 M solution, 5 mmol) and the mixture heated at 50° C. for 3 h. The reaction was cooled, quenched with MeOH (5 mL) and heated at 50° C. for 1 h. The resultant mixture was cooled, concentrated under reduced pressure, diluted with 3 N HCl (5 mL) and heated at 80° C. for 6 h. After cooling, an aqueous 15% NaOH solution was added until a basic pH (pH=13) was obtained and the mixture was extracted with CH₂Cl₂ (3×10 mL). The phases were separated and the combined organic fractions were dried (Na₂SO₄), concentrated under reduced pressure and purified by column chromatography on silica gel (CH₂Cl₂/MeOH/NH₄OH, 100:10:1) to afford benzyl-2-[2-(hydroxymethyl)-pyridin-3-yl]-ethylamine (86 mg, 41%) as a yellow oil. ¹H NMR (CDCl₃) δ 2.75 (t, 2H, J=6.8 Hz), 2.88 (t, 2H, J=6.8 Hz), 4.75 (s, 2H), 7.18-7.34 (m, 6H), 7.50 (d, 1H, J=7.8 Hz), 8.43 (d, 1H, J=4.9 Hz). ES-MS m/z 243 (M+H).

To a stirred solution of triphenylphosphine (150 mg, 0.62 mmol) in CH₂Cl₂ (10 mL) 0° C. was added bromine (0.075 mL, 1.5 mmol) followed by a solution of benzyl-2-[2-(hydroxymethyl)-pyridin-3-yl]-ethylamine (150 mg, 0.62 mmol) in CH₂Cl₂ (5 mL) and the reaction stirred overnight at room temperature. The mixture was then concentrated under reduced pressure and purified by column chromatography on silica gel (CH₂Cl₂/MeOH, 20:1) to afford the desired benzyl-protected product (106 mg, 76%) as a white powder. ¹H NMR (CDCl₃) δ 3.14 (m, 4H), 4.09 (s, 2H), 4.15 (s, 2H), 7.13 (t, 1H, J=6.6 Hz), 7.19 (m, 3H), 7.36 (d, 1H, J=6.6 Hz), 7.46 (m, 2H), 8.35 (d, 1H, J=5.2 Hz). ES-MS m/z 225 (M+H).

To a solution of the solid from above (106 mg, 0.473 mmol) in MeOH (20 mL) and AcOH (5 mL) in a Parr bottle was added 10% palladium on carbon (106 mg) and the mixture hydrogenated at 50 psi hydrogen in a Parr hydrogenator for 16 h. The product mixture was filtered through celite and the solvent from the eluent removed in vacuo. The resultant residue was purified by column chromatography on silica gel (CH₂Cl₂/MeOH, 10:1) to afford the title compound (54 mg, 85%), 5,6,7,8-tetrahydro-[1,7]-naphthylpyridine, as a yellow crystalline solid. ¹H NMR (CDCl₃) δ 3.14 (t, 2H, J=6.8 Hz), 3.40 (t, 2H, J=6.8 Hz), 4.35 (s, 2H), 7.34 (dd, 1H, J=8.1, 5.2 Hz), 7.63 (d, 1H, J=8.1 Hz), 8.41 (d, 1H, J=5.2 Hz).

Using General Procedure A: To a solution of 5,6,7,8-tetrahydro-[1,7]-naphthylpyridine (40 mg, 0.3 mmol) and 4-{[(1H-Benzimidazol-2-ylmethyl)-(5,6,7,8-tetrahydro-quinolin-8-yl)-amino]-methyl}-benzaldehyde (70 mg, 0.141 mmol) in MeOH (8 mL) was added NaBH$_3$CN (50 mg, 0.8 mmol) and the mixture stirred at room temperature for 16 h. Purification by column chromatography on silica gel (CH$_2$Cl$_2$/MeOH, 10:1) afforded the alkylated product (48 mg, 55%), (1H-N-t-butoxycarbonyl-benzimidazol-2-ylmethyl)-[4-(5,8-dihydro-6H-[1,7]naphthylpyridine-7-ylmethyl)-benzyl]-(5,6,7,8-tetrahydroquinolin-8-yl)-amine. $^1$H NMR (CDCl$_3$) □1.44 (s, 9H), 1.88 (m, 1H), 2.01 (m, 4H), 2.51 (t, 2H, J=6.8 Hz), 2.77 (m, 2H), 2.79 (t, 2H, J=6.8 Hz), 3.49 (m, 2H), 3.62 (m, 3H), 4.33 (t, 1H, J=5.8 Hz), 4.63 (s, 2H), 6.98 (m, 2H), 7.14-7.22 (m, 6H), 7.31 (m, 2H), 7.55 (d, 1H, J=8.1 Hz), 7.64 (d, 1H, J=5.8 Hz), 8.36 (d, 1H, J=4.8 Hz), 8.44 (d, 1H, J=5.1 Hz).

Using General Procedure D: Conversion of the material from above (34 mg, 0.055 mmol) to the hydrobromide salt with simultaneous removal of the BOC-protecting group, followed by re-precipitation of the intermediate solid from methanol/ether, gave AMD9670 (36 mg) as a white solid. $^1$H NMR (D$_2$O) □ 1.88 (m, 1H), 2.21 (m, 2H), 2.43 (m, 1H), 3.01 (m, 2H), 3.13 (br s, 4H), 3.85 (dd, 2H, J=12.6, 12.3 Hz), 4.09 (s, 2H), 4.17 (s, 2H), 4.48 (d, 1H, J=17.4 Hz), 4.66 (d, 1H, J=17.4 Hz), 4.86 (m, 1H), 7.14 (d, 2H, J=8.1 Hz), 7.21 (dd, 2H, J=6.1, 3.3 Hz), 7.29 (d, 2H, J=8.1 Hz), 7.51 (dd, 2H, J=6.0, 3.1 Hz), 7.65 (dd, 1H, J=8.1, 5.4 Hz), 7.92 (dd, 1H, J=7.8, 5.7 Hz), 8.04 (d, 1H, J=7.8 Hz), 8.40 (d, 1H, J=7.8 Hz), 8.53 (d, 1H, J=4.2 Hz), 8.77 (d, 1H, J=5.1 Hz). $^{13}$C NMR (D$_2$O) □ 20.97, 24.04, 27.85, 48.24, 50.33, 51.48, 57.22, 58.78, 63.41, 113.73 (2C), 125.69, 126.15, 126.53 (2C), 127.41, 130.04, 130.39, 131.00 (2C), 130.55, 131.76 (2C), 138.92, 139.70, 141.12, 142.64, 145.42, 148.34, 152.50, 156.69.ES-MS m/z 515 (M+H); Anal. Calcd. for (C$_{33}$H$_{34}$N$_6$×4 HBr×1.6 H$_2$O×1.4 HOAc): C,45.20; H, 4.96; N, 8.84; Br 33.60. Found: C, 45.45; H, 5.03; N, 8.86; Br, 33.26.

EXAMPLE 131

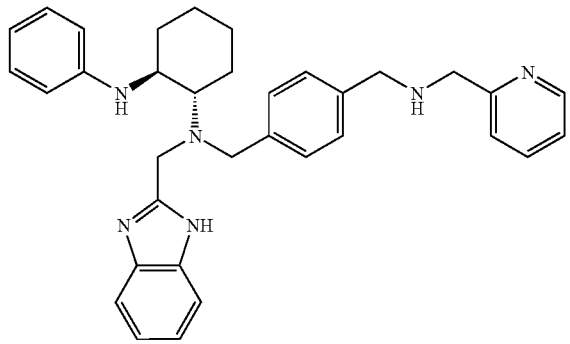

AMD9407: Preparation of N-(2-pyridinylmethyl)-N'-[1H-benzimidazol-2-ylmethyl)]-N'-[trans-2-(N-phenylamino)cyclohexyl]-1,4-benzenedimethanamine(hydrobromide salt)

Preparation of 2-[N-(t-butyloxycarbonyl)]amino-cyclohexanone

To a suspension of trans-2-aminocyclohexanol hydrochloride (1.69 g, 11.1 mmol) and triethylamine (3.1 mL, 22.2 mmol) in THF (25 mL) was added di-tert-butyl dicarbonate (2.78 g, 12.7 mmol) and the mixture stirred at room temperature for 5 hours. The reaction was diluted with ethyl acetate (10 mL) and water (30 mL). The phases were separated and the aqueous phase washed with ethyl acetate (2×25 mL). The combined organic extracts were washed with brine (1×30 mL), dried (Na$_2$SO$_4$), filtered and concentrated under reduced pressure. The resultant white solid (2.39 g) was used without further purification in the next reaction.

To a suspension of the alcohol from above (0.620 g) and powdered 3 Å molecular sieves (0.550 g) in CH$_2$Cl$_2$ (7 mL) was added 4-methylmorpholine N-oxide (0.505 g, 4.32 mmol) and tetrapropylammonium perruthenate (0.070 g, 0.20 mmol) and the mixture stirred for 2 hours. The reaction was concentrated under reduced pressure and purified by column chromatography through a plug of silica gel (ethyl acetate) to afford the title compound (0.542 g, 88% over 2 steps) as a clear oil. $^1$H NMR (CDCl$_3$) □1.44 (br s, 9H), 1.58-1.87 (m, 4H), 2.08-2.17 (m, 1H), 2.32-2.43 (m, 1H), 2.48-2.62 (m, 2H), 4.19-4.27 (m, 1H), 5.48 (br s, 1H, NH); $^{13}$C NMR (D$_2$O) □ 23.85, 27.10, 27.65, 28.04, 35.59, 40.80, 58.85, 155.00, 207.30.

Preparation of trans-N-phenyl-cyclohexane-1,2-diamine

To a solution of 2-[N-(t-butyloxycarbonyl)]amino-cyclohexanone (0.785 g, 3.69 mmol, aniline (0.68 mL, 7.46 mmol) and glacial acetic acid (0.22 mL) in THF (10 mL) was added NaBH(OAc)$_3$ (1.173 g, 5.53 mmol) and the mixture was stirred at 60 □□Covernight. The reaction was cooled to room temperature, diluted with CH$_2$Cl$_2$ (60 mL) and washed with saturated aqueous NaHCO$_3$ (50 mL). The aqueous phase was washed with CH$_2$Cl$_2$ (2×25 mL) and the combined organic extracts dried (Na$_2$SO$_4$), filtered and concentrated under reduced pressure. Purification and separation of the resultant brown oil by flash chromatography on silica gel (Hexanes/EtOAc, 9:1) afforded the low polarity cis-N-phenyl-N'-(t-butyloxycarbonyl)-cyclohexane-1,2-diamine isomer (0.095 g, 9%) and the high polarity trans-N-phenyl-N'-(t-butyloxycarbonyl)-cyclohexane-1,2-diamine isomer (0.412 g, 39%), both as pale yellow solids.

The trans isomer from above (0.223 g, 0.77 mmol) was dissolved in CH$_2$Cl$_2$ (2 mL) and treated with trifluoroacetic acid (2 mL) and the mixture stirred overnight. The reaction was concentrated under reduced pressure then diluted with CH$_2$Cl$_2$ (45 mL) and 1 N NaOH (35 mL). The phases were separated and the aqueous phase was washed with CH$_2$Cl$_2$ (2×30 mL). The combined organic extracts were dried (Na$_2$SO$_4$), filtered and concentrated under reduced pressure to provide trans-N-phenyl-cyclohexane-1,2-diamine (0.138 g) as a yellow oil. $^1$H NMR (CDCl$_3$) □1.21-1.36 (m, 4H), 1.45-1.55 (m, 3H), 1.73-1.76 (m, 2H), 1.97-2.01 (m, 1H), 2.12-2.16 (m, 1H), 2.52 (td, 1H, J=9.6, 2.7 Hz), 2.95 (td, 1H, J=9.6, 3.3 Hz), 6.66-6.72 (m, 3H), 7.17 (td, 2H, J=7.5, 1.8 Hz).

1-[[2-(trimethylsilyl)ethoxy]methyl]-benzimidazole-2-carboxaldehyde

To a stirred solution of benzimidazole (2.00 g, 16.9 mmol) in anhydrous DMF (25 mL) was added N,N-diisopropylethylamine (7.3 mL, 42.2 mmol) followed by 2-(trimethylsilyl)ethoxymethyl chloride (3.3 mL, 18.6 mmol) and the resultant solution was heated to 80 □C for 4 hours. Purification of the crude brown oil through a plug of silica gel (CH$_2$Cl$_2$/MeOH, 19:1) provided the 1-(2-trimethylsilylethoxymethyl)-benzimidazole (3.19 g, 76%) as an orange oil. $^1$H NMR (CDCl$_3$) □-0.05 (s, 9H), 0.90 (t, 2H, J=9 Hz), 3.51 (t, 2H, J=9 Hz), 5.55 (s, 2H), 7.32-7.37 (m, 2H), 7.55 (br d, 1H, J=6 Hz), 7.83 (br d, 1H, J=6 Hz), 7.98 (s, 1H).

To a cold (−40 °C), stirred solution of the 1-(2-trimethyl-silylethoxymethyl)-benzimidazole (0.678 g, 2.73 mmol) in dry THF (10 mL) was added a 2.5 M solution of n-butyllithium in hexanes (1.4 mL, 3.5 mmol). The reaction mixture turned deep red. After 30 minutes, DMF (1.3 mL, 16.8 mmol) was added to the reaction mixture and the resultant solution was allowed to warm to room temperature overnight. After the usual work up, the resultant yellow oil was used without further purification in the reductive amination step. $^1$H NMR (CDCl$_3$)) δ −0.05 (s, 9H), 0.90 (t, 2H, J=9 Hz), 3.56 (t, 2H, J=9 Hz), 6.05 (s, 2H), 7.43-7.53 (m, 2H), 7.66 (d, 1H, J=6 Hz), 7.95 (d, 1H, J=6 Hz), 10.13 (s, 1H).

Using General Procedure B: To a stirred solution of trans-N-phenyl-cyclohexane-1,2-diamine (0.137 g, 0.72 mmol) and 4-[[N-(-t-butoxycarbonyl)-N-(2-pyridinylmethyl)amino]methyl]benzaldehyde (0.239 g, 0.66 mmol) in CH$_2$Cl$_2$ (10 mL) was added NaBH(OAc)$_3$ (0.229 g, 1.08 mmol) and the mixture was stirred at room temperature for 4.5 hours. Purification of the crude material by flash chromatography on silica gel (CH$_2$Cl$_2$/MeOH, 96:4) afforded the protected amine (0.198 g) as a yellow foam.

To a solution of the foam from above (0.198 g) and 1-[[2-(trimethylsilyl)ethoxy]methyl]-benzimidazole-2-carboxaldehyde (0.110 g, 0.40 mmol) in MeOH (4 mL) was added NaBH$_3$CN (0.036 g, 0.57 mmol) and the mixture stirred at room temperature overnight. Purification of the crude material by flash chromatography on silica gel (CH$_2$Cl$_2$/MeOH, 98:2 followed by 96:4) afforded the desired benzimidazole derivative (0.211 g, 42% over 2 steps) as a pale yellow oil.

Simultaneous BOC and SEM Deprotection: A solution of the oil from above (0.211 g, 0.28 mmol) in 5 M HCl/THF (5:1, 12 mL) was stirred at 60° C for 4 hours. The reaction was cooled to room temperature, diluted with 10 N NaOH (15 mL, pH >10) and extracted with CH$_2$Cl$_2$ (3×25 mL). The combined organic layers were dried (Na$_2$SO$_4$), filtered and concentrated under reduced pressure. Purification of the crude brown oil by radial chromatography (2 mm plate, CH$_2$Cl$_2$/MeOH, 96:4) afforded the title compound (0.050 g, 34%) as a clear, colourless oil.

Using General Procedure D: The free base from above (0.050 g, 0.094 mmol) was converted to the hydrobromide salt with HBr(g) saturated MeOH (2 mL) to provide AMD9407 (0.080 g) as an off-white solid. $^1$H NMR (D$_2$O) δ 1.21-1.61 (m, 3H), 1.61-1.78 (m, 2H), 1.87-2.00 (m, 2H), 2.27-2.32 (m, 1H), 3.29 (td, 1H, J=10.5, 2.4 Hz), 3.85 (s, 2H), 3.85-3.98 (m, 2H), 4.21-4.41 (m, 2H), 4.26 (s, 2H), 4.62 (d, 1H, J=16.5 Hz), 7.07 (d, 2H, J=8.1 Hz), 7.31 (d, 2H, J=8.1 Hz), 7.35-7.39 (m, 2H), 7.46-7.52 (m, 4H), 7.58-7.63 (m, 3H), 7.76 (d, 1H, J=8.1 Hz), 7.81 (dd, 1H, J=7.8, 15.7 Hz), 8.30 (td, 1H, J=8.1, 1.5 Hz), 8.70 (d, 1H, J=5.7 Hz); $^{13}$C NMR (D$_2$O) δ 23.67, 24.09, 24.48, 27.94, 48.45 (2 carbons), 50.62 (2 carbons), 62.23 (2 carbons), 113.88 (2 carbons), 124.06 (2 carbons), 126.63 (2 carbons), 126.96 (2 carbons), 129.93, 130.32 (2 carbons), 130.52 (2 carbons), 130.69, 130.91 (2 carbons), 130.98 (2 carbons), 132.87, 138.49, 144.19, 146.31, 147.25, 151.50. ES-MS m/z 531 (M+H). Anal. Calcd. for C$_{34}$H$_{38}$N$_6$·4.1HBr·3.5H$_2$O: C, 44.12; H, 5.35; N, 9.08; Br, 35.40. Found: C, 44.34; H, 5.28; N, 8.70; Br, 35.11.

EXAMPLE 132

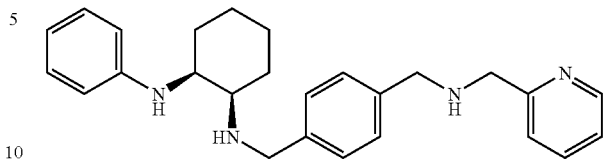

AMD9423: Preparation of N-(2-pyridinylmethyl)-N'-[cis-2-(N-phenylamino)cyclohexyl]-1,4-benzene-dimethanamine(hydrobromide salt)

Preparation of cis-N-phenyl-cyclohexane-1,2-diamine

The cis-N-phenyl-N'-(t-butyloxycarbonyl)-cyclohexane-1,2-diamine isomer from above (0.095 g, 0.33 mmol) was dissolved in CH$_2$Cl$_2$ (2 mL) and treated with trifluoroacetic acid (2 mL) and the mixture stirred overnight. The reaction was worked up to afford the title compound (0.069 g) as a pale yellow solid. $^1$H NMR (CDCl$_3$) δ 1.28-1.37 (m, 5H), 1.50-1.63 (m, 6H), 3.18 (br s, 1H), 3.42-3.45 (m, 1H), 6.63-6.70 (m, 3H), 7.16 (br t, 2H, J=7.5 Hz).

Using General Procedure B: To a stirred solution of cis-N-phenyl-cyclohexane-1,2-diamine (0.069 g) and 4-[[N-(-t-butoxycarbonyl)-N-(2-pyridinylmethyl)amino]methyl]benzaldehyde (PCT International Application PCT/CA00/00321) (0.239 g, 0.66 mmol) in CH$_2$Cl$_2$ (5 mL) was added NaBH(OAc)$_3$ (0.112 g, 0.53 mmol) and the mixture stirred at room temperature for 2 hours. Purification of the crude material by flash chromatography on silica gel (CH$_2$Cl$_2$/MeOH, 96:4) afforded the protected amine (0.128 g, 78% over 2 steps) as a clear oil.

Using General Procedure D: The oil from above (0.050 g, 0.10 mmol) was converted to the hydrobromide salt with simultaneous deprotection of the BOC group to provide AMD9423 (0.071 g) as a white solid. $^1$H NMR (D$_2$O) δ 1.47-1.58 (m, 4H), 1.70-1.91 (m, 4H), 3.48-3.55 (m, 1H), 3.96-3.98 (m, 1H), 4.19 (d, 1H, J=13.2 Hz), 4.31 (d, 1H, J=13.2 Hz), 4.37 (s, 2H), 4.65 (s, 2H), 6.74-6.81 (m, 3H), 7.19 (t, 2H, J=7.8 Hz), 7.39 (s, 4H), 8.00 (t, 1H, J=6.9 Hz), 8.05 (d, 1H, J=8.1 Hz), 8.52 (t, 1H, J=7.8 Hz), 8.80 (d, 1H, J=5.8 Hz); $^{13}$C NMR D$_2$O) δ 20.08, 22.34, 24.16, 27.22, 47.69, 48.48, 48.99, 51.61, 57.02, 114.95 (2 carbons), 119.37, 127.97, 128.25, 130.11 (2 carbons), 131.06 (2 carbons), 131.20 (2 carbons), 131.43, 132.67, 144.50, 145.78, 146.29, 146.91. ES-MS m/z 401 (M+H). Anal. Calcd. for C$_{26}$H$_{32}$N$_4$·4.3HBr·3.0H$_2$O·0.7C$_4$H$_{10}$O: C, 40.49; H, 5.82; N, 6.56; Br, 40.21. Found: C, 40.60; H, 5.52; N, 6.43; Br, 39.97.

EXAMPLE 133

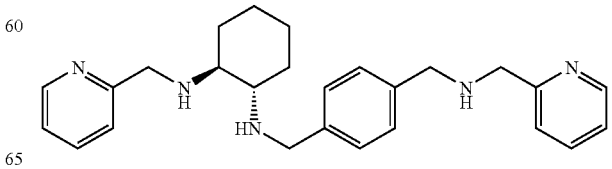

AMD9469: Preparation of N-(2-pyridinylmethyl)-
N'-[trans-2-[(pyridin-2-ylmethyl)amino]cyclohexyl]-
1,4-benzenedimethanamine(hydrobromide salt)

Preparation of trans-N-(t-butoxycarbonyl)-N'-pyridin-2-ylmethyl-cyclohexane-1,2-diamine.

Using General Procedure B: To a solution of 2-[N-(t-butyloxycarbonyl)]amino-cyclohexanone (117 mg, 0.55 mmol) and 2-(aminomethyl)pyridine (0.065 mL, 0.63 mmol in $CH_2Cl_2$ (5 mL) was added $NaBH(OAc)_3$ (167 mg, 0.79 mmol) and the mixture stirred at room temperature overnight. The resultant crude pale yellow oil (168 mg) was used without further purification in the next step. $^1H$ NMR ($CDCl_3$) □1.08-1.22 (m, 4H), 1.43 (s, 9H), 1.61-1.67 (m, 2H), 2.04-2.16 (m, 2H), 2.29 (td, 1H, J=9, 3 Hz), 2.31 (br s, 1H, NH), 3.27-3.33 (m, 1H), 3.85 (d, 1H, J=15 Hz), 4.02 (d, 1H, J=15 Hz), 5.37 (br s, 1H, NH), 7.14 (dd, 1H, J=9, 6 Hz), 7.28 (d, 1H, J=9 Hz), 7.59 (td, 1H, J=9, 3 Hz), 8.53 (d, 1H, J=3 Hz).

To a solution of the oil from above (168 mg) and N,N-diisopropylethylamine (0.15 mL, 0.87 mmol) in $CH_2Cl_2$ (2.5 mL) was added benzylchloroformate (0.10 mL, 0.70 mmol) and the mixture stirred at room temperature for 4 hours. The reaction was diluted with $CH_2Cl_2$ (15 mL) and saturated aqueous $NaHCO_3$ (15 mL) and the phases separated. The aqueous phase was washed with $CH_2Cl_2$ (2×10 mL) and the combined organic extracts were dried ($Na_2SO_4$), filtered and concentrated under reduced pressure. The resultant crude yellow oil (256 mg) was used without further purification in the next step.

BOC Deprotection: The oil from above (256 mg) was dissolved in $CH_2Cl_2$ (2 mL) and treated with trifluoroacetic acid (2 mL) and the mixture stirred for 40 minutes. The resultant crude orange oil (188 mg) was used without further purification in the next step.

Using General Procedure B: To a solution of the oil from above (188 mg) and 4-[[N-(t-butoxycarbonyl)-N-(2-pyridinylmethyl)amino]methyl]benzaldehyde (190 mg, 0.58 mmol) in $CH_2Cl_2$ (4 mL) was added $NaBH(OAc)_3$ (175 mg, 0.83 mmol) and the mixture stirred at room temperature overnight. Purification of the crude material by flash chromatography on silica gel ($CH_2Cl_2$/MeOH/$NH_4OH$, 96:4:0 followed by 95:4: 1) afforded the desired amine (270 mg, 76% over 4 steps) as a clear oil.

BOC Deprotection: The oil from above (136 mg, 0.21 mmol) was dissolved in $CH_2Cl_2$ (2 mL) and treated with trifluoroacetic acid (2 mL) and the mixture stirred overnight. Purification of the resultant crude oil by flash chromatography on silica gel ($CH_2Cl_2$/MeOH/$NH_4OH$, 95:4:1) afforded the desired amine (94 mg) as a clear oil.

CBz Deprotection: To a solution of the oil from above (94 mg) in MeOH (5 mL) was added palladium on activated carbon (10%, 14 mg) and the mixture was hydrogenated (1 atmosphere) at room temperature overnight. The reaction mixture was filtered through celite and the cake was washed with methanol. The combined filtrates were evaporated under reduced pressure and the resultant clear oil was purified by radial chromatography on silica gel (1 mm plate, 50:1:1 $CH_2Cl_2$/MeOH/$NH_4OH$) to afford the free amine (34 mg, 39% over 2 steps) as a clear oil.

Using General Procedure D: The free base from above (34 mg, 0.082 mmol) was converted to the hydrobromide salt with HBr(g) saturated MeOH (2 mL) to provide AMD9469 (62 mg) as a pale yellow solid. $^1H$ NMR ($D_2O$) □1.18-1.30 (m, 3H), 1.47-1.54 (m, 1H), 1.79-1.84 (m, 2H), 2.31-2.36 (m, 2H), 2.86-2.92 (m, 1H), 3.20 (td, 1H, J=10.8, 3.6 Hz), 4.18 (d, 1H, J=16.8 Hz), 4.29 (d, 1H, J=13.5 Hz), 4.43-4.49 (m, 4H), 4.65 (s, 2H), 7.57 (s, 4H), 7.78-7.87 (m, 2H), 7.92 (t, 1H, J=6.9 Hz), 7.98 (d, 1H, J=7.8 Hz), 8.36-8.46 (m, 3H), 8.78 (d, 1H, J=5.4 Hz); $^{13}C$ NMR ($D_2O$) □ 23.64, 23.87, 27.23, 30.15, 47.17, 47.79, 48.36, 51.45, 58.69, 60.14, 125.99, 126.22, 127.47, 127.63, 131.08 (2 carbons), 131.35 (2 carbons), 131.85, 133.07, 142.30, 145.47, 145.55, 145.88, 146.58, 153.84. ES-MS m/z 416 (M+H). Anal. Calcd. for $C_{26}H_{33}N_5.5.2HBr.2.6H_2O$: C, 35.36; H, 4.95; N, 7.93; Br, 47.05. Found: C, 35.29; H, 5.02; N, 7.63; Br, 47.24.

EXAMPLE 134

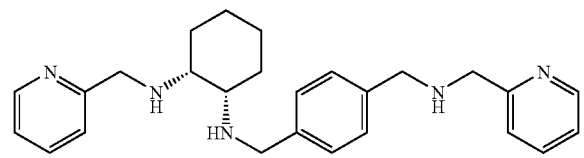

AMD9470: Preparation of N-(2-pyridinylmethyl)-
N'-[cis-2-[(N-pyridin-2-ylmethyl)amino]cyclohexyl]-1,4-benzenedimethanamine(hydrobromide salt)

Preparation of trans-2-[N-(t-butoxycarbonyl)amino]-1-methanesulfonyloxycyclohexane To a suspension of trans-2-aminocyclohexanol hydrochloride (4.95 g, 32.6 mmol) and triethylamine (10 mL, 71.7 mmol) in THF (75 mL) was added di-tert-butyl dicarbonate (8.25 g, 37.8 mmol) and the mixture stirred at room temperature for 1.5 hours. The reaction was diluted with ethyl acetate (75 mL) and water (25 mL) and the phases separated. The aqueous phase was washed with ethyl acetate (3×25 mL) and the combined organic extracts were washed with brine (3×30 mL), dried ($MgSO_4$), filtered and concentrated under reduced pressure to give the Boc-protected amine (8.00 g) as a white solid.

To a stirred solution of trans-2-[N-(t-butoxycarbonyl)aminocyclohexanol (8.00 g, 37.2 mmol) and triethylamine (8.0 mL, 57.4 mmol) in $CH_2Cl_2$ (100 mL) at −78° C. was added methanesulfonyl chloride (3.5 mL, 45.2 mmol) dropwise and the mixture stirred for 10 minutes. The reaction was warmed to room temperature and stirred for another 40 minutes. The mixture was then diluted with water (10 mL) and brine (15 mL) and the phases separated. The organic layer was washed with brine (2×25 mL), dried ($Na_2SO_4$), filtered and concentrated to give the crude mesylate (11.04 g) as a white solid. $^1H$ NMR ($CDCl_3$) □1.26-1.37 (m, 3H), 1.44 (s, 9H), 1.59-1.69 (m, 2H), 1.70-1.79 (m, 1H), 2.10-2.21 (m, 2H), 3.03 (s, 3H), 3.58-3.61 (m, 1H), 4.44 (dt, 1H, J=9, 3 Hz), 4.68 (br s, 1H, NH).

Preparation of cis-1-[N-(t-butoxycarbonyl)]-cyclohexane-1,2-diamine:

To a solution of the mesylate from above (11.04 g) in DMF (125 mL) was added sodium azide (15.45 g, 237.7 mmol) and the mixture stirred at 80° C. for 16 hours. The reaction was cooled to room temperature, concentrated under reduced pressure and the resultant residue diluted with ethyl acetate (100 mL), water (10 mL) and brine (15 mL). The phases were separated and the organic phase was washed with brine (3×25 mL), dried ($MgSO_4$), filtered and concentrated to give the crude azide (6.17 g) as a yellow oil. Purification and separation of the crude product by flash chromatography on silica gel (Hexanes/ethyl acetate, 10:1) afforded the cis azide (2.17 g, 28% over 3 steps) and trans azide (2.20 g, 28% over 3 steps)

both as white solids. cis-1-[N-(t-butoxycarbonyl)]-cyclohexane-1,2-diamine: $^1$H NMR (CDCl$_3$) δ1.27-1.37 (m, 3H), 1.44 (s, 9H), 1.58-1.73 (m, 3H), 1.94-2.01 (m, 2H), 3.56-3.63 (m, 1H), 3.92-3.95 (m, 1H), 4.72 (br s, 1H, NH). $^{13}$C NMR (CDCl$_3$) δ 18.36, 23.03, 26.38, 27.03, 27.39, 49.77, 60.28, 78.24, 153.73. ES-MS m/z 263 (M+Na). trans-1-[N-(t-butoxycarbonyl)]-cyclohexane-1,2-diamine: $^1$H NMR (CDCl$_3$) δ1.19-1.39 (m, 3H), 1.46 (s, 9H), 1.64-1.78 (m, 3H), 2.02-2.07 (m, 2H), 3.08-3.13 (m, 1H), 3.36-3.42 (m, 1H), 4.50 (br s, 1H, NH). $^{13}$C NMR (CDCl$_3$) δ 24.44, 24.68, 28.76, 31.06, 32.66, 54.27, 64.79, 80.08, 155.75. ES-MS m/z 263 (M+Na).

To a solution of the cis azide from above (2.12 g, 8.83 mmol) in MeOH (44 mL) was added palladium on activated carbon (10%, 227 mg) and the mixture was hydrogenated (30 psi) at room temperature for 17.5 hours. The reaction mixture was filtered through celite and the cake was washed with methanol. The combined filtrates were evaporated under reduced pressure to afford the title compound as a clear, colourless oil (1.85 g, 98%). $^1$H NMR (CDCl$_3$) δ1.41-1.68 (m, 10H), 1.45 (s, 9H), 2.98-3.00 (m, 1H), 3.57-3.59 (m, 1H), 5.00 (br s, 1H, NH).

Using General Procedure B: To a solution of cis-1-[N-(t-butoxycarbonyl)]-cyclohexane-1,2-diamine (0.79 g, 3.69 mmol) and 2-pyridinecarboxaldehyde (0.35 mL, 3.68 mmol) in CH$_2$Cl$_2$ (20 mL) was added NaBH(OAc)$_3$ (0.036 g, 0.57 mmol) and the mixture stirred at room temperature overnight. The resultant crude oil was used without further purification in the next step. $^1$H NMR (CDCl$_3$) δ1.35-1.51 (m, 4H), 1.44 (s, 9H), 1.54-1.64 (m, 3H), 2.01-2.04 (m, 2H), 2.75-2.79 (m, 1H), 3.66-3.70 (m, 1H), 3.87 (d, 1H, J=15 Hz), 3.96 (d, 1H, J=15 Hz), 5.42 (br s, 1H, NH), 7.16 (dd, 1H, J=9, 6 Hz), 7.30 (d, 1H, J=9 Hz), 7.61 (td, 1H, J=9, 3 Hz), 8.56 (d, 1H, J=3 Hz).

CBz Protection: To a solution of the oil from above and N,N-diisopropylethylamine (0.96 mL, 5.52 mmol) in CH$_2$Cl$_2$ (10 mL) was added benzylchloroformate (0.64 mL, 4.48 mmol) and the mixture was stirred at room temperature for 3 hours. The reaction was diluted with CH$_2$Cl$_2$ (15 mL) and brine (25 mL) and the phases separated. The aqueous phase was washed with CH$_2$Cl$_2$ (2×20 mL) and the combined organic extracts were dried (Na$_2$SO$_4$), filtered and concentrated under reduced pressure. Purification of the crude product by flash chromatography on silica gel (CH$_2$Cl$_2$/MeOH, 97:3) afforded the di-protected diamine (1.44 g, 89% over 2 steps) as an orange oil.

BOC Deprotection: The oil from above (1.44 g, 3.28 mmol) was dissolved in CH$_2$Cl$_2$ (2 mL) and treated with trifluoroacetic acid (2 mL) and the mixture stirred overnight. The usual work-up afforded an orange oil (1.17 g) which was use without further purification in the next reaction.

Using General Procedure B: To a solution of the oil from above (296 mg) and 4-[[N-(t-butoxycarbonyl)-N-(2-pyridinylmethyl)amino]methyl]benzaldehyde (322 mg, 0.89 mmol) in CH$_2$Cl$_2$ (10 mL) was added NaBH(OAc)$_3$ (280 mg, 1.32 mmol) and the mixture stirred at room temperature overnight. Purification of the crude material by flash chromatography on silica gel (CH$_2$Cl$_2$/MeOH, 96:4) afforded the desired amine (350 mg, 62% over 2 steps) as a clear oil.

CBz deprotection: To a solution of the oil from above (160 mg) in MeOH (3 mL) was added palladium on activated carbon (10%, 30 mg) and the mixture was hydrogenated (1 atmosphere) at room temperature for 3.5 hours. The reaction mixture was filtered through celite and the cake was washed with methanol. The combined filtrates were evaporated under reduced pressure and the resultant clear oil was purified by radial chromatography on silica gel (1 mm plate, 95:4:1 CH$_2$Cl$_2$/MeOH/NH$_4$OH) to afford the free amine (80 mg, 63%) as a clear oil.

Using General Procedure D: The free base from above (80 mg, 0.16 mmol) was converted to the hydrobromide salt with simultaneous deprotection of the BOC group using HBr(g) saturated MeOH (2 mL) to provide AMD9470 (144 mg) as a grey solid. $^1$H NMR (D$_2$O) δ1.38-1.65 (m, 5H), 1.75-1.79 (m, 1H), 1.95-2.01 (m, 2H), 3.30-3.34 (m, 1H), 3.42-3.48 (m, 1H), 4.04 (d, 1H, J=17.4 Hz), 4.28 (d, 1H, J=13.5 Hz), 4.37 (d, 1H, J=13.5 Hz), 4.42 (s, 2H), 4.49 (d, 1H, J=17.4 Hz), 4.67 (s, 2H), 7.54 (s, 4H), 7.89-8.04 (m, 4H), 8.45-8.52 (m, 2H), 8.61 (d, 1H, J=5.4 Hz), 8.80 (d, 1H, J=5.4 Hz); $^{13}$C NMR (D$_2$O) δ 18.74, 23.04, 24.14, 26.51, 47.86, 48.13, 48.22, 51.47, 53.90, 58.63, 126.09, 126.33, 127.67, 127.88, 131.29 (4 carbons), 131.74, 133.04, 140.90, 145.11, 146.08, 146.26, 146.91, 155.12. ES-MS m/z 416 (M+H). Anal. Calcd. for C$_{26}$H$_{33}$N$_5$.4.7HBr.2.3H$_2$O: C, 37.30; H, 5.09; N, 8.36; Br, 44.85. Found: C, 37.41; H, 5.00; N, 8.19; Br, 44.72.

EXAMPLE 135

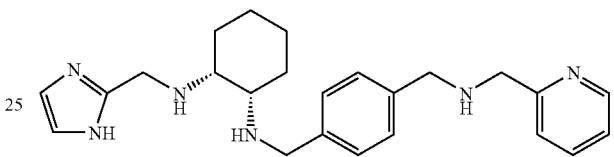

AMD9526: Preparation of N-(2-pyridinylmethyl)-N'-[cis-2-[(1H-imidazol-2-ylmethyl)amino]cyclohexyl]-1,4-benzenedimethanamine(hydrobromide salt)

Cis-1-[N-(t-butoxycarbonyl)]-cyclohexane-1,2-diamine (540 mg, 2.52 mmol) was stirred with 2-imidazole carboxaldehyde (250 mg, 2.60 mmol) in methanol (10 mL) overnight. Palladium on activated carbon (10%, 76 mg) was then added and the mixture was hydrogenated (1 atmosphere) at room temperature for 3 hours. The reaction mixture was filtered through celite and the cake was washed with methanol. The combined filtrates were evaporated under reduced pressure to give a pale yellow oil (785 mg) which was used without further purification in the next reaction.

Using General Procedure B: To a solution of the oil from above (115 mg) and 4-[[N-(t-butoxycarbonyl)-N-(2-pyridinylmethyl)amino]methyl]benzaldehyde (221 mg, 0.68 mmol) in CH$_2$Cl$_2$ (5 mL) was added NaBH(OAc)$_3$ (178 mg, 0.84 mmol) and the mixture stirred at room temperature overnight. Purification of the crude material by flash chromatography on silica gel (CH$_2$Cl$_2$/MeOH/NH$_4$OH, 96:4:0 then 95:4:1) afforded the product (135 mg, 45%) as a clear foam.

Using General Procedure D: The product from above (135 mg, 0.27 mmol) was converted to the hydrobromide salt (156 mg) with simultaneous deprotection of the Boc group. The salt was then dissolved in MeOH (1 mL) and diluted with 10 N NaOH (2 mL) and CH$_2$Cl$_2$ (10 mL). The aqueous phase was washed with CH$_2$Cl$_2$ (3×10 mL) and the combined organic layers dried (Na$_2$SO$_4$), filtered and concentrated under reduced pressure. Purification of the resultant yellow oil (76 mg) by radial chromatography on silica gel (1 mm plate, 40:1:1 CH$_2$Cl$_2$/MeOH/NH$_4$OH) afforded pure free base (52 mg, 48%) as a colourless oil.

Using General Procedure D: Conversion of the oil from above (77 mg, 0.14 mmol) to the hydrobromide salt followed by re-precipitation of the intermediate solid from methanol/ether gave AMD9526 (89 mg, 80%) as a white solid. $^1$H NMR (D$_2$O) ☐1.35-1.61 (m, 5H), 1.70-1.74 (m, 1H), 1.85-1.90 (m, 2H), 3.20-3.22 (m, 1H), 3.33-3.40 (m, 1H), 3.84 (d, 1H, J=16.5 Hz), 4.20-4.33 (m, 3H), 4.42 (s, 2H), 4.66 (s, 2H), 7.34 (s, 2H), 7.52 (s, 4H), 7.96 (t, 1H, J=6.9 Hz), 8.02 (d, 1H, J=8.1 Hz), 8.48 (td, 1H, J=7.8, 0.9 Hz), 8.79 (d, 1H, J=5.4 Hz); $^{13}$C NMR (D$_2$O) ☐ 18.82, 22.91, 24.19, 26.30, 41.93, 48.07, 48.12, 51.50, 53.26, 58.28, 119.08 (2 carbons), 127.73, 127.96, 131.26 (4 carbons), 131.73, 133.01, 144.99, 146.17, 146.25, 146.89. ES-MS m/z 405 (M+H). Anal. Calcd. for C$_{24}$H$_{32}$N$_6$.4.9HBr.3.6H$_2$O: C, 33.29; H, 5.13; N, 9.71; Br, 45.22. Found: C, 33.46; H, 5.23; N, 9.53; Br, 45.01.

EXAMPLE 136

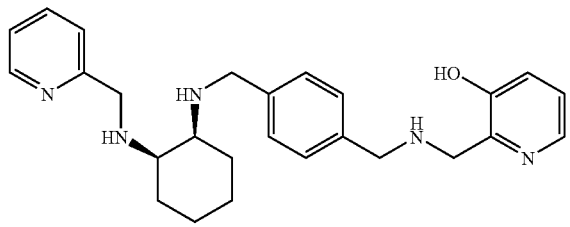

AMD9527: Preparation of 2-{[4-({2-[(pyridin-2-ylmethyl)-amino]-cyclohexylamino}-methyl)-benzylamino]-methyl}-pyridin-3-ol(hydrobromide salt)

Preparation of (4-hydroxymethyl-benzyl)-(3-hydroxy-pyridin-2-ylmethyl)-carbamic acid tert-butyl ester.

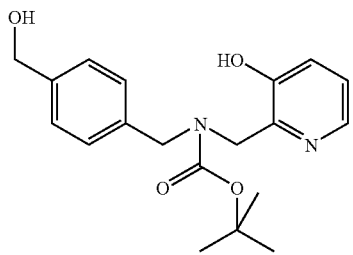

Using General Procedure B: (4-Aminomethyl-phenyl)-methanol (1.20 g, 8.75 mmol), 3-hydroxy-pyridine-2-carbaldehyde (1.18 g, 9.58 mmol), acetic acid (0.50 mL, 8.7 mmol), and NaBH(OAc)$_3$ (5.60 g, 26.4 mmol) were reacted for 1 hour. Standard work-up gave a yellow foam that was used in the next step without further purification.

A solution of the crude yellow foam and di-t-butyl dicarbonate (2.3 g, 11 mmol) in THF (34 mL) was stirred at room temperature for 1 hour then concentrated. Purification of the crude material on silica gel (60% EtOAc/hexanes) gave the title compound as an orange foam (1.39 g, 46%). $^1$H NMR (CDCl$_3$) ☐ 1.47 (s, 9H), 4.48 (s, 2H), 4.51 (s, 2H), 4.70 (d, 2H, J=6.0 Hz), 7.16 (dd, 1H, J=8.1, 4.5 Hz), 7.26 (m, 3H), 7.34 (d, 2H, J=8.1 Hz), 8.05 (dd, 1H, J=4.5, 1.2 Hz), 9.69 (s, 1H).

(4-Formyl-benzyl)-(3-hydroxy-pyridin-2-ylmethyl)-carbamic acid tert-butyl ester.

A solution of (4-hydroxymethyl-benzyl)-(3-hydroxy-pyridin-2-ylmethyl)-carbamic acid tert-butyl ester (0.99 g, 2.9 mmol) in CH$_2$Cl$_2$ (14 mL) was stirred at room temperature with a suspension of 85% MnO$_2$ (3.0 g, 29 mmol) for 15 hours. The catalyst was removed by filtration, and the filtrate was concentrated to give orange crystals (818 mg, 83%). $^1$H NMR (CDCl$_3$) ☐ 1.44 (s, 9H), 4.54 (s, 2H), 4.61 (s, 2H), 7.17 (dd, 1H, J=8.1, 4.5 Hz), 7.26 (dd, 1H, J=8.1, 1.5 Hz), 7.37 (d, 2H, J=8.1 Hz), 7.84 (d, 2H, J=8.1 Hz), 8.03 (dd, 1H, J=4.5, 1.2 Hz), 9.55 (s, 1H), 10.00 (s, 1H).

(3-Hydroxy-pyridin-2-ylmethyl)-[4-({2-[(pyridin-2-ylmethyl)-amino]-cyclohexylamino}-methyl)-benzyl]-carbamic acid tert-butyl ester.

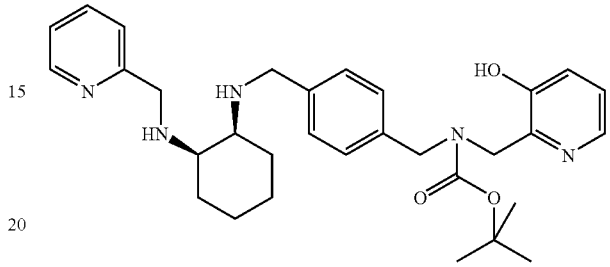

Using General Procedure B: (2-Amino-cyclohexyl)-pyridin-2-ylmethyl-carbamic acid benzyl ester (198 mg, 0.583 mmol), (4-formyl-benzyl)-(3-hydroxy-pyridin-2-ylmethyl)-carbamic acid tert-butyl ester (200 mg, 0.584 mmol), acetic acid (0.033 mL, 0.58 mmol), and NaBH(OAc)$_3$ (371 mg, 1.75 mmol) in dichloromethane were reacted for 2.5 hours. The crude yellow oil was filtered through silica gel using 100:3:0.2 CH$_2$Cl$_2$/MeOH/NH$_4$OH to give a colourless foam (229 mg).

A solution of the crude material (224 mg) in MeOH (4 mL) was stirred at room temperature with a suspension of 10% Pd/C (25 mg, 0.023 mmol) under hydrogen atmosphere (1 atm) for 70 hours. The catalyst was removed by filtration, and the filtrate was concentrated. Purification of the crude material on silica gel (10% MeOH/CH$_2$Cl$_2$ and 30:5:1 CH$_2$Cl$_2$/MeOH/NH$_4$OH) gave the title compound as a colourless oil (40 mg, 13%). $^1$H NMR (CDCl$_3$) δ 1.34 (m, 4H), 1.47 (s, 9H), 1.70 (m, 4H), 2.77 (m, 2H), 3.62-3.90 (m, 4H), 4.46 (s, 2H), 4.48 (s, 2H), 7.13-7.31 (m, 8H), 7.63 (m, 1H), 8.06 (dd, 1H, J=4.5, 1.4 Hz), 8.52 (d, 1H, J=4.5 Hz), 9.74 (br s, 1H).

Using General Procedure D: (3-Hydroxy-pyridin-2-ylmethyl)-[4-({2-[(pyridin-2-ylmethyl)-amino]-cyclohexylamino}-methyl)-benzyl]-carbamic acid tert-butyl ester (40 mg, 0.075 mmol) was treated with saturated hydrogen bromide/acetic acid to provide AMD9527 as a colourless solid (60 mg, 91%). $^1$H NMR (D$_2$O) ☐1.34-1.78 (m, 6H), 1.99 (m, 2H), 3.31 (m, 1H), 3.42 (m, 1H), 4.02 (d, 1H, J=17.4 Hz), 4.29 (m, 2H), 4.38 (s, 2H), 4.46 (d, 1H, J=17.4 Hz), 4.58 (s, 2H), 7.49 (m, 4H), 7.82-7.98 (m, 4H), 8.27 (dd, 1H, J=5.4, 1.2 Hz), 8.46 (m, 1H), 8.59 (d, 1H, J=5.7 Hz); $^{13}$C NMR (D$_2$O) ☐ 18.73, 23.05, 24.13, 26.53, 44.10, 47.87, 48.18, 51.40, 53.87, 58.62, 126.06, 126.31, 129.42, 131.18, 131.65, 132.74, 133.00, 134.89, 140.88, 146.89, 155.18, 155.88. ES-MS m/z 432 (M+H). Anal Calcd for (C$_{26}$H$_{33}$N$_5$O) 4.8(HBr) 3.4 (H$_2$O): C, 35.44; H, 5.10; N, 7.95; Br, 43.52. Found: C, 35.50; H, 5.01; N, 7.84; Br, 43.55.

The following examples (137-204) were prepared by the reaction of commercially available aldehydes/ketones with N-(1H-benzimidazol-2-ylmethyl)-N-(5,6,7,8-tetrahydro-8-quinolinyl)-1,4-benzenedimethanamine (AMD9381) using a reductive amination procedure with sodium cyanoborohydride in methanol/acetic acid, in a similar manner to the procedures described above:

Example 137

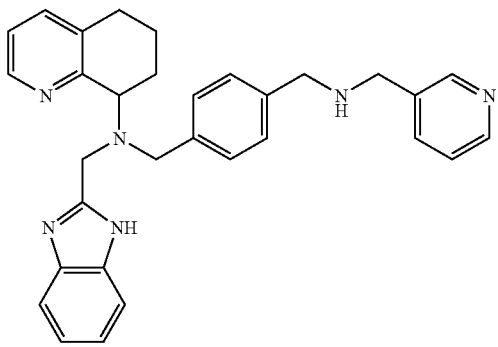

9162

(1H-Benzoimidazol-2-ylmethyl)-(4-{[(pyridin-3-ylmethyl)-amino]-methyl}-benzyl)-(5,6,7,8-tetrahydro-quinolin-8-yl)-amine Example 138

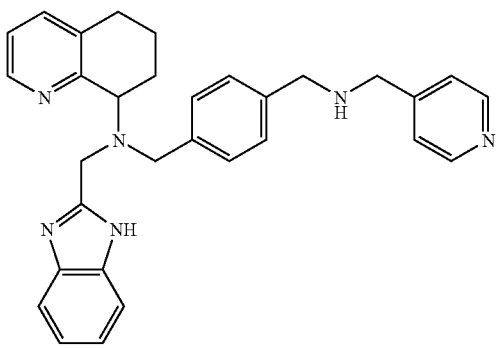

9163

(1H-Benzoimidazol-2-ylmethyl)-(4-{[(pyridin-4-ylmethyl)-amino]-methyl}-benzyl)-(5,6,7,8-tetrahydro-quinolin-8-yl)-amine Example 139

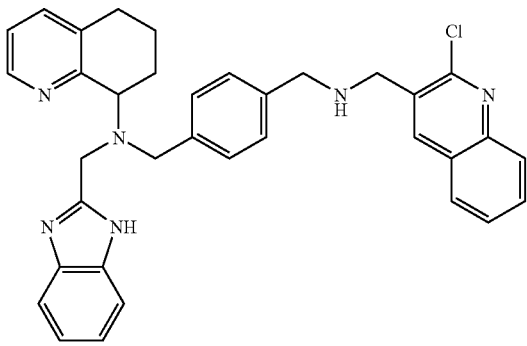

9164

(1H-Benzoimidazol-2-ylmethyl)-(4-{[(2-chloro-quinolin-3-ylmethyl)-amino]-methyl}-benzyl)-(5,6,7,8-tetrahydro-quinolin-8-yl)-amine Example 140

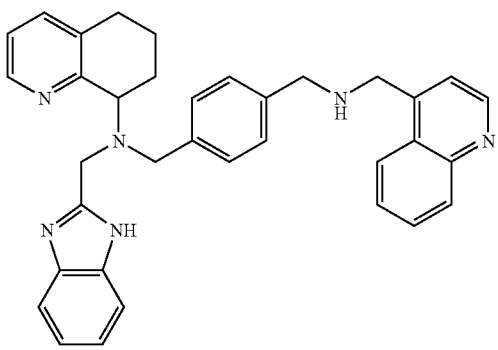

9165

(1H-Benzoimidazol-2-ylmethyl)-4-{[(quinolin-4-ylmethyl)-amino]-methyl}-benzyl)-(5,6,7,8-tetrahydro-quinolin-8-yl)-amine -continued Example 141 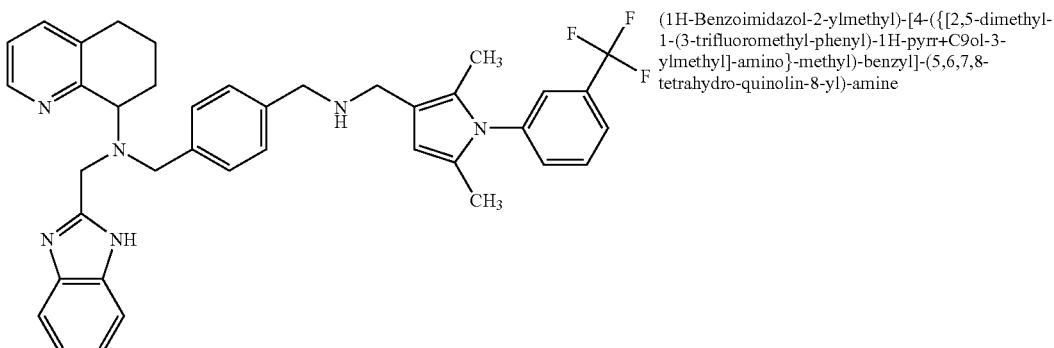
9166

(1H-Benzoimidazol-2-ylmethyl)-[4-({[2,5-dimethyl-1-(3-trifluoromethyl-phenyl)-1H-pyrr+C9ol-3-ylmethyl]-amino}-methyl)-benzyl]-(5,6,7,8-tetrahydro-quinolin-8-yl)-amine Example 142 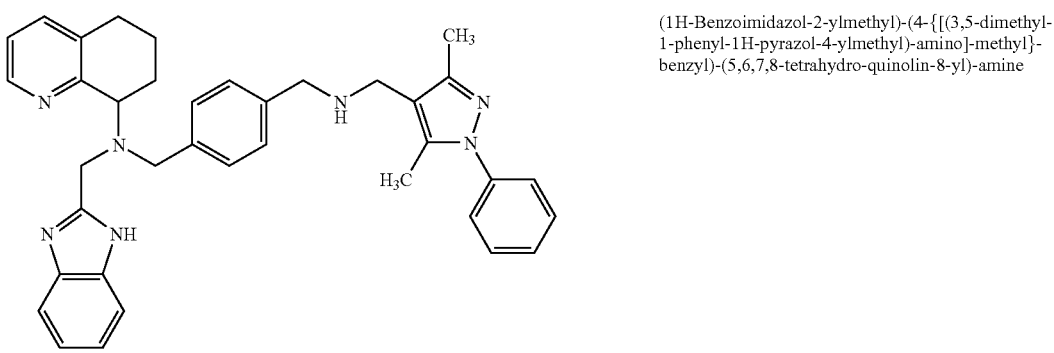
9167

(1H-Benzoimidazol-2-ylmethyl)-(4-{[(3,5-dimethyl-1-phenyl-1H-pyrazol-4-ylmethyl)-amino]-methyl}-benzyl)-(5,6,7,8-tetrahydro-quinolin-8-yl)-amine Example 143 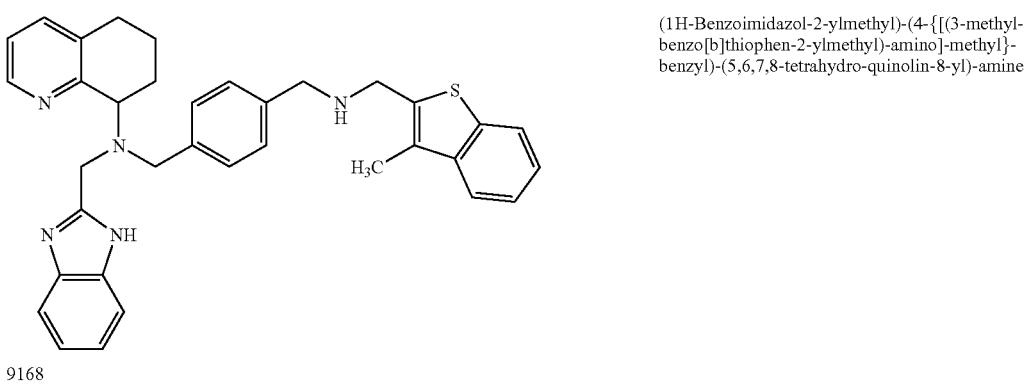
9168

(1H-Benzoimidazol-2-ylmethyl)-(4-{[(3-methyl-benzo[b]thiophen-2-ylmethyl)-amino]-methyl}-benzyl)-(5,6,7,8-tetrahydro-quinolin-8-yl)-amine Example 144 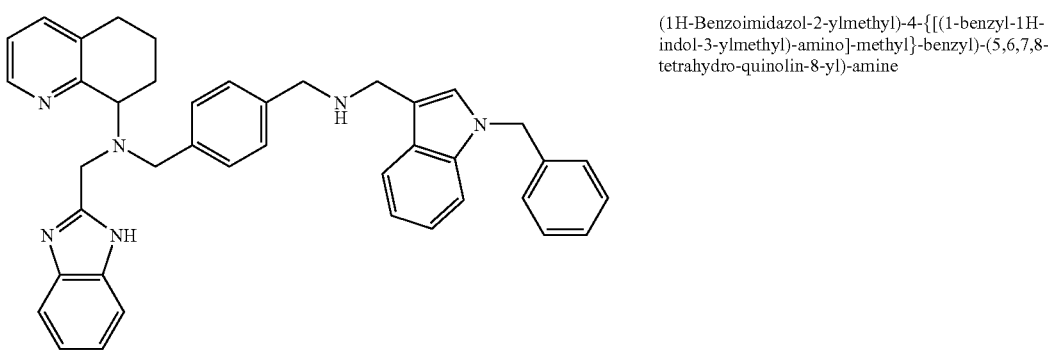
9169

(1H-Benzoimidazol-2-ylmethyl)-4-{[(1-benzyl-1H-indol-3-ylmethyl)-amino]-methyl}-benzyl)-(5,6,7,8-tetrahydro-quinolin-8-yl)-amine -continued Example 145

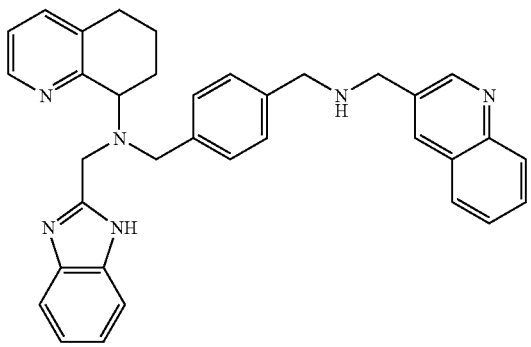

9170

(1H-Benzoimidazol-2-ylmethyl)-(4-{[(quinolin-3-ylmethyl)-amino]-methyl}-benzyl)-(5,6,7,8-tetrahydro-quinolin-8-yl)-amine Example 146

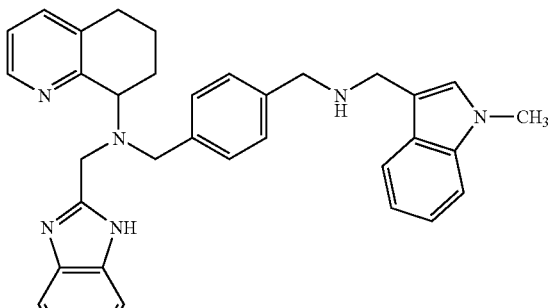

9171

(1H-Benzoimidazol-2-ylmethyl)-(4-{[(1-methyl-1H-indol-3-ylmethyl)-amino]-methyl}-benzyl)-(5,6,7,8-tetrahydro-quinolin-8-yl)-amine Example 147

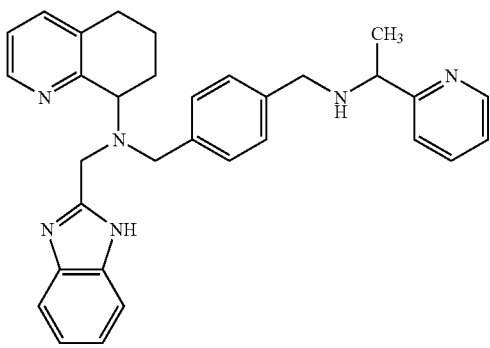

9173

(1H-Benzoimidazol-2-ylmethyl)-{4-[(1-pyridin-3-yl-ethylamino)-methyl]-benzyl}-(5,6,7,8-tetrahydro-quinolin-8-yl)-amine Example 148

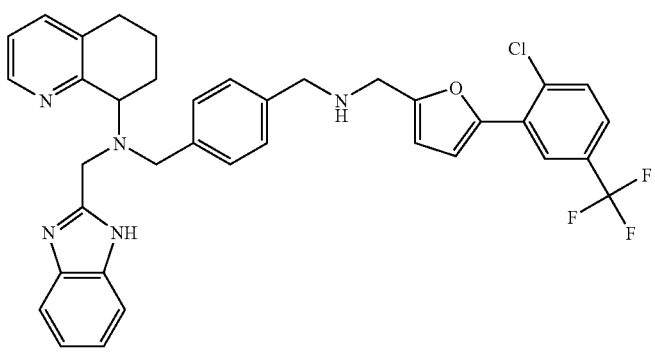

9174

(1H-Benzoimidazol-2-ylmethyl)-[4-({[5-(2-chloro-5-trifluoromethyl-phenyl)-furan-2-ylmethyl]-amino}-methyl)-benzyl]-(5,6,7,8-tetrahydro-quinolin-8-yl)-amine -continued
Example 149 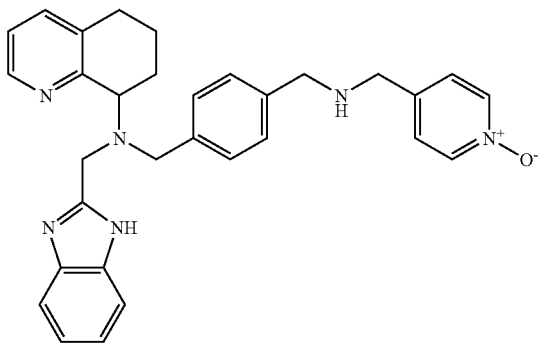
9175
(1H-Benzoimidazol-2-ylmethyl)-(4-{[(1-oxy-pyridin-4-ylmethyl)-amino]-methyl}-benzyl)-(5,6,7,8-tetrahydro-quinolin-8-yl)-amine
Example 150 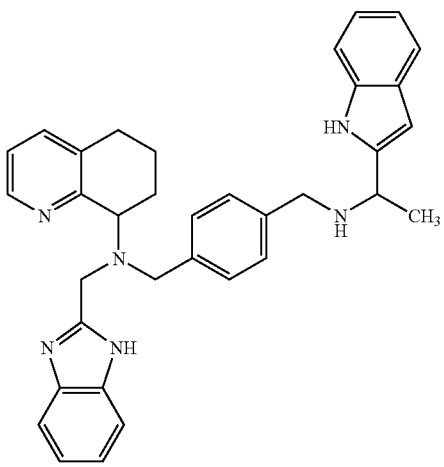
9176
(1H-Benzoimidazol-2-ylmethyl)-(4-{[1-(1H-indol-2-yl)-ethylamino]-methyl}-benzyl)-(5,6,7,8-tetrahydro-quinolin-8-yl)-amine
Example 151 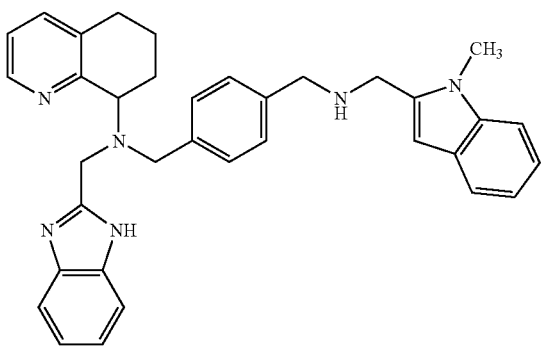
9177
(1H-Benzoimidazol-2-ylmethyl)-(4-{[(1-methyl-1H-indol-2-ylmethyl)-amino]-methyl}-benzyl)-(5,6,7,8-tetrahydro-quinolin-8-yl)-amine -continued Example 152

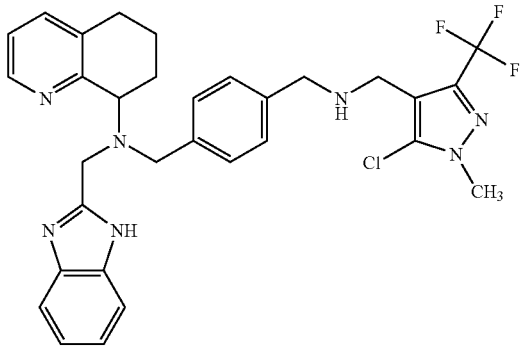

9178

(1H-Benzoimidazol-2-ylmethyl)-(4-{[(5-chloro-1-methyl-3-trifluoromethyl-1H-pyrazol-4-ylmethyl)-amino]-methyl}-benzyl)-(5,6,7,8-tetrahydro-quinolin-8-yl)-amine Example 153

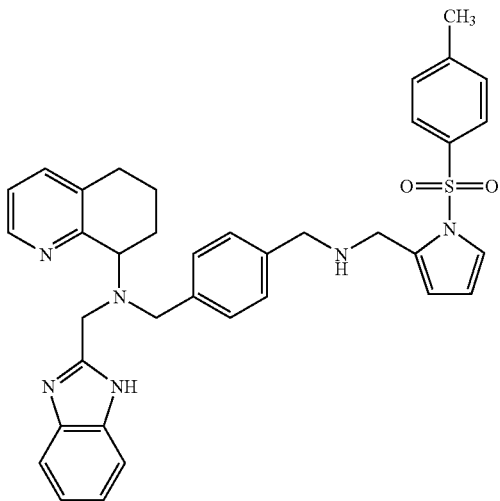

9179

(1H-Benzoimidazol-2-ylmethyl)-(5,6,7,8-tetrahydro-quinolin-8-yl)-[4-({[1-(toluene-4-sulfonyl)-1H-pyrrol-2-ylmethyl]-amino}-methyl)-benzyl]-amine Example 154

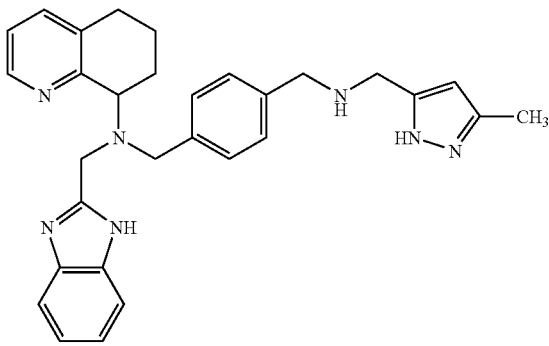

9180

(1H-Benzoimidazol-2-ylmethyl)-(4-{[(5-methyl-2H-pyrazol-3-ylmethyl)-amino]-methyl}-benzyl)-(5,6,7,8-tetrahydro-quinolin-8-yl)-amine -continued Example 155 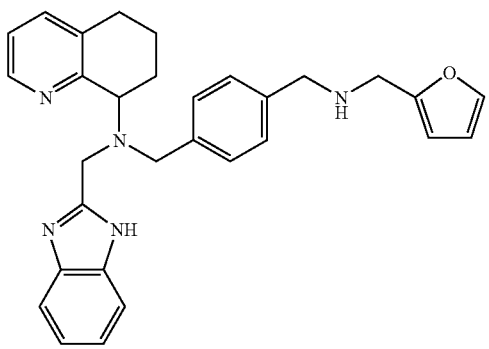
9181

(H-Benzoimidazol-2-ylmethyl)-(4-{[(furan-2-ylmethyl)-amino]-methyl}-benzyl)-(5,6,7,8-tetrahydro-quinolin-8-yl)-amine Example 156 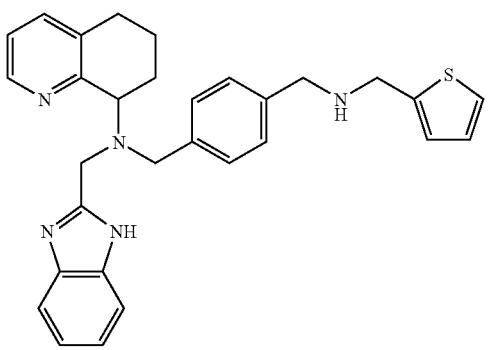
9182

(1H-Benzoimidazol-2-ylmethyl)-(5,6,7,8-tetrahydro-quinolin-8-yl)-(4-{[(thiophen-2-ylmethyl)-amino]-methyl}-benzyl)-amine Example 157 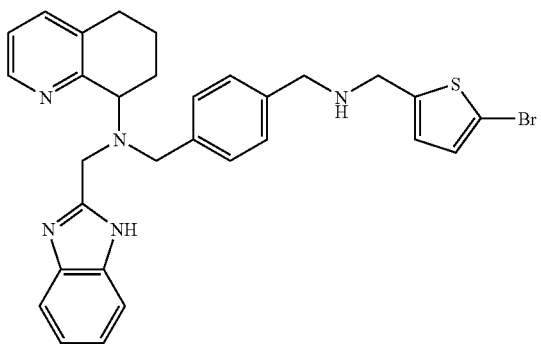
9183

(1H-Benzoimidazol-2-ylmethyl)-(4-{[(5-bromo-thiophen-2-ylmethyl)-amino]-methyl}-benzyl)-(5,6,7,8-tetrahydro-quinolin-8-yl)-amine Example 158 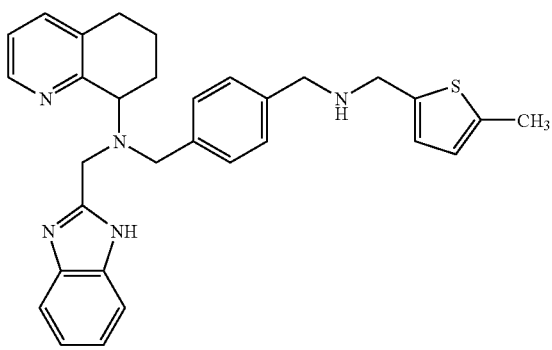
9184

(1H-Benzoimidazol-2-ylmethyl)-(4-{[(5-methyl-thiophen-2-ylmethyl)-amino]-methyl}-benzyl)-(5,6,7,8-tetrahydro-quinolin-8-yl)-amine -continued Example 159 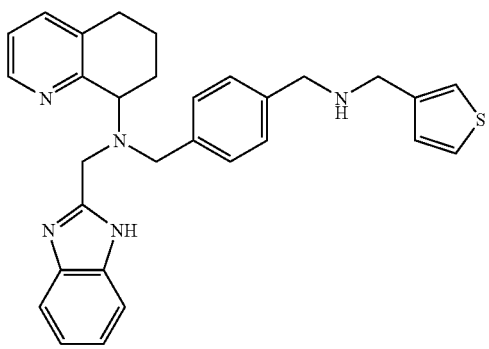

9185

(1H-Benzoimidazol-2-ylmethyl)-(5,6,7,8-tetrahydro-quinolin-8-yl)-(4-{[(thiophen-3-ylmethyl)-amino]-methyl}-benzyl)-amine Example 160 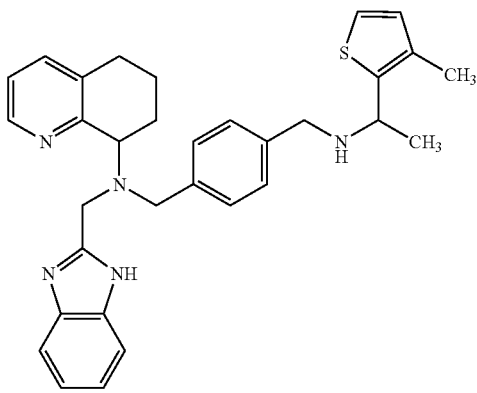

9186

(1H-Benzoimidazol-2-ylmethyl)-(4-{[1-(3-methyl-thiophen-2-yl)-ethylamino]-methyl}-benzyl)-(5,6,7,8-tetrahydro-quinolin-8-yl)-amine Example 161 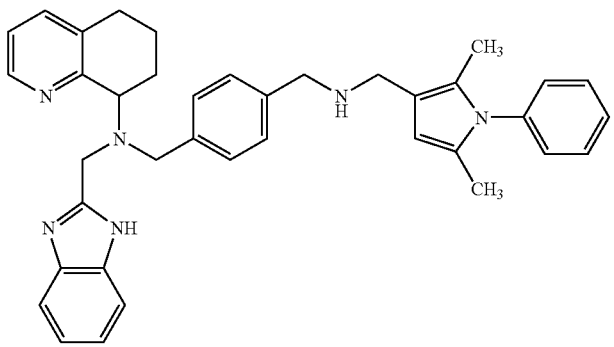

9187

(1H-Benzoimidazol-2-ylmethyl)-(4-{[(2,5-dimethyl-1-phenyl-1H-pyrrol-3-ylmethyl)-amino]-methyl}-benzyl)-(5,6,7,8-tetrahydro-quinolin-8-yl)-amine Example 162 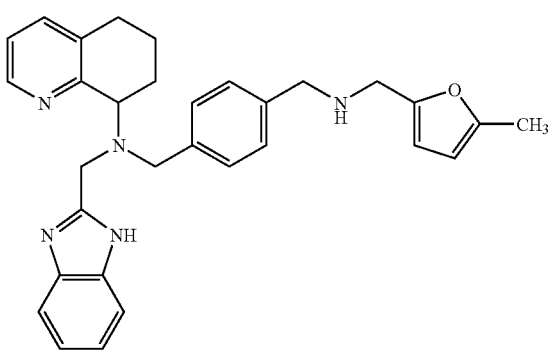

9188

(1H-Benzoimidazol-2-ylmethyl)-(4-{[(5-methyl-furan-2-ylmethyl)-amino]-methyl}-benzyl)-(5,6,7,8-tetrahydro-quinolin-8-yl)-amine -continued
Example 163 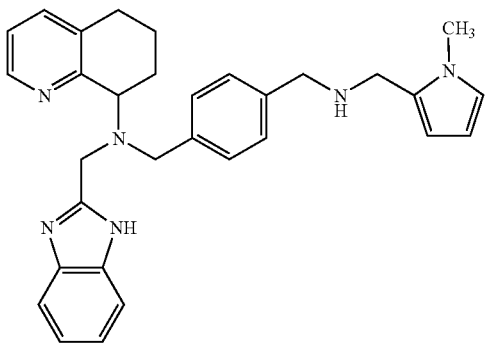
9189
(1H-Benzoimidazol-2-ylmethyl)-(4-{[(1-methyl-1H-pyrrol-2-ylmethyl)-amino]-methyl}-benzyl)-(5,6,7,8-tetrahydro-quinolin-8-yl)-amine
Example 164 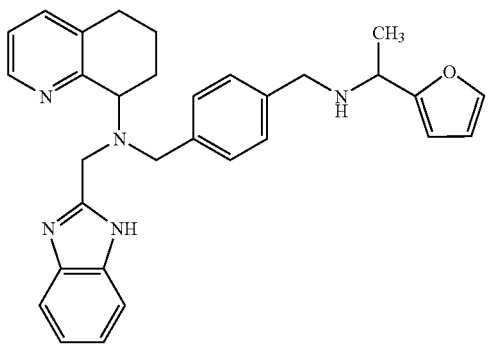
9190
(1H-Benzoimidazol-2-ylmethyl)-{4-[(1-furan-2-yl-ethylamino)-methyl]-benzyl}-(5,6,7,8-tetrahydro-quinolin-8-yl)-amine
Example 165 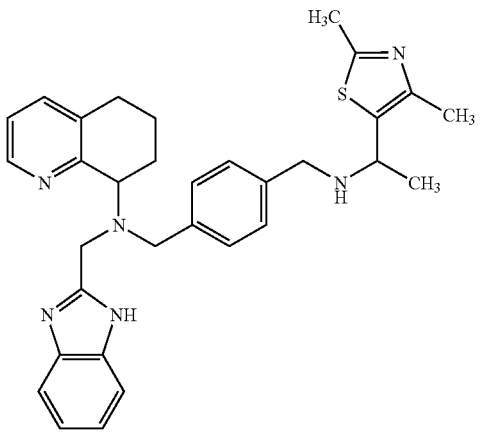
9191
(1H-Benzoimidazol-2-ylmethyl)-(4-{[1-(2,4-dimethyl-thiazol-5-yl)-ethylamino]-methyl}-benzyl)-(5,6,7,8-tetrahydro-quinolin-8-yl)-amine -continued Example 166 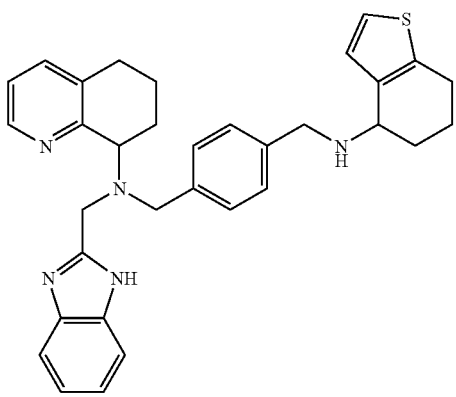

9192

(1H-Benzoimidazol-2-ylmethyl)-{4-[(4,5,6,7-tetrahydro-benzo[b]thiophen-4-ylamino)-methyl]-benzyl}-(5,6,7,8-tetrahydro-quinolin-8-yl)-amine Example 167 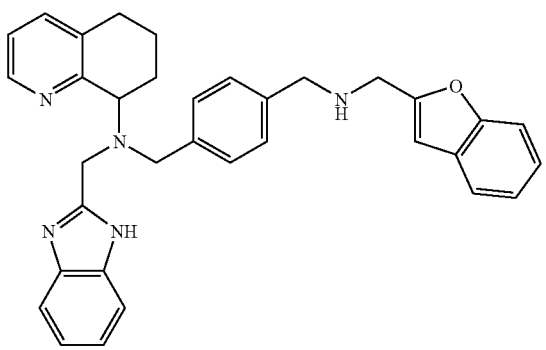

9194

4-{[(Benzofuran-2-ylmethyl)-amino]-methyl}-benzyl)-(1H-benzoimidazol-2-ylmethyl)-(5,6,7,8-tetrahydro-quinolin-8-yl)-amine Example 168 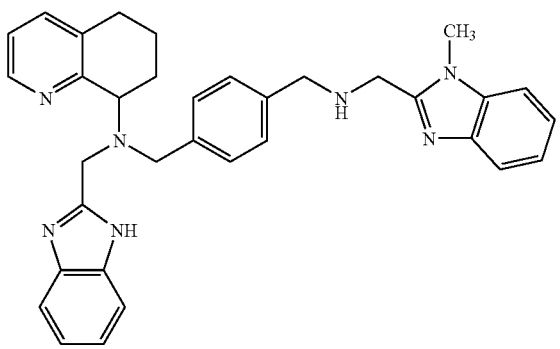

9195

(1H-Benzoimidazol-2-ylmethyl)-(4-{[(1-methyl-1H-benzoimidazol-2-ylmethyl)-amino]-methyl}-benzyl)-(5,6,7,8-tetrahydro-quinolin-8-yl)-amine Example 169 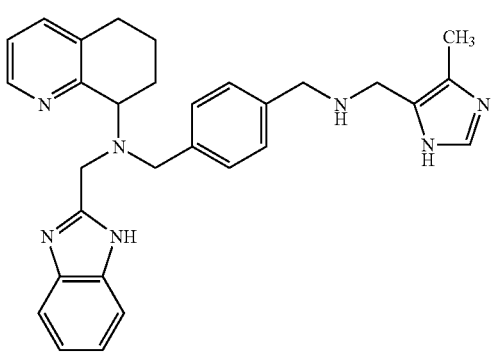

9196

(1H-Benzoimidazol-2-ylmethyl)-(4-{[(5-methyl-3H-imidazol-4-ylmethyl)-amino]-methyl}-benzyl)-(5,6,7,8-tetrahydro-quinolin-8-yl)-amine -continued Example 170 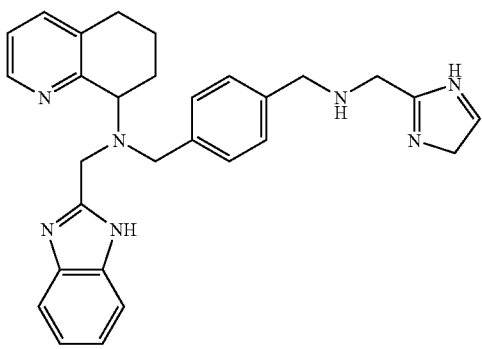
9197

(1H-Benzoimidazol-2-ylmethyl)-(4-{[(1H-imidazol-2-ylmethyl)-amino]methyl}-benzyl)-(5,6,7,8-tetrahydro-quinolin-8-yl)-amine Example 171 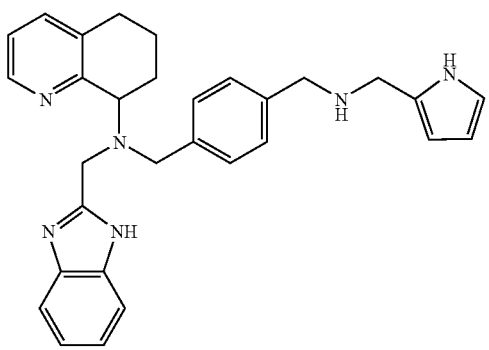
9198

(1H-Benzoimidazol-2-ylmethyl)-(4-{[(1H-pyrrol-2-ylmethyl)-amino]-methyl}-benzyl)-(5,6,7,8-tetrahydro-quinolin-8-yl)-amine Example 172 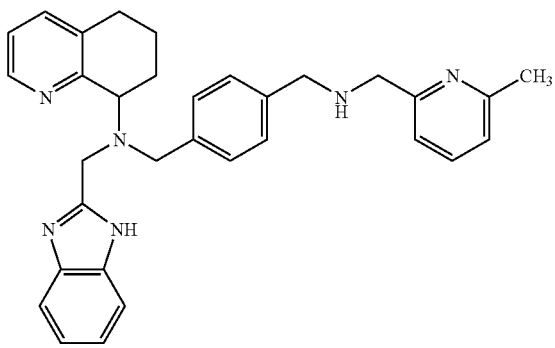
9199

(1H-Benzoimidazol-2-ylmethyl)-(4-{[(6-methyl-pyridin-2-ylmethyl)-amino]-methyl}-benzyl)-(5,6,7,8-tetrahydro-quinolin-8-yl)-amine Example 173 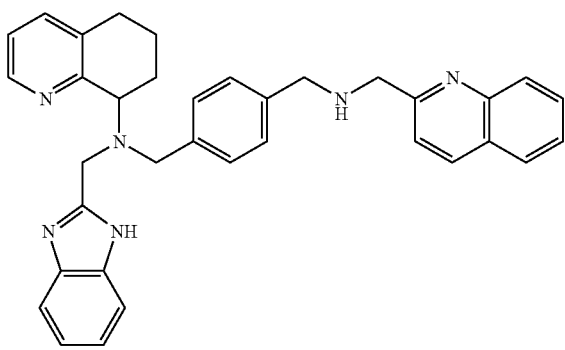
9200

(1H-Benzoimidazol-2-ylmethyl)-(4-{[(quinolin-2-ylmethyl)-amino]-methyl}-benzyl)-(5,6,7,8-tetrahydro-quinolin-8-yl)-amine -continued Example 174

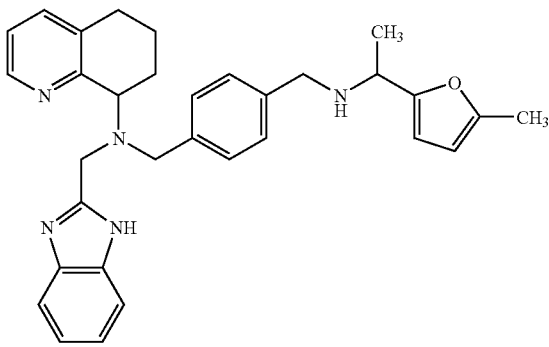

9201

(1H-Benzoimidazol-2-ylmethyl)-(4-{[1-(5-methyl-furan-2-yl)-ethylamino]-methyl}-benzyl)-(5,6,7,8-tetrahydro-quinolin-8-yl)-amine Example 175

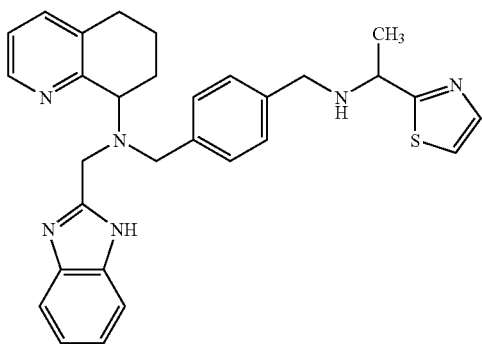

9202

(1H-Benzoimidazol-2-ylmethyl)-(5,6,7,8-tetrahydro-quinolin-8-yl)-{4-[(1-thiazol-2-yl-ethylamino)-methyl]-benzyl}-amine Example 176

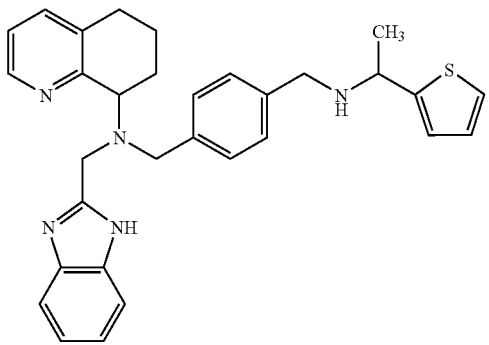

9203

(1H-Benzoimidazol-2-ylmethyl)-(5,6,7,8-tetrahydro-quinolin-8-yl)-{4-[(1-thiophen-2-yl-ethylamino)-methyl]-benzyl}-amine Example 177

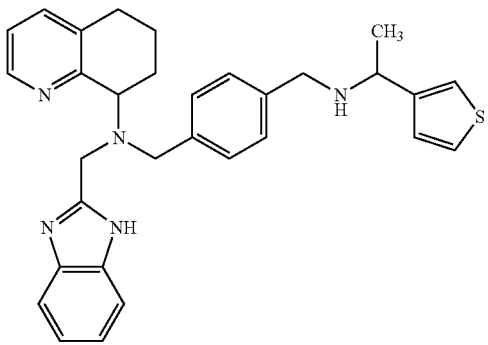

9204

(1H-Benzoimidazol-2-ylmethyl)-(5,6,7,8-tetrahydro-quinolin-8-yl)-(4-[(1-thiophen-3-yl-ethylamino)-methyl]-benzyl}-amine -continued Example 178 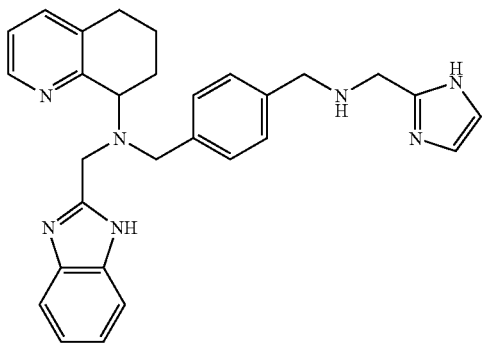
9197

(1H-Benzoimidazol-2-ylmethyl)-(4-{[(1-H-imidazol-2-ylmethyl)-amino]methyl}-benzyl)-(5,6,7,8-tetrahydro-quinolin-8-yl)-amine Example 179 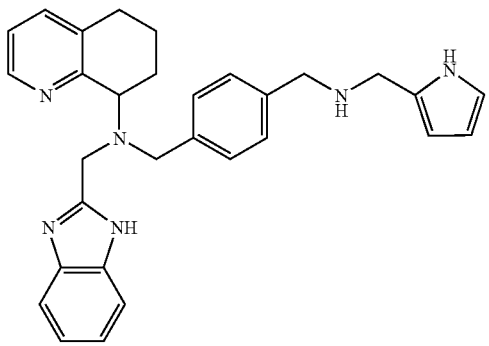
9198

(1H-Benzoimidazol-2-ylmethyl)-(4-{[(1H-pyrrol-2-ylmethyl)-amino]-methyl}-benzyl)-(5,6,7,8-tetrahydro-quinolin-8-yl)-amine Example 180 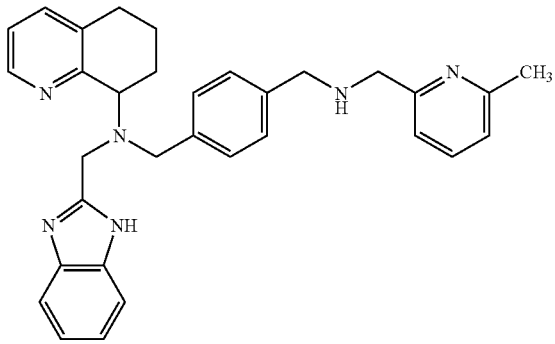
9199

(1H-Benzoimidazol-2-ylmethyl)-(4-{[(6-methyl-pyridin-2-ylmethyl)-amino]-methyl}-benzyl)-(5,6,7,8-tetrahydro-quinolin-8-yl)-amine Example 181 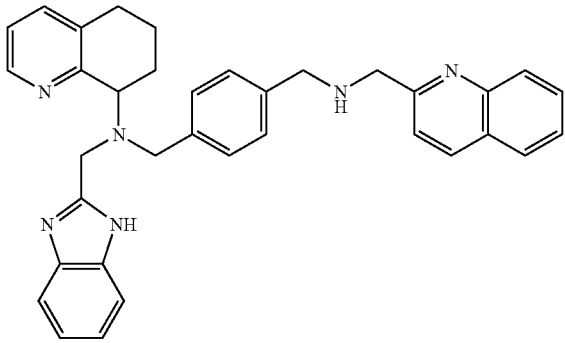
9200

(1H-Benzoimidazol-2-ylmethyl)-(4-{[(quinolin-2-ylmethyl)-amino]-methyl}-benzyl)-(5,6,7,8-tetrahydro-quinolin-8-yl)-amine Example 182 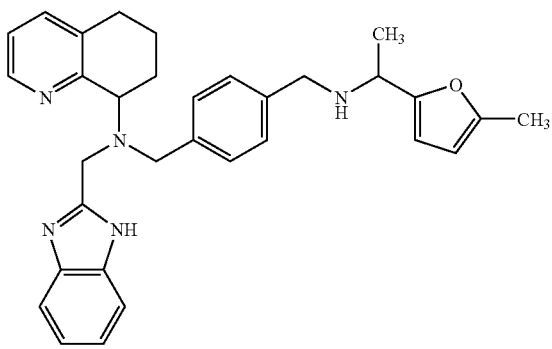
9201

(1H-Benzoimidazol-2-ylmethyl)-(4-{[1-(5-methyl-furan-2-yl)-ethylamino]-methyl}-benzyl)-(5,6,7,8-tetrahydro-quinolin-8-yl)-amine Example 183 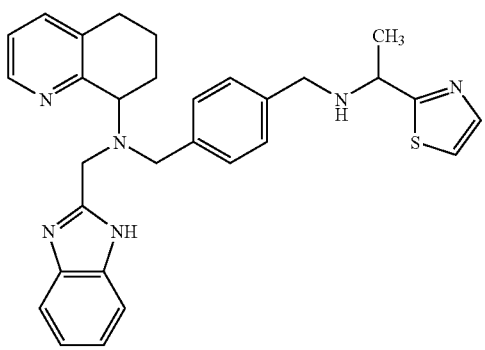
9202

(1H-Benzoimidazol-2-ylmethyl)-(5,6,7,8-tetrahydro-quinolin-8-yl)-{4-[(1-thiazol-2-yl-ethylamino)-methyl]-benzyl}-amine Example 184 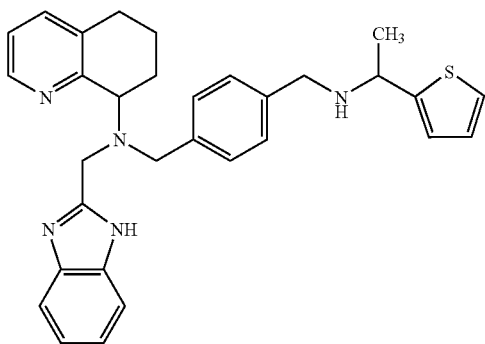
9203

(1H-Benzoimidazol-2-ylmethyl)-(5,6,7,8-tetrahydro-quinolin-8-yl)-{4-[(1-thiophen-2-yl-ethylamino)-methyl]-benzyl}-amine Example 185 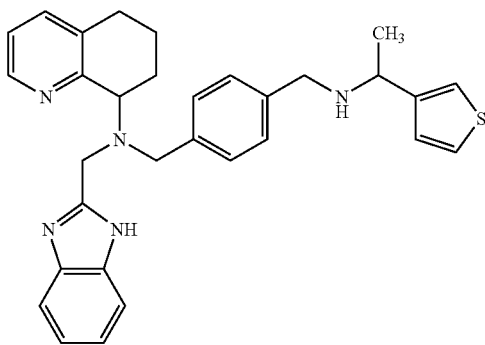
9204

(1H-Benzoimidazol-2-ylmethyl)-(5,6,7,8-tetrahydro-quinolin-8-yl)-{4-[(1-thiophen-3-yl-ethylamino)-methyl]-benzyl}-amine -continued Example 186 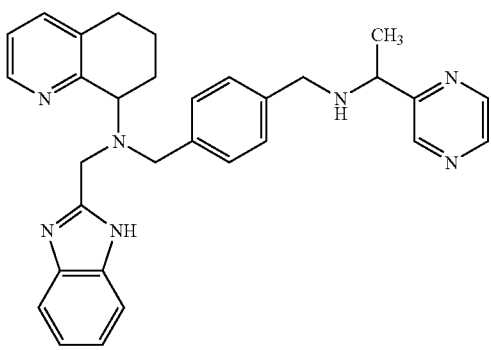
9205

(1H-Benzoimidazol-2-ylmethyl)-{4-[(1-pyrazin-2-yl-ethylamino)-methyl]-benzyl}-(5,6,7,8-tetrahydro-quinolin-8-yl)-amine Example 187 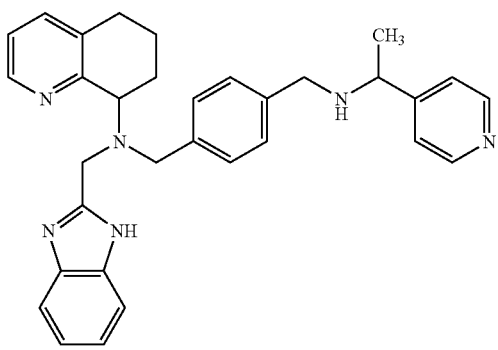
9206

(1H-Benzoimidazol-2-ylmethyl)-{4-[(1-pyridin-4-yl-ethylamino)-methyl]-benzyl}-(5,6,7,8-tetrahydro-quinolin-8-yl)-amine Example 188 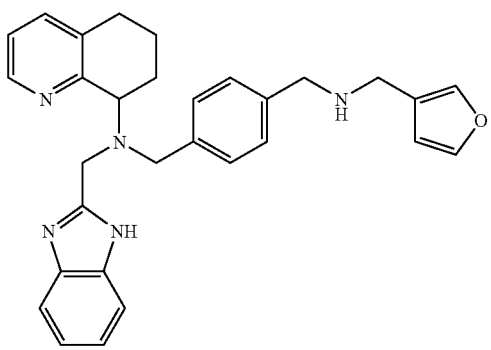
9207

(1H-Benzoimidazol-2-ylmethyl)-(4-{[(furan-3-ylmethyl)-amino]-methyl}-benzyl)-(5,6,7,8-tetrahydro-quinolin-8-yl)-amine Example 189 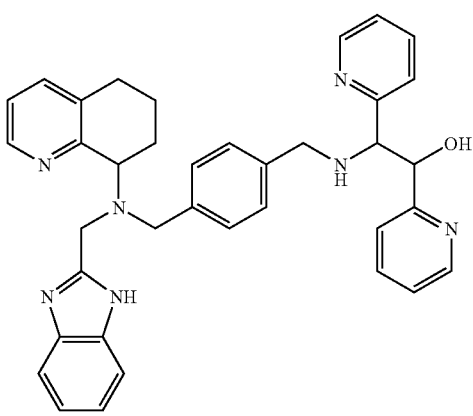
9208

2-(4-{[(1H-Benzoimidazol-2-ylmethyl)-(5,6,7,8-tetrahydro-quinolin-8-yl)-amino]-methyl}-benzylamino)-1,2-di-pyridin-2-yl-ethanol -continued Example 190 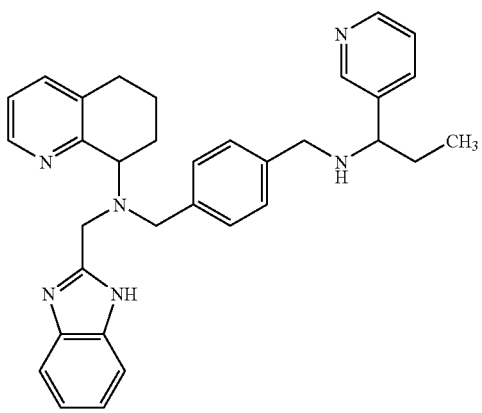
9209

1H-Benzoimidazol-2-ylmethyl)-{4-[(1-pyridin-3-yl-propylamino)-methyl]-benzyl}-(5,6,7,8-tetrahydro-quinolin-8-yl)-amine Example 191 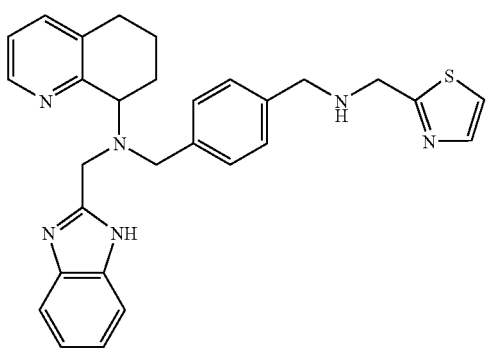
9210

1H-Benzoimidazol-2-ylmethyl)-(5,6,7,8-tetrahydro-quinolin-8-yl)-(4-{[(thiazol-2-ylmethyl)-amino]-methyl}-benzyl)-amine Example 192 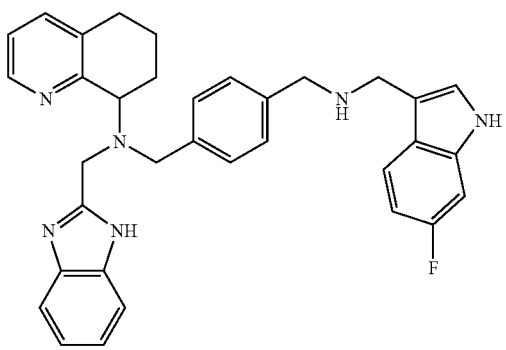
9211

(1H-Benzoimidazol-2-ylmethyl)-(4-{[(6-fluoro-1H-indol-3-ylmethyl)-amino]-methyl}-benzyl)-(5,6,7,8-tetrahydro-quinolin-8-yl)-amine Example 193 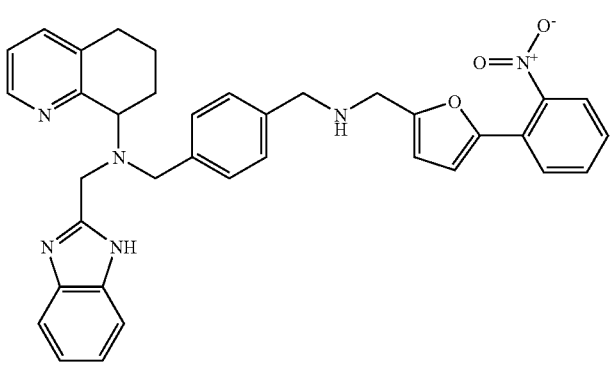
9212

1H-Benzoimidazol-2-ylmethyl)-[4-({[5-(2-nitro-phenyl)-furan-2-ylmethyl]-amino}-methyl)-benzyl]-(5,6,7,8-tetrahydro-quinolin-8-yl)-amine -continued Example 194

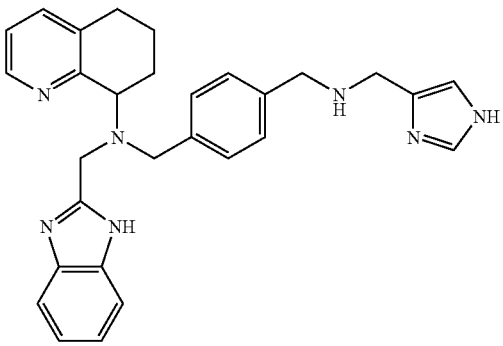

9213

(1H-Benzoimidazol-2-ylmethyl)-(4-{[(1H-imidazol-4-ylmethyl)-amino]methyl}-benzyl)-(5,6,7,8-tetrahydro-quinolin-8-yl)-amine Example 195

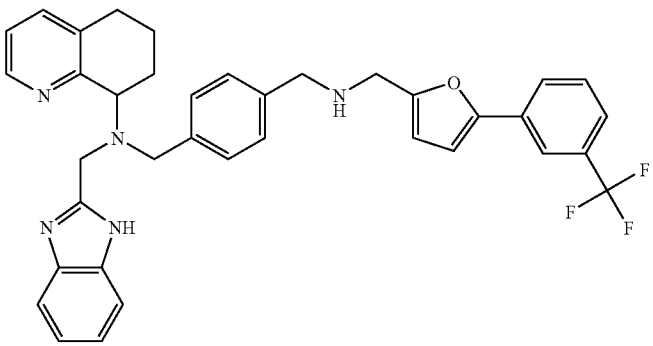

9214

(1H-Benzoimidazol-2-ylmethyl)-(5,6,7,8-tetrahydro-quinolin-8-yl)-[4-({[5-(3-trifluoromethyl-phenyl)-furan-2-ylmethyl]-amino}-methyl)-benzyl]-amine Example 196

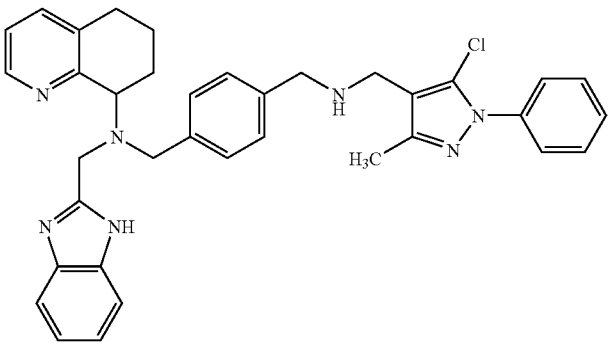

9215

(1H-Benzoimidazol-2-ylmethyl)-(4-{[(5-chloro-3-methyl-1-phenyl-1H-pyrazol-4-ylmethyl)-amino]-methyl}-benzyl)-(5,6,7,8-tetrahydro-quinolin-8-yl)-amine Example 197

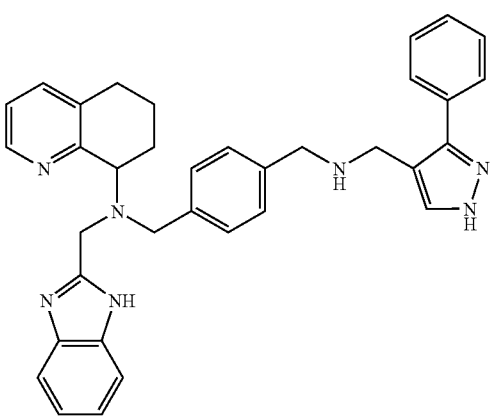

9216

(1H-Benzoimidazol-2-ylmethyl)-(4-{[(3-phenyl-1H-pyrazol-4-ylmethyl)-amino]-methyl}-benzyl)-(5,6,7,8-tetrahydro-quinolin-8-yl)-amine -continued Example 198

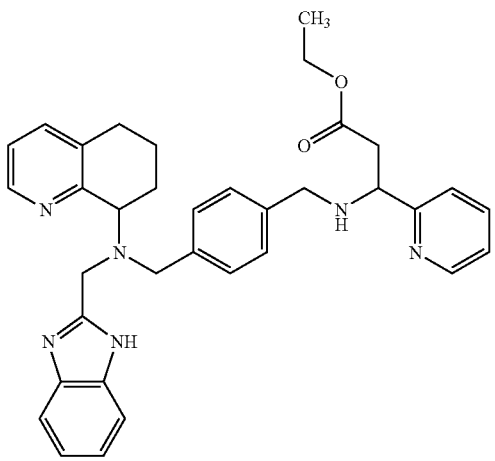

9217

3-(4-{[(1H-Benzoimidazol-2-ylmethyl)-(5,6,7,8-tetrahydro-quinolin-8-yl)-amino]-methyl}-benzylamino)-3-pyridin-2-yl-propionic acid ethylester Example 199

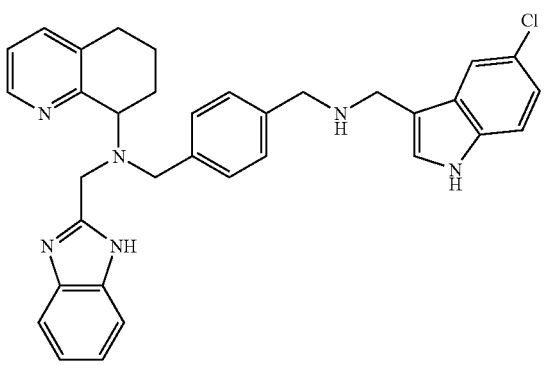

9218

1H-Benzoimidazol-2-ylmethyl)-(4-{[(5-chloro-1H-indol-4-ylmethyl)-amino]-methyl}-benzyl)-(5,6,7,8-tetrahydro-quinolin-8-yl)-amine Example 200

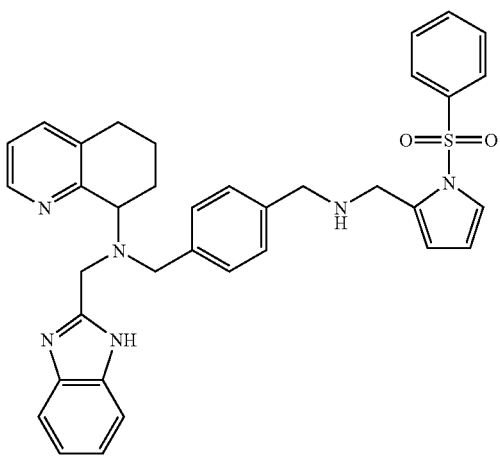

9219

4-{[(1-Benzenesulfonyl-1H-pyrrol-2-ylmethyl)-amino]-methyl}-benzyl)-(1H-benzoimidazol-2-ylmethyl)-(5,6,7,8-tetrahydro-quinolin-8-yl)-amine -continued Example 201

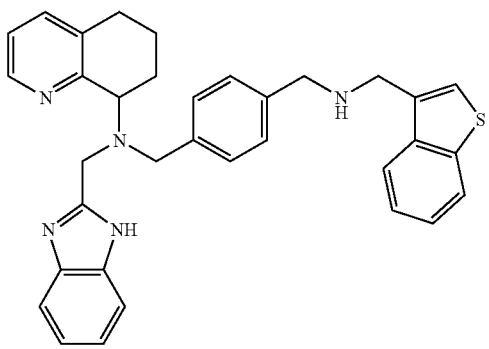

9220

4-{[(Benzo[b]thiophen-3-ylmethyl)-amino]-methyl}-benzyl)-(1H-benzoimidazol-2-ylmethyl)-(5,6,7,8-tetrahydro-quinolin-8-yl)-amine Example 202

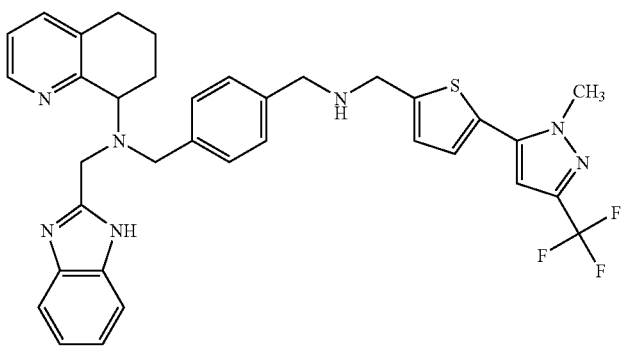

9221

(1H-Benzoimidazol-2-ylmethyl)-[4-({[5-(2-methyl-5-trifluoromethyl-2H-pyrazol-3-yl)-thiophen-2-ylmethyl]-amino}-methyl)-benzyl]-(5,6,7,8-tetrahydro-quinolin-8-yl)-amine Example 203

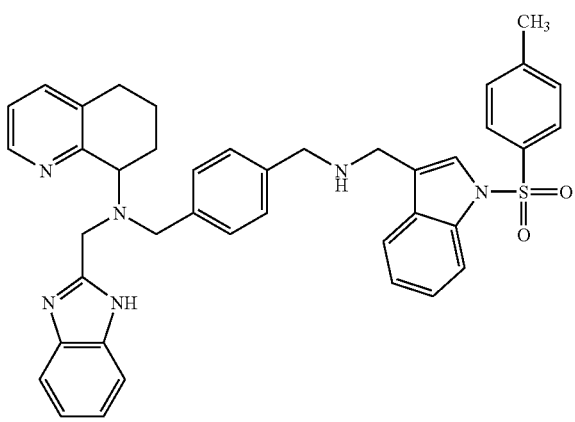

9222

(1H-Benzoimidazol-2-ylmethyl)-(5,6,7,8-tetrahydro-quinolin-8-yl)-[4-({[1-(tolene-4-sulfonyl)-1H-indol-3-ylmethyl]-amino}-methyl)-benzyl]-amine -continued Example 204 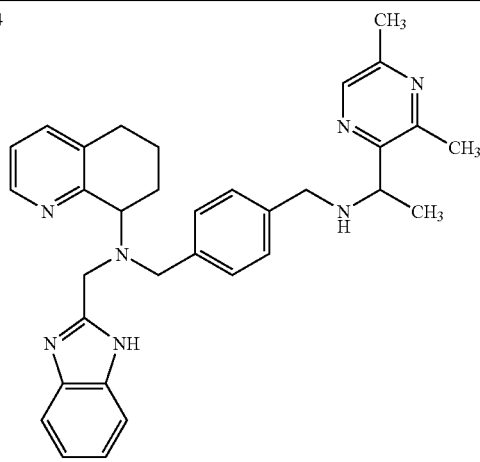
9223

(1H-Benzoimidazol-2-ylmethyl)-(4-{[1-(3,5-dimethyl-pyrazin-2-yl)-ethylamino]-methyl}-benzyl)-(5,6,7,8-tetrahydro-quinolin-8-yl)-amine Example 205 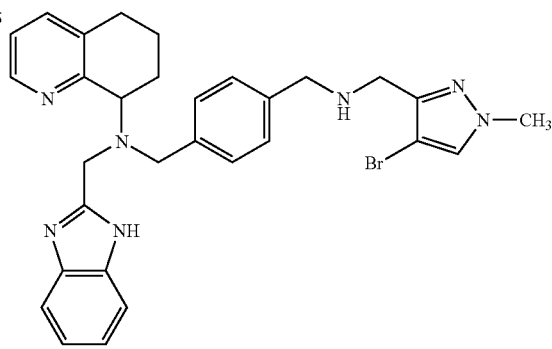
9224

(1H-Benzoimidazol-2-ylmethyl)-(4-{[(4-bromo-1-methyl-1H-pyrazol-3-ylmethyl)-amino]-methyl}-benzyl)-(5,6,7,8-tetrahydro-quinolin-8-yl)amine Example 206 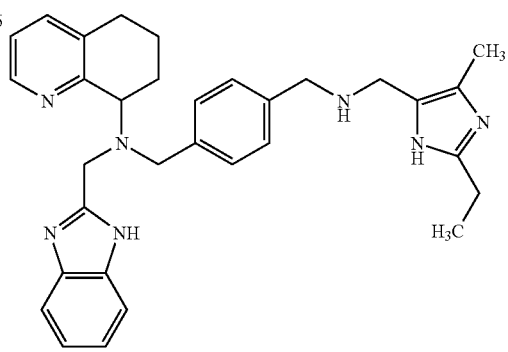
9225

(1H-Benzoimidazol-2-ylmethyl)-(4-{[(2-ethyl-5-methyl-3H-imidazol-4-ylmethyl)-amino]-methyl}-benzyl)-(5,6,7,8-tetrahydro-quinolin-8-yl)-amine Example 207 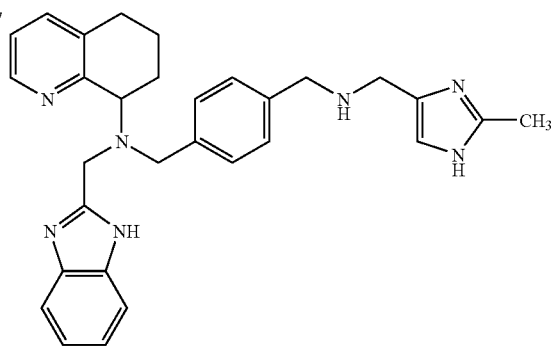
9226

(1H-Benzoimidazol-2-ylmethyl)-(4-{[(2-methyl-1H-imidazol-4-ylmethyl)-amino]-methyl}-benzyl)-(5,6,7,8-tetrahydro-quinolin-8-yl)-amine -continued Example 208
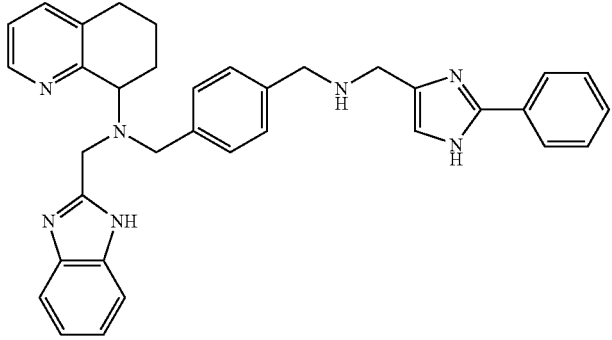
9227

(1H-Benzoimidazol-2-ylmethyl)-(4-{[(2-phenyl-1H-imidazol-4-ylmethyl)-amino]-methyl}-benzyl)-(5,6,7,8-tetrahydro-quinolin-8-yl)-amine Example 209
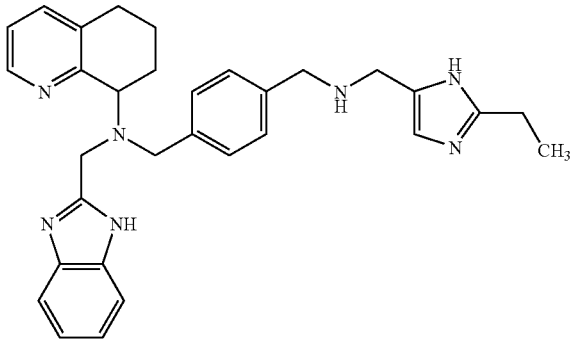
9228

(1H-Benzoimidazol-2-ylmethyl)-(4-{[(2-ethyl-3H-imidazol-4-ylmethyl)amino]-methyl}-benzyl)-(5,6,7,8-tetrahydro-quinolin-8-yl)-amine Example 210
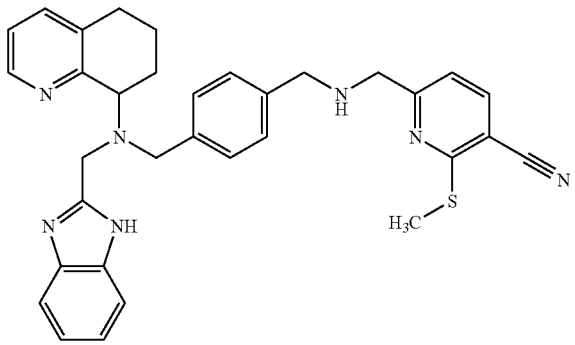
9229

6-[(4-{[(1H-Benzoimidazol-2-ylmethyl)-(5,6,7,8-tetrahydro-quinolin-8-yl)-amino]-methyl)-benzylamino)-methyl]-2-methylsulfanyl-nicotinonitrile Example 211
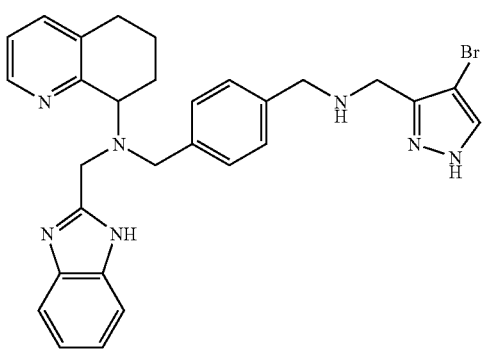
9230

(1H-Benzoimidazol-2-ylmethyl)-(4-({[4-bromo-1H-pyrazol-3-ylmethyl)-amino]-methyl}-benzyl)-(5,6,7,8-tetrahydro-quinolin-8-yl)-amine Example 212

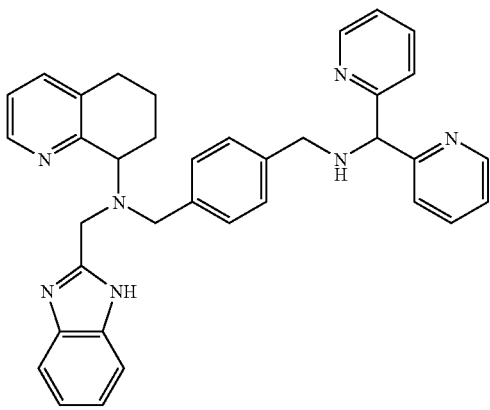

9231

(1H-Benzoimidazol-2-ylmethyl)-(4-{[(di-pyridin-2-yl-methyl)-amino]-methyl}-benzyl)-(5,6,7,8-tetrahydro-quinolin-8-yl)-amine

EXAMPLE 213

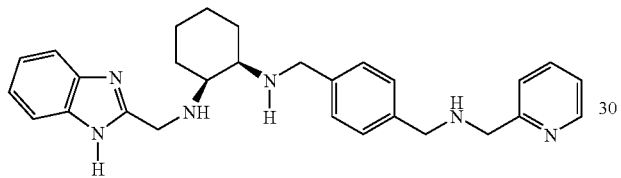

AMD 9536: Preparation of N-(2-pyridinylmethyl)-N'-[cis-2-[[(1H)-benzimidazol-2-ylmethyl]amino]]cyclohexyl]-1,4-benzenedimethanamine(hydrobromide salt)

Preparation of cis-1-[N-(t-butoxycarbonyl)]-2-[N-(2-nitrobenzenesulfonyl)]-cyclohexane-1,2-diamine

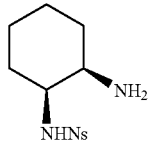

To a solution of cis-1-[N-(t-butoxycarbonyl)]-cyclohexane-1,2-diamine (1.01 g, 4.72 mmol) in CH$_2$Cl$_2$ (24 mL) was added triethylamine (1 mL, 7.17 mmol) followed by 2-nitrobenzenesulfonyl chloride (1.12 g, 5.06 mmol) The resultant solution was stirred at room temperature for 2 hours then poured into water and diluted with CH$_2$Cl$_2$ (25 mL). The phases were separated and the organic phase was washed with brine (2×20 mL), dried (Na$_2$SO$_4$), and concentrated. The resultant white solid (1.73 g) was used without further purification. $^1$H NMR (CDCl$_3$) ☐ 1.36-1.71 (m, 17H), 3.54-3.61 (m, 1H), 3.71-3.77 (m, 1H), 4.79 (br d, 1H J=7.8 Hz), 5.71 (br d, 1H J=8.1 Hz), 7.73-7.78 (m, 2H), 7.86-7.89 (m, 1H), 8.13-8.16 (m, 1H).

Preparation of cis-1 [N-(2-nitrobenzenesulfonyl)]-cyclohexane-1,2-diamine

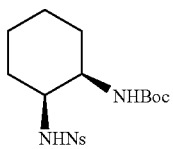

The solid (0.38 g, 0.97 mmol) from above was dissolved in CH$_2$Cl$_2$ (4 mL) and treated with trifluoroacetic acid (2 mL) and the mixture was stirred for 60 minutes. The resultant yellow foam (0.258 g) was used without further purification. $^1$H NMR (CDCl$_3$) ☐ 1.25-1.58 (m, 8H), 2.86-2.91 (m, 1H), 3.39-3.44 (m, 1H), 7.71-7.75 (m, 2H), 7.85-7.88 (m, 1H), 8.14-8.17 (m, 1H);

Using General Procedure B: To a solution of cis-1 [N-(2-nitrobenzenesulfonyl)]-cyclohexane-1,2-diamine (0.258 g, 0.862 mmol) and 4-[[N-(t-butoxycarbonyl)-N-(2-pyridinylmethyl)amino]methyl]benzaldehyde (0.281 g, 0.86 mmol) in CH$_2$Cl$_2$ (8 mL) was added NaBH(OAc)$_3$ (0.362 g, 1.71 mmol) and the mixture was stirred at room temperature for 2 hours. Purification of the crude material by column chromatography on silica gel (20:1 CH$_2$Cl$_2$—MeOH) afforded the desired amine (0.400 g) as a white solid.

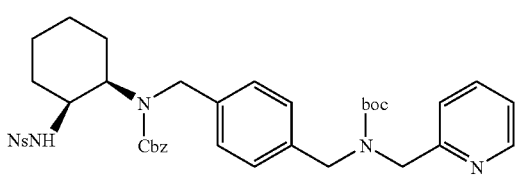

To a solution of the solid from above (0.20 g, 0.33 mmol) and N,N,-diisopropylethylamine (0.17 mL, 0.98 mmol) in CH$_2$Cl$_2$ (5 mL) was added benzylchloroformate (0.14 mL, 0.98 mmol) dropwise and the mixture was stirred at room temperature for 90 minutes. The crude oil was purified by column chromatography on silica gel (20:1 CH$_2$Cl$_2$—MeOH) and provided the protected amine (0.24 g) as a yellow foam.

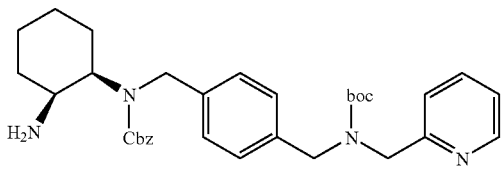

Using General Procedure C: The yellow foam (0.46 g, 0.62 mmol) was treated with thiophenol (0.63 mL, 6.2 mmol) and K$_2$CO$_3$ (1.20 g, 8.70 mmol) in CH$_3$CN (12 mL) for 30 minutes. Purification of the crude material by radial chromatography on silica gel (2 mm plate, 10:1:1 CH$_2$Cl$_2$—MeOH—NH$_4$OH) provided 0.20 g of a yellow oil.

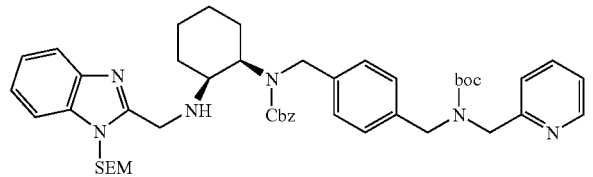

Using General Procedure B: To a solution of the above oil (0.10 g, 0.36 mmol) and 1-[2-(trimethylsilyl)ethoxy]methyl]-1H-benzimidazole-2-carboxaldehyde (0.281 g, 0.46 mmol) in CH$_2$Cl$_2$ (3.5 mL) was added NaBH(OAc)$_3$ (0.229 g, 1.08 mmol) and the mixture was stirred at room temperature overnight. Purification of the crude material by radial chromatography on silica gel (2 mm plate, 40:1:1 CH$_2$Cl$_2$—MeOH—NH$_4$OH) afforded the desired amine (0.199 g) as a white solid.

Global deprotection of SEM, Cbz & BOC protecting groups: The white solid (0.323 g) was dissolved in glacial acetic acid (2 mL), treated with HBr saturated acetic acid (7 mL) and stirred at room temperature overnight. The resultant hydrobromide salt was partitioned between CH$_2$Cl$_2$ (20 mL) and 10 N NaOH (4 mL). The aqueous phase was extracted with CH$_2$Cl$_2$ (3×10 mL) and the combined organic extracts were dried (Na$_2$SO$_4$), filtered and concentrated under reduced pressure to give the deprotected crude amine as a yellow oil. Purification of the crude material by radial chromatography on silica gel (1 mm plate, 40:1:1 CH$_2$Cl$_2$—MeOH—NH$_4$OH) gave 0.043 g of the free base of the title compound as a colorless oil.

Using General Procedure D: Conversion of the free base to the hydrobromide salt, followed by re-precipitation of the intermediate solid from methanol/ether, gave AMD 9536 (0.087 g) as a white solid. $^1$H NMR (D$_2$O) □ 1.40-1.75 (m, 6H), 1.89-1.96 (m, 2H), 3.32 (br s, 1H), 3.44-3.48 (m, 1H), 3.89 (d, 1H, J=13.2 Hz), 4.03-4.18 (m, 2H), 4.20 (d, 1H, J=13.8 Hz), 4.38 (d, 1H, J=13.5 Hz), 4.47 (s, 2H), 4.52 (d, 1H; J=18 Hz), 7.30 (d, 2H, J=8.1 Hz), 7.48 (d, 2H, J=8.1 Hz), 7.51-7.57 (m, 2H), 7.67-7.73 (m, 2H), 7.80-7.89 (m, 2H), 8.31 (td, 1H, J=8.1, 1.5 Hz), 8.71 (br d, 1H, J=6.0 Hz); $^{13}$C NMR (D$_2$O) □ 19.01, 22.78, 24.45, 26.63, 42.73, 48.31, 48.71, 50.70, 53.63, 58.75, 114.14, 126.66, 126.98, 127.01, 130.74, 131.09, 131.14, 131.73, 133.28, 144.20, 146.37, 147.22, 153.63; ES-MS m/z455 (M+H). Anal. Calcd. for C$_{28}$H$_{34}$N$_6$.4.4 HBr.4.5 H$_2$O: C, 37.68; H, 5.36; N, 9.42; Br, 39.39. Found: C, 37.83; H, 4.96; N, 9.11; Br, 39.00.

EXAMPLE: 214

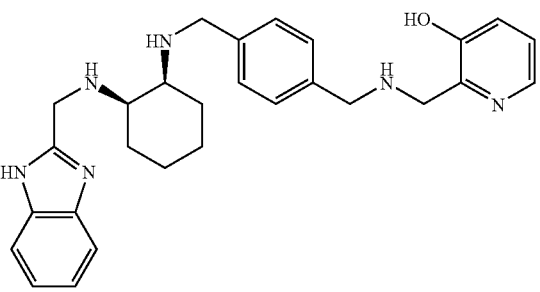

AMD9576: Preparation of N-[2-(3-hydroxy)pyridinylmethyl]-N'-{cis-2-[[(1H)-benzimidazol-2-ylmethyl]amino]cyclohexyl}-1,4-benzenedimethanamine(hydrobromide salt)

Using General Procedure B: To a solution of cis-1-[N-(2-nitrobenzenesulfonyl)]-cyclohexane-1,2-diamine (prepared as described for EXAMPLE, AMD9536) (780 mg, 2.6 mmol) and (4-formylbenzyl)-[(3-hydroxy)pyridin-2-ylmethyl]-carbamic acid tert-butyl ester (890 mg, 2.6 mmol) in THF (25 mL) was added acetic acid (0.15 mL, 2.6 mmol) and NaBH(OAc)$_3$ (1.65 g, 7.79 mmol) and the reaction stirred for 16 h to give a yellow foam (1.7 g).

A solution of the foam from above (1.7 g), N,N-diisopropylethylamine (1.5 mL, 8.6 mmol) and benzyl chloroformate (1.11 mL, 7.78 mmol) in CH$_2$Cl$_2$ (25 mL) was stirred at room temperature for 1.5 h. The mixture was diluted with saturated, aqueous NaHCO$_3$ (20 mL) and the aqueous phase was extracted with CH$_2$Cl$_2$ (3×15 mL). The phases were separated and the combined organic phases dried (MgSO$_4$), filtered and concentrated under reduced pressure. Purification of the crude material by column chromatography on silica gel (CH$_2$Cl$_2$/MeOH, 98:2) gave a yellow foam (2.16 g) which was used without further purification in the next step.

Using General Procedure C: The foam from above (2.16 g) in CH$_3$CN (50 mL) was reacted with thiophenol (0.80 mL, 7.8 mmol) and potassium carbonate (1.44 g, 10.4 mmol) at 40° C. for 20 h. Purification of the crude material by chromatography on neutral alumina (CH$_2$Cl$_2$/MeOH, 100:0 followed by 9:1) gave the deprotected material (976 mg, 65%) as a yellow foam. $^1$H NMR (CDCl$_3$) □ 1.26-1.90 (m, 17H), 3.45 (s, 1H), 4.06 (m, 1H), 4.46 (s, 4H), 4.60 (d, 1H, J=17 Hz), 4.78 (d, 1H, J=17 Hz), 5.16 (m, 2H), 7.13-7.38 (m, 11H), 8.05 (d, 1H, J=4.2 Hz), 9.69 (br s, 1H).

General Procedure for Alkylation: To a solution of the foam from above (972 mg, 1.69 mmol) and N-(tert-butoxycarbonyl)-2-chloromethylbenzimidazole (451 mg, 1.69 mmol) in CH$_3$CN (17 mL) was added potassium iodide (14 mg, 0.084 mmol) and N,N-diisopropylethylamine (0.44 mL, 2.5 mmol) and the mixture heated at 60° C. for 16 h. Purification of the crude material by chromatography on silica gel (CH$_2$Cl$_2$/MeOH/NH$_4$OH, 200:3:0.2) gave the N-alkylated product (1.10 g, 81%) as a yellow foam. $^1$H NMR (CDCl$_3$) □ 1.26-1.96 (m, 26H), 2.35 (s, 1H), 3.27 (s, 1H), 4.05 (s, 1H), 4.24 (m, 2H), 4.48 (m, 4H), 4.66 (m, 1H), 4.77-5.16 (m, 3H), 7.13-7.37 (m, 13H), 7.71 (m, 1H), 7.90 (m, 1H), 8.04 (dd, 1H, J=4.5, 1.5 Hz), 9.70 (s, 1H).

Using General Procedure D: The foam from above (190 mg, 0.236 mmol) was treated with HBr saturated acetic acid (5 mL) and stirred at room temperature overnight. Conversion of this material to the hydrobromide salt with simultaneous removal of the Boc and Cbz protecting groups gave a precipitate which was partitioned between $CH_2Cl_2$ (20 mL) and 10 N NaOH (4 mL). The aqueous phase was extracted with $CH_2Cl_2$ (3×10 mL) and the combined organic extracts were dried ($MgSO_4$), filtered and concentrated under reduced pressure to give the deprotected crude amine. Purification of the crude material by chromatography on silica gel ($CH_2Cl_2$/MeOH/ $NH_4OH$, 100:5:1) gave a colourless oil (53 mg, 48%).

Using General Procedure D: Conversion of the oil from above (53 mg, 0.11 mmol) to the hydrobromide salt followed by re-precipitation of the intermediate solid from methanol/ether gave AMD9576 (89 mg, 82%) as a colourless solid (89 mg, 82%). $^1H$ NMR $D_2O$) ☐ 1.38-1.76 (m, 6H), 1.93 (m, 2H), 3.33 (br s, 1H), 3.47 (m, 1H), 3.98 (m, 3H), 4.20 (d, 1H, J=14 Hz), 4.38 (d, 1H, J=14 Hz), 4.52 (m, 3H), 7.29 (d, 2H, J=8.1 Hz), 7.47 (d, 2H, J=8.4 Hz), 7.54 (m, 2H), 7.69 (m, 2H), 7.85 (dd, 1H, J=8.7, 5.4 Hz), 7.95 (dd, 1H, J=8.7, 0.9 Hz), 8.27 (dd, 1H, J=5.4, 1.2 Hz); $^{13}C$ NMR ($D_2O$) ☐ 20.55, 22.36, 24.34, 25.99, 28.18, 44.30, 45.47, 49.82, 52.38, 55.17, 60.33, 115.69, 128.18, 130.96, 132.26, 132.55, 132.67, 133.01, 134.11, 134.21, 134.84, 136.45, 155.16, 157.35. ES-MS m/z 471 (M+H). Anal Calcd for ($C_{28}H_{34}N_6O$) 5.0(HBr) 2.0($H_2O$) 1.0(AcOH): C, 37.10; H, 4.88; N, 8.65; Br, 41.13. Found: C, 37.04; H, 4.70; N, 8.70; Br, 41.21.

EXAMPLE 215

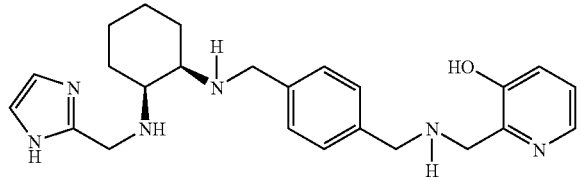

AMD 9537: Preparation of N-(3-hydroxy-2-pyridinylmethyl)-N'-[cis-2-[[imidazol-2-ylmethyl]amino]cyclohexyl]-1,4-benzenedimethanamine(hydrobromide salt)

Using General Procedure B: To a solution of cis-1 [N-(2-nitrobenzenesulfonyl)]-cyclohexane-1,2-diamine (0.318 g, 1.06 mmol) and 4-[[N-(t-butoxycarbonyl)-N-(3-hydroxy-2-pyridinylmethyl)amino]methyl]benzaldehyde (0.361 g, 1.04 mmol) in THF (10 mL) was added glacial acetic acid (60 ☐L, 1.05 mmol) followed by NaBH(OAc)$_3$ (0.424 g, 2.00 mmol) and the mixture was stirred at room temperature for 3 hours. The resultant yellow foam (0.67 g) was used without further purification.

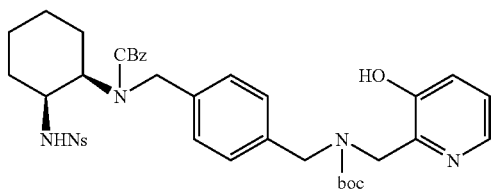

To a solution of the foam (0.66 g, 1.06 mmol) from above and N,N,-diisopropylethylamine (0.90 mL, 5.15 mmol) in $CH_2Cl_2$ (10 mL) was added benzylchloroformate (0.50 mL, 3.50 mmol) dropwise and the mixture was stirred at room temperature for 30 minutes. The crude oil was purified by column chromatography on silica gel (40:1 $CH_2Cl_2$— MeOH) and provided the protected amine (0.63 g) as a white foam.

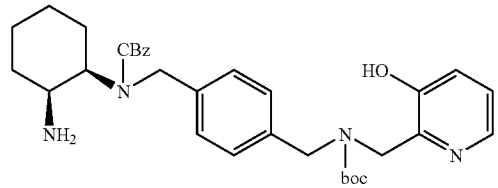

Using General Procedure C: The white foam (0.63 g, 0.83 mmol) was treated with thiophenol (0.65 mL, 6.33 mmol) and $K_2CO_3$ (1.50 g, 10.88 mmol) in $CH_3CN$ (16 mL) for 30 minutes. Purification of the crude material by radial chromatography on silica gel (2 mm plate, 10:1:1 $CH_2Cl_2$— MeOH—$NH_4OH$) provided 0.185 g of a white foam. $^1H$ NMR (CDCl$_3$) ☐ 1.26-1.90 (m, 17H), 3.45 (br s, 1H), 4.06 (br d, 1H, J=12.6 Hz), 4.46 (br s, 4H), 4.59 (d, 1H, J=16.6 Hz), 4.75-4.80 (m, 1H), 5.15 (br s, 2H), 7.13-7.36 (m, 11H), 8.05 (dd, 1H, J=4.5, 1.5 Hz), 9.70 (br s, 1H);

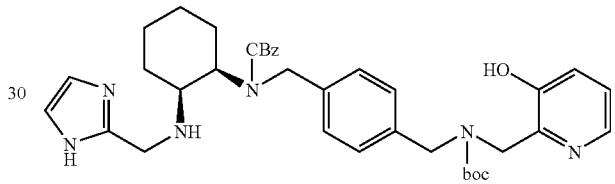

Using General Procedure A: To a solution of the above foam (0.185 g, 0.322 mmol) and imidazole-2-carboxaldehyde (0.030 g, 0.314 mmol) in MeOH (3.5 mL) was added NaBH$_3$CN (0.047 g, 0.75 mmol) and the mixture was stirred at room temperature for 3 days. Purification of the crude material by radial chromatography on silica gel (2 mm plate, 20:1 $CH_2Cl_2$—MeOH) afforded the desired amine (0.114 g) as a white solid.

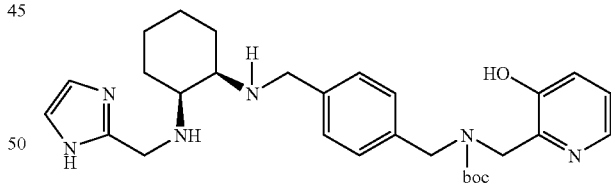

Removal of Cbz Protecting group: To a solution of the above solid (0.113 g, 0.172 mmol) in MeOH (2 mL) was added palladium on activated carbon (10%, 22 mg) and the mixture was hydrogenated (1 atm) at room temperature overnight. The crude material was purified by radial chromatography on silica gel (1 mm plate, 100:1:1 $CH_2Cl_2$—MeOH— $NH_4OH$) and afforded the amine as a white solid (42 mg).

Using General Procedure D: Conversion of the white solid (42 mg) to the hydrobromide salt with simultaneous removal of the BOC-protecting group, followed by re-precipitation of the intermediate solid from methanol/ether, gave AMD 9537 (54 mg) as a white solid.

$^1H$ NMR ($D_2O$) ☐ 1.37-1.63 (m, 5H), 1.72-1.77 (m, 2H), 1.88-1.94 (m, 1H), 3.22 (br s, 1H), 3.35-3.40 (m, 1H), 3.86 (d,

1H, J=16.5 Hz), 4.21-4.35 (m, 3H), 4.44 (s, 2H), 4.62 (s, 2H), 7.36 (s, 2H), 7.52 (s, 4H), 7.88 (dd, 1H, J=8.7, 5.4 Hz), 8.00 (d, 1H, J=8.7 Hz), 8.30 (d, 1H, J=5.1 Hz); $^{13}$C NMR (D$_2$O) □ 16.45, 20.55, 21.82, 23.95, 39.57, 41.70, 45.72, 49.06, 50.89, 55.91, 116.69 (2 carbons), 127.09, 128.81 (4 carbons), 129.28, 130.29, 130.49, 130.60, 132.43, 144.57, 153.57; ES-MS m/z 421 (M+H).

EXAMPLE 216

Inhibition of Chemokine Induced Ca Flux Measured on a FLIPR (Molecular Devices)

Reagents:
Loading dye: Fluo-3, AM (Molecular Probes F-1241) is dissolved in anhydrous DMSO and stored frozen in aliquots. To increase the solubility of the dye in the loading medium, 10% (w/v) pluronic acid (Molecular Probes F-127) is added to the Fluo-3 stock solution immediately before use.
Flux Buffer:
HBSS+20 mM Hepes buffer+0.2% BSA, pH 7.4. HBSS 10× [(w/o phenol red and sodium bicarbonate (Gibco 14 065-049)]; Hepes buffer 1M (Gibco 15 630-056), BSA (Sigma A3675). The flux buffer is vacuum-filtered and stored refrigerated for a maximum of 5 days. Before use in the experiment, the buffer is warmed at 37° C. in a waterbath.
Antagonists:
The test compounds were diluted in flux buffer to the desired concentration and added to 4 wells of a black microplate (4 parallel measurements per compound). The following control wells were used: 100% response control (no inhibition), flux buffer was added; 100% inhibition control: chemokine was added at 5-times the concentration required to induce a Ca flux.
Preparation of the Agonist (Chemokine) Plate
The chemokines are diluted in flux buffer to concentrations that are 4-fold higher than the desired concentrations required for stimulation of the cells (i.e. 2.5 nM for SDF-1□ and 0.6 nM for RANTES). The chemokines were added to untreated 96-well Sero well compound plates (International Medical, Sterilin code 611F96). In the negative control well's (baseline monitoring), flux buffer is added instead of chemokine. As a positive control to check for dye loading efficiency, 20 µM digitonin (final concentration) was also included. The agonist plate was incubated in the FLIPR (37° C.) for 15-30 min.
Cell Loading Protocol for Measuring Inhibition of SDF-1□ Induced Ca Flux in SUP-T1 Cells.
SUP-T1 cells were centrifuged at room temperature (RT) and re-suspended in loading medium (RPMI-1640 containing 2% FBS and 4 µM Fluo-3, AM). The cells were incubate at room temperature for 45 min. then washed twice in flux buffer then incubated in flux buffer at room temperature for 10 min. The cells were centrifuged and re-suspended in flux buffer at a density of 3×10$^6$ cells per mL. A 100 µL aliquot of the cell suspension (3×10$^5$ cells) was added to each well of a black microplate (Costar 3603), which already contains 50 µL of a solution of the test compound (at concentrations that are 3-fold higher than the desired final compound concentrations). The microplate is then gently centrifuged at room temperature. Homogeneous spreading of the cells on the bottom of the microplate wells was then confirmed with a microscope and the microplate was incubated in the FLIPR (37° C.) for 10 min. prior to testing.
Fluorescence Measurements as a Function of Time on the FLIPR
The FLIPR settings (camera exposure time and laser power) are adjusted to obtain initial fluorescence values between 8,000 and 10,000 units. After monitoring a 20 second-baseline, the agonist (chemokine) (50 µL) is added by automatic pipettor with black pipette tips. Fluorescence is measured simultaneously in all wells of the microplate every 2 seconds (first 2 min) and thereafter every 6 seconds (additional 2 min). The average ca-flux measured in each set of 4 identical wells (one test compound) was calculated by the FLIPR software.
The compounds of the current invention were tested for inhibition of SDF-1□ induced Ca flux in SUP-T1 cells using the method described above. The following compounds inhibited SDF-1□ induced Ca flux greater than 20% at 20 □g/mL:
Example numbers: 1, 2, 3, 4, 5, 6, 7, 9, 10, 11, 12, 13, 14, 15, 20, 21, 22, 23, 24, 25, 26, 27, 28, 29, 30, 35, 36, 38, 40, 42, 44, 54-68 and 132-134.

EXAMPLE 217

Assay for Inhibition of HIV-1 (NL4.3) Replication in MT-4 Cells

Inhibition of HIV-1 NL4.3 (or III$_B$, CXCR4 using) replication assays were performed as previously described (Bridger et al. J. Med. Chem. 1999, 42, 3971-3981; De Clercq et al. Proc. Natl. Acad. Sci, 1992, 89, 5286-5290; De Clercq et al. Antimicrob. Agents Chemother. 1994, 38, 668-674; Bridger et al. J. Med. Chem. 1995, 38, 366-378; Schols et al. J. Exp. Med., 1997, 186, 1383-1388). Anti-HIV activity and cytotoxicity measurements were carried out in parallel. They were based on the viability of MT-4 cells that had been infected with HIV in the presence of various concentrations of the test compounds. After the MT-4 cells were allowed to proliferate for 5 days, the number of viable cells was quantified by a tetrazolium-based colorimetric 3-(4,5-dimethylthiazol-2-yl)-2,5-diphenyltetrazolium bromide (MTT) procedure in 96-well microtrays. In all of these assays, viral input (viral multiplicity of infection, MOI) was 0.01, or 100 times the 50% cell culture infective dose (CCID$_{50}$). The EC$_{50}$ was defined as the concentration required to protect 50% of the virus-infected cells against viral cytopathicity.
When compounds of the current invention were tested for inhibition of HIV-1 NL4.3 or III$_B$ replication in MT-4 cells, the following compounds exhibited EC$_{50}$'s of less than 20 µg/mL:
Examples numbers: 1, 2, 3, 4, 5, 6, 7, 8, 9, 10, 11, 12, 13, 14, 15, 16, 17, 19, 20, 21, 22, 23, 24, 25, 26, 27, 28, 29, 30, 31, 32, 33, 35, 36, 38, 40, 42, 44, 54-70 and 131-134

EXAMPLE 218

Assay for Inhibition of HIV-1 (BaL) Replication in PBMC's

When compounds of the current invention were tested for inhibition of HIV-1 BaL (CCR5 using) replication in PHA-stimulated PBMC's (peripheral blood mononuclear cells) using viral p24 antigen expression (De Clercq et al. Antimicrob. Agents Chemother. 1994, 38, 668-674; Schols et al. J. Exp. Med., 1997, 186, 1383-1388), the following compounds exhibited EC$_{50}$'s of less than 20 µg/mL:
Example numbers: 1, 2, 8, 13, 14, 17, 19, 25, 27, 28, 29, 30, 31, 32, 33, 35, 37, 54, 55, 61-64, 66-68 and 132-134.

The invention claimed is:
1. A compound of the formula

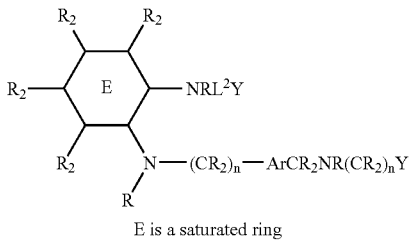

(2)

E is a saturated ring and the pharmaceutically acceptable salts thereof wherein:
each n is independently 0-2;
each R is independently H or alkyl (1-6C);
Ar is phenylene;
each Y is independently optionally substituted pyrimidyl, imidazole, pyridyl, benzimidazole, or benzooxazole; and
$L^2$ is a covalent bond or a C1-6 alkylene,
wherein said optional substituents are independently halogen, nitro, cyano, carboxylic acid, alkyl, alkenyl, cycloalkyl, hydroxyl, thiol, or amino, acyl;
wherein the hydroxyl and thiol groups may be substituted by $C_{1-10}$ alkyl or by $C_{2-4}$ alkanoyl; and
wherein an amino group may also be substituted once or twice with $C_{1-10}$ alkyl, alkenyl or $C_{2-4}$ alkanoyl.

2. The compound of claim 1, wherein $L^2$ is methylene or ethylene.

3. The compound of claim 1, wherein all R coupled directly to ring E are H.

4. A composition comprising the compound of claim 1 or a pharmaceutically acceptable salt thereof, and a pharmaceutically acceptable carrier.

5. The compound of claim 1, wherein all R are H.

6. The compound of claim 1, wherein each Y is independently imicazole, benzimidazole or pyridyl.

7. The compound of claim 6, wherein all R are H.

8. The compound of claim 6, wherein $L^2$ is methylene or ethylene.

9. The compound of claim 6 which is
N-(2-pyridinylmethyl)-N'-[cis-2-(N-phenylamino)cyclohexyl]-1,4-benzenedimethanamine;
N-(2-pyridinylmethyl)-N'-[trans-2-[(pyridin-2-ylmethyl)amino]cyclohexyl]-1,4-benzenedimethanamine;
N-(2-pyridinylmethyl)-N'-[cis-2-[(N-pyridin-2-ylmethyl)amino]cyclohexyl]-1,4-benzenedimethanamine;
N-(2-pyridinylmethyl)-N'-[cis-2-[(1H-imidazol-2-ylmethyl)amino]cyclohexyl]-1,4-benzenedimethanamine;
2-{[4-({2-[(pyridin-2-ylmethyl)-amino]-cyclohexylamino}-methyl)-benzylamino]-methyl}-pyridin-3-ol;
N-(2-pyridinylmethyl)-N'-[cis-2-[[(1H)-benzimidazol-2-ylmethyl]amino]]cyclohexyl]-1,4-benzenedimethanamine;
N-[2-(3-hydroxy)pyridinylmethyl]-N'-{cis-2-[[(1H)-benzimidazol-2-ylmethyl]amino]cyclohexyl}-1,4-benzenedimethanamine;
N-(3-hydroxy-2-pyridinylmethyl)-N'-[cis-2-[[imidazol-2-ylmethyl]amino]cyclohexyl]-1,4-benzenedimethanamine;
or a pharmaceutically acceptable salt thereof.

* * * * *